US009988400B2

(12) United States Patent
Jiang et al.

(10) Patent No.: US 9,988,400 B2
(45) Date of Patent: Jun. 5, 2018

(54) THIAZOLOPYRIMIDINONES AND METHODS OF USE THEREOF

(71) Applicant: Genentech, Inc., South San Francisco, CA (US)

(72) Inventors: Yu Jiang, Beijing (CN); Guosheng Wu, Beijing (CN); Po-Wai Yuen, Beijing (CN); Elisia Villemure, San Francisco, CA (US); Jacob Schwarz, San Ramon, CA (US); Cuong Ly, Burlingame, CA (US); Benjamin Sellers, Larkspur, CA (US); Matthew Volgraf, Oakland, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days. days.

(21) Appl. No.: 15/094,687

(22) Filed: Apr. 8, 2016

(65) Prior Publication Data

US 2016/0222033 A1    Aug. 4, 2016

Related U.S. Application Data

(63) Continuation of application No. PCT/EP2014/071522, filed on Oct. 8, 2014.

(30) Foreign Application Priority Data

Oct. 11, 2013  (WO) ................ PCT/CN2013/085031
Sep. 5, 2014   (WO) ................ PCT/CN2014/085959

(51) Int. Cl.
*C07D 513/04*  (2006.01)
*C07D 513/10*  (2006.01)
*C07D 513/14*  (2006.01)
*C07D 519/00*  (2006.01)

(52) U.S. Cl.
CPC ......... *C07D 513/14* (2013.01); *C07D 513/04* (2013.01); *C07D 513/10* (2013.01); *C07D 519/00* (2013.01)

(58) Field of Classification Search
CPC ... C07D 513/04; C07D 513/10; C07D 191/00
See application file for complete search history.

(56) References Cited

U.S. PATENT DOCUMENTS 3,888,983 A * 6/1975 Baetz ................... C07D 513/04
                                             514/259.2
2007/0155779 A1    7/2007 Verhoest et al.

FOREIGN PATENT DOCUMENTS

WO    2004/074270 A2    9/2004
WO    2014/202493 A1    12/2014
WO    2016/166078       10/2016

OTHER PUBLICATIONS

Agamennone et al., "Identification of small molecules acting against H1N1 influenza A virus" Virology 488:249-258 (Dec. 3, 2015).
Costa et al., "A Novel Family of Negative and Positive Allosteric Modulators of NMDA Receptors" Journal of Pharmacology and Experimental Therapeutics 335(3):614-621 (Dec. 1, 2010).
Ferrarini et al., "Study on Affinity Profile toward Native Human and Bovine Adenosine Receptors of a Series of 1,8-Naphthyridine Derivatives" Journal of Medicinal Chemistry 47(12):3019-3031 (Jan. 1, 2004).
Guo Chuangxing et al., "Discovery of 2-((1H-benzo[d]imidazol-1-yl)methyl)-4H-pyrido[1,2-a]pyrimidin-4-ones as novel PKM2 activators" Bioorganic & Medicinal Chemistry Letters 23(11):3358-3363 (Apr. 1, 2013).
Hackos et al., "Positive Allosteric Modulators of GluN2A-Containing NMDARs with Distinct Modes of Action and Impacts on Circuit Function" Neuron 89:983-999 ( 2016).
Kennis et al., "New substituted 1,2,3,4-tetrahydrobenzofuro[3,2-c]pyridine having highly active and potent central a2-antagonistic activity as potential antidepressants" Bioorganic & Medicinal Chemistry Letters 10:71-74 (Jan. 1, 2000).
Molnár et al., "Suzuki-Miyaura cross-coupling reactions of halo derivatives of 4H-pyrido[1,2-a]pyrimidin-4-ones" Organic & Biomolecular Chemistry 9(19):6559 (Jan. 1, 2011).
Villemure et al., "GluN2A-Selective Pyridopyrimidinone Series of NMDAR Positive Allosteric Modulators with an Improved in Vivo Profile" ACS Medicinal Chemistry Letters 8:84-89 ( 2017)
Volgraf et al., "Discovery of GluN2A-Selective NMDA Receptor Positive Allosteric Modulators (PAMs): Tuning Deactivation Kinetics via Structure-Based Design" Journal of Medicinal Chemistry 59:2760-2779 ( 2016).

* cited by examiner

*Primary Examiner* — Zohreh A Fay
(74) *Attorney, Agent, or Firm* — Jonathan Duffield

(57) ABSTRACT

The present invention relates to certain thiazolopyrimidinone compounds, pharmaceutical compositions comprising such compounds, and methods of treatment using such compounds.

70 Claims, No Drawings

THIAZOLOPYRIMIDINONES AND METHODS OF USE THEREOF

FIELD OF THE INVENTION

The present invention relates to certain thiazolopyrimidinone compounds, pharmaceutical compositions comprising such compounds, and methods of treating neurological and psychiatric conditions, and other diseases and medical conditions, with such compounds and pharmaceutical compositions. The present invention also relates to certain thiazolopyrimidinone compounds for use in modulating NMDA receptor activity.

BACKGROUND OF THE INVENTION

N-Methyl-D-aspartate (NMDA) receptors play an important role in various central nervous system functions, such as synaptic transmission and synaptic plasticity, and underlying functions such as regulation of long-term potentiation, long-term depression, and experience, dependent synaptic refinement. Costa et al., "A Novel Family of Negative and Positive Allosteric Modulators of NMDA Receptors," *J. Pharmacol. Exp. Ther.* 2010, 335, 614-621, at 614. Excitatory nerve transmission in these receptors is regulated by the neurotransmitter, L-glutamate, and the agonist, NMDA. PCT Intl. Publ. No. WO2007/006175, paras. 2-3. NMDA receptors are ligand-gated ion channels comprising seven subunits: GluN1, GluN2A-D, and GluN3A-B. Costa at 615. The NR2A and NR2B subunits have been implicated in glutamate binding to the receptor, while the NR1 subunit may play a role in the binding of the receptor co-agonist, glycine. The three-dimensional structures of the glutamate- and glycine-binding pockets of NMDA receptors have been characterized, allowing for design of more subtype-specific modulators.

Modulation of these receptors effects changes in learning and memory, and modulators of NMDA receptor activity are considered as potential treatments for neurological and psychiatric conditions including pain, neuropathic pain, inflammatory pain, peripheral neuropathy, stroke, epilepsy, neurodegeneration, schizophrenia, drug addiction, mood disorders, post-traumatic stress disorder, seizures, convulsions, age-associated memory impairment, and depression. Costa at 614. Modulation of NMDA receptor activity is linked with a neuroprotective role, with applications in treatments for stroke, traumatic brain injury, ischemia, and neurodegenerative diseases such as Alzheimer's disease, Parkinson's disease, Huntington's disease, amyotrophic lateral sclerosis, and Creutzfeldt-Jakob disease. Costa at 614-615.

There is a particular need for NMDA receptor modulators that demonstrate subtype selectivity among members of the NMDA receptor family. Selective agents will allow for optimal therapeutic activity with a reduced potential for adverse side effects. Costa at 615.

There remains a need for potent NMDA receptor modulators with desirable pharmaceutical properties. Certain thiazolopyrimidinone derivatives have been found in the context of this invention to have NMDA receptor-modulating activity.

SUMMARY OF THE INVENTION

In one aspect, the invention is directed to a compound of Formula II:

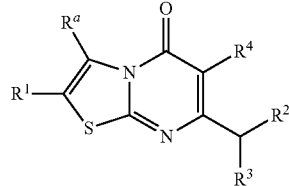

(II)

wherein
$R^a$ is $C_{1-6}$alkyl or $C_{2-6}$alkenyl, each optionally substituted with one or more $R^b$ substituents; $C_{2-6}$alkynyl; halo; —C(O)$R^c$; —N$R^d R^e$; C(O)N$R^d R^e$; —C(S)N$R^d R^e$; —C(=N—OH)—$C_{1-4}$alkyl; —O$C_{1-4}$alkyl; —O$C_{1-4}$haloalkyl; —S$C_{1-4}$ alkyl; —SO$_2 C_{1-4}$alkyl; cyano; $C_{3-6}$cycloalkyl optionally substituted with one or more $R^f$ substituents; or a phenyl, monocyclic heteroaryl, or heterocycloalkyl ring, each ring optionally substituted with one or more $R^g$ substituents;
  wherein each $R^b$ substituent is independently selected from the group consisting of —OH, —$C_{1-4}$alkoxy, —N$R^d R^e$, —C(O)N$R^d R^e$, —S$C_{1-4}$alkyl, —SO$_2 C_{1-4}$alkyl, cyano, halo, $C_{3-6}$cycloalkyl, and monocyclic heteroaryl;
  $R^c$ is $C_{1-4}$alkyl, —$C_{1-4}$haloalkyl, $C_{3-6}$cycloalkyl, or a monocyclic, carbon-linked heterocycloalkyl;
  $R^d$ is H or $C_{1-4}$alkyl;
  $R^e$ is H; $C_{1-4}$alkyl optionally substituted with —CN, —CF$_3$, —OH, or a monocyclic heterocycloalkyl; $C_{3-6}$cycloalkyl; —OH; or —O$C_{1-4}$alkoxy;
  or $R^d$ and $R^e$ taken together with the nitrogen to which they are attached form a heterocycloalkyl, optionally substituted with $C_{1-4}$alkyl or —OH;
  each $R^f$ substituent is independently selected from the group consisting of: $C_{1-4}$alkyl optionally substituted with —OH, cyano, or $C_{1-4}$alkoxy; —OH; halo; $C_{1-4}$haloalkyl; —CONH$_2$; and cyano; and
  each $R^g$ substituent is independently selected from the group consisting of $C_{1-4}$alkyl, —CF$_3$, halo, —NH$_2$, —OCH$_3$, cyano, and —OH;
$R^1$ is selected from the group consisting of H, $C_{1-6}$alkyl, $C_{1-4}$haloalkyl, $C_{3-6}$cycloalkyl, halo, —O$C_{1-4}$alkyl, —O$C_{1-4}$haloalkyl, cyano, and —C(O)$C_{1-4}$alkyl; or $R^a$ and $R^1$ taken together with the carbons to which they are attached form a 5- to 7-membered ring, optionally containing an O or NH, and optionally substituted with one or more $R^h$ substituents;
  wherein each $R^h$ substituent is independently —C(O)N$R^i R^j$, cyano, or is $C_{1-4}$alkyl optionally substituted with —OH, —OCH$_3$, cyano, or —C(O)N$R^i R^j$; or two $R^h$ groups attached to the same carbon and taken together with the carbon to which they are attached form a carbonyl or a $C_{3-6}$cycloalkyl;
  wherein $R^i$ and $R^j$ are each independently H or $C_{1-4}$alkyl;
$R^2$ is —$R^m$, —O$R^m$, or —N$R^m R^n$;
  wherein $R^m$ is aryl or heteroaryl, each optionally substituted with one or more $R^s$ substituents;
    wherein each $R^s$ substituent is independently selected from the group consisting of $C_{1-4}$alkyl, $C_{2-4}$alkenyl (optionally substituted with halo), $C_{2-4}$alkynyl, $C_{1-4}$haloalkyl, $C_{1-4}$alkoxy, $C_{1-4}$alkyl-OH, $C_{1-4}$haloalkoxy, halo, cyano, $C_{3-6}$cycloalkyl (optionally substituted with —OH or halo), monocyclic heteroaryl, —NH$_2$, —NO$_2$, —NHSO$_2$C$_{1-4}$alkyl, and —SO$_2$C$_{1-4}$alkyl;
R$''$ is H, C$_{1-4}$haloalkyl, or C$_{1-4}$alkyl optionally substituted with —OH or C$_{1-4}$alkoxy;
or R$'$ and R$''$ taken together with the nitrogen to which they are attached form a pyrrolidine or piperidine ring, optionally substituted with C$_{1-4}$alkyl and optionally fused to phenyl, wherein said phenyl is optionally substituted with halo;
R$^3$ is H or methyl; and
R$^4$ is H or fluoro;
or a pharmaceutically acceptable salt thereof.

In one aspect, the invention is directed to a compound of Formula I:

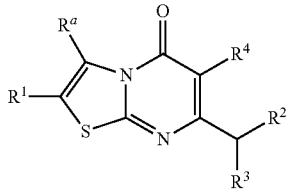

(I)

wherein
R$^a$ is C$_{1-6}$alkyl optionally substituted with one or more R$^b$ substituents; C$_{2-6}$alkenyl; C$_{2-6}$alkynyl; halo; —C(O)R$^c$; —NR$^d$R$^e$; —C(O)NR$^d$R$^e$; —C(S)NR$^d$R$^e$; —C(═N—OH)—C$_{1-4}$alkyl; —SO$_2$C$_{1-4}$alkyl; cyano; C$_{3-6}$cycloalkyl optionally substituted with one or more R$^f$ substituents; or a phenyl, monocyclic heteroaryl, or heterocycloalkyl ring, each ring optionally substituted with one or more R$^g$ substituents;
wherein each R$^b$ substituent is independently selected from the group consisting of —OH, —C$_{1-4}$alkoxy, —NR$^d$R$^e$, —C(O)NR$^d$R$^e$, —SC$_{1-4}$alkyl, —SO$_2$C$_{1-4}$alkyl, cyano, halo, and monocyclic heteroaryl;
R$^c$ is C$_{1-4}$alkyl, —C$_{1-4}$haloalkyl, C$_{3-6}$cycloalkyl, or a monocyclic, carbon-linked heterocycloalkyl;
R$^d$ is H or C$_{1-4}$alkyl;
R$^e$ is H; C$_{1-4}$alkyl optionally substituted with —CN, —CF$_3$, —OH, or a monocyclic heterocycloalkyl; C$_{3-6}$cycloalkyl; —OH; or —OC$_{1-4}$alkoxy;
or R$^d$ and R$^e$ taken together with the nitrogen to which they are attached form a heterocycloalkyl, optionally substituted with C$_{1-4}$alkyl or —OH;
each R$^f$ substituent is independently selected from the group consisting of: C$_{1-4}$alkyl optionally substituted with —OH, cyano, or C$_{1-4}$alkoxy; C$_{1-4}$haloalkyl; —CONH$_2$; and cyano; and
each R$^g$ substituent is independently selected from the group consisting of C$_{1-4}$alkyl, —CF$_3$, halo, —NH$_2$, —OCH$_3$, cyano, and —OH;
R$^1$ is selected from the group consisting of H, C$_{1-6}$alkyl, C$_{1-4}$haloalkyl, and C$_{3-6}$cycloalkyl; or R$^a$ and R$^1$ taken together with the carbons to which they are attached form a 5- to 7-membered ring, optionally containing an O or NH, and optionally substituted with one or more R$^h$ substituents;
wherein each R$^h$ substituent is independently —C(O)NR$^i$R$^j$, cyano, or is C$_{1-4}$alkyl optionally substituted with —OH, —OCH$_3$, cyano, or —C(O)NR$^i$R$^j$; or two R$^h$ groups attached to the same carbon and taken together with the carbon to which they are attached form a carbonyl or a C$_{3-6}$cycloalkyl;
wherein R$^i$ and R$^j$ are each independently H or C$_{1-4}$alkyl;
R$^2$ is —R$^m$, —OR$^m$, or —NR$^m$R$^n$;
wherein R$^m$ is aryl or heteroaryl, each optionally substituted with one or more R$^s$ substituents; wherein each R$^s$ substituent is independently selected from the group consisting of C$_{1-4}$alkyl, C$_{1-4}$haloalkyl, C$_{1-4}$alkoxy, C$_{1-4}$alkyl-OH, C$_{1-4}$haloalkoxy, halo, cyano, C$_{3-6}$cycloalkyl, —NHSO$_2$C$_{1-4}$alkyl, and —SO$_2$C$_{1-4}$alkyl;
R$^n$ is H, C$_{1-4}$haloalkyl, or C$_{1-4}$alkyl optionally substituted with —OH or C$_{1-4}$alkoxy;
or R$^m$ and R$^n$ taken together with the nitrogen to which they are attached form a pyrrolidine or piperidine ring, optionally substituted with C$_{1-4}$alkyl and optionally fused to phenyl, wherein said phenyl is optionally substituted with halo;
R$^3$ is H or methyl; and
R$^4$ is H or fluoro;
or a pharmaceutically acceptable salt thereof.

In a further aspect, the invention relates to pharmaceutical compositions each comprising an effective amount of at least one compound of Formula I or II or a pharmaceutically acceptable salt of a compound of Formula I or II. Pharmaceutical compositions according to the invention may further comprise at least one pharmaceutically acceptable excipient.

In another aspect, the invention is directed to a method of treating a subject suffering from a disease or medical condition mediated by NMDA receptor activity, comprising administering to the subject in need of such treatment an effective amount of at least one compound of Formula I or II or a pharmaceutically acceptable salt of a compound of Formula I or II, or comprising administering to the subject in need of such treatment an effective amount of a pharmaceutical composition comprising an effective amount of at least one compound of Formula I or II or a pharmaceutically acceptable salt of a compound of Formula I or II.

An aspect of the present invention concerns the use of compound of Formula I or II, or a pharmaceutically acceptable salt thereof, for the preparation of a medicament used in the treatment, prevention, inhibition, or elimination of a disease or medical condition mediated by NMDA receptor activity.

An aspect of the present invention concerns the use of a compound of Formula I or II, or a pharmaceutically acceptable salt thereof, for the preparation of a medicament used in the treatment, prevention, inhibition or elimination of a disease or medical condition mediated by NMDA receptor activity.

In another aspect, the compounds of Formula I or II, and pharmaceutically acceptable salts thereof, are useful as NMDA receptor modulators. Thus, the invention is directed to a method for modulating NMDA receptor activity, including when the NMDA receptor is in a subject, comprising exposing the NMDA receptor to an effective amount of at least one compound of Formula I or II, or a pharmaceutically acceptable salt of a compound of Formula I or II.

In yet another aspect, the present invention is directed to methods of making compounds of Formula I or II, and pharmaceutically acceptable salts thereof.

In certain embodiments of the compounds, pharmaceutical compositions, and methods of the invention, the compound of Formula I or II is a compound selected from those species described or exemplified in the detailed description below, or is a pharmaceutically acceptable salt of such a compound.

Additional embodiments, features, and advantages of the invention will be apparent from the following detailed description and through practice of the invention.

DETAILED DESCRIPTION AND PREFERRED EMBODIMENTS

For the sake of brevity, the disclosures of the publications cited in this specification, including patents and patent applications, are herein incorporated by reference in their entirety.

Most chemical names were generated using IUPAC nomenclature herein. Some chemical names were generated using different nomenclatures or alternative or commercial names known in the art. In the case of conflict between names and structures, the structures prevail.

General Definitions

As used above, and throughout this disclosure, the following terms, unless otherwise indicated, shall be understood to have the following meanings. If a definition is missing, the conventional definition as known to one skilled in the art controls. If a definition provided herein conflicts or is different from a definition provided in any cited publication, the definition provided herein controls.

As used herein, the terms "including," "containing," and "comprising" are used in their open, non-limiting sense.

As used herein, the singular forms "a," "an," and "the" include plural referents unless the context clearly dictates otherwise.

To provide a more concise description, some of the quantitative expressions given herein are not qualified with the term "about." It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, 4$^{th}$ edition, New York: Oxford University Press, 2002, pp. 360-361, 1084-1085; Smith and March, March's Advanced Organic Chemistry: Reactions, Mechanisms, and Structure, 5$^{th}$ edition, Wiley-Interscience, 2001.

Chemical Definitions

As used herein, "alkyl" refers to a saturated, straight- or branched-chain hydrocarbon group having from 1 to 10 carbon atoms. Representative alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl, and the like, and longer alkyl groups, such as heptyl, octyl, and the like. As used herein, "lower alkyl" means an alkyl having from 1 to 6 carbon atoms.

The term "alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "alkoxy" as used herein includes —O-(alkyl), wherein alkyl is defined above.

"Aryl" means a mono-, bi-, or tricyclic aromatic group, wherein all rings of the group are aromatic and all ring atoms are carbon atoms. For bi- or tricyclic systems, the individual aromatic rings are fused to one another. Examples of aryl groups are 6 and 10 membered aryls. Further examples of aryl groups include, but are not limited to, phenyl, naphthalene, and anthracene.

The term "cyano" as used herein means a substituent having a carbon atom joined to a nitrogen atom by a triple bond.

The term "deuterium" as used herein means a stable isotope of hydrogen having one proton and one neutron.

The term "halo" represents chloro, fluoro, bromo, or iodo. In some embodiments, halo is chloro, fluoro, or bromo. The term "halogen" as used herein refers to fluorine, chlorine, bromine, or iodine.

The term "haloalkyl" represents an alkyl group substituted with one, two, three, or more halogen atoms. Examples of haloalkyl groups include fluoromethyl, difluoromethyl, trifluoromethyl, fluoroethyl, trifluoroethyl, and trifluoropropyl.

The term "hydroxy" means an —OH group.

The term "oxo" means an =O group and may be attached to a carbon atom or a sulfur atom.

The term "N-oxide" refers to the oxidized form of a nitrogen atom.

As used herein, the term "cycloalkyl" refers to a saturated or partially saturated, monocyclic, fused polycyclic, bridged polycyclic, or spiro polycyclic carbocycle having from 3 to 15 carbon ring atoms. A non limiting category of cycloalkyl groups are saturated or partially saturated, monocyclic carbocycles having from 3 to 6 carbon atoms. Illustrative examples of cycloalkyl groups include, but are not limited to, the following moieties:

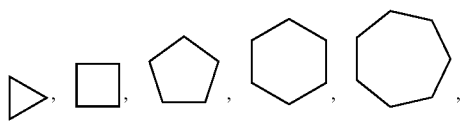

"Heterocycloalkyl" as used herein refers to a monocyclic, or fused, bridged, or spiro polycyclic ring structure that is saturated or partially saturated and has from three to 12 ring atoms selected from carbon atoms and up to three heteroatoms selected from nitrogen, oxygen, and sulfur. The ring structure may optionally contain up to two oxo groups on carbon or sulfur ring members, or an N-oxide. Illustrative heterocycloalkyl entities include, but are not limited to:

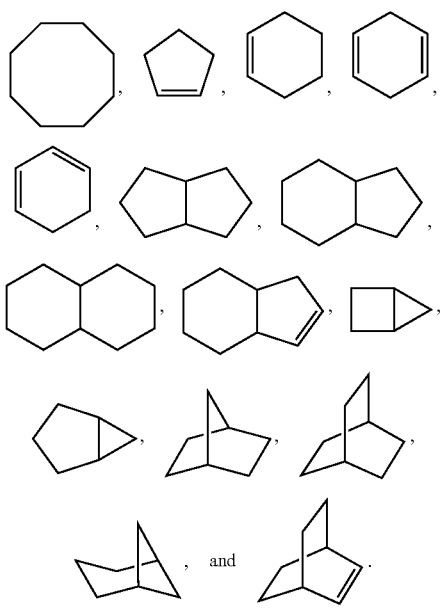

Heterocycloalkyl groups may be carbon-linked, meaning they are attached to the remainder of the molecule via a carbon atom, or nitrogen-linked, meaning they are attached to the remainder of the molecule via a nitrogen atom.

As used herein, the term "heteroaryl" refers to a monocyclic, or fused polycyclic, aromatic heterocycle having from three to 15 ring atoms that are selected from carbon, oxygen, nitrogen, and sulfur. Suitable heteroaryl groups do not include ring systems that must be charged to be aromatic, such as pyrylium. Suitable 5-membered heteroaryl rings (as a monocyclic heteroaryl or as part of a polycyclic heteroaryl) have one oxygen, sulfur, or nitrogen ring atom, or one nitrogen plus one oxygen or sulfur, or 2, 3, or 4 nitrogen ring atoms. Suitable 6-membered heteroaryl rings (as a monocyclic heteroaryl or as part of a polycyclic heteroaryl) have 1, 2, or 3 nitrogen ring atoms. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

Those skilled in the art will recognize that the species of heteroaryl, cycloalkyl, and heterocycloalkyl groups listed or illustrated above are not exhaustive, and that additional species within the scope of these defined terms may also be selected.

As used herein, the term "substituted" means that the specified group or moiety bears one or more suitable substituents. As used herein, the term "unsubstituted" means that the specified group bears no substituents. As used herein, the term "optionally substituted" means that the specified group is unsubstituted or substituted by the specified number of substituents. Where the term "substituted" is used to describe a structural system, the substitution is meant to occur at any valency-allowed position on the system.

As used herein, the expression "one or more substituents" denotes one to maximum possible number of substitution(s) that can occur at any valency-allowed position on the system. In a certain embodiment, one or more substituent means 1, 2, 3, 4, or 5 substituents. In another embodiment, one or more substituent means 1, 2, or 3 substituents.

Any atom that is represented herein with an unsatisfied valence is assumed to have the sufficient number of hydrogen atoms to satisfy the atom's valence.

When any variable (e.g., alkyl or $R^a$) appears in more than one place in any formula or description provided herein, the definition of that variable on each occurrence is independent of its definition at every other occurrence.

Numerical ranges, as used herein, are intended to include sequential whole numbers. For example, a range expressed as "from 0 to 4" or "0-4" includes 0, 1, 2, 3 and 4.

When a multifunctional moiety is shown, the point of attachment to the remainder of the formula can be at any point on the multifunctional moiety. In some embodiments, the point of attachment is indicated by a line or hyphen. For example, aryloxy—refers to a moiety in which an oxygen atom is the point of attachment to the core molecule while aryl is attached to the oxygen atom.

The nomenclature used herein to name the subject compounds is illustrated in the Examples herein. This nomenclature has generally been derived using the commercially-available LexiChem TK software (OpenEye, Santa Fe, N. Mex.).

Any formula given herein is intended to represent compounds having structures depicted by the structural formula as well as certain variations or forms. For example, compounds of any formula given herein may have asymmetric or chiral centers and therefore exist in different stereoisomeric forms. All stereoisomers, including optical isomers, enantiomers, and diastereomers, of the compounds of the general formula, and mixtures thereof, are considered to fall within the scope of the formula. Furthermore, certain structures may exist as geometric isomers (i.e., cis and trans isomers), as tautomers, or as atropisomers. All such isomeric forms, and mixtures thereof, are contemplated herein as part of the present invention. Thus, any formula given herein is intended to represent a racemate, one or more enantiomeric forms, one or more diastereomeric forms, one or more tautomeric or atropisomeric forms, and mixtures thereof.

The compounds described herein include pharmaceutically acceptable salt forms of compounds of Formula I or II. A "pharmaceutically acceptable salt" refers to a salt form of a free acid or base of a compound of Formula I or II that is non-toxic, is physiologically tolerable, is compatible with the pharmaceutical composition in which it is formulated, and is otherwise suitable for formulation and/or administration to a subject. Reference to a compound herein is understood to include reference to a pharmaceutically acceptable salt of said compound unless otherwise indicated.

Compound salts include acidic salts formed with inorganic and/or organic acids, as well as basic salts formed with inorganic and/or organic bases. In addition, where a given compound contains both a basic moiety, such as, but not limited to, a pyridine or imidazole, and an acidic moiety, such as, but not limited to, a carboxylic acid, one of skill in the art will recognize that the compound may exist as a zwitterion ("inner salt"); such salts are included within the term "salt" as used herein. Salts of the compounds of the invention may be prepared, for example, by reacting a compound with an amount of a suitable acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, isonicotinates, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like.

Additionally, acids and bases which are generally considered suitable for the formation of pharmaceutically useful salts from pharmaceutical compounds are discussed, for example, by P. Stahl et al., Camille G. (eds.) Handbook of Pharmaceutical Salts: Properties, Selection and Use. (2002) Zurich: Wiley-VCH; S. Berge et al., *J. Pharm. Sci.* (1977) 66(1) 1-19. These disclosures are incorporated herein by reference thereto.

Additionally, any compound described herein is intended to refer also to any unsolvated form, or a hydrate or solvate of such a compound, and mixtures thereof, even if such forms are not listed explicitly. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of a crystalline solid. "Solvate" encompasses both solution-phase and isolatable solvates. Suitable solvates include those formed with pharmaceutically acceptable solvents such as water, ethanol, and the like. In some embodiments, the solvent is water and the solvates are hydrates. A compound of Formula I or II, including any hydrate or solvate forms, may be in the form of a crystalline polymorph, an amorphous solid, or a non-solid form.

The invention also relates to pharmaceutically acceptable prodrugs of the compounds of Formula I or II, and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula I or II). A "pharmaceutically acceptable prodrug" is a prodrug that is non-toxic, biologically tolerable, and otherwise suitable for formulation and/or administration to the subject. Illustrative procedures for the selection and preparation of suitable prodrug derivatives are described, for example, in "Design of Prodrugs", ed. H. Bundgaard, Elsevier, 1985. Prodrugs include, but are not limited to, esters, amides, sulfonates, and phosphonate esters.

The present invention also relates to pharmaceutically active metabolites of compounds of Formula I or II, and uses of such metabolites in the methods of the invention. A "pharmaceutically active metabolite" means a pharmacologically active product of metabolism in the body of a compound of Formula I or II, or salts thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labelled compounds are useful in metabolic studies (for example with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly suitable for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

The use of the terms "salt," "solvate," "polymorph," "prodrug," and the like, with respect to the compounds described herein is intended to apply equally to the salt, solvate, polymorph, and prodrug forms of enantiomers, stereoisomers, rotamers, tautomers, atropisomers, and racemates of the inventive compounds.

Also contemplated herein are methods of synthesizing compounds of Formula I or II.

Compounds of the Invention

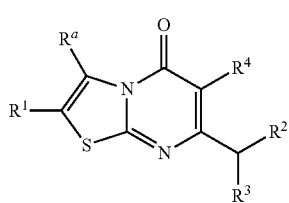

(I)

In some embodiments of (a) Formula I or (b) Formula II, $R^a$ is $C_{1-6}$alkyl optionally substituted with one or more $R^b$ substituents. In some embodiments, $R^a$ is methyl, ethyl, propyl, isopropyl, butyl, isobutyl, sec-butyl, tert-butyl, pentyl, or isopentyl, each optionally substituted with one or more $R^b$ substituents. In some embodiments, $R^a$ is $C_{1-6}$alkyl optionally substituted with one or two $R^b$ substituents.

In some embodiments, each $R^b$ is independently —OH, methoxy, ethoxy, —NR$^d$R$^e$, —C(O)NR$^d$R$^e$, thiomethyl, thioethyl, methanesulfonyl, ethanesulfonyl, cyano, fluoro, chloro, bromo, pyrrolyl, pyrazolyl, imidazolyl, furanyl, thiophenyl, triazolyl, tetrazolyl, oxazolyl, or thiazolyl. In other embodiments, each $R^b$ is independently —OH, —C(O)NHCH$_3$, —CF$_3$, methoxy, ethoxy, fluoro, —C(O)NH$_2$, —C(O)N(CH$_3$)$_2$, —N(CH$_3$)$_2$, methanesulfonyl, thiomethyl, cyano, pyrazolyl, 6-oxa-1-azaspiro[3.3]heptan-1-yl, azetidinyl, 3-hydroxyazetidinyl, pyrrolidinyl, or hydroxyethylamino.

In other embodiments, $R^a$ is $C_{1-6}$alkenyl or $C_{1-6}$alkynyl. In some embodiments, $R^a$ is ethenyl, isopropenyl, or propynyl.

In some embodiments, $R^a$ is halo. In some embodiments, $R^a$ is bromo, chloro, fluoro, or iodo.

In other embodiments, $R^a$ is —C(O)R$^c$; —NR$^d$R$^e$; —C(O)NR$^d$R$^e$; —C(S)NR$^d$R$^e$; —C(=N—OH)—C$_{1-4}$alkyl; or —SO$_2$C$_{1-4}$alkyl. In other embodiments, $R^a$ is —C(O)NR$^d$R$^e$.

In some embodiments, $R^c$ is methyl, ethyl, propyl, isopropyl, butyl, fluoromethyl, difluoromethyl, trifluoromethyl, cyclopropyl, cyclobutyl, cyclopentyl, cyclohexyl, azetidinyl, pyrrolidinyl, piperidinyl, morpholinyl, thiomorpholinyl, oxetanyl, tetrahydrofuranyl, or tetrahydropyranyl. In other embodiments, $R^c$ is ethyl, cyclopropyl, methyl, oxetanyl, or trifluoromethyl.

In some embodiments, $R^d$ is H, methyl, ethyl, propyl, isopropyl, butyl, isobutyl, or tert-butyl. In some embodiments, $R^e$ is H, methyl, ethyl, propyl, isopropyl, butyl, isobutyl, tert-butyl, cyanomethyl, trifluoroethyl, hydroxyethyl, 2-hydroxy-1-methylethyl, hydroxypropyl, cyclopropyl, hydroxy, methoxy, or oxetanylmethyl. In other embodiments, $R^d$ and $R^e$ taken together with the nitrogen to which they are attached form azetidinyl, pyrrolidinyl, piperidinyl, morpholinyl, thiomorpholinyl, oxetanyl, tetrahydrofuranyl, tetrahydropyranyl, or 6-oxa-1-azaspiro[3.3]heptan-1-yl, each optionally substituted with $C_{1-4}$alkyl or —OH.

In other embodiments, $R^a$ is cyano.

In other embodiments, $R^a$ is $C_{3-6}$cycloalkyl optionally substituted with one or more $R^f$ substituents. In some embodiments, $R^a$ is cyclopropyl, cyclobutyl, cyclopentyl, or cyclohexyl, each optionally substituted with one or more $R^f$ substituents. In other embodiments, $R^a$ is cyclopropyl, optionally substituted with one or more $R^f$ substituents.

In some embodiments, each $R^f$ is independently: methyl, ethyl, propyl, or isopropyl, each optionally substituted with —OH, cyano, methoxy, or ethoxy; $C_{1-4}$fluoroalkyl; —CONH$_2$; or cyano. In other embodiments, each $R^f$ is independently hydroxymethyl, methyl, cyano, trifluoromethyl, cyanomethyl, methoxymethyl, fluoromethyl, hydroxymethyl, 1-hydroxy-1-methyl-ethyl, or —CONH$_2$.

In some embodiments, $R^a$ is a phenyl, monocyclic heteroaryl, or heterocycloalkyl ring, each ring optionally substituted with one or more $R^g$ substituents. In other embodiments, $R^a$ is a phenyl, pyrrolyl, furanyl, thiophenyl, pyrazolyl, imidazolyl, oxazolyl, thiazolyl, triazolyl, pyridyl, pyrimidinyl, pyridazinyl, pyrazinyl, or pyrimidinyl, each optionally substituted with one or more $R^g$ substituents. In some embodiments, $R^a$ is optionally substituted with one or two $R^g$ substituents. In some embodiments, each $R^g$ is independently methyl, ethyl, propyl, isopropyl, —CF$_3$, fluoro, chloro, —NH$_2$, —OCH$_3$, cyano, or —OH. In other embodiments, each $R^g$ is independently fluoro, methyl, —NH$_2$, —CF$_3$, chloro, methoxy, or cyano.

In some embodiments, $R^a$ and $R^1$ taken together with the carbons to which they are attached form a 5- to 7-membered ring, optionally containing an O or NH, and optionally substituted with one or more $R^h$ substituents. In other embodiments, $R^a$ and $R^1$ taken together with the carbons to which they are attached form cyclopentenyl, cyclohexenyl, dihydrofuranyl, dihydropyranyl, dihydropyrrolyl, or tetrahydropyridine, each optionally substituted with one or more $R^h$ substituents. In some embodiments, each $R^h$ is independently: methyl, ethyl, or propyl, each optionally substituted with hydroxy, cyano, methoxy, or —C(O)N(CH$_3$)$_2$; —C(O)NR$^i$R$^j$; or cyano. In other embodiments, each $R^h$ is independently hydroxypropyl, hydroxyethyl, hydroxymethyl, methyl, cyano, methoxymethyl, —C(O)NH$_2$, or —CH$_2$C(O)N(CH$_3$)$_2$. Alternatively, two $R^h$ groups attached to the same carbon are taken together with the carbon to which they are attached to form cyclopentyl or a carbonyl.

In some embodiments, $R^1$ is H, methyl, ethyl, propyl, isopropyl, butyl, isobutyl, sec-butyl, tert-butyl, pentyl, fluoromethyl, fluoromethyl, trifluoromethyl, fluoroethyl, trifluoroethyl, cyclopropyl, cyclobutyl, cyclopentyl, or cyclohexyl. In other embodiments, $R^1$ is H, methyl, isopropyl, trifluoromethyl, or cyclopropyl.

In some embodiments, $R^2$ is $R^m$. In other embodiments, $R^2$ is —OR$^m$. In other embodiments, $R^2$ is —NR$^m$R$^n$. In some embodiments, $R^m$ is phenyl, naphthyl, pyridyl, pyrazinyl, pyridazinyl, pyrrolyl, pyrazolyl, triazolyl, imidazolyl, furanyl, oxazolyl, isoxazolyl, thiophenyl, thiazolyl, isothiazolyl, indolyl, indazolyl, quinolinyl, or isoquinolinyl, each optionally substituted with one or more $R^s$ substituents. In other embodiments, $R^m$ is phenyl, naphthyl, pyridyl, indazolyl, or isoquinolinyl, each optionally substituted with one or more $R^s$ substituents. In other embodiments, $R^m$ is pyrazolyl, optionally substituted with one or more $R^s$ substituents. In other embodiments, $R^m$ is phenyl, optionally substituted with one or more $R^s$ substituents. In other embodiments, $R^m$ is optionally substituted with one or two $R^s$ substituents. In some embodiments, each $R^s$ is independently methyl, ethyl, propyl, isopropyl, butyl, fluoromethyl, difluoromethyl, trifluoromethyl, fluoroethyl, trifluoroethyl, methoxy, ethoxy, isopropoxy, hydroxymethyl, hydroxyethyl, trifluoromethoxy, fluoro, chloro, bromo, iodo, cyano, cyclopropyl, cyclobutyl, cyclopentyl, cyclohexyl, —NHSO$_2$C$_{1-2}$alkyl, or —SO$_2$C$_{1-2}$alkyl. In other embodiments, each $R^s$ is independently fluoro, chloro, trifluoromethyl, cyano, methyl, methoxy, cyclopropyl, —NHSO$_2$CH$_3$, fluoroethyl, ethyl, propyl, difluoromethyl, hydroxymethyl, fluoromethyl, or methanesulfonyl.

In other embodiments, $R^2$ is $R^m$ and $R^m$ is

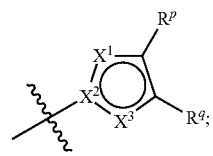

wherein at least one of $X^1$, $X^2$, and $X^3$ is N, and the other two are independently N, NR$^r$, O, S, or C—R$^r$;

$R^p$ and $R^r$ are each independently H; C$_{1-4}$haloalkyl; C$_{1-4}$alkyl optionally substituted with —OH; halo; cyano; or C$_{3-6}$cycloalkyl; and $R^q$ is H or fluoro;

or $R^q$ and $R^r$ taken together with the carbons to which they are attached form phenyl, optionally substituted with halo.

In some embodiments, $X^1$ and $X^2$ are each N and $X^3$ is C—R$^r$. In other embodiments, $X^2$ is N and $X^1$ and $X^3$ are each independently C—R$^r$. In other embodiments, $X^1$, $X^2$, and $X^3$ are each N.

In some embodiments, $R^p$ and $R^r$ are each independently H, fluoromethyl, difluoromethyl, trifluoromethyl, fluoroethyl, trifluoroethyl, methyl, ethyl, hydroxymethyl, hydroxyethyl, chloro, cyano, cyclopropyl, cyclobutyl, or cyclopentyl. In other embodiments, $R^p$ is trifluoromethyl, chloro, methyl, hydroxyethyl, cyclopropyl, cyano, difluoromethyl, or ethyl. In other embodiments, $R^r$ is ethyl, trifluoromethyl, methyl, chloro, H, hydroxyethyl, cyclopropyl, or cyano.

In some embodiments, $R^q$ is H or fluoro. In other embodiments, $R^q$ and $R^r$ taken together with the carbons to which they are attached form phenyl, optionally substituted with fluoro.

In some embodiments, $R^n$ is H, fluoromethyl, difluoromethyl, trifluoromethyl, fluoroethyl, difluoroethyl, or trifluoroethyl, or is methyl or ethyl optionally substituted with —OH, methoxy, or ethoxy. In other embodiments, $R^n$ is H, methyl, ethyl, fluoroethyl, difluoroethyl, or trifluoroethyl.

In other embodiments, $R^m$ and $R^n$ taken together with the nitrogen to which they are attached form dihydroindole, optionally substituted with methyl or fluoro.

In some embodiments, $R^3$ is H. In other embodiments, $R^3$ is methyl.

In some embodiments, $R^4$ is H. In other embodiments, $R^4$ is fluoro.

In some embodiments, the compound of Formula (I) is a compound of Formula (I-A):

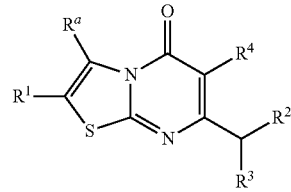

(I-A)

wherein
$R^a$ is —C(O)NR$^d$R$^e$;
  wherein $R^d$ is H or C$_{1-4}$alkyl;
  $R^e$ is H; C$_{1-4}$alkyl optionally substituted with —CN, —CF$_3$, —OH, or a monocyclic heterocycloalkyl; C$_{3-6}$cycloalkyl; —OH; or —OC$_{1-4}$alkoxy;
  or $R^d$ and $R^e$ taken together with the nitrogen to which they are attached form a heterocycloalkyl, optionally substituted with C$_{1-4}$alkyl or —OH;
$R^1$ is selected from the group consisting of H, C$_{1-6}$alkyl, C$_{1-4}$haloalkyl, and C$_{3-6}$cycloalkyl;
$R^2$ is —R$^m$, —OR$^m$, or —NR$^m$R$^n$;
  wherein $R^m$ is aryl or heteroaryl, each optionally substituted with one or more $R^s$ substituents;
    wherein each $R^s$ substituent is independently selected from the group consisting of C$_{1-4}$alkyl, C$_{1-4}$haloalkyl, $C_{1-4}$alkoxy, $C_{1-4}$alkyl-OH, $C_{1-4}$haloalkoxy, halo, cyano, $C_{3-6}$cycloalkyl, —$NHSO_2C_{1-4}$alkyl, and —$SO_2C_{1-4}$alkyl;

$R''$ is H, $C_{1-4}$haloalkyl, or $C_{1-4}$alkyl optionally substituted with —OH or $C_{1-4}$alkoxy;

or $R'''$ and $R''$ taken together with the nitrogen to which they are attached form a pyrrolidine or piperidine ring, optionally substituted with $C_{1-4}$alkyl and optionally fused to phenyl, wherein said phenyl is optionally substituted with halo;

$R^3$ is H or methyl; and $R^4$ is H or fluoro;

or a pharmaceutically acceptable salt thereof.

In some embodiments of compounds of Formula (I-A), $R^d$ is H, methyl, ethyl, propyl, isopropyl, butyl, isobutyl, or tert-butyl. In some embodiments, $R^e$ is H, methyl, ethyl, propyl, isopropyl, butyl, isobutyl, tert-butyl, cyanomethyl, trifluoroethyl, hydroxyethyl, 2-hydroxy-1-methylethyl, hydroxypropyl, cyclopropyl, hydroxy, methoxy, or oxetanylmethyl. In other embodiments, $R^d$ and $R^e$ taken together with the nitrogen to which they are attached form azetidinyl, pyrrolidinyl, piperidinyl, morpholinyl, thiomorpholinyl, oxetanyl, tetrahydrofuranyl, tetrahydropyranyl, or 6-oxa-1-azaspiro[3.3]heptan-1-yl, each optionally substituted with $C_{1-4}$alkyl or —OH.

In some embodiments, $R^1$ is H, methyl, ethyl, propyl, isopropyl, butyl, isobutyl, sec-butyl, tert-butyl, pentyl, fluoromethyl, fluoromethyl, trifluoromethyl, fluoroethyl, trifluoroethyl, cyclopropyl, cyclobutyl, cyclopentyl, or cyclohexyl. In other embodiments, $R^1$ is H, methyl, isopropyl, trifluoromethyl, or cyclopropyl.

In some embodiments, $R^2$ is $R^m$. In other embodiments, $R^2$ is —$OR^m$. In other embodiments, $R^2$ is —$NR'''R''$. In some embodiments, $R^m$ is phenyl, naphthyl, pyridyl, pyrazinyl, pyridazinyl, pyrrolyl, pyrazolyl, triazolyl, imidazolyl, furanyl, oxazolyl, isoxazolyl, thiophenyl, thiazolyl, isothiazolyl, indolyl, indazolyl, quinolinyl, or isoquinolinyl, each optionally substituted with one or more $R^s$ substituents. In other embodiments, $R^m$ is phenyl, naphthyl, pyridyl, indazolyl, or isoquinolinyl, each optionally substituted with one or more $R^s$ substituents. In other embodiments, $R^m$ is pyrazolyl, optionally substituted with one or more $R^s$ substituents. In other embodiments, $R^m$ is phenyl, optionally substituted with one or more $R^s$ substituents. In other embodiments, $R^m$ is optionally substituted with one or two $R^s$ substituents. In some embodiments, each $R^s$ is independently methyl, ethyl, propyl, isopropyl, butyl, fluoromethyl, difluoromethyl, trifluoromethyl, fluoroethyl, trifluoroethyl, methoxy, ethoxy, isopropoxy, hydroxymethyl, hydroxyethyl, trifluoromethoxy, fluoro, chloro, bromo, iodo, cyano, cyclopropyl, cyclobutyl, cyclopentyl, cyclohexyl, —$NHSO_2C_{1-2}$alkyl, or —$SO_2C_{1-2}$alkyl. In other embodiments, each $R^s$ is independently fluoro, chloro, trifluoromethyl, cyano, methyl, methoxy, cyclopropyl, —$NHSO_2CH_3$, fluoroethyl, ethyl, propyl, difluoromethyl, hydroxymethyl, fluoromethyl, or methanesulfonyl.

In other embodiments, $R^2$ is $R^m$ and $R^m$ is

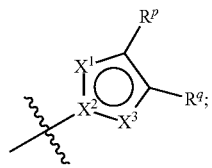

wherein at least one of $X^1$, $X^2$, and $X^3$ is N, and the other two are independently N, NR, O, S, or C—$R^r$;

$R^p$ and $R^r$ are each independently H; $C_{1-4}$haloalkyl; $C_{1-4}$alkyl optionally substituted with —OH; halo; cyano; or $C_{3-6}$cycloalkyl; and $R^q$ is H or fluoro;

or $R^q$ and $R^r$ taken together with the carbons to which they are attached form phenyl, optionally substituted with halo.

In some embodiments, $X^1$ and $X^2$ are each N and $X^3$ is C—$R^r$. In other embodiments, $X^2$ is N and $X^1$ and $X^3$ are each independently C—$R^r$. In other embodiments, $X^1$, $X^2$, and $X^3$ are each N.

In some embodiments, $R^p$ and $R^r$ are each independently H, fluoromethyl, difluoromethyl, trifluoromethyl, fluoroethyl, trifluoroethyl, methyl, ethyl, hydroxymethyl, hydroxyethyl, chloro, cyano, cyclopropyl, cyclobutyl, or cyclopentyl. In other embodiments, $R^p$ is trifluoromethyl, chloro, methyl, hydroxyethyl, cyclopropyl, cyano, difluoromethyl, or ethyl. In other embodiments, $R^r$ is ethyl, trifluoromethyl, methyl, chloro, H, hydroxyethyl, cyclopropyl, or cyano.

In some embodiments, $R^q$ is H or fluoro. In other embodiments, $R^q$ and $R^r$ taken together with the carbons to which they are attached form phenyl, optionally substituted with fluoro.

In some embodiments, $R''$ is H, fluoromethyl, difluoromethyl, trifluoromethyl, fluoroethyl, difluoroethyl, or trifluoroethyl, or is methyl or ethyl optionally substituted with —OH, methoxy, or ethoxy. In other embodiments, $R''$ is H, methyl, ethyl, fluoroethyl, difluoroethyl, or trifluoroethyl.

In some embodiments, $R'''$ and $R''$ taken together with the nitrogen to which they are attached form dihydroindole, optionally substituted with methyl or fluoro.

In some embodiments, $R^3$ is H. In other embodiments, $R^3$ is methyl.

In some embodiments, $R^4$ is H. In other embodiments, $R^4$ is fluoro.

In some embodiments, the compound of Formula (I) is a compound of Formula (I-B):

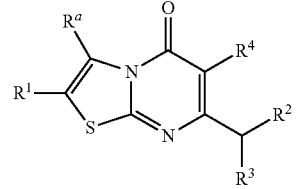

(I-B)

wherein $R^a$ is cyclopropyl, optionally substituted with one or more $R^f$ substituents;

each $R^f$ substituent is independently selected from the group consisting of: $C_{1-4}$alkyl optionally substituted with —OH, cyano, or $C_{1-4}$alkoxy; $C_{1-4}$haloalkyl; —$CONH_2$; and cyano; and $R^1$ is selected from the group consisting of H, $C_{1-6}$alkyl, $C_{1-4}$haloalkyl, and $C_{3-6}$cycloalkyl;

$R^2$ is —$R^m$, —$OR^m$, or —$NR'''R''$;

wherein $R^m$ is aryl or heteroaryl, each optionally substituted with one or more $R^s$ substituents;

wherein each $R^s$ substituent is independently selected from the group consisting of $C_{1-4}$alkyl, $C_{1-4}$haloalkyl, $C_{1-4}$alkoxy, $C_{1-4}$alkyl-OH, $C_{1-4}$haloalkoxy, halo, cyano, $C_{3-6}$cycloalkyl, —NHSO$_2$C$_{1-4}$alkyl, and —SO$_2$C$_{1-4}$alkyl;

$R''$ is H, $C_{1-4}$haloalkyl, or $C_{1-4}$alkyl optionally substituted with —OH or $C_{1-4}$alkoxy;

or $R'''$ and $R''$ taken together with the nitrogen to which they are attached form a pyrrolidine or piperidine ring, optionally substituted with $C_{1-4}$alkyl and optionally fused to phenyl, wherein said phenyl is optionally substituted with halo;

$R^3$ is H or methyl; and $R^4$ is H or fluoro;

or a pharmaceutically acceptable salt thereof.

In some embodiments of Formula (I-B), each $R^f$ is independently: methyl, ethyl, propyl, or isopropyl, each optionally substituted with —OH, cyano, methoxy, or ethoxy; $C_{1-4}$fluoroalkyl; —CONH$_2$; or cyano. In other embodiments, each $R^f$ is independently hydroxymethyl, methyl, cyano, trifluoromethyl, cyanomethyl, methoxymethyl, fluoromethyl, hydroxymethyl, 1-hydroxy-1-methyl-ethyl, or —CONH$_2$. In some embodiments, $R^a$ is cyclopropyl, optionally substituted with one or two $R^f$ substituents.

In some embodiments, $R^1$ is H, methyl, ethyl, propyl, isopropyl, butyl, isobutyl, sec-butyl, tert-butyl, pentyl, fluoromethyl, fluoromethyl, trifluoromethyl, fluoroethyl, trifluoroethyl, cyclopropyl, cyclobutyl, cyclopentyl, or cyclohexyl. In other embodiments, $R^1$ is H, methyl, isopropyl, trifluoromethyl, or cyclopropyl.

In some embodiments, $R^2$ is $R'''$. In other embodiments, $R^2$ is —O$R'''$. In other embodiments, $R^2$ is —N$R'''R''$. In some embodiments, $R'''$ is phenyl, naphthyl, pyridyl, pyrazinyl, pyridazinyl, pyrrolyl, pyrazolyl, triazolyl, imidazolyl, furanyl, oxazolyl, isoxazolyl, thiophenyl, thiazolyl, isothiazolyl, indolyl, indazolyl, quinolinyl, or isoquinolinyl, each optionally substituted with one or more $R^s$ substituents. In other embodiments, $R'''$ is phenyl, naphthyl, pyridyl, indazolyl, or isoquinolinyl, each optionally substituted with one or more $R^s$ substituents. In other embodiments, $R'''$ is pyrazolyl, optionally substituted with one or more $R^s$ substituents. In other embodiments, $R'''$ is phenyl, optionally substituted with one or more $R^s$ substituents. In other embodiments, $R'''$ is optionally substituted with one or two $R^s$ substituents. In some embodiments, each $R^s$ is independently methyl, ethyl, propyl, isopropyl, butyl, fluoromethyl, difluoromethyl, trifluoromethyl, fluoroethyl, trifluoroethyl, methoxy, ethoxy, isopropoxy, hydroxymethyl, hydroxyethyl, trifluoromethoxy, fluoro, chloro, bromo, iodo, cyano, cyclopropyl, cyclobutyl, cyclopentyl, cyclohexyl, —NHSO$_2$C$_{1-2}$alkyl, or —SO$_2$C$_{1-2}$alkyl. In other embodiments, each $R^s$ is independently fluoro, chloro, trifluoromethyl, cyano, methyl, methoxy, cyclopropyl, —NHSO$_2$CH$_3$, fluoroethyl, ethyl, propyl, difluoromethyl, hydroxymethyl, fluoromethyl, or methanesulfonyl.

In other embodiments, $R^2$ is $R'''$ and $R'''$ is

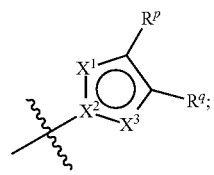

wherein at least one of $X^1$, $X^2$, and $X^3$ is N, and the other two are independently N, N$R^r$, O, S, or C—$R^r$;

$R^p$ and $R^r$ are each independently H; $C_{1-4}$haloalkyl; $C_{1-4}$alkyl optionally substituted with —OH; halo; cyano; or $C_{3-6}$cycloalkyl; and $R^q$ is H or fluoro;

or $R^q$ and $R^r$ taken together with the carbons to which they are attached form phenyl, optionally substituted with halo.

In some embodiments, $X^1$ and $X^2$ are each N and $X^3$ is C—$R^r$. In other embodiments, $X^2$ is N and $X^1$ and $X^3$ are each independently C—$R^r$. In other embodiments, $X^1$, $X^2$, and $X^3$ are each N.

In some embodiments, $R^p$ and $R^r$ are each independently H, fluoromethyl, difluoromethyl, trifluoromethyl, fluoroethyl, trifluoroethyl, methyl, ethyl, hydroxymethyl, hydroxyethyl, chloro, cyano, cyclopropyl, cyclobutyl, or cyclopentyl. In other embodiments, $R^p$ is trifluoromethyl, chloro, methyl, hydroxyethyl, cyclopropyl, cyano, difluoromethyl, or ethyl. In other embodiments, $R^r$ is ethyl, trifluoromethyl, methyl, chloro, H, hydroxyethyl, cyclopropyl, or cyano.

In some embodiments, $R^q$ is H or fluoro. In other embodiments, $R^q$ and $R^r$ taken together with the carbons to which they are attached form phenyl, optionally substituted with fluoro.

In some embodiments, $R''$ is H, fluoromethyl, difluoromethyl, trifluoromethyl, fluoroethyl, difluoroethyl, or trifluoroethyl, or is methyl or ethyl optionally substituted with —OH, methoxy, or ethoxy. In other embodiments, $R''$ is H, methyl, ethyl, fluoroethyl, difluoroethyl, or trifluoroethyl.

In some embodiments, $R'''$ and $R''$ taken together with the nitrogen to which they are attached form dihydroindole, optionally substituted with methyl or fluoro.

In some embodiments, $R^3$ is H. In other embodiments, $R^3$ is methyl.

In some embodiments, $R^4$ is H. In other embodiments, $R^4$ is fluoro.

In some embodiments, the compound of Formula (I) is a compound of Formula (I-C):

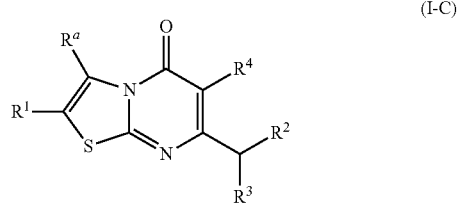

(I-C)

$R^a$ is a monocyclic heteroaryl ring, optionally substituted with one or more $R^g$ substituents;

each $R^g$ substituent is independently selected from the group consisting of $C_{1-4}$alkyl, —CF$_3$, halo, —NH$_2$, —OCH$_3$, cyano, and —OH;

$R^1$ is selected from the group consisting of H, $C_{1-6}$alkyl, $C_{1-4}$haloalkyl, and $C_{3-6}$cycloalkyl;

$R^2$ is —$R'''$, —O$R'''$, or —N$R'''R''$;

wherein $R'''$ is aryl or heteroaryl, each optionally substituted with one or more $R^s$ substituents;

wherein each $R^s$ substituent is independently selected from the group consisting of $C_{1-4}$alkyl, $C_{1-4}$haloalkyl, $C_{1-4}$alkoxy, $C_{1-4}$alkyl-OH, $C_{1-4}$haloalkoxy, halo, cyano, $C_{3-6}$cycloalkyl, —NHSO$_2$C$_{1-4}$alkyl, and —SO$_2$C$_{1-4}$alkyl;

$R''$ is H, $C_{1-4}$haloalkyl, or $C_{1-4}$alkyl optionally substituted with —OH or $C_{1-4}$alkoxy;

or R''' and R'' taken together with the nitrogen to which they are attached form a pyrrolidine or piperidine ring, optionally substituted with $C_{1-4}$alkyl and optionally fused to phenyl, wherein said phenyl is optionally substituted with halo;

$R^3$ is H or methyl; and $R^4$ is H or fluoro;

or a pharmaceutically acceptable salt thereof.

In some embodiments of Formula (I-C), $R^a$ is pyrrolyl, furanyl, thiophenyl, pyrazolyl, imidazolyl, oxazolyl, thiazolyl, triazolyl, pyridyl, pyrimidinyl, pyridazinyl, pyrazinyl, or pyrimidinyl, each optionally substituted with one or more $R^g$ substituents. In some embodiments, $R^a$ is optionally substituted with one or two $R^g$ substituents. In some embodiments, each $R^g$ is independently methyl, ethyl, propyl, isopropyl, —$CF_3$, fluoro, chloro, —$NH_2$, —$OCH_3$, cyano, or —OH. In other embodiments, each $R^g$ is independently fluoro, methyl, —$NH_2$, —$CF_3$, chloro, methoxy, or cyano.

In some embodiments, $R^1$ is H, methyl, ethyl, propyl, isopropyl, butyl, isobutyl, sec-butyl, tert-butyl, pentyl, fluoromethyl, fluoromethyl, trifluoromethyl, fluoroethyl, trifluoroethyl, cyclopropyl, cyclobutyl, cyclopentyl, or cyclohexyl. In other embodiments, $R^1$ is H, methyl, isopropyl, trifluoromethyl, or cyclopropyl.

In some embodiments, $R^2$ is $R'''$. In other embodiments, $R^2$ is —$OR'''$. In other embodiments, $R^2$ is —$NR'''R''$. In some embodiments, $R'''$ is phenyl, naphthyl, pyridyl, pyrazinyl, pyridazinyl, pyrrolyl, pyrazolyl, triazolyl, imidazolyl, furanyl, oxazolyl, isoxazolyl, thiophenyl, thiazolyl, isothiazolyl, indolyl, indazolyl, quinolinyl, or isoquinolinyl, each optionally substituted with one or more $R^s$ substituents. In other embodiments, $R'''$ is phenyl, naphthyl, pyridyl, indazolyl, or isoquinolinyl, each optionally substituted with one or more $R^s$ substituents. In other embodiments, $R'''$ is pyrazolyl, optionally substituted with one or more $R^s$ substituents. In other embodiments, $R'''$ is phenyl, optionally substituted with one or more $R^s$ substituents. In other embodiments, $R'''$ is optionally substituted with one or two $R^s$ substituents. In some embodiments, each $R^s$ is independently methyl, ethyl, propyl, isopropyl, butyl, fluoromethyl, difluoromethyl, trifluoromethyl, fluoroethyl, trifluoroethyl, methoxy, ethoxy, isopropoxy, hydroxymethyl, hydroxyethyl, trifluoromethoxy, fluoro, chloro, bromo, iodo, cyano, cyclopropyl, cyclobutyl, cyclopentyl, cyclohexyl, —$NHSO_2C_{1-2}$alkyl, or —$SO_2C_{1-2}$alkyl. In other embodiments, each $R^s$ is independently fluoro, chloro, trifluoromethyl, cyano, methyl, methoxy, cyclopropyl, —$NHSO_2CH_3$, fluoroethyl, ethyl, propyl, difluoromethyl, hydroxymethyl, fluoromethyl, or methanesulfonyl.

In other embodiments, $R^2$ is $R'''$ and $R'''$ is

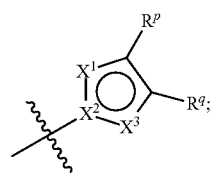

wherein at least one of $X^1$, $X^2$, and $X^3$ is N, and the other two are independently N, $NR^r$, O, S, or C—$R^r$;

$R^p$ and $R^r$ are each independently H; $C_{1-4}$haloalkyl; $C_{1-4}$alkyl optionally substituted with —OH; halo; cyano; or $C_{3-6}$cycloalkyl; and $R^q$ is H or fluoro;

or $R^q$ and $R^r$ taken together with the carbons to which they are attached form phenyl, optionally substituted with halo.

In some embodiments, $X^1$ and $X^2$ are each N and $X^3$ is C—$R^1$. In other embodiments, $X^2$ is N and $X^1$ and $X^3$ are each independently C—$R^r$. In other embodiments, $X^1$, $X^2$, and $X^3$ are each N.

In some embodiments, $R^p$ and $R^r$ are each independently H, fluoromethyl, difluoromethyl, trifluoromethyl, fluoroethyl, trifluoroethyl, methyl, ethyl, hydroxymethyl, hydroxyethyl, chloro, cyano, cyclopropyl, cyclobutyl, or cyclopentyl. In other embodiments, $R^p$ is trifluoromethyl, chloro, methyl, hydroxyethyl, cyclopropyl, cyano, difluoromethyl, or ethyl. In other embodiments, $R^r$ is ethyl, trifluoromethyl, methyl, chloro, H, hydroxyethyl, cyclopropyl, or cyano.

In some embodiments, $R^q$ is H or fluoro. In other embodiments, $R^q$ and $R^r$ taken together with the carbons to which they are attached form phenyl, optionally substituted with fluoro.

In some embodiments, $R''$ is H, fluoromethyl, difluoromethyl, trifluoromethyl, fluoroethyl, difluoroethyl, or trifluoroethyl, or is methyl or ethyl optionally substituted with —OH, methoxy, or ethoxy. In other embodiments, $R''$ is H, methyl, ethyl, fluoroethyl, difluoroethyl, or trifluoroethyl.

In some embodiments, $R'''$ and $R''$ taken together with the nitrogen to which they are attached form dihydroindole, optionally substituted with methyl or fluoro.

In some embodiments, $R^3$ is H. In other embodiments, $R^3$ is methyl.

In some embodiments, $R^4$ is H. In other embodiments, $R^4$ is fluoro.

In some embodiments, compounds described herein are compounds of Formula II or pharmaceutically acceptable salts thereof. Compounds of Formula II include those in which each variable is defined independently as described herein for Formula I, I-A, I-B, or I-C, or combinations of said definitions. Additional embodiments of Formula II include compounds in which $R^a$ is —$SCH_3$, —$CH_2$-cyclopropyl, difluorocyclopropyl, hydroxycyclopropyl, —$OCH_2CF_3$, —CH=CH—CN, or —CH=CH—$CONH_2$. Additional embodiments of Formula II include compounds in which $R^1$ is chloro, methoxy, cyano, ethoxy, trifluoroethoxy, or acetyl. Additional embodiments of Formula II include compounds in which $R^s$ is fluoro-isopropenyl, ethynyl, hydroxycyclopropyl, fluorocyclopropyl, —$NH_2$, —$NO_2$, or thiazolyl.

In other embodiments are compounds of Formula III:

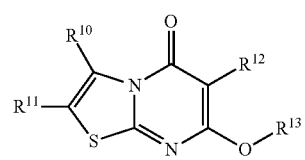

wherein:

$R^{10}$ is $C_{1-4}$alkyl, $C_{1-4}$haloalkyl, or cyano, or $C_{3-6}$cycloalkyl optionally substituted with —$C_{1-4}$alkyl-OH, $R^{11}$ is $C_{1-4}$alkyl; or $R^{10}$ and $R^{11}$ taken together with the carbons to which they are attached form a $C_{5-6}$ cycloalkyl;

$R^{12}$ is —H or halo; and $R^{13}$ is phenyl, optionally substituted with one or more substituents selected from the group consisting of halo, $C_{1-4}$haloalkyl, and cyano;

and pharmaceutically acceptable salts thereof.

Additional embodiments include pharmaceutical compositions comprising at least one compound of Formula III, or a pharmaceutically acceptable salt thereof, and a pharmaceutically acceptable excipient, and a method of treating a subject suffering from a disease or medical condition mediated by NMDA receptor activity, comprising administering to the subject in need of such treatment an effective amount of at least one compound of Formula III, or a pharmaceutically acceptable salt thereof.

Embodiments of the invention also include compounds in which each variable is defined independently as described above.

In certain embodiments, the compound of Formula I or II is a compound selected from the group consisting of the compounds in Table 1, and pharmaceutically acceptable salts thereof:

TABLE 1

| Ex. | Chemical Name |
|---|---|
| 1.1 | N-(cyanomethyl)-7-((4-fluorophenoxy)methyl)-2-methyl-5-oxo-5H-thiazolo[3,2-a]pyrimidine-3-carboxamide |
| 1.2 | 7-(4-Fluorophenoxymethyl)-N,2-dimethyl-5-oxo-5H-[1,3]thiazolo[3,2-a]pyrimidine-3-carboxamide |
| 1.3 | 3-[(Azetidin-1-yl)carbonyl]-7-(4-fluorophenoxymethyl)-2-methyl-5H-[1,3]thiazolo[3,2-a]pyrimidin-5-one |
| 1.4 | N-ethyl-7-(4-fluorophenoxymethyl)-2-methyl-5-oxo-5H-[1,3]thiazolo[3,2-a]pyrimidine-3-carboxamide |
| 1.5 | 7-(4-Fluorophenoxymethyl)-2-methyl-5-oxo-N-(2,2,2-trifluoroethyl)-5H-[1,3]thiazolo[3,2-a]pyrimidine-3-carboxamide |
| 1.6 | 7-(3,4-Difluorophenoxymethyl)-N,2-dimethyl-5-oxo-5H-[1,3]thiazolo[3,2-a]pyrimidine-3-carboxamide |
| 1.7 | N-ethyl-7-(4-fluorophenoxymethyl)-5-oxo-5H-[1,3]thiazolo[3,2-a]pyrimidine-3-carboxamide |
| 1.8 | 7-((4-fluorophenoxy)methyl)-2-methyl-5-oxo-5H-thiazolo[3,2-a]pyrimidine-3-carboxamide |
| 1.9 | 7-((4-fluorophenoxy)methyl)-N-hydroxy-2-methyl-5-oxo-5H-thiazolo[3,2-a]pyrimidine-3-carboxamide |
| 1.10 | 7-(4-Fluorophenoxymethyl)-2-methyl-5-oxo-N-(propan-2-yl)-5H-[1,3]thiazolo[3,2-a]pyrimidine-3-carboxamide |
| 1.11 | 7-(4-Fluorophenoxymethyl)-N-(2-hydroxyethyl)-2-methyl-5-oxo-5H-[1,3]thiazolo[3,2-a]pyrimidine-3-carboxamide |
| 1.12 | 7-(4-Fluorophenoxymethyl)-N-(1-hydroxypropan-2-yl)-2-methyl-5-oxo-5H-[1,3]thiazolo[3,2-a]pyrimidine-3-carboxamide |
| 1.13 | 7-((4-fluorophenoxy)methyl)-2-methyl-N-(oxetan-3-ylmethyl)-5-oxo-5H-thiazolo[3,2-a]pyrimidine-3-carboxamide |
| 1.14 | 7-((4-fluorophenoxy)methyl)-N-(3-hydroxypropyl)-2-methyl-5-oxo-5H-thiazolo[3,2-a]pyrimidine-3-carboxamide |
| 1.15 | N-cyclopropyl-7-((4-fluorophenoxy)methyl)-2-methyl-5-oxo-5H-thiazolo[3,2-a]pyrimidine-3-carboxamide |
| 1.16 | 7-((4-fluorophenoxy)methyl)-N-methoxy-2-methyl-5-oxo-5H-thiazolo[3,2-a]pyrimidine-3-carboxamide |
| 1.17 | 7-(4-Fluorophenoxymethyl)-N,2-dimethyl-5-oxo-5H-[1,3]thiazolo[3,2-a]pyrimidine-3-carbothioamide |
| 2.1 | 7-((4-fluorophenoxy)methyl)-2-methyl-3-propionyl-5H-thiazolo[3,2-a]pyrimidin-5-one |
| 2.2 | 7-((4-fluorophenoxy)methyl)-3-(1-hydroxypropyl)-2-methyl-5H-thiazolo[3,2-a]pyrimidin-5-one |
| 2.3 | 7-(4-Fluorophenoxymethyl)-3-(1-hydroxyethyl)-2-methyl-5H-[1,3]thiazolo[3,2-a]pyrimidin-5-one |
| 2.4 | 7-(4-Fluorophenoxymethyl)-3-(2-hydroxypropan-2-yl)-2-methyl-5H-[1,3]thiazolo[3,2-a]pyrimidin-5-one |
| 2.5 | 3-acetyl-7-((4-fluorophenoxy)methyl)-2-methyl-5H-thiazolo[3,2-a]pyrimidin-5-one |
| 2.6 | 2-(7-((4-fluorophenoxy)methyl)-2-methyl-5-oxo-5H-thiazolo[3,2-a]pyrimidin-3-yl)-N-methylacetamide |
| 2.7 | 3-Cyclopropanecarbonyl-7-(4-fluorophenoxymethyl)-2-methyl-5H-[1,3]thiazolo[3,2-a]pyrimidin-5-one |
| 2.8 | 7-(4-Fluorophenoxymethyl)-3-[1-(hydroxyimino)ethyl]-2-methyl-5H-[1,3]thiazolo[3,2-a]pyrimidin-5-one |
| 2.9 | 7-((4-fluorophenoxy)methyl)-2-methyl-3-(oxetane-3-carbonyl)-5H-thiazolo[3,2-a]pyrimidin-5-one |
| 2.10 | 7-((4-fluorophenoxy)methyl)-2-methyl-3-(2,2,2-trifluoro-1-hydroxyethyl)-5H-thiazolo[3,2-a]pyrimidin-5-one |
| 2.11 | 7-(4-Fluorophenoxymethyl)-2-methyl-3-(trifluoroacetyl)-5H-[1,3]thiazolo[3,2-a]pyrimidin-5-one |
| 3.1 | 2-cyclopropyl-N-ethyl-7-((4-fluorophenoxy)methyl)-5-oxo-5H-thiazolo[3,2-a]pyrimidine-3-carboxamide |
| 3.2 | 7-(4-Fluorophenoxymethyl)-N-methyl-5-oxo-2-(trifluoromethyl)-5H-[1,3]thiazolo[3,2-a]pyrimidine-3-carboxamide |
| 3.3 | 2-Cyclopropyl-7-(4-fluorophenoxymethyl)-N-methyl-5-oxo-5H-[1,3]thiazolo[3,2-a]pyrimidine-3-carboxamide |
| 3.4 | N-Ethyl-7-(4-fluorophenoxymethyl)-5-oxo-2-(trifluoromethyl)-5H-[1,3]thiazolo[3,2-a]pyrimidine-3-carboxamide |
| 3.5 | 7-((4-fluorophenoxy)methyl)-N-methyl-5-oxo-5H-thiazolo[3,2-a]pyrimidine-3-carboxamide |
| 3.6 | N-ethyl-7-[[(5-fluoropyridin-2-yl)oxy]methyl]-2-methyl-5-oxo-5H-[1,3]thiazolo[3,2-a]pyrimidine-3-carboxamide |

TABLE 1-continued

| Ex. | Chemical Name |
|---|---|
| 4.1 | 7-(4-Fluorophenoxymethyl)-3-[trans-2-(hydroxymethyl)cyclopropyl]-2-methyl-5H-[1,3]thiazolo[3,2-a]pyrimidin-5-one |
| 4.2 | 7-(4-Fluorophenoxymethyl)-3-[trans-2-(hydroxymethyl)cyclopropyl]-2-methyl-5H-[1,3]thiazolo[3,2-a]pyrimidin-5-one (enantiomer 1) |
| 4.3 | 7-(4-Fluorophenoxymethyl)-3-[trans-2-(hydroxymethyl)cyclopropyl]-2-methyl-5H-[1,3]thiazolo[3,2-a]pyrimidin-5-one (enantiomer 2) |
| 4.4 | 7-((3-fluorophenoxy)methyl)-3-(trans-2-(hydroxymethyl)cyclopropyl)-2-methyl-5H-thiazolo[3,2-a]pyrimidin-5-one |
| 4.5 | 7-((4-fluorophenoxy)methyl)-2-methyl-3-(pyrimidin-5-yl)-5H-thiazolo[3,2-a]pyrimidin-5-one |
| 4.6 | 7-(2,4-Difluorophenoxymethyl)-3-[trans-2-(hydroxymethyl)cyclopropyl]-2-methyl-5H-[1,3]thiazolo[3,2-a]pyrimidin-5-one |
| 4.7 | 7-(3,4-Difluorophenoxymethyl)-3-[trans-2-(hydroxymethyl)cyclopropyl]-2-methyl-5H-[1,3]thiazolo[3,2-a]pyrimidin-5-one |
| 4.8 | 7-(4-Chlorophenoxymethyl)-3-[trans-2-(hydroxymethyl)cyclopropyl]-2-methyl-5H-[1,3]thiazolo[3,2-a]pyrimidin-5-one |
| 4.9 | 7-[[(5-Fluoropyridin-2-yl)oxy]methyl]-3-[trans-2-(hydroxymethyl)cyclopropyl]-2-methyl-5H-[1,3]thiazolo[3,2-a]pyrimidin-5-one |
| 4.10 | 3-(trans-2-(hydroxymethyl)cyclopropyl)-2-methyl-7-((4-(trifluoromethyl)phenoxy)methyl)-5H-thiazolo[3,2-a]pyrimidin-5-one |
| 4.11 | 7-((4-fluorophenoxy)methyl)-2-methyl-3-(oxazol-2-yl)-5H-thiazolo[3,2-a]pyrimidin-5-one |
| 4.12 | 7-((2-fluorophenoxy)methyl)-3-(trans-2-(hydroxymethyl)cyclopropyl)-2-methyl-5H-thiazolo[3,2-a]pyrimidin-5-one |
| 4.13 | 4-((3-(trans-2-(hydroxymethyl)cyclopropyl)-2-methyl-5-oxo-5H-thiazolo[3,2-a]pyrimidin-7-yl)methoxy)benzonitrile |
| 4.14 | 7-((4-fluorophenoxy)methyl)-3-(trans-2-(hydroxymethyl)cyclopropyl)-5H-thiazolo[3,2-a]pyrimidin-5-one |
| 4.15 | 7-((4-fluorophenoxy)methyl)-2-methyl-3-(1H-pyrazol-5-yl)-5H-thiazolo[3,2-a]pyrimidin-5-one |
| 4.16 | 7-((4-fluorophenoxy)methyl)-2-methyl-3-(4H-1,2,4-triazol-3-yl)-5H-thiazolo[3,2-a]pyrimidin-5-one |
| 4.17 | 3-cyclopropyl-7-[(4-fluorophenoxy)methyl]-2-methyl-thiazolo[3,2-a]pyrimidin-5-one |
| 4.18 | cis-2-[7-(4-Fluorophenoxymethyl)-2-methyl-5-oxo-5H-[1,3]thiazolo[3,2-a]pyrimidin-3-yl]cyclopropane-1-carbonitrile |
| 4.18A | trans-2-[7-(4-Fluorophenoxymethyl)-2-methyl-5-oxo-5H-[1,3]thiazolo[3,2-a]pyrimidin-3-yl]cyclopropane-1-carbonitrile |
| 4.19 | cis-2-[7-(4-Fluorophenoxymethyl)-2-methyl-5-oxo-5H-[1,3]thiazolo[3,2-a]pyrimidin-3-yl]cyclopropane-1-carbonitrile (enantiomer 1) |
| 4.20 | cis-2-[7-(4-Fluorophenoxymethyl)-2-methyl-5-oxo-5H-[1,3]thiazolo[3,2-a]pyrimidin-3-yl]cyclopropane-1-carbonitrile (enantiomer 2) |
| 4.21 | trans-2-[7-(4-Fluorophenoxymethyl)-2-methyl-5-oxo-5H-[1,3]thiazolo[3,2-a]pyrimidin-3-yl]cyclopropane-1-carbonitrile (enantiomer 1) |
| 4.22 | trans-2-[7-(4-Fluorophenoxymethyl)-2-methyl-5-oxo-5H-[1,3]thiazolo[3,2-a]pyrimidin-3-yl]cyclopropane-1-carbonitrile (enantiomer 2) |
| 4.23 | 7-(4-Fluorophenoxymethyl)-3-[cis-2-(hydroxymethyl)cyclopropyl]-2-methyl-5H-[1,3]thiazolo[3,2-a]pyrimidin-5-one |
| 4.24 | trans-7-(4-Fluorophenoxymethyl)-2-methyl-3-[2-(trifluoromethyl)cyclopropyl]-5H-[1,3]thiazolo[3,2-a]pyrimidin-5-one |
| 4.25 | 7-(4-Fluorophenoxymethyl)-2-methyl-3-(2-methylcyclopropyl)-5H-[1,3]thiazolo[3,2-a]pyrimidin-5-one |
| 4.26 | trans-2-[2-[7-(4-Fluorophenoxymethyl)-2-methyl-5-oxo-5H-[1,3]thiazolo[3,2-a]pyrimidin-3-yl]cyclopropyl]acetonitrile |
| 4.27 | 7-(4-Fluorophenoxymethyl)-3-[2-(methoxymethyl)cyclopropyl]-2-methyl-5H-[1,3]thiazolo[3,2-a]pyrimidin-5-one |
| 4.28 | 3-(2-(fluoromethyl)cyclopropyl)-7-((4-fluorophenoxy)methyl)-2-methyl-5H-thiazolo[3,2-a]pyrimidin-5-one |
| 4.29 | 6-fluoro-7-((4-fluorophenoxy)methyl)-3-(trans-2-(hydroxymethyl)cyclopropyl)-2-methyl-5H-thiazolo[3,2-a]pyrimidin-5-one |
| 4.30 | 7-(4-Fluorophenoxymethyl)-3-(3-hydroxypropyl)-2-methyl-5H-[1,3]thiazolo[3,2-a]pyrimidin-5-one |
| 4.31 | 7-(4-Fluorophenoxymethyl)-3-(methoxymethyl)-2-methyl-5H-[1,3]thiazolo[3,2-a]pyrimidin-5-one |
| 4.32 | 7-((4-fluorophenoxy)methyl)-3-(3-hydroxyoxetan-3-yl)-2-methyl-5H-thiazolo[3,2-a]pyrimidin-5-one |
| 4.33 | 7-(4-Fluorophenoxymethyl)-3-(4-hydroxybutan-2-yl)-2-methyl-5H-[1,3]thiazolo[3,2-a]pyrimidin-5-one |
| 4.34 | 7-(4-Fluorophenoxymethyl)-3-[2-(2-hydroxypropan-2-yl)cyclopropyl]-2-methyl-5H-[1,3]thiazolo[3,2-a]pyrimidin-5-one |
| 5.1 | 7-[(N-ethyl-4-fluoro-anilino)methyl]-2-methyl-3-pyrimidin-5-yl-thiazolo[3,2-a]pyrimidin-5-one |
| 5.2 | 7-(((4-fluorophenyl)(methyl)amino)methyl)-2-methyl-3-(pyrimidin-5-yl)-5H-thiazolo[3,2-a]pyrimidin-5-one |
| 5.3 | 7-(((4-fluorophenyl)(2,2,2-trifluoroethyl)amino)methyl)-2-methyl-3-(pyrimidin-5-yl)-5H-thiazolo[3,2-a]pyrimidin-5-one |
| 5.4 | 7-(((3,4-difluorophenyl)(ethyl)amino)methyl)-2-methyl-3-(pyrimidin-5-yl)-5H-thiazolo[3,2-a]pyrimidin-5-one |

TABLE 1-continued

| Ex. | Chemical Name |
|---|---|
| 5.5 | 7-((ethyl(3-fluorophenyl)amino)methyl)-2-methyl-3-(pyrimidin-5-yl)-5H-thiazolo[3,2-a]pyrimidin-5-one |
| 5.6 | 7-(((2,2-difluoroethyl)(4-fluorophenyl)amino)methyl)-2-methyl-3-(pyrimidin-5-yl)-5H-thiazolo[3,2-a]pyrimidin-5-one |
| 5.7 | 7-((ethyl(pyridine-2-yl)amino)methyl)-3-(trans-2-(hydroxymethyl)cyclopropyl)-2-methyl-5H-thiazolo[3,2-a]pyrimidin-5-one |
| 5.8 | 7-((ethyl(4-fluorophenyl)amino)methyl)-2-methyl-3-(thiazol-2-yl)-5H-thiazolo[3,2-a]pyrimidin-5-one |
| 5.9 | 7-((ethyl(4-fluorophenyl)amino)methyl)-2-methyl-3-(thiophen-2-yl)-5H-thiazolo[3,2-a]pyrimidin-5-one |
| 5.10 | 3-(ethyl((2-methyl-5-oxo-3-(pyrimidin-5-yl)-5H-thiazolo[3,2-a]pyrimidin-7-yl)methyl)amino)benzonitrile |
| 5.11 | 3-(2-aminopyridin-3-yl)-7-((ethyl(4-fluorophenyl)amino)methyl)-2-methyl-5H-thiazolo[3,2-a]pyrimidin-5-one |
| 5.12 | 7-((ethyl(pyridine-2-yl)amino)methyl)-2-methyl-3-(pyrimidin-5-yl)-5H-thiazolo[3,2-a]pyrimidin-5-one |
| 5.13 | 7-((4-fluorophenylamino)methyl)-2-methyl-3-(pyrimidin-5-yl)-5H-thiazolo[3,2-a]pyrimidin-5-one |
| 5.14 | 3-butyl-7-((ethyl(4-fluorophenyl)amino)methyl)-2-methyl-5H-thiazolo[3,2-a]pyrimidin-5-one |
| 5.15 | 2-cyclopropyl-7-[(N-ethyl-4-fluoro-anilino)methyl]-3-pyrimidin-5-yl-thiazolo[3,2-a]pyrimidin-5-one |
| 5.16 | 2-ethyl-7-((ethyl(4-fluorophenyl)amino)methyl)-3-(pyrimidin-5-yl)-5H-thiazolo[3,2-a]pyrimidin-5-one |
| 5.17 | 7-((ethyl(4-fluorophenyl)amino)methyl)-3-(trans-2-(hydroxymethyl)cyclopropyl)-2-methyl-5H-thiazolo[3,2-a]pyrimidin-5-one |
| 5.18 | 7-((ethyl(4-fluorophenyl)amino)methyl)-3-(trans-2-(hydroxymethyl)cyclopropyl)-2-methyl-5H-thiazolo[3,2-a]pyrimidin-5-one (enantiomer 1) |
| 5.19 | 7-((ethyl(4-fluorophenyl)amino)methyl)-3-(trans-2-(hydroxymethyl)cyclopropyl)-2-methyl-5H-thiazolo[3,2-a]pyrimidin-5-one (enantiomer 2) |
| 5.20 | 7-[(N-ethyl-4-fluoro-anilino)methyl]-2-methyl-3-thiazol-4-yl-thiazolo[3,2-a]pyrimidin-5-one |
| 5.21 | 7-[(N-ethyl-4-fluoro-anilino)methyl]-2-methyl-3-(3-pyridyl)thiazolo[3,2-a]pyrimidin-5-one |
| 5.22 | 7-[(N-ethyl-4-fluoro-anilino)methyl]-2-methyl-3-phenyl-thiazolo[3,2-a]pyrimidin-5-one |
| 5.23 | 7-[(N-ethyl-4-fluoro-anilino)methyl]-2,3-dimethyl-thiazolo[3,2-a]pyrimidin-5-one |
| 5.24 | 7-[(N-ethyl-4-fluoro-anilino)methyl]-3-(5-fluoro-3-pyridyl)-2-methyl-thiazolo[3,2-a]pyrimidin-5-one |
| 5.25 | 7-[(N-ethyl-4-fluoro-anilino)methyl]-3-(2-fluoro-3-pyridyl)-2-methyl-thiazolo[3,2-a]pyrimidin-5-one |
| 5.26 | 3-cyclopropyl-7-[(N-ethyl-4-fluoro-anilino)methyl]-2-methyl-thiazolo[3,2-a]pyrimidin-5-one |
| 5.27 | 7-[(N-ethyl-4-fluoro-anilino)methyl]-2-methyl-3-pyrazin-2-yl-thiazolo[3,2-a]pyrimidin-5-one |
| 5.28 | 7-[(N-ethyl-4-fluoro-anilino)methyl]-3-[trans-2-(hydroxymethyl)cyclopropyl]thiazolo[3,2-a]pyrimidin-5-one |
| 5.29 | 7-[(N-ethyl-4-fluoro-anilino)methyl]-3-isopropenyl-2-methyl-thiazolo[3,2-a]pyrimidin-5-one |
| 5.30 | 7-[(N-ethyl-4-fluoro-anilino)methyl]-2-methyl-3-pyridazin-4-yl-thiazolo[3,2-a]pyrimidin-5-one |
| 5.31 | 3-(5-chloro-3-pyridyl)-7-[(N-ethyl-4-fluoro-anilino)methyl]-2-methyl-thiazolo[3,2-a]pyrimidin-5-one |
| 5.32 | 7-[(N-ethyl-4-fluoro-anilino)methyl]-2-methyl-3-(4-pyridyl)thiazolo[3,2-a]pyrimidin-5-one |
| 5.33 | 7-[(N-ethyl-4-fluoro-anilino)methyl]-2-methyl-3-(1-methylpyrazol-4-yl)thiazolo[3,2-a]pyrimidin-5-one |
| 5.34 | 7-[(N-ethyl-4-fluoro-anilino)methyl]-2-methyl-3-(1H-pyrazol-4-yl)thiazolo[3,2-a]pyrimidin-5-one |
| 5.35 | 5-[7-[(N-ethyl-4-fluoro-anilino)methyl]-2-methyl-5-oxo-thiazolo[3,2-a]pyrimidin-3-yl]pyridine-3-carbonitrile |
| 5.36 | 7-[(N-ethyl-4-fluoro-anilino)methyl]-2-methyl-3-[5-(trifluoromethyl)-3-pyridyl]thiazolo[3,2-a]pyrimidin-5-one |
| 5.37 | 7-[(N-ethyl-4-fluoro-anilino)methyl]-2-methyl-3-oxazol-2-yl-thiazolo[3,2-a]pyrimidin-5-one |
| 5.38 | 7-((ethyl(4-fluorophenyl)amino)methyl)-2-methyl-3-(trifluoromethyl)-5H-thiazolo[3,2-a]pyrimidin-5-one |
| 5.39 | 7-((ethyl(4-fluorophenyl)amino)methyl)-3-(trans-2-(fluoromethyl)cyclopropyl)-2-methyl-5H-thiazolo[3,2-a]pyrimidin-5-one |
| 5.40 | 3-ethyl-7-((ethyl(4-fluorophenyl)amino)methyl)-2-methyl-5H-thiazolo[3,2-a]pyrimidin-5-one |
| 5.41 | 7-((ethyl(4-fluorophenyl)amino)methyl)-2-methyl-3-propyl-5H-thiazolo[3,2-a]pyrimidin-5-one |
| 5.42 | 7-[[4-fluoro-N-(2-fluoroethyl)anilino]methyl]-3-[trans-2-(hydroxymethyl)cyclopropyl]-2-methyl-thiazolo[3,2-a]pyrimidin-5-one (enantiomer 1) |
| 5.43 | 7-[[4-fluoro-N-(2-fluoroethyl)anilino]methyl]-3-[trans-2-(hydroxymethyl)cyclopropyl]-2-methyl-thiazolo[3,2-a]pyrimidin-5-one (enantiomer 2) |
| 5.44 | 7-((ethyl(4-fluorophenyl)amino)methyl)-3-(furan-3-yl)-2-methyl-5H-thiazolo[3,2-a]pyrimidin-5-one |

TABLE 1-continued

| Ex. | Chemical Name |
|---|---|
| 5.45 | 7-((ethyl(4-fluorophenyl)amino)methyl)-3-(furan-2-yl)-2-methyl-5H-thiazolo[3,2-a]pyrimidin-5-one |
| 5.46 | 7-((5-fluoro-2-methylindolin-1-yl)methyl)-3-(furan-2-yl)-2-methyl-5H-thiazolo[3,2-a]pyrimidin-5-one |
| 5.47 | 7-((ethyl(4-fluorophenyl)amino)methyl)-2-methyl-3-(thiophen-3-yl)-5H-thiazolo[3,2-a]pyrimidin-5-one |
| 5.48 | 7-((5-fluoro-2-methylindolin-1-yl)methyl)-2-methyl-3-(pyrimidin-5-yl)-5H-thiazolo[3,2-a]pyrimidin-5-one |
| 5.49 | 7-((ethyl(4-fluorophenyl)amino)methyl)-2-methyl-3-(4-methylthiazol-2-yl)-5H-thiazolo[3,2-a]pyrimidin-5-one |
| 5.50 | 7-((ethyl(4-fluorophenyl)amino)methyl)-2-methyl-3-(6-oxo-1,6-dihydropyridin-3-yl)-5H-thiazolo[3,2-a]pyrimidin-5-one |
| 5.51 | 3-(6-aminopyridin-3-yl)-7-((ethyl(4-fluorophenyl)amino)methyl)-2-methyl-5H-thiazolo[3,2-a]pyrimidin-5-one |
| 5.52 | 7-((ethyl(4-fluorophenyl)amino)methyl)-2-methyl-3-(prop-1-ynyl)-5H-thiazolo[3,2-a]pyrimidin-5-one |
| 5.53 | 7-((ethyl(4-fluorophenyl)amino)methyl)-2-methyl-3-vinyl-5H-thiazolo[3,2-a]pyrimidin-5-one |
| 5.54 | 3-bromo-2-cyclopropyl-7-[(N-ethyl-4-fluoro-anilino)methyl]thiazolo[3,2-a]pyrimidin-5-one |
| 5.55 | 3-(3,5-difluorophenyl)-7-[(N-ethyl-4-fluoro-anilino)methyl]-2-methyl-thiazolo[3,2-a]pyrimidin-5-one |
| 5.56 | 7-[(N-ethyl-4-fluoro-anilino)methyl]-2-methyl-3-(1-methylpyrazol-3-yl)thiazolo[3,2-a]pyrimidin-5-one |
| 5.57 | 3-(2-amino-4-pyridyl)-7-[(N-ethyl-4-fluoro-anilino)methyl]-2-methyl-thiazolo[3,2-a]pyrimidin-5-one |
| 5.58 | 7-[(N-ethyl-4-fluoro-anilino)methyl]-3-(5-methoxy-3-pyridyl)-2-methyl-thiazolo[3,2-a]pyrimidin-5-one |
| 6.1 | 7-((ethyl(4-fluorophenyl)amino)methyl)-2-methyl-3-morpholino-5H-thiazolo[3,2-a]pyrimidin-5-one |
| 6.2 | 3-(dimethylamino)-7-((ethyl(4-fluorophenyl)amino)methyl)-2-methyl-5H-thiazolo[3,2-a]pyrimidin-5-one |
| 6.3 | 7-((ethyl(4-fluorophenyl)amino)methyl)-2-methyl-3-(pyrrolidin-1-yl)-5H-thiazolo[3,2-a]pyrimidin-5-one |
| 7.1 | 7-(((3,4-difluorophenyl)(ethyl)amino)methyl)-2-methyl-5-oxo-5H-thiazolo[3,2-a]pyrimidine-3-carbonitrile |
| 7.2 | 7-((ethyl(3-fluorophenyl)amino)methyl)-2-methyl-5-oxo-5H-thiazolo[3,2-a]pyrimidine-3-carbonitrile |
| 7.3 | 7-[(N-ethyl-4-fluoro-anilino)methyl]-2-methyl-5-oxo-thiazolo[3,2-a]pyrimidine-3-carbonitrile |
| 7.4 | 7-[(N-ethyl-4-fluoro-anilino)methyl]-5-oxo-thiazolo[3,2-a]pyrimidine-3-carbonitrile |
| 7.5 | 7-((5-fluoro-2-methylindolin-1-yl)methyl)-2-methyl-5-oxo-5H-thiazolo[3,2-a]pyrimidine-3-carbonitrile |
| 7.6 | 7-(((3-cyanophenyl)(ethyl)amino)methyl)-2-methyl-5-oxo-5H-thiazolo[3,2-a]pyrimidine-3-carbonitrile |
| 7.7 | 7-((ethyl(pyridin-2-yl)amino)methyl)-2-methyl-5-oxo-5H-thiazolo[3,2-a]pyrimidine-3-carbonitrile |
| 7.8 | 2-methyl-7-((2-methylindolin-1-yl)methyl)-5-oxo-5H-thiazolo[3,2-a]pyrimidine-3-carbonitrile |
| 7.9 | 7-(((3,5-difluorophenyl)(ethyl)amino)methyl)-2-methyl-5-oxo-5H-thiazolo[3,2-a]pyrimidine-3-carbonitrile |
| 8.1 | 6-[(N-ethyl-4-fluoro-anilino)methyl]-2,3-dihydro-1H-cyclopenta[3,4]thiazolo[1,4-a]pyrimidin-8-one |
| 8.2 | 2-[(N-ethyl-4-fluoro-anilino)methyl]-6,7,8,9-tetrahydropyrimido[2,1-b][1,3]benzothiazol-4-one |
| 8.3 | 6-[(N-ethyl-4-fluoro-anilino)methyl]-1-(hydroxymethyl)-2,3-dihydro-1H-cyclopenta[3,4]thiazolo[1,4-a]pyrimidin-8-one |
| 8.4 | 6-[(N-ethyl-4-fluoro-anilino)methyl]-1-(hydroxymethyl)-2,3-dihydro-1H-cyclopenta[3,4]thiazolo[1,4-a]pyrimidin-8-one (enantiomer 1) |
| 8.5 | 6-[(N-ethyl-4-fluoro-anilino)methyl]-1-(hydroxymethyl)-2,3-dihydro-1H-cyclopenta[3,4]thiazolo[1,4-a]pyrimidin-8-one (enantiomer 2) |
| 8.6 | 6-[(N-ethyl-4-fluoro-anilino)methyl]spiro[2,3-dihydrocyclopenta[3,4]thiazolo[1,4-a]pyrimidine-1,1'-cyclopentane]-8-one |
| 8.7 | 6-[(N-ethyl-4-fluoro-anilino)methyl]-2,3-dihydrocyclopenta[3,4]thiazolo[1,4-a]pyrimidine-1,8-dione |
| 8.8 | 6-[(N-ethyl-4-fluoro-anilino)methyl]-1,1-dimethyl-2,3-dihydrocyclopenta[3,4]thiazolo[1,4-a]pyrimidin-8-one |
| 8.9 | 2-[(N-ethyl-4-fluoro-anilino)methyl]-8,9-dihydro-6H-pyrano[3,4]thiazolo[1,4-a]pyrimidin-4-one |
| 8.10 | 2-[(N-ethyl-4-fluoro-anilino)methyl]-7-methyl-8,9-dihydro-6H-pyrido[3,4]thiazolo[1,4-a]pyrimidin-4-one |
| 8.11 | 6-[(N-ethyl-4-fluoro-anilino)methyl]-8-oxo-2,3-dihydro-1H-cyclopenta[3,4]thiazolo[1,4-a]pyrimidine-1-carboxamide |
| 8.12 | 6-[(N-ethyl-4-fluoro-anilino)methyl]-8-oxo-2,3-dihydro-1H-cyclopenta[3,4]thiazolo[1,4-a]pyrimidine-1-carbonitrile |
| 8.13 | 2-[6-[(N-ethyl-4-fluoro-anilino)methyl]-8-oxo-2,3-dihydro-1H-cyclopenta[3,4]thiazolo[1,4-a]pyrimidin-1-yl]acetonitrile |

TABLE 1-continued

| Ex. | Chemical Name |
|---|---|
| 8.14 | 6-[(N-ethyl-4-fluoro-anilino)methyl]-1-(2-hydroxyethyl)-2,3-dihydro-1H-cyclopenta[3,4]thiazolo[1,4-a]pyrimidin-8-one |
| 8.15 | 2-((ethyl(4-fluorophenyl)amino)methyl)-6-(methoxymethyl)-7,8-dihydrocyclopenta[4,5]thiazolo[3,2-a]pyrimidin-4(6H)-one |
| 8.16 | 2-[6-[(N-ethyl-4-fluoro-anilino)methyl]-8-oxo-2,3-dihydro-1H-cyclopenta[3,4]thiazolo[1,4-a]pyrimidin-1-yl]acetamide |
| 9.1 | 3-cyclohexyl-7-[[ethyl(4-fluorophenyl)amino]methyl]-2-methyl-5H-[1,3]thiazolo[3,2-a]pyrimidin-5-one |
| 9.2 | 7-[(N-ethyl-4-fluoro-anilino)methyl]-3-isopropyl-2-methyl-thiazolo[3,2-a]pyrimidin-5-one |
| 9.3 | 3-cyclopentyl-7-[(N-ethyl-4-fluoro-anilino)methyl]-2-methyl-thiazolo[3,2-a]pyrimidin-5-one |
| 9.4 | 7-[(N-ethyl-4-fluoro-anilino)methyl]-2-methyl-3-tetrahydropyran-4-yl-thiazolo[3,2-a]pyrimidin-5-one |
| 10.1 | 3-cyclobutyl-7-[(N-ethyl-4-fluoro-anilino)methyl]-2-methyl-thiazolo[3,2-a]pyrimidin-5-one |
| 10.2 | 3-tert-butyl-7-[(N-ethyl-4-fluoro-anilino)methyl]-2-methyl-thiazolo[3,2-a]pyrimidin-5-one |
| 10.3 | 3-acetyl-7-((ethyl(4-fluorophenyl)amino)methyl)-2-methyl-5H-thiazolo[3,2-a]pyrimidin-5-one |
| 10.4 | 7-[(N-ethyl-4-fluoro-anilino)methyl]-N,2-dimethyl-5-oxo-thiazolo[3,2-a]pyrimidine-3-carboxamide |
| 10.5 | 7-[(N-ethyl-4-fluoro-anilino)methyl]-3-(1-hydroxy-1-methyl-ethyl)-2-methyl-thiazolo[3,2-a]pyrimidin-5-one |
| 10.6 | 7-[(N-ethyl-4-fluoro-anilino)methyl]-3-(1-hydroxyethyl)-2-methyl-thiazolo[3,2-a]pyrimidin-5-one |
| 10.7 | 3-[(dimethylamino)methyl]-7-[[ethyl(4-fluorophenyl)amino]methyl]-2-methyl-5H-[1,3]thiazolo[3,2-a]pyrimidin-5-one |
| 10.8 | 3-(azetidin-1-ylmethyl)-7-[(N-ethyl-4-fluoro-anilino)methyl]-2-methyl-thiazolo[3,2-a]pyrimidin-5-one |
| 10.9 | 7-[(N-ethyl-4-fluoro-anilino)methyl]-2-methyl-3-(pyrrolidin-1-ylmethyl)thiazolo[3,2-a]pyrimidin-5-one |
| 10.10 | 7-[(N-ethyl-4-fluoro-anilino)methyl]-3-[(3-hydroxyazetidin-1-yl)methyl]-2-methyl-thiazolo[3,2-a]pyrimidin-5-one |
| 10.11 | 7-[(N-ethyl-4-fluoro-anilino)methyl]-2-methyl-3-(2,2,2-trifluoro-1-hydroxy-ethyl)thiazolo[3,2-a]pyrimidin-5-one |
| 10.12 | 7-((ethyl(4-fluorophenyl)amino)methyl)-3-(hydroxymethyl)-2-methyl-5H-thiazolo[3,2-a]pyrimidin-5-one |
| 10.13 | 7-[[ethyl(4-fluorophenyl)amino]methyl]-3-(methoxymethyl)-2-methyl-5H-[1,3]thiazolo[3,2-a]pyrimidin-5-one |
| 10.14 | 7-[[Ethyl(4-fluorophenyl)amino]methyl]-2-methyl-3-(1H-pyrazol-1-ylmethyl)-5H-[1,3]thiazolo[3,2-a]pyrimidin-5-one |
| 10.15 | 7-[(N-ethyl-4-fluoro-anilino)methyl]-2-methyl-3-(methylsulfonylmethyl)thiazolo[3,2-a]pyrimidin-5-one |
| 10.16 | 3-(ethoxymethyl)-7-[(N-ethyl-4-fluoro-anilino)methyl]-2-methyl-thiazolo[3,2-a]pyrimidin-5-one |
| 10.17 | 2-[7-[(N-ethyl-4-fluoro-anilino)methyl]-2-methyl-5-oxo-thiazolo[3,2-a]pyrimidin-3-yl]acetonitrile |
| 10.18 | 3-tert-butyl-7-[(N-ethyl-4-fluoro-anilino)methyl]thiazolo[3,2-a]pyrimidin-5-one |
| 10.19 | 7-[(N-ethyl-4-fluoro-anilino)methyl]-3-(1-hydroxy-1-methyl-ethyl)thiazolo[3,2-a]pyrimidin-5-one |
| 10.20 | 7-[(N-ethyl-4-fluoro-anilino)methyl]-3-(1-hydroxyethyl)thiazolo[3,2-a]pyrimidin-5-one |
| 10.21 | 7-[(N-ethyl-4-fluoro-anilino)methyl]-2-methyl-3-(6-oxa-1-azaspiro[3.3]heptan-1-ylmethyl)thiazolo[3,2-a]pyrimidin-5-one |
| 10.22 | 7-[(N-ethyl-4-fluoro-anilino)methyl]-3-[(2-hydroxyethylamino)methyl]-2-methyl-thiazolo[3,2-a]pyrimidin-5-one |
| 10.23 | 3-(ethyl((3-(hydroxymethyl)-2-methyl-5-oxo-5H-thiazolo[3,2-a]pyrimidin-7-yl)methyl)amino)benzonitrile |
| 10.24 | 3-[ethyl-[[3-(methoxymethyl)-2-methyl-5-oxo-thiazolo[3,2-a]pyrimidin-7-yl]methyl]amino]benzonitrile |
| 10.25 | 7-((ethyl(4-fluorophenyl)amino)methyl)-2-methyl-3-((methylthio)methyl)-5H-thiazolo[3,2-a]pyrimidin-5-one |
| 11.1 | 3-chloro-7-[[ethyl(4-fluorophenyl)amino]methyl]-2-methyl-5H-[1,3]thiazolo[3,2-a]pyrimidin-5-one |
| 11.2 | 7-[(N-ethyl-4-fluoro-anilino)methyl]-3-fluoro-2-methyl-thiazolo[3,2-a]pyrimidin-5-one |
| 11.3 | 7-[(N-ethyl-4-fluoro-anilino)methyl]-2-methyl-thiazolo[3,2-a]pyrimidin-5-one |
| 11.4 | 7-[(N-ethyl-4-fluoro-anilino)methyl]-3-iodo-2-methyl-thiazolo[3,2-a]pyrimidin-5-one |
| 11.5 | 3-chloro-7-[(N-ethyl-4-fluoro-anilino)methyl]thiazolo[3,2-a]pyrimidin-5-one |
| 11.6 | 7-[(N-ethylanilino)methyl]-2-methyl-thiazolo[3,2-a]pyrimidin-5-one |
| 12.1 | 3-(1,3-dihydroxypropyl)-7-[(N-ethyl-4-fluoro-anilino)methyl]-2-methyl-thiazolo[3,2-a]pyrimidin-5-one |
| 12.2 | 7-[(N-ethyl-4-fluoro-anilino)methyl]-3-(1-fluoro-3-hydroxy-propyl)-2-methyl-thiazolo[3,2-a]pyrimidin-5-one |
| 12.3 | 3-(1,3-dihydroxypropyl)-7-[(N-ethyl-4-fluoro-anilino)methyl]-2-methyl-thiazolo[3,2-a]pyrimidin-5-one (enantiomer 1) |
| 12.4 | 3-(1,3-dihydroxypropyl)-7-[(N-ethyl-4-fluoro-anilino)methyl]-2-methyl-thiazolo[3,2-a]pyrimidin-5-one (enantiomer 2) |

TABLE 1-continued

| Ex. | Chemical Name |
| --- | --- |
| 12.5 | 3-(1,2-dihydroxyethyl)-7-[(N-ethyl-4-fluoro-anilino)methyl]-2-methyl-thiazolo[3,2-a]pyrimidin-5-one |
| 13.1 | 7-[(N-ethyl-4-fluoro-anilino)methyl]-3-(3-hydroxypropyl)-2-methyl-thiazolo[3,2-a]pyrimidin-5-one |
| 13.2 | 7-((Ethyl(4-fluorophenyl)amino)methyl)-3-(3-methoxypropyl)-2-methyl-5H-thiazolo[3,2-a]pyrimidin-5-one |
| 13.3 | 7-((Ethyl(4-fluorophenyl)amino)methyl)-3-(4-hydroxybutyl)-2-methyl-5H-thiazolo[3,2-a]pyrimidin-5-one |
| 13.4 | 7-((Ethyl(4-fluorophenyl)amino)methyl)-3-(2-hydroxyethyl)-2-methyl-5H-thiazolo[3,2-a]pyrimidin-5-one |
| 13.5 | 7-[[Ethyl(4-fluorophenyl)amino]methyl]-3-(2-methoxyethyl)-2-methyl-5H-[1,3]thiazolo[3,2-a]pyrimidin-5-one |
| 13.6 | 3-(7-[[ethyl(4-fluorophenyl)amino]methyl]-2-methyl-5-oxo-5H-[1,3]thiazolo[3,2-a]pyrimidin-3-yl)propanamide |
| 13.7 | 3-[7-[(N-ethyl-4-fluoro-anilino)methyl]-2-methyl-5-oxo-thiazolo[3,2-a]pyrimidin-3-yl]propanenitrile |
| 13.8 | 3-[7-[(N-ethyl-4-fluoro-anilino)methyl]-2-methyl-5-oxo-thiazolo[3,2-a]pyrimidin-3-yl]-N,N-dimethyl-propanamide |
| 13.9 | 7-[[Ethyl(4-fluorophenyl)amino]methyl]-3-(3-hydroxy-3-methylbutyl)-2-methyl-5H-[1,3]thiazolo[3,2-a]pyrimidin-5-one |
| 14.1 | 2-[7-[(N-ethyl-4-fluoro-anilino)methyl]-2-methyl-5-oxo-thiazolo[3,2-a]pyrimidin-3-yl]cyclopropanecarboxamide |
| 14.2 | 2-[7-[(N-ethyl-4-fluoro-anilino)methyl]-2-methyl-5-oxo-thiazolo[3,2-a]pyrimidin-3-yl]cyclopropanecarboxamide |
| 15.1 | 7-((5-ethyl-3-(trifluoromethyl)-1H-pyrazol-1-yl)methyl)-3-(2-(hydroxymethyl)cyclopropyl)-2-methyl-5H-thiazolo[3,2-a]pyrimidin-5-one |
| 15.2 | 7-((3,5-bis(trifluoromethyl)-1H-pyrazol-1-yl)methyl)-3-(trans-2-(hydroxymethyl)cyclopropyl)-2-methyl-5H-thiazolo[3,2-a]pyrimidin-5-one |
| 15.3 | 7-((3-chloro-5-methyl-1H-pyrazol-1-yl)methyl)-3-(trans-2-(hydroxymethyl)cyclopropyl)-2-methyl-5H-thiazolo[3,2-a]pyrimidin-5-one |
| 15.4 | 7-((5-chloro-3-methyl-1H-pyrazol-1-yl)methyl)-3-(trans-2-(hydroxymethyl)cyclopropyl)-2-methyl-5H-thiazolo[3,2-a]pyrimidin-5-one |
| 15.5 | 3-(trans-2-(hydroxymethyl)cyclopropyl)-2-methyl-7-((3-(trifluoromethyl)-1H-pyrazol-1-yl)methyl)-5H-thiazolo[3,2-a]pyrimidin-5-one |
| 15.6 | 7-((1H-indazol-1-yl)methyl)-3-(trans-2-(hydroxymethyl)cyclopropyl)-2-methyl-5H-thiazolo[3,2-a]pyrimidin-5-one |
| 15.7 | 7-((5-(2-hydroxyethyl)-3-(trifluoromethyl)-1H-pyrazol-1-yl)methyl)-3-(trans-2-(hydroxymethyl)cyclopropyl)-2-methyl-5H-thiazolo[3,2-a]pyrimidin-5-one |
| 15.8 | 7-((3-(2-hydroxyethyl)-5-(trifluoromethyl)-1H-pyrazol-1-yl)methyl)-3-(trans-2-(hydroxymethyl)cyclopropyl)-2-methyl-5H-thiazolo[3,2-a]pyrimidin-5-one |
| 15.9 | 7-((3-cyclopropyl-4-fluoro-5-(trifluoromethyl)-1H-pyrazol-1-yl)methyl)-3-(trans-2-(hydroxymethyl)cyclopropyl)-2-methyl-5H-thiazolo[3,2-a]pyrimidin-5-one |
| 15.10 | 7-((5-cyclopropyl-4-fluoro-3-(trifluoromethyl)-1H-pyrazol-1-yl)methyl)-3-(trans-2-(hydroxymethyl)cyclopropyl)-2-methyl-5H-thiazolo[3,2-a]pyrimidin-5-one |
| 15.11 | 7-((5-cyclopropyl-3-(trifluoromethyl)-1H-pyrazol-1-yl)methyl)-3-(trans-2-(hydroxymethyl)cyclopropyl)-2-methyl-5H-thiazolo[3,2-a]pyrimidin-5-one |
| 15.12 | 7-((3-cyclopropyl-5-(trifluoromethyl)-1H-pyrazol-1-yl)methyl)-3-(trans-2-(hydroxymethyl)cyclopropyl)-2-methyl-5H-thiazolo[3,2-a]pyrimidin-5-one |
| 15.13 | 7-[(5-cyclopropyl-3-methyl-pyrazol-1-yl)methyl]-3-[trans-2-(hydroxymethyl)cyclopropyl]-2-methyl-thiazolo[3,2-a]pyrimidin-5-one (enantiomer 1) |
| 15.14 | 7-[(5-cyclopropyl-3-methyl-pyrazol-1-yl)methyl]-3-[trans-2-(hydroxymethyl)cyclopropyl]-2-methyl-thiazolo[3,2-a]pyrimidin-5-one (enantiomer 2) |
| 15.15 | 7-[(3-cyclopropyl-5-methyl-pyrazol-1-yl)methyl]-3-[trans-2-(hydroxymethyl)cyclopropyl]-2-methyl-thiazolo[3,2-a]pyrimidin-5-one (enantiomer 1) |
| 15.16 | 7-[(3-cyclopropyl-5-methyl-pyrazol-1-yl)methyl]-3-[trans-2-(hydroxymethyl)cyclopropyl]-2-methyl-thiazolo[3,2-a]pyrimidin-5-one (enantiomer 2) |
| 15.17 | 7-[(3,5-dicyclopropylpyrazol-1-yl)methyl]-3-[trans-2-(hydroxymethyl)cyclopropyl]-2-methyl-thiazolo[3,2-a]pyrimidin-5-one |
| 15.18 | 7-((3,5-dimethyl-1H-pyrazol-1-yl)methyl)-6-fluoro-3-(trans-2-(hydroxymethyl)cyclopropyl)-2-methyl-5H-thiazolo[3,2-a]pyrimidin-5-one |
| 15.19 | 1-((3-(trans-2-(hydroxymethyl)cyclopropyl)-2-methyl-5-oxo-5H-thiazolo[3,2-a]pyrimidin-7-yl)methyl)-3-(trifluoromethyl)-1H-pyrazole-5-carbonitrile |
| 15.20 | 7-((5-cyclopropyl-3-(trifluoromethyl)-1H-pyrazol-1-yl)methyl)-6-fluoro-3-(trans-2-(hydroxymethyl)cyclopropyl)-2-methyl-5H-thiazolo[3,2-a]pyrimidin-5-one |
| 15.21 | 1-[[3-[trans-2-(hydroxymethyl)cyclopropyl]-2-methyl-5-oxo-thiazolo[3,2-a]pyrimidin-7-yl]methyl]-5-methyl-pyrazole-3-carbonitrile |
| 15.22 | 7-[[3-(difluoromethyl)-5-methyl-pyrazol-1-yl]methyl]-3-[trans-2-(hydroxymethyl)cyclopropyl]-2-methyl-thiazolo[3,2-a]pyrimidin-5-one |
| 15.23 | 7-[(6-fluoroindazol-1-yl)methyl]-3-[trans-2-(hydroxymethyl)cyclopropyl]-2-methyl-thiazolo[3,2-a]pyrimidin-5-one |
| 15.24 | 7-[[5-cyclopropyl-3-(trifluoromethyl)pyrazol-1-yl]methyl]-3-[2-(hydroxymethyl)cyclopropyl]-2-isopropyl-thiazolo[3,2-a]pyrimidin-5-one |
| 15.25 | 7-[(3,5-dimethylpyrazol-1-yl)methyl]-3-[trans-2-(hydroxymethyl)cyclopropyl]-2-methyl-thiazolo[3,2-a]pyrimidin-5-one |
| 15.26 | 7-[(5-fluoroindazol-1-yl)methyl]-3-[trans-2-(hydroxymethyl)cyclopropyl]-2-methyl-thiazolo[3,2-a]pyrimidin-5-one |
| 15.27 | 5-ethyl-3-(trifluoromethyl)-1H-pyrazol-1-yl)methyl)-2-methyl-3-(pyrimidin-5-yl)-5H-thiazolo[3,2-a]pyrimidin-5-one |

TABLE 1-continued

| Ex. | Chemical Name |
|---|---|
| 15.28 | 7-((3-cyclopropyl-5-(trifluoromethyl)-1H-pyrazol-1-yl)methyl)-2-methyl-3-(pyrimidin-5-yl)-5H-thiazolo[3,2-a]pyrimidin-5-one |
| 15.29 | 7-((5-cyclopropyl-3-(trifluoromethyl)-1H-pyrazol-1-yl)methyl)-2-methyl-3-(pyrimidin-5-yl)-5H-thiazolo[3,2-a]pyrimidin-5-one |
| 15.30 | 7-((3,5-bis(trifluoromethyl)-1H-pyrazol-1-yl)methyl)-2-methyl-3-(pyrimidin-5-yl)-5H-thiazolo[3,2-a]pyrimidin-5-one |
| 15.31 | 2-methyl-3-(pyrimidin-5-yl)-7-((5-(trifluoromethyl)-1H-pyrazol-1-yl)methyl)-5H-thiazolo[3,2-a]pyrimidin-5-one |
| 15.32 | 2-methyl-7-((5-methyl-3-(trifluoromethyl)-1H-pyrazol-1-yl)methyl)-3-(pyrimidin-5-yl)-5H-thiazolo[3,2-a]pyrimidin-5-one |
| 15.33 | 7-((3,5-bis(trifluoromethyl)-1H-pyrazol-1-yl)methyl)-2-methyl-5H-thiazolo[3,2-a]pyrimidin-5-one |
| 15.34 | 7-((1H-indazol-1-yl)methyl)-2-methyl-3-(pyrimidin-5-yl)-5H-thiazolo[3,2-a]pyrimidin-5-one |
| 16.1 | 7-((5-cyclopropyl-3-(trifluoromethyl)-1H-pyrazol-1-yl)methyl)-N,2-dimethyl-5-oxo-5H-thiazolo[3,2-a]pyrimidine-3-carboxamide |
| 16.2 | 7-((3-cyclopropyl-5-(trifluoromethyl)-1H-pyrazol-1-yl)methyl)-N,2-dimethyl-5-oxo-5H-thiazolo[3,2-a]pyrimidine-3-carboxamide |
| 16.3 | 7-((5-cyclopropyl-3-(trifluoromethyl)-1H-pyrazol-1-yl)methyl)-N-ethyl-5-oxo-2-(trifluoromethyl)-5H-thiazolo[3,2-a]pyrimidine-3-carboxamide |
| 16.4 | 7-((3-cyclopropyl-5-(trifluoromethyl)-1H-pyrazol-1-yl)methyl)-N-ethyl-5-oxo-2-(trifluoromethyl)-5H-thiazolo[3,2-a]pyrimidine-3-carboxamide |
| 16.5 | 7-((5-cyclopropyl-3-(trifluoromethyl)-1H-pyrazol-1-yl)methyl)-N-ethyl-5-oxo-5H-thiazolo[3,2-a]pyrimidine-3-carboxamide |
| 16.6 | 2-cyclopropyl-7-((5-cyclopropyl-3-(trifluoromethyl)-1H-pyrazol-1-yl)methyl)-N-ethyl-5-oxo-5H-thiazolo[3,2-a]pyrimidine-3-carboxamide |
| 16.7 | 2-cyclopropyl-7-((3-cyclopropyl-5-(trifluoromethyl)-1H-pyrazol-1-yl)methyl)-N-ethyl-5-oxo-5H-thiazolo[3,2-a]pyrimidine-3-carboxamide |
| 17.1 | 2-methyl-5-oxo-7-((3-(trifluoromethyl)-1H-pyrazol-1-yl)methyl)-5H-thiazolo[3,2-a]pyrimidine-3-carbonitrile |
| 17.2 | 7-((5-cyclopropyl-3-(trifluoromethyl)-1H-pyrazol-1-yl)methyl)-2-methyl-5-oxo-5H-thiazolo[3,2-a]pyrimidine-3-carbonitrile |
| 17.3 | 7-((3-cyclopropyl-5-(trifluoromethyl)-1H-pyrazol-1-yl)methyl)-2-methyl-5-oxo-5H-thiazolo[3,2-a]pyrimidine-3-carbonitrile |
| 18.1 | 3-(1-hydroxyethyl)-2-methyl-7-((3-(trifluoromethyl)-1H-pyrazol-1-yl)methyl)-5H-thiazolo[3,2-a]pyrimidin-5-one |
| 18.2 | 3-acetyl-7-((5-cyclopropyl-3-(trifluoromethyl)-1H-pyrazol-1-yl)methyl)-2-methyl-5H-thiazolo[3,2-a]pyrimidin-5-one |
| 18.3 | 3-acetyl-7-((3-cyclopropyl-5-(trifluoromethyl)-1H-pyrazol-1-yl)methyl)-2-methyl-5H-thiazolo[3,2-a]pyrimidin-5-one |
| 18.4 | 3-(2-hydroxypropan-2-yl)-2-methyl-7-((3-(trifluoromethyl)-1H-pyrazol-1-yl)methyl)-5H-thiazolo[3,2-a]pyrimidin-5-one |
| 18.5 | 7-((5-fluoro-3-methyl-1H-indazol-1-yl)methyl)-3-(1-hydroxyethyl)-2-methyl-5H-thiazolo[3,2-a]pyrimidin-5-one |
| 19.1 | 7-(1-(5-cyclopropyl-3-(trifluoromethyl)-1H-pyrazol-1-yl)ethyl)-3-(trans-2-(hydroxymethyl)cyclopropyl)-2-methyl-5H-thiazolo[3,2-a]pyrimidin-5-one |
| 19.2 | 7-(1-(5-cyclopropyl-3-(trifluoromethyl)-1H-pyrazol-1-yl)ethyl)-3-(2-(hydroxymethyl)-1-methylcyclopropyl)-2-methyl-5H-thiazolo[3,2-a]pyrimidin-5-one |
| 20.1 | 3-((3-(trans-2-(hydroxymethyl)cyclopropyl)-2-methyl-5-oxo-5H-thiazolo[3,2-a]pyrimidin-7-yl)methyl)benzonitrile |
| 20.2 | 3-((6-fluoro-3-(2-(hydroxymethyl)cyclopropyl)-2-methyl-5-oxo-5H-thiazolo[3,2-a]pyrimidin-7-yl)methyl)benzonitrile |
| 20.3 | 2-fluoro-3-((3-(trans-2-(hydroxymethyl)cyclopropyl)-2-methyl-5-oxo-5H-thiazolo[3,2-a]pyrimidin-7-yl)methyl)benzonitrile |
| 20.4 | 3-(trans-2-(hydroxymethyl)cyclopropyl)-7-(isoquinolin-4-ylmethyl)-2-methyl-5H-thiazolo[3,2-a]pyrimidin-5-one |
| 20.5 | 3-(trans-2-(hydroxymethyl)cyclopropyl)-2-methyl-7-(3-(trifluoromethyl)benzyl)-5H-thiazolo[3,2-a]pyrimidin-5-one |
| 20.6 | 3-((3-(trans-2-(hydroxymethyl)cyclopropyl)-2-methyl-5-oxo-5H-thiazolo[3,2-a]pyrimidin-7-yl)methyl)-4-methylbenzonitrile |
| 20.7 | 4-fluoro-3-((3-(trans-2-(hydroxymethyl)cyclopropyl)-2-methyl-5-oxo-5H-thiazolo[3,2-a]pyrimidin-7-yl)methyl)benzonitrile |
| 20.8 | 3-fluoro-5-((3-(trans-2-(hydroxymethyl)cyclopropyl)-2-methyl-5-oxo-5H-thiazolo[3,2-a]pyrimidin-7-yl)methyl)benzonitrile |
| 20.9 | 2-fluoro-5-((3-(trans-2-(hydroxymethyl)cyclopropyl)-2-methyl-5-oxo-5H-thiazolo[3,2-a]pyrimidin-7-yl)methyl)benzonitrile |
| 20.10 | 3-[[3-[trans-2-(hydroxymethyl)cyclopropyl]-2-methyl-5-oxo-thiazolo[3,2-a]pyrimidin-7-yl]methyl]-4-methoxy-benzonitrile |
| 20.11 | 3-(2-(hydroxymethyl)cyclopropyl)-2-methyl-7-(4-(trifluoromethyl)benzyl)-5H-thiazolo[3,2-a]pyrimidin-5-one |
| 20.12 | 4-((3-(trans-2-(hydroxymethyl)cyclopropyl)-2-methyl-5-oxo-5H-thiazolo[3,2-a]pyrimidin-7-yl)methyl)picolinonitrile |
| 20.13 | 4-cyclopropyl-3-((3-(trans-2-(hydroxymethyl)cyclopropyl)-2-methyl-5-oxo-5H-thiazolo[3,2-a]pyrimidin-7-yl)methyl)benzonitrile |
| 21.1 | 7-(3-cyanobenzyl)-N,2-dimethyl-5-oxo-5H-thiazolo[3,2-a]pyrimidine-3-carboxamide |
| 21.2 | 7-(3-cyano-2-fluorobenzyl)-N,2-dimethyl-5-oxo-5H-thiazolo[3,2-a]pyrimidine-3-carboxamide |

TABLE 1-continued

| Ex. | Chemical Name |
|---|---|
| 21.3 | 7-(3-chloro-2-fluorobenzyl)-N-ethyl-2-methyl-5-oxo-5H-thiazolo[3,2-a]pyrimidine-3-carboxamide |
| 21.4 | N-ethyl-7-(2-fluoro-3-(trifluoromethyl)benzyl)-2-methyl-5-oxo-5H-thiazolo[3,2-a]pyrimidine-3-carboxamide |
| 21.5 | N-ethyl-7-(2-fluoro-3-methylbenzyl)-2-methyl-5-oxo-5H-thiazolo[3,2-a]pyrimidine-3-carboxamide |
| 21.6 | 7-(2-chloro-5-cyanobenzyl)-N-ethyl-2-methyl-5-oxo-5H-thiazolo[3,2-a]pyrimidine-3-carboxamide |
| 21.7 | N-ethyl-2-methyl-5-oxo-7-(3-(trifluoromethyl)benzyl)-5H-thiazolo[3,2-a]pyrimidine-3-carboxamide |
| 21.8 | 7-(3-cyanobenzyl)-N-ethyl-2-methyl-5-oxo-5H-thiazolo[3,2-a]pyrimidine-3-carboxamide |
| 21.9 | 7-(3-cyano-2-fluorobenzyl)-2-cyclopropyl-N-ethyl-5-oxo-5H-thiazolo[3,2-a]pyrimidine-3-carboxamide |
| 21.10 | 7-(3-cyano-5-fluorobenzyl)-N-ethyl-2-methyl-5-oxo-5H-thiazolo[3,2-a]pyrimidine-3-carboxamide |
| 21.11 | 7-(3-cyanobenzyl)-N-ethyl-2-methyl-5-oxo-5H-thiazolo[3,2-a]pyrimidine-3-carboxamide |
| 21.12 | N-ethyl-7-(2-fluoro-3-(trifluoromethyl)benzyl)-2-methyl-5-oxo-5H-thiazolo[3,2-a]pyrimidine-3-carboxamide |
| 21.13 | 7-(3-cyano-2-fluorobenzyl)-N-ethyl-2-methyl-5-oxo-5H-thiazolo[3,2-a]pyrimidine-3-carboxamide |
| 21.14 | 7-[(3-chloro-2-fluoro-phenyl)methyl]-N,2-dimethyl-5-oxo-thiazolo[3,2-a]pyrimidine-3-carboxamide |
| 21.15 | N,2-dimethyl-5-oxo-7-[[3-(trifluoromethyl)phenyl]methyl]thiazolo[3,2-a]pyrimidine-3-carboxamide |
| 21.16 | 7-[(3-chlorophenyl)methyl]-N,2-dimethyl-5-oxo-thiazolo[3,2-a]pyrimidine-3-carboxamide |
| 21.17 | 7-[[2-cyclopropyl-5-(trifluoromethyl)phenyl]methyl]-N,2-dimethyl-5-oxo-thiazolo[3,2-a]pyrimidine-3-carboxamide |
| 21.18 | N-ethyl-2-methyl-5-oxo-7-((6-(trifluoromethyl)pyridine-2-yl)methyl)-5H-thiazolo[3,2-a]pyrimidine-3-carboxamide |
| 21.19 | N-ethyl-7-(2-ethyl-4,5-difluorobenzyl)-2-methyl-5-oxo-5H-thiazolo[3,2-a]pyrimidine-3-carboxamide |
| 21.20 | 7-[[3-(difluoromethyl)-2-fluoro-phenyl]methyl]-N-ethyl-2-methyl-5-oxo-thiazolo[3,2-a]pyrimidine-3-carboxamide |
| 21.21 | N-ethyl-7-(2-ethyl-4,5-difluorobenzyl)-2-methyl-5-oxo-5H-thiazolo[3,2-a]pyrimidine-3-carboxamide |
| 21.22 | 7-((6-cyanopyridin-2-yl)methyl)-N-ethyl-2-methyl-5-oxo-5H-thiazolo[3,2-a]pyrimidine-3-carboxamide |
| 21.23 | 7-[[3-(difluoromethyl)-2-fluoro-phenyl]methyl]-N,2-dimethyl-5-oxo-thiazolo[3,2-a]pyrimidine-3-carboxamide |
| 21.24 | 7-[[2-fluoro-3-(hydroxymethyl)phenyl]methyl]-N,2-dimethyl-5-oxo-thiazolo[3,2-a]pyrimidine-3-carboxamide |
| 21.25 | 7-(3-cyclopropyl-2-fluorobenzyl)-N-ethyl-2-methyl-5-oxo-5H-thiazolo[3,2-a]pyrimidine-3-carboxamide |
| 21.26 | 7-(3-cyano-2-fluorobenzyl)-N-ethyl-6-fluoro-5-oxo-5H-thiazolo[3,2-a]pyrimidine-3-carboxamide |
| 21.27 | 7-(3-cyano-2-fluorobenzyl)-6-fluoro-N,N-dimethyl-5-oxo-5H-thiazolo[3,2-a]pyrimidine-3-carboxamide |
| 21.28 | 7-(3-cyano-2-fluorobenzyl)-N-ethyl-6-fluoro-2-methyl-5-oxo-5H-thiazolo[3,2-a]pyrimidine-3-carboxamide |
| 21.29 | 6-fluoro-7-(2-fluoro-3-(trifluoromethyl)benzyl)-N,2-dimethyl-5-oxo-5H-thiazolo[3,2-a]pyrimidine-3-carboxamide |
| 21.30 | 7-(5-cyano-2-methylbenzyl)-N-ethyl-2-methyl-5-oxo-5H-thiazolo[3,2-a]pyrimidine-3-carboxamide |
| 21.31 | 7-(5-cyano-2-fluorobenzyl)-N-ethyl-2-methyl-5-oxo-5H-thiazolo[3,2-a]pyrimidine-3-carboxamide |
| 21.32 | 7-(2-chloro-5-fluorobenzyl)-N-ethyl-2-methyl-5-oxo-5H-thiazolo[3,2-a]pyrimidine-3-carboxamide |
| 21.33 | 7-(3-cyano-2-fluorobenzyl)-N-ethyl-5-oxo-5H-thiazolo[3,2-a]pyrimidine-3-carboxamide |
| 21.34 | N-ethyl-7-(5-fluoro-2-(trifluoromethyl)benzyl)-2-methyl-5-oxo-5H-thiazolo[3,2-a]pyrimidine-3-carboxamide |
| 21.35 | N-ethyl-2-methyl-7-(naphthalen-1-ylmethyl)-5-oxo-5H-thiazolo[3,2-a]pyrimidine-3-carboxamide |
| 21.36 | N-ethyl-7-(5-fluoro-2-methylbenzyl)-2-methyl-5-oxo-5H-thiazolo[3,2-a]pyrimidine-3-carboxamide |
| 21.37 | 7-(3-cyano-4-fluorobenzyl)-N-ethyl-2-methyl-5-oxo-5H-thiazolo[3,2-a]pyrimidine-3-carboxamide |
| 21.38 | N-ethyl-2-methyl-7-((1-methyl-1H-indazol-4-yl)methyl)-5-oxo-5H-thiazolo[3,2-a]pyrimidine-3-carboxamide |
| 21.39 | N-ethyl-2-methyl-7-(3-(methylsulfonamido)benzyl)-5-oxo-5H-thiazolo[3,2-a]pyrimidine-3-carboxamide |
| 21.40 | 7-(5-cyano-2-(trifluoromethyl)benzyl)-N-ethyl-2-methyl-5-oxo-5H-thiazolo[3,2-a]pyrimidine-3-carboxamide |

TABLE 1-continued

| Ex. | Chemical Name |
|---|---|
| 21.41 | 7-(4-chloro-2-methylbenzyl)-N,2-dimethyl-5-oxo-5H-thiazolo[3,2-a]pyrimidine-3-carboxamide |
| 21.42 | 7-(2,5-difluorobenzyl)-N-ethyl-2-methyl-5-oxo-5H-thiazolo[3,2-a]pyrimidine-3-carboxamide |
| 21.43 | 7-(3-cyanobenzyl)-2-cyclopropyl-N-ethyl-5-oxo-5H-thiazolo[3,2-a]pyrimidine-3-carboxamide |
| 21.44 | N-ethyl-7-(2-fluorobenzyl)-2-methyl-5-oxo-5H-thiazolo[3,2-a]pyrimidine-3-carboxamide |
| 21.45 | 7-(2,3-difluorobenzyl)-N-ethyl-2-methyl-5-oxo-5H-thiazolo[3,2-a]pyrimidine-3-carboxamide |
| 21.46 | N-ethyl-7-(3-fluorobenzyl)-2-methyl-5-oxo-5H-thiazolo[3,2-a]pyrimidine-3-carboxamide |
| 21.47 | 7-[(3-chloro-4-fluoro-phenyl)methyl]-N,2-dimethyl-5-oxo-thiazolo[3,2-a]pyrimidine-3-carboxamide |
| 21.48 | 7-[(2,5-dichlorophenyl)methyl]-N,2-dimethyl-5-oxo-thiazolo[3,2-a]pyrimidine-3-carboxamide |
| 21.49 | N,2-dimethyl-5-oxo-7-[[3-(trifluoromethoxy)phenyl]methyl]thiazolo[3,2-a]pyrimidine-3-carboxamide |
| 21.50 | 7-[(5-cyano-2-fluoro-phenyl)methyl]-N,2-dimethyl-5-oxo-thiazolo[3,2-a]pyrimidine-3-carboxamide |
| 21.51 | 7-[(3-chloro-5-cyano-phenyl)methyl]-N,2-dimethyl-5-oxo-thiazolo[3,2-a]pyrimidine-3-carboxamide |
| 21.52 | 7-[(3-cyclopropylphenyl)methyl]-N,2-dimethyl-5-oxo-thiazolo[3,2-a]pyrimidine-3-carboxamide |
| 21.53 | 7-[(2,5-difluorophenyl)methyl]-N,2-dimethyl-5-oxo-thiazolo[3,2-a]pyrimidine-3-carboxamide |
| 21.54 | 7-[(3,4-difluorophenyl)methyl]-N,2-dimethyl-5-oxo-thiazolo[3,2-a]pyrimidine-3-carboxamide |
| 21.55 | 7-[(2,3-difluorophenyl)methyl]-N,2-dimethyl-5-oxo-thiazolo[3,2-a]pyrimidine-3-carboxamide |
| 21.56 | 7-[(4-chloro-2-fluoro-phenyl)methyl]-N,2-dimethyl-5-oxo-thiazolo[3,2-a]pyrimidine-3-carboxamide |
| 21.57 | 7-[(2,4-dichlorophenyl)methyl]-N,2-dimethyl-5-oxo-thiazolo[3,2-a]pyrimidine-3-carboxamide |
| 21.58 | 7-[(3-fluoro-4-methyl-phenyl)methyl]-N,2-dimethyl-5-oxo-thiazolo[3,2-a]pyrimidine-3-carboxamide |
| 21.59 | 7-[[4-fluoro-2-(trifluoromethyl)phenyl]methyl]-N,2-dimethyl-5-oxo-thiazolo[3,2-a]pyrimidine-3-carboxamide |
| 21.60 | 7-[(2-cyclopropyl-4-fluoro-phenyl)methyl]-N,2-dimethyl-5-oxo-thiazolo[3,2-a]pyrimidine-3-carboxamide |
| 21.61 | 7-(5-cyano-2-(2-fluoroethyl)benzyl)-N-ethyl-2-methyl-5-oxo-5H-thiazolo[3,2-a]pyrimidine-3-carboxamide |
| 21.62 | 7-(2-chloro-3-cyanobenzyl)-N-ethyl-2-methyl-5-oxo-5H-thiazolo[3,2-a]pyrimidine-3-carboxamide |
| 21.63 | N-ethyl-7-(6-ethyl-2,3-difluorobenzyl)-2-methyl-5-oxo-5H-thiazolo[3,2-a]pyrimidine-3-carboxamide |
| 21.64 | 7-(5-cyano-2-ethylbenzyl)-N-ethyl-2-methyl-5-oxo-5H-thiazolo[3,2-a]pyrimidine-3-carboxamide |
| 21.65 | 7-(2-cyclopropyl-5-fluorobenzyl)-N-ethyl-2-methyl-5-oxo-5H-thiazolo[3,2-a]pyrimidine-3-carboxamide |
| 21.66 | 7-(5-cyano-2-cyclopropylbenzyl)-N-ethyl-2-methyl-5-oxo-5H-thiazolo[3,2-a]pyrimidine-3-carboxamide |
| 21.67 | N-ethyl-7-(5-fluoro-2-propylbenzyl)-2-methyl-5-oxo-5H-thiazolo[3,2-a]pyrimidine-3-carboxamide |
| 21.68 | 7-[[2-fluoro-3-(fluoromethyl)phenyl]methyl]-N,2-dimethyl-5-oxo-thiazolo[3,2-a]pyrimidine-3-carboxamide |
| 22.1 | N-ethyl-7-(1-(2-fluoro-3-(trifluoromethyl)phenyl)ethyl)-2-methyl-5-oxo-5H-thiazolo[3,2-a]pyrimidine-3-carboxamide |
| 22.2 | N-ethyl-7-(2-fluoro-3-(trifluoromethyl)benzyl)-N,2-dimethyl-5-oxo-5H-thiazolo[3,2-a]pyrimidine-3-carboxamide |
| 23.1 | 3-((3-(2-cyanocyclopropyl)-2-methyl-5-oxo-5H-thiazolo[3,2-a]pyrimidin-7-yl)methyl)benzonitrile |
| 23.2 | 3-((3-(2-cyanocyclopropyl)-2-methyl-5-oxo-5H-thiazolo[3,2-a]pyrimidin-7-yl)methyl)-2-fluorobenzonitrile |
| 23.3 | 6-((3-(2-cyanocyclopropyl)-2-methyl-5-oxo-5H-thiazolo[3,2-a]pyrimidin-7-yl)methyl)picolinonitrile |
| 23.4 | 3-((3-(2-cyanocyclopropyl)-2-methyl-5-oxo-5H-thiazolo[3,2-a]pyrimidin-7-yl)methyl)-4-methoxybenzonitrile |
| 24.1 | 2-methyl-3-(pyrimidin-5-yl)-7-(3-(trifluoromethyl)benzyl)-5H-thiazolo[3,2-a]pyrimidin-5-one |
| 24.2 | 7-(2-fluoro-3-(trifluoromethyl)benzyl)-2-methyl-3-(pyrimidin-5-yl)-5H-thiazolo[3,2-a]pyrimidin-5-one |
| 24.3 | 2-fluoro-3-((2-methyl-5-oxo-3-(pyrimidin-5-yl)-5H-thiazolo[3,2-a]pyrimidin-7-yl)methyl)benzonitrile |
| 24.4 | 3-((3-cyclopropyl-2-methyl-5-oxo-5H-thiazolo[3,2-a]pyrimidin-7-yl)methyl)-2-fluorobenzonitrile |

TABLE 1-continued

| Ex. | Chemical Name |
|---|---|
| 24.5 | 7-(isoquinolin-4-ylmethyl)-2-methyl-3-(pyrimidin-5-yl)-5H-thiazolo[3,2-a]pyrimidin-5-one |
| 24.6 | 3-((2-methyl-5-oxo-3-(pyrimidin-5-yl)-5H-thiazolo[3,2-a]pyrimidin-7-yl)methyl)benzonitrile |
| 24.7 | 7-(5-fluoro-2-methoxybenzyl)-2-methyl-3-(pyrimidin-5-yl)-5H-thiazolo[3,2-a]pyrimidin-5-one |
| 24.8 | 2-fluoro-3-((3-(furan-2-yl)-2-methyl-5-oxo-5H-thiazolo[3,2-a]pyrimidin-7-yl)methyl)benzonitrile |
| 24.9 | 3-bromo-2-methyl-7-(3-(methylsulfonyl)benzyl)-5H-thiazolo[3,2-a]pyrimidin-5-one |
| 25.1 | 7-(3-cyano-2-fluorobenzyl)-2-methyl-5-oxo-N-(2,2,2-trifluoroethyl)-5H-thiazolo[3,2-a]pyrimidine-3-carboxamide |
| 25.2 | N-(cyanomethyl)-7-(2-fluoro-3-(trifluoromethyl)benzyl)-2-methyl-5-oxo-5H-thiazolo[3,2-a]pyrimidine-3-carboxamide |
| 26.1 | 7-(3-cyanobenzyl)-2-methyl-5-oxo-5H-thiazolo[3,2-a]pyrimidine-3-carbonitrile |
| 26.2 | 7-(2-fluoro-3-(trifluoromethyl)benzyl)-2-methyl-5-oxo-5H-thiazolo[3,2-a]pyrimidine-3-carbonitrile |
| 27.1 | 10-(4-fluorophenoxymethyl)-3-(hydroxymethyl)-7-thia-1,9-diazatricyclo[6.4.0.0^[2,6]]dodeca-2(6),8,10-trien-12-one |
| 27.2 | 10-(4-Fluorophenoxymethyl)-3-(2-hydroxyethyl)-7-thia-1,9-diazatricyclo[6.4.0.0^[2,6]]dodeca-2(6),8,10-trien-12-one |
| 27.3 | 7-[(N-ethyl-4-fluoro-anilino)methyl]-2-methyl-3-methylsulfonyl-thiazolo[3,2-a]pyrimidin-5-one |
| 27.4 | 3-(hydroxymethyl)-10-[[3-(trifluoromethyl)-1H-pyrazol-1-yl]methyl]-7-thia-1,9-diazatricyclo[6.4.0.0^[2,6]]dodeca-2(6),8,10-trien-12-one |
| 27.5 | 10-{[5-cyclopropyl-3-(trifluoromethyl)-1H-pyrazol-1-yl]methyl}-7-thia-1,9-diazatricyclo[6.4.0.0^{2,6}]dodeca-2(6),8,10-trien-12-one |
| 27.6 | 10-{[3-cyclopropyl-5-(trifluoromethyl)-1H-pyrazol-1-yl]methyl}-7-thia-1,9-diazatricyclo[6.4.0.0^{2,6}]dodeca-2(6),8,10-trien-12-one |
| 27.7 | 10-{[5-cyclopropyl-3-(trifluoromethyl)-1H-pyrazol-1-yl]methyl}-3,3-dimethyl-7-thia-1,9-diazatricyclo[6.4.0.0^{2,6}]dodeca-2(6),8,10-trien-12-one |
| 27.8 | 10-{[3-cyclopropyl-5-(trifluoromethyl)-1H-pyrazol-1-yl]methyl}-3,3-dimethyl-7-thia-1,9-diazatricyclo[6.4.0.0^{2,6}]dodeca-2(6),8,10-trien-12-one |
| 27.9 | 10-{[3,5-bis(trifluoromethyl)-1H-pyrazol-1-yl]methyl}-3,3-dimethyl-7-thia-1,9-diazatricyclo[6.4.0.0^{2,6}]dodeca-2(6),8,10-trien-12-one |
| 27.10 | 3-((3-acetyl-2-methyl-5-oxo-5H-thiazolo[3,2-a]pyrimidin-7-yl)methyl)-2-fluorobenzonitrile |
| 27.11 | 7-(2-fluoro-3-(trifluoromethyl)benzyl)-3-(1-hydroxyethyl)-2-methyl-5H-thiazolo[3,2-a]pyrimidin-5-one (enantiomer 1) |
| 27.12 | 7-(2-fluoro-3-(trifluoromethyl)benzyl)-3-(1-hydroxyethyl)-2-methyl-5H-thiazolo[3,2-a]pyrimidin-5-one (enantiomer 2) |
| 27.13 | 3-((3-acetyl-2-methyl-5-oxo-5H-thiazolo[3,2-a]pyrimidin-7-yl)methyl)benzonitrile |
| 27.14 | 7-(2-fluoro-3-(trifluoromethyl)benzyl)-3-(hydroxymethyl)-2-methyl-5H-thiazolo[3,2-a]pyrimidin-5-one |
| 27.15 | 7-(2-fluoro-3-(trifluoromethyl)benzyl)-2-methyl-3-((methylamino)methyl)-5H-thiazolo[3,2-a]pyrimidin-5-one |

In certain embodiments, the compound of Formula I or II is a compound selected from the group consisting of the compounds in Table 2, and pharmaceutically acceptable salts thereof:

TABLE 2

| Ex. | Chemical Name |
|---|---|
| 1 | 7-[(3-cyclopropyl-2-fluoro-phenyl)methyl]-N,2-dimethyl-5-oxo-thiazolo[3,2-a]pyrimidine-3-carboxamide |
| 2 | N-ethyl-2-methyl-5-oxo-7-[(2,3,6-trifluorophenyl)methyl]thiazolo[3,2-a]pyrimidine-3-carboxamide |
| 3 | 2-fluoro-3-[(2-methyl-3-oxazol-2-yl-5-oxo-thiazolo[3,2-a]pyrimidin-7-yl)methyl]benzonitrile |
| 4 | 7-[(5-cyano-3-cyclopropyl-2-fluoro-phenyl)methyl]-N-ethyl-2-methyl-5-oxo-thiazolo[3,2-a]pyrimidine-3-carboxamide |
| 5 | N-ethyl-7-[(2-fluoro-3-methoxy-phenyl)methyl]-2-methyl-5-oxo-thiazolo[3,2-a]pyrimidine-3-carboxamide |
| 6 | 7-[(3-cyclopropyl-2-fluoro-phenyl)methyl]-6-fluoro-N,2-dimethyl-5-oxo-thiazolo[3,2-a]pyrimidine-3-carboxamide |
| 7 | 2-[7-[(3-chloro-2-fluoro-phenyl)methyl]-2-methyl-5-oxo-thiazolo[3,2-a]pyrimidin-3-yl]-N-methyl-acetamide |
| 8 | 7-[(3-chloro-2-fluoro-phenyl)methyl]-N-ethyl-6-fluoro-2-methyl-5-oxo-thiazolo[3,2-a]pyrimidine-3-carboxamide |
| 9 | 7-[(4,5-difluoro-2-methoxy-phenyl)methyl]-N,2-dimethyl-5-oxo-thiazolo[3,2-a]pyrimidine-3-carboxamide |
| 10 | 2-fluoro-3-[[2-methyl-3-(2-methylcyclopropyl)-5-oxo-thiazolo[3,2-a]pyrimidin-7-yl]methyl]benzonitrile |

TABLE 2-continued

| Ex. | Chemical Name |
|---|---|
| 11 | 2-[7-[(3-cyclopropyl-2-fluoro-phenyl)methyl]-2-methyl-5-oxo-thiazolo[3,2-a]pyrimidin-3-yl]-N-methyl-acetamide |
| 13 | N-ethyl-6-fluoro-7-[[2-fluoro-3-(trifluoromethyl)phenyl]methyl]-2-methyl-5-oxo-thiazolo[3,2-a]pyrimidine-3-carboxamide |
| 14 | 7-[[2-chloro-5-(trifluoromethyl)phenyl]methyl]-N,2-dimethyl-5-oxo-thiazolo[3,2-a]pyrimidine-3-carboxamide |
| 15 | 7-[(3-cyano-2-fluoro-phenyl)methyl]-6-fluoro-2-methyl-5-oxo-N-(2,2,2-trifluoroethyl)thiazolo[3,2-a]pyrimidine-3-carboxamide |
| 16 | 7-[(2-chloro-4,5-difluoro-phenyl)methyl]-N,2-dimethyl-5-oxo-thiazolo[3,2-a]pyrimidine-3-carboxamide |
| 17 | 7-[[4,5-difluoro-2-(2-fluoroethyl)phenyl]methyl]-N-ethyl-2-methyl-5-oxo-thiazolo[3,2-a]pyrimidine-3-carboxamide |
| 18 | 2-[7-[[5-cyclopropyl-3-(trifluoromethyl)pyrazol-1-yl]methyl]-2-methyl-5-oxo-thiazolo[3,2-a]pyrimidin-3-yl]-N-methyl-acetamide |
| 19 | 2-[7-[[2-fluoro-3-(trifluoromethyl)phenyl]methyl]-2-methyl-5-oxo-thiazolo[3,2-a]pyrimidin-3-yl]-N-methyl-acetamide |
| 20 | 7-[(5-chloro-3-methyl-pyrazol-1-yl)methyl]-N-ethyl-2-methyl-5-oxo-thiazolo[3,2-a]pyrimidine-3-carboxamide |
| 21 | 7-[(3-chloro-5-methyl-pyrazol-1-yl)methyl]-N-ethyl-2-methyl-5-oxo-thiazolo[3,2-a]pyrimidine-3-carboxamide |
| 22 | 7-[(3-chloro-5-cyclopropyl-pyrazol-1-yl)methyl]-N-ethyl-2-methyl-5-oxo-thiazolo[3,2-a]pyrimidine-3-carboxamide |
| 23 | 7-[(5-chloro-3-cyclopropyl-pyrazol-1-yl)methyl]-N-ethyl-2-methyl-5-oxo-thiazolo[3,2-a]pyrimidine-3-carboxamide |
| 24 | 3-[2-(hydroxymethyl)cyclopropyl]-2-methyl-7-[[4-(trifluoromethyl)thiazol-2-yl]methyl]thiazolo[3,2-a]pyrimidin-5-one |
| 25 | 2-[7-[(N-ethyl-4-fluoro-anilino)methyl]-2-methyl-5-oxo-thiazolo[3,2-a]pyrimidin-3-yl]-N-methyl-acetamide |
| 26 | N-ethyl-2-methyl-7-[[5-methyl-3-(trifluoromethyl)pyrazol-1-yl]methyl]-5-oxo-thiazolo[3,2-a]pyrimidine-3-carboxamide |
| 27 | N-ethyl-2-methyl-7-[[3-methyl-5-(trifluoromethyl)pyrazol-1-yl]methyl]-5-oxo-thiazolo[3,2-a]pyrimidine-3-carboxamide |
| 28 | 7-[[5-chloro-3-(trifluoromethyl)pyrazol-1-yl]methyl]-N-ethyl-2-methyl-5-oxo-thiazolo[3,2-a]pyrimidine-3-carboxamide |
| 29 | 7-[[3-chloro-5-(trifluoromethyl)pyrazol-1-yl]methyl]-N-ethyl-2-methyl-5-oxo-thiazolo[3,2-a]pyrimidine-3-carboxamide |
| 30 | 7-[[3-(difluoromethyl)-2-fluoro-phenyl]methyl]-6-fluoro-N,2-dimethyl-5-oxo-thiazolo[3,2-a]pyrimidine-3-carboxamide |
| 31 | 7-[[3-(difluoromethyl)-2-fluoro-phenyl]methyl]-N-ethyl-6-fluoro-2-methyl-5-oxo-thiazolo[3,2-a]pyrimidine-3-carboxamide |
| 32 | 7-(4-bicyclo[4.2.0]octa-1,3,5-trienylmethyl)-N,2-dimethyl-5-oxo-thiazolo[3,2-a]pyrimidine-3-carboxamide |
| 33 | N-ethyl-7-[[2-fluoro-3-(1-hydroxycyclopropyl)phenyl]methyl]-2-methyl-5-oxo-thiazolo[3,2-a]pyrimidine-3-carboxamide |
| 35 | N-ethyl-7-[[2-fluoro-3-(1-fluorocyclopropyl)phenyl]methyl]-2-methyl-5-oxo-thiazolo[3,2-a]pyrimidine-3-carboxamide |
| 36 | N-ethyl-7-[[2-fluoro-3-[1-(fluoromethyl)vinyl]phenyl]methyl]-2-methyl-5-oxo-thiazolo[3,2-a]pyrimidine-3-carboxamide |
| 37 | 7-[(2-ethynyl-4,5-difluoro-phenyl)methyl]-N,2-dimethyl-5-oxo-thiazolo[3,2-a]pyrimidine-3-carboxamide |
| 38 | 2-fluoro-3-[[2-methyl-5-oxo-3-[2-(trifluoromethyl)cyclopropyl]thiazolo[3,2-a]pyrimidin-7-yl]methyl]benzonitrile |
| 39 | 3-[[3-(2,2-difluorocyclopropyl)-2-methyl-5-oxo-thiazolo[3,2-a]pyrimidin-7-yl]methyl]-2-fluoro-benzonitrile |
| 40 | N-ethyl-7-[[2-fluoro-3-(trifluoromethyl)phenyl]methyl]-5-oxo-2-(trifluoromethyl)thiazolo[3,2-a]pyrimidine-3-carboxamide |
| 41 | 7-[(3-cyano-2-fluoro-phenyl)methyl]-N-ethyl-5-oxo-2-(trifluoromethyl)thiazolo[3,2-a]pyrimidine-3-carboxamide |
| 42 | 7-[[3-(difluoromethyl)-2-fluoro-phenyl]methyl]-N-ethyl-5-oxo-2-(trifluoromethyl)thiazolo[3,2-a]pyrimidine-3-carboxamide |
| 43 | 7-[[5-chloro-3-(trifluoromethyl)pyrazol-1-yl]methyl]-N-ethyl-5-oxo-2-(trifluoromethyl)thiazolo[3,2-a]pyrimidine-3-carboxamide |
| 44 | 7-[[3-chloro-5-(trifluoromethyl)pyrazol-1-yl]methyl]-N-ethyl-5-oxo-2-(trifluoromethyl)thiazolo[3,2-a]pyrimidine-3-carboxamide |
| 45 | N-ethyl-7-[[5-methyl-3-(trifluoromethyl)pyrazol-1-yl]methyl]-5-oxo-2-(trifluoromethyl)thiazolo[3,2-a]pyrimidine-3-carboxamide |
| 46 | N-ethyl-7-[[3-methyl-5-(trifluoromethyl)pyrazol-1-yl]methyl]-5-oxo-2-(trifluoromethyl)thiazolo[3,2-a]pyrimidine-3-carboxamide |
| 47 | 7-[[2-fluoro-3-(trifluoromethyl)phenyl]methyl]-3-(1H-imidazol-2-yl)-2-methyl-thiazolo[3,2-a]pyrimidin-5-one |
| 49 | 7-[(3-cyano-2-fluoro-5-methyl-phenyl)methyl]-N-ethyl-2-methyl-5-oxo-thiazolo[3,2-a]pyrimidine-3-carboxamide |
| 50 | 7-[(3-chloro-2-fluoro-phenyl)methyl]-N-ethyl-5-oxo-2-(trifluoromethyl)thiazolo[3,2-a]pyrimidine-3-carboxamide |
| 51 | 7-[[2-fluoro-3-(trifluoromethyl)phenyl]methyl]-2-methyl-5-oxo-N-(2,2,2-trifluoroethyl)thiazolo[3,2-a]pyrimidine-3-carboxamide |
| 52 | 2-methyl-7-[[5-methyl-3-(trifluoromethyl)pyrazol-1-yl]methyl]-5-oxo-N-(2,2,2-trifluoroethyl)thiazolo[3,2-a]pyrimidine-3-carboxamide |

TABLE 2-continued

| Ex. | Chemical Name |
|---|---|
| 53 | 7-[[5-cyclopropyl-3-(trifluoromethyl)pyrazol-1-yl]methyl]-N-methyl-5-oxo-2-(trifluoromethyl)thiazolo[3,2-a]pyrimidine-3-carboxamide |
| 54 | 7-[[3-cyclopropyl-5-(trifluoromethyl)pyrazol-1-yl]methyl]-N-methyl-5-oxo-2-(trifluoromethyl)thiazolo[3,2-a]pyrimidine-3-carboxamide |
| 55 | 7-[[5-chloro-3-(trifluoromethyl)pyrazol-1-yl]methyl]-N-methyl-5-oxo-2-(trifluoromethyl)thiazolo[3,2-a]pyrimidine-3-carboxamide |
| 56 | 7-[[3-chloro-5-(trifluoromethyl)pyrazol-1-yl]methyl]-N-methyl-5-oxo-2-(trifluoromethyl)thiazolo[3,2-a]pyrimidine-3-carboxamide |
| 57 | 7-[[5-cyclopropyl-3-(trifluoromethyl)pyrazol-1-yl]methyl]-2-methyl-5-oxo-N-(2,2,2-trifluoroethyl)thiazolo[3,2-a]pyrimidine-3-carboxamide |
| 58 | 7-[[3-cyclopropyl-5-(trifluoromethyl)pyrazol-1-yl]methyl]-2-methyl-5-oxo-N-(2,2,2-trifluoroethyl)thiazolo[3,2-a]pyrimidine-3-carboxamide |
| 60 | 2-chloro-N-ethyl-7-[[2-fluoro-3-(trifluoromethyl)phenyl]methyl]-5-oxo-thiazolo[3,2-a]pyrimidine-3-carboxamide |
| 61 | N-methyl-7-[[5-methyl-3-(trifluoromethyl)pyrazol-1-yl]methyl]-5-oxo-2-(trifluoromethyl)thiazolo[3,2-a]pyrimidine-3-carboxamide |
| 62 | N-methyl-7-[[3-methyl-5-(trifluoromethyl)pyrazol-1-yl]methyl]-5-oxo-2-(trifluoromethyl)thiazolo[3,2-a]pyrimidine-3-carboxamide |
| 63 | 7-[[2-fluoro-3-(trifluoromethyl)phenyl]methyl]-N-methyl-5-oxo-2-(trifluoromethyl)thiazolo[3,2-a]pyrimidine-3-carboxamide |
| 64 | 7-[(3-chloro-2-fluoro-phenyl)methyl]-N-methyl-5-oxo-2-(trifluoromethyl)thiazolo[3,2-a]pyrimidine-3-carboxamide |
| 65 | 7-[[5-chloro-3-(trifluoromethyl)pyrazol-1-yl]methyl]-2-methyl-5-oxo-N-(2,2,2-trifluoroethyl)thiazolo[3,2-a]pyrimidine-3-carboxamide |
| 66 | 7-[[3-chloro-5-(trifluoromethyl)pyrazol-1-yl]methyl]-2-methyl-5-oxo-N-(2,2,2-trifluoroethyl)thiazolo[3,2-a]pyrimidine-3-carboxamide |
| 67 | 2-methyl-7-[[3-methyl-5-(trifluoromethyl)pyrazol-1-yl]methyl]-5-oxo-N-(2,2,2-trifluoroethyl)thiazolo[3,2-a]pyrimidine-3-carboxamide |
| 69 | 2-chloro-7-[(3-cyano-2-fluoro-phenyl)methyl]-N-ethyl-5-oxo-thiazolo[3,2-a]pyrimidine-3-carboxamide |
| 70 | 7-[(3-cyano-2-fluoro-phenyl)methyl]-N-methyl-5-oxo-2-(trifluoromethyl)thiazolo[3,2-a]pyrimidine-3-carboxamide |
| 71 | N-ethyl-2-[7-[[2-fluoro-3-(trifluoromethyl)phenyl]methyl]-2-methyl-5-oxo-thiazolo[3,2-a]pyrimidin-3-yl]acetamide |
| 72 | N,2-dimethyl-5-oxo-7-[[4-(trifluoromethyl)pyrazol-1-yl]methyl]thiazolo[3,2-a]pyrimidine-3-carboxamide |
| 74 | 3-[[2-chloro-5-oxo-3-[2-(trifluoromethyl)cyclopropyl]thiazolo[3,2-a]pyrimidin-7-yl]methyl]-2-fluoro-benzonitrile |
| 75 | 2-[7-[[2-fluoro-3-(trifluoromethyl)phenyl]methyl]-5-oxo-2-(trifluoromethyl)thiazolo[3,2-a]pyrimidin-3-yl]-N-methyl-acetamide |
| 76 | 7-[[5-cyclopropyl-3-(trifluoromethyl)pyrazol-1-yl]methyl]-N-ethyl-2-methyl-5-oxo-thiazolo[3,2-a]pyrimidine-3-carboxamide |
| 78 | 2-[7-[[5-cyclopropyl-3-(trifluoromethyl)pyrazol-1-yl]methyl]-5-oxo-2-(trifluoromethyl)thiazolo[3,2-a]pyrimidin-3-yl]-N-methyl-acetamide |
| 79 | 2-[7-[[3-cyclopropyl-5-(trifluoromethyl)pyrazol-1-yl]methyl]-5-oxo-2-(trifluoromethyl)thiazolo[3,2-a]pyrimidin-3-yl]-N-methyl-acetamide |
| 80 | 7-[[2-fluoro-3-(trifluoromethyl)phenyl]methyl]-2-methyl-3-(methylsulfonylmethyl)thiazolo[3,2-a]pyrimidin-5-one |
| 81 | 7-[[2-fluoro-3-(trifluoromethyl)phenyl]methyl]-3-(1H-imidazol-2-ylmethyl)-2-methyl-thiazolo[3,2-a]pyrimidin-5-one |
| 82 | N-ethyl-7-[(N-ethyl-4-fluoro-anilino)methyl]-2-methyl-5-oxo-thiazolo[3,2-a]pyrimidine-3-carboxamide |
| 83 | N-ethyl-7-[(N-ethyl-4-fluoro-anilino)methyl]-5-oxo-2-(trifluoromethyl)thiazolo[3,2-a]pyrimidine-3-carboxamide |
| 84 | 2-fluoro-3-[[3-(2-methylcyclopropyl)-5-oxo-2-(trifluoromethyl)thiazolo[3,2-a]pyrimidin-7-yl]methyl]benzonitrile |
| 85 | 3-[[2-chloro-3-(2-methylcyclopropyl)-5-oxo-thiazolo[3,2-a]pyrimidin-7-yl]methyl]-2-fluoro-benzonitrile |
| 87 | N-ethyl-7-[[2-fluoro-3-(trifluoromethyl)phenyl]methyl]-2-isopropyl-5-oxo-thiazolo[3,2-a]pyrimidine-3-carboxamide |
| 88 | 2-fluoro-3-[[5-oxo-2-(trifluoromethyl)-3-[2-(trifluoromethyl)cyclopropyl]thiazolo[3,2-a]pyrimidin-7-yl]methyl]benzonitrile |
| 89 | 6-[[5-chloro-3-(trifluoromethyl)pyrazol-1-yl]methyl]-2,3-dihydro-1H-cyclopenta[3,4]thiazolo[1,4-a]pyrimidin-8-one |
| 90 | 6-[[3-chloro-5-(trifluoromethyl)pyrazol-1-yl]methyl]-2,3-dihydro-1H-cyclopenta[3,4]thiazolo[1,4-a]pyrimidin-8-one |
| 91 | N-ethyl-7-[[2-fluoro-3-(trifluoromethyl)phenyl]methyl]-2-methoxy-5-oxo-thiazolo[3,2-a]pyrimidine-3-carboxamide |
| 92 | 6-[[2-fluoro-3-(trifluoromethyl)phenyl]methyl]-1-(hydroxymethyl)-2,3-dihydro-1H-cyclopenta[3,4]thiazolo[1,4-a]pyrimidin-8-one |
| 93 | 2-ethyl-7-[[2-fluoro-3-(trifluoromethyl)phenyl]methyl]-N-methyl-5-oxo-thiazolo[3,2-a]pyrimidine-3-carboxamide |
| 94 | 2-[7-[[2-fluoro-3-(trifluoromethyl)phenyl]methyl]-5-oxo-2-(trifluoromethyl)thiazolo[3,2-a]pyrimidin-3-yl]cyclopropanecarbonitrile |
| 95 | 6-[[5-cyclopropyl-3-(trifluoromethyl)pyrazol-1-yl]methyl]-1-(hydroxymethyl)-2,3-dihydro-1H-cyclopenta[3,4]thiazolo[1,4-a]pyrimidin-8-one |
| 96 | 7-[[5-chloro-3-(trifluoromethyl)pyrazol-1-yl]methyl]-N,2-dimethyl-5-oxo-thiazolo[3,2-a]pyrimidine-3-carboxamide |

TABLE 2-continued

| Ex. | Chemical Name |
|---|---|
| 97 | 7-[[3-chloro-5-(trifluoromethyl)pyrazol-1-yl]methyl]-N,2-dimethyl-5-oxo-thiazolo[3,2-a]pyrimidine-3-carboxamide |
| 98 | 2-[7-[[5-chloro-3-(trifluoromethyl)pyrazol-1-yl]methyl]-2-methyl-5-oxo-thiazolo[3,2-a]pyrimidin-3-yl]-N-methyl-acetamide |
| 99 | 2-[7-[[3-chloro-5-(trifluoromethyl)pyrazol-1-yl]methyl]-2-methyl-5-oxo-thiazolo[3,2-a]pyrimidin-3-yl]-N-methyl-acetamide |
| 100 | 7-[[2-fluoro-3-(trifluoromethyl)phenyl]methyl]-3-(2-hydroxycyclopropyl)-2-methyl-thiazolo[3,2-a]pyrimidin-5-one |
| 102 | 7-[[5-chloro-3-(trifluoromethyl)pyrazol-1-yl]methyl]-3-[2-(hydroxymethyl)cyclopropyl]-2-methyl-thiazolo[3,2-a]pyrimidin-5-one |
| 103 | 7-[[3-chloro-5-(trifluoromethyl)pyrazol-1-yl]methyl]-3-[2-(hydroxymethyl)cyclopropyl]-2-methyl-thiazolo[3,2-a]pyrimidin-5-one |
| 104 | 2-[7-[[5-chloro-3-(trifluoromethyl)pyrazol-1-yl]methyl]-2-methyl-5-oxo-thiazolo[3,2-a]pyrimidin-3-yl]cyclopropanecarbonitrile |
| 105 | 2-cyano-N-ethyl-7-[[2-fluoro-3-(trifluoromethyl)phenyl]methyl]-5-oxo-thiazolo[3,2-a]pyrimidine-3-carboxamide |
| 106 | 7-[[2-fluoro-3-(trifluoromethyl)phenyl]methyl]-N-isopropyl-2-methyl-5-oxo-thiazolo[3,2-a]pyrimidine-3-carboxamide |
| 108 | 7-[[5-chloro-3-(trifluoromethyl)pyrazol-1-yl]methyl]-3-(1-hydroxy-1-methyl-ethyl)-2-methyl-thiazolo[3,2-a]pyrimidin-5-one |
| 109 | 7-[[3-chloro-5-(trifluoromethyl)pyrazol-1-yl]methyl]-3-(1-hydroxy-1-methyl-ethyl)-2-methyl-thiazolo[3,2-a]pyrimidin-5-one |
| 110 | 7-[[5-chloro-3-(trifluoromethyl)pyrazol-1-yl]methyl]-3-(1-hydroxyethyl)-2-methyl-thiazolo[3,2-a]pyrimidin-5-one |
| 111 | 7-[[3-chloro-5-(trifluoromethyl)pyrazol-1-yl]methyl]-3-(1-hydroxyethyl)-2-methyl-thiazolo[3,2-a]pyrimidin-5-one |
| 112 | 7-[[2-fluoro-3-(trifluoromethyl)phenyl]methyl]-2-methyl-5-oxo-N-sec-butyl-thiazolo[3,2-a]pyrimidine-3-carboxamide |
| 113 | 3-[[3-(azetidin-1-yl)-2-methyl-5-oxo-thiazolo[3,2-a]pyrimidin-7-yl]methyl]-2-fluoro-benzonitrile |
| 114 | 7-[[5-chloro-3-(trifluoromethyl)pyrazol-1-yl]methyl]-2-methyl-5-oxo-thiazolo[3,2-a]pyrimidine-3-carbonitrile |
| 115 | 7-[[3-chloro-5-(trifluoromethyl)pyrazol-1-yl]methyl]-2-methyl-5-oxo-thiazolo[3,2-a]pyrimidine-3-carbonitrile |
| 116 | 7-[[5-chloro-3-(trifluoromethyl)pyrazol-1-yl]methyl]-3-cyclopropyl-2-methyl-thiazolo[3,2-a]pyrimidin-5-one |
| 117 | 7-[[3-chloro-5-(trifluoromethyl)pyrazol-1-yl]methyl]-3-cyclopropyl-2-methyl-thiazolo[3,2-a]pyrimidin-5-one |
| 118 | 7-[[5-chloro-3-(trifluoromethyl)pyrazol-1-yl]methyl]-2-methyl-3-(2-methylcyclopropyl)thiazolo[3,2-a]pyrimidin-5-one |
| 119 | 3-acetyl-7-[[5-chloro-3-(trifluoromethyl)pyrazol-1-yl]methyl]-2-methyl-thiazolo[3,2-a]pyrimidin-5-one |
| 120 | 3-acetyl-7-[[3-chloro-5-(trifluoromethyl)pyrazol-1-yl]methyl]-2-methyl-thiazolo[3,2-a]pyrimidin-5-one |
| 121 | 2-chloro-7-[[2-fluoro-3-(trifluoromethyl)phenyl]methyl]-3-(2-methylcyclopropyl)thiazolo[3,2-a]pyrimidin-5-one |
| 122 | 7-[[3-chloro-5-(trifluoromethyl)pyrazol-1-yl]methyl]-2-methyl-3-pyrimidin-5-yl-thiazolo[3,2-a]pyrimidin-5-one |
| 123 | 7-[[3-cyclopropyl-5-(trifluoromethyl)pyrazol-1-yl]methyl]-N-ethyl-2-methyl-5-oxo-thiazolo[3,2-a]pyrimidine-3-carboxamide |
| 124 | 7-[[[(5-chloro-2-pyridyl)-methyl-amino]methyl]-N-ethyl-2-methyl-5-oxo-thiazolo[3,2-a]pyrimidine-3-carboxamide |
| 125 | 2-[7-[[5-chloro-3-(trifluoromethyl)pyrazol-1-yl]methyl]-2-methyl-5-oxo-thiazolo[3,2-a]pyrimidin-3-yl]cyclopropanecarbonitrile (cis enantiomer 1) |
| 126 | 2-[7-[[5-chloro-3-(trifluoromethyl)pyrazol-1-yl]methyl]-2-methyl-5-oxo-thiazolo[3,2-a]pyrimidin-3-yl]cyclopropanecarbonitrile (cis enantiomer 2) |
| 127 | 7-[[3-chloro-5-(trifluoromethyl)pyrazol-1-yl]methyl]-N-ethyl-2-methoxy-5-oxo-thiazolo[3,2-a]pyrimidine-3-carboxamide |
| 128 | 7-[[5-chloro-3-(trifluoromethyl)pyrazol-1-yl]methyl]-N-ethyl-2-methoxy-5-oxo-thiazolo[3,2-a]pyrimidine-3-carboxamide |
| 129 | 7-[[5-cyclopropyl-3-(trifluoromethyl)pyrazol-1-yl]methyl]-N-ethyl-2-methoxy-5-oxo-thiazolo[3,2-a]pyrimidine-3-carboxamide |
| 130 | 7-[[3-cyclopropyl-5-(trifluoromethyl)pyrazol-1-yl]methyl]-N-ethyl-2-methoxy-5-oxo-thiazolo[3,2-a]pyrimidine-3-carboxamide |
| 131 | 2-[7-[[2-fluoro-3-(trifluoromethyl)phenyl]methyl]-2-methyl-5-oxo-thiazolo[3,2-a]pyrimidin-3-yl]cyclopropanecarbonitrile |
| 132 | 7-[[5-chloro-3-(trifluoromethyl)pyrazol-1-yl]methyl]-2-methyl-3-(1H-pyrazol-5-yl)thiazolo[3,2-a]pyrimidin-5-one |
| 133 | 7-[[3-chloro-5-(trifluoromethyl)pyrazol-1-yl]methyl]-2-methyl-3-(1H-pyrazol-5-yl)thiazolo[3,2-a]pyrimidin-5-one |
| 134 | 7-[[5-chloro-3-(trifluoromethyl)pyrazol-1-yl]methyl]-2-methyl-3-(3-pyridyl)thiazolo[3,2-a]pyrimidin-5-one |
| 135 | 7-[[5-chloro-3-(trifluoromethyl)pyrazol-1-yl]methyl]-3-isopropenyl-2-methyl-thiazolo[3,2-a]pyrimidin-5-one |
| 136 | 7-[[5-chloro-3-(trifluoromethyl)pyrazol-1-yl]methyl]-3-[2-(hydroxymethyl)cyclopropyl]-2-methyl-thiazolo[3,2-a]pyrimidin-5-one (trans enantiomer 1) |
| 137 | 7-[[5-chloro-3-(trifluoromethyl)pyrazol-1-yl]methyl]-3-[2-(hydroxymethyl)cyclopropyl]-2-methyl-thiazolo[3,2-a]pyrimidin-5-one (trans enantiomer 2) |

TABLE 2-continued

| Ex. | Chemical Name |
|---|---|
| 138 | 7-[[5-chloro-3-(trifluoromethyl)pyrazol-1-yl]methyl]-3-(5-fluoro-3-pyridyl)-2-methyl-thiazolo[3,2-a]pyrimidin-5-one |
| 139 | 7-[[3-chloro-5-(trifluoromethyl)pyrazol-1-yl]methyl]-3-(5-fluoro-3-pyridyl)-2-methyl-thiazolo[3,2-a]pyrimidin-5-one |
| 140 | 7-[[5-chloro-3-(trifluoromethyl)pyrazol-1-yl]methyl]-2-methyl-3-propanoyl-thiazolo[3,2-a]pyrimidin-5-one |
| 141 | 7-[[3-chloro-5-(trifluoromethyl)pyrazol-1-yl]methyl]-2-methyl-3-propanoyl-thiazolo[3,2-a]pyrimidin-5-one |
| 142 | 7-[[5-chloro-3-(trifluoromethyl)pyrazol-1-yl]methyl]-2-methyl-3-thiazol-2-yl-thiazolo[3,2-a]pyrimidin-5-one |
| 143 | N-ethyl-7-[[(5-fluoro-2-pyridyl)-methyl-amino]methyl]-2-methyl-5-oxo-thiazolo[3,2-a]pyrimidine-3-carboxamide |
| 144 | 2-[7-[[5-chloro-3-(trifluoromethyl)pyrazol-1-yl]methyl]-5-oxo-2-(trifluoromethyl)thiazolo[3,2-a]pyrimidin-3-yl]cyclopropanecarbonitrile |
| 145 | 2-[7-[[3-chloro-5-(trifluoromethyl)pyrazol-1-yl]methyl]-5-oxo-2-(trifluoromethyl)thiazolo[3,2-a]pyrimidin-3-yl]cyclopropanecarbonitrile |
| 146 | 2-fluoro-3-[[5-oxo-2-(trifluoromethyl)-3-[2-(trifluoromethyl)cyclopropyl]thiazolo[3,2-a]pyrimidin-7-yl]methyl]benzonitrile |
| 147 | N-ethyl-7-[[ethyl-(5-fluoro-2-pyridyl)amino]methyl]-2-methyl-5-oxo-thiazolo[3,2-a]pyrimidine-3-carboxamide |
| 148 | N-ethyl-7-[[ethyl(2-pyridyl)amino]methyl]-2-methyl-5-oxo-thiazolo[3,2-a]pyrimidine-3-carboxamide |
| 149 | 3-(5-chloro-3-pyridyl)-7-[[5-chloro-3-(trifluoromethyl)pyrazol-1-yl]methyl]-2-methyl-thiazolo[3,2-a]pyrimidin-5-one |
| 150 | 3-(5-chloro-3-pyridyl)-7-[[3-chloro-5-(trifluoromethyl)pyrazol-1-yl]methyl]-2-methyl-thiazolo[3,2-a]pyrimidin-5-one |
| 151 | 7-[[5-chloro-3-(trifluoromethyl)pyrazol-1-yl]methyl]-2-methyl-3-thiazol-4-yl-thiazolo[3,2-a]pyrimidin-5-one |
| 152 | 7-[[(5-chloro-2-pyridyl)-ethyl-amino]methyl]-N-ethyl-2-methyl-5-oxo-thiazolo[3,2-a]pyrimidine-3-carboxamide |
| 153 | 7-[(5-cyclopropyltriazol-1-yl)methyl]-3-[2-(hydroxymethyl)cyclopropyl]-2-methyl-thiazolo[3,2-a]pyrimidin-5-one |
| 154 | 7-[[5-chloro-3-(trifluoromethyl)pyrazol-1-yl]methyl]-2-methyl-3-[2-methylcyclopropyl]thiazolo[3,2-a]pyrimidin-5-one (trans enantiomer 1) |
| 155 | 7-[[5-chloro-3-(trifluoromethyl)pyrazol-1-yl]methyl]-2-methyl-3-[2-methylcyclopropyl]thiazolo[3,2-a]pyrimidin-5-one (trans enantiomer 2) |
| 156 | 2-ethoxy-N-ethyl-7-[[2-fluoro-3-(trifluoromethyl)phenyl]methyl]-5-oxo-thiazolo[3,2-a]pyrimidine-3-carboxamide |
| 157 | 7-[[5-chloro-3-(trifluoromethyl)pyrazol-1-yl]methyl]-3-(2-fluoro-3-pyridyl)-2-methyl-thiazolo[3,2-a]pyrimidin-5-one |
| 158 | 7-[[5-chloro-3-(trifluoromethyl)pyrazol-1-yl]methyl]-2-methyl-3-oxazol-2-yl-thiazolo[3,2-a]pyrimidin-5-one |
| 159 | 7-[[3-chloro-5-(trifluoromethyl)pyrazol-1-yl]methyl]-2-methyl-3-oxazol-2-yl-thiazolo[3,2-a]pyrimidin-5-one |
| 160 | 7-[[5-chloro-3-(trifluoromethyl)pyrazol-1-yl]methyl]-2-methyl-3-(trifluoromethyl)thiazolo[3,2-a]pyrimidin-5-one |
| 161 | 7-[[3-chloro-5-(trifluoromethyl)pyrazol-1-yl]methyl]-2-methyl-3-(trifluoromethyl)thiazolo[3,2-a]pyrimidin-5-one |
| 162 | 2-[7-[[2-fluoro-3-(trifluoromethyl)phenyl]methyl]-5-oxo-2-(trifluoromethyl)thiazolo[3,2-a]pyrimidin-3-yl]cyclopropanecarbonitrile |
| 163 | 7-[[(5-chloro-2-pyridyl)-methyl-amino]methyl]-3-[2-(hydroxymethyl)cyclopropyl]-2-methyl-thiazolo[3,2-a]pyrimidin-5-one |
| 164 | 7-[(3,5-dichloropyrazol-1-yl)methyl]-N-ethyl-2-methyl-5-oxo-thiazolo[3,2-a]pyrimidine-3-carboxamide |
| 165 | N-ethyl-7-[[2-fluoro-3-(trifluoromethyl)phenyl]methyl]-5-oxo-2-(2,2,2-trifluoroethoxy)thiazolo[3,2-a]pyrimidine-3-carboxamide |
| 166 | 3-acetyl-7-[[5-chloro-3-(trifluoromethyl)pyrazol-1-yl]methyl]-2-(trifluoromethyl)thiazolo[3,2-a]pyrimidin-5-one |
| 167 | 3-acetyl-7-[[3-chloro-5-(trifluoromethyl)pyrazol-1-yl]methyl]-2-(trifluoromethyl)thiazolo[3,2-a]pyrimidin-5-one |
| 168 | 3-[(4-chloropyrazol-1-yl)methyl]-7-[[5-chloro-3-(trifluoromethyl)pyrazol-1-yl]methyl]-2-methyl-thiazolo[3,2-a]pyrimidin-5-one |
| 169 | 7-[[5-chloro-3-(trifluoromethyl)pyrazol-1-yl]methyl]-3-isopropenyl-2-(trifluoromethyl)thiazolo[3,2-a]pyrimidin-5-one |
| 170 | 7-[[5-chloro-3-(trifluoromethyl)pyrazol-1-yl]methyl]-3-(1H-imidazol-2-yl)-2-methyl-thiazolo[3,2-a]pyrimidin-5-one |
| 171 | 7-[[5-chloro-3-(trifluoromethyl)pyrazol-1-yl]methyl]-3-pyrimidin-5-yl-2-(trifluoromethyl)thiazolo[3,2-a]pyrimidin-5-one |
| 172 | 7-[[3-chloro-5-(trifluoromethyl)pyrazol-1-yl]methyl]-3-pyrimidin-5-yl-2-(trifluoromethyl)thiazolo[3,2-a]pyrimidin-5-one |
| 173 | 7-[[3-chloro-5-(trifluoromethyl)pyrazol-1-yl]methyl]-3-(3-pyridyl)-2-(trifluoromethyl)thiazolo[3,2-a]pyrimidin-5-one |
| 174 | 7-[[5-chloro-3-(trifluoromethyl)pyrazol-1-yl]methyl]-N-ethyl-5-oxo-2-(2,2,2-trifluoroethoxy)thiazolo[3,2-a]pyrimidine-3-carboxamide |
| 175 | 7-[[5-chloro-3-(trifluoromethyl)pyrazol-1-yl]methyl]-2-ethoxy-N-ethyl-5-oxo-thiazolo[3,2-a]pyrimidine-3-carboxamide |
| 176 | 7-[[3-chloro-5-(trifluoromethyl)pyrazol-1-yl]methyl]-2-ethoxy-N-ethyl-5-oxo-thiazolo[3,2-a]pyrimidine-3-carboxamide |

TABLE 2-continued

| Ex. | Chemical Name |
|---|---|
| 177 | 7-[[5-chloro-3-(trifluoromethyl)pyrazol-1-yl]methyl]-2-methyl-3-(2-methylpropanoyl)thiazolo[3,2-a]pyrimidin-5-one |
| 178 | 7-[[3-chloro-5-(trifluoromethyl)pyrazol-1-yl]methyl]-2-methyl-3-(2-methylpropanoyl)thiazolo[3,2-a]pyrimidin-5-one |
| 179 | 7-[[2-fluoro-3-(trifluoromethyl)phenyl]methyl]-2-methyl-N-[((1R)-1-methylpropyl]-5-oxo-thiazolo[3,2-a]pyrimidine-3-carboxamide |
| 180 | 7-[[2-fluoro-3-(trifluoromethyl)phenyl]methyl]-2-methyl-N-[(1S)-1-methylpropyl]-5-oxo-thiazolo[3,2-a]pyrimidine-3-carboxamide |
| 191 | 7-[[(4-chloro-2-pyridyl)-ethyl-amino]methyl]-N-ethyl-2-methyl-5-oxo-thiazolo[3,2-a]pyrimidine-3-carboxamide |
| 182 | 7-[[(5-fluoro-2-pyridyl)-methyl-amino]methyl]-3-[2-(hydroxymethyl)cyclopropyl]-2-methyl-thiazolo[3,2-a]pyrimidin-5-one |
| 183 | 7-[[5-chloro-3-(trifluoromethyl)pyrazol-1-yl]methyl]-3-(methoxymethyl)-2-methyl-thiazolo[3,2-a]pyrimidin-5-one |
| 184 | 7-[[5-chloro-3-(trifluoromethyl)pyrazol-1-yl]methyl]-3-cyclopropyl-2-(trifluoromethyl)thiazolo[3,2-a]pyrimidin-5-one |
| 185 | 7-[[5-chloro-3-(trifluoromethyl)pyrazol-1-yl]methyl]-2-methyl-3-(methylsulfonylmethyl)thiazolo[3,2-a]pyrimidin-5-one |
| 186 | 7-[[5-chloro-3-(trifluoromethyl)pyrazol-1-yl]methyl]-2-methyl-3-(pyrazol-1-ylmethyl)thiazolo[3,2-a]pyrimidin-5-one |
| 187 | 2-[7-[[2-chloro-5-(trifluoromethyl)phenyl]methyl]-2-methyl-5-oxo-thiazolo[3,2-a]pyrimidin-3-yl]cyclopropanecarbonitrile |
| 188 | 7-[[5-chloro-3-(trifluoromethyl)pyrazol-1-yl]methyl]-3-cyclobutyl-2-methyl-thiazolo[3,2-a]pyrimidin-5-one |
| 189 | 7-[[3-chloro-5-(trifluoromethyl)pyrazol-1-yl]methyl]-3-cyclobutyl-2-methyl-thiazolo[3,2-a]pyrimidin-5-one |
| 190 | 2-[7-[[(5-chloro-2-pyridyl)-methyl-amino]methyl]-2-methyl-5-oxo-thiazolo[3,2-a]pyrimidin-3-yl]cyclopropanecarbonitrile |
| 191 | 7-[[ethyl-(5-fluoro-2-pyridyl)amino]methyl]-3-[2-(hydroxymethyl)cyclopropyl]-2-methyl-thiazolo[3,2-a]pyrimidin-5-one |
| 192 | 3-chloro-7-[[5-chloro-3-(trifluoromethyl)pyrazol-1-yl]methyl]-2-methyl-thiazolo[3,2-a]pyrimidin-5-one |
| 193 | 3-chloro-7-[[3-chloro-5-(trifluoromethyl)pyrazol-1-yl]methyl]-2-methyl-thiazolo[3,2-a]pyrimidin-5-one |
| 194 | 2-[7-[(4,5-difluoro-2-methoxy-phenyl)methyl]-2-methyl-5-oxo-thiazolo[3,2-a]pyrimidin-3-yl]cyclopropanecarbonitrile |
| 195 | 2-[7-[[ethyl-(5-fluoro-2-pyridyl)amino]methyl]-2-methyl-5-oxo-thiazolo[3,2-a]pyrimidin-3-yl]cyclopropanecarbonitrile |
| 196 | 7-[[(5-chloro-2-pyridyl)-ethyl-amino]methyl]-3-[2-(hydroxymethyl)cyclopropyl]-2-methyl-thiazolo[3,2-a]pyrimidin-5-one |
| 197 | 5-[7-[[5-chloro-3-(trifluoromethyl)pyrazol-1-yl]methyl]-2-methyl-5-oxo-thiazolo[3,2-a]pyrimidin-3-yl]pyridine-3-carbonitrile |
| 198 | 7-[[5-chloro-3-(trifluoromethyl)pyrazol-1-yl]methyl]-2-methyl-3-(2,2,2-trifluoroacetyl)thiazolo[3,2-a]pyrimidin-5-one |
| 199 | 7-[[5-chloro-3-(trifluoromethyl)pyrazol-1-yl]methyl]-3-(2-methylcyclopropyl)-2-(trifluoromethyl)thiazolo[3,2-a]pyrimidin-5-one |
| 200 | 7-[[3-chloro-5-(trifluoromethyl)pyrazol-1-yl]methyl]-3-(2-methylcyclopropyl)-2-(trifluoromethyl)thiazolo[3,2-a]pyrimidin-5-one |
| 201 | 7-[[5-chloro-3-(trifluoromethyl)pyrazol-1-yl]methyl]-2-methyl-3-pyrimidin-5-yl-thiazolo[3,2-a]pyrimidin-5-one |
| 202 | 7-[[5-chloro-3-(trifluoromethyl)pyrazol-1-yl]methyl]-2-ethyl-3-(3-pyridyl)thiazolo[3,2-a]pyrimidin-5-one |
| 203 | 7-[[5-chloro-3-(trifluoromethyl)pyrazol-1-yl]methyl]-2-methyl-3-(2,2,2-trifluoro-1-hydroxy-ethyl)thiazolo[3,2-a]pyrimidin-5-one |
| 204 | 7-[[(5-bromo-2-pyridyl)-ethyl-amino]methyl]-N-ethyl-2-methyl-5-oxo-thiazolo[3,2-a]pyrimidine-3-carboxamide |
| 205 | N-ethyl-7-[[ethyl-(5-fluoro-2-pyridyl)amino]methyl]-5-oxo-2-(trifluoromethyl)thiazolo[3,2-a]pyrimidine-3-carboxamide |
| 206 | 3-(azetidin-1-yl)-7-[[5-chloro-3-(trifluoromethyl)pyrazol-1-yl]methyl]-2-(trifluoromethyl)thiazolo[3,2-a]pyrimidin-5-one |
| 207 | 2-[7-[[5-chloro-3-(trifluoromethyl)pyrazol-1-yl]methyl]-5-oxo-2-(trifluoromethyl)thiazolo[3,2-a]pyrimidin-3-yl]cyclopropanecarbonitrile (cis enantiomer 1) |
| 208 | 2-[7-[[5-chloro-3-(trifluoromethyl)pyrazol-1-yl]methyl]-5-oxo-2-(trifluoromethyl)thiazolo[3,2-a]pyrimidin-3-yl]cyclopropanecarbonitrile (cis enantiomer 2) |
| 209 | 2-[7-[[5-methoxy-3-(trifluoromethyl)pyrazol-1-yl]methyl]-2-methyl-5-oxo-thiazolo[3,2-a]pyrimidin-3-yl]cyclopropanecarbonitrile |
| 210 | 2-[7-[[3-methoxy-5-(trifluoromethyl)pyrazol-1-yl]methyl]-2-methyl-5-oxo-thiazolo[3,2-a]pyrimidin-3-yl]cyclopropanecarbonitrile |
| 211 | 3-acetyl-7-[[5-chloro-3-(trifluoromethyl)pyrazol-1-yl]methyl]-2-ethyl-thiazolo[3,2-a]pyrimidin-5-one |
| 212 | 3-acetyl-7-[[3-chloro-5-(trifluoromethyl)pyrazol-1-yl]methyl]-2-ethyl-thiazolo[3,2-a]pyrimidin-5-one |
| 213 | 2-[7-[[5-chloro-3-(trifluoromethyl)pyrazol-1-yl]methyl]-2-ethyl-5-oxo-thiazolo[3,2-a]pyrimidin-3-yl]cyclopropanecarbonitrile |
| 214 | 2-[7-[[3-chloro-5-(trifluoromethyl)pyrazol-1-yl]methyl]-2-ethyl-5-oxo-thiazolo[3,2-a]pyrimidin-3-yl]cyclopropanecarbonitrile |

TABLE 2-continued

| Ex. | Chemical Name |
|---|---|
| 215 | 3-bromo-7-[[5-chloro-3-(trifluoromethyl)pyrazol-1-yl]methyl]-2-methyl-thiazolo[3,2-a]pyrimidin-5-one |
| 216 | 3-bromo-7-[[3-chloro-5-(trifluoromethyl)pyrazol-1-yl]methyl]-2-methyl-thiazolo[3,2-a]pyrimidin-5-one |
| 217 | 3-chloro-7-[[5-chloro-3-(trifluoromethyl)pyrazol-1-yl]methyl]-2-methoxy-thiazolo[3,2-a]pyrimidin-5-one |
| 218 | 3-chloro-7-[[3-chloro-5-(trifluoromethyl)pyrazol-1-yl]methyl]-2-methoxy-thiazolo[3,2-a]pyrimidin-5-one |
| 219 | 7-[[5-chloro-3-(trifluoromethyl)pyrazol-1-yl]methyl]-3-methylsulfanyl-2-(trifluoromethyl)thiazolo[3,2-a]pyrimidin-5-one |
| 220 | 2-[7-[(N-ethyl-4-fluoro-anilino)methyl]-5-oxo-thiazolo[3,2-a]pyrimidin-3-yl]-1-(hydroxymethyl)cyclopropane carbonitrile |
| 221 | 7-[[5-chloro-3-(trifluoromethyl)pyrazol-1-yl]methyl]-3-(cyclopropylmethyl)-2-methyl-thiazolo[3,2-a]pyrimidin-5-one |
| 222 | 7-[[5-chloro-3-(trifluoromethyl)pyrazol-1-yl]methyl]-3-(2-hydroxy-1-methyl-ethyl)-2-methyl-thiazolo[3,2-a]pyrimidin-5-one |
| 223 | 7-[[3-chloro-5-(trifluoromethyl)pyrazol-1-yl]methyl]-3-(2-hydroxy-1-methyl-ethyl)-2-methyl-thiazolo[3,2-a]pyrimidin-5-one |
| 224 | 7-[[5-chloro-3-(trifluoromethyl)pyrazol-1-yl]methyl]-3-(cyclopropanecarbonyl)-2-methyl-thiazolo[3,2-a]pyrimidin-5-one |
| 225 | 3-bromo-7-[[5-chloro-3-(trifluoromethyl)pyrazol-1-yl]methyl]thiazolo[3,2-a]pyrimidin-5-one |
| 226 | 3-bromo-7-[[3-chloro-5-(trifluoromethyl)pyrazol-1-yl]methyl]thiazolo[3,2-a]pyrimidin-5-one |
| 227 | 7-[(3-amino-5-chloro-pyrazol-1-yl)methyl]-3-bromo-2-methyl-thiazolo[3,2-a]pyrimidin-5-one |
| 228 | 7-[(5-amino-3-chloro-pyrazol-1-yl)methyl]-3-bromo-2-methyl-thiazolo[3,2-a]pyrimidin-5-one |
| 229 | 2-[7-[[5-chloro-3-(trifluoromethyl)pyrazol-1-yl]methyl]-2-methyl-5-oxo-thiazolo[3,2-a]pyrimidin-3-yl]acetonitrile |
| 230 | N-ethyl-7-[[(5-fluoro-2-pyridyl)-methyl-amino]methyl]-5-oxo-2-(trifluoromethyl)thiazolo[3,2-a]pyrimidine-3-carboxamide |
| 231 | 7-[[5-chloro-3-(trifluoromethyl)pyrazol-1-yl]methyl]-3-(3,3-difluoroazetidin-1-yl)-2-(trifluoromethyl)thiazolo[3,2-a]pyrimidin-5-one |
| 233 | 7-[[5-chloro-3-(trifluoromethyl)pyrazol-1-yl]methyl]-2-methoxy-3-(3-pyridyl)thiazolo[3,2-a]pyrimidin-5-one |
| 234 | 2-[7-[[5-bromo-3-(trifluoromethyl)pyrazol-1-yl]methyl]-2-methyl-5-oxo-thiazolo[3,2-a]pyrimidin-3-yl]cyclopropanecarbonitrile |
| 235 | 3-chloro-7-[[5-chloro-3-(trifluoromethyl)pyrazol-1-yl]methyl]thiazolo[3,2-a]pyrimidin-5-one |
| 236 | 3-chloro-7-[[3-chloro-5-(trifluoromethyl)pyrazol-1-yl]methyl]thiazolo[3,2-a]pyrimidin-5-one |
| 237 | 2-acetyl-7-[[5-chloro-3-(trifluoromethyl)pyrazol-1-yl]methyl]-N-ethyl-5-oxo-thiazolo[3,2-a]pyrimidine-3-carboxamide |
| 238 | 2-acetyl-7-[[3-chloro-5-(trifluoromethyl)pyrazol-1-yl]methyl]-N-ethyl-5-oxo-thiazolo[3,2-a]pyrimidine-3-carboxamide |
| 239 | 7-[[5-chloro-3-(trifluoromethyl)pyrazol-1-yl]methyl]-3-(trifluoromethyl)thiazolo[3,2-a]pyrimidin-5-one |
| 240 | 7-[[2-fluoro-3-(trifluoromethyl)phenyl]methyl]-2-methyl-3-(1H-1,2,4-triazol-5-yl)thiazolo[3,2-a]pyrimidin-5-one |
| 241 | 2-[7-[[5-chloro-3-(trifluoromethyl)pyrazol-1-yl]methyl]-5-oxo-thiazolo[3,2-a]pyrimidin-3-yl]cyclopropanecarbonitrile |
| 242 | 3-acetyl-7-[[5-chloro-3-(trifluoromethyl)pyrazol-1-yl]methyl]thiazolo[3,2-a]pyrimidin-5-one |
| 243 | 7-[[5-chloro-3-(trifluoromethyl)pyrazol-1-yl]methyl]-3-(2,2,2-trifluoroethoxy)-2-(trifluoromethyl)thiazolo[3,2-a]pyrimidin-5-one |
| 244 | 3-acetyl-7-[[5-chloro-3-(trifluoromethyl)pyrazol-1-yl]methyl]-2-methoxy-thiazolo[3,2-a]pyrimidin-5-one |
| 245 | 3-acetyl-7-[[3-chloro-5-(trifluoromethyl)pyrazol-1-yl]methyl]-2-methoxy-thiazolo[3,2-a]pyrimidin-5-one |
| 246 | 3-bromo-7-[(5-chloro-3-nitro-pyrazol-1-yl)methyl]-2-methyl-thiazolo[3,2-a]pyrimidin-5-one |
| 247 | 7-[[5-chloro-3-(trifluoromethyl)pyrazol-1-yl]methyl]-3-(1H-pyrazol-5-yl)-2-(trifluoromethyl)thiazolo[3,2-a]pyrimidin-5-one |
| 248 | 7-[[5-chloro-3-(trifluoromethyl)pyrazol-1-yl]methyl]-3-thiazol-4-yl-2-(trifluoromethyl)thiazolo[3,2-a]pyrimidin-5-one |
| 249 | 7-[[5-chloro-3-(trifluoromethyl)pyrazol-1-yl]methyl]-3-(5-fluoro-3-pyridyl)-2-(trifluoromethyl)thiazolo[3,2-a]pyrimidin-5-one |
| 250 | 7-[[5-chloro-3-(trifluoromethyl)pyrazol-1-yl]methyl]-3-propanoyl-2-(trifluoromethyl)thiazolo[3,2-a]pyrimidin-5-one |
| 251 | 2-[7-[(3,5-dichloropyrazol-1-yl)methyl]-2-methyl-5-oxo-thiazolo[3,2-a]pyrimidin-3-yl]cyclopropanecarbonitrile |
| 251A | 2-[7-[[5-chloro-3-(trifluoromethyl)pyrazol-1-yl]methyl]-2-methyl-5-oxo-thiazolo[3,2-a]pyrimidin-3-yl]propanenitrile |
| 252 | 2-[7-[[3-chloro-5-(trifluoromethyl)pyrazol-1-yl]methyl]-2-methyl-5-oxo-thiazolo[3,2-a]pyrimidin-3-yl]propanenitrile |
| 253 | 2-fluoro-3-[[3-[2-methylcyclopropyl]-5-oxo-2-(trifluoromethyl)thiazolo[3,2-a]pyrimidin-7-yl]methyl]benzonitrile |

TABLE 2-continued

| Ex. | Chemical Name |
|---|---|
| 254 | 7-[[5-chloro-3-(trifluoromethyl)pyrazol-1-yl]methyl]-3-(3-fluoroazetidin-1-yl)-2-(trifluoromethyl)thiazolo[3,2-a]pyrimidin-5-one |
| 255 | 3-(5-chloro-3-pyridyl)-7-[[5-chloro-3-(trifluoromethyl)pyrazol-1-yl]methyl]-2-(trifluoromethyl)thiazolo[3,2-a]pyrimidin-5-one |
| 256 | 7-[(3,5-dichloropyrazol-1-yl)methyl]-N-ethyl-5-oxo-2-(trifluoromethyl)thiazolo[3,2-a]pyrimidine-3-carboxamide |
| 257 | 3-[[3-acetyl-5-oxo-2-(trifluoromethyl)thiazolo[3,2-a]pyrimidin-7-yl]methyl]-2-fluoro-benzonitrile |
| 258 | 7-[[5-chloro-3-(trifluoromethyl)pyrazol-1-yl]methyl]-2-(difluoromethyl)-N-ethyl-5-oxo-thiazolo[3,2-a]pyrimidine-3-carboxamide |
| 259 | 7-[[3-chloro-5-(trifluoromethyl)pyrazol-1-yl]methyl]-2-(difluoromethyl)-N-ethyl-5-oxo-thiazolo[3,2-a]pyrimidine-3-carboxamide |
| 260 | (Z)-3-[7-[(N-ethyl-4-fluoro-anilino)methyl]-2-methyl-5-oxo-thiazolo[3,2-a]pyrimidin-3-yl]prop-2-enenitrile |
| 261 | (E)-3-[7-[(N-ethyl-4-fluoro-anilino)methyl]-2-methyl-5-oxo-thiazolo[3,2-a]pyrimidin-3-yl]prop-2-enamide |
| 262 | (E)-3-[7-[[5-chloro-3-(trifluoromethyl)pyrazol-1-yl]methyl]-2-methyl-5-oxo-thiazolo[3,2-a]pyrimidin-3-yl]prop-2-enenitrile |
| 263 | (Z)-3-[7-[[5-chloro-3-(trifluoromethyl)pyrazol-1-yl]methyl]-2-methyl-5-oxo-thiazolo[3,2-a]pyrimidin-3-yl]prop-2-enenitrile |
| 264 | (E)-3-[7-[[5-chloro-3-(trifluoromethyl)pyrazol-1-yl]methyl]-2-methyl-5-oxo-thiazolo[3,2-a]pyrimidin-3-yl]prop-2-enamide |
| 265 | N-ethyl-7-[[5-isobutyl-3-(trifluoromethyl)pyrazol-1-yl]methyl]-2-methyl-5-oxo-thiazolo[3,2-a]pyrimidine-3-carboxamide |
| 266 | 2-[2-chloro-7-[[5-chloro-3-(trifluoromethyl)pyrazol-1-yl]methyl]-5-oxo-thiazolo[3,2-a]pyrimidin-3-yl]cyclopropanecarbonitrile (cis enantiomer 1) |
| 267 | 2-[2-chloro-7-[[5-chloro-3-(trifluoromethyl)pyrazol-1-yl]methyl]-5-oxo-thiazolo[3,2-a]pyrimidin-3-yl]cyclopropanecarbonitrile (cis enantiomer 2) |
| 268 | 2-[2-chloro-7-[[3-chloro-5-(trifluoromethyl)pyrazol-1-yl]methyl]-5-oxo-thiazolo[3,2-a]pyrimidin-3-yl]cyclopropanecarbonitrile |
| 269 | 7-[[5-chloro-3-(trifluoromethyl)pyrazol-1-yl]methyl]-3-[2-(hydroxymethyl)cyclopropyl]-2-(trifluoromethyl)thiazolo[3,2-a]pyrimidin-5-one (trans enantiomer 1) |
| 270 | 7-[[5-chloro-3-(trifluoromethyl)pyrazol-1-yl]methyl]-3-[2-(hydroxymethyl)cyclopropyl]-2-(trifluoromethyl)thiazolo[3,2-a]pyrimidin-5-one (trans enantiomer 2) |
| 271 | 2-[7-[(4-chloro-1-methyl-pyrazol-3-yl)methyl]-2-methyl-5-oxo-thiazolo[3,2-a]pyrimidin-3-yl]cyclopropanecarbonitrile |
| 272 | 2-[2-methyl-5-oxo-7-[[3-(trifluoromethyl)pyrazol-1-yl]methyl]thiazolo[3,2-a]pyrimidin-3-yl]cyclopropanecarbonitrile (cis enantiomer 1) |
| 273 | 2-[2-methyl-5-oxo-7-[[3-(trifluoromethyl)pyrazol-1-yl]methyl]thiazolo[3,2-a]pyrimidin-3-yl]cyclopropanecarbonitrile (cis enantiomer 2) |
| 274 | 2-[7-[[5-bromo-3-(trifluoromethyl)pyrazol-1-yl]methyl]-2-methyl-5-oxo-thiazolo[3,2-a]pyrimidin-3-yl]cyclopropanecarbonitrile (cis enantiomer 1) |
| 275 | 2-[7-[[5-bromo-3-(trifluoromethyl)pyrazol-1-yl]methyl]-2-methyl-5-oxo-thiazolo[3,2-a]pyrimidin-3-yl]cyclopropanecarbonitrile (cis enantiomer 2) |
| 276 | 2-[7-[[5-chloro-3-(trifluoromethyl)pyrazol-1-yl]methyl]-6-fluoro-5-oxo-2-(trifluoromethyl)thiazolo[3,2-a]pyrimidin-3-yl]cyclopropanecarbonitrile (cis enantiomer 1) |
| 277 | 2-[7-[[5-chloro-3-(trifluoromethyl)pyrazol-1-yl]methyl]-6-fluoro-5-oxo-2-(trifluoromethyl)thiazolo[3,2-a]pyrimidin-3-yl]cyclopropanecarbonitrile (cis enantiomer 2) |
| 278 | 2-[2-methyl-7-[[1-methyl-4-(trifluoromethyl)imidazol-2-yl]methyl]-5-oxo-thiazolo[3,2-a]pyrimidin-3-yl]cyclopropanecarbonitrile |
| 279 | (E)-3-[7-[(N-ethyl-4-fluoro-anilino)methyl]-2-methyl-5-oxo-thiazolo[3,2-a]pyrimidin-3-yl]prop-2-enenitrile |
| 280 | 7-[(4-fluorophenoxy)methyl]-3-[[2-hydroxyethyl(methyl)amino]methyl]-2-methyl-thiazolo[3,2-a]pyrimidin-5-one |
| 281 | 7-[(4-fluorophenoxy)methyl]-3-[(2-hydroxyethylamino)methyl]-2-methyl-thiazolo[3,2-a]pyrimidin-5-one |
| 282 | 2-[7-[(4-fluorophenoxy)methyl]-2-methyl-5-oxo-thiazolo[3,2-a]pyrimidin-3-yl]-N,N-dimethyl-acetamide |
| 283 | 7-[(2-cyano-4,5-difluoro-phenyl)methyl]-N,2-dimethyl-5-oxo-thiazolo[3,2-a]pyrimidine-3-carboxamide |
| 284 | 7-[(2-cyclopropyl-4,5-difluoro-phenyl)methyl]-N-ethyl-2-methyl-5-oxo-thiazolo[3,2-a]pyrimidine-3-carboxamide |
| 285 | 3-[2-(azetidin-1-yl)-2-oxo-ethyl]-7-[[2-fluoro-3-(trifluoromethyl)phenyl]methyl]-2-methyl-thiazolo[3,2-a]pyrimidin-5-one |
| 286 | 7-[(4-fluorophenoxy)methyl]-2-methyl-3-(4H-1,2,4-triazol-3-ylmethyl)thiazolo[3,2-a]pyrimidin-5-one |
| 287 | 2-[7-[[2-fluoro-3-(trifluoromethyl)phenyl]methyl]-2-methyl-5-oxo-thiazolo[3,2-a]pyrimidin-3-yl]-N-methyl-propanamide |
| 288 | 3-[7-[[2-fluoro-3-(trifluoromethyl)phenyl]methyl]-2-methyl-5-oxo-thiazolo[3,2-a]pyrimidin-3-yl]-N-methyl-propanamide |
| 289 | 7-[[5-chloro-2-(trifluoromethyl)phenyl]methyl]-N,2-dimethyl-5-oxo-thiazolo[3,2-a]pyrimidine-3-carboxamide |
| 290 | 7-[(5-ethyl-1,3-benzoxazol-6-yl)methyl]-N,2-dimethyl-5-oxo-thiazolo[3,2-a]pyrimidine-3-carboxamide |
| 291 | 7-[(3-chloropyrazol-1-yl)methyl]-N-ethyl-2-methyl-5-oxo-thiazolo[3,2-a]pyrimidine-3-carboxamide |

TABLE 2-continued

| Ex. | Chemical Name |
|---|---|
| 292 | 7-[(5-chloropyrazol-1-yl)methyl]-N-ethyl-2-methyl-5-oxo-thiazolo[3,2-a]pyrimidine-3-carboxamide |
| 293 | 2-[7-[(3-cyano-2-fluoro-phenyl)methyl]-2-methyl-5-oxo-thiazolo[3,2-a]pyrimidin-3-yl]-N-methyl-acetamide |
| 294 | N-ethyl-7-[[2-fluoro-3-(1-hydroxypropyl)phenyl]methyl]-2-methyl-5-oxo-thiazolo[3,2-a]pyrimidine-3-carboxamide |
| 295 | 7-[(4,5-difluoro-2-oxazol-2-yl-phenyl)methyl]-N,2-dimethyl-5-oxo-thiazolo[3,2-a]pyrimidine-3-carboxamide |
| 296 | 2-fluoro-3-[(2-methyl-5-oxo-3-propanoyl-thiazolo[3,2-a]pyrimidin-7-yl)methyl]benzonitrile |
| 297 | 7-[[4,5-difluoro-2-(trifluoromethyl)phenyl]methyl]-N,2-dimethyl-5-oxo-thiazolo[3,2-a]pyrimidine-3-carboxamide |
| 299 | 7-[[2-chloro-5-(trifluoromethyl)phenyl]methyl]-N-ethyl-5-oxo-2-(trifluoromethyl)thiazolo[3,2-a]pyrimidine-3-carboxamide |
| 300 | 7-[[2-chloro-5-(trifluoromethyl)phenyl]methyl]-N-ethyl-2-methyl-5-oxo-thiazolo[3,2-a]pyrimidine-3-carboxamide |
| 301 | 7-[[2-chloro-5-(trifluoromethyl)phenyl]methyl]-2-methyl-5-oxo-N-(2,2,2-trifluoroethyl)thiazolo[3,2-a]pyrimidine-3-carboxamide |
| 303 | 3-[(2-chloro-3-cyclopropyl-5-oxo-thiazolo[3,2-a]pyrimidin-7-yl)methyl]-2-fluoro-benzonitrile |
| 304 | 7-[[2-fluoro-3-(trifluoromethyl)phenyl]methyl]-2-methyl-3-(pyrazol-1-ylmethyl)thiazolo[3,2-a]pyrimidin-5-one |
| 305 | N,2-dimethyl-7-[[3-methyl-4-(trifluoromethyl)pyrazol-1-yl]methyl]-5-oxo-thiazolo[3,2-a]pyrimidine-3-carboxamide |
| 306 | N,2-dimethyl-7-[[5-methyl-4-(trifluoromethyl)pyrazol-1-yl]methyl]-5-oxo-thiazolo[3,2-a]pyrimidine-3-carboxamide |
| 307 | 2-fluoro-3-[(8-oxo-2,3-dihydro-1H-cyclopenta[3,4]thiazolo[1,4-a]pyrimidin-6-yl)methyl]benzonitrile |
| 308 | 7-[[2-fluoro-3-(trifluoromethyl)phenyl]methyl]-3-[hydroxy(thiazol-2-yl)methyl]-2-methyl-thiazolo[3,2-a]pyrimidin-5-one |
| 309 | 2-fluoro-3-[(3-methyl-8-oxo-2,3-dihydro-1H-cyclopenta[3,4]thiazolo[1,4-a]pyrimidin-6-yl)methyl]benzonitrile |
| 310 | 2-[7-[(4-fluorophenoxy)methyl]-5-oxo-2-(trifluoromethyl)thiazolo[3,2-a]pyrimidin-3-yl]-N-methyl-acetamide |
| 312 | 2-fluoro-3-[[1-(hydroxymethyl)-8-oxo-2,3-dihydro-1H-cyclopenta[3,4]thiazolo[1,4-a]pyrimidin-6-yl]methyl]benzonitrile |
| 313 | 7-[[2-fluoro-3-(trifluoromethyl)phenyl]methyl]-N-(2-hydroxy-1-methyl-ethyl)-2-methyl-5-oxo-thiazolo[3,2-a]pyrimidine-3-carboxamide |
| 314 | 3-[[3-(2,3-dimethylcyclopropyl)-2-methyl-5-oxo-thiazolo[3,2-a]pyrimidin-7-yl]methyl]-2-fluoro-benzonitrile |
| 315 | 6-[[3-cyclopropyl-5-(trifluoromethyl)pyrazol-1-yl]methyl]-1-(hydroxymethyl)-2,3-dihydro-1H-cyclopenta[3,4]thiazolo[1,4-a]pyrimidin-8-one |
| 316 | 7-[[2-fluoro-3-(trifluoromethyl)phenyl]methyl]-2-methyl-3-(2-oxa-6-azaspiro[3.3]heptan-6-yl)thiazolo[3,2-a]pyrimidin-5-one |
| 317 | N-ethyl-6-fluoro-7-[[2-fluoro-3-(trifluoromethyl)phenyl]methyl]-5-oxo-2-(trifluoromethyl)thiazolo[3,2-a]pyrimidine-3-carboxamide |
| 318 | 7-[(4-fluorophenoxy)methyl]-5-oxo-N-(2,2,2-trifluoroethyl)-2-(trifluoromethyl)thiazolo[3,2-a]pyrimidine-3-carboxamide |
| 319 | N-cyclopentyl-7-[[2-fluoro-3-(trifluoromethyl)phenyl]methyl]-2-methyl-5-oxo-thiazolo[3,2-a]pyrimidine-3-carboxamide |
| 320 | 7-[(4,5-dichloropyrazol-1-yl)methyl]-N-ethyl-2-methyl-5-oxo-thiazolo[3,2-a]pyrimidine-3-carboxamide |
| 321 | 7-[(3,4-dichloropyrazol-1-yl)methyl]-N-ethyl-2-methyl-5-oxo-thiazolo[3,2-a]pyrimidine-3-carboxamide |
| 322 | N-ethyl-2-methyl-7-[[methyl(thiazol-2-yl)amino]methyl]-5-oxo-thiazolo[3,2-a]pyrimidine-3-carboxamide |
| 323 | 7-[(4-chloropyrazol-1-yl)methyl]-N-ethyl-2-methyl-5-oxo-thiazolo[3,2-a]pyrimidine-3-carboxamide |
| 324 | N-ethyl-2-methyl-7-[[methyl-(1-methylpyrazol-4-yl)amino]methyl]-5-oxo-thiazolo[3,2-a]pyrimidine-3-carboxamide |
| 325 | 7-[(4-fluorophenoxy)methyl]-2-(trifluoromethyl)-3-[2-(trifluoromethyl)cyclopropyl]thiazolo[3,2-a]pyrimidin-5-one |
| 326 | 7-[[[(3-ethoxy-2-pyridyl)-methyl-amino]methyl]-N-ethyl-2-methyl-5-oxo-thiazolo[3,2-a]pyrimidine-3-carboxamide |
| 327 | 7-[[[(3,5-dimethylisoxazol-4-yl)-methyl-amino]methyl]-N-ethyl-2-methyl-5-oxo-thiazolo[3,2-a]pyrimidine-3-carboxamide |
| 328 | 3-cyclopropyl-7-[(4-fluorophenoxy)methyl]-2-(trifluoromethyl)thiazolo[3,2-a]pyrimidin-5-one |
| 329 | 7-[(4-fluorophenoxy)methyl]-3-pyrimidin-5-yl-2-(trifluoromethyl)thiazolo[3,2-a]pyrimidin-5-one |
| 330 | 7-[(4-fluorophenoxy)methyl]-3-[2-(hydroxymethyl)cyclopropyl]-2-(trifluoromethyl)thiazolo[3,2-a]pyrimidin-5-one |
| 331 | 7-[[2-fluoro-3-(trifluoromethyl)phenyl]methyl]-2-methyl-3-(4-methyl-1,2,4-triazol-3-yl)thiazolo[3,2-a]pyrimidin-5-one |
| 332 | 2-fluoro-3-[[5-oxo-2-(trifluoromethyl)-3-[2-(trifluoromethyl)cyclopropyl]thiazolo[3,2-a]pyrimidin-7-yl]methyl]benzonitrile |
| 333 | N-ethyl-7-[[ethyl(4-pyridyl)amino]methyl]-2-methyl-5-oxo-thiazolo[3,2-a]pyrimidine-3-carboxamide |

TABLE 2-continued

| Ex. | Chemical Name |
|---|---|
| 334 | N-ethyl-7-[[ethyl(3-pyridyl)amino]methyl]-2-methyl-5-oxo-thiazolo[3,2-a]pyrimidine-3-carboxamide |
| 335 | 7-[[5-chloro-3-(trifluoromethyl)pyrazol-1-yl]methyl]-3-(2-methoxy-3-pyridyl)-2-methyl-thiazolo[3,2-a]pyrimidin-5-one |
| 336 | 2-[7-[[2-fluoro-3-(trifluoromethyl)phenyl]methyl]-5-oxo-2-(trifluoromethyl)thiazolo[3,2-a]pyrimidin-3-yl]cyclopropanecarbonitrile |
| 337 | 7-[[3-chloro-5-(trifluoromethyl)pyrazol-1-yl]methyl]-3-isopropenyl-2-(trifluoromethyl)thiazolo[3,2-a]pyrimidin-5-one |
| 338 | 3-(5-chloro-3-pyridyl)-7-[[(5-chloro-2-pyridyl)-methyl-amino]methyl]-2-methyl-thiazolo[3,2-a]pyrimidin-5-one |
| 339 | 7-[[5-chloro-3-(trifluoromethyl)pyrazol-1-yl]methyl]-3-(3-pyridyl)-2-(trifluoromethyl)thiazolo[3,2-a]pyrimidin-5-one |
| 340 | 7-[[3-chloro-5-(trifluoromethyl)pyrazol-1-yl]methyl]-N-ethyl-5-oxo-2-(2,2,2-trifluoroethoxy)thiazolo[3,2-a]pyrimidine-3-carboxamide |
| 341 | 7-[[3-chloro-6-(trifluoromethyl)-2-pyridyl]methyl]-2-methyl-3-(2-methylcyclopropyl)thiazolo[3,2-a]pyrimidin-5-one |
| 342 | 7-[(5-chloro-2-pyridyl)oxymethyl]-N-ethyl-2-methyl-5-oxo-thiazolo[3,2-a]pyrimidine-3-carboxamide |
| 343 | 7-[[3-chloro-5-(trifluoromethyl)pyrazol-1-yl]methyl]-2-ethyl-3-(3-pyridyl)thiazolo[3,2-a]pyrimidin-5-one |
| 344 | 7-[[5-chloro-3-(trifluoromethyl)pyrazol-1-yl]methyl]-3-pyrrolidin-1-yl-2-(trifluoromethyl)thiazolo[3,2-a]pyrimidin-5-one |
| 345 | N-ethyl-7-[[(5-methoxy-2-pyridyl)-methyl-amino]methyl]-2-methyl-5-oxo-thiazolo[3,2-a]pyrimidine-3-carboxamide |
| 346 | 3-(2-chloro-3-pyridyl)-7-[[5-chloro-3-(trifluoromethyl)pyrazol-1-yl]methyl]-2-methyl-thiazolo[3,2-a]pyrimidin-5-one |
| 347 | 3-(2-chloro-3-pyridyl)-7-[[3-chloro-5-(trifluoromethyl)pyrazol-1-yl]methyl]-2-methyl-thiazolo[3,2-a]pyrimidin-5-one |
| 348 | 7-[[5-chloro-3-(trifluoromethyl)pyrazol-1-yl]methyl]-3-(3-pyridyl)thiazolo[3,2-a]pyrimidin-5-one |
| 349 | 7-[[3-chloro-5-(trifluoromethyl)pyrazol-1-yl]methyl]-3-(3-pyridyl)thiazolo[3,2-a]pyrimidin-5-one |
| 350 | 7-[[5-chloro-3-(trifluoromethyl)pyrazol-1-yl]methyl]-3-(3-methoxyazetidin-1-yl)-2-(trifluoromethyl)thiazolo[3,2-a]pyrimidin-5-one |
| 351 | 7-[[5-chloro-3-(trifluoromethyl)pyrazol-1-yl]methyl]-3-(cyclopropylmethyl)-2-methyl-thiazolo[3,2-a]pyrimidin-5-one |
| 352 | 5-[7-[[2-fluoro-3-(trifluoromethyl)phenyl]methyl]-2-methyl-5-oxo-thiazolo[3,2-a]pyrimidin-3-yl]pyridine-3-carbonitrile |
| 353 | 2-fluoro-3-[[3-[2-methylcyclopropyl]-5-oxo-2-(trifluoromethyl)thiazolo[3,2-a]pyrimidin-7-yl]methyl]benzonitrile |
| 354 | 7-[(3,5-diisopropylpyrazol-1-yl)methyl]-N-ethyl-2-methyl-5-oxo-thiazolo[3,2-a]pyrimidine-3-carboxamide |
| 355 | 2-[7-[(4-chloro-2-methyl-pyrazol-3-yl)methyl]-2-methyl-5-oxo-thiazolo[3,2-a]pyrimidin-3-yl]cyclopropanecarbonitrile |
| 356 | 7-[[5-chloro-3-(trifluoromethyl)pyrazol-1-yl]methyl]-3-(2-methylazetidin-1-yl)-2-(trifluoromethyl)thiazolo[3,2-a]pyrimidin-5-one |
| 357 | 2-[7-[(3,5-dichloropyrazol-1-yl)methyl]-5-oxo-2-(trifluoromethyl)thiazolo[3,2-a]pyrimidin-3-yl]cyclopropanecarbonitrile (cis enantiomer 1) |
| 358 | 2-[7-[(3,5-dichloropyrazol-1-yl)methyl]-5-oxo-2-(trifluoromethyl)thiazolo[3,2-a]pyrimidin-3-yl]cyclopropanecarbonitrile (cis enantiomer 2) |
| 359 | 7-[[5-chloro-3-(trifluoromethyl)pyrazol-1-yl]methyl]-3-[2-(2-hydroxyethyl)cyclopropyl]-2-(trifluoromethyl)thiazolo[3,2-a]pyrimidin-5-one (trans enantiomer 1) |
| 360 | 7-[[5-chloro-3-(trifluoromethyl)pyrazol-1-yl]methyl]-3-[2-(2-hydroxyethyl)cyclopropyl]-2-(trifluoromethyl)thiazolo[3,2-a]pyrimidin-5-one (trans enantiomer 2) |
| 361 | 3-chloro-7-[[5-chloro-3-(trifluoromethyl)pyrazol-1-yl]methyl]-2-(trifluoromethyl)thiazolo[3,2-a]pyrimidin-5-one |
| 362 | 5-chloro-1-[[3-[2-methylcyclopropyl]-5-oxo-2-(trifluoromethyl)thiazolo[3,2-a]pyrimidin-7-yl]methyl]pyrazole-3-carbonitrile (cis enantiomer 1) |
| 363 | 5-chloro-1-[[3-[2-methylcyclopropyl]-5-oxo-2-(trifluoromethyl)thiazolo[3,2-a]pyrimidin-7-yl]methyl]pyrazole-3-carbonitrile (cis enantiomer 2) |
| 364 | 5-chloro-2-[[3-[(2-methylcyclopropyl)-5-oxo-2-(trifluoromethyl)thiazolo[3,2-a]pyrimidin-7-yl]methyl]pyrazole-3-carbonitrile |
| 365 | 7-[[5-ethoxy-3-(trifluoromethyl)pyrazol-1-yl]methyl]-N-ethyl-2-methyl-5-oxo-thiazolo[3,2-a]pyrimidine-3-carboxamide |
| 366 | N-ethyl-7-[[5-isobutyl-3-(trifluoromethyl)pyrazol-1-yl]methyl]-5-oxo-2-(trifluoromethyl)thiazolo[3,2-a]pyrimidine-3-carboxamide |
| 367 | 2-[2-[7-[[5-chloro-3-(trifluoromethyl)pyrazol-1-yl]methyl]-5-oxo-2-(trifluoromethyl)thiazolo[3,2-a]pyrimidin-3-yl]cyclopropyl]acetonitrile (trans enantiomer 1) |
| 368 | 2-[2-[7-[[5-chloro-3-(trifluoromethyl)pyrazol-1-yl]methyl]-5-oxo-2-(trifluoromethyl)thiazolo[3,2-a]pyrimidin-3-yl]cyclopropyl]acetonitrile (trans enantiomer 2) |

In certain embodiments, the compound of Formula III is a compound selected from the group consisting of the compounds in Table 3, and pharmaceutically acceptable salts thereof

TABLE 3

| Ex. | Chemical Name |
|---|---|
| 12 | 3-[2-(hydroxymethyl)cyclopropyl]-2-methyl-7-[3-(trifluoromethyl)phenoxy]thiazolo[3,2-a]pyrimidin-5-one |
| 34 | 6-fluoro-3-[2-(hydroxymethyl)cyclopropyl]-2-methyl-7-[3-(trifluoromethyl)phenoxy]thiazolo[3,2-a]pyrimidin-5-one |
| 48 | N-ethyl-7-[2-fluoro-3-(trifluoromethyl)phenoxy]-2-methyl-5-oxo-thiazolo[3,2-a]pyrimidine-3-carboxamide |
| 59 | 7-[2-fluoro-3-(trifluoromethyl)phenoxy]-N,2-dimethyl-5-oxo-thiazolo[3,2-a]pyrimidine-3-carboxamide |
| 68 | 7-(3-cyano-2-fluoro-phenoxy)-N-ethyl-2-methyl-5-oxo-thiazolo[3,2-a]pyrimidine-3-carboxamide |
| 73 | 3-cyclopropyl-7-[2-fluoro-3-(trifluoromethyl)phenoxy]-2-methyl-thiazolo[3,2-a]pyrimidin-5-one |
| 77 | 2-fluoro-3-[2-methyl-5-oxo-3-[2-(trifluoromethyl)cyclopropyl]thiazolo[3,2-a]pyrimidin-7-yl]oxy-benzonitrile |
| 86 | 7-[2-fluoro-3-(trifluoromethyl)phenoxy]-2-methyl-3-(2-methylcyclopropyl)thiazolo[3,2-a]pyrimidin-5-one |
| 101 | 2-[7-[2-fluoro-3-(trifluoromethyl)phenoxy]-2-methyl-5-oxo-thiazolo[3,2-a]pyrimidin-3-yl]cyclopropanecarbonitrile |
| 107 | 2-fluoro-3-[2-methyl-3-(2-methylcyclopropyl)-5-oxo-thiazolo[3,2-a]pyrimidin-7-yl]oxy-benzonitrile |
| 298 | N,2-dimethyl-5-oxo-7-[3-(trifluoromethyl)phenoxy]thiazolo[3,2-a]pyrimidine-3-carboxamide |
| 302 | N-ethyl-2-methyl-5-oxo-7-[3-(trifluoromethyl)phenoxy]thiazolo[3,2-a]pyrimidine-3-carboxamide |
| 311 | 2-fluoro-3-[(8-oxo-2,3-dihydro-1H-cyclopenta[3,4]thiazolo[1,4-a]pyrimidin-6-yl)oxy]benzonitrile |

Pharmaceutical Description

As used herein, the term "subject" encompasses mammals and non-mammals. Examples of mammals include, but are not limited to, any member of the Mammalian class: humans; non-human primates such as chimpanzees, and other apes and monkey species; farm animals such as cattle, horses, sheep, goats, swine; domestic animals such as rabbits, dogs, and cats; and laboratory animals including rodents, such as rats, mice and guinea pigs, and the like. Examples of non-mammals include, but are not limited to, birds, fish and the like. In one embodiment of the present invention, the mammal is a human.

"Patient" encompasses a human or animal subject.

The term "inhibitor" refers to a molecule such as a compound, a drug, an enzyme activator, or a hormone that blocks or otherwise interferes with a particular biologic activity.

The term "modulator" refers to a molecule, such as a compound of the present invention, that increases or decreases, or otherwise affects the activity of a given enzyme or protein.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying metabolic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

The terms "effective amount" or "therapeutically effective amount" refer to a sufficient amount of the agent to provide the desired biological result. That result can be reduction and/or alleviation of the signs, symptoms, or causes of a disease or medical condition, or any other desired alteration of a biological system. For example, an "effective amount" for therapeutic use is the amount of a compound, or of a composition comprising the compound, that is required to provide a clinically relevant change in a disease state, symptom, or medical condition. An appropriate "effective" amount in any individual case may be determined by one of ordinary skill in the art using routine experimentation. Thus, the expression "effective amount" generally refers to the quantity for which the active substance has a therapeutically desired effect. Effective amounts or doses of the compounds of the embodiments may be ascertained by routine methods, such as modeling, dose escalation, or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose is in the range of about 1 μg to 2 mg of active agent per kilogram of subject's body weight per day, preferably about 0.05 to 100 mg/kg/day, or about 1 to 35 mg/kg/day, or about 0.1 to 10 mg/kg/day. The total dosage may be given in single or divided dosage units (e.g., BID, TID, QID).

Once improvement of the patient's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

A pharmaceutical composition according to the invention comprises at least one compound of Formula (I), or a pharmaceutically acceptable salt thereof. The pharmaceutical compositions may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, anti-caking agents, glidants, surfactants, diluents, anti-oxidants, binders, chelating agents, coating agents, coloring agents, bulking agents, emulsifiers, buffers, pH modifiers, or taste-modifying agents. In preferred embodiments, pharmaceutical compositions according to the embodiments are sterile compositions. Sterile compositions include compositions that are in accord with national and local regulations governing such compositions. Pharmaceutical compositions may be prepared using compounding techniques known or that become available to those skilled in the art.

The pharmaceutical compositions and compounds described herein may be formulated as solutions, emulsions, suspensions, dispersions, or inclusion complexes such as cyclodextrins in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the embodiments may be administered by a suitable route of delivery, such as oral, parenteral, rectal, nasal, topical, or ocular routes, or by inhalation. Preferably, the compositions are formulated for intravenous or oral administration.

A further embodiment of the invention is a method of preparing a pharmaceutical formulation comprising mixing at least one compound of the present invention, and, optionally, one or more pharmaceutically acceptable excipients.

In certain aspects, the invention relates to methods of treating diseases or conditions mediated by activation or deactivation of NMDA receptors, or which are generally mediated by NMDA receptor activity. Such disease or condition is one or more selected from the group consisting of pain, neuropathic pain, inflammatory pain, peripheral neuropathy, stroke, epilepsy, neurodegeneration, schizophrenia, drug addiction, mood disorders, post-traumatic stress disorder, seizures, convulsions, age-associated memory impairment, depression, stroke, traumatic brain injury, ischemia, Alzheimer's disease, Parkinson's disease, Huntington's disease, amyotrophic lateral sclerosis, or Creutzfeldt-Jakob disease. In particular, the disease or condition is schizophrenia.

Still another aspect of this invention is to provide a method for treating, preventing, inhibiting or eliminating a disease or condition in a patient by modulating, activating, or inhibiting NMDA receptor activity in said patient by administering a therapeutically effective amount of at least one compound of this disclosure, wherein said disease or condition is selected from the group consisting of pain, neuropathic pain, inflammatory pain, peripheral neuropathy, stroke, epilepsy, neurodegeneration, schizophrenia, drug addiction, mood disorders, post-traumatic stress disorder, seizures, convulsions, age-associated memory impairment, depression, stroke, traumatic brain injury, ischemia, Alzheimer's disease, Parkinson's disease, Huntington's disease, amyotrophic lateral sclerosis, or Creutzfeldt-Jakob disease.

Still another aspect of this invention is the use of a compound as described herein as a positive allosteric modulator (PAM) of an NMDA receptor. The invention includes a method of modulating and/or amplifying the activity an NMDA receptor by contacting the receptor at an allosteric binding site with at least one compound as described herein or a pharmaceutical composition comprising such a compound. Further, compounds of the invention are useful as subtype selective for NR2A-containing NMDA receptors. The invention is also directed toward a method of modulating an NR2A-containing NMDA receptor by contacting the receptor with at least one compound of the invention or a pharmaceutical composition comprising such a compound.

The pharmaceutical compositions and compounds described herein may be formulated as solutions, emulsions, suspensions, dispersions, or inclusion complexes such as cyclodextrins in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the embodiments may be administered by a suitable route of delivery, such as oral, parenteral, rectal, nasal, topical, or ocular routes, or by inhalation. Preferably, the compositions are formulated for intravenous or oral administration.

For oral administration, the compounds the embodiments may be provided in a solid form, such as a tablet or capsule, or as a solution, emulsion, or suspension. To prepare the oral compositions, the compounds of the embodiments may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The inventive compositions may be formulated for rectal administration as a suppository. For parenteral use, including intravenous, intramuscular, intraperitoneal, intranasal, or subcutaneous routes, the agents of the embodiments may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For nasal, inhaled, or oral administration, the inventive pharmaceutical compositions may be administered using, for example, a spray formulation also containing a suitable carrier.

For topical applications, the compounds of the present embodiments are preferably formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the embodiments may utilize a patch formulation to effect transdermal delivery.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Still another embodiment of the invention is a pharmaceutical formulation comprising at least one compound of Formula I or II, or a pharmaceutically acceptable salt thereof, and a pharmaceutically acceptable excipient, and further comprising one or more adjunctive active agent. Methods of treatment as described herein include regimes in which the compound of the invention and at least one adjunctive active agent are administered simultaneously or sequentially.

The expression "adjunctive active agent" generally refers to agents which targets the same or a different disease, symptom, or medical condition as the primary therapeutic agent. Adjunctive active agents may treat, alleviate, relieve, or ameliorate side effects caused by administration of the primary therapeutic agents.

EXAMPLES

Exemplary, non-limiting, chemical entities and methods useful in preparing compounds of the invention will now be described by reference to the specific examples that follow. Those skilled in the art will appreciate that other synthetic routes may be used to synthesize the compounds according to the invention. Although specific starting materials and reagents are depicted and discussed herein, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Each of the reactions depicted in the reaction schemes is preferably run at a temperature from about 0° C. to the reflux temperature of the solvent used.

In the methods of preparing compounds according to the invention, it may be advantageous to separate reaction products from one another and/or from starting materials. The desired products of each step or series of steps may be separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Diastereomeric mixtures may be separated into their individual diastereomers on the basis of their physical chemical differences by methods well known to those skilled in the art, such as, for example, by chromatography and/or fractional crystallization. Enantiomers may be separated by converting the enantiomeric mixture into a diastereomeric mixture by reaction with an appropriate optically active compound (e.g., chiral auxiliary such as a chiral alcohol or Mosher's acid chloride, or formation of a mixture of diastereomeric salts, for example, with tartaric acid or a chiral amine), separating the diastereomers by, for example, fractional crystallization or chromatography, and converting (e.g., hydrolyzing or de-salting) the individual diastereomers to the corresponding pure enantiomers. Enantiomers may also be separated by use of chiral HPLC column or prepared directly by chiral synthesis. The chiral centers of compounds of the present invention may be designated as "R" or "S" as defined by the IUPAC 1974 Recommendations. Enriched or purified enantiomers can be distinguished by methods used to distinguish other chiral molecules with asymmetric carbon atoms, such as optical rotation and circular dichroism.

General Experimental Conditions

Unless otherwise indicated, $^1$H NMR spectra were recorded at ambient temperature using a Varian Unity Inova (400 MHz) spectrometer with a triple resonance 5 mm probe. Chemical shifts are expressed in ppm relative to tetramethylsilane. The following abbreviations have been used: br=broad signal, s=singlet, d=doublet, dd=double doublet, t=triplet, q=quartet, m=multiplet.

Microwave experiments were carried out using a CEM Discover, Smith Synthesiser or a Biotage Initiator 60™, which uses a single-mode resonator and dynamic field tuning, both of which give reproducibility and control. Temperatures from 40-250° C. can be achieved and pressures of up to 30 bars can be reached.

High Pressure Liquid Chromatography—Mass Spectrometry (LCMS) experiments was used to detect associated mass ions. The spectrometers have an electrospray source operating in positive and negative ion mode. Additional detection was achieved using a Sedex 85 evaporative light scattering detector.

The following examples illustrate the preparation of representative compounds of the invention. Unless otherwise specified, all reagents and solvents were of standard commercial grade and were used without further purification. Those having skill in the art will recognize that the starting materials, reagents, and conditions described in the examples may be varied and additional steps employed to produce compounds encompassed by the present inventions.

Method 1

Example 1.1: N-(cyanomethyl)-7-((4-fluorophenoxy)methyl)-2-methyl-5-oxo-5H-thiazolo[3,2-a]pyrimidine-3-carboxamide

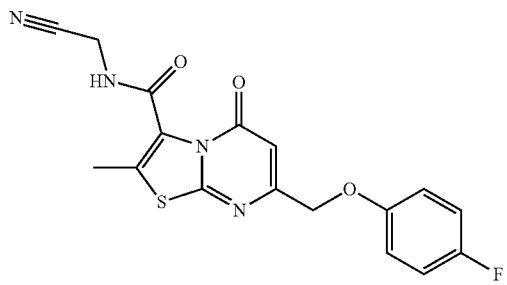 [SMILES: Cc1sc2nc(COc3ccc(F)cc3)cc(=O)n2c1C(=O)NCC#N]

Step 1: Methyl 3-bromo-2-oxobutanoate

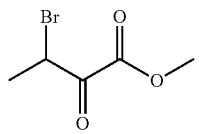

To a solution of methyl 2-oxobutanoate (1.00 g, 8.61 mmol) in chloroform (20 mL) were added hydrogen bromide in acetic acid (40%, 1 mL) and bromine (1.40 g, 8.76 mmol) dropwise with stirring at room temperature. The reaction mixture was stirred for 1 h at 70° C. After cooling down to room temperature, the resulting solution was concentrated in vacuo to afford methyl 3-bromo-2-oxobutanoate as yellow oil (1.60 g, 95%). No LCMS signal.

Step 2: Methyl 2-amino-5-methyl-1,3-thiazole-4-carboxylate

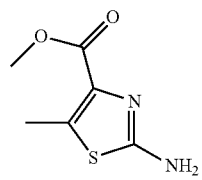

To a solution of methyl 3-bromo-2-oxobutanoate (1.60 g, 8.20 mmol) in 1,4-dioxane (30 mL) was added thiourea (625 mg, 8.21 mmol) with stirring. The resulting solution was refluxed for 3 h in an oil bath. After cooling down to room temperature, the solids were collected by filtration and dried in vacuo to afford methyl 2-amino-5-methyl-1,3-thiazole-4-carboxylate as a gray solid (900 mg, 64%). LCMS (ESI): M+H$^+$=173.

Step 3: Methyl 7-(chloromethyl)-2-methyl-5-oxo-5H-thiazolo[3,2-a]pyrimidine-3-carboxylate

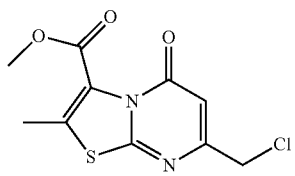 [SMILES: COC(=O)c1c(C)sc2nc(CCl)cc(=O)n12]

To a mixture of methyl 2-amino-5-methyl-1,3-thiazole-4-carboxylate (200 mg, 1.16 mmol) and ethyl 4-chloro-3-oxobutanoate (390 mg, 2.32 mmol) was added polyphosphoric acid (5 mL). The reaction mixture was stirred 1 h at 110° C. The reaction was then quenched with water (20 mL). The pH value of the solution was adjusted to pH 8 with sodium hydroxide (aq., 10 mol/L) and extracted with dichloromethane (2×100 mL), washed with brine, dried over anhydrous sodium sulfate and concentrated in vacuo. The residue was purified by chromatography with ethyl acetate/petroleum ether (1:1) to afford methyl 7-(chloromethyl)-2-methyl-5-oxo-5H-thiazolo[3,2-a]pyrimidine-3-carboxylate as a light yellow solid (120 mg, 38%). LCMS (ESI): M+H$^+$=273.

Step 4: Methyl 7-(4-fluorophenoxymethyl)-2-methyl-5-oxo-5H-[1,3]thiazolo[3,2-a]pyrimidine-3-carboxylate

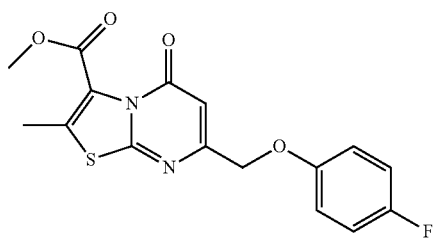 [SMILES: COC(=O)c1c(C)sc2nc(COc3ccc(F)cc3)cc(=O)n12]

To a solution of methyl 7-(chloromethyl)-2-methyl-5-oxo-5H-thiazolo[3,2-a]pyrimidine-3-carboxylate (200 mg, 0.73 mmol), potassium iodide (60 mg, 0.37 mmol) and potassium carbonate (200 mg, 1.45 mmol) in acetonitrile (15 mL) was added 4-fluorophenol (125 mg, 1.12 mmol). After stirring 2 h at 85° C., the reaction mixture was cooled down to room temperature and concentrated under vacuum. The residue was purified by chromatography with ethyl acetate/petroleum ether (1:1) to afford methyl 7-(4-fluorophenoxymethyl)-2-methyl-5-oxo-5H-[1,3]thiazolo[3,2-a]pyrimidine-3-carboxylate as a white solid (220 mg, 86%). LCMS (ESI): M+H$^+$=349; $^1$H NMR (300 MHz, CDCl$_3$) δ 7.02-6.92 (m, 2H), 6.91-6.86 (m, 2H), 6.48 (s, 1H), 4.92 (s, 2H), 3.98 (s, 3H), 2.45 (s, 3H).

Step 5: 7-((4-fluorophenoxy)methyl)-2-methyl-5-oxo-5H-thiazolo[3,2-a]pyrimidine-3-carboxylic acid

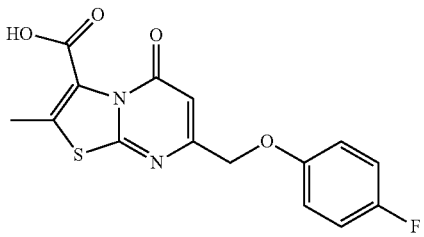 [SMILES: Cc1sc2nc(COc3ccc(F)cc3)cc(=O)n2c1C(=O)O]

To a solution of methyl 7-(4-fluorophenoxymethyl)-2-methyl-5-oxo-5H-[1,3]thiazolo[3,2-a]pyrimidine-3-carboxylate (5.00 g, 14.3 mmol) in tetrahydrofuran (400 mL) and water (200 mL) was added lithium hydroxide (7.00 g, 167 mmol). The resulting solution was stirred at 25° C. for 30 h. After the starting material was consumed (by TLC), the pH of the solution was adjusted to 7 with 2 N hydrogen chloride. Then the solution was concentrated in vacuo until a solid precipitated. The solids were filtered and washed with tetrahydrofuran to afford 7-((4-fluorophenoxy)methyl)-2-methyl-5-oxo-5H-thiazolo[3,2-a]pyrimidine-3-carboxylic acid as white solid (1.70 g, 36%). LCMS (ESI): M+H$^+$=335.

Step 6: N-(Cyanomethyl)-7-(4-fluorophenoxymethyl)-2-methyl-5-oxo-5H-[1,3]thiazolo[3,2-a]pyrimidine-3-carboxamide

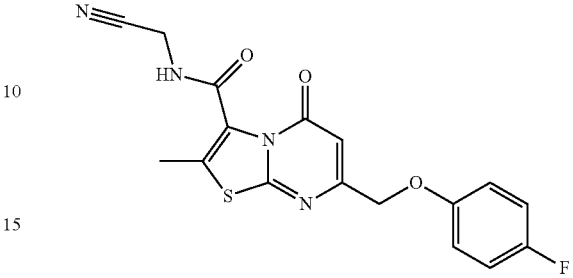

To a solution of 7-((4-fluorophenoxy)methyl)-2-methyl-5-oxo-5H-thiazolo[3,2-a]pyrimidine-3-carboxylic acid (100 mg, 0.30 mmol), 2-aminoacetonitrile hydrochloride (56 mg, 0.61 mmol), triethylamine (90 mg, 0.90 mmol), 4-dimethylaminopyridine (4 mg, 0.03 mmol) and 1-hydroxybenzotrizole (80 mg, 0.60 mmol) in N,N-dimethylformamide (8 mL) was added N-(3-dimethylaminopropyl)-N'-ethylcarbodiimide hydrochloride (115 mg, 0.6 mmol) with stirring. The resulting solution was stirred overnight and was concentrated under vacuum. The residue was purified on a silica gel column eluting with dichloromethane/methanol (30:1) to afford N-(cyanomethyl)-7-(4-fluorophenoxymethyl)-2-methyl-5-oxo-5H-[1,3]thiazolo[3,2-a]pyrimidine-3-carboxamide as white solid (22.7 mg, 20%). LCMS (ESI): M+H$^+$=373; $^1$H NMR (300 MHz, DMSO-d$_6$) δ 9.22 (m, 1H), 7.18-7.03 (m, 4H), 6.30 (s, 1H), 5.02 (s, 2H), 4.36-4.31 (m, 2H), 2.34 (s, 3H).

The following examples were prepared in a manner similar to Example 1.1:

| No. | Structure/Name | LCMS (M + H) | $^1$H NMR |
|---|---|---|---|
| 1.2 | 7-(4-Fluorophenoxymethyl)-N,2-dimethyl-5-oxo-5H-[1,3]thiazolo[3,2-a]pyrimidine-3-carboxamide | 348.0 | $^1$H NMR (300 MHz, CDCl$_3$) δ 7.01-6.95 (m, 2H), 6.91-6.86 (m, 2H), 6.44 (s, 1H), 6.01 (br, 1H), 4.91 (s, 2H), 3.09-3.04 (m, 3H), 2.42 (s, 3H) |
| 1.3 | 3-[(Azetidin-1-yl)carbonyl]-7-(4-fluorophenoxymethyl)-2-methyl-5H-[1,3]thiazolo[3,2-a]pyrimidin-5-one | 374.0 | $^1$H NMR (300 MHz, CDCl$_3$) δ 7.03-6.87 (m, 4H), 6.48 (s, 1H), 4.93 (s, 2H), 4.43-4.34 (m, 1H), 4.20-4.02 (m, 2H), 3.93-3.86 (m, 1H), 2.41-2.33 (m, 5H) |

| No. | Structure/Name | LCMS (M + H) | ¹H NMR |
|---|---|---|---|
| 1.4 | 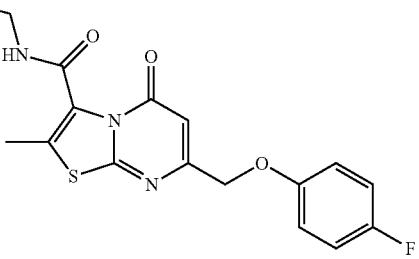<br>N-ethyl-7-(4-fluorophenoxymethyl)-2-methyl-5-oxo-5H-[1,3]thiazolo[3,2-a]pyrimidine-3-carboxamide | 361.9 | ¹H NMR (300 MHz, CDCl$_3$) δ 7.01-6.95 (m, 2H), 6.90-6.86 (m, 2H), 6.45 (s, 1H), 5.89 (s, 1H), 4.91 (s, 2H), 3.57-3.50 (m, 2H), 2.42 (s, 3H) 1.31-1.27 (m, 3H) |
| 1.5 | 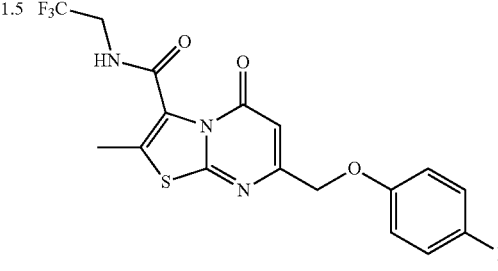<br>7-(4-Fluorophenoxymethyl)-2-methyl-5-oxo-N-(2,2,2-trifluoroethyl)-5H-[1,3]thiazolo[3,2-a]pyrimidine-3-carboxamide | 415.9 | ¹H NMR (400 MHz, DMSO-d$_6$) δ 9.21-9.19 (m, 1H), 7.17-7.04 (m, 4H), 6.29 (s, 1H), 5.01 (s, 2H), 4.05-4.14 (m, 2H), 2.33 (s, 3H) |
| 1.6 | 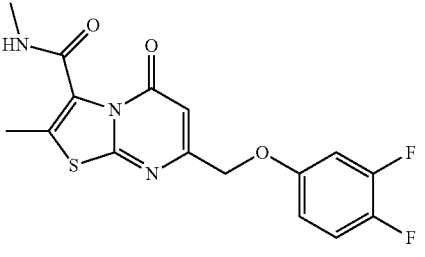 [SMILES: CNC(=O)c1c(C)sc2nc(COc3ccc(F)c(F)c3)cc(=O)n12]<br>7-(3,4-Difluorophenoxymethyl)-N,2-dimethyl-5-oxo-5H-[1,3]thiazolo[3,2-a]pyrimidine-3-carboxamide | 365.95 | ¹H NMR (300 MHz, DMSO-d$_6$) δ 8.38-8.36 (m, 1H), 7.39-7.36 (m, 1H), 7.25-7.24 (m, 1H), 6.91-6.89 (m, 1H), 6.28 (s, 1H), 5.02 (s, 2H), 2.77-2.74 (m, 3H), 2.29 (s, 3H) |
| 1.7 | 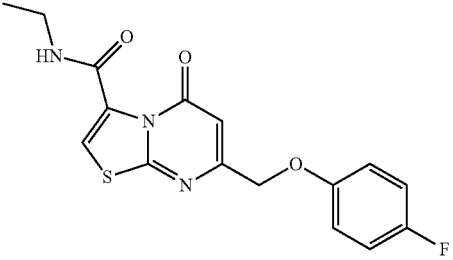 [SMILES: CCNC(=O)c1csc2nc(COc3ccc(F)cc3)cc(=O)n12]<br>N-ethyl-7-(4-fluorophenoxymethyl)-5-oxo-5H-[1,3]thiazolo[3,2-a]pyrimidine-3-carboxamide | 348.0 | ¹H NMR (300 MHz, CDCl$_3$) δ 9.64 (br, 1H), 8.03 (s, 1H), 6.87-7.03 (m, 4H), 6.58 (s, 1H), 4.96 (s, 2H), 3.42-3.51 (m, 2H), 1.24-1.28 (m, 3H) |

| No. | Structure/Name | LCMS (M + H) | ¹H NMR |
|---|---|---|---|
| 1.8 | 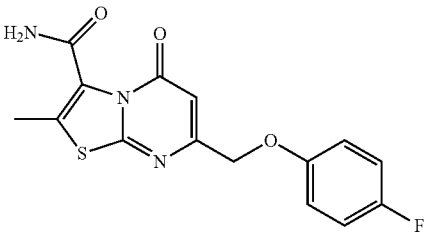 [SMILES: Cc1sc2nc(COc3ccc(F)cc3)cc(=O)n2c1C(N)=O]<br>7-((4-fluorophenoxy)methyl)-2-methyl-5-oxo-5H-thiazolo[3,2-a]pyrimidine-3-carboxamide | 334.1 | ¹H NMR (400 MHz, DMSO-d6) δ 7.90 (s, 1H), 7.77 (s, 1H), 7.20-7.10 (m, 2H), 7.10-6.98 (m, 2H), 6.28 (s, 1H), 5.00 (s, 2H), 2.36 (s, 3H). |
| 1.9 | 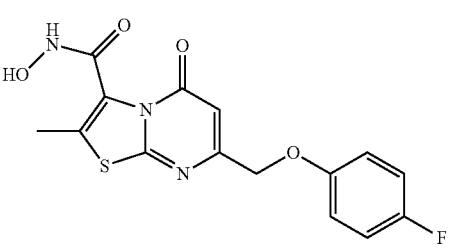 [SMILES: Cc1sc2nc(COc3ccc(F)cc3)cc(=O)n2c1C(=O)NO]<br>7-((4-fluorophenoxy)methyl)-N-hydroxy-2-methyl-5-oxo-5H-thiazolo[3,2-a]pyrimidine-3-carboxamide | 350.1 | ¹H NMR (400 MHz, DMSO-d6) δ 10.91 (s, 1H), 9.36 (s, 1H), 7.19-7.09 (m, 2H), 7.09-6.98 (m, 2H), 6.29 (s, 1H), 5.00 (s, 2H), 2.35 (d, J = 1.9 Hz, 3H) |

The following additional compounds were prepared using the methods described above.

| No. | Structure/Name | LCMS (M + H) | ¹H NMR |
|---|---|---|---|
| 1.10 | 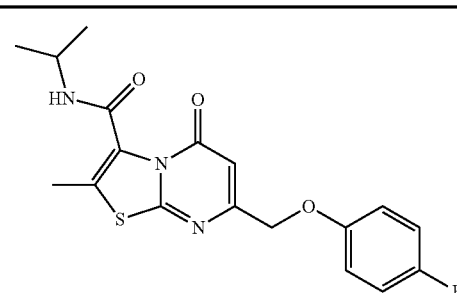<br>7-(4-Fluorophenoxymethyl)-2-methyl-5-oxo-N-(propan-2-yl)-5H-[1,3]thiazolo[3,2-a]pyrimidine-3-carboxamide | 376.10 | ¹H NMR (300 MHz, CDCl₃) δ 7.02-6.99 (m, 2H), 6.95-6.91 (m, 2H), 6.48 (s, 1H), 5.74 (s, 1H), 4.94 (s, 2H), 4.36-4.34 (m, 1H), 2.46 (s, 3H), 1.32 (s, 6H) |

| No. | Structure/Name | LCMS (M + H) | ¹H NMR |
|---|---|---|---|
| 1.11 | 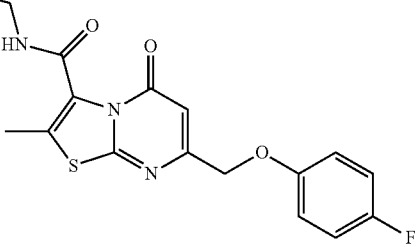<br>7-(4-Fluorophenoxymethyl)-N-(2-hydroxyethyl)-2-methyl-5-oxo-5H-[1,3]thiazolo[3,2-a]pyrimidine-3-carboxamide | 378.0 | ¹H NMR (300 MHz, CD₃OD) δ 7.04 (m, 4H), 6.45 (s, 1H), 5.01 (s, 2H), 3.80-3.73 (m, 2H), 3.56-3.51 (m, 2H), 2.46 (s, 3H) |
| 1.12 | 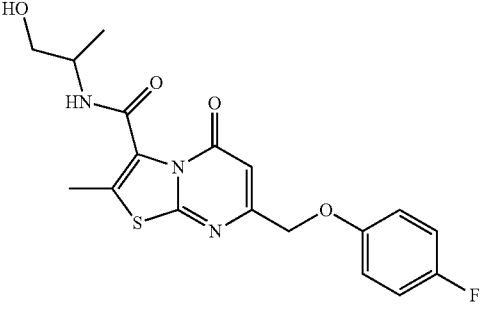 [SMILES: Cc1sc2nc(COc3ccc(F)cc3)cc(=O)n2c1C(=O)NC(C)CO]<br>7-(4-Fluorophenoxymethyl)-N-(1-hydroxypropan-2-yl)-2-methyl-5-oxo-5H-[1,3]thiazolo[3,2-a]pyrimidine-3-carboxamide | 392.0 | ¹H NMR (300 MHz, CDCl₃) δ 7.01-6.96 (m, 2H), 6.91-6.85 (m, 2H), 6.50 (s, 1H), 5.87-5.03 (m, 1H), 4.93 (s, 2H), 4.23-4.25 (m, 1H), 4.08-03 (m, 1H), 3.55-3.50 (m, 1H), 2.45 (s, 3H), 1.30-1.27 (m, 3H) |
| 1.13 | 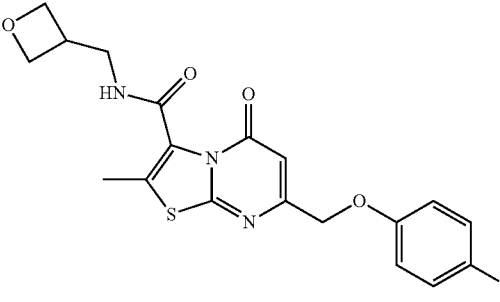<br>7-((4-fluorophenoxy)methyl)-2-methyl-N-(oxetan-3-ylmethyl)-5-oxo-5H-thiazolo[3,2-a]pyrimidine-3-carboxamide | 404.0 | ¹H NMR (300 MHz, CD₃OD) δ 7.09-7.00 (m, 4H), 6.44 (s, 1H), 5.01 (s, 2H), 4.87-4.85 (m, 2H), 4.57-4.53 (m, 2H), 3.72-3.70 (m, 2H), 3.41-3.38 (m, 1H), 2.45 (s, 3H) |
| 1.14 | 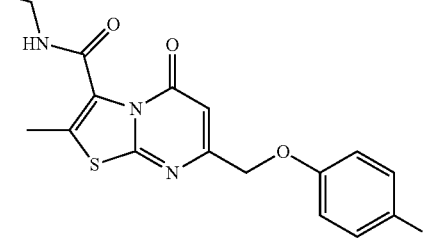<br>7-((4-fluorophenoxy)methyl)-N-(3-hydroxypropyl)-2-methyl-5-oxo-5H-thiazolo[3,2-a]pyrimidine-3-carboxamide | 392.0 | ¹H NMR (300 MHz, CDCl₃) δ 7.02-6.97 (m, 2H), 6.91-6.88 (m, 2H), 6.53 (br, 1H), 6.49 (s, 1H), 4.94 (s, 2H), 3.90-3.85 (m, 2H), 3.70-3.66 (m, 2H), 2.46 (s, 3H), 1.95-1.89 (m, 2H) |

| No. | Structure/Name | LCMS (M + H) | ¹H NMR |
|---|---|---|---|
| 1.15 | 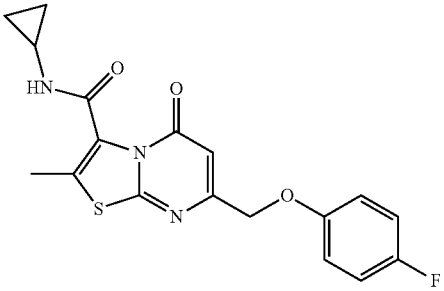 [SMILES: Cc1sc2nc(COc3ccc(F)cc3)cc(=O)n2c1C(=O)NC1CC1]<br>N-cyclopropyl-7-((4-fluorophenoxy)methyl)-2-methyl-5-oxo-5H-thiazolo[3,2-a]pyrimidine-3-carboxamide | 374.0 | ¹H NMR (300 MHz, CDCl₃) δ 7.01-6.95 (m, 2H), 6.89-6.85 (m, 2H), 6.45 (s, 1H), 6.03 (s, 1H), 4.91 (s, 2H), 2.93-2.90 (m, 1H), 2.42 (s, 3H), 0.93-0.87 (m, 2H), 0.81-0.74 (m, 2H). |
| 1.16 | 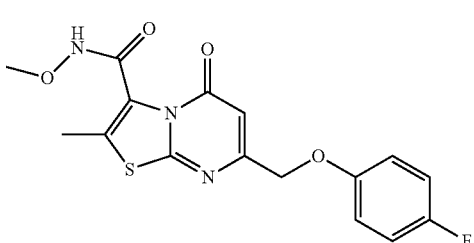<br>7-((4-fluorophenoxy)methyl)-N-methoxy-2-methyl-5-oxo-5H-thiazolo[3,2-a]pyrimidine-3-carboxamide | 364.1 | ¹H NMR (400 MHz, DMSO-d₆) δ 11.50 (s, 1H), 7.19-7.09 (m, 2H), 7.09-6.99 (m, 2H), 6.30 (s, 1H), 5.01 (s, 2H), 3.73 (s, 3H), 2.36 (s, 3H). |
| 1.17 | 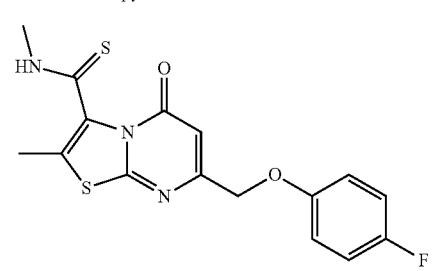<br>7-(4-Fluorophenoxymethyl)-N,2-dimethyl-5-oxo-5H-[1,3]thiazolo[3,2-a]pyrimidine-3-carbothioamide | 363.9 | ¹H NMR (300 MHz, CD₃OD) δ 7.04-6.97 (m, 4H), 6.38 (s, 1H), 5.06 (s, 2H), 3.22 (s, 3H), 2.36 (s, 3H). |

Method 2

Example 2.1: 7-((4-fluorophenoxy)methyl)-2-methyl-3-propionyl-5H-thiazolo[3,2-a]pyrimidin-5-one

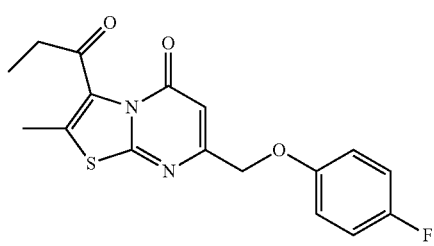

To a solution of methyl 7-((4-fluorophenoxy)methyl)-2-methyl-5-oxo-5H-thiazolo[3,2-a]pyrimidine-3-carboxylate (from Example 1.1, Step 4; 100 mg, 0.29 mmol) in tetrahydrofuran (2 mL) was added ethylmagnesium bromide (0.14 mL, 0.32 mmol). The reaction mixture was stirred for 1 h at room temperature. The reaction was then quenched by addition of water, extracted with dichloromethane (3×30 mL), washed with brine, dried over anhydrous sodium sulfate and concentrated in vacuo. The residue was purified on a silica gel column with ethyl acetate/petroleum ether (1:3) to provide 7-((4-fluorophenoxy)methyl)-2-methyl-3-propionyl-5H-thiazolo[3,2-a]pyrimidin-5-one as a white solid (91.9 mg, 92%). LCMS (ESI): M+H⁺=347.0.

Example 2.2: 7-((4-fluorophenoxy)methyl)-3-(1-hydroxypropyl)-2-methyl-5H-thiazolo[3,2-a]pyrimidin-5-one

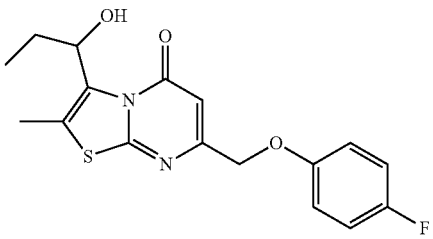 [SMILES: CCC(O)c1c(C)sc2nc(COc3ccc(F)cc3)cc(=O)n12]

To a solution of 7-((4-fluorophenoxy)methyl)-2-methyl-3-propionyl-5H-thiazolo[3,2-a]pyrimidin-5-one (from Example 2.1; 20.0 mg, 0.060 mmol) in methanol (10 mL) was added sodium borohydride (4.70 mg, 0.13 mmol). The reaction mixture was stirred overnight at room temperature. The reaction was then quenched by saturated aqueous ammonium chloride (20 mL), extracted with dichloromethane (3×30 mL), washed with brine, dried over sodium sulfate and concentrated in vacuo. The residue was purified by chromatography with dichloromethane/methanol (50:1) to afford 7-((4-fluorophenoxy)methyl)-3-(1-hydroxypropyl)-2-methyl-5H-thiazolo[3,2-a]pyrimidin-5-one as a white solid (4.50 mg, 21%). LCMS (ESI): M+H$^+$=349.0; $^1$H NMR (300 MHz, CD$_3$OD) δ 7.05-7.03 (m, 4H), 6.50 (s, 1H), 5.11-5.01 (m, 1H), 4.89 (s, 2H), 2.51 (s, 3H), 1.96-1.83 (m, 2H), 0.97-0.92 (m, 3H).

The following examples were prepared in a manner similar to Example 2.1 and 2.2:

| No. | Structure/Name | LCMS (M + H) | $^1$H NMR |
|---|---|---|---|
| 2.3 | 7-(4-Fluorophenoxymethyl)-3-(1-hydroxyethyl)-2-methyl-5H-[1,3]thiazolo[3,2-a]pyrimidin-5-one | 335.20 | $^1$H NMR (300 MHz, DMSO-d$_6$) δ 7.18-7.12 (m, 2H), 7.08-7.03 (m, 2H), 6.33 (s, 1H), 5.68-5.62 (m, 2H), 5.00 (s, 2H), 2.49 (s, 3H), 1.43-1.41 (m, 3H) |
| 2.4 | 7-(4-Fluorophenoxymethyl)-3-(2-hydroxypropan-2-yl)-2-methyl-5H-[1,3]thiazolo[3,2-a]pyrimidin-5-one | 349.10 | $^1$H NMR (300 MHz, CD$_3$OD) δ 7.18-7.13 (s, 2H), 7.08-7.05 (s, 2H), 6.66 (s, 1H), 6.41 (s, 1H), 5.02 (s, 2H), 2.54 (s, 3H), 1.65 (s, 6H) |
| 2.5 | 3-acetyl-7-((4-fluorophenoxy)methyl)-2-methyl-5H-thiazolo[3,2-a]pyrimidin-5-one | 333.0 | $^1$H NMR (300 MHz, CD$_3$OD) δ 7.08-7.01 (m, 4H), 6.46 (s, 1H), 5.06 (s, 2H), 2.50 (s, 3H), 2.40 (s, 3H). |

Example 2.6: 2-(7-((4-fluorophenoxy)methyl)-2-methyl-5-oxo-5H-thiazolo[3,2-a]pyrimidin-3-yl)-N-methylacetamide

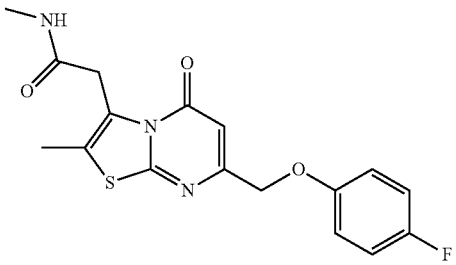 [SMILES: CNC(=O)Cc1c(C)sc2nc(COc3ccc(F)cc3)cc(=O)n12]

Step 1: 7-((4-fluorophenoxy)methyl)-3-(hydroxymethyl)-2-methyl-5H-thiazolo[3,2-a]pyrimidin-5-one

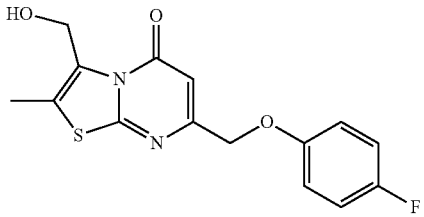 [SMILES: Cc1sc2nc(COc3ccc(F)cc3)cc(=O)n2c1CO]

Into a 25-mL round bottom flask under nitrogen was added a solution of methyl 7-((4-fluorophenoxy)methyl)-2-methyl-5-oxo-5H-thiazolo[3,2-a]pyrimidine-3-carboxylate (from Example 1.1, Step 5) (200 mg, 0.57 mmol) in tetrahydrofuran (20 mL) and a solution of diisobutylaluminum hydride in toluene (1.1 mol/L, 1 mL). The resulting solution was stirred overnight at room temperature. The reaction was quenched with water (30 mL), extracted with dichloromethane (3×50 mL), washed with brine, dried over sodium sulfate and concentrated in vacuo. The residue was purified by silica gel chromatography with dichloromethane/methanol (50:1) to afford 7-((4-fluorophenoxy)methyl)-3-(hydroxymethyl)-2-methyl-5H-thiazolo[3,2-a]pyrimidin-5-one as an off-white solid (150 mg, 77%). LCMS (ESI): M+H$^+$= 321.0; $^1$H NMR (300 MHz, CDCl$_3$) δ 7.02-6.87 (m, 4H), 6.48 (s, 1H), 4.93 (s, 2H), 4.76 (s, 2H), 2.44 (s, 3H).

Step 2: 3-(Chloromethyl)-7-(4-fluorophenoxymethyl)-2-methyl-5H-[1,3]thiazolo[3,2-a]pyrimidin-5-one

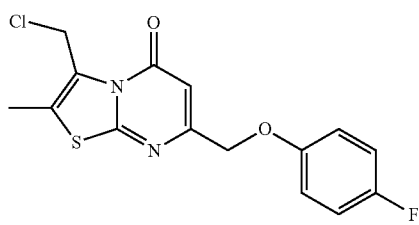 [SMILES: Cc1sc2nc(COc3ccc(F)cc3)cc(=O)n2c1CCl]

To a solution of 7-(4-fluorophenoxymethyl)-3-(hydroxymethyl)-2-methyl-5H-[1,3]thiazolo[3,2-a]pyrimidin-5-one (200 mg, 0.62 mmol) in dichloromethane (5 mL) was added thionyl chloride (0.5 mL) and N,N-dimethylformamide (10 mg, 0.14 mmol). The resulting solution was stirred overnight at room temperature and then concentrated in vacuo. The residue was purified by chromatography with dichloromethane/ethyl acetate (50/1) to afford 3-(chloromethyl)-7-(4-fluorophenoxymethyl)-2-methyl-5H-[1,3]thiazolo[3,2-a]pyrimidin-5-one as a white solid (150 mg, 71%). LCMS (ESI): M+H$^+$=339.0; $^1$H NMR (400 MHz, CDCl$_3$) δ 7.01-6.96 (m, 2H), 6.92-6.89 (m, 2H), 6.47 (s, 1H), 5.26 (s, 2H), 4.91 (s, 2H), 2.45 (s, 3H).

Step 3: Methyl 2-[7-(4-fluorophenoxymethyl)-2-methyl-5-oxo-5H-[1,3]thiazolo[3,2-a]pyrimidin-3-yl]acetate

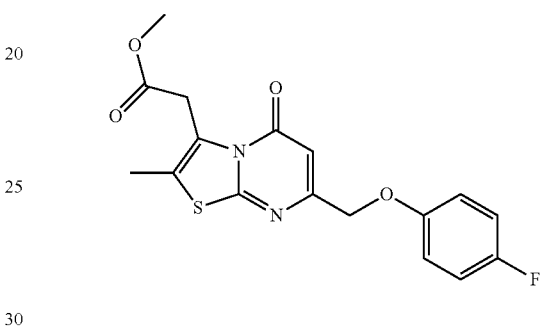

To a solution of 3-(chloromethyl)-7-(4-fluorophenoxymethyl)-2-methyl-5H-[1,3]thiazolo[3,2-a]pyrimidin-5-one (200 mg, 0.59 mmol) in methanol (5 mL) was added 1,1'-bis(diphenylphosphino)ferrocenepalladium dichloride (60 mg, 0.08 mmol), potassium carbonate (163 mg, 1.18 mmol). The reaction mixture was stirred for 3 h at 25° C. under carbon monoxide (5 atm) atmosphere. After filtration, the filtrate was concentrated in vacuo. The residue was purified by chromatography with dichloromethane/ethyl acetate (50/1) to afford methyl 2-[7-(4-fluorophenoxymethyl)-2-methyl-5-oxo-5H-[1,3]thiazolo[3,2-a]pyrimidin-3-yl]acetate as a white solid (120 mg, 56%). LCMS (ESI): M+H$^+$=363.2; $^1$H NMR (400 MHz, CDCl$_3$) δ 7.01-6.95 (m, 2H), 6.91-6.86 (m, 2H), 6.37 (s, 1H), 4.89 (s, 2H), 4.19 (s, 2H), 3.75 (s, 3H), 2.33 (s, 3H).

Step 4: 2-[7-(4-Fluorophenoxymethyl)-2-methyl-5-oxo-5H-[1,3]thiazolo[3,2-a]pyrimidin-3-yl]-N-methylacetamide

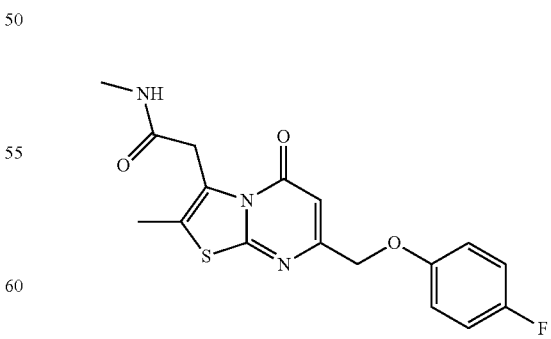

Methyl 2-[7-(4-fluorophenoxymethyl)-2-methyl-5-oxo-5H-[1,3]thiazolo[3,2-a]pyrimidin-3-yl]acetate (70 mg, 0.19 mmol) and a methylamine in ethanol solution (30%, 5 mL) were added to a 25-mL round-bottom flask. The resulting solution was stirred for 30 min at 40° C. and then concentrated in vacuo. The residue was purified by chromatography with dichloromethane/ethyl acetate (10/1) to afford 2-[7-(4-fluorophenoxymethyl)-2-methyl-5-oxo-5H-[1,3]thiazolo[3,2-a]pyrimidin-3-yl]-N-methylacetamide as a white solid (38 mg, 54%). LCMS (ESI): M+H$^+$=362.0; $^1$H NMR (300 MHz, CDCl$_3$) δ 7.02-6.87 (m, 5H), 6.44 (s, 1H), 4.92 (s, 2H), 4.12 (s, 2H), 2.78-2.76 (m, 3H), 2.51 (s, 3H).

The following examples were prepared using methods analogous to those described above:

| No. | Structure/Name | LCMS (M + H) | $^1$H NMR |
|---|---|---|---|
| 2.7 | 3-Cyclopropanecarbonyl-7-(4-fluorophenoxymethyl)-2-methyl-5H-[1,3]thiazolo[3,2-a]pyrimidin-5-one | 359.0 | $^1$H NMR (300 MHz, CDCl$_3$) δ 7.02-6.87 (m, 4H), 6.50 (s, 1H), 4.94 (s, 2H), 2.38 (s, 3H), 2.19-2.10 (m, 1H), 1.38-1.31 (m, 2H), 1.17-1.11 (m, 2H) |
| 2.8 | 7-(4-Fluorophenoxymethyl)-3-[1-(hydroxyimino)ethyl]-2-methyl-5H-[1,3]thiazolo[3,2-a]pyrimidin-5-one | 348.0 | $^1$H NMR (300 MHz, CDCl$_3$) δ 7.07-6.98 (m, 4H), 6.38 (s, 1H), 4.98 (s, 2H), 2.36 (s, 2H), 2.29 (s, 1H), 2.18 (s, 1H), 2.10 (s, 2H) |
| 2.9 | 7-((4-fluorophenoxy)methyl)-2-methyl-3-(oxetane-3-carbonyl)-5H-thiazolo[3,2-a]pyrimidin-5-one | 375.0 | $^1$H NMR (300 MHz, DMSO-d$_6$) δ 7.17-7.03 (m, 4H), 6.28 (s, 1H), 6.04 (s, 1H), 5.69 (s, 1H), 5.16-5.12 (m, 1H), 5.00 (s, 2H), 4.35-4.25 (m, 2H), 2.30 (s, 3H) |
| 2.10 | 7-((4-fluorophenoxy)methyl)-2-methyl-3-(2,2,2-trifluoro-1-hydroxyethyl)-5H-thiazolo[3,2-a]pyrimidin-5-one | 389.0 | $^1$H NMR (300 MHz, CDCl$_3$) δ 7.95 (s, 1H), 7.03-6.96 (m, 2H), 6.93-6.87 (m, 2H), 6.66 (s, 1H), 5.35-5.33 (m, 1H), 4.96 (s, 2H), 2.50 (s, 3H) |

| No. | Structure/Name | LCMS (M + H) | $^1$H NMR |
|---|---|---|---|
| 2.11 | 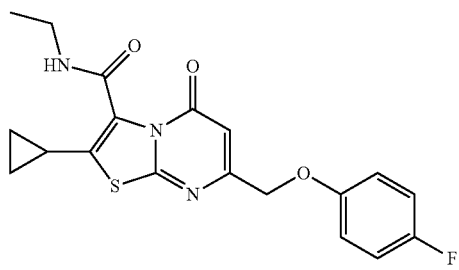 [SMILES: CCNC(=O)c1c(C2CC2)sc2nc(COc3ccc(F)cc3)cc(=O)n12]<br>7-(4-Fluorophenoxymethyl)-2-methyl-3-(trifluoroacetyl)-5H-[1,3]thiazolo[3,2-a]pyrimidin-5-one | 386.8 | $^1$HNMR (300 MHz, CDCl$_3$) δ 7.03-6.96 (m, 2H), 6.93-6.87 (m, 2H), 6.59 (s, 1H), 4.95 (s, 2H), 2.44 (s, 3H) |

Method 3

Example 3.1: 2-cyclopropyl-N-ethyl-7-((4-fluorophenoxy)methyl)-5-oxo-5H-thiazolo[3,2-a]pyrimidine-3-carboxamide

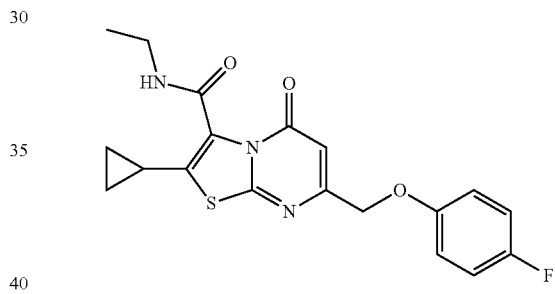

Step 1: 7-(chloromethyl)-2-cyclopropyl-N-ethyl-5-oxo-5H-thiazolo[3,2-a]pyrimidine-3-carboxamide

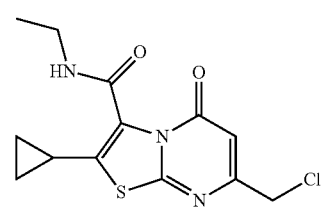 [SMILES: CCNC(=O)c1c(C2CC2)sc2nc(CCl)cc(=O)n12]

To a solution of 2-amino-5-cyclopropyl-N-ethylthiazole-4-carboxamide (2.53 g, 12.8 mmol) in polyphosphoric acid (16.0 g) was added ethyl 4-chloro-3-oxobutanoate (4.20 g, 25.5 mmol). The resulting solution was stirred for 1 h at 110° C. The reaction was then quenched by water (80 mL) and the pH value of the solution was adjusted to pH 7 with a sodium hydroxide solution (1 mol/L). The reaction mixture was extracted with dichloromethane (3×50 mL), washed with brine (30 mL), dried over anhydrous magnesium sulfate and concentrated in vacuo. The residue was purified by chromatography with dichloromethane/ethyl acetate (5/1) to afford 7-(chloromethyl)-2-cyclopropyl-N-ethyl-5-oxo-5H-thiazolo[3,2-a]pyrimidine-3-carboxamide as a brown solid (905 mg, 24%). LCMS (ESI): M+H$^+$=312.0.

Step 2: 2-cyclopropyl-N-ethyl-7-((4-fluorophenoxy)methyl)-5-oxo-5H-thiazolo[3,2-a]pyrimidine-3-carboxamide A solution of 7-(chloromethyl)-2-cyclopropyl-N-ethyl-5-oxo-5H-thiazolo[3,2-a]pyrimidine-3-carboxamide (100 mg, 0.32 mmol) in acetonitrile (10 mL) was treated with potassium iodide (27.0 mg, 0.16 mmol), potassium carbonate (88.0 mg, 0.64 mmol) and 4-fluorophenol (72.0 mg, 0.64 mmol,). The reaction mixture was then stirred overnight at 80° C. After cooling down to room temperature, the reaction mixture was concentrated in vacuo. The residue was purified by chromatography with dichloromethane/methanol (50/1) to afford 2-cyclopropyl-N-ethyl-7-(4-fluorophenoxymethyl)-5-oxo-5H-[1,3]Thiazolo[3,2-a]pyrimidine-3-carboxamide as a white solid (36.4 mg, 29%). LCMS (ESI): M+H$^+$=388.0; $^1$HNMR (300 MHz, CDCl$_3$) δ 7.00-6.95 (m, 2H), 6.90-6.84 (m, 2H), 6.44 (s, 1H), 5.91 (s, 1H), 4.90 (s, 2H), 3.57-3.53 (m, 2H), 2.19-2.09 (m, 1H), 1.32-1.27 (m, 3H), 1.22-1.08 (m, 2H), 0.90-0.83 (m, 2H).

The following examples were prepared in a manner similar to Example 3.1:

| No. | Structure/Name | LCMS (M + H) | ¹H NMR |
|---|---|---|---|
| 3.2 | 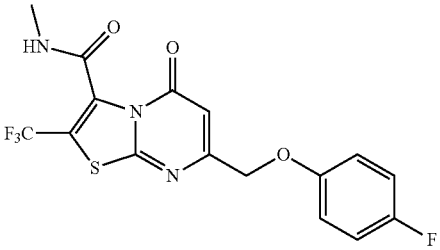 [SMILES: CNC(=O)c1c(C(F)(F)F)sc2nc(COc3ccc(F)cc3)cc(=O)n12]<br>7-(4-Fluorophenoxymethyl)-N-methyl-5-oxo-2-(trifluoromethyl)-5H-[1,3]thiazolo[3,2-a]pyrimidine-3-carboxamide | 401.9 | ¹H NMR(300 MHz, CDCl$_3$) δ 7.02-6.95 (m, 2H), 6.92-6.85 (m, 2H), 6.53 (s, 1H), 5.89 (bs, 1H), 4.92 (s, 2H), 3.10-3.06 (m, 3H) |
| 3.3 | 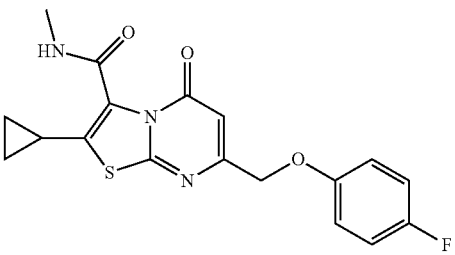 [SMILES: CNC(=O)c1c(C2CC2)sc2nc(COc3ccc(F)cc3)cc(=O)n12]<br>2-Cyclopropyl-7-(4-fluorophenoxymethyl)-N-methyl-5-oxo-5H-[1,3]thiazolo[3,2-a]pyrimidine-3-carboxamide | 374.0 | ¹H NMR (300 MHz, CDCl$_3$) δ 7.02-6.91 (m, 2H), 6.90-6.85 (m, 2H), 6.42 (s, 1H), 6.11 (s, 1H), 4.89 (s, 2H), 3.07 (s, 3H), 2.21-2.12 (m, 1H), 1.29-1.08 (m, 2H), 0.92-0.81 (m, 2H) |
| 3.4 | 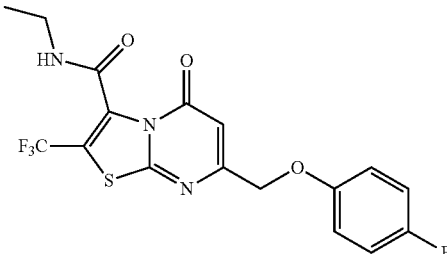<br>N-Ethyl-7-(4-fluorophenoxymethyl)-5-oxo-2-(trifluoromethyl)-5H-[1,3]thiazolo[3,2-a]pyrimidine-3-carboxamide | 415.95 | ¹H NMR (300 MHz, CDCl$_3$) δ 7.02-6.96 (m, 2H), 6.91-6.85 (m, 2H), 6.53 (s, 1H), 5.87 (br, 1H), 4.92 (s, 2H), 3.60-3.51 (m, 2H), 1.31-1.27 (m, 3H) |
| 3.5 | 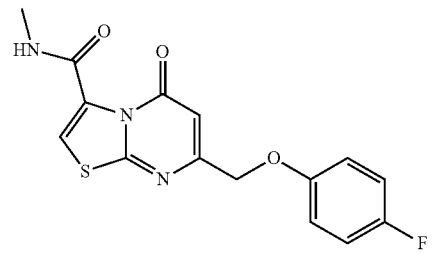 [SMILES: CNC(=O)c1csc2nc(COc3ccc(F)cc3)cc(=O)n12]<br>7-((4-fluorophenoxy)methyl)-N-methyl-5-oxo-5H-thiazolo[3,2-a]pyrimidine-3-carboxamide | 334.0 | ¹H NMR (300 MHz, CDCl$_3$) δ 8.07 (s, 1H), 7.03-6.96 (m, 2H), 6.94-6.88 (m, 2H), 6.59 (s, 1H), 4.96 (s, 2H), 2.99 (s, 3H) |

The following example was prepared using methods analogous to those described above.

| No. | Structure/Name | LCMS (M + H) | $^1$H NMR |
|---|---|---|---|
| 3.6 | ![structure] N-ethyl-7-[[(5-fluoropyridin-2-yl)oxy]methyl]-2-methyl-5-oxo-5H-[1,3]thiazolo[3,2-a]pyrimidine-3-carboxamide | 363.15 | $^1$H NMR (300 MHz, CD$_3$OD) δ 7.99-7.98 (m, 1H), 7.61-7.54 (m, 1H), 7.00-6.96 (m, 1H), 6.32 (s, 1H), 5.27 (s, 2H), 3.45-3.38 (m, 2H), 2.42 (s, 3H), 1.26-1.22 (m, 3H) |

Method 4

Example 4.1: 7-(4-Fluorophenoxymethyl)-3-[trans-2-(hydroxymethyl)cyclopropyl]-2-methyl-5H-[1,3]thiazolo[3,2-a]pyrimidin-5-one Example 4.2: 7-(4-Fluorophenoxymethyl)-3-[trans-2-(hydroxymethyl)cyclopropyl]-2-methyl-5H-[1,3]thiazolo[3,2-a]pyrimidin-5-one (enantiomer 1)

Example 4.3: 7-(4-Fluorophenoxymethyl)-3-[trans-2-(hydroxymethyl)cyclopropyl]-2-methyl-5H-[1,3]thiazolo[3,2-a]pyrimidin-5-one (enantiomer 2)

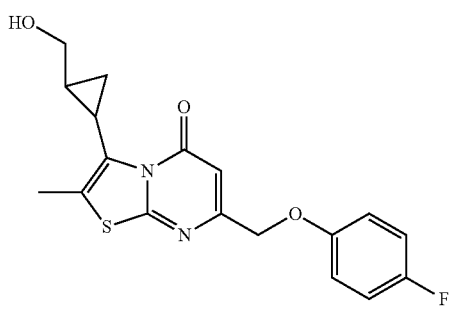 [SMILES: Cc1sc2nc(COc3ccc(F)cc3)cc(=O)n2c1C1CC1CO]

Step 1: tert-butyldimethyl((2-(4,4,5,5-tetramethyl-1,3,2-dioxaborolan-2-yl)cyclopropyl)methoxy)silane

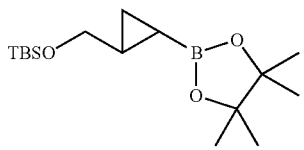 [SMILES: CC1(C)OB(C2CC2CO[Si](C)(C)C(C)(C)C)OC1(C)C]

Diethylzinc (1.0 M in hexane) (200 mL, 200 mmol) was added to freshly distilled dichloromethane (200 mL) under nitrogen. Then a solution of trifluoroacetic acid (15.4 mL, 200 mmol) in dichloromethane (100 mL) was added dropwise at 0° C. Upon stirring for 30 min, a solution of diiodomethane (16.1 mL, 200 mmol) in dichloromethane (100 mL) was added at 0° C. After an additional 30 min of stirring, a solution of (E)-tert-butyldimethyl(3-(4,4,5,5-tetramethyl-1,3,2-dioxaborolan-2-yl)allyloxy)silane (30.0 g, 100 mmol) in dichloromethane (100 mL) was added at 0° C. The resulting solution was stirred 2 h at room temperature and was then quenched with water. The reaction was extracted with dichloromethane (1000 mL×2), washed with brine, and the organic layer was then dried over anhydrous sodium sulfate and concentrated to afford tert-butyldimethyl ((2-(4,4,5,5-tetramethyl-1,3,2-dioxaborolan-2-yl)cyclopropyl)methoxy)silane as a colorless oil (30 g, 96%). $^1$H NMR (300 MHz, CDCl$_3$) δ 3.58-3.53 (m, 1H), 3.44-3.38 (m, 1H), 1.17 (s, 12H), 0.87 (s, 9H), 0.66-0.63 (m, 1H), 0.54-0.49 (m, 1H), 0.06 (s, 6H), −0.35 to −0.25 (m, 2H).

Step 2: Potassium trans-2-(hydroxymethyl)cyclopropyltrifluoroborate

To a solution of tert-butyldimethyl((2-(4,4,5,5-tetramethyl-1,3,2-dioxaborolan-2-yl)cyclopropyl)methoxy)silane (30.0 g, 100 mmol) in methanol (300 mL) was added a solution of potassium difluoride (32.0 g, 400 mmol) in water (100 mL) dropwise at 0° C. After stirring 1.5 h at room temperature, the reaction mixture was concentrated under reduce pressure. The resulting solid was suspended in acetone (1 L) and was refluxed 20 min. The heterogeneous mixture was then filtered to remove potassium difluoride and the filtrate was concentrated. The extraction was repeated for the filtered solid. The combined filtrates were concentrated and dissolved in minimal acetone followed by the slow addition of ethyl ether until the solution become cloudy. The mixture was filtered and the solid was collected to provide potassium trans-2-(hydroxymethyl)cyclopropyltrifluoroborate (7.00 g, 40%). $^1$H NMR (300 MHz, CDCl$_3$) δ 4.01-3.97 (m, 1H), 3.44-3.37 (m, 1H), 2.83-2.75 (m, 1H), 0.58-0.48 (m, 1H), 0.01 to −0.03 (m, 1H), −0.21 to −0.25 (m, 1H), −0.94 to −0.97 (m, 1H).

Step 3: 2-(5-methylthiazol-2-yl)isoindoline-1,3-dione

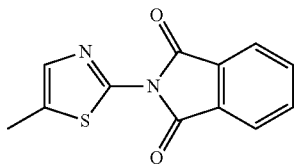 [SMILES: Cc1cnc(N2C(=O)c3ccccc3C2=O)s1]

5-Methylthiazol-2-amine (200 g, 1.75 mol) and phthalic acid anhydride (272.4 g, 1.84 mol) were suspended in dioxane (2.5 L) and heated at 110° C. overnight. TLC (DCM/MeOH=20:1) showed the reaction was complete. The mixture was concentrated, and the residue was purified via column chromatography on silica gel (DCM/MeOH=50: 1-20:1) to give 2-(5-methylthiazol-2-yl)isoindoline-1,3-dione (240 g, 56%) as an off-white solid. LCMS (ESI): M+H$^+$=245.1; $^1$H NMR (400 MHz, CDCl$_3$) δ 8.01-7.99 (m, 2H), 7.84-7.82 (m, 2H), 7.46 (s, 1H), 2.51 (s, 3H).

Step 4: 2-(4-bromo-5-methylthiazol-2-yl)isoindoline-1,3-dione

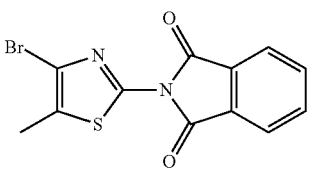 [SMILES: Cc1sc(N2C(=O)c3ccccc3C2=O)nc1Br]

To a mixture of 2-(5-methylthiazol-2-yl)isoindoline-1,3-dione (250 g, 0.819 mol) in THF (2 L) was added N-bromosuccinimide (330 g, 1.85 mol) portionwise at room temperature. Then the mixture was stirred overnight at 30° C. LCMS showed the reaction was complete. The mixture was diluted with water and ethyl acetate. The mixture was filtered and the filter cake was dried to give 2-(4-bromo-5-methylthiazol-2-yl)isoindoline-1,3-dione (210 g, 75%) as a yellow solid. LCMS (ESI): M+H$^+$=323.1, 325.1; $^1$H NMR (400 MHz, DMSO-d$_6$) δ 8.03-8.00 (m, 2H), 7.95-7.93 (s, 2H), 2.41 (s, 3H).

Step 5: 4-bromo-5-methylthiazol-2-amine

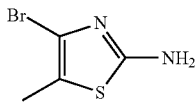

A mixture of 2-(4-bromo-5-methylthiazol-2-yl)isoindoline-1,3-dione (152 g, 0.471 mol) and hydrazine monohydrate (29.5 g, 0.495 mol) in EtOH (1.5 L) was stirred overnight at 20° C. TLC (100% DCM) showed the reaction was complete. The mixture was then concentrated and the residue was purified via column chromatography on silica (100% DCM) to give 4-bromo-5-methylthiazol-2-amine (67 g, 73%) as a white solid. LCMS (ESI): M+H$^+$=193.1; $^1$H NMR (400 MHz, CDCl$_3$) δ 8.52 (br, 1H), 5.11 (br, 1H), 2.23 (s, 1H).

Step 6: 3-bromo-7-(chloromethyl)-2-methyl-5H-thiazolo[3,2-a]pyrimidin-5-one

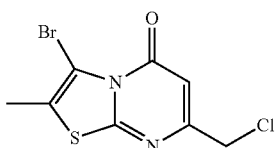

A mixture of 4-bromo-5-methylthiazol-2-amine (60 g, 0.31 mol) and 4-chloro-3-oxo-butanoate (62 g, 0.37 mol) in PPA (500 g) was stirred for 2 h at 110° C. LCMS showed the reaction was complete. The aqueous layer was extracted with DCM (300 mL×3). The combined organic layers were washed with water (200 mL×3) and brine (200 mL), dried over Na$_2$SO$_4$ and concentrated. The residue was purified via chromatography on silica gel (DCM/MeOH=100:1-50:1) to give 3-bromo-7-(chloromethyl)-2-methyl-5H-thiazolo[3,2-a]pyrimidin-5-one (50 g, 55%) as a brown solid. LCMS (ESI): M+H$^+$=293.1, 295.1; $^1$H NMR (400 MHz, CDCl$_3$) δ 6.39 (s, 1H), 4.39 (s, 2H), 2.38 (s, 3H).

Step 7: 3-bromo-7-((4-fluorophenoxy)methyl)-2-methyl-5H-thiazolo[3,2-a]pyrimidin-5-one

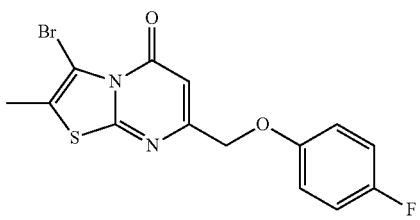 [SMILES: Cc1sc2nc(COc3ccc(F)cc3)cc(=O)n2c1Br]

To a solution of 3-bromo-7-(chloromethyl)-2-methyl-5H-thiazolo[3,2-a]pyrimidin-5-one (20 g, 0.068 mmol) in acetonitrile (300 ml) was added 4-fluorophenol (9.20 g, 0.082 mmol), potassium iodide (5.68 g, 0.034 mmol), and potassium carbonate (26.1 g, 0.136 mmol). The mixture was stirred for 3 h at 80° C. and then cooled down room temperature. After filtration and concentration, the residue was purified by chromatography by ethyl acetate/petroleum ether (1/1) to afford 3-bromo-7-((4-fluorophenoxy)methyl)-2-methyl-5H-thiazolo[3,2-a]pyrimidin-5-one (20 g, 80%) as a yellow solid. LCMS (ESI): M+H$^+$=369.1, 371.1; $^1$H NMR (300 MHz, CDCl$_3$) δ 7.01-6.95 (m, 2H), 6.92-6.86 (m, 2H), 6.44 (s, 1H), 4.88 (s, 2H), 2.36 (s, 3H).

Step 8: 7-(4-Fluorophenoxymethyl)-3-[trans-2-(hydroxymethyl)cyclopropyl]-2-methyl-5H-[1,3]thiazolo[3,2-a]pyrimidin-5-one and 7-(4-Fluorophenoxymethyl)-3-[trans-2-(hydroxymethyl)cyclopropyl]-2-methyl-5H-[1,3]thiazolo[3,2-a]pyrimidin-5-one (enantiomer 1 and enantiomer 2)

3-Bromo-7-((4-fluorophenoxy)methyl)-2-methyl-5H-thiazolo[3,2-a]pyrimidin-5-one (500 mg, 1.36 mmol), sodium carbonate (430 mg, 4.07 mmol), 1,1'-bis(diphenylphosphino)-ferrocenepalladiumdichloride (200 mg, 0.27 mmol), potassium organotrifluoroborates (500 mg, 2.80 mmol), 1,4-dioxane (12 mL) and water (3 mL) were placed in a 30-mL sealed tube. The reaction was stirred at 120° C. for 1.5 h under microwave irradiation. The reaction was then extracted with dichloromethane, washed with brine, dried over sodium sulfate and concentrated in vacuo. The residue was purified by chromatography with dichloromethane/ethyl acetate (2/1) to afford 7-(4-fluorophenoxymethyl)-3-[trans-2-(hydroxymethyl)cyclopropyl]-2-methyl-5H-[1,3]thiazolo[3,2-a]pyrimidin-5-one (Example 4.1) as a light yellow solid (3.00 g, 30%). LCMS(ESI): M+H$^+$=361.1; 1HNMR (300 MHz, CDCl$_3$) δ 7.04-6.98 (m, 2H), 6.93-6.89 (m, 2H), 6.48 (s, 1H), 4.92 (s, 2H), 4.09-4.05 (m, 1H), 3.16-3.09 (m, 1H), 2.41 (s, 3H), 2.36-2.28 (m, 1H), 1.31-1.28 (m, 1H), 1.07-1.00 (m, 2H).

Example 4.1 was purified by Chiral-Prep-HPLC with the following conditions (Prep-SFC80): Column, Chiralpak IC, 2*25 cm, 5 um; mobile phase, CO$_2$ and EtOH (0.2% DEA) (hold 65% CO$_2$ in 13 mins); Detector, UV 220 nm to afford two enantiomers.

Peak (9.93 min): Enantiomer 1 (1.09 g, 10%). LCMS (ESI): M+H$^+$=361.0; 1H NMR (300 MHz, CDCl$_3$) δ 7.03-6.87 (m, 4H), 6.46 (s, 1H), 4.91 (s, 2H), 4.08-4.03 (m, 1H), 3.16-3.08 (m, 1H), 2.40 (s, 3H), 2.31-2.23 (m, 1H), 1.32-1.26 (m, 1H), 1.07-0.96 (m, 2H).

Peak (11.06 min): Enantiomer 2 (0.96 g, 10%). LCMS (ESI): M+H$^+$=361.0; $^1$H NMR (300 MHz, CDCl$_3$) δ 7.02-6.89 (m, 4H), 6.47 (s, 1H), 4.91 (s, 2H), 4.08-4.03 (m, 1H), 3.16-3.09 (m, 1H), 2.40 (s, 3H), 2.30-2.28 (m, 1H), 1.30-1.25 (m, 1H), 1.07-1.01 (m, 2H).

The following examples were prepared in a manner similar to Example 4.1, 4.2, and 4.3:

| No. | Structure/Name | LCMS (M + H) | $^1$H NMR |
|---|---|---|---|
| 4.4 | 7-((3-fluorophenoxy)methyl)-3-(trans-2-(hydroxymethyl)cyclopropyl)-2-methyl-5H-thiazolo[3,2-a]pyrimidin-5-one | 361.0 | $^1$H NMR (300 MHz, CDCl$_3$) δ 7.26-7.21 (m, 1H), 6.76-6.64 (m, 3H), 6.45 (s, 1H), 4.93 (s, 2H), 4.08-4.03 (m, 1H), 3.16-3.09 (m, 1H), 2.39 (s, 3H), 2.32-2.26 (m, 1H), 1.31-1.23 (m, 1H), 1.07-0.97 (m, 2H) |
| 4.5 | 7-((4-fluorophenoxy)methyl)-2-methyl-3-(pyrimidin-5-yl)-5H-thiazolo[3,2-a]pyrimidin-5-one | 369.1 | $^1$H NMR (300 MHz, CDCl$_3$) δ 9.26 (s, 1H), 8.69 (s, 2H), 7.01-6.87 (m, 4H), 6.40 (s, 1H), 4.94 (s, 2H), 2.29 (s, 3H) |
| 4.6 | 7-(2,4-Difluorophenoxymethyl)-3-[trans-2-(hydroxymethyl)cyclopropyl]-2-methyl-5H-[1,3]thiazolo[3,2-a]pyrimidin-5-one | 379.10 | $^1$H NMR (300 MHz, CDCl$_3$) δ 6.95-6.86 (m, 2H), 6.81-6.74 (m, 1H), 6.50 (s, 1H), 4.96 (s, 2H), 4.08-4.03 (m, 2H), 3.15-3.08 (m, 1H), 2.41 (s, 3H), 2.40-2.27 (m, 1H), 1.30-1.25 (m, 1H), 1.07-0.96 (m, 2H) |

| No. | Structure/Name | LCMS (M + H) | ¹H NMR |
|---|---|---|---|
| 4.7 | 7-(3,4-Difluorophenoxymethyl)-3-[trans-2-(hydroxymethyl)cyclopropyl]-2-methyl-5H-[1,3]thiazolo[3,2-a]pyrimidin-5-one | 379.25 | ¹H NMR (300 MHz, CDCl₃) δ 7.14-7.05 (m, 1H), 6.82-6.75 (m, 1H), 6.68-6.64 (m, 1H), 6.43 (s, 1H), 4.90 (s, 1H), 4.10-4.05 (m, 1H), 3.16-3.09 (m, 1H), 2.41 (s, 3H), 2.37-2.29 (m, 1H), 1.34-1.27 (m, 2H), 1.08-0.98 (m, 2H) |
| 4.8 | 7-(4-Chlorophenoxymethyl)-3-[trans-2-(hydroxymethyl)cyclopropyl]-2-methyl-5H-[1,3]thiazolo[3,2-a]pyrimidin-5-one | 377.0 | ¹H NMR (300 MHz, CDCl₃) δ 7.26-7.24 (m, 2H), 6.91-6.87 (m, 2H), 6.45 (s, 1H), 4.97 (s, 2H), 4.11-4.03 (m, 1H), 3.16-3.09 (m, 1H), 2.43 (s, 3H), 2.40-2.28 (m, 1H), 1.27-1.19 (m, 1H), 1.07-1.01 (m, 2H) |
| 4.9 | 7-[[(5-Fluoropyridin-2-yl)oxy]methyl]-3-[trans-2-(hydroxymethyl)cyclopropyl]-2-methyl-5H-[1,3]thiazolo[3,2-a]pyrimidin-5-one | 362.0 | ¹H NMR (300 MHz, CD₃OD) δ 8.02-8.01 (m, 1H), 7.60-7.59 (m, 1H), 7.01-6.97 (m, 1H), 6.27 (s, 1H), 5.25 (s, 2H), 3.64-3.60 (m, 2H), 2.45 (s, 3H), 2.23-2.17 (m, 1H), 1.41-1.32 (m, 1H), 1.07-1.01 (m, 2H) |
| 4.10 | 3-(trans-2-(hydroxymethyl)cyclopropyl)-2-methyl-7-((4-(trifluoromethyl)phenoxy)methyl)-5H-thiazolo[3,2-a]pyrimidin-5-one | 411.0 | ¹H NMR (300 MHz, CDCl₃) δ 7.60-7.56 (m, 2H), 7.04-7.01 (m, 2H), 6.45 (s, 1H), 5.04 (s, 2H), 4.07-4.02 (m, 1H), 3.17-3.13 (m, 1H), 2.41 (s, 3H), 2.34-2.27 (m, 1H), 1.30-1.26 (m, 1H), 1.08-1.01 (m, 2H). |

| No. | Structure/Name | LCMS (M + H) | ¹H NMR |
|---|---|---|---|
| 4.11 | 7-((4-fluorophenoxy)methyl)-2-methyl-3-(oxazol-2-yl)-5H-thiazolo[3,2-a]pyrimidin-5-one | 358.0 | ¹H NMR (300 MHz, CDCl₃) δ 7.85 (s, 1H), 7.34 (s, 1H), 7.01-6.86 (m, 4H), 6.42 (s, 1H), 4.93 (s, 2H), 2.37 (s, 3H). |
| 4.12 | 7-((2-fluorophenoxy)methyl)-3-(trans-2-(hydroxymethyl)cyclopropyl)-2-methyl-5H-thiazolo[3,2-a]pyrimidin-5-one | 361.0 | ¹HNMR (300 MHz, CDCl₃) δ 7.17-6.96 (m, 4H), 6.57 (s, 1H), 5.08 (s, 2H), 4.09-4.08 (m, 1H), 3.20-3.15 (m, 1H), 2.44 (s, 3H), 2.32-2.17 (m, 1H), 1.31-1.28 (m, 1H), 1.09-1.02 (m, 2H) |
| 4.13 | 4-((3-(trans-2-(hydroxymethyl)cyclopropyl)-2-methyl-5-oxo-5H-thiazolo[3,2-a]pyrimidin-7-yl)methoxy)benzonitrile | 368.0 | ¹H NMR (300 MHz, DMSO-d₆) δ 7.82-7.79 (m, 2H), 7.23-7.20 (m, 2H), 6.22 (s, 1H), 5.07 (s, 2H), 4.59-4.55 (m, 1H), 3.48-3.44 (m, 2H), 2.37 (s, 3H), 2.05-2.01 (m, 1H), 1.33-1.25 (m, 1H), 0.89-0.86 (m, 2H) |
| 4.14 | 7-((4-fluorophenoxy)methyl)-3-(trans-2-(hydroxymethyl)cyclopropyl)-5H-thiazolo[3,2-a]pyrimidin-5-one | 347.1 | ¹H NMR (400 MHz, DMSO-d₆) δ 7.18-7.10 (m, 2H), 7.10-7.03 (m, 2H), 7.02 (s, 1H), 6.23 (s, 1H), 4.97 (s, 2H), 4.43 (dd, J = 6.6, 4.6 Hz, 1H), 3.55-3.36 (m, 2H), 2.63-2.54 (m, 1H), 1.41-1.26 (m, 1H), 1.01 (dt, J = 8.5, 5.2 Hz, 1H), 0.87 (dt, J = 8.4, 5.2 Hz, 1H). |

| No. | Structure/Name | LCMS (M + H) | $^1$H NMR |
|---|---|---|---|
| 4.15 | 7-((4-fluorophenoxy)methyl)-2-methyl-3-(1H-pyrazol-5-yl)-5H-thiazolo[3,2-a]pyrimidin-5-one | 357.1 | $^1$H NMR (400 MHz, DMSO-d$_6$) δ 12.97 (s, 1H), 7.78 (s, 1H), 7.19-7.09 (m, 2H), 7.09-6.97 (m, 2H), 6.47-6.26 (m, 1H), 6.16 (s, 1H), 4.99 (s, 2H), 2.20 (s, 3H). |
| 4.16 | 7-((4-fluorophenoxy)methyl)-2-methyl-3-(4H-1,2,4-triazol-3-yl)-5H-thiazolo[3,2-a]pyrimidin-5-one | 358.1 | $^1$H NMR (400 MHz, DMSO-d$_6$) δ 9.64 (s, 1H), 7.18-7.08 (m, 2H), 7.08-7.00 (m, 2H), 6.19 (s, 1H), 5.01 (s, 2H), 2.22 (d, J = 13.2 Hz, 3H). |
| 4.17 | 3-cyclopropyl-7-[(4-fluorophenoxy)methyl]-2-methyl-thiazolo[3,2-a]pyrimidin-5-one | 331.1 | $^1$H NMR (400 MHz, DMSO-d$_6$) δ 7.20-7.09 (m, 2H), 7.09-6.96 (m, 2H), 6.18 (s, 1H), 4.94 (s, 2H), 2.35 (d, J = 1.5 Hz, 3H), 2.16 (tdd, J = 8.5, 5.1, 1.9 Hz, 1H), 0.99-0.87 (m, 2H), 0.75-0.58 (m, 2H). |

Example 4.18: cis-2-[7-(4-Fluorophenoxymethyl)-2-methyl-5-oxo-5H-[1,3]thiazolo[3,2-a]pyrimidin-3-yl]cyclopropane-1-carbonitrile Example 4.18A trans-2-[7-(4-Fluorophenoxymethyl)-2-methyl-5-oxo-5H-[13]thiazolo[3,2-a]pyrimidin-3-yl]cyclopropane-1-carbonitrile

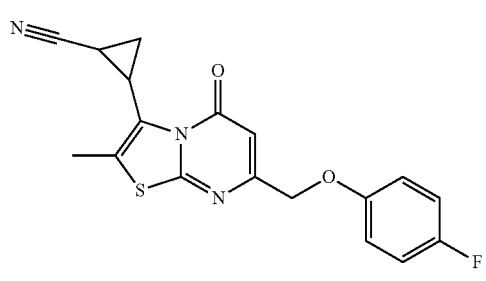 [SMILES: Cc1sc2nc(COc3ccc(F)cc3)cc(=O)n2c1C1CC1C#N]

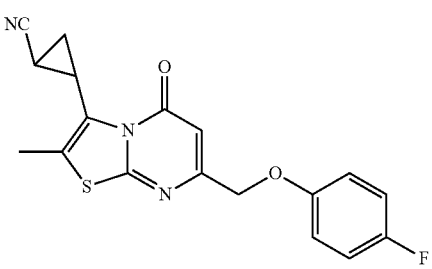 [SMILES: Cc1sc2nc(COc3ccc(F)cc3)cc(=O)n2c1C1CC1C#N]

and

Step 1: Ethyl 2-(4,4,5,5-tetramethyl-1,3,2-dioxaborolan-2-yl)cyclopropanecarboxylate

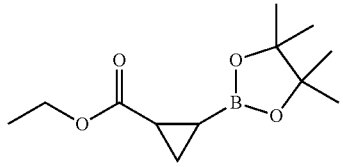 [SMILES: CCOC(=O)C1CC1B1OC(C)(C)C(C)(C)O1]

To a solution of 2-ethenyl-4,4,5,5-tetramethyl-1,3,2-dioxaborolane (10.0 g, 4.38 mmol) and palladium acetate (166 mg, 0.44 mmol) in ether (50 mL) was added ethyl 2-diazoacetate (6.60 g, 5.47 mmol) in ether (20 mL) dropwise for 10 min at room temperature. Palladium acetate (166 mg, 0.44 mmol) and ethyl 2-diazoacetate (6.60 g, 5.47 mmol) in ether (20 mL) were again added dropwise for another 10 min. The resulting solution was then stirred for 1 h at room temperature. After filtration through active aluminum oxide, the filtrate was concentrated in vacuo to afford ethyl 2-(tetramethyl-1,3,2-dioxaborolan-2-yl)cyclopropane-1-carboxylate as yellow oil (24.0 g). The crude product was used in the next step without further purification.

Step 2: Ethyl 2-[7-(4-fluorophenoxymethyl)-2-methyl-5-oxo-5H-[1,3]thiazolo[3,2-a]pyrimidin-3-yl]cyclopropane-1-carboxylate

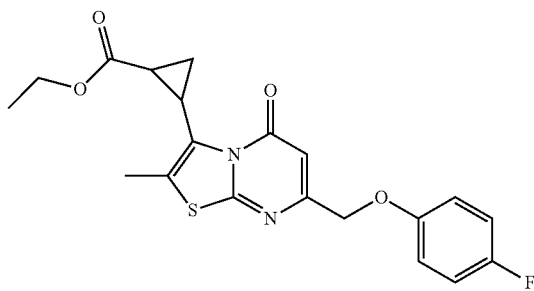 [SMILES: CCOC(=O)C1CC1c1c(C)sc2nc(COc3ccc(F)cc3)cc(=O)n12]

To a solution of 3-bromo-7-(4-fluorophenoxymethyl)-2-methyl-5H-[1,3]thiazolo[3,2-a]pyrimidin-5-one (from Example 4.1, Step 7) (500 mg, 1.35 mmol), ethyl 2-(4,4,5,5-tetramethyl-1,3-dioxolan-2-yl)cyclopropane-1-carboxylate (2.25 g, 6.37 mmol) and potassium carbonate (697 mg, 5.20 mmol) in 5:1 acetonitrile/water (12 mL) was added 1,1'-bis(diphenylphosphino)ferrocenepalladium dichloride (54.7 mg, 0.06 mmol). The resulting solution was stirred for 1 h at 120° C. in a 20-mL microwave tube. The process was then scaled up to 5 g (10 batches) using the same method. After concentration in vacuo, the residue was purified by chromatography with ethyl acetate/petroleum ether (1/2) to afford ethyl 2-[7-(4-fluorophenoxymethyl)-2-methyl-5-oxo-5H-[1,3]thiazolo[3,2-a]pyrimidin-3-yl]cyclopropane-1-carboxylate as a red oil (1.50 g, 28%). LCMS (ESI): M+H$^+$= 403.0.

Step 3: 2-[7-(4-Fluorophenoxymethyl)-2-methyl-5-oxo-5H-[1,3]thiazolo[3,2-a]pyrimidin-3-yl]cyclopropane-1-carboxylic acid

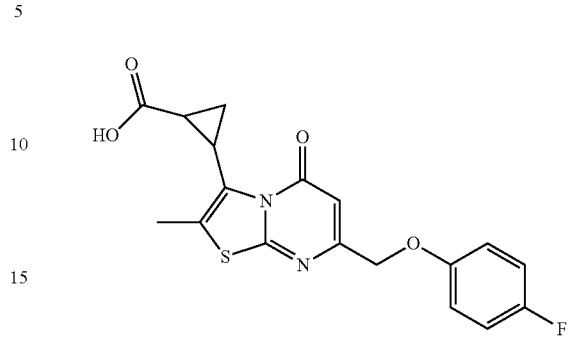

To a solution of ethyl 2-[7-(4-fluorophenoxymethyl)-2-methyl-5-oxo-5H-[1,3]thiazolo[3,2-a]pyrimidin-3-yl]cyclopropane-1-carboxylate (1.50 g, 3.75 mmol) in tetrahydrofuran/water (100/10 mL) was added lithium hydroxide (850 mg, 35.5 mmol) and the solution was stirred overnight at room temperature. The pH value of the solution was adjusted to 4-5 with hydrogen chloride (1 mol/L). The resulting solution was extracted with ethyl acetate (2×200 mL) and dried over anhydrous magnesium sulfate. After filtration, the filtrate was concentrated in vacuo to afford 2-(7-[[ethyl(4-fluorophenyl)amino]methyl]-2-methyl-5-oxo-5H-[1,3]thiazolo[3,2-a]pyrimidin-3-yl)cyclopropane-1-carboxylic acid as a yellow oil (800 mg, 57%). LCMS (ESI): M+H$^+$=375.0.

Step 4: 2-(7-((4-fluorophenoxy)methyl)-2-methyl-5-oxo-5H-thiazolo[3,2-a]pyrimidin-3-yl)cyclopropanecarboxamide

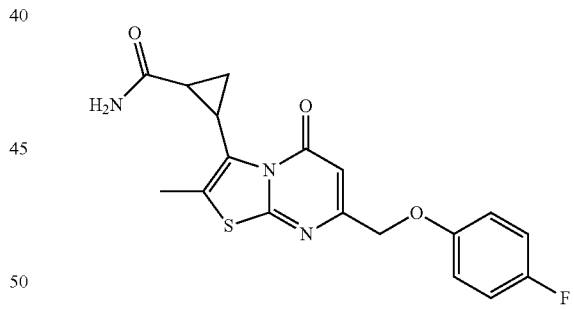

To a solution of 2-[7-(4-fluorophenoxymethyl)-2-methyl-5-oxo-5H-[1,3]thiazolo[3,2-a]pyrimidin-3-yl]cyclopropane-1-carboxylic acid (800 mg, 2.25 mmol), triethylamine (325 mg, 3.25 mmol,) in tetrahydrofuran (100 mL) was added propan-2-ylchloroformate (325 mg, 2.75 mmol). The solution was stirred for 20 min at room temperature. Then ammonium hydroxide (10 mL, 2.60 mmol) was added and the solution was stirred for an additional 20 min at room temperature. The resulting solution was extracted with ethyl acetate (2×100 mL), washed with brine, dried over anhydrous magnesium sulfate and concentrated in vacuo. The residue was purified by chromatography with 3% methanol in dichloromethane to afford 2-(7-((4-fluorophenoxy)methyl)-2-methyl-5-oxo-5H-thiazolo[3,2-a]pyrimidin-3-yl)cyclopropanecarboxamide as a white solid (500 mg, 62%).

Step 5: 2-(7-((4-fluorophenoxy)methyl)-2-methyl-5-oxo-5H-thiazolo[3,2-a]pyrimidin-3-yl)cyclopropanecarbonitrile

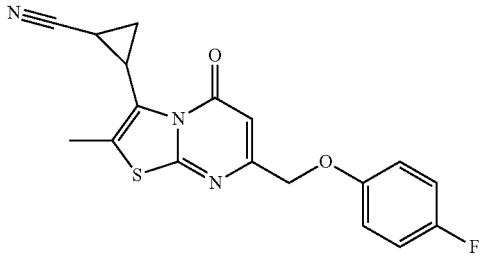 [SMILES: Cc1sc2nc(COc3ccc(F)cc3)cc(=O)n2c1C1CC1C#N]

To a solution of 2-(7-((4-fluorophenoxy)methyl)-2-methyl-5-oxo-5H-thiazolo[3,2-a]pyrimidin-3-yl)cyclopropanecarboxamide (500 mg, 1.20 mmol) in dichloromethane (100 mL) was added 1,8-diazabicyclo[5.4.0]undec-7-ene (100 mL) and ethyl dichlorophosphate (50 mL). After stirring for 30 min at room temperature, the reaction was quenched with water (50 mL) and extracted with dichloromethane (3×20 mL) and the combined organic layer was washed with brine, dried over anhydrous sodium sulfate and concentrated in vacuo. The residue was purified by preparative HPLC with the following conditions: (1#-Pre-HPLC-005(Waters)): Column, SunFire Prep $C_{18}$ OBD Column, 5 um, 19*150 mm; mobile phase, water with 10 mmol $NH_4HCO_3$ and $CH_3CN$ (50.0% $CH_3CN$ up to 82.0% in 10 min, down to 50.0% in 2 min); Detector, UV 254/220 nm to afford the cis (Example 4.18; 200 mg, 42%) and trans (Example 4.18A; 60 mg, 12%) isomers.

Example 4.18

LCMS (ESI): M+H$^+$=356.2; $^1$H NMR (300 Mhz, CD$_3$OD) δ 7.07-7.01 (M, 4H), 6.40 (s, 1H), 4.97 (s, 2H), 3.10-2.92 (m, 1H), 2.42 (s, 3H), 2.05-1.96 (m, 1H), 1.84-1.77 (m, 1H), 1.62-1.55 (m, 1H).

Examples 4.19 and 4.20

The racemic cis isomer (Ex. 4.18) was purified by Chiral-Prep-HPLC with the following conditions (Prep-HPLC-032): Column, Chiralpak IA, 2*25 cm, 5 um; mobile phase, Hex (1% TEA)/EtOH (hold 50.0% EtOH in 12 mins), flow, 1.0 mL/min; Detector, UV 254 nm to afford two enantiomers.

Example 4.19: Cis Enantiomer 1

Obtained as a white solid (58.6 mg, 16%). Chrial-Prep-HPLC retention time, 6.48 min; LCMS(ESI): M+H$^+$=356.2; $^1$H NMR (400 MHz, CDCl$_3$) δ 7.03-7.00 (m, 2H), 6.92-6.89 (m, 2H), 6.46 (s, 1H), 4.90 (s, 2H), 3.02-3.01 (m, 1H), 2.42 (s, 3H), 1.88-1.83 (m, 1H), 1.74-1.69 (m, 1H), 1.48-1.42 (m, 1H).

Example 4.20: Cis Enantiomer 2

Obtained as a white solid (67.8 mg, 19%). Chrial-Prep-HPLC retention time, 8.80 min; LCMS (ESI): M+H$^+$=356.2; $^1$H NMR (300 MHz, CD$_3$OD) δ 7.08-7.01 (m, 4H), 6.40 (s, 1H), 4.96 (s, 2H), 2.98-2.94 (m, 1H), 2.42 (s, 3H), 2.05-1.96 (m, 1H), 1.84-1.77 (m, 1H), 1.62-1.55 (m, 1H).

Examples 4.21 and 4.22

The racemic trans isomer (Ex. 4.18A) was purified by Chiral-Prep-HPLC with the following conditions (Prep-HPLC-032): Column, Chiralpak IA, 2*25 cm, 5 um; mobile phase, Hex (1% TEA)/IPA (hold 50.0% IPA in 8 mins), flow, 1.0 mL/min; Detector, UV 254 nm to afford two enantiomers.

Example 4.21: Trans Enantiomer 1

Obtained as a white solid (7.1 mg, 1%). Chrial-Prep-HPLC retention time, 2.28 min; LCMS (ESI): M+H$^+$=356.2; $^1$H NMR (400 MHz, CDCl$_3$) δ 7.05-6.91 (m, 4H), 6.47 (s, 1H), 4.92 (s, 2H), 3.01-2.95 (m, 1H), 2.43 (s, 3H), 2.06-2.00 (m, 1H), 1.86-1.70 (m, 1H), 1.62-1.57 (m, 1H).

Example 4.22: Trans Enantiomer 2

Obtained (4.4 mg, 0.5%). Chrial-Prep-HPLC retention time, 3.97 min; LCMS (ESI): M+H$^+$=356.2; $^1$H NMR (400 MHz, CDCl$_3$) δ 7.05-6.93 (m, 2H), 6.95-6.91 (m, 2H), 6.47 (s, 1H), 4.92 (s, 2H), 3.01-2.95 (m, 1H), 2.43 (s, 3H), 2.06-2.66 (m, 1H), 1.86-1.80 (m, 1H), 1.60-1.52 (m, 1H).

Example 4.23: 7-(4-Fluorophenoxymethyl)-3-[cis-2-(hydroxymethyl)cyclopropyl]-2-methyl-5H-[1,3]thiazolo[3,2-a]pyrimidin-5-one

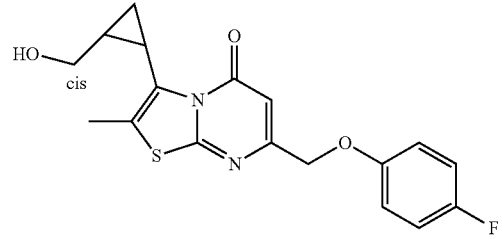 [SMILES: Cc1sc2nc(COc3ccc(F)cc3)cc(=O)n2c1C1CC1CO]

Step 1: tert-Butyldimethyl[[3-(tetramethyl-1,3,2-dioxaborolan-2-yl)prop-2-yn-1-yl]oxy]silane

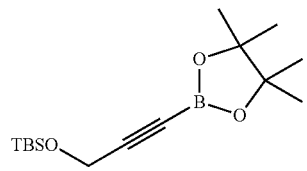 [SMILES: CC1(C)OB(C#CCO[Si](C)(C)C(C)(C)C)OC1(C)C]

To a solution of tert-butyldimethyl(prop-2-yn-1-yloxy)silane (200 mg, 1.17 mmol) in tetrahydrofuran (6 mL) was added 2.5 M n-butyl lithium (0.57 mL, 1.42 mmol) dropwise at −78° C. The resulting solution was stirred for 0.5 h at −78° C. Then 4,4,5,5-tetramethyl-2-(propan-2-yloxy)-1,3,2-dioxaborolane (230 mg, 1.24 mmol) was added dropwise at −78° C. The resulting solution was allowed to react for an additional 4 h while the temperature was maintained at −78° C. The reaction was then quenched by hydrogen chloride in ethyl ether (1 mol/L). After concentration in vacuo, the residue was diluted with ethyl ether (20 mL) and the solids were filtered off. The filtrate was concentrated to afford tert-butyldimethyl[[3-(tetramethyl-1,3,2-dioxaborolan-2-yl)prop-2-yn-1-yl]oxy]silane as a light yellow liquid (260 mg, 75%). ¹H NMR (300 MHz, CDCl₃) δ 4.35 (s, 2H), 1.27 (s, 12H), 0.90 (s, 9H), 0.12 (s, 6H).

Step 2: tert-butyldimethyl[[(2Z)-3-(tetramethyl-1,3,2-dioxaborolan-2-yl)prop-2-en-1-yl]oxy]silane

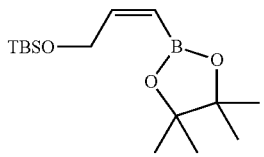 [SMILES: CC1(C)OB(/C=C\CO[Si](C)(C)C(C)(C)C)OC1(C)C]

To a suspension of bis(cyclopentadienyl)zirconium chloride hydride (230 mg, 0.88 mmol) in tetrahydrofuran (5 mL) was added tert-butyldimethyl[[3-(tetramethyl-1,3,2-dioxaborolan-2-yl)prop-2-yn-1-yl]oxy]silane (260 mg, 0.88 mmol) in tetrahydrofuran (2 mL) dropwise with stirring at room temperature. The resulting solution was stirred overnight at room temperature and then quenched by water (5 mL). The resulting mixture was stirred for an additional 1 h at room temperature and was extracted with dichloromethane (2×20 mL). The combined organic layers were washed with brine, dried over anhydrous sodium sulfate and concentrated in vacuo. The residue was purified by silica gel chromatography with ethyl acetate/petroleum ether (1/50) to afford tert-butyldimethyl[[(2Z)-3-(tetramethyl-1,3,2-dioxaborolan-2-yl)prop-2-en-1-yl]oxy]silane as a colorless oil (200 mg, 76%). ¹H NMR (400 MHz, CDCl₃) δ 6.58-6.47 (m, 1H), 5.35-5.30 (m, 1H), 4.34-4.33 (m, 2H), 1.27 (s, 12H), 0.90 (s, 9H), 0.12 (s, 6H).

Step 3: tert-Butyldimethyl[[2-(tetramethyl-1,3,2-dioxaborolan-2-yl)cyclopropyl]methoxy]silane

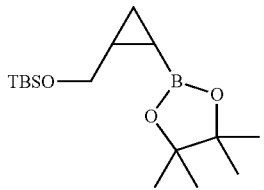 [SMILES: CC1(C)OB(C2CC2CO[Si](C)(C)C(C)(C)C)OC1(C)C]

Diethylzinc (1.0 M in hexanes) (4 mL, 4 mmol) was added to freshly distilled dichloromethane (4 mL) under nitrogen. Then trifluoroacetic acid (0.31 mL, 4.00 mmol) in dichloromethane (2 mL) was added dropwise at 0° C. Upon stirring for 20 min, a solution of diethylzinc in hexanes (0.32 mL, 4.00 mmol) in dichloromethane (2 mL) was added at 0° C. After an additional 20 min of stirring, a solution of tert-butyldimethyl[[(2Z)-3-(tetramethyl-1,3,2-dioxaborolan-2-yl)prop-2-en-1-yl]oxy]silane (600 mg, 2.01 mmol) in dichloromethane (2 mL) was added at 0° C. Then the resulting solution was stirred 1 h at room temperature and was quenched with water. The reaction was extracted with dichloromethane (100 mL×2), washed with brine, dried over anhydrous sodium sulfate and concentrated to afford tert-butyldimethyl((2-(4,4,5,5-tetramethyl-1,3,2-dioxaborolan-2-yl)cyclopropyl)methoxy)silane as a colorless oil (600 mg, 96%).

Step 4: Potassium cis-2-(hydroxymethyl)cyclopropyltrifluoroborate

To a solution of tert-butyldimethyl((2-(4,4,5,5-tetramethyl-1,3,2-dioxaborolan-2-yl)cyclopropyl)methoxy)silane (600 mg, 2.00 mmol) in methanol (4 mL) was added potassium difluoride (630 mg, 8 mmol) in water (2 mL) drop wise at 0° C. After stirred 1.5 h at room temperature, the reaction mixture was concentrated in vacuo. The resulting solid was suspended in acetone (20 mL) and refluxed 20 min. The heterogeneous mixture was then filtered to remove potassium difluoride and the filtrate was concentrated. The extraction process was repeated for the filtered solid. The combined filtrates were concentrated and dissolved in minimal acetone followed by the slow addition of ethyl ether until the solution become cloudy. The solids were collected by filtration and dried to afford the title compound as a white solid (150 mg, 43%).

Step 5: 7-(4-Fluorophenoxymethyl)-3-[cis-2-(hydroxymethyl)cyclopropyl]-2-methyl-5H-[1,3]thiazolo[3,2-a]pyrimidin-5-one

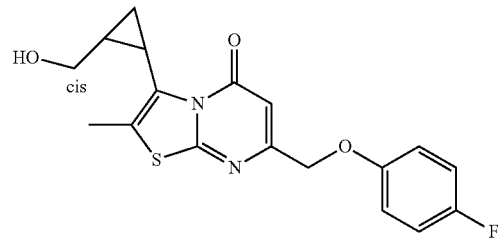 [SMILES: Cc1sc2nc(COc3ccc(F)cc3)cc(=O)n2c1C1CC1CO]

3-Bromo-7-(4-fluorophenoxymethyl)-2-methyl-5H-[1,3]thiazolo[3,2-a]pyrimidin-5-one (from Example 4.1, Step 7) (100 mg, 0.27 mmol,), 1,1'-bis(diphenylphosphino)ferrocene-palladium dichloride (20.0 mg, 0.03 mmol), sodium carbonate (60.0 mg, 0.57 mmol), potassium cis-2-(hydroxymethyl)cyclopropyltrifluoroborate (100 mg, 0.56 mmol), acetonitrile (3 mL) and water (0.5 mL) were placed in a 10-mL sealed tube. The final reaction mixture was heated in a microwave reactor for 1.5 h at 120° C. The mixture was extracted with dichloromethane (20 mL), washed with brine (10 mL), dried over anhydrous sodium sulfate and concentrated. The residue was purified by chromatography with ethyl acetate/petroleum ether (2:1) to give 7-(4-fluorophenoxymethyl)-3-[2-(hydroxymethyl)cyclopropyl]-2-methyl-5H-[1,3]thiazolo[3,2-a]pyrimidin-5-one as a white solid (23.5 mg, 24%). LCMS (ESI): M+H⁺=361.0; ¹H NMR (300 MHz, CDCl₃) δ 7.02-6.88 (m, 4H), 6.45 (s, 1H), 4.90 (s, 2H), 3.69-3.64 (m, 1H), 3.17-3.11 (m, 1H), 2.55-2.47 (m, 1H), 2.42 (s, 3H), 1.68-1.59 (m, 1H), 1.47-1.40 (m, 1H), 0.83-0.77 (m, 1H).

Example 4.24: trans-7-(4-Fluorophenoxymethyl)-2-methyl-3-[2-(trifluoromethyl)cyclopropyl]-5H-[1,3]thiazolo[3,2-a]pyrimidin-5-one

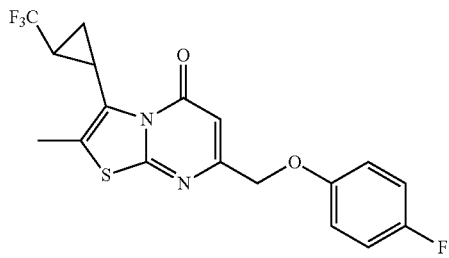 [SMILES: Cc1sc2nc(COc3ccc(F)cc3)cc(=O)n2c1C1CC1C(F)(F)F]

Step 1: 2-Diazo-1,1,1-trifluoroethane

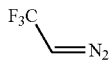

To a solution of 2,2,2-trifluoroethan-1-amine hydrochloride (3.24 g, 23.9 mmol) in water (5 mL) and ethyl ether (10 mL) was added dropwise a solution of sodium nitrite (1.84 g, 26.7 mmol) in water (2 mL). The resulting solution was stirred for 3 h at room temperature. The solids were filtered out to afford 2-diazo-1,1,1-trifluoroethane as a light yellow liquid (1.32 g, 51%). No LCMS signal.

Step 2: 4,4,5,5-Tetramethyl-2-[2-(trifluoromethyl)cyclopropyl]-1,3,2-dioxaborolane

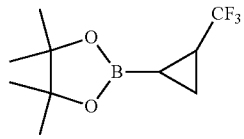 [SMILES: CC1(C)OB(C2CC2C(F)(F)F)OC1(C)C]

To a solution of 2-diazo-1,1,1-trifluoroethane (530 mg, 4.82 mmol) in ether (100 mL) was added palladium acetate (50.0 mg, 0.22 mmol). Then 2-ethenyl-4,4,5,5-tetramethyl-1,3,2-dioxaborolane (0.66 g, 4.29 mmol) and palladium acetate (50.0 mg, 0.22 mmol) were added with stirring over 20 min. After the resulting solution was stirred for 1 h at room temperature, the solids were filtered off. The resulting solution was concentrated in vacuo to afford 4,4,5,5-tetramethyl-2-[2-(trifluoromethyl)cyclopropyl]-1,3,2-dioxaborolane as dark green oil (580 mg, 51%).

Step 3: trans-7-(4-Fluorophenoxymethyl)-2-methyl-3-[2-(trifluoromethyl)cyclopropyl]-5H-[1,3]thiazolo[3,2-a]pyrimidin-5-one

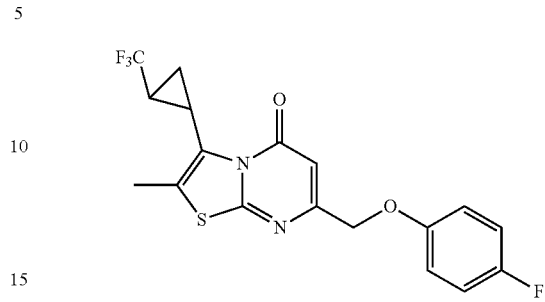

To a solution of 4,4,5,5-tetramethyl-2-[2-(trifluoromethyl)cyclopropyl]-1,3,2-dioxaborolane (384 mg, 1.63 mmol) in acetonitrile (3 mL) and water (1 mL) was added 3-bromo-7-(4-fluorophenoxymethyl)-2-methyl-5H-[1,3]thiazolo[3,2-a]pyrimidin-5-one (300 mg, 0.81 mmol), 1,1'-bis(diphenylphosphino)ferrocenepalladium dichloride (59 mg, 0.08 mmol) and sodium carbonate (12 mg). The resulting solution was stirred for 1.5 h at 120° C. under nitrogen atmosphere and then diluted with water (5 mL). After extraction with dichloromethane (3×30 mL), the combined organic layers were washed with brine, dried over anhydrous sodium sulfate and concentrated in vacuo. The crude product was purified by Prep-HPLC (Conditions: (Prep-HPLC-005): Column, Xbridge Prep $C_{18}$ OBD Column, 5 um, 19×150 mm; mobile phase, water with 10 mmol ammonium dicarbonate and acetonitrile (35.0% acetonitrile up to 59.0% in 10 min); Detector, UV 254/220 nm) to afford 7-(4-fluorophenoxymethyl)-2-methyl-3-[2-(trifluoromethyl)cyclopropyl]-5H-[1,3]thiazolo[3,2-a]pyrimidin-5-one as a white solid (4.40 mg, 1%). LCMS (ESI): M+H$^+$=399.2; $^1$H NMR (300 MHz, CDCl$_3$) δ 7.02-6.96 (m, 2H), 6.92-6.87 (m, 1H), 6.42 (s, 1H), 4.90 (s, 2H), 2.81-2.76 (m, 1H), 2.42 (s, 3H), 1.98-1.87 (m, 1H), 1.55-1.48 (m, 1H), 1.18-1.10 (m, 1H).

Example 4.25: 7-(4-Fluorophenoxymethyl)-2-methyl-3-(2-methylcyclopropyl)-5H-[1,3]thiazolo[3,2-a]pyrimidin-5-one

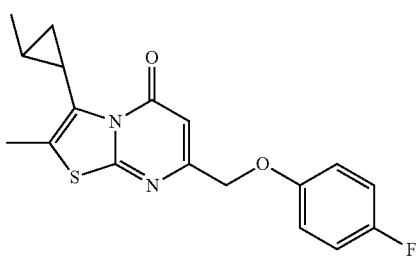 [SMILES: Cc1sc2nc(COc3ccc(F)cc3)cc(=O)n2c1C1CC1C]

Step 1: 4,4,5,5-Tetramethyl-2-(2-methylcyclopropyl)-1,3,2-dioxaborolane

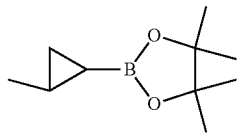

To a solution of 1 M diethylzinc in hexanes (0.36 mL, 0.36 mmol) in dichloromethane (4 mL) was added a solution of trifluoroacetic acid (408 mg, 3.58 mmol) in dichloromethane (4.0 mL), followed by a solution of diiodomethane (957 mg, 3.57 mmol) in dichloromethane (4.0 mL) under nitrogen and the reaction solution was stirred for 40 min at 0° C. Then a solution of 4,4,5,5-tetramethyl-2-[(1E)-prop-1-en-1-yl]-1,3,2-dioxaborolane (300 mg, 1.79 mmol) in dichloromethane (2 mL) was added and the reaction mixture was stirred for an additional 50 min at room temperature. The reaction was quenched by a saturated ammonium chloride solution (10 mL), extracted with petroleum ether (3×20 mL), washed with brine, dried with anhydrous sodium sulfate and concentrated in vacuo to afford 4,4,5,5-tetramethyl-2-(2-methylcyclopropyl)-1,3,2-dioxaborolane as a yellow solid (300 mg). The crude product was used in next step without further purification. LCMS (ESI): M+H$^+$=376.1; $^1$H NMR (300 MHz, CD$_3$OD) δ 1.21 (s, 12H), 1.08-1.06 (m, 3H), 0.95-0.91 (m, 1H), 0.69-0.65 (m, 1H), 0.38-0.32 (m, 1H), −0.42 to −0.47 (m, 1H).

Step 2: 7-(4-Fluorophenoxymethyl)-2-methyl-3-(2-methylcyclopropyl)-5H-[1,3]thiazolo[3,2-a]pyrimidin-5-one

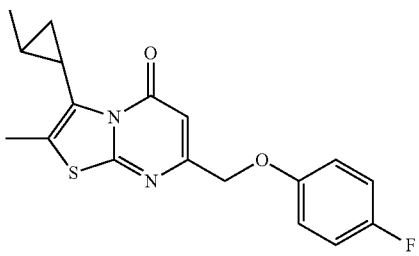 [SMILES: Cc1sc2nc(COc3ccc(F)cc3)cc(=O)n2c1C1CC1C]

To a solution of 3-bromo-7-(4-fluorophenoxymethyl)-2-methyl-5H-[1,3]thiazolo[3,2-a]pyrimidin-5-one (from Example 4.1, Step 7) (100 mg, 0.27 mmol) in acetonitrile/water (1.5/0.5 mL) was added 4,4,5,5-tetramethyl-2-(2-methylcyclopropyl)-1,3,2-dioxaborolane (100 mg, 0.55 mmol), 1,1'-bis(diphenylphosphino)ferrocenepalladium dichloride (20.3 mg, 0.03 mmol) and sodium carbonate (57.0 mg, 0.54 mmol). The reaction mixture was heated under microwave yridine ra for 90 min at 120° C. The reaction was then concentrated under vacuum and the resulting residue was purified by chromatography with dichloromethane/methanol (50/1) to afford 7-(4-fluorophenoxymethyl)-2-methyl-3-(2-methylcyclopropyl)-5H-[1,3]thiazolo[3,2-a]pyrimidin-5-one as an off-white solid (17.6 mg, 18%). LCMS (ESI): M+H$^+$=345.1; $^1$H NMR (300 MHz, CDCl$_3$) δ 7.01-6.95 (m, 2H), 6.91-6.86 (m, 2H), 6.38 (s, 1H), 4.88 (s, 2H), 2.36 (s, 3H), 1.94-1.90 (m, 1H), 1.24-1.22 (m, 3H), 1.03-0.95 (m, 1H), 0.93-0.85 (m, 2H).

Example 4.26: trans-2-[2-[7-(4-Fluorophenoxymethyl)-2-methyl-5-oxo-5H-[1,3]thiazolo[3,2-a]pyrimidin-3-yl]cyclopropyl]acetonitrile

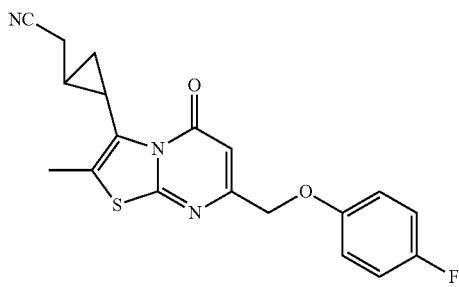 [SMILES: Cc1sc2nc(COc3ccc(F)cc3)cc(=O)n2c1C1CC1CC#N]

Step 1: [2-[7-(4-Fluorophenoxymethyl)-2-methyl-5-oxo-5H-[1,3]thiazolo[3,2-a]pyrimidin-3-yl]cyclopropyl]methylmethanesulfonate

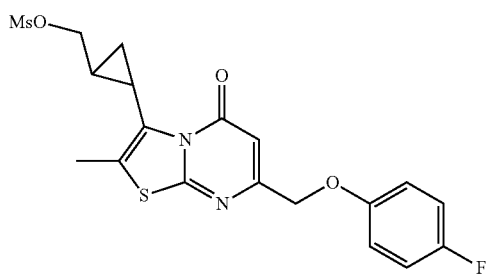 [SMILES: Cc1sc2nc(COc3ccc(F)cc3)cc(=O)n2c1C1CC1COS(C)(=O)=O]

To a solution of 7-((3-fluorophenoxy)methyl)-3-(trans-2-(hydroxymethyl)cyclopropyl)-2-methyl-5H-thiazolo[3,2-a]pyrimidin-5-one (from Example 4.1, Step 8) (40.0 mg, 0.11 mmol) in dichloromethane (51 mL) was added triethylamine (34.0 mg, 0.34 mmol) and methanesulfonyl chloride (38.0 mg). After stirring for 1 h at room temperature, the resulting mixture was concentrated in vacuo. The residue was purified by silica gel chromatography with 2% methanol in dichloromethane to afford [2-[7-(4-fluorophenoxymethyl)-2-methyl-5-oxo-5H-[1,3]thiazolo[3,2-a]pyrimidin-3-yl]cyclopropyl]methyl methanesulfonate as an off-white solid (40.0 mg, 82%). LCMS (ESI): M+H$^+$=439; $^1$H NMR (300 MHz, CDCl$_3$) δ 7.03-6.89 (m, 4H), 6.41 (s, 1H), 4.95 (s, 2H), 4.65-4.59 (s, 2H), 2.43 (s, 3H), 2.42-2.21 (m, 1H), 1.56-1.02 (m, 3H).

Step 2: trans-2-[2-[7-(4-Fluorophenoxymethyl)-2-methyl-5-oxo-5H-[1,3]thiazolo[3,2-a]pyrimidin-3-yl]cyclopropyl]acetonitrile

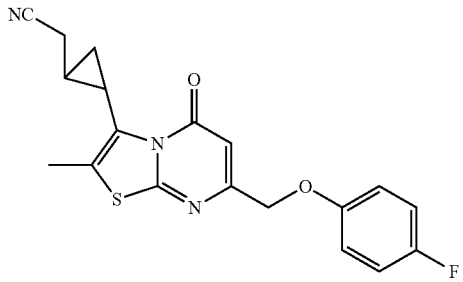 [SMILES: Cc1sc2nc(COc3ccc(F)cc3)cc(=O)n2c1C1CC1CC#N]

To a solution of [2-[7-(4-fluorophenoxymethyl)-2-methyl-5-oxo-5H-[1,3]thiazolo[3,2-a]pyrimidin-3-yl]cyclopropyl]methyl methanesulfonate (50.0 mg, 0.11 mmol) in dimethyl sulfoxide (5 mL) was added sodium cyanide (50.0 mg). The resulting solution was stirred for 1 h at 90° C. After cooling down to room temperature, the reaction mixture was diluted with dichloromethane (10 mL), washed with water (4×5 mL), dried over anhydrous sodium sulfate and concentrated in vacuo. The residue was purified by Prep-HPLC (Conditions: Column, SunFire Prep $C_{18}$ OBD Column, 5 um, 19*150 mm; mobile phase, Water with 10 mmol ammonium bicarbonate and acetonitrile (18.0% acetonitrile up to 28.0% in 10 min, up to 95.0% in 2 min, down to 18.0% in 2 min); Detector, UV 254/220 nm) to afford 2-[2-[7-(4-fluorophenoxymethyl)-2-methyl-5-oxo-5H-[1,3]thiazolo[3,2-a]pyrimidin-3-yl]cyclopropyl]acetonitrile as a white solid (8.90 mg, 21%). LCMS (ESI): M+H$^+$=370.0; $^1$H NMR (300 MHz, CDCl$_3$) δ 7.04-6.89 (m, 4H), 6.41 (s, 1H), 4.94 (s, 2H), 3.02-2.95 (m, 1H), 2.56-2.45 (m, 1H), 2.42 (s, 3H), 2.06-1.96 (m, 1H), 1.32-1.23 (m, 2H), 1.20-1.09 (m, 1H).

The following examples were prepared in a manner similar to Example 4.26:

| No. | Structure/Name | LCMS (M + H) | $^1$H NMR |
|---|---|---|---|
| 4.27 | ![structure] 7-(4-Fluorophenoxymethyl)-3-[2-(methoxymethyl)cyclopropyl]-2-methyl-5H-[1,3]thiazolo[3,2-a]pyrimidin-5-one | 375.1 | $^1$H NMR (300 MHz, CDCl$_3$) δ 7.01-6.96 (m, 2H), 6.92-6.87 (m, 2H), 6.39 (s, 1H), 4.91 (s, 2H), 3.69-3.64 (m, 1H), 3.38 (s, 3H), 3.32-3.12 (m, 1H), 2.42 (s, 3H), 2.19-2.16 (m, 1H), 1.45-1.34 (m, 1H), 1.13-1.07 (m, 1H), 0.98-0.92 (m, 1H) |
| 4.28 | ![structure] 3-(2-(fluoromethyl)cyclopropyl)-7-((4-fluorophenoxy)methyl)-2-methyl-5H-thiazolo[3,2-a]pyrimidin-5-one | 363.0 | $^1$H NMR (300 MHz, CDCl$_3$) δ 7.03-6.89 (m, 4H), 6.38 (s, 1H), 4.95 (s, 2H), 4.73-4.27 (m, 2H), 2.40 (s, 3H), 2.28-2.26 (m, 1H), 1.48-1.40 (m, 1H), 1.26-1.02 (m, 2H) |

Example 4.29: 6-fluoro-7-((4-fluorophenoxy)methyl)-3-(trans-2-(hydroxymethyl)cyclopropyl)-2-methyl-5H-thiazolo[3,2-a]pyrimidin-5-one

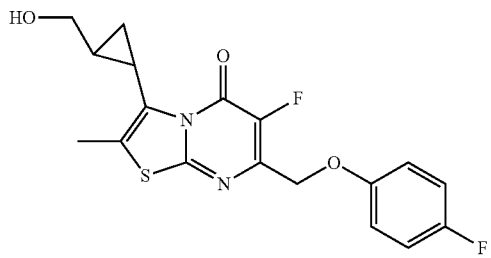 [SMILES: Cc1sc2nc(COc3ccc(F)cc3)c(F)c(=O)n2c1C1CC1CO]

Step 1: 3-bromo-7-(chloromethyl)-6-fluoro-2-methyl-5H-thiazolo[3,2-a]pyrimidin-5-one

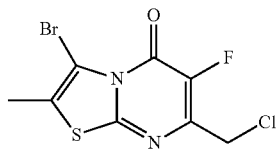

Into a 30-mL sealed tube purged and maintained with nitrogen was added a solution of 3-bromo-7-(chloromethyl)-2-methyl-5H-thiazolo[3,2-a]pyrimidin-5-one (from Example 4.1, Step 6) (500 mg, 1.70 mmol) in acetonitrile (20 mL) and 1-chloromethyl-4-fluoro-1,4-diazoniabicyclo[2.2.2]octane bis(tetrafluoroborate) (Selectfluor®; 600 mg, 1.69 mmol). The resulting solution was stirred for 3 h at 75° C. After cooling down to room temperature, the reaction mixture was concentrated in vacuo. The residue was purified by silica gel chromatography with dichloromethane to afford 3-bromo-7-(chloromethyl)-6-fluoro-2-methyl-5H-[1,3]thiazolo[3,2-a]pyrimidin-5-one as off-white solid (250 mg, 40%). LCMS (ESI): M+H$^+$=311.0, 313.0; $^1$H NMR (300 MHz, CDCl$_3$) δ 4.55 (s, 2H), 2.41 (s, 3H).

Step 2: 3-bromo-6-fluoro-7-((4-fluorophenoxy)methyl)-2-methyl-5H-thiazolo[3,2-a]pyrimidin-5-one

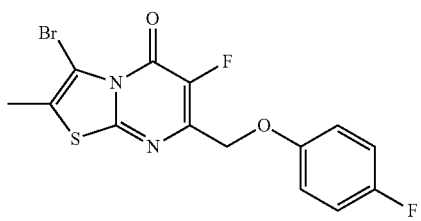 [SMILES: Cc1sc2nc(COc3ccc(F)cc3)c(F)c(=O)n2c1Br]

To a solution of 3-bromo-7-(chloromethyl)-6-fluoro-2-methyl-5H-[1,3]thiazolo[3,2-a]pyrimidin-5-one (300 mg, 0.96 mmol,) in acetonitrile (20 mL) was added potassium iodide (83.0 mg, 0.48 mmol), potassium carbonate (276 mg, 2.00 mmol) and 4-fluorophenol (224 mg, 2.00 mmol). The reaction mixture was stirred overnight at 80° C. After cooling down to room temperature, the reaction mixture was concentrated in vacuo. The residue was purified on a silica gel column with ethyl acetate/petroleum ether (1/2) to afford 3-bromo-6-fluoro-7-(4-fluorophenoxymethy)-2-methyl-5H-[1,3]thiazolo[3,2-a]pyrimidin-5-one as an off-white solid (50.0 mg, 11%). LCMS (ESI): M+H=387.0, 389.0.

Step 3: 6-fluoro-7-((4-fluorophenoxy)methyl)-3-(2-(hydroxymethyl)cyclopropyl)-2-methyl-5H-thiazolo[3,2-a]pyrimidin-5-one

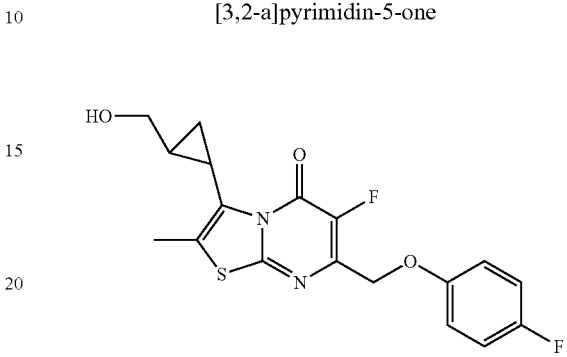

Into a 10-mL sealed tube purged and maintained with nitrogen was added a solution of 3-bromo-6-fluoro-7-(4-fluorophenoxymethyl)-2-methyl-5H-[1,3]thiazolo[3,2-a]pyrimidin-5-one (150 mg, 0.39 mmol) in acetonitrile/water (3/1 mL), 1,1'-bis(diphenylphosphino)ferrocene-palladium-dichloride (29.0 mg, 0.04 mmol), sodium carbonate (82.0 mg, 0.77 mmol) and potassium trans-2-(hydroxymethyl)cyclopropyltrifluoroborate (from Example 4.1, Step 2) (138 mg, 0.78 mmol). The reaction mixture was stirred for 1.5 h at 120° C. After cooling down to room temperature, the reaction mixture was concentrated in vacuo. The residue was purified on a silica gel column with dichloromethane/methanol (100/1) to afford 6-fluoro-7-((4-fluorophenoxy)methyl)-3-(trans-2-(hydroxymethyl)cyclopropyl)-2-methyl-5H-thiazolo[3,2-a]pyrimidin-5-one as off-white solid (26.1 mg, 18%). LCMS (ESI): M+H$^+$=379.0; $^1$H NMR (300 MHz, CDCl$_3$) δ 6.98-6.91 (m, 4H), 5.02 (s, 2H), 4.06-4.01 (m, 1H), 3.25-3.18 (m, 1H), 2.39 (s, 3H), 2.33-2.27 (m, 1H), 1.30-1.25 (m, 1H), 1.08-0.99 (m, 2H).

Example 4.30: 7-(4-Fluorophenoxymethyl)-3-(3-hydroxypropyl)-2-methyl-5H-[1,3]thiazolo[3,2-a]pyrimidin-5-one

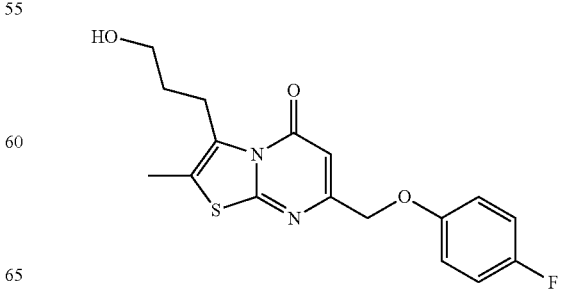

Step 1: Ethyl (E)-ethyl 3-(7-((4-fluorophenoxy)methyl)-2-methyl-5-oxo-5H-thiazolo[3,2-a]pyrimidin-3-yl)acrylate

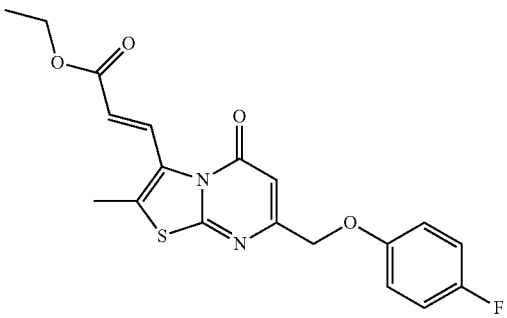 [SMILES: CCOC(=O)/C=C/c1c(C)sc2nc(COc3ccc(F)cc3)cc(=O)n12]

To a solution of 3-bromo-7-((3-fluorophenoxy)methyl)-2-methyl-5H-thiazolo[3,2-a]pyrimidin-5-one (from Example 4.1, Step 7) (205 mg, 0.56 mmol) in acetonitrile (5 mL) was added ethyl prop-2-enoate (110 mg, 1.10 mmol), tri-tolylphosphine (25 mg), tris(dibenzylideneacetone)dipalladium (33.0 mg, 0.04 mmol) and triethylamine (110 mg, 1.09 mmol). The reaction mixture was stirred overnight at 90° C. under a nitrogen atmosphere. After cooling down to room temperature, the reaction mixture was concentrated in vacuo and the residue was purified by chromatography with 3% ethyl acetate in petroleum ether to afford ethyl (E)-ethyl 3-(7-((4-fluorophenoxy)methyl)-2-methyl-5-oxo-5H-thiazolo[3,2-a]pyrimidin-3-yl)acrylate as an off-white solid (58.0 mg, 27%). LCMS (ESI): M+H$^+$=389.0.

Step 2: ethyl 3-(7-((4-fluorophenoxy)methyl)-2-methyl-5-oxo-5H-thiazolo[3,2-a]pyrimidin-3-yl)propanoate

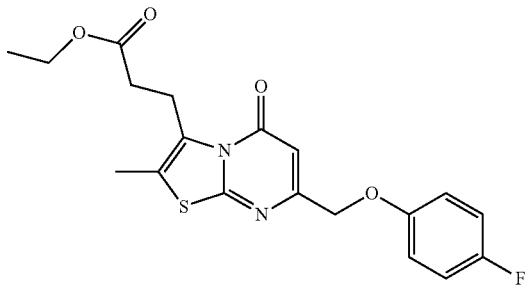 [SMILES: CCOC(=O)CCc1c(C)sc2nc(COc3ccc(F)cc3)cc(=O)n12]

To a solution of ethyl (E)-ethyl 3-(7-((4-fluorophenoxy)methyl)-2-methyl-5-oxo-5H-thiazolo[3,2-a]pyrimidin-3-yl)acrylate (58.0 mg, 0.15 mmol) in methanol (5 mL) was added palladium on carbon (50.0 mg). The reaction mixture was stirred overnight at room temperature under a hydrogen atmosphere (1.5 atm). After the solids were filtered off, the resulting mixture was concentrated in vacuo to afford ethyl 3-(7-((4-fluorophenoxy)methyl)-2-methyl-5-oxo-5H-thiazolo[3,2-a]pyrimidin-3-yl)propanoate (52.0 mg, 89%) as a white solid. LCMS (ESI): M+H$^+$=391.0.

Step 3: 7-(4-Fluorophenoxymethyl)-3-(3-hydroxypropyl)-2-methyl-5H-[1,3]thiazolo[3,2-a]pyrimidin-5-one

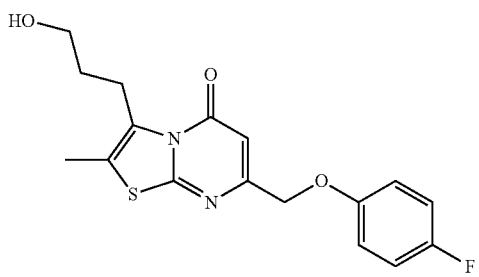 [SMILES: Cc1sc2nc(COc3ccc(F)cc3)cc(=O)n2c1CCCO]

To a solution of ethyl 3-[7-(4-fluorophenoxymethyl)-2-methyl-5-oxo-5H-[1,3]thiazolo[3,2-a]pyrimidin-3-yl]propanoate (42.0 mg, 0.11 mmol) in tetrahydrofuran (4 mL) and methanol (1 mL) was added lithium borohydride (23.0 mg). The reaction mixture was stirred overnight at room temperature. The reaction was then quenched with water (5 mL), extracted with dichloromethane (3×10 mL), washed with brine, dried over anhydrous sodium sulfate and concentrated in vacuo. The residue was purified by silica gel chromatography with 3% methanol in dichloromethane to afford 7-(4-Fluorophenoxymethyl)-3-(3-hydroxypropyl)-2-methyl-5H-[1,3]thiazolo[3,2-a]pyrimidin-5-one as a white solid (6.3 mg, 1.7%). LCMS (ESI): M+H$^+$=349.1; $^1$H NMR (300 MHz, CDCl$_3$,) δ 7.02-6.91 (m, 4H), 6.46 (s, 1H), 4.92 (s, 2H), 3.70-3.65 (m, 2H), 3.36-3.32 (m, 2H), 2.36 (s, 3H), 1.96-1.89 (m, 2H).

The following compounds were prepared using methods analogous to those described above:

| No. | Structure/Name | LCMS (M + H) | $^1$H NMR |
|---|---|---|---|
| 4.31 | 7-(4-Fluorophenoxymethyl)-3-(methoxymethyl)-2-methyl-5H-[1,3]thiazolo[3,2-a]pyrimidin-5-one | 335.20 | $^1$H NMR (300 MHz, CD$_3$OD) δ 7.08-6.98 (m, 4H), 6.39 (s, 1H), 5.01-4.96 (m, 4H), 3.41 (s, 3H), 2.49 (s, 3H). |

-continued

| No. | Structure/Name | LCMS (M + H) | ¹H NMR |
|---|---|---|---|
| 4.32 | 7-((4-fluorophenoxy)methyl)-3-(3-hydroxyoxetan-3-yl)-2-methyl-5H-thiazolo[3,2-a]pyrimidin-5-one | 363.1 | ¹H NMR (400 MHz, DMSO-d₆) δ 8.49 (s, 1H), 7.20-7.09 (m, 2H), 7.09-6.93 (m, 2H), 6.25 (s, 1H), 4.98 (s, 2H), 4.92 (d, J = 7.8 Hz, 2H), 4.63-4.45 (m, 2H), 2.26 (s, 3H). |
| 4.33 | 7-(4-Fluorophenoxymethyl)-3-(4-hydroxybutan-2-yl)-2-methyl-5H-[1,3]thiazolo[3,2-a]pyrimidin-5-one | 363.0 | ¹H NMR (400 MHz, DMSO-d₆) δ 7.03-6.98 (m, 2H), 6.93-6.90 (m, 2H), 6.46 (s, 1H), 5.06 (s, 1H), 4.94 (s, 2H), 3.70-3.66 (m, 1H), 3.57 (m, 1H), 2.46 (m, 4H), 2.08-1.92 (m, 2H), 1.36-1.33 (m, 3H) |
| 4.34 | 7-(4-Fluorophenoxymethyl)-3-[2-(2-hydroxypropan-2-yl)cyclopropyl]-2-methyl-5H-[1.3]thiazolo[3,2-a]pyrimidin-5-one | 371.1 | ¹H NMR (300 MHz, CDCl₃) δ 7.01-6.96 (m, 2H), 6.91-6.86 (m, 2H), 6.45 (s, 1H), 4.90 (s, 2H), 2.57-2.50 (m, 1H), 2.39 (s, 3H), 1.28 (s, 3H), 1.25-1.20 (m, 1H), 1.06 (s, 3H), 1.05-0.90 (m, 2H) |

Method 5

Example 5.1: 7-[(N-ethyl-4-fluoro-anilino)methyl]-2-methyl-3-pyrimidin-5-yl-thiazolo[3,2-a]pyrimidin-5-one

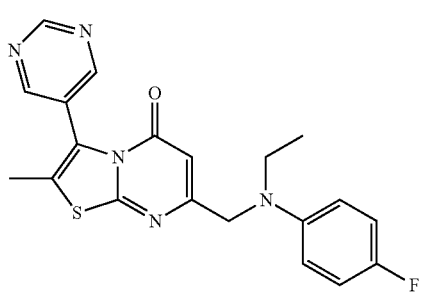

Step 1: 3-bromo-7-((ethyl(4-fluorophenyl)amino)methyl)-2-methyl-5H-thiazolo[3,2-a]pyrimidin-5-one

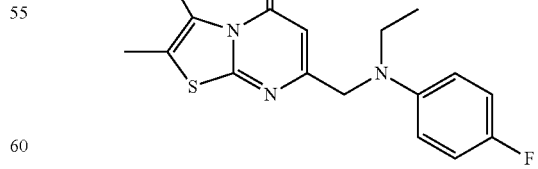

A mixture of 3-bromo-7-(chloromethyl)-2-methyl-5H-thiazolo[3,2-a]pyrimidin-5-one (from Example 4.1, Step 6) (30 g, 0.1 mol), N-ethyl-4-fluoroaniline (18.5 g, 0.13 mol), potassium carbonate (28.2 g, 0.2 mol) and sodium iodide (7.66 g, 0.05 mol) in acetonitrile was heated overnight at 80°

C. The mixture was then cooled to room temperature, diluted with a saturated aqueous solution of ammonium chloride (300 mL) and extracted with dichloromethane (200 mL×3). The combined organic layers were washed with water and brine, dried over sodium sulfate and concentrated. The residue was triturated with dichloromethane to give 3-bromo-7-((ethyl(4-fluorophenyl)amino)methyl)-2-methyl-5H-thiazolo[3,2-a]pyrimidin-5-one (21 g, 54%) as an off-white solid.

Step 2

7-[(N-ethyl-4-fluoro-anilino)methyl]-2-methyl-3-pyrimidin-5-yl-thiazolo[3,2-a]pyrimidin-5-one

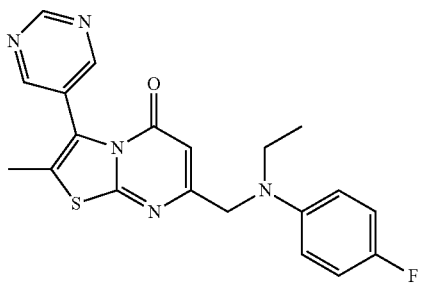 [SMILES: CCN(Cc1cc(=O)n2c(-c3cncnc3)c(C)sc2n1)c1ccc(F)cc1]

To a solution of 3-bromo-7-((ethyl(4-fluorophenyl)amino)methyl)-2-methyl-5H-thiazolo[3,2-a]pyrimidin-5-one (50 mg, 0.13 mmol) in acetonitrile/H$_2$O (1.3/0.5 mL) was added (pyrimidin-5-yl) boronic acid (20.3 mg, 0.16 mmol), sodium carbonate (40.5 mg, 0.379 mmol) and [1,1'-bis(diphenylphosphino)ferrocene]palladium(II) dichloride (9.7 mg, 0.013 mmol). The reaction mixture was heated under microwave irradiation for 20 min at 120° C. After cooling down room temperature, the resulting mixture was concentrated in vacuo. The residue was purified by silica gel chromatography with dichloromethane/methanol (95/5) to afford 7-[(N-ethyl-4-fluoro-anilino)methyl]-2-methyl-3-pyrimidin-5-yl-thiazolo[3,2-a]pyrimidin-5-one (14.8 mg, 30.0%) as an off-white solid. LCMS (ESI): M+H$^+$=396.1; 1H NMR (400 MHz, DMSO-d6) δ 9.18 (s, 1H), 8.83 (s, 2H), 6.98 (t, J=8.8 Hz, 2H), 6.62 (dd, J=9.2, 4.4 Hz, 2H), 5.85 (s, 1H), 4.36 (s, 2H), 3.47 (q, J=7.0 Hz, 2H), 2.22 (s, 3H), 1.13 (t, J=7.0 Hz, 3H).

The following examples were prepared in a manner similar to Example 5.1:

| No. | Structure/Name | LCMS (M + H) | $^1$H NMR |
|---|---|---|---|
| 5.2 | 7-(((4-fluorophenyl)(methyl)amino)methyl)-2-methyl-3-(pyrimidin-5-yl)-5H-thiazolo[3,2-a]pyrimidin-5-one | 382.1 | $^1$H NMR (300 MHz, CDCl$_3$) δ 9.90 (s, 1H), 9.24 (s, 2H), 6.96-6.88 (m, 2H), 6.63-6.59 (m, 2H), 6.07 (s, 1H), 4.35 (s, 2H), 3.06 (s, 3H), 2.25 (s, 3H). |
| 5.3 | 7-(((4-fluorophenyl)(2,2,2-trifluoroethyl)amino)methyl)-2-methyl-3-(pyrimidin-5-yl)-5H-thiazolo[3,2-a]pyrimidin-5-one | 450.1 | $^1$H NMR (300 MHz, CD$_3$OD) δ 9.13 (s, 1H), 8.76 (s, 2H), 6.94-6.86 (m, 2H), 6.79-6.75 (m, 2H), 5.97 (s, 1H), 5.54 (s, 2H), 4.25-4.16 (m, 2H), 2.25 (s, 3H). |

| No. | Structure/Name | LCMS (M + H) | ¹H NMR |
|---|---|---|---|
| 5.4 | 7-(((3,4-difluorophenyl)(ethyl)amino)methyl)-2-methyl-3-(pyrimidin-5-yl)-5H-thiazolo[3,2-a]pyrimidin-5-one | 413.8 | ¹H NMR (300 MHz, CD₃OD) δ 9.17 (s, 1H), 8.81 (s, 2H), 7.07-6.97 (m, 1H), 6.57-6.49 (m, 1H), 6.42-6.38 (m, 1H), 6.01 (s, 1H), 4.40 (s, 2H), 3.52 (m, 2H), 2.29 (s, 3H), 1.22 (m, 3H). |
| 5.5 | 7-((ethyl(3-fluorophenyl)amino)methyl)-2-methyl-3-(pyrimidin-5-yl)-5H-thiazolo[3,2-a]pyrimidin-5-one | 396.09 | ¹H NMR (400 MHz, DMSO-d₆) δ 9.19 (s, 1H), 8.84 (s, 2H), 7.15-7.12 (m, 1H), 6.47-6.39 (m, 3H), 5.84 (s, 1H), 4.42 (s, 2H), 3.51-3.49 (m, 2H), 2.23 (s, 3H), 1.16-1.13 (m, 3H). |
| 5.6 | 7-(((2,2-difluoroethyl)(4-fluorophenyl)amino)methyl)-2-methyl-3-(pyrimidin-5-yl)-5H-thiazolo[3,2-a]pyrimidin-5-one | 432.0 | ¹H NMR (300 MHz, CD₃OD) δ 9.20 (s, 1H), 8.89 (s, 2H), 6.90-6.77 (m, 2H), 6.30-5.93 (m, 2H), 4.63 (s, 2H), 3.93-3.83 (m, 2H), 2.29 (s, 3H). |
| 5.7 | 7-((ethyl(pyridine-2-yl)amino)methyl)-3-(trans-2-(hydroxymethyl)cyclopropyl)-2-methyl-5H-thiazolo[3,2-a]pyrimidin-5-one | 371.0 | ¹H NMR (300 MHz, CDCl₃) δ 8.15-8.13 (m, 1H), 7.48-7.42 (m, 1H), 6.60-6.50 (m, 2H), 6.10 (s, 1H), 4.61 (s, 2H), 4.24-4.21 (m, 1H), 4.07-4.01 (m, 1H), 3.62-3.55 (m, 2H), 3.10-3.03 (m, 1H), 2.37 (s, 3H), 2.27-2.25 (m, 1H), 1.26-1.21 (m, 4H), 1.05-0.95 (m, 2H). |

| No. | Structure/Name | LCMS (M + H) | ¹H NMR |
|---|---|---|---|
| 5.8 | 7-((ethyl(4-fluorophenyl)amino)methyl)-2-methyl-3-(thiazol-2-yl)-5H-thiazolo[3,2-a]pyrimidin-5-one | 401.0 | ¹H NMR (300 MHz, DMSO-$d_6$) δ 8.00-7.91 (m, 2H), 7.00-6.94 (m, 2H), 6.70-6.62 (m, 2H), 5.84 (s, 1H), 4.35 (s, 2H), 3.48-3.45 (m, 2H), 2.20 (s, 3H), 1.14-1.10 (m, 3H). |
| 5.9 | 7-((ethyl(4-fluorophenyl)amino)methyl)-2-methyl-3-(thiophen-2-yl)-5H-thiazolo[3,2-a]pyrimidin-5-one | 400.1 | ¹H NMR (300 MHz, CD$_3$OD) δ 7.61-7.59 (m, 1H), 7.11-7.07 (m, 2H), 6.92-6.85 (m, 2H), 6.67-6.62 (m, 2H), 6.00 (s, 1H), 4.36 (s, 2H), 3.52-3.49 (m, 2H), 2.24 (s, 3H), 1.21-1.18 (m, 3H). |
| 5.10 | 3-(ethyl((2-methyl-5-oxo-3-(pyrimidin-5-yl)-5H-thiazolo[3,2-a]pyrimidin-7-yl)methyl)amino)benzonitrile | 402.9 | ¹H NMR (300 MHz, CD$_3$OD) δ 9.06 (s, 1H), 8.71 (s, 2H), 7.23-7.18 (m, 1H), 6.87-6.84 (m, 3H), 5.88 (s, 1H), 4.38 (s, 2H), 3.52-3.45 (m, 2H), 2.19 (s, 3H), 1.19-1.12 (m, 3H). |
| 5.11 | 3-(2-aminopyridin-3-yl)-7-((ethyl(4-fluorophenyl)amino)methyl)-2-methyl-5H-thiazolo[3,2-a]pyrimidin-5-one | 409.8 | ¹H NMR (300 MHz, DMSO-$d_6$) δ 7.94-7.90 (m, 1H), 7.25-7.24 (m, 1H), 7.00-6.94 (m, 2H), 6.63-6.52 (m, 3H), 5.90 (br, 2H), 5.74 (s, 1H), 4.31 (s, 2H), 3.46-3.44 (m, 2H), 2.05 (s, 3H), 1.14-1.10 (m, 3H) |

| No. | Structure/Name | LCMS (M + H) | ¹H NMR |
|---|---|---|---|
| 5.12 | 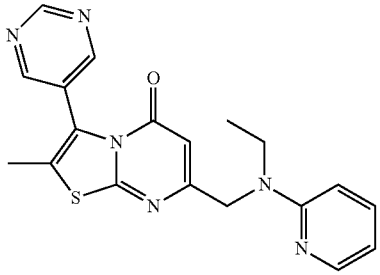 [SMILES: CCN(Cc1cc(=O)n2c(-c3cncnc3)c(C)sc2n1)c1ccccn1]<br>7-((ethyl(pyridine-2-yl)amino)methyl)-2-methyl-3-(pyrimidin-5-yl)-5H-thiazolo[3,2-a]pyrimidin-5-one | 379.0 | ¹H NMR (300 MHz, CD$_3$OD) δ 9.13 (s, 1H), 8.77 (s, 2H), 7.99-7.97 (m, 1H), 7.51-7.45 (m, 1H), 6.66-6.55 (m, 2H), 5.91 (s, 1H), 4.61 (s, 2H), 3.65-3.57 (m, 2H), 2.26 (s, 3H), 1.21-1.19 (m, 3H). |
| 5.13 | 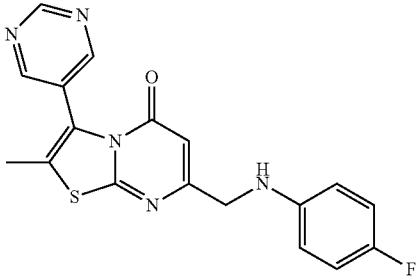 [SMILES: Cc1sc2nc(CNc3ccc(F)cc3)cc(=O)n2c1-c1cncnc1]<br>7-((4-fluorophenylamino)methyl)-2-methyl-3-(pyrimidin-5-yl)-5H-thiazolo[3,2-a]pyrimidin-5-one | 368.0 | ¹H NMR (300 MHz, CDCl$_3$) δ 9.25 (s, 1H), 8.72 (s, 2H), 6.95-6.86 (m, 2H), 6.69-6.65 (m, 2H), 6.23 (s, 1H), 4.25 (s, 2H), 2.32 (s, 3H). |
| 5.14 | 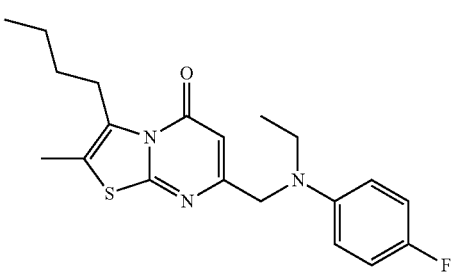 [SMILES: CCCCc1c(C)sc2nc(CN(CC)c3ccc(F)cc3)cc(=O)n12]<br>3-butyl-7-((ethyl(4-fluorophenyl)amino)methyl)-2-methyl-5H-thiazolo[3,2-a]pyrimidin-5-one | 374.1 | ¹H NMR (300 MHz, CD$_3$OD) δ 6.91-6.83 (m, 2H), 6.65-6.59 (m, 2H), 6.00 (s, 1H), 4.30 (s, 2H), 3.51-3.44 (m, 2H), 3.14-3.09 (m, 2H), 1.61-1.51 (m, 2H), 1.42-1.30 (m, 2H), 1.17-1.11 (m, 3H), 0.92-0.85 (m, 3H) |
| 5.15 | 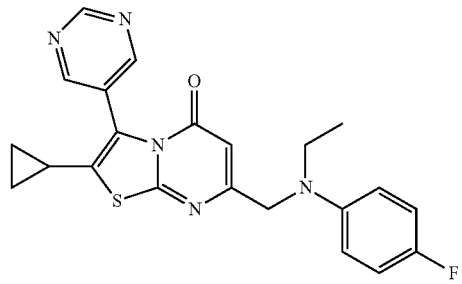 [SMILES: CCN(Cc1cc(=O)n2c(-c3cncnc3)c(C3CC3)sc2n1)c1ccc(F)cc1]<br>2-cyclopropyl-7-[(N-ethyl-4-fluoro-anilino)methyl]-3-pyrimidin-5-yl-thiazolo[3,2-a]pyrimidin-5-one | 422.1 | ¹H NMR (300 MHz, CD$_3$OD) δ 9.17 (s, 1H), 8.89 (s, 2H), 6.93-6.87 (m, 2H), 6.68-6.64 (m, 2H), 6.05 (s, 1H), 4.38 (s, 2H), 3.57-3.51 (m, 2H), 1.99-1.91 (m, 1H), 1.23-1.20 (m, 3H), 1.11-1.04 (m, 2H), 0.91-0.79 (m, 2H). |

| No. | Structure/Name | LCMS (M + H) | ¹H NMR |
|---|---|---|---|
| 5.16 | 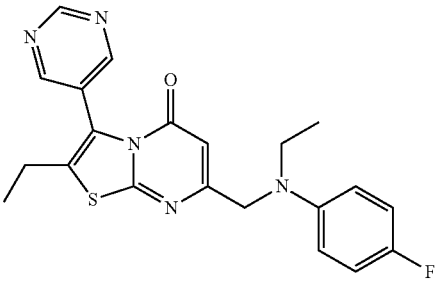 [SMILES: CCc1sc2nc(CN(CC)c3ccc(F)cc3)cc(=O)n2c1-c1cncnc1]<br>2-ethyl-7-((ethyl(4-fluorophenyl)amino)methyl)-3-(pyrimidin-5-yl)-5H-thiazolo[3,2-a]pyrimidin-5-one | 410.0 | ¹H NMR (300 MHz, CD$_3$OD) δ 9.18 (s, 1H), 8.82 (s, 2H), 6.92-6.89 (m, 2H), 6.68-6.64 (m, 2H), 6.04 (s, 1H), 4.39 (s, 2H), 3.37-3.34 (m, 2H), 2.69-2.67 (m, 2H), 1.29-1.14 (m, 6H). |
| 5.17 | 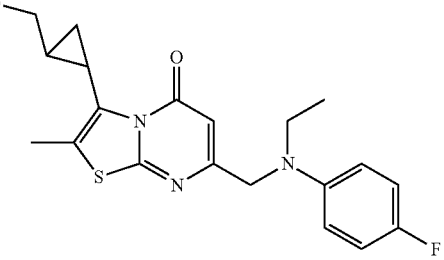<br>7-((ethyl(4-fluorophenyl)amino)methyl)-3-(trans-2-(hydroxymethyl)cyclopropyl)-2-methyl-5H-thiazolo[3,2-a]pyrimidin-5-one | 402.1 | ¹H NMR (300 MHz, CDCl$_3$) δ 6.94-6.77 (m, 2H), 6.58-6.34 (m, 2H), 6.19 (s, 1H), 4.28 (s, 2H), 4.17-4.03 (m, 2H), 3.50-3.43 (m, 2H), 3.08-3.05 (m, 1H), 2.38 (s, 3H), 2.29-2.24 (m, 1H), 1.29-1.19 (m, 4H), 1.06-0.94 (m, 2H) |
| 5.18 | 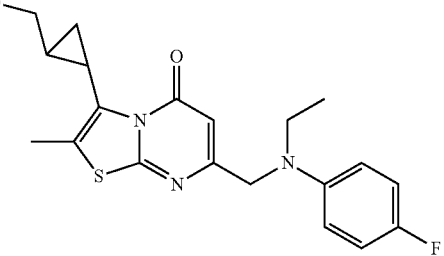<br>7-((ethyl(4-fluorophenyl)amino)methyl)-3-(trans-2-(hydroxymethyl)cyclopropyl)-2-methyl-5H-thiazolo[3,2-a]pyrimidin-5-one (enantiomer 1) | 402.1 | ¹H NMR (300 MHz, CDCl$_3$) δ 6.94-6.77 (m, 2H), 6.58-6.34 (m, 2H), 6.19 (s, 1H), 4.28 (s, 2H), 4.17-4.03 (m, 2H), 3.50-3.43 (m, 2H), 3.08-3.05 (m, 1H), 2.38 (s, 3H), 2.29-2.24 (m, 1H), 1.29-1.19 (m, 4H), 1.06-0.94 (m, 2H) |
| 5.19 | 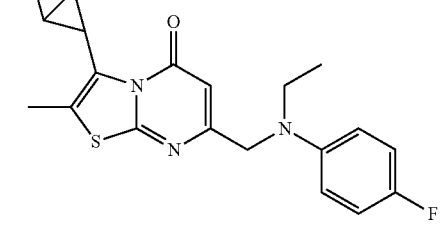<br>7-((ethyl(4-fluorophenyl)amino)methyl)-3-(trans-2-(hydroxymethyl)cyclopropyl)-2-methyl-5H-thiazolo[3,2-a]pyrimidin-5-one (enantiomer 2) | 402.1 | ¹H NMR (300 MHz, CDCl$_3$) δ 6.94-6.77 (m, 2H), 6.58-6.34 (m, 2H), 6.19 (s, 1H), 4.28 (s, 2H), 4.17-4.03 (m, 2H), 3.50-3.43 (m, 2H), 3.08-3.05 (m, 1H), 2.38 (s, 3H), 2.29-2.24 (m, 1H), 1.29-1.19 (m, 4H), 1.06-0.94 (m, 2H) |

| No. | Structure/Name | LCMS (M + H) | ¹H NMR |
|---|---|---|---|
| 5.20 | 7-[(N-ethyl-4-fluoro-anilino)methyl]-2-methyl-3-thiazol-4-yl-thiazolo[3,2-a]pyrimidin-5-one | 401.2 | |
| 5.21 | 7-[(N-ethyl-4-fluoro-anilino)methyl]-2-methyl-3-(3-pyridyl)thiazolo[3,2-a]pyrimidin-5-one | 395.1 | ¹H NMR (400 MHz, DMSO-$d_6$) δ 8.57 (dd, J = 5.0, 1.5 Hz, 1H), 8.54 (d, J = 2.0 Hz, 1H), 7.78 (dt, J = 8.1, 1.9 Hz, 1H), 7.42 (dd, J = 7.8, 5.0 Hz, 1H), 6.97 (t, J = 8.9 Hz, 2H), 6.62 (dd, J = 9.2, 4.3 Hz, 2H), 5.81 (s, 1H), 4.35 (s, 2H), 3.46 (q, J = 7.0 Hz, 2H), 2.16 (s, 3H), 1.13 (t, J = 6.9 Hz, 3H). |
| 5.22 | 7-[(N-ethyl-4-fluoro-anilino)methyl]-2-methyl-3-phenyl-thiazolo[3,2-a]pyrimidin-5-one | 394.1 | ¹H NMR (400 MHz, DMSO-$d_6$) δ 7.39 (d, J = 5.5 Hz, 3H), 7.32 (d, J = 5.2 Hz, 2H), 6.98 (t, J = 8.6 Hz, 2H), 6.62 (dd, J = 9.1, 4.3 Hz, 2H), 5.78 (s, 1H), 4.34 (s, 2H), 3.47 (q, J = 7.0 Hz, 2H), 2.13 (s, 3H), 1.13 (t, J = 7.0 Hz, 3H). |
| 5.23 | 7-[(N-ethyl-4-fluoro-anilino)methyl]-2,3-dimethyl-thiazolo[3,2-a]pyrimidin-5-one | 332.1 | ¹H NMR (400 MHz, DMSO-$d_6$) δ 6.98 (t, J = 8.6 Hz, 2H), 6.61 (dd, J = 9.0, 4.3 Hz, 2H), 5.81 (s, 1H), 4.30 (s, 2H), 3.47 (q, J = 7.0 Hz, 2H), 2.59 (s, 3H), 2.28 (s, 3H), 1.13 (t, J = 7.0 Hz, 3H). |

-continued

| No. | Structure/Name | LCMS (M + H) | ¹H NMR |
|---|---|---|---|
| 5.24 | 7-[(N-ethyl-4-fluoro-anilino)methyl]-3-(5-fluoro-3-pyridyl)-2-methyl-thiazolo[3,2-a]pyrimidin-5-one | 413.1 | ¹H NMR (400 MHz, DMSO-d₆) δ 8.62 (d, J = 2.6 Hz, 1H), 8.45 (s, 1H), 7.91-7.79 (m, 1H), 6.98 (t, J = 8.7 Hz, 2H), 6.62 (dd, J = 9.1, 4.3 Hz, 2H), 5.83 (s, 1H), 4.36 (s, 2H), 3.47 (q, J = 7.0 Hz, 2H), 2.19 (s, 3H), 1.13 (t, J = 6.9 Hz, 3H). |
| 5.25 | 7-[(N-ethyl-4-fluoro-anilino)methyl]-3-(2-fluoro-3-pyridyl)-2-methyl-thiazolo[3,2-a]pyrimidin-5-one | 412 | |
| 5.26 | 3-cyclopropyl-7-[(N-ethyl-fluoro-anilino)methyl]-2-methyl-thiazolo[3,2-a]pyrimidin-5-one | 358.1 | ¹H NMR (400 MHz, DMSO-d₆) δ 6.98 (t, J = 8.8 Hz, 2H), 6.61 (dd, J = 9.2, 4.3 Hz, 2H), 5.82 (s, 1H), 4.28 (s, 2H), 3.46 (q, J = 7.0 Hz, 2H), 2.34 (s, 3H), 2.14 (p, J = 7.4 Hz, 1H), 1.13 (t, J = 7.0 Hz, 3H), 0.97-0.88 (m, 2H), 0.72-0.60 (m, 2H). |
| 5.27 | 7-[(N-ethyl-4-fluoro-anilino)methyl]-2-methyl-3-pyrazin-2-yl-thiazolo[3,2-a]pyrimidin-5-one | 396.1 | |

| No. | Structure/Name | LCMS (M + H) | ¹H NMR |
|---|---|---|---|
| 5.28 | 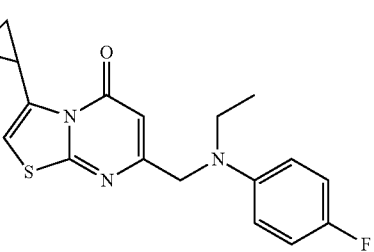<br>7-[(N-ethyl-4-fluoro-anilino)methyl]-3-[trans-2-(hydroxymethyl)cyclopropyl]thiazolo[3,2-a]pyrimidin-5-one | 374.1 | |
| 5.29 | 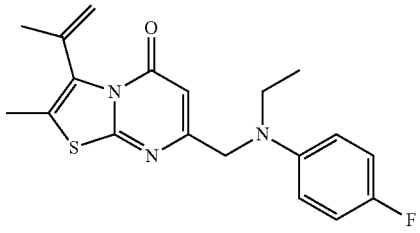 [SMILES: C=C(C)c1c(C)sc2nc(CN(CC)c3ccc(F)cc3)cc(=O)n12]<br>7-[(N-ethyl-4-fluoro-anilino)methyl]-3-isopropenyl-2-methyl-thiazolo[3,2-a]pyrimidin-5-one | 358.1 | ¹H NMR (400 MHz, DMSO-$d_6$) δ 6.98 (t, J = 8.6 Hz, 2H), 6.61 (dd, J = 9.0, 4.3 Hz, 2H), 5.86 (s, 1H), 5.35 (s, 1H), 5.00 (s, 1H), 4.33 (s, 2H), 3.47 (q, J = 7.0 Hz, 2H), 2.28 (s, 2H), 1.94 (s, 3H), 1.13 (t, J = 7.0 Hz, 3H). |
| 5.30 | 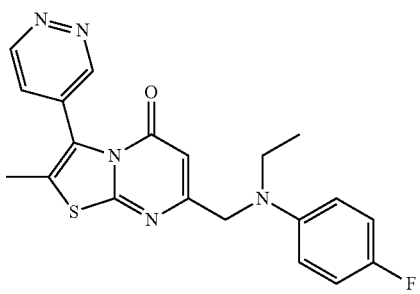 [SMILES: CCN(Cc1cc(=O)n2c(-c3ccnnc3)c(C)sc2n1)c1ccc(F)cc1]<br>7-[(N-ethyl-4-fluoro-anilino)methyl]-2-methyl-3-pyridazin-4-yl-thiazolo[3,2-a]pyrimidin-5-one | 396.1 | ¹H NMR (400 MHz, DMSO-$d_6$) δ 9.28 (d, J = 6.7 Hz, 1H), 9.22 (d, J = 1.5 Hz, 1H), 7.72 (d, J = 5.1 Hz, 1H), 7.03-6.91 (m, 2H), 6.69-6.55 (m, 2H), 5.87 (s, 1H), 4.36 (s, 2H), 3.47 (q, J = 7.0 Hz, 2H), 2.22 (s, 3H), 1.13 (t, J = 7.0 Hz, 3H). |
| 5.31 | 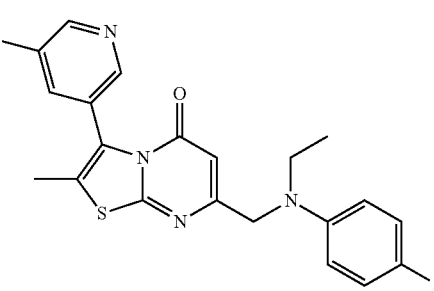<br>3-(5-chloro-3-pyridyl)-7-[(N-ethyl-4-fluoro-anilino)methyl]-2-methyl-thiazolo[3,2-a]pyrimidin-5-one | 429.1 | ¹H NMR (400 MHz, DMSO-$d_6$) δ 8.65 (d, J = 3.0 Hz, 1H), 8.54 (s, 1H), 8.03 (s, 1H), 6.98 (t, J = 8.7 Hz, 2H), 6.62 (dd, J = 9.2, 4.3 Hz, 2H), 5.83 (s, 1H), 4.36 (s, 2H), 3.47 (q, J = 7.0 Hz, 2H), 2.19 (s, 3H), 1.13 (t, J = 7.0 Hz, 3H). |

| No. | Structure/Name | LCMS (M + H) | ¹H NMR |
|---|---|---|---|
| 5.32 | 7-[(N-ethyl-4-fluoro-anilino)methyl]-2-methyl-3-(4-pyridyl)thiazolo[3,2-a]pyrimidin-5-one | 395.1 | |
| 5.33 | 7-[(N-ethyl-4-fluoro-anilino)methyl]-2-methyl-3-(1-methylpyrazol-4-yl)thiazolo[3,2-a]pyrimidin-5-one | 398.2 | |
| 5.34 | 7-[(N-ethyl-4-fluoro-anilino)methyl]-2-methyl-3-(1H-pyrazol-4-yl)thiazolo[3,2-a]pyrimidin-5-one | 384.1 | |
| 5.35 | 5-[7-[(N-ethyl-4-fluoro-anilino)methyl]-2-methyl-5-oxo-thiazolo[3,2-a]pyrimidin-3-yl]pyridine-3-carbonitrile | 420.1 | ¹H NMR (400 MHz, DMSO-$d_6$) δ 9.04 (s, 1H), 8.87 (d, J = 1.7 Hz, 1H), 8.41 (s, 1H), 6.98 (t, J = 8.7 Hz, 2H), 6.62 (dd, J = 9.3, 4.3 Hz, 2H), 5.84 (s, 1H), 4.36 (s, 2H), 3.47 (q, J = 7.0 Hz, 2H), 2.21 (s, 3H), 1.13 (t, J = 7.0 Hz, 3H). |

| No. | Structure/Name | LCMS (M + H) | ¹H NMR |
|---|---|---|---|
| 5.36 | 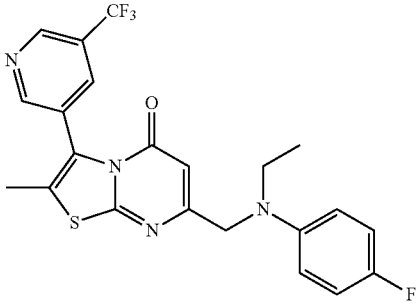 [SMILES: CCN(Cc1cc(=O)n2c(-c3cncc(C(F)(F)F)c3)c(C)sc2n1)c1ccc(F)cc1]  7-[(N-ethyl-4-fluoro-anilino)methyl]-2-methyl-3-[5-(trifluoromethyl)-3-pyridyl]thiazolo[3,2-a]pyrimidin-5-one | 463.1 | ¹H NMR (400 MHz, DMSO-$d_6$) δ 9.00 (s, 1H), 8.89 (s, 1H), 8.31 (s, 1H), 6.98 (t, J = 8.7 Hz, 2H), 6.62 (dd, J = 9.0, 4.1 Hz, 2H), 5.83 (s, 1H), 4.36 (s, 2H), 3.47 (q, J = 7.0 Hz, 2H), 2.20 (s, 3H), 1.13 (t, J = 7.0 Hz, 3H). |
| 5.37 | 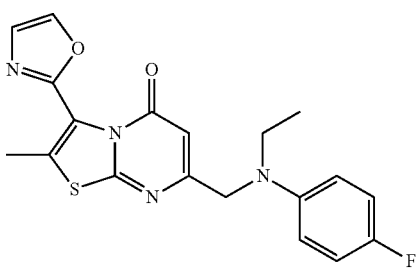 [SMILES: CCN(Cc1cc(=O)n2c(-c3ncco3)c(C)sc2n1)c1ccc(F)cc1]  7-[(N-ethyl-4-fluoro-anilino)methyl]-2-methyl-3-oxazol-2-yl-thiazolo[3,2-a]pyrimidin-5-one | 385.1 | ¹H NMR (300 MHz, CD₃OD) δ 8.09 (s, 1H), 7.38 (s, 1H), 6.94-6.88 (m, 2H), 6.69-6.65 (m, 2H), 6.09 (s, 1H), 4.40 (s, 2H), 3.56-3.51 (m, 2H), 2.36 (s, 3H), 1.24-1.19 (m, 3H) |

Example 5.38: 7-((ethyl(4-fluorophenyl)amino)methyl)-2-methyl-3-(trifluoromethyl)-5H-thiazolo[3,2-a]pyrimidin-5-one

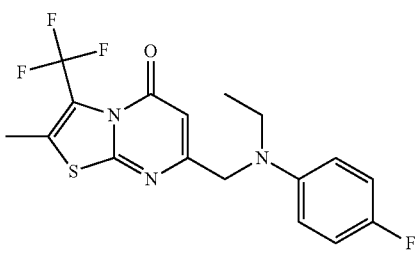 [SMILES: CCN(Cc1cc(=O)n2c(C(F)(F)F)c(C)sc2n1)c1ccc(F)cc1]

To a solution of 3-bromo-7-[[ethyl(4-fluorophenyl)amino]methyl]-2-methyl-5H-[1,3]thiazolo[3,2-a]pyrimidin-5-one (from Example 5.1, Step 1) (200 mg, 0.50 mmol) in N-methyl-pyrrolidone (5 mL) was added copper(I) iodide (12 mg, 0.06 mmol) and methyl 2,2-difluoro-2-(fluorosulfonyl)acetate (146 mg, 0.76 mmol). The reaction solution was stirred for 8 h at 120° C. The resulting mixture was concentrated in vacuo. The residue was purified by chromatography with ethyl acetate/petroleum ether (1/2) to afford 7-[[ethyl(4-fluorophenyl)amino]methyl]-2-methyl-3-(trifluoromethyl)-5H-[1,3]thiazolo[3,2-a]pyrimidin-5-one (21.1 mg, 11%) as a white solid. LCMS (ESI): M+H⁺=385.8; ¹H NMR (300 MHz, CDCl₃) δ 6.94-6.88 (m, 2H), 6.59-6.54 (m, 2H), 6.24 (s, 1H), 4.28 (s, 2H), 3.46-3.43 (m, 2H), 2.60-2.51 (m, 3H), 1.24-1.22 (m, 3H).

Example 5.39: 7-((ethyl(4-fluorophenyl)amino)methyl)-3-(trans-2-(fluoromethyl)cyclopropyl)-2-methyl-5H-thiazolo[3,2-a]pyrimidin-5-one

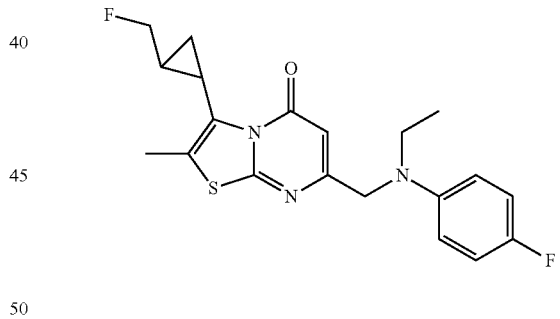

Step 1: (2-(7-((ethyl(4-fluorocyclohexa-2,4-dienyl)amino)methyl)-2-methyl-1-oxo-5H-thiazolo[3,2-a]pyrimidin-3-yl)cyclopropyl)methyl methanesulfonate

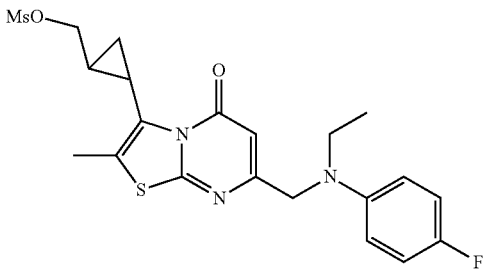 [SMILES: CCN(Cc1cc(=O)n2c(C3CC3COS(C)(=O)=O)c(C)sc2n1)c1ccc(F)cc1]

To a solution of 7-((ethyl(4-fluorocyclohexa-2,4-dienyl)amino)methyl)-3-(2-(hydroxymethyl)cyclopropyl)-2-methyl-5H-thiazolo[3,2-a]pyrimidin-5-one (from Example 5.17) (50 mg, 0.13 mmol) in dichloromethane (5 mL) was added methanesulfonyl chloride (22 mg, 0.19 mmol) and triethylamine (26 mg, 0.26 mmol). The reaction mixture was stirred 30 mins at room temperature. The reaction solution was concentrated in vacuo to afford (2-(7-((ethyl(4-fluorocyclohexa-2,4-dienyl)amino)methyl)-2-methyl-5-oxo-5H-thiazolo[3,2-a]pyrimidin-3-yl)cyclopropyl)methyl methanesulfonate (60 mg, crude). The crude product was used in next step without further purification.

Step 2: 7-((ethyl(4-fluorophenyl)amino)methyl)-3-(trans-2-(fluoromethyl)cyclopropyl)-2-methyl-5H-thiazolo[3,2-a]pyrimidin-5-one

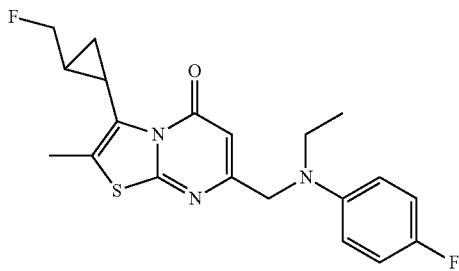 [SMILES: CCN(Cc1cc(=O)n2c(C3CC3CF)c(C)sc2n1)c1ccc(F)cc1]

To a solution of [2-(7-[[ethyl(4-fluorophenyl)amino]methyl]-2-methyl-5-oxo-5H-[1,3]thiazolo[3,2-a]pyrimidin-3-yl)cyclopropyl]methyl methanesulfonate (60 mg, 0.13 mmol) in propan-2-ol (0.5 mL) was added cesium fluoride (45.6 mg, 0.30 mmol). The reaction mixture was stirred for 90 min at 80° C. and then concentrated in vacuo. The residue was purified by Prep-HPLC to afford 7-[[ethyl(4-fluorophenyl)amino]methyl]-3-[trans-2-(fluoromethyl)cyclopropyl]-2-methyl-5H-[1,3]thiazolo[3,2-a]pyrimidin-5-one as a yellow solid (3.1 mg, 6.0%). LCMS (ESI):M+H$^+$=390.1; $^1$H NMR (300 MHz, CDCl$_3$) δ 6.95-6.89 (m, 2H), 6.72-6.65 (m, 2H), 6.12 (s, 1H), 4.72-4.26 (m, 2H), 3.52-3.45 (m, 2H), 2.41 (s, 3H), 2.28-2.22 (m, 1H), 1.71-1.58 (m, 1H), 1.26-1.15 (m, 4H), 1.08-1.01 (m, 1H).

Example 5.40: 3-ethyl-7-((ethyl(4-fluorophenyl)amino)methyl)-2-methyl-5H-thiazolo[3,2-a]pyrimidin-5-one

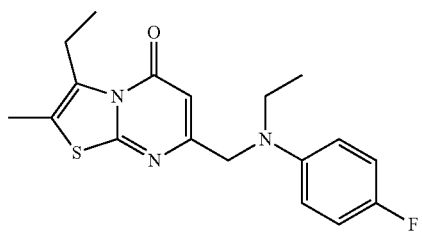 [SMILES: CCc1c(C)sc2nc(CN(CC)c3ccc(F)cc3)cc(=O)n12]

To a solution of 3-ethenyl-7-[[ethyl(4-fluorophenyl)amino]methyl]-2-methyl-5H-[1,3]thiazolo[3,2-a]pyrimidin-5-one (prepared via a method similar to Example 5.1) (75.0 mg, 0.22 mmol) in methanol (15 mL) was added palladium on carbon (100 mg). The reaction mixture was stirred overnight at room temperature under a hydrogen atmosphere. After filtration, the filtrate was concentrated in vacuo. The residue was purified by chromatography with ethyl acetate/petroleum ether (1/5) to afford 3-ethyl-7-[[ethyl(4-fluorophenyl)amino]methyl]-2-methyl-5H-[1,3]thiazolo[3,2-a]pyrimidin-5-one as a yellow solid (50 mg, 60%). LCMS (ESI): M+H$^+$=346.1; $^1$H NMR (300 MHz, CDCl$_3$) δ 6.96-6.90 (m, 2H), 6.73-6.67 (m, 2H), 6.14 (s, 1H), 4.30 (s, 2H), 3.54-3.47 (m, 2H), 3.19-3.14 (m, 2H), 2.32 (s, 3H), 1.38-1.24 (m, 6H).

The following compound was prepared using methods analogous to Example 5.40:

| No. | Structure/Name | LCMS (M + H) | $^1$H NMR |
|---|---|---|---|
| 5.41 | 7-((ethyl(4-fluorophenyl)amino)methyl)-2-methyl-3-propyl-5H-thiazolo[3,2-a]pyrimidin-5-one | 360.1 | $^1$HNMR (300 MHz, CDCl$_3$) δ 6.92-6.86 (m, 2H), 6.67-6.63 (m, 2H), 6.09 (s, 1H), 4.26 (s, 2H), 3.48-3.44 (m, 2H), 3.10-3.05 (m, 2H), 1.71-1.43 (m, 2H), 1.22-1.17 (m, 3H), 0.95-0.90 (m, 3H) |

The following compounds were prepared using methods analogous to those described above:

| No. | Structure/Name | LCMS (M + H) | ¹H NMR |
|---|---|---|---|
| 5.42 | 7-[[4-fluoro-N-(2-fluoroethyl)anilino]methyl]-3-trans-2-(hydroxymethyl)cyclopropyl]-2-methyl-thiazolo[3,2-a]pyrimidin-5-one (enantiomer 1) | 406.0 | ¹H NMR (300 MHz, CDCl₃) δ 6.95-6.90 (m, 2H). 6.66-6.64 (m, 2H), 6.16 (s, 1H), 4.73-4.71 (m, 1H), 4.62-4.95 (m, 1H), 4.45 (s, 2H), 4.05-4.02 (m, 1H), 4.01-3.72 (m, 2H) 3.14-3.08 (m, 1H), 2.39 (s, 3H), 2.27-2.00 (m, 1H), 1.29-1.24 (m, 1H), 1.05-0.97 (m, 2H). |
| 5.43 | 7-[[4-fluoro-N-(2-fluoroethyl)anilino]methyl]-3-[trans-2-(hydroxymethyl)cyclopropyl]-2-methyl-thiazolo[3,2-a]pyrimidin-5-one (enantiomer 2) | 406.0 | ¹H NMR (300 MHz, CDCl₃) δ 6.94-6.89 (m, 2H), 6.63-6.60 (m, 2H), 6.15 (s, 1H), 4.73-4.70 (m, 1H), 4.61-4.59 (m, 1H ), 4.43 (s, 2H), 4.05-4.02 (m, 1H), 3.80-3.71 (m, 2H) 3.12-3.07 (m, 1H), 2.39 (s, 3H), 2.27-2.23 (m, 1H), 1.28-1.25 (m, 1H), 1.05-0.96 (m, 2H). |
| 5.44 | 7-((ethyl(4-fluorophenyl)amino)methyl)-3-(furan-3-yl)-2-methyl-5H-thiazolo[3,2-a]pyrimidin-5-one | 384.0 | ¹H NMR (300 MHz, CDCl₃) δ 7.49-7.47 (m, 2H), 6.90-6.85 (m, 2H), 6.58-6.54 (m, 2H), 6.45-6.44 (m, 1H), 6.09 (s, 1H), 4.28 (s, 2H), 3.50-3.41 (m, 2H), 2.27 (s, 3H), 1.22-1.18 (m, 3H). |
| 5.45 | 7-((ethyl(4-fluorophenyl)amino)methyl)-3-(furan-2-yl)-2-methyl-5H-thiazolo[3,2-a]pyrimidin-5-one | 384.0 | ¹H NMR (300 MHz, CD₃OD) δ 7.63 (s, 1H), 6.93-6.87 (m, 2H), 6.67-6.52 (m, 4H), 6.04 (s, 1H), 4.37 (s, 2H), 3.57-3.48 (m, 2H), 2.32 (s, 3H), 1.23-1.20 (m, 3H). |

| No. | Structure/Name | LCMS (M + H) | ¹H NMR |
|---|---|---|---|
| 5.46 | 7-((5-fluoro-2-methylindolin-1-yl)methyl)-3-(furan-2-yl)-2-methyl-5H-thiazolo[3,2-a]pyrimidin-5-one | 396.0 | ¹H NMR (300 MHz, CD₃OD) δ 7.65 (s, 1H), 6.81-6.63 (m, 1H), 6.72-6.54 (m, 3H), 6.26 (s, 1H), 6.24-6.19 (m, 1H), 4.13 (m, 2H), 3.84-3.76 (m, 1H), 3.23-3.15 (m, 1H), 2.71-2.63 (m, 1H), 2.33 (s, 3H), 1.31 (m, 3H) |
| 5.47 | 7-((ethyl(4-fluorophenyl)amino)methyl)-2-methyl-3-(thiophen-3-yl)-5H-thiazolo[3,2-a]pyrimidin-5-one | 400.0 | ¹H NMR (300 MHz, CD₃OD) δ 7.45-7.42 (m, 2H), 7.07-7.06 (m, 1H), 6.93-6.87 (m, 2H), 6.67-6.63 (m, 2H), 6.00 (s, 1H), 4.36 (s, 2H), 3.51 (m, 2H), 2.23 (s, 3H), 1.21 (m, 3H). |
| 5.48 | 7-((5-fluoro-2-methylindolin-1-yl)methyl)-2-methyl-3-(pyrimidin-5-yl)-5H-thiazolo[3,2-a]pyrimidin-5-one | 408.0 | ¹H NMR (300 MHz, CD₃OD) δ 9.19 (s, 1H), 8.84 (s, 2H), 6.84-6.81 (m, 1H), 6.71-6.64 (m, 1H), 6.26 (s, 1H), 6.24-6.20 (m, 1H), 4.25-4.05 (m, 2H), 3.84-3.76 (m, 1H), 3.22-3.17 (m, 1H), 2.68-2.62 (m, 1H), 2.31 (s, 3H), 1.35-1.33 (m, 3H). |
| 5.49 | 7-((ethyl(4-fluorophenyl)amino)methyl)-2-methyl-3-(4-methylthiazol-2-yl)-5H-thiazolo[3,2-a]pyrimidin-5-one | 415.1 | ¹H NMR (300 MHz, CD₃OD) δ 7.40 (s, 1H), 6.91-6.84 (m, 2H), 6.65-6.59 (m, 2H), 6.00 (s, 1H), 4.35 (s, 2H), 3.49-3.46 (m, 2H), 2.45 (s, 3H), 2.25 (s, 3H), 1.19-1.15 (m, 3H) |

| No. | Structure/Name | LCMS (M + H) | ¹H NMR |
|---|---|---|---|
| 5.50 | 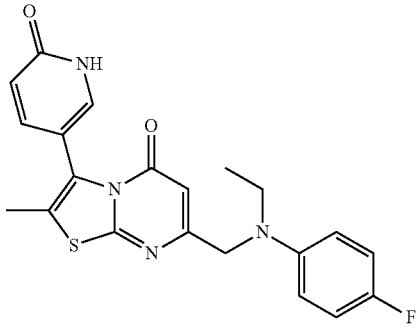 [SMILES: CCN(Cc1cc(=O)n2c(-c3ccc(=O)[nH]c3)c(C)sc2n1)c1ccc(F)cc1]<br>7-((ethyl(4-fluorophenyl)amino)methyl)-2-methyl-3-(6-oxo-1,6-dihydropyridin-3-yl)-5H-thiazolo[3,2-a]pyrimidin-5-one | 411.2 | ¹H NMR (300 MHz, DMSO-d$_6$) δ 7.39-7.34 (m, 2H), 6.70-6.95 (m, 2H), 6.64-6.59 (m, 2H), 6.26 (m, 1H), 5.81 (s, 1H), 4.33 (s, 2H), 3.50-3.43 (m, 2H), 2.21 (s, 3H), 1.13-1.10 (m, 3H) |
| 5.51 | 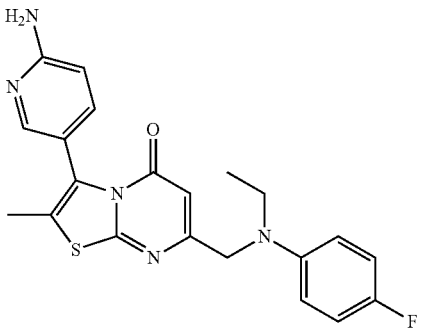 [SMILES: CCN(Cc1cc(=O)n2c(-c3ccc(N)nc3)c(C)sc2n1)c1ccc(F)cc1]<br>3-(6-aminopyridin-3-yl)-7-((ethyl(4-fluorophenyl)amino)methyl)-2-methyl-5H-thiazolo[3,2-a]pyrimidin-3-one | 409.9 | ¹H NMR (300 MHz, DMSO-d$_6$) δ 7.77 (s, 1H), 7.36-7.26 (m, 1H), 6.96-6.90 (m, 2H), 6.59-6.54 (m, 2H), 6.40-6.32 (m, 1H), 6.22 (br, 2H), 5.74 (s, 1H), 4.28 (s, 2H), 3.45-3.38 (m, 2H), 2.12 (s, 3H), 1.10-1.02 (m, 3H) |
| 5.52 | 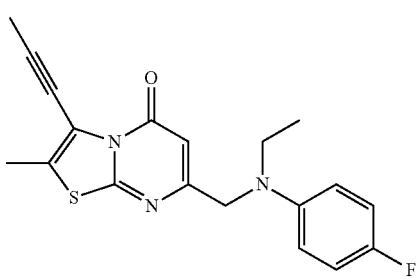 [SMILES: CC#Cc1c(C)sc2nc(CN(CC)c3ccc(F)cc3)cc(=O)n12]<br>7-((ethyl(4-fluorophenyl)amino)methyl)-2-methyl]-3-(prop-1-ynyl)-5H-thiazolo[3,2-a]pyrimidin-5-one | 356.0 | ¹H NMR (300 MHz, CDCl$_3$) δ 6.93-6.87 (m, 2H), 6.59-6.55 (m, 2H), 6.16 (s, 1H), 4.28 (s, 2H), 3.50-3.43 (m, 2H), 2.45 (s, 3H), 2.23 (s, 3H), 1.27-1.20 (m, 3H) |
| 5.53 | 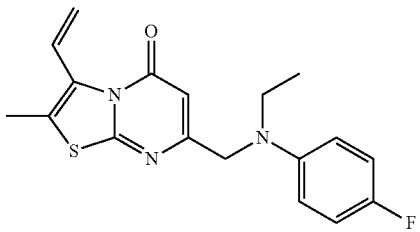 [SMILES: C=Cc1c(C)sc2nc(CN(CC)c3ccc(F)cc3)cc(=O)n12]<br>7-((ethyl(4-fluorophenyl)amino)methyl)-2-methyl-3-vinyl-5H-thiazolo[3,2-a]pyrimidin-5-one | 344.0 | ¹H NMR (300 MHz, CDCl$_3$) δ 7.17-7.13 (m, 1H), 6.92-6.87 (m, 2H), 6.59-6.55 (m, 2H), 6.15 (s, 1H), 5.64-5.60 (m, 1H), 5.35-5.29 (m, 1H), 4.28 (s, 2H), 3.50-3.43 (m, 2H), 2.42 (s, 3H), 1.24-1.19 (m, 3H) |

-continued

| No. | Structure/Name | LCMS (M + H) | ¹H NMR |
|---|---|---|---|
| 5.54 | 3-bromo-2-cyclopropyl-7-[(N-ethyl-4-fluoro-anilino)methyl]thiazolo[3,2-a]pyrimidin-5-one | 424.0 | ¹H NMR (300 MHz, CDCl$_3$) δ 6.92-6.86 (m, 2H), 6.58-6.52 (m, 2H), 6.14 (s, 1H), 4.25 (s, 2H), 3.46-3.40 (m, 2H), 2.18-2.10 (m, 1H), 1.25-1.15 (m, 5H), 0.89-0.78 (m, 2H). |
| 5.55 | 3-(3,5-difluorophenyl)-7-[(N-ethyl-4-fluoro-anilino)methyl]-2-methyl-thiazolo[3,2-a]pyrimidin-5-one | 430.1 | 1H NMR (400 MHz, DMSO-d$_6$) δ 7.29 (tt, J = 9.4, 2.5 Hz, 1H), 7.16 (h, J = 4.8 Hz, 2H), 6.98 (t, J = 8.9 Hz, 2H), 6.62 (dd, J = 9.1, 4.3 Hz, 2H), 5.82 (s, 1H), 4.34 (s, 2H), 3.46 (q, J = 7.0 Hz, 2H), 2.16 (s, 3H), 1.13 (t, J = 7.0 Hz, 3H). |
| 5.56 | 7-[(N-ethyl-4-fluoro-anilino)methyl]-2-methyl-3-(1-methylpyrazol-3-yl)thiazolo[3,2-a]pyrimidin-5-one | 398.34 | |
| 5.57 | 3-(2-amino-4-pyridyl)-7-[(N-ethyl-4-fluoro-anilino)methyl]-2-methyl-thiazolo[3,2-a]pyrimidin-5-one | 410.1 | |

| No. | Structure/Name | LCMS (M + H) | ¹H NMR |
|---|---|---|---|
| 5.58 | 7-[(N-ethyl-4-fluoro-anilino)methyl]-3-(5-methoxy-3-pyridyl)-2-methyl-thiazolo[3,2-a]pyrimidin-5-one | 425.1 | 1H NMR (400 MHz, DMSO-d₆) δ 8.31 (d, J = 2.9 Hz, 1H), 8.14 (s, 1H), 7.43 (d, J = 2.3 Hz, 1H), 6.98 (t, J = 8.7 Hz, 2H), 6.62 (dd, J = 9.3, 4.3 Hz, 2H), 5.81 (s, 1H), 4.35 (s, 2H), 3.81 (s, 3H), 3.47 (q, J = 7.0 Hz, 2H), 2.16 (s, 3H), 1.13 (t, J = 7.0 Hz, 3H). |

Method 6

Example 6.1: 7-((ethyl(4-fluorophenyl)amino)methyl)-2-methyl-3-morpholino-5H-thiazolo[3,2-a]pyrimidin-5-one

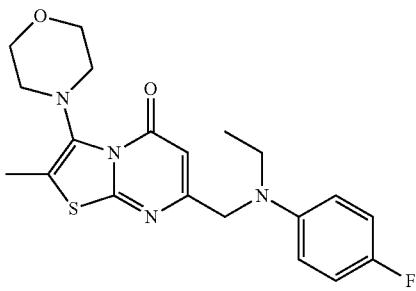 [SMILES: CCN(Cc1cc(=O)n2c(N3CCOCC3)c(C)sc2n1)c1ccc(F)cc1]

To a solution of 3-bromo-7-[[ethyl(4-fluorophenyl)amino]methyl]-2-methyl-5H-[1,3]thiazolo[3,2-a]pyrimidin-5-one (250 mg, 0.63 mmol) (from Example 5.1, Step 1) in dimethyl sulfoxide (3 mL) was added potassium phosphate (268 mg, 1.26 mmol), L-proline (22.0 mg, 0.19 mmol), morpholine (165 mg, 1.89 mmol) and cuprous iodide (18.0 mg, 0.09 mmol). The reaction mixture was stirred overnight at 90° C. The resulting mixture was quenched with water (50 mL), extracted with ethyl acetate (30 mL×3), washed with brine, dried over anhydrous sodium sulfate and concentrated in vacuo. The residue was purified by chromatography with ethyl acetate/petroleum ether (1/2) to afford 7-[[ethyl(4-fluorophenyl)amino]methyl]-2-methyl-3-(morpholin-4-yl)-5H-[1,3]thiazolo[3,2-a]pyrimidin-5-one as a white solid (29.5 mg, 12%). LCMS (ESI): M+H⁺=403.0; ¹H NMR (300 MHz, CDCl₃) δ 6.93-6.87 (m, 2H), 6.61-6.57 (m, 2H), 6.15 (s, 1H), 3.91-3.87 (m, 2H), 3.76-3.59 (m, 4H), 3.50-3.43 (m, 2H), 2.64-2.60 (m, 2H), 2.40 (s, 3H), 1.25-1.20 (m, 3H).

The following examples were prepared in a manner similar to Example 6.1:

| No. | Structure/Name | LCMS (M + H) | ¹H NMR |
|---|---|---|---|
| 6.2 | 3-(dimethylamino)-7-((ethyl(4-fluorophenyl)amino)methyl)-2-methyl-5H-thiazolo[3,2-a]pyrimidin-5-one | 361.0 | ¹H NMR (300 MHz, CDCl₃) δ 6.93-6.87 (m, 2H), 6.60-6.55 (m, 2H), 6.12 (s, 1H), 4.28 (s, 2H), 3.50-3.43 (m, 2H), 2.76 (s, 6H), 2.31 (s, 3H), 1.26-1.20 (m, 3H) |

| No. | Structure/Name | LCMS (M + H) | ¹H NMR |
|---|---|---|---|
| 6.3 | 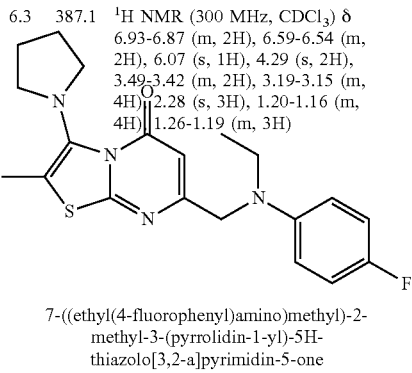<br>7-((ethyl(4-fluorophenyl)amino)methyl)-2-methyl-3-(pyrrolidin-1-yl)-5H-thiazolo[3,2-a]pyrimidin-5-one | 387.1 | ¹H NMR (300 MHz, CDCl₃) δ 6.93-6.87 (m, 2H), 6.59-6.54 (m, 2H), 6.07 (s, 1H), 4.29 (s, 2H), 3.49-3.42 (m, 2H), 3.19-3.15 (m, 4H), 2.28 (s, 3H), 1.20-1.16 (m, 4H), 1.26-1.19 (m, 3H) |

Method 7

Example 7.1: 7-(((3,4-difluorophenyl)(ethyl)amino)methyl)-2-methyl-5-oxo-5H-thiazolo[3,2-a]pyrimidine-3-carbonitrile

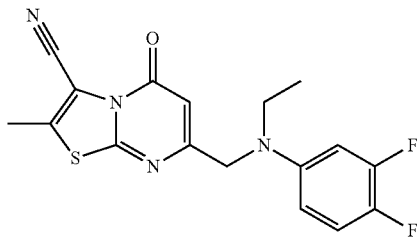 [SMILES: CCN(Cc1cc(=O)n2c(C#N)c(C)sc2n1)c1ccc(F)c(F)c1]

To a solution of 3-bromo-7-[[(3,4-difluorophenyl)(ethyl)amino]methyl]-2-methyl-5H-[1,3]thiazolo[3,2-a]pyrimidin-5-one (prepared via a method similar to Example 5.1, Step 1) (100 mg, 0.24 mmol) in N,N-dimethylformamide (5 mL) was added cuprous cyanide (43.0 mg, 0.48 mmol). The reaction solution was stirred for 1.5 h at 100° C. The reaction solution was quenched by water (50 mL), extracted with dichloromethane, washed with brine, dried over anhydrous magnesium sulfate and concentration in vacuo. The residue was purified by chromatography with dichloromethane/methanol (20/1) to afford 7-[[(3,4-difluorophenyl)(ethyl)amino]methyl]-2-methyl-5-oxo-5H-[1,3]thiazolo[3,2-a]pyrimidine-3-carbonitrile (43.1 mg, 47%) as an off-white solid. LCMS (ESI): M+H⁺=361.0; ¹H NMR (400 MHz, CD₃OD) δ 7.08-7.01 (m, 1H), 6.59-6.53 (m, 1H), 6.430-6.40 (m, 1H), 6.16 (s, 1H), 4.41 (s, 2H), 3.56-3.51 (m, 2H), 2.67 (s, 3H), 1.31-1.21 (m, 3H).

The following examples were prepared in a manner similar to Example 7.1:

| No. | Structure/Name | LCMS (M + H) | ¹H NMR |
|---|---|---|---|
| 7.2 | 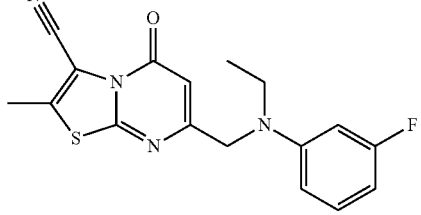<br>7-((ethyl(3-fluorophenyl)amino)methyl)-2-methyl-5-oxo-5H-thiazolo[3,2-a]pyrimidine-3-carbonitrile | 343.1 | ¹H NMR (300 MHz, CDCl₃) δ 7.19-7.17 (m, 1H), 6.46-6.32 (m, 3H), 6.25 (s, 1H), 4.34 (s, 2H), 3.53-3.50 (m, 2H), 2.66 (s, 3H), 1.27-1.24 (m, 3H). |

-continued

| No. | Structure/Name | LCMS (M + H) | ¹H NMR |
|---|---|---|---|
| 7.3 | 7-[(N-ethyl-4-fluoro-anilino)methyl]-2-methyl-5-oxo-thiazolo[3,2-a]pyrimidine-3-carbonitrile | 343.0 | ¹H NMR (400 MHz, DMSO-$d_6$) δ 6.99 (t, J = 8.7 Hz, 2H), 6.62 (dd, J = 9.1, 4.2 Hz, 2H), 6.01 (s, 1H), 4.36 (s, 2H), 3.48 (q, J = 7.0 Hz, 2H), 2.61 (s, 3H), 1.13 (t, J = 7.0 Hz, 3H). |
| 7.4 | 7-[(N-ethyl-4-fluoro-anilino)methyl]-5-oxo-thiazolo[3,2-a]pyrimidine-3-carbonitrile | 329.1 | ¹H NMR (400 MHz, DMSO-$d_6$) δ 8.70 (s, 1H), 7.05-6.87 (m, 2H), 6.71-6.54 (m, 2H), 6.02 (s, 2H), 4.37 (s, 2H), 3.47 (q, J = 7.0 Hz, 2H), 1.13 (t, J = 7.0 Hz, 3H). |

The following compounds were prepared using methods analogous to those described above:

| No. | Structure/Name | LCMS (M + H) | ¹H NMR |
|---|---|---|---|
| 7.5 | 7-((5-fluoro-2-methylindolin-1-yl)methyl)-2-methyl-5-oxo-5H-thiazolo[3,2-a]pyrimidine-3-carbonitrile | 355.0 | ¹H NMR (300 MHz, CD$_3$OD) δ 6.84-6.81 (m, 1H), 6.70-6.64 (m, 1H), 6.38 (s, 1H), 6.21-6.20 (m, 1H), 4.23-4.04 (m, 2H), 3.80-3.75 (m, 1H), 3.22-3.14 (m, 1H), 2.72-2.67 (m, 1H), 2.66 (s, 3H), 1.34-1.32 (m, 3H). |
| 7.6 | 7-(((3-cyanophenyl)(ethyl)amino)methyl)-2-methyl-5-oxo-5H-thiazolo[3,2-a]pyrimidine-3-carbonitrile | 350.0 | ¹H NMR (300 MHz, CD$_3$OD) δ 7.35-7.29 (m, 1H), 7.00-6.97 (m, 3H), 6.13 (s, 1H), 4.49 (s, 2H), 3.64-3.56 (m, 2H), 2.66 (s, 3H), 1.30-1.23 (m, 3H). |

-continued

| No. | Structure/Name | LCMS (M + H) | ¹H NMR |
|---|---|---|---|
| 7.7 | 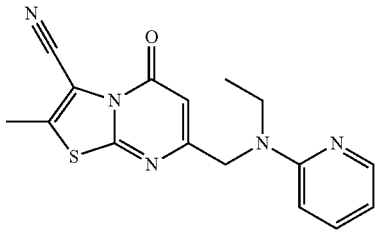<br>7-((ethyl(pyridin-2-yl)amino)methyl)-2-methyl-5-oxo-5H-thiazolo[3,2-a]pyrimidine-3-carbonitrile | 326.1 | ¹H NMR (300 MHz, CDCl₃) δ 8.12-8.11 (m, 1H), 7.50-7.45 (m, 1H), 6.61-6.52 (m, 2H), 6.19 (s, 1H), 4.65 (s, 2H), 3.61-3.54 (m, 2H), 2.65 (s, 3H), 1.26-1.21 (m, 3H). |
| 7.8 | 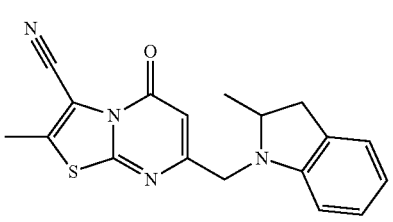<br>2-methyl-7-((2-methylindolin-1-yl)methyl)-5-oxo-5H-thiazolo[3,2-a]pyrimidine-3-carbonitrile | 336.8 | ¹H NMR (300 MHz, CD₃OD) δ 7.05-7.03 (m, 1H), 6.98-6.93 (m, 1H), 6.65-6.60 (m, 1H), 6.38 (s, 1H), 6.28-6.26 (m, 1H), 4.26-4.09 (m, 2H), 3.83-3.73 (m, 1H), 2.24-2.16 (m, 1H), 2.69-2.66 (m, 1H), 2.64 (s, 3H), 1.34-1.21 (m, 3H). |
| 7.9 | 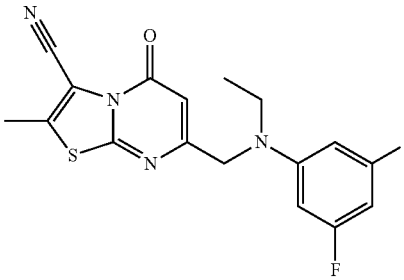<br>7-(((3,5-difluorophenyl)(ethyl)amino)methyl)-2-methyl-5-oxo-5H-thiazolo[3,2-a]pyrimidine-3-carbonitrile | 361.1 | ¹H NMR (300 MHz, CDCl₃) δ 6.19-6.05 (m, 4H), 4.31 (s, 2H), 3.48-3.45 (m, 2H), 2.66 (s, 3H), 1.26-1.23 (m, 3H) |

Method 8

Example 8.1: 6-[(N-ethyl-4-fluoro-anilino)methyl]-2,3-dihydro-1H-cyclopenta[3,4]thiazolo[1,4-a]pyrimidin-8-one

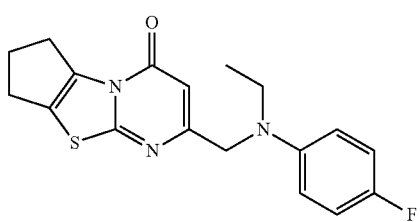 [SMILES: CCN(Cc1cc(=O)n2c3c(sc2n1)CCC3)c1ccc(F)cc1]

Step 1: 2-bromocyclopentan-1-one

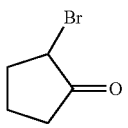

To a solution of cyclohexanone (5.00 g, 50.9 mmol) in dimethyl sulfoxide (30 mL) was added N-bromosuccinimide (11.1 g, 62.4 mmol). The reaction mixture was stirred 20 min at room temperature and then quenched with water (300 mL). The reaction mixture was extracted with dichloromethane (100 mL×2), washed with brine, dried over anhydrous sodium sulfate and concentrated in vacuo to afford 2-bromocyclopentan-1-one as a light yellow oil (5.6 g, 58%). The crude product was used in next step without further purification. No LCMS signal.

Step 2: 4H,5H,6H-cyclopenta[d][1,3]thiazol-2-amine

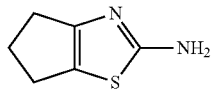

To a solution of 2-bromocyclopentan-1-one (5.50 g, 33.7 mmol) in ethanol (50 mL) was added thiourea (3.30 g, 43.4 mmol) and sodium bicarbonate (4.80 g, 57.1 mmol). The reaction mixture was stirred at reflux overnight. After cooling to room temperature, the reaction was quenched with water (200 mL), extracted with dichloromethane (100 mL×3), washed with brine, dried over anhydrous sodium sulfate and concentrated in vacuo to afford 4H,5H,6H-cyclopenta[d][1,3]thiazol-2-amine as a brown solid (2.0 g, 42%). LCMS (ESI): M+H$^+$=141.1.

Step 3: 10-(chloromethyl)-7-thia-1,9-diazatricyclo[6.4.0.0'[2,6]]dodeca-2(6),8,10-trien-12-one

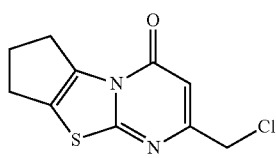 [SMILES: O=c1cc(CCl)nc2sc3c(n12)CCC3]

Step 4: 6-[(N-ethyl-4-fluoro-anilino)methyl]-2,3-dihydro-1H-cyclopenta[3,4]thiazolo[1,4-a]pyrimidin-8-one

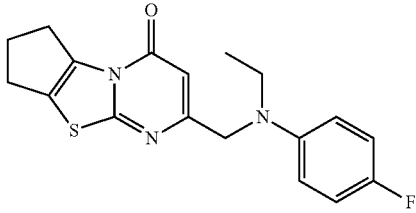 [SMILES: CCN(Cc1cc(=O)n2c3c(sc2n1)CCC3)c1ccc(F)cc1]

To a solution of 10-(chloromethyl)-7-thia-1,9-diazatricyclo[6.4.0.0'[2,6]]dodeca-2(6),8,10-trien-12-one (150 mg, 0.62 mmol) in acetonitrile (20 mL) was added N-ethyl-4-fluoroaniline (105 mg, 0.75 mmol), potassium carbonate (150 mg, 0.62 mmol), and potassium iodide (52 mg, 0.31 mmol). The reaction mixture was stirred overnight at 60° C. After cooling to room temperature, the reaction was quenched with water (100 mL), extracted with dichloromethane (50 mL×3), washed with brine, dried over sodium sulfate and concentrated in vacuo. The residue was purified by chromatography with 33% ethyl acetate in petroleum ether to afford 6-[(N-ethyl-4-fluoro-anilino)methyl]-2,3-dihydro-1H-cyclopenta[3,4]thiazolo[1,4-a]pyrimidin-8-one as a brown solid (47.8 mg, 22%). LCMS (ESI): M+H$^+$=343.7; $^1$H NMR (300 MHz, DMSO-d$_6$) δ 7.00-6.94 (m, 2H), 6.61-6.58 (m, 2H), 5.87 (s, 1H), 4.32 (s, 2H), 3.50-3.43 (m, 2H), 3.19-3.13 (m, 2H), 2.85-2.72 (m, 2H), 3.37-2.30 (m, 2H), 1.16-1.09 (m, 3H).

The following examples were prepared in a manner similar to Example 8.1:

| No. | Structure/Name | LCMS (M + H) | $^1$H NMR |
|---|---|---|---|
| 8.2 | ![structure] 2-[(N-ethyl-4-fluoro-anilino)methyl]-6,7,8,9-tetrahydropyrimido[2,1-b][1,3]benzothiazol-4-one | 358.1 | $^1$H NMR (300 MHz, DMSO-d$_6$) δ 7.19-6.96 (m, 2H), 6.61-6.57 (m, 2H), 5.80 (s, 1H), 4.29 (s, 2H), 3.46-3.42 (m, 2H), 3.14 (m, 2H), 2.72-2.70 (m, 2H), 1.75 (m, 4H), 1.14-1.09 (m, 3H). |

A mixture of 4H,5H,6H-cyclopenta[d][1,3]thiazol-2-amine (2.00 g, 14.3 mmol) and ethyl 4-chloro-3-oxobutanoate (3.50 g, 21.3 mmol) in polyphosphoric acid (15 mL) was stirred for 1 h at 110° C. The reaction mixture cooled to room temperature, diluted with water (30 mL) and stirred for 1 h at 80° C. After cooling to room temperature, the reaction was quenched by water (200 mL), and the pH value of the solution was adjusted to pH 8-9 with potassium carbonate, extracted with dichloromethane (100 mL×3), washed with brine, dried over sodium sulfate and concentrated in vacuo. The residue was purified by chromatography with 20% ethyl acetate in petroleum ether to afford 10-(chloromethyl)-7-thia-1,9-diazatricyclo[6.4.0.0'[2,6]]dodeca-2(6),8,10-trien-12-one as a brown solid (150 mg, 4.0%). LCMS (ESI): M+H$^+$=241.1.

Example 8.3: 6-[(N-ethyl-4-fluoro-anilino)methyl]-1-(hydroxymethyl)-2,3-dihydro-1H-cyclopenta[3,4]thiazolo[1,4-a]pyrimidin-8-one

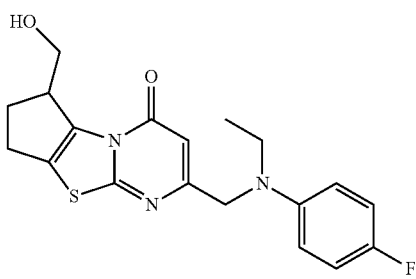 [SMILES: CCN(Cc1cc(=O)n2c3c(sc2n1)CCC3CO)c1ccc(F)cc1]

Step 1: ethyl 3-bromo-2-oxocyclopentanecarboxylate

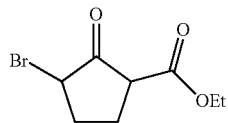 [SMILES: CCOC(=O)C1CCC(Br)C1=O]

To a solution of ethyl 3-bromo-2-oxocyclopentanecarboxylate (780 mg, 5.00 mmol) in chloroform (15 mL) was added bromine (800 mg, 5.01 mmol) dropwise with stirring. The resulting solution was stirred for 2 h at room temperature. The resulting mixture was concentrated in vacuo to afford ethyl 3-bromo-2-oxocyclopentanecarboxylate as light yellow oil (1.30 g). The crude product was used in the next step without further purification. No LCMS signal.

Step 2: ethyl 2-amino-5,6-dihydro-4H-cyclopenta[d]thiazole-4-carboxylate

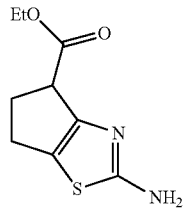

To a solution of ethyl 3-bromo-2-oxocyclopentanecarboxylate (1.30 g, 5.53 mmol) in 1,4-dioxane (20 mL) was added thiourea (420 mg, 5.52 mmol). The resulting solution was refluxed for 12 h. After cooled down to room temperature, the reaction mixture was concentrated in vacuo. The residue was purified by chromatography with dichloromethane/methanol (20/1) to afford ethyl-2-amino-5,6-dihydro-4H-cyclopenta[d]thiazole-4-carboxylate as light yellow solid (600 mg, 51%). LCMS (ESI): M+H$^+$=213; $^1$H NMR (300 MHz, DMSO-d$_6$) δ 6.90 (br, 2H), 4.12-4.08 (m, 2H), 3.68-3.63 (m, 1H), 2.82-2.40 (m, 4H), 1.29-1.25 (m, 3H).

Step 3: Ethyl 6-(chloromethyl)-8-oxo-2,3-dihydro-1H-cyclopenta[3,4]thiazolo[1,4-a]pyrimidine-1-carboxylate

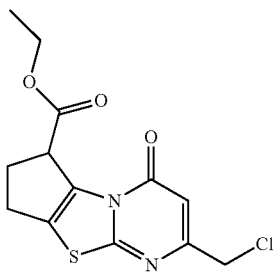 [SMILES: CCOC(=O)C1CCc2sc3nc(CCl)cc(=O)n3c21]

To a solution of ethyl-2-amino-5,6-dihydro-4H-cyclopenta[d]thiazole-4-carboxylate (1.00 g, 4.70 mmol) and 4-methylbenzenesulfonic acid (170 mg, 1.00 mmol) in toluene (30 mL) was added methyl 4-chloro-3-oxobutanoate (1.40 g, 9.40 mmol). The reaction mixture was stirred for 12 h at 125° C. with a Dean-Stark apparatus to separate water. After cooled down to room temperature, the reaction mixture was concentrated in vacuo. The residue was purified by chromatography with ethyl acetate/petroleum ether (1:2) to afford ethyl 6-(chloromethyl)-8-oxo-2,3-dihydro-1H-cyclopenta[3,4]thiazolo[1,4-a]pyrimidine-1-carboxylate as light yellow solid (150 mg, 10%). LCMS (ESI): M+H$^+$=313.0; $^1$H NMR (300 MHz, CDCl$_3$) δ 6.30 (s, 1H), 4.46-4.40 (m, 1H), 4.33 (s, 2H), 4.22-4.18 (m, 2H), 3.03-2.87 (m, 3H), 2.62-2.54 (m, 1H), 1.29-1.25 (m, 3H).

Step 4: ethyl 2-((ethyl(4-fluorophenyl)amino)methyl)-4-oxo-4,6,7,8-tetrahydrocyclopenta[4,5]thiazolo[3,2-a]pyrimidine-6-carboxylate

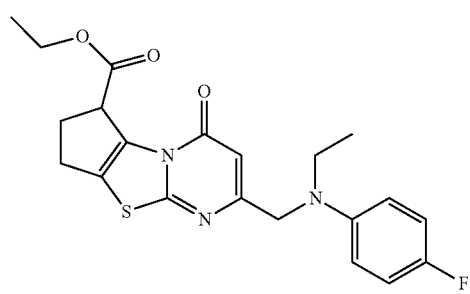 [SMILES: CCOC(=O)C1CCc2sc3nc(CN(CC)c4ccc(F)cc4)cc(=O)n3c21]

To a solution of ethyl 10-(chloromethyl)-12-oxo-7-thia-1,9-diazatricyclo[6.4.0.0^[2,6]]dodeca-2(6),8,10-triene-3-carboxylate (50.0 mg, 0.16 mmol), potassium iodide (14 mg, 0.08 mmol) and potassium carbonate (45 mg, 0.33 mmol) in acetonitrile (5 mL) was added N-ethyl-4-fluoroaniline (33.0 mg, 0.24 mmol). The reaction mixture was stirred overnight at 80° C. After filtration and concentration in vacuo, the residue was purified by chromatography with ethyl acetate/petroleum ether (1/2) to afford ethyl 10-[[ethyl(4-fluorophenyl)amino]methyl]-12-oxo-7-thia-1,9-diazatricyclo[6.4.0.0^[2,6]]dodeca-2(6),8,10-triene-3-carboxylate as a light yellow semi-solid (17.2 mg, 26%). LCMS (ESI): M+H$^+$=416.0; $^1$H NMR (300 MHz, CDCl$_3$) δ 6.92-6.87 (m, 2H), 6.60-6.55 (m, 2H), 6.14 (s, 1H), 4.50-4.45 (m, 1H), 4.30 (s, 2H), 4.22-4.17 (m, 2H), 3.48-3.41 (m, 2H), 3.02-2.85 (m, 3H), 2.60-2.55 (m, 1H), 1.29-1.19 (m, 6H).

Step 5: 10-[[Ethyl(4-fluorophenyl)amino]methyl]-12-oxo-7-thia-1,9-diazatricyclo[6.4.0.0^[2,6]]dodeca-2(6),8,10-triene-3-carboxylic acid

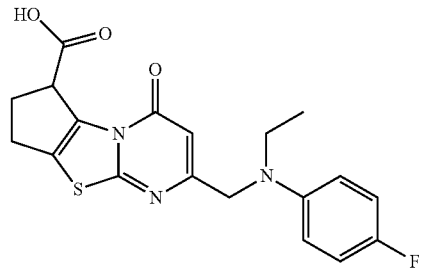 [SMILES: CCN(Cc1cc(=O)n2c3c(sc2n1)CCC3C(=O)O)c1ccc(F)cc1]

To a solution of ethyl 10-[[ethyl(4-fluorophenyl)amino]methyl]-12-oxo-7-thia-1,9-diazatricyclo[6.4.0.0^[2,6]]dodeca-2(6),8,10-triene-3-carboxylate (40 mg, 0.10 mmol), tetrahydrofuran (2 mL) and water (2 mL) was added lithium hydroxide (12 mg, 0.50 mmol). The resulting solution was stirred overnight at room temperature. The pH value of the solution was adjusted to pH 2 with hydrochloric acid (1 mol/L) and extracted with dichloromethane (2×20 mL). The combined organic layers were washed with brine, dried over anhydrous sodium sulfate and concentrated in vacuo to afford 10-[[ethyl(4-fluorophenyl)amino]methyl]-12-oxo-7-thia-1,9-diazatricyclo[6.4.0.0^[2,6]]dodeca-2(6),8,10-triene-3-carboxylic acid (30 mg, 80%) as a light yellow solid. The crude product was used in the next step without further purification.

Step 6: 6-[(N-ethyl-4-fluoro-anilino)methyl]-1-(hydroxymethyl)-2,3-dihydro-1H-cyclopenta[3,4]thiazolo[1,4-a]pyrimidin-8-one

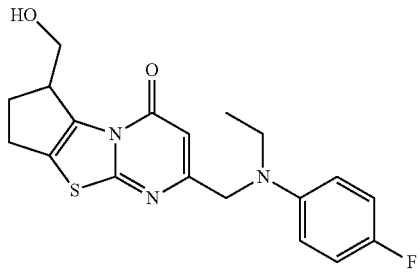 [SMILES: CCN(Cc1cc(=O)n2c3c(sc2n1)CCC3CO)c1ccc(F)cc1]

To a solution of 10-[[ethyl(4-fluorophenyl)amino]methyl]-12-oxo-7-thia-1,9-diazatricyclo[6.4.0.0^[2,6]]dodeca-2(6),8,10-triene-3-carboxylic acid (110 mg, 0.28 mmol) and triethylamine (60 mg, 0.57 mmol) in tetrahydrofuran (10 mL) was added chloro(propan-2-yloxy)methanone (70 mg, 0.57 mmol) and the reaction mixture was stirred 0.5 h at room temperature. Then sodium borohydride (22 mg, 0.58 mmol) in water (0.5 mL) was added. The resulting solution was stirred for an additional 1 h at room temperature. The reaction was quenched with saturated aqueous ammonium chloride and extracted with dichloromethane (3×20 mL). The combined organic layers were washed with brine, dried over anhydrous sodium sulfate and concentrated in vacuo. The residue was purified by chromatography with ethyl acetate/petroleum ether (1/1) to afford 6-[(N-ethyl-4-fluoro-anilino)methyl]-1-(hydroxymethyl)-2,3-dihydro-1H-cyclopenta[3,4]thiazolo[1,4-a]pyrimidin-8-one (51.2 mg, 48%) as a white solid. LCMS (ESI): M+H$^+$=374.0; $^1$H NMR (400 MHz, CDCl$_3$) δ 6.94-6.90 (m, 2H), 6.60-6.57 (m, 2H), 6.27 (s, 1H), 4.35 (s, 2H), 3.98-3.91 (m, 2H), 3.75-3.70 (m, 2H), 3.49-3.47 (m, 2H), 3.01-2.95 (m, 1H), 2.88-2.82 (m, 1H), 2.74-2.68 (m, 1H), 2.27-2.22 (m, 1H), 1.26-1.23 (m, 3H).

Examples 8.4 and 8.5: 6-[(N-ethyl-4-fluoro-anilino)methyl]-1-(hydroxymethyl)-2,3-dihydro-1H-cyclopenta[3,4]thiazolo[1,4-a]pyrimidin-8-one (enantiomers 1 and 2)

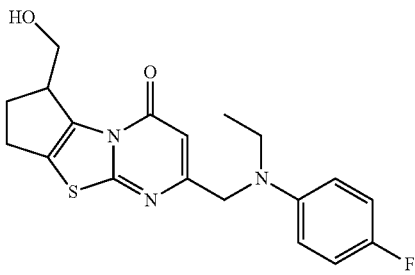 [SMILES: CCN(Cc1cc(=O)n2c3c(sc2n1)CCC3CO)c1ccc(F)cc1]

The product of Example 8.3 was further purified by chiral SFC on a Chiralpak AD (2×15 cm) column eluting with 25% methanol (0.1% NH$_4$OH)/CO$_2$ at 100 bar at a flow rate of 70 mL/min. The peaks isolated were analyzed on Chiralpak AD (50×0.46 cm) column eluting with 25% methanol (0.1% NH$_4$OH)/CO$_2$, at 120 bar (flow rate 5 mL/min, 220 nm). From this separation two isomers were isolated.

Example 8.4: Peak 2; Enantiomer 2

Retention time=1.45 min; LCMS (ESI): M+H$^+$=374.0; $^1$H NMR (400 MHz, CDCl$_3$) δ 6.94-6.90 (m, 2H), 6.60-6.57 (m, 2H), 6.27 (s, 1H), 4.35 (s, 2H), 3.98-3.91 (m, 2H), 3.75-3.70 (m, 2H), 3.49-3.47 (m, 2H), 3.01-2.95 (m, 1H), 2.88-2.82 (m, 1H), 2.74-2.68 (m, 1H), 2.27-2.22 (m, 1H), 1.26-1.23 (m, 3H).

Example 8.5: Peak 1, Enantiomer 1

Retention time=0.59 min; LCMS (ESI): M+H$^+$=374.0 $^1$H NMR (400 MHz, CDCl$_3$) δ 6.94-6.90 (m, 2H), 6.60-6.57 (m, 2H), 6.27 (s, 1H), 4.35 (s, 2H), 3.98-3.91 (m, 2H), 3.75-3.70 (m, 2H), 3.49-3.47 (m, 2H), 3.01-2.95 (m, 1H), 2.88-2.82 (m, 1H), 2.74-2.68 (m, 1H), 2.27-2.22 (m, 1H), 1.26-1.23 (m, 3H).

The following compounds were prepared using methods analogous to those described above:

| No. | Structure/Name | LCMS (M + H) | $^1$H NMR |
|---|---|---|---|
| 8.6 | 6-[(N-ethyl-4-fluoro-anilino)methyl]spiro[2,3-dihydrocyclopenta[3,4]thiazolo[1,4-a]pyrimidine-1,1'-cyclopentane]-8-one | 398.0 | $^1$H NMR (300 MHz, CDCl$_3$) δ 6.91-6.88 (m, 2H), 6.65-6.60 (m, 2H), 6.14 (s, 1H), 4.30 (s, 2H), 3.50-3.43 (m, 2H), 2.84-2.80 (m, 2H), 2.43-2.34 (m, 4H), 1.98-1.86 (m, 2H), 1.74-1.48 (m, 4H), 1.19-1.23 (m, 3H). |

-continued

| No. | Structure/Name | LCMS (M + H) | ¹H NMR |
|---|---|---|---|
| 8.7 | 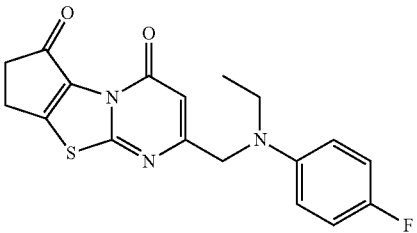<br>6-[(N-ethyl-4-fluoro-anilino)methyl]-2,3-dihydrocyclopenta[3,4]thiazolo[1,4-a]pyrimidine-1,8-dione | 358.2 | ¹H NMR (300 MHz, CDCl₃) δ 7.01-6.74 (m, 4H), 6.17 (s, 1H), 5.54 (s, 2H), 3.47-3.43 (m, 2H), 3.22-3.19 (m, 2H), 3.09-3.07 (m, 2H), 1.20-1.13 (m, 3H) |
| 8.8 | 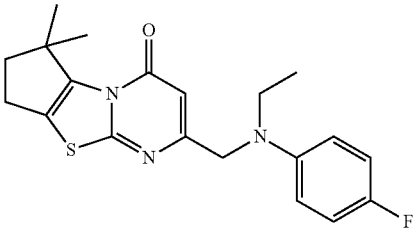<br>6-[(N-ethyl-4-fluoro-anilino)methyl]-1,1-dimethyl-2,3-dihydrocyclopenta[3,4]thiazolo[1,4-a]pyrimidin-8-one | 372.0 | ¹H NMR (300 MHz, CD₃OD) δ 6.94-6.88 (m, 2H), 6.68-6.63 (m, 2H), 6.09 (s, 1H), 4.36 (s, 2H), 3.56-3.49 (m, 2H), 2.92-2.89 (m, 2H), 2.39-2.37 (m, 2H), 1.49 (s, 6H), 1.22-1.20 (m, 3H). |
| 8.9 | 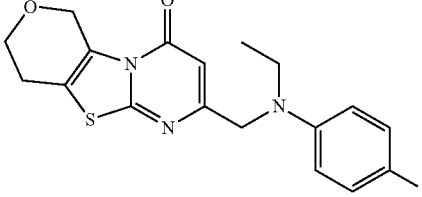<br>2-[(N-ethyl-4-fluoro-anilino)methyl]-8,9-dihydro-6H-pyrano[3,4]thiazolo[1,4-a]pyrimidin-4-one | 360.0 | ¹HNMR (300 MHz, CDCl₃) δ 6.94-6.92 (m, 2H), 6.72 (m, 2H), 6.14 (s, 1H), 4.33-4.27 (m, 2H), 3.50-3.46 (m, 2 H), 3.35-3.32 (m, 2H), 2.13-2.19 (m, 2H), 1.28-1.26 (m, 3H). |
| 8.10 | 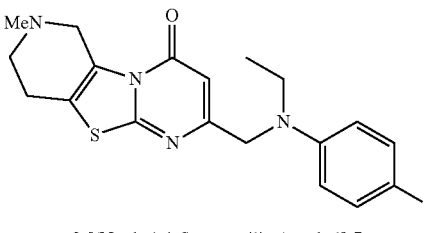<br>2-[(N-ethyl-4-fluoro-anilino)methyl]-7-methyl-8,9-dihydro-6H-pyrido[3,4]thiazolo[1,4-a]pyrimidin-4-one | 373.0 | ¹H NMR (300 MHz, CDCl₃) δ 6.94-6.86 (m, 2H), 6.59-6.52 (m, 2H), 6.12 (s, 1H), 4.28 (s, 2H), 4.22 (s, 2H), 3.47-3.45 (m, 2H), 2.86 (s, 4H), 2.58 (s, 3H), 1.23-1.21 (m, 3H). |

-continued

| No. | Structure/Name | LCMS (M + H) | ¹H NMR |
|---|---|---|---|
| 8.11 | 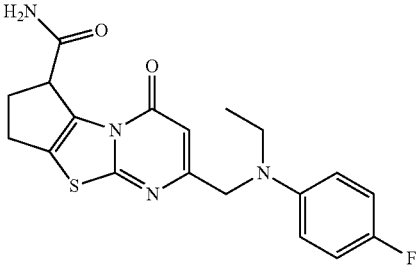<br>6-[(N-ethyl-4-fluoro-anilino)methyl]-8-oxo-2,3-dihydro-1H-cyclopenta[3,4]thiazolo[1,4-a]pyrimidine-1-carboxamide | 387.0 | ¹H NMR (400 MHz, CDCl₃) δ 7.34 (s, 1H), 6.97-6.93 (m, 2H), 6.72-6.67 (m, 2H), 6.29 (s, 1H), 5.26 (s, 1H), 4.51-4.49 (m, 1H), 4.37 (s, 2H), 3.52-3.49 (m, 2H), 3.26-3.19 (m, 1H), 3.07-3.02 (m, 1H), 2.90-2.83 (m, 1H), 2.68-2.59 (m, 1H), 1.25-1.22 (m, 3H) |
| 8.12 | 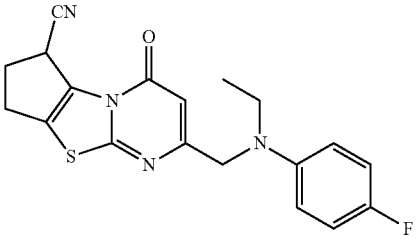<br>6-[N-ethyl-4-fluoro-anilino)methyl]-8-oxo-2,3-dihydro-1H-cyclopenta[3,4]thiazolo[1,4-a]pyrimidine-1-carbonitrile | 369.0 | ¹H NMR (300 MHz, CDCl₃) δ 6.94-6.87 (m, 2H), 6.60-6.56 (m, 2H), 6.24 (s, 1H), 4.71-4.68 (m, 1H), 4.31 (s, 2H), 3.49-3.46 (m, 2H), 3.21-2.87 (m, 4H), 1.24-1.21 (m, 3H). |
| 8.13 | 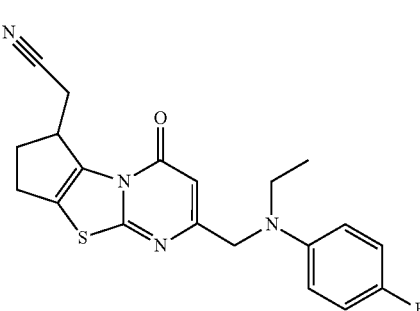<br>2-[6-[(N-ethyl-4-fluoro-anilino)methyl]-8-oxo-2,3-dihydro-1H-cyclopenta[3,4]thiazolo[1,4-a]pyrimidin-1-yl]acetonitrile | 383.3 | ¹H NMR (300 MHz, CD₃OD) δ 6.93-6.90 (m, 2H), 6.70-6.65 (m, 2H), 6.14 (s, 1H), 4.40 (s, 2H), 4.02-3.90 (m, 1H), 3.57-3.50 (m, 2H), 3.17-2.85 (m, 5H), 2.48-2.41 (m, 1H), 1.25-1.22 (m, 3H). |
| 8.14 | 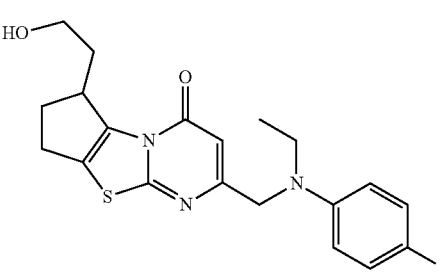<br>6-[(N-ethyl-4-fluoro-anilino)methyl]-1-(2-hydroxyethyl)-2,3-dihydro-1H-cyclopenta[3,4]thiazolo[1,4-a]pyrimidin-8-one | 388.2 | ¹H NMR (300 MHz, CDCl₃) δ 6.96-6.92 (m, 2H), 6.82-6.72 (m, 2H), 6.24 (s, 1H), 4.34 (s, 2H), 3.92-3.90 (m, 1H), 3.66-3.55 (m, 2H), 3.52-3.47 (m, 2H), 2.98-2.90 (m, 1H), 2.84-2.66 (m, 2H), 2.28-2.22 (m, 1H), 1.99-1.89 (m, 2H), 1.28-1.22 (m, 3H). |

| No. | Structure/Name | LCMS (M + H) | ¹H NMR |
|---|---|---|---|
| 8.15 | 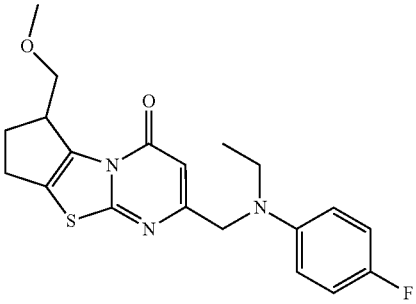<br>2-((ethyl(4-fluorophenyl)amino)methyl)-6-(methoxymethyl)-7,8-dihydrocyclopenta[4,5]thiazolo[3,2-a]pyrimidin-4(6H)-one | 388.0 | ¹H NMR (300 MHz, CDCl₃) δ 6.94-6.90 (m, 2H), 6.61-6.58 (m, 2H), 6.18 (s, 1H), 4.33 (s, 2H), 3.91-3.88 (m, 1H), 3.70-3.64 (m, 2H), 3.51-3.48 (m, 2H), 3.32 (s, 3H), 2.99-2.48 (m, 4H), 1.26-1.23 (m, 3H). |
| 8.16 | 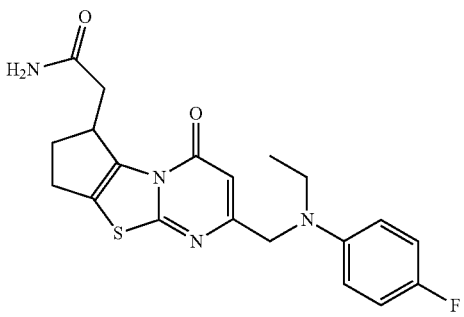<br>2-[6-[(N-ethyl-4-fluoro-anilino)methyl]-8-oxo-2,3-dihydro-1H-cyclopenta[3,4]thiazolo[1,4-a]pyrimidin-1-yl]acetamide | 401.2 | ¹H NMR (300 MHz, CD₃OD) δ 6.23-6.19 (m, 2H), 6.69-6.65 (m, 2H), 6.12 (s, 1H), 4.38 (s, 2H), 4.08-3.97 (m, 1H), 3.57-3.50 (m, 2H), 2.96-2.73 (m, 4H), 2.48-2.36 (m, 2H), 1.25-1.21 (m, 3H). |

Method 9

Example 9.1: 3-cyclohexyl-7-[[ethyl(4-fluorophenyl)amino]methyl]-2-methyl-5H-[1,3]thiazolo[3,2-a]pyrimidin-5-one

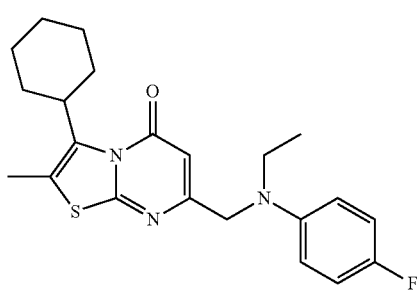 [SMILES: CCN(Cc1cc(=O)n2c(C3CCCCC3)c(C)sc2n1)c1ccc(F)cc1]

Step 1: 4-(cyclohex-1-en-1-yl)-5-methyl-1,3-thiazol-2-amine

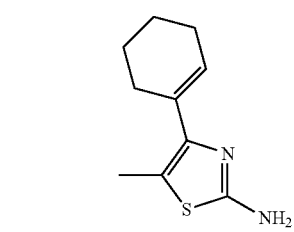

To a solution of 4-bromo-5-methyl-1,3-thiazol-2-amine (from Example 4.1, Step 5) (130 mg, 0.67 mmol) in 1,4-dioxane (2 mL) was added 2-(cyclohex-1-en-1-yl)-4,4,5,5-tetramethyl-1,3,2-dioxaborolane (140 mg, 0.67 mmol), potassium phosphate (171 mg, 0.81 mmol) and tetrakis(triphenylphosphine)palladium (78 mg, 0.070 mmol). The reaction mixture was stirred for 2 h at 90° C. and concentrated in vacuo. The residue was purified by silica gel chromatography with 3.3% methanol in dichloromethane to afford 4-(cyclohex-1-en-1-yl)-5-methyl-1,3-thiazol-2-amine as a yellow solid (140 mg). The crude product was used in next step without further purification. LCMS (ESI): M+H$^+$= 194.8.

Step 2: 4-cyclohexyl-5-methyl-1,3-thiazol-2-amine

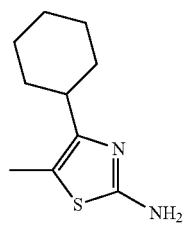

To a solution of 4-(cyclohex-1-en-1-yl)-5-methyl-1,3-thiazol-2-amine (140 mg, 0.72 mmol) in MeOH (20 mL) was added Pd/C (100 mg) and hydrogen chloride (0.1 mL, 12 mol/L). The reaction mixture was stirred overnight at 40° C. under a hydrogen atmosphere (5 atm), then filtered and concentrated in vacuo to afford 4-cyclohexyl-5-methyl-1,3-thiazol-2-amine as a yellow solid (130 mg). The crude product was used in next step without further purification. LCMS (ESI): M+H$^+$=197.1.

Step 3: 7-(chloromethyl)-3-cyclohexyl-2-methyl-5H-[1,3]thiazolo[3,2-a]pyrimidin-5-one

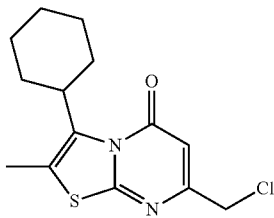 [SMILES: Cc1sc2nc(CCl)cc(=O)n2c1C1CCCCC1]

To a solution of 4-cyclohexyl-5-methyl-1,3-thiazol-2-amine (130 mg, 0.66 mmol) in polyphosphoric acid (10 mL) was added ethyl 4-chloro-3-oxobutanoate (164 mg, 1.00 mmol). The reaction mixture was stirred for 1 h at 100° C. and then quenched by water (100 mL). The pH value was adjusted to pH 8-9 with a sodium hydroxide solution (1 M). The resulting solution was extracted with dichloromethane (50 mL×3), washed with brine, dried over anhydrous sodium sulfate, and concentrated in vacuo. The residue was purified by chromatography with ethyl acetate/petroleum ether (1/1) to afford 7-(chloromethyl)-3-cyclohexyl-2-methyl-5H-[1,3]thiazolo[3,2-a]pyrimidin-5-one as a white solid (49 mg, 25%). LCMS (ESI): M+H$^+$=297.1.

Step 4: 3-cyclohexyl-7-[[ethyl(4-fluorophenyl)amino]methyl]-2-methyl-5H-[1,3]thiazolo[3,2-a]pyrimidin-5-one

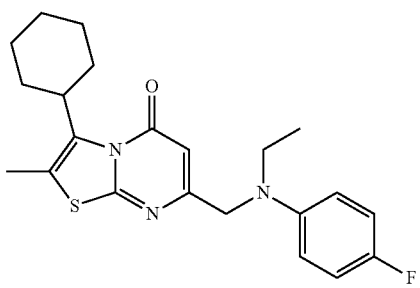 [SMILES: CCN(Cc1cc(=O)n2c(C3CCCCC3)c(C)sc2n1)c1ccc(F)cc1]

To a solution of 7-(chloromethyl)-3-cyclohexyl-2-methyl-5H-[1,3]thiazolo[3,2-a]pyrimidin-5-one (49 mg, 0.17 mmol) in acetonitrile (20 mL) was added potassium carbonate (46 mg, 0.33 mmol), potassium iodide (14 mg, 0.08 mmol) and N-ethyl-4-fluoroaniline (28 mg, 0.20 mmol). The reaction mixture was stirred overnight at 60° C. and then quenched by water (100 mL). The reaction mixture was extracted with dichloromethane (50 mL×3), washed with brine, dried over anhydrous sodium sulfate, and concentrated in vacuo. The residue was purified by chromatography with ethyl acetate/petroleum ether (1/2) to afford 3-cyclohexyl-7-[[ethyl(4-fluorophenyl)amino]methyl]-2-methyl-5H-[1,3]thiazolo[3,2-a]pyrimidin-5-one as a gray solid (8.8 mg, 13%). LCMS (ESI): M+H$^+$=399.9; $^1$H NMR (300 MHz, CDCl$_3$) δ 6.94-6.85 (m, 2H), 6.58-6.54 (m, 2H), 6.07 (s, 1H), 4.25 (s, 2H), 3.48-3.41 (m, 2H), 2.41 (s, 3H), 1.87-1.71 (m, 6H), 1.41-1.30 (m, 4H), 1.25-1.20 (m, 3H).

The following example was prepared in a manner similar to Example 9.1:

| No. | Structure/Name | LCMS (M + H) | $^1$H NMR |
|---|---|---|---|
| 9.2 | ![structure] 7-[(N-ethyl-4-fluoro-anilino)methyl]-3-isopropyl-2-methyl-thiazolo[3,2-a]pyrimidin-5-one | 360.0 | $^1$H NMR (300 MHz, CD$_3$OD) δ 6.91-6.87 (m, 2H), 6.69-6.19 (m, 2H), 6.05 (s, 1H), 4.33 (s, 2H), 3.55-3.51 (m, 2H), 2.44 (s, 3H), 2.10 (m, 1H), 1.41-1.38 (m, 6H), 1.19-1.21 (m, 3H). |

The following compounds were prepared using methods analogous to those described above:

| No. | Structure/Name | LCMS (M + H) | ¹H NMR |
|---|---|---|---|
| 9.3 | 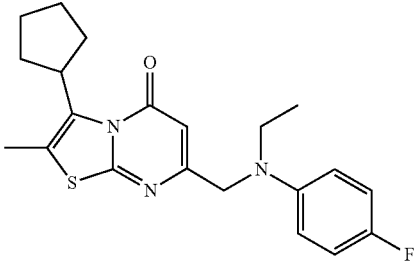<br>3-cyclopentyl-7-[(N-ethyl-4-fluoro-anilino)methyl]-2-methyl-thiazolo[3,2-a]pyrimidin-5-one | 386.0 | ¹H NMR (300 MHz, CD$_3$OD) δ 6.93-6.87 (m, 2H), 6.67-6.63 (m, 2H), 6.04 (s, 1H), 4.33 (s, 2H), 4.17-4.08 (m, 1H), 3.53-3.47 (m, 2H), 2.41 (s, 3H), 1.96-1.88 (m, 6H), 1.69-1.65 (m, 2H), 1.22-1.19 (m, 3H). |
| 9.4 | 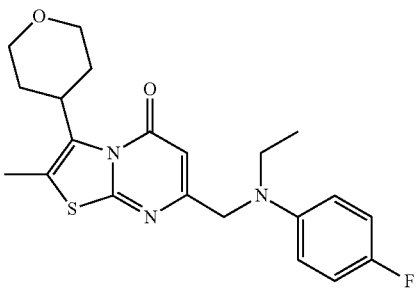<br>7-[(N-ethyl-4-fluoro-anilino)methyl]-2-methyl-3-tetrahydropyran-4-yl-thiazolo[3,2-a]pyrimidin-5-one | 401.8 | ¹H NMR (300 MHz, CDCl$_3$) δ 6.92-6.85 (m, 2H), 6.62-6.58 (m, 2H), 6.10 (s, 1H), 4.67 (br, 1H), 4.26 (s, 2H), 4.06-4.01 (m, 2H), 3.55-3.42 (m, 4H), 2.46 (s, 3H), 2.18-2.07 (m, 2H), 1.84-1.80 (m, 2H), 1.30-1.19 (m, 3H). |

Method 10

Example 10.1: 3-cyclobutyl-7-[(N-ethyl-4-fluoro-anilino)methyl]-2-methyl-thiazolo[3,2-a]pyrimidin-5-one

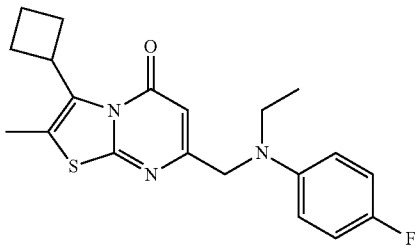 [SMILES: CCN(Cc1cc(=O)n2c(C3CCC3)c(C)sc2n1)c1ccc(F)cc1]

Step 1: 2-Bromo-1-cyclobutylpropan-1-one

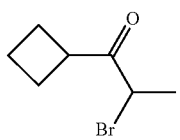

To a solution of 1-cyclobutylpropan-1-one (2.50 g, 22.3 mmol) in methanol (50 mL) was added bromine (3.87 g, 24.2 mmol) under nitrogen atmosphere. The reaction solution was stirred overnight at room temperature and was then concentrated in vacuo to afford 2-bromo-1-cyclobutylpropan-1-one as yellow oil (3.5 g). The crude product was used for the next step without further purification.

Step 2: 4-Cyclobutyl-5-methyl-1,3-thiazol-2-amine

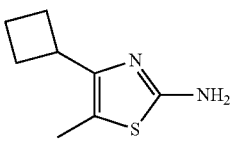

To a solution of 2-bromo-1-cyclobutylpropan-1-one (3.50 g, 31.3 mmol) in ethanol (30 mL) was added thiourea (1.5 g, 19.71 mmol). The reaction solution was heated to reflux for 1 h and then concentrated in vacuo. The residue was dissolved in dichloromethane (50 mL) and the solids were filtered off. The resulting solution was concentrated in vacuo to afford 4-cyclobutyl-5-methyl-1,3-thiazol-2-amine as a yellow solid (600 mg, 18%). LCMS (ESI): M+H$^+$=169.0.

Step 3: 6-(Chloromethyl)-3-cyclobutyl-2-methyl-3aH,4H-thieno[2,3-b]yridine-4-one Step 4: 3-Cyclobutyl-7-[[ethyl(4-fluorophenyl)amino]methyl]-2-methyl-5H-[1,3]thiazolo[3,2-a]pyrimidin-5-one

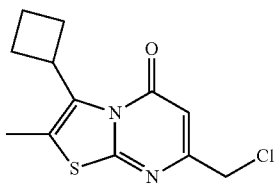 [SMILES: Cc1sc2nc(CCl)cc(=O)n2c1C1CCC1]

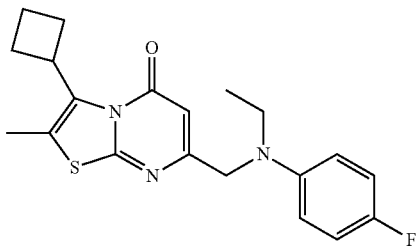 [SMILES: CCN(Cc1cc(=O)n2c(C3CCC3)c(C)sc2n1)c1ccc(F)cc1]

To a solution of 4-cyclobutyl-5-methyl-1,3-thiazol-2-amine (335 mg, 1.99 mmol) was added polyphosphoric acid (5 mL) and ethyl 4-chloro-3-oxobutanoate (492 mg, 2.99 mmol). The reaction solution was stirred for 1 h at 110° C. The pH value of the solution was adjusted to pH 9-10 with an aqueous sodium hydroxide solution (2 M). The reaction mixture was extracted with dichloromethane (5×100 mL), washed with brine, dried over sodium sulfate and concentrated in vacuo to afford 6-(chloromethyl)-3-cyclobutyl-2-methyl-3aH,4H-thieno[2,3-b]yridine-4-one as a brown solid (300 mg). The crude product was used in next step without further purification. LCMS (ESI): M+H$^+$=269.0.

To a solution of 7-(chloromethyl)-3-cyclobutyl-2-methyl-5H-[1,3]thiazolo[3,2-a]pyrimidin-5-one (300 mg, 1.12 mmol) in acetonitrile (20 mL) was added potassium iodide (93 mg, 0.56 mmol), potassium carbonate (309 mg, 2.24 mmol), and N-ethyl-4-fluoroaniline (311 mg, 2.23 mmol). The resulting solution was stirred for 5 h at 70° C. After concentrating in vacuo, the crude product was purified by Prep-HPLC with the following conditions (Agilent 1200: Column, X-Brigde C18; mobile phase, 0.05% NH$_4$HCO$_3$ in water and CH$_3$CN (CH$_3$CN 20% up to 60% in 15 min); Detector, UV254) to afford 3-cyclobutyl-7-[[ethyl(4-fluorophenyl)amino]methyl]-2-methyl-5H-[1,3]thiazolo[3,2-a]pyrimidin-5-one as a yellow solid (36.1 mg, 8%). LCMS (ESI): M+H$^+$=371.8; $^1$H NMR (300 MHz, CD$_3$OD) δ 6.93-6.86 (m, 2H), 6.69-6.62 (m, 2H), 6.01 (s, 1H), 4.44-4.35 (m, 1H), 4.31 (s, 2H), 3.53-3.49 (m, 2H), 2.48 (s, 3H), 2.45-2.35 (m, 2H), 1.89-1.80 (m, 1H), 2.06-1.94 (m, 1H), 1.22-1.19 (m, 3H).

The following examples were prepared in a manner similar to Example 10.1:

| No. | Structure/Name | LCMS (M + H) | $^1$H NMR |
|---|---|---|---|
| 10.2 | 3-tert-butyl-7-[(N-ethyl-4-fluoro-anilino)methyl]-2-methyl-thiazolo[3,2-a]pyrimidin-5-one | 374.0 | $^1$H NMR (300 MHz, CD$_3$OD) 6.94-6.91 (m, 2H), 6.68-6.63 (m, 2H), 6.04 (s, 1H), 4.31 (s, 2H), 3.53-3.50 (m, 2H), 2.54 (s, 3H), 1.59 (s, 9H), 1.23-1.20 (m, 3H). |
| 10.3 | 3-acetyl-7-((ethyl(4-fluorophenyl)amino)methyl)-2-methyl-5H-thiazolo[3,2-a]pyrimidin-5-one | 360.1 | $^1$H NMR (300 MHz, CD$_3$OD) δ 6.95-6.89 (m, 2H), 6.70-6.65 (m, 2H), 6.16 (s, 1H), 4.40 (s, 2H), 3.54-3.52 (m, 2H), 2.40 (m, 6H), 1.24-1.21 (m, 3H). |

| No. | Structure/Name | LCMS (M + H) | ¹H NMR |
|---|---|---|---|
| 10.4 | 7-[N-ethyl-4-fluoro-anilino)methyl]-N,2-dimethyl-5-oxo-thiazolo[3,2-a]pyrimidine-3-carboxamide | 375.2 | ¹H NMR (300 MHz, DMSO-$d_6$) δ 8.37-8.36 (m, 1H), 7.14-6.95 (m, 2H), 6.68-6.59 (m, 2H), 5.90 (s, 1H), 4.42 (s, 2H), 3.48-3.35 (m, 2H), 2.73-2.71 (m, 3H), 2.30 (s, 3H), 1.13-1.11 (m, 3H). |

Example 10.5: 7-[(N-ethyl-4-fluoro-anilino)methyl]-3-(1-hydroxy-1-methyl-ethyl)-2-methyl-thiazolo[3,2-a]pyrimidin-5-one

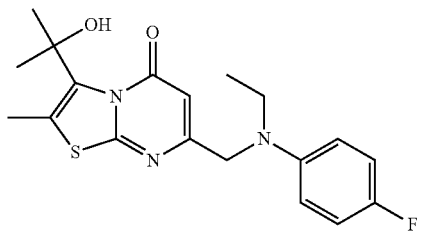 [SMILES: CCN(Cc1cc(=O)n2c(C(C)(C)O)c(C)sc2n1)c1ccc(F)cc1]

To a solution of 3-acetyl-7-[[ethyl(4-fluorophenyl)amino]methyl]-2-methyl-5H-[1,3]thiazolo[3,2-a]pyrimidin-5-one (from Example 10.3) (70 mg, 0.19 mmol) in tetrahydrofuran (15 mL) was added methylmagnesium bromide in tetrahydrofuran (1 mol/L, 0.42 mL). The reaction was stirred for 48 h at room temperature and was then quenched by a saturated aqueous ammonium chloride solution (20 mL). The resulting mixture was extracted with dichloromethane (3×30 mL), washed with brine, dried over anhydrous sodium sulfate, and concentrated in vacuo. The residue was purified chromatography with dichloromethane/methanol (50/1) to afford 7-[[ethyl(4-fluorophenyl)amino]methyl]-3-(2-hydroxypropan-2-yl)-2-methyl-5H-[1,3]thiazolo[3,2-a]pyrimidin-5-one as a yellow solid (40 mg, 52%). LCMS (ESI): M+H⁺=376.1; ¹H NMR (300 MHz, CD$_3$OD) δ 6.95-6.89 (m, 2H), 6.70-6.65 (m, 2H), 6.24 (s, 1H), 4.39 (s, 2H), 3.56-3.50 (m, 2H), 2.58 (s, 3H), 1.73 (s, 6H), 1.24-1.21 (m, 3H).

Example 10.6: 7-[(N-ethyl-4-fluoro-anilino)methyl]-3-(1-hydroxyethyl)-2-methyl-thiazolo[3,2-a]pyrimidin-5-one

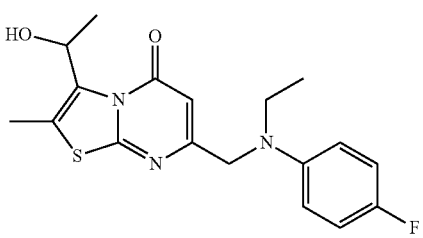 [SMILES: CCN(Cc1cc(=O)n2c(C(C)O)c(C)sc2n1)c1ccc(F)cc1]

Step 1: 7-((ethyl(4-fluorophenyl)amino)methyl)-2-methyl-5-oxo-5H-thiazolo[3,2-a]pyrimidine-3-carbaldehyde To a solution of 3-bromo-7-((ethyl(4-fluorophenyl)amino)methyl)-2-methyl-5H-thiazolo[3,2-a]pyrimidin-5-one (from Example 5.1, Step 1) (200 mg, 0.51 mmol) in tetrahydrofuran (10 mL) was added n-butyl lithium (0.3 ml, 2.5 mol/L) at −78° C., then was stirred 30 min at the same temperature. Ethyl formate (75.8 mg, 1.02 mmol) was added to the reaction mixture at −78° C. and allowed to warm to room temperature for 1 hour. The resulting reaction was quenched by water (20 mL), extracted with dichloromethane (30 mL×3), washed with brine, dried over anhydrous sodium sulfate, and concentrated under vacuum. The residue was purified by chromatography with 20% ethyl acetate in petroleum ether to afford 7-((ethyl(4-fluorophenyl)amino)methyl)-2-methyl-5-oxo-5H-thiazolo[3,2-a]pyrimidine-3-carbaldehyde. LCMS (ESI): M+H⁺=345.1.

Step 2: 7-[(N-ethyl-4-fluoro-anilino)methyl]-3-(1-hydroxyethyl)-2-methyl-thiazolo[3,2-a]pyrimidin-5-one

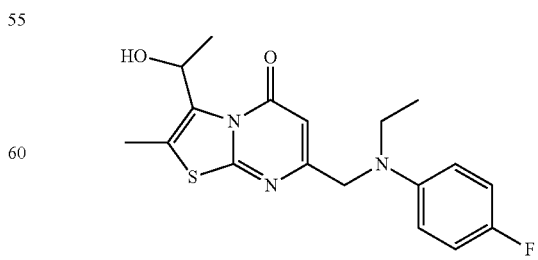

To a solution of 7-[[ethyl(4-fluorophenyl)amino]methyl]-2-methyl-5-oxo-5H-[1,3]thiazolo[3,2-a]pyrimidine-3-carbaldehyde (200 mg, 0.58 mmol) (from example 11.4) in tetrahydrofuran (15 mL) was added methylmagnesium bromide (1.3 mL, 0.5 mol/L). The resulting solution was stirred for overnight at room temperature. The reaction was then quenched by ammonium chloride (sat., 20 mL), extracted with dichloromethane (3×30 mL), washed with brine, dried over sodium sulfate and concentrated in vacuo. The residue was purified by chromatography with ethyl acetate/petroleum ether (1/2) to afford 7-[[ethyl(4-fluorophenyl)amino]methyl]-3-(1-hydroxyethyl)-2-methyl-5H-[1,3]thiazolo[3,2-a]pyrimidin-5-one as an off-white solid (67.5 mg, 31%). LCMS (ESI): M+H+=362.1; $^1$H NMR (300 MHz, CD$_3$OD) δ 6.95-6.88 (m, 2H), 6.71-6.65 (m, 2H), 6.20 (s, 1H), 5.43-5.36 (m, 1H), 4.39 (s, 2H), 3.56-3.51 (m, 2H), 2.50 (s, 3H), 1.54-1.51 (m, 3H), 1.24-1.21 (m, 3H).

Example 10.7: 3-[(dimethylamino)methyl]-7-[[ethyl(4-fluorophenyl)amino]methyl]-2-methyl-5H-[1,3]thiazolo[3,2-a]pyrimidin-5-one

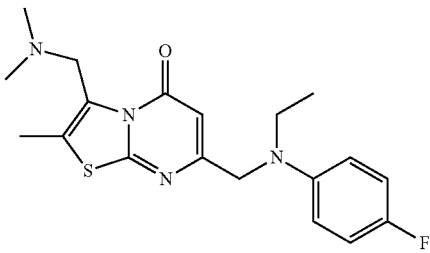 [SMILES: CCN(Cc1cc(=O)n2c(CN(C)C)c(C)sc2n1)c1ccc(F)cc1]

To a solution of 7-[[ethyl(4-fluorophenyl)amino]methyl]-2-methyl-5-oxo-5H-[1,3]thiazolo[3,2-a]pyrimidine-3-carbaldehyde (from Example 10.6, Step 1) (100 mg, 0.29 mmol) in methanol (30 mL) was added dimethylamine hydrochloride (118 mg, 1.45 mmol), triethylamine (161 mg, 1.59 mmol) and sodium cyanoborohydride (55 mg, 0.88 mmol). The reaction mixture was stirred overnight at room temperature and then quenched by water (50 mL). The reaction mixture was extracted with dichloromethane (30 mL×3), washed with brine, dried over anhydrous sodium sulfate, and concentrated under vacuum. The residue was purified by chromatography with 25% ethyl acetate in petroleum ether to afford 3-[(dimethylamino)methyl]-7-[[ethyl(4-fluorophenyl)amino]methyl]-2-methyl-5H-[1,3]thiazolo[3,2-a]pyrimidin-5-one as a light yellow solid (11.1 mg, 10%). LCMS [M+H]+=374.85; $^1$H NMR (300 MHz, CDCl$_3$) δ 6.92-6.84 (m, 2H), 6.58-6.54 (m, 2H), 6.14 (s, 1H), 4.28 (s, 2H), 4.05 (bs, 2H), 3.48-3.41 (m, 2H), 2.44-2.39 (m, 9H), 1.26-1.19 (m, 3H).

The following examples were prepared in a manner similar to Example 10.7:

| No. | Structure/Name | LCMS (M + H) | $^1$H NMR |
|---|---|---|---|
| 10.8 | 3-(azetidin-1-ylmethyl)-7-[(N-ethyl-4-fluoro-anilino)methyl]-2-methyl-thiazolo[3,2-a]pyrimidin-5-one | 387.1 | $^1$H NMR (300 MHz, CD$_3$OD) δ 6.93-6.89 (m, 2H), 6.69-6.63 (m, 2H), 6.08 (s, 1H), 4.36 (s, 2H), 4.27 (s, 2H), 3.56-3.52 (m, 2H), 3.33-3.31 (m, 4H), 2.41 (s, 3H), 2.13-2.06 (m, 2H), 1.23-1.21 (m, 3H) |
| 10.9 | 7-[(N-ethyl-4-fluoro-anilino)methyl]-2-methyl-3-(pyrrolidin-1-ylmethyl)thiazolo[3,2-a]pyrimidin-5-one | 401.1 | $^1$H NMR (300 MHz, DMSO-d$_6$) δ 7.01-6.95 (m, 2H), 6.65-6.59 (m, 2H), 5.84 (s, 1H), 4.31 (s, 2H), 4.13 (s, 2H), 3.48-3.43 (m, 2H), 2.50-2.49 (m, 4H), 2.38 (s, 3H), 1.75-1.73 (m, 4H), 1.15-1.10 (m, 3H) |

| No. | Structure/Name | LCMS (M + H) | ¹H NMR |
|---|---|---|---|
| 10.10 | 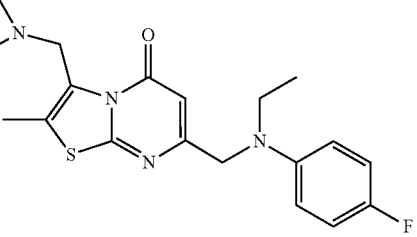<br>7-[(N-ethyl-4-fluoro-anilino)methyl]-3-[(3-hydroxyazetidin-1-yl)methyl]-2-methyl-thiazolo[3,2-a]pyrimidin-5-one | 402.9 | ¹H NMR (300 MHz, DMSO-d$_6$) δ 7.01-6.95 (m, 2H), 6.63-6.59 (m, 2H), 5.83 (s, 1H), 5.22-5.20 (m, 1H), 4.31 (s, 2H), 4.11-4.01 (m, 3H), 3.50-3.37 (m, 4H), 2.83-2.78 (m, 2H), 2.38 (s, 3H), 1.15-1.10 (m, 3H). |

Example 10.11: 7-[(N-ethyl-4-fluoro-anilino)methyl]-2-methyl-3-(2,2,2-trifluoro-1-hydroxyethyl)thiazolo[3,2-a]pyrimidin-5-one

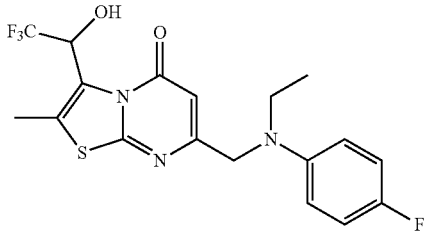 [SMILES: CCN(Cc1cc(=O)n2c(C(O)C(F)(F)F)c(C)sc2n1)c1ccc(F)cc1]

To a solution of tetrabutylammonium fluoride (113 mg, 0.43 mmol) in tetrahydrofuran (10 mL) was added 4 Å-molecular sieves (200 mg) and then was stirred for 0.5 h at −20° C. A solution of 7-[[ethyl(4-fluorophenyl)amino]methyl]-2-methyl-5-oxo-5H-[1,3]thiazolo[3,2-a]pyrimidine-3-carbaldehyde (from Example 10.6, Step 1) (300 mg, 0.87 mmol), trimethyl(trifluoromethyl)silane (617 mg, 4.35 mmol) and 4 Å molecular sieve (100 mg) in tetrahydrofuran (20 mL) was added. The reaction mixture was stirred for an additional 3 h at −30° C. The reaction was quenched with water (50 mL), extracted with dichloromethane (3×50 mL), washed with brine, dried over anhydrous magnesium sulfate and concentrated in vacuo. The residue was purified by silica gel chromatography with dichloromethane/methanol (50/1) to afford 7-[[ethyl(4-fluorophenyl)amino]methyl]-2-methyl-3-(2,2,2-trifluoro-1-hydroxyethyl)-5H-[1,3]thiazolo[3,2-a]pyrimidin-5-one as a off-white solid (32.4 mg, 9.0%). LCMS (ESI): M+H$^+$=416.0; ¹H NMR (300 MHz, CD$_3$OD) δ 6.95-6.89 (m, 2H), 6.69-6.64 (m, 2H), 6.12 (s, 1H), 4.87 (s, 1H), 4.37 (s, 2H), 3.55-3.50 (m, 2H), 2.63 (s, 3H), 1.24-1.20 (m, 3H).

Example 10.12: 7-((ethyl(4-fluorophenyl)amino)methyl)-3-(hydroxymethyl)-2-methyl-5H-thiazolo[3,2-a]pyrimidin-5-one

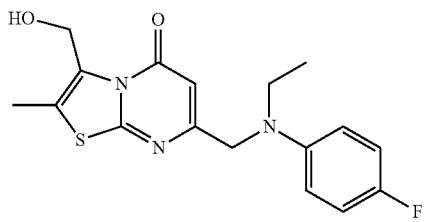 [SMILES: CCN(Cc1cc(=O)n2c(CO)c(C)sc2n1)c1ccc(F)cc1]

To a solution of 7-[[ethyl(4-fluorophenyl)amino]methyl]-2-methyl-5-oxo-5H-[1,3]thiazolo[3,2-a]pyrimidine-3-carbaldehyde (from Example 10.6, Step 1) (100 mg, 0.29 mmol) in tetrahydrofuran (10 mL) was added water (2 mL) and sodium borohydride (33 mg, 0.87 mmol). The reaction mixture was stirred overnight at room temperature and then quenched with water (50 mL). The resulting solution was extracted with ethyl acetate (30 mL×3), washed with brine, dried over anhydrous sodium sulfate, and concentrated in vacuo. The residue was purified by chromatography with 50% ethyl acetate in petroleum ether to afford 7-[[ethyl(4-fluorophenyl)amino]methyl]-3-(hydroxymethyl)-2-methyl-5H-[1,3]thiazolo[3,2-a]pyrimidin-5-one as a off-white solid (60 mg, 60%). LCMS (ESI): M+H$^+$=347.9; ¹H NMR (300 MHz, CDCl$_3$) δ 6.93-6.86 (m, 2H), 6.59-6.54 (m, 2H), 6.26 (s, 1H), 4.75-4.73 (m, 2H), 4.49-4.45 (m, 1H), 4.32 (s, 2H), 3.52-3.44 (m, 2H), 2.44 (s, 3H), 1.25-1.19 (m, 3H).

Example 10.13: 7-[[ethyl(4-fluorophenyl)amino]methyl]-3-(methoxymethyl)-2-methyl-5H-[1,3]thiazolo[3,2-a]pyrimidin-5-one

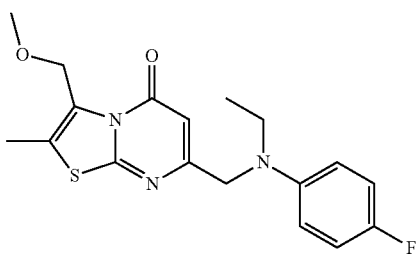 [SMILES: CCN(Cc1cc(=O)n2c(COC)c(C)sc2n1)c1ccc(F)cc1]

To a solution of 7-[[ethyl(4-fluorophenyl)amino]methyl]-3-(hydroxymethyl)-2-methyl-5H-[1,3]thiazolo[3,2-a]pyrimidin-5-one (60 mg, 0.17 mmol) in tetrahydrofuran (10 mL) was added sodium hydride (11 mg, 0.28 mmol) and iodomethane (30 mg, 0.21 mmol). The reaction mixture was stirred overnight at room temperature and then quenched by water (100 mL). The resulting solution was extracted with dichloromethane (50 mL×3), washed with brine, dried over anhydrous sodium sulfate, and concentrated in vacuo. The residue was purified by chromatography with 50% ethyl acetate in petroleum ether to afford 7-[[ethyl(4-fluorophenyl)amino]methyl]-3-(methoxymethyl)-2-methyl-5H-[1,3]thiazolo[3,2-a]pyrimidin-5-one as a yellow semi-solid (1.4 mg, 2.0%). LCMS (ESI): M+H⁺=362.1; $^1$H NMR (300 MHz, CDCl$_3$) δ 6.93-6.87 (m, 2H), 6.61-6.60 (m, 2H), 6.16 (s, 1H), 4.93 (s, 2H), 4.28 (s, 2H), 3.45-3.42 (m, 5H), 2.45 (s, 3H), 1.33-1.21 (m, 3H).

Example 10.14: 7-[[Ethyl(4-fluorophenyl)amino]methyl]-2-methyl-3-(1H-pyrazol-1-ylmethyl)-5H-[1,3]thiazolo[3,2-a]pyrimidin-5-one

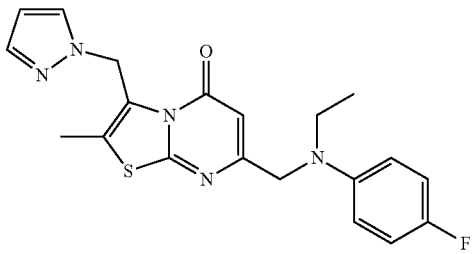 [SMILES: CCN(Cc1cc(=O)n2c(Cn3cccn3)c(C)sc2n1)c1ccc(F)cc1]

To a solution of 7-[[ethyl(4-fluorophenyl)amino]methyl]-3-(hydroxymethyl)-2-methyl-5H-[1,3]thiazolo[3,2-a]pyrimidin-5-one (from Example 10.12) (100 mg, 0.29 mmol), 1H-pyrazole (39.2 mg, 0.58 mmol) and triphenylphosphine (135 mg, 0.52 mmol) in tetrahydrofuran (5 mL) was added diisopropyl azodicarboxylate (105 mg, 0.52 mmol). The reaction mixture was stirred at room temperature overnight. After concentrating in vacuo, the crude residue was purified by silica gel chromatography with dichloromethane/methanol (100/1) to afford 7-[[ethyl(4-fluorophenyl)amino]methyl]-2-methyl-3-(1H-pyrazol-1-ylmethyl)-5H-[1,3]thiazolo[3,2-a]pyrimidin-5-one as an off-white solid (10.0 mg, 8.0%). LCMS (ESI): M+H⁺=398.1; $^1$H NMR (300 MHz, CD$_3$OD) δ 7.76 (s, 1H), 7.45 (s, 1H), 6.93-6.87 (m, 2H), 6.68-6.62 (m, 2H), 6.25 (s, 1H), 6.05 (s, 1H), 5.90 (s, 2H), 4.34 (s, 2H), 3.53-3.47 (m, 2H), 2.58 (s, 3H), 1.22-1.19 (m, 3H).

Example 10.15: 7-[(N-ethyl-4-fluoro-anilino)methyl]-2-methyl-3-(methylsulfonylmethyl)thiazolo[3,2-a]pyrimidin-5-one

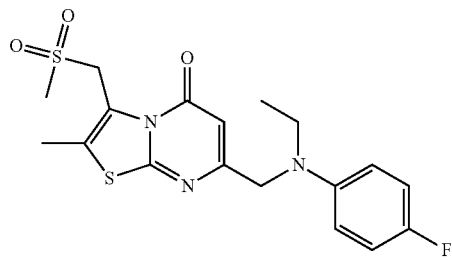 [SMILES: CCN(Cc1cc(=O)n2c(CS(C)(=O)=O)c(C)sc2n1)c1ccc(F)cc1]

Step 1: (7-[[ethyl(4-fluorophenyl)amino]methyl]-2-methyl-5-oxo-5H-[1,3]thiazolo[3,2-a]pyrimidin-3-yl)methyl methanesulfonate

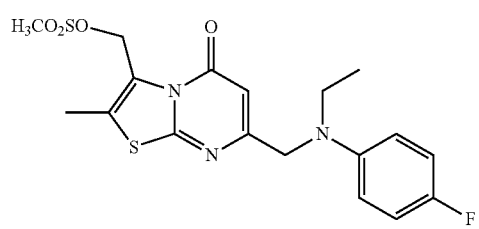

To a solution of 7-[[ethyl(4-fluorophenyl)amino]methyl]-3-(hydroxymethyl)-2-methyl-5H-[1,3]thiazolo[3,2-a]pyrimidin-5-one (from Example 10.12) (100 mg, 0.28 mmol) in dichloromethane (15 mL) was added triethylamine (58 mg, 0.58 mmol) and methanesulfonyl chloride (50 mg, 0.44 mmol) at 0° C. The reaction mixture was stirred for 30 min at 0° C. and then concentrated under vacuum. The crude product was used directly in the next step.

Step 2: 7-[[ethyl(4-fluorophenyl)amino]methyl]-3-(methanesulfonylmethyl)-2-methyl-5H-[1,3]thiazolo[3,2-a]pyrimidin-5-one

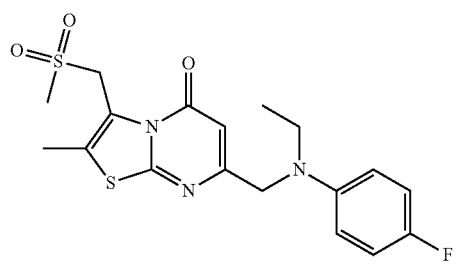 [SMILES: CCN(Cc1cc(=O)n2c(CS(C)(=O)=O)c(C)sc2n1)c1ccc(F)cc1]

To a solution of (7-[[ethyl(4-fluorophenyl)amino]methyl]-2-methyl-5-oxo-5H-[1,3]thiazolo[3,2-a]pyrimidin-3-yl)methyl methanesulfonate (120 mg, 0.28 mmol) in ethanol (30 mL) was added sodium methanesulfinate (202 mg, 1.98 mmol). The reaction mixture was stirred at reflux for 2 h at 80° C. and then concentrated in vacuo. The residue was purified by silica gel chromatography with dichloromethane/methanol (30/1) to afford 7-[[ethyl(4-fluorophenyl)amino]methyl]-3-(methanesulfonylmethyl)-2-methyl-5H-[1,3]thiazolo[3,2-a]pyrimidin-5-one as an off-white solid (2.8 mg, 2%). LCMS (ESI): M+H⁺=409.9; $^1$H NMR (300 MHz, DMSO-d$_6$) δ 6.94-6.88 (m, 2H), 6.57-6.52 (m, 2H), 5.84 (s, 1H), 5.28 (s, 2H), 4.27 (s, 2H), 3.41-3.36 (m, 2H), 2.93 (s, 3H), 2.39 (s, 3H), 1.08-1.03 (m, 3H) and 3-(ethoxymethyl)-7-[[ethyl(4-fluorophenyl)amino]methyl]-2-methyl-5H-[1,3]thiazolo[3,2-a]pyrimidin-5-one as a off-white solid (22.1 mg, 21%). LCMS (ESI): M+H⁺=409.9; $^1$H NMR (300 MHz, DMSO-d$_6$) δ 6.94-6.88 (m, 2H), 6.57-6.52 (m, 2H), 5.84 (s, 1H), 5.28 (s, 2H), 4.27 (s, 2H), 3.41-3.36 (m, 2H), 2.93 (s, 3H), 2.39 (s, 3H), 1.08-1.03 (m, 3H).

The following examples were prepared in a manner similar to Example 10.15:

| No. | Structure/Name | LCMS (M + H) | ¹H NMR |
|---|---|---|---|
| 10.16 | 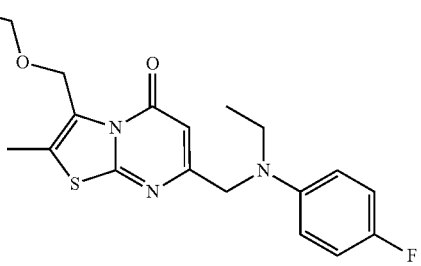<br>3-(ethoxymethyl)-7-[(N-ethyl-4-fluoro-anilino)methyl]-2-methyl-thiazolo[3,2-a]pyrimidin-5-one | 376.1 | ¹H NMR (300 MHz, DMSO-$d_6$) δ 7.00-6.94 (m, 2H), 6.64-6.60 (m, 2H), 5.86 (s, 1H), 4.87 (s, 2H), 4.32 (s, 2H), 3.49-3.47 (m, 4H), 2.41 (s, 3H), 1.15-1.05 (m, 6H). |
| 10.17 | 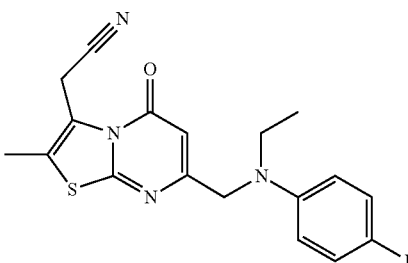<br>2-[7-[(N-ethyl-4-fluoro-anilino)methyl]-2-methyl-5-oxo-thiazolo[3,2-a]pyrimidin-3-yl]acetonitrile | 357.1 | ¹H NMR (300 MHz, CDCl₃) δ 6.94-6.87 (m, 2H), 6.59-6.53 (m, 2H), 6.18 (s, 1H), 4.41 (s, 2H), 4.28 (s, 2H), 3.48-3.41 (m, 2H), 2.41 (s, 3H), 1.25-1.19 (m, 3H). |

The following compounds were prepared using methods analogous to those described above:

| No. | Structure/Name | LCMS (M + H) | ¹H NMR |
|---|---|---|---|
| 10.18 | 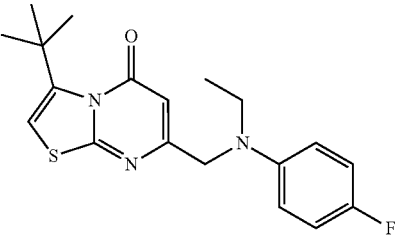<br>3-tert-butyl-7-[(N-ethyl-4-fluoro-anilino)methyl]thiazolo[3,2-a]pyrimidin-5-one | 360.0 | ¹H NMR (300 MHz, CDCl₃) 6.92-6.89 (m, 2H), 6.64 (s, 1H), 6.61-6.56 (m, 2H), 6.17 (s, 1H), 4.29 (s, 2H), 3.48-3.45 (m, 2H), 1.55 (s, 9H), 1.24-1.21 (m, 3H). |
| 10.19 | 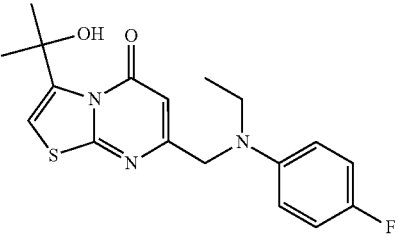<br>7-[(N-ethyl-4-fluoro-anilino)methyl]-3-(1-hydroxy-1-methyl-ethyl)thiazolo[3,2-a]pyrimidin-5-one | 362.1 | ¹H NMR (400 MHz, DMSO-$d_6$) δ 7.46-7.36 (m, 1H), 7.03-6.93 (m, 2H), 6.69-6.58 (m, 2H), 6.48 (s, 1H), 6.11 (s, 1H), 4.40 (s, 2H), 3.49 (q, J = 7.0 Hz, 2H), 1.56 (s, 6H), 1.14 (t, J = 7.0 Hz, 3H). |

| No. | Structure/Name | LCMS (M + H) | ¹H NMR |
|---|---|---|---|
| 10.20 | 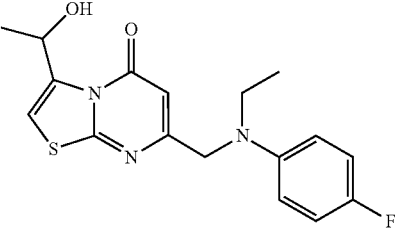<br>7-[(N-ethyl-4-fluoro-anilino)methyl]-3-(1-hydroxyethyl)thiazolo[3,2-a]pyrimidin-5-one | 348.1 | ¹H NMR (400 MHz, DMSO-$d_6$) δ 7.03-6.92 (m, 2H), 6.67-6.59 (m, 2H), 5.92 (s, 1H), 5.48 (td, J = 6.6, 5.4 Hz, 1H), 7.31-7.25 (m, 1H), 4.34 (s, 2H), 3.47 (q, J = 7.0 Hz, 2H), 1.37 (d, J = 6.3 Hz, 3H), 1.13 (t, J = 7.0 Hz, 3H). |
| 10.21 | 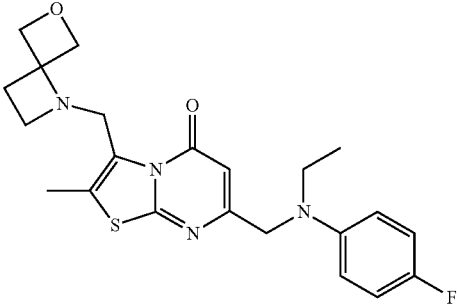<br>7-[(N-ethyl-4-fluoro-anilino)methyl]-2-methyl-3-(6-oxa-1-azaspiro[3,3]heptan-1-ylmethyl)thiazolo[3,2-a]pyrimidin-5-one | 429.0 | ¹H NMR (300 MHz, CD$_3$OD) δ 6.96-6.88 (m, 2H), 6.70-6.64 (m, 2H), 6.08 (s, 1H), 5.14-5.10 (m, 2H), 4.66-4.43 (m, 2H), 4.52 (s, 2H), 4.35 (s, 2H), 3.56-3.51 (m, 2H), 3.19-3.16 (m, 2H), 2.46 (s, 3H), 2.34-2.31 (m, 2H), 1.24-1.21 (m, 3H). |
| 10.22 | 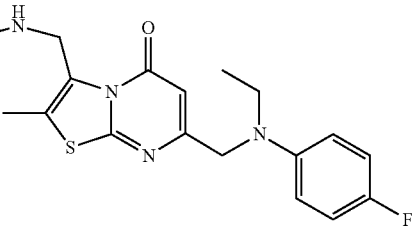<br>7-[(N-ethyl-4-fluoro-anilino)methyl]-3-[(2-hydroxyethylamino)methyl]-2-methyl-thiazolo[3,2-a]pyrimidin-5-one | 391.1 | ¹H NMR (300 MHz, CD$_3$OD) δ 6.89-6.83 (m, 2H), 6.64-6.59 (m, 2H), 6.08 (s, 1H), 4.32 (s, 2H), 4.11 (s, 2H), 3.62-3.60 (m, 2H), 3.50-3.45 (m, 2H), 2.69-2.66 (m, 2H), 2.41 (s, 3H), 1.19-1.16 (m, 3H). |
| 10.23 | 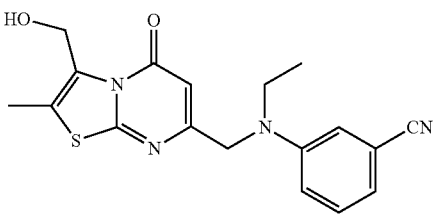<br>3-(ethyl((3-(hydroxymethyl)-2-methyl-5-oxo-5H-thiazolo[3,2-a]pyrimidin-7-yl)methyl)amino)benzonitrile | 354.9 | ¹H NMR (300 MHz, DMSO-$d_6$) δ 7.34-7.28 (m, 1H), 7.01-6.92 (m, 3H), 5.92 (s, 1H), 4.76 (s, 2H), 4.44 (s, 2H), 3.57-3.50 (m, 2H), 2.41 (s, 3H), 1.16-1.12 (m, 3H). |

| No. | Structure/Name | LCMS (M + H) | ¹H NMR |
|---|---|---|---|
| 10.24 | 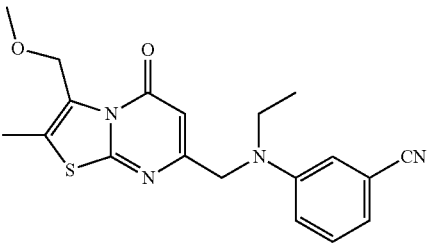<br>3-[ethyl-[[3-(methoxymethyl)-2-methyl-5-oxo-thiazolo[3,2-a]pyrimidin-7-yl]methyl]amino]benzonitrile | 369.0 | ¹H NMR (300 MHz, DMSO-d₆) δ 7.34-7.28 (m, 1H), 7.02-6.93 (m, 3H), 5.85 (s, 1H), 4.83 (s, 2H), 4.42 (s, 2H), 3.56-3.49 (m, 2H), 3.23 (s, 3H), 2.42 (s, 3H), 1.16-1.11 (m, 3H). |
| 10.25 | 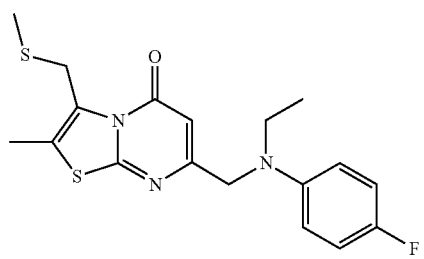<br>7-((ethyl(4-fluorophenyl)amino)methyl)-2-methyl-3-((methylthio)methyl)-5H-thiazolo[3,2-a]pyrimidin-5-one | 378.0 | ¹H NMR (300 MHz, DMSO-d₆) δ 7.01-6.95 (m, 2H), 6.63-6.57 (m, 2H), 5.85 (s, 1H), 4.32 (s, 2H), 4.22 (s, 2H), 3.50-3.43 (m, 2H), 2.37 (s, 3H), 1.98 (s, 3H), 1.14-1.10 (m, 3H). |

Method 11

Example 11.1: 3-chloro-7-[[ethyl(4-fluorophenyl)amino]methyl]-2-methyl-5H-[1,3]thiazolo[3,2-a]pyrimidin-5-one

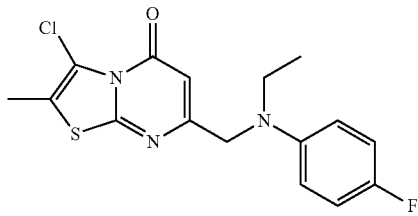 [SMILES: CCN(Cc1cc(=O)n2c(Cl)c(C)sc2n1)c1ccc(F)cc1]

To a solution of 3-bromo-7-[[ethyl(4-fluorophenyl)amino]methyl]-2-methyl-5H-[1,3]thiazolo[3,2-a]pyrimidin-5-one (from Example 5.1, Step 1) (100 mg, 0.25 mmol) in tetrahydrofuran (20 mL) was added n-butyl lithium (0.12 mL, 2.5 mol/L) dropwise at −80° C. The reaction solution was stirred for 30 min at −80° C. To the reaction was added N-chlorosuccinimide (40 mg, 0.30 mmol) at −80° C. The reaction was slowly warmed to room temperature for 30 min. The reaction was then quenched by the addition of 100 mL of water, extracted with ethyl acetate (30 mL×3), washed with brine, dried over anhydrous sodium sulfate, and concentrated in vacuo. The residue was purified by chromatography with 33% ethyl acetate in petroleum ether to afford 3-chloro-7-[[ethyl(4-fluorophenyl)amino]methyl]-2-methyl-5H-[1,3]thiazolo[3,2-a]pyrimidin-5-one as a yellow solid (16.4 mg, 18%). LCMS (ESI): M+H⁺=351.9; ¹H NMR (300 MHz, CDCl₃) δ 6.94-6.88 (m, 2H), 6.61-6.57 (m, 2H), 6.16 (s, 1H), 4.27 (s, 2H), 4.50-4.43 (m, 2H), 2.36 (s, 3H), 1.26-1.20 (m, 3H).

The following examples were prepared in a manner similar to Example 11.1:

| No. | Structure/Name | LCMS (M + H) | ¹H NMR |
|---|---|---|---|
| 11.2 | 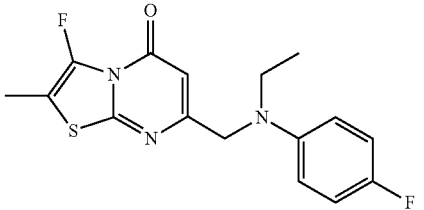<br>7-[(N-ethyl-4-fluoro-anilino)methyl]-3-fluoro-2-methyl-thiazolo[3,2-a]pyrimidin-5-one | 336.0 | ¹H NMR (300 MHz, CDCl₃) δ 7.63-7.00 (m, 2H), 6.88-6.70 (m, 2H), 6.46 (s, 1H), 4.20 (s, 2H), 3.30-3.21 (m, 2H), 2.40 (s, 3H), 1.14-1.11 (m, 3H). |

-continued

| No. | Structure/Name | LCMS (M + H) | $^1$H NMR |
|---|---|---|---|
| 11.3 | 7-[(N-ethyl-4-fluoro-anilino)methyl]-2-methyl-thiazolo[3,2-a]pyrimidin-5-one | 318.1 | $^1$H NMR (400 MHz, DMSO-d$_6$) δ 7.84 (d, J = 1.8 Hz, 1H), 7.07-6.90 (m, 2H), 6.66-6.50 (m, 2H), 5.93 (s, 1H), 4.35 (s, 2H), 3.47 (q, J = 7.0 Hz, 2H), 2.42 (d, J = 1.4 Hz, 3H), 1.13 (t, J = 7.0 Hz, 3H). |

The following compounds were prepared using methods analogous to those described above:

| No. | Structure/Name | LCMS (M + H) | $^1$H NMR |
|---|---|---|---|
| 11.4 | 7-[(N-ethyl-4-fluoro-anilino)methyl]-3-iodo-2-methyl-thiazolo[3,2-a]pyrimidin-5-one | 443.6 | $^1$H NMR (300 MHz, CDCl$_3$) δ 6.95-6.90 (m, 2H), 6.71-6.68 (m, 2H), 6.19 (s, 1H), 4.29 (s, 2H), 4.52-4.45 (m, 2H), 2.39 (s, 3H), 1.25-1.21 (m, 3H). |
| 11.5 | 3-chloro-7-[(N-ethyl-4-fluoro-anilino)methyl]thiazolo[3,2-a]pyrimidin-5-one | 338.1 | $^1$H NMR (300 MHz, CDCl$_3$) δ 7.57 (s, 1H), 7.55-7.52 (m, 2H), 7.44-7.40 (m, 1H), 4.06-4.00 (m, 3H), 3.22-3.17 (m, 1H), 2.37 (s, 3H), 2.31-2.26 (m, 1H), 1.34-1.25 (m, 1H), 1.06-0.98 (m, 2H). |
| 11.6 | 7-[(N-ethylanilino)methyl]-2-methyl-thiazolo[3,2-a]pyrimidin-5-one | 300.0 | $^1$H NMR (400 MHz, DMSO-d$_6$) δ 7.84 (s, 1H), 7.14 (t, J = 7.8 Hz, 2H), 6.62 (t, J = 7.5 Hz, 2H), 5.92 (s, 1H), 4.38 (s, 2H), 3.50 (q, J = 7.0 Hz, 2H), 2.42 (s, 3H), 1.15 (t, J = 7.0 Hz, 3H). |

Method 12

Example 12.1: 3-(1,3-dihydroxypropyl)-7-[(N-ethyl-4-fluoro-anilino)methyl]-2-methyl-thiazolo[3,2-a]pyrimidin-5-one

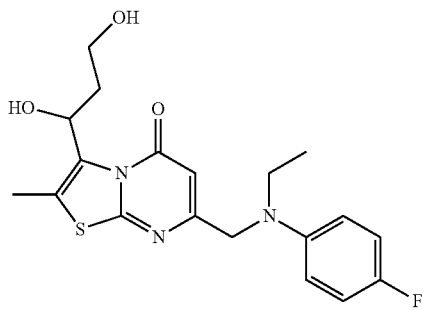 [SMILES: CCN(Cc1cc(=O)n2c(C(O)CCO)c(C)sc2n1)c1ccc(F)cc1]

Step 1: 3-[3-(Benzyloxy)-1-hydroxypropyl]-7-[[ethyl(4-fluorophenyl)amino]methyl]-2-methyl-5H-[1,3]thiazolo[3,2-a]pyrimidin-5-one

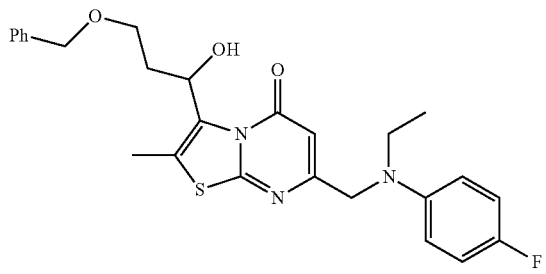 [SMILES: CCN(Cc1cc(=O)n2c(C(O)CCOCc3ccccc3)c(C)sc2n1)c1ccc(F)cc1]

To a solution of 3-bromo-7-[[ethyl(4-fluorophenyl)amino]methyl]-2-methyl-5H-[1,3]thiazolo[3,2-a]pyrimidin-5-one (from Example 5.1, Step 1) (600 mg, 1.51 mmol) in tetrahydrofuran (50 mL) was added n-butyl lithium in tetrahydrofuran (2.4 M, 3 mL, 7.2 mmol) at −80° C. After stirring at −80° C. for 0.5 h, 3-(benzyloxy)propanal (500 mg, 3.05 mmol) was added to the reaction. The resulting solution was stirred for 1.5 h at −80° C. The reaction was then quenched by water (50 mL), extracted with dichloromethane (3×50 mL), washed with brine, dried over sodium sulfate and concentrated in vacuo to afford 3-[3-(benzyloxy)-1-hydroxypropyl]-7-[[ethyl(4-fluorophenyl)amino]methyl]-2-methyl-5H-[1,3]thiazolo[3,2-a]pyrimidin-5-one as a yellow solid (500 mg). The crude product was used in next step without purification. LCMS (ESI): M+H$^+$=482.0.

Step 2: 3-(1,3-Dihydroxypropyl)-7-((ethyl(4-fluorophenyl)amino)methyl)-2-methyl-5H-thiazolo[3,2-a]pyrimidin-5-one.

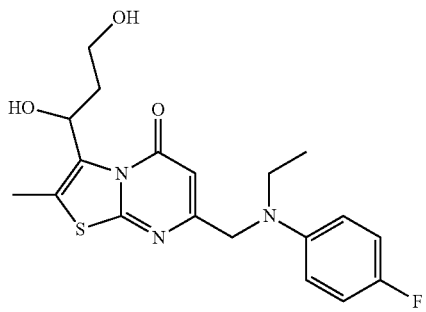 [SMILES: CCN(Cc1cc(=O)n2c(C(O)CCO)c(C)sc2n1)c1ccc(F)cc1]

To a solution of 3-[3-(benzyloxy)-1-hydroxypropyl]-7-[[ethyl(4-fluorophenyl)amino]methyl]-2-methyl-5H-[1,3]thiazolo[3,2-a]pyrimidin-5-one (500 mg, 1.04 mmol) in dichloromethane (50 mL) was added a solution of boron trichloride (10 mL, 1 mol/L) in dichloromethane (10 mL) at −20° C. The reaction mixture was stirred overnight at room temperature. The reaction was quenched by a saturated aqueous ammonium chloride solution (50 mL), extracted with dichloromethane (3×50 mL), washed with brine, dried over sodium sulfate and concentrated in vacuo. The residue was purified by chromatography with ethyl acetate/petroleum ether (1/1) to afford 3-(1,3-dihydroxypropyl)-7-[[ethyl(4-fluorophenyl)amino]methyl]-2-methyl-5H-[1,3]thiazolo[3,2-a]pyrimidin-5-one as a off-white solid (136.4 mg, 32%). LCMS (ESI): M+H$^+$=392.1; $^1$H NMR (300 MHz, CD$_3$OD) δ 6.95-6.88 (m, 2H), 6.70-6.65 (m, 2H), 6.22 (s, 1H), 5.32-5.27 (m, 1H), 4.40 (s, 2H), 3.75-3.67 (m, 1H), 3.57-3.49 (m, 3H), 2.51 (s, 3H), 2.22-2.10 (m, 1H), 2.00-1.94 (m, 1H), 1.24-1.22 (m, 3H).

Example 12.2: 7-[(N-ethyl-4-fluoro-anilino)methyl]-3-(1-fluoro-3-hydroxy-propyl)-2-methyl-thiazolo[3,2-a]pyrimidin-5-one

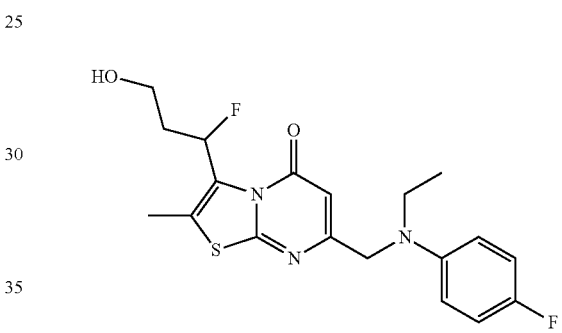

Step 1: 3-(3-(tert-butyldimethylsilyloxy)-1-fluoropropyl)-7-((ethyl(4-fluorophenyl)amino)methyl)-2-methyl-5H-thiazolo[3,2-a]pyrimidin-5-one

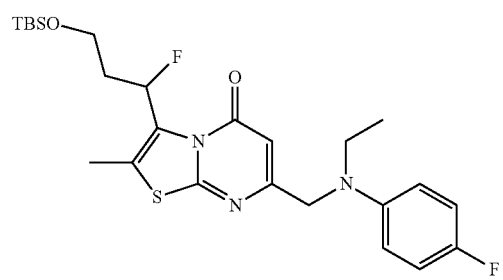 [SMILES: CCN(Cc1cc(=O)n2c(C(F)CCO[Si](C)(C)C(C)(C)C)c(C)sc2n1)c1ccc(F)cc1]

To a solution of 3-[3-[(tert-butyldimethylsilyl)oxy]-1-hydroxypropyl]-7-[[ethyl(4-fluorophenyl)amino]methyl]-2-methyl-5H-[1,3]thiazolo[3,2-a]pyrimidin-5-one (prepared via a similar method as Example 12.1, Step 1) (120 mg, 0.24 mmol) in dichloromethane (20 mL) was added diethylaminosulfurtrifluoride (57.4 mg, 0.36 mmol) dropwise at −78° C. The resulting solution was stirred at room temperature. The reaction was then quenched by a saturated aqueous sodium bicarbonate solution (20 mL), extracted with dichloromethane (3×20 mL), washed with brine, dried over sodium sulfate and concentrated in vacuo to afford 3-[3-[(tert-butyldimethylsilyl)oxy]-1-fluoropropyl]-7-[[ethyl(4-fluorophenyl)amino]methyl]-2-methyl-5H-[1,3]thiazolo[3,2-a]pyrimidin-5-one as a yellow oil (100 mg). LCMS (ESI): M+H+=508.1.

Step 2: 7-[[ethyl(4-fluorophenyl)amino]methyl]-3-(1-fluoro-3-hydroxypropyl)-2-methyl-5H-[1,3]thiazolo[3,2-a]pyrimidin-5-one

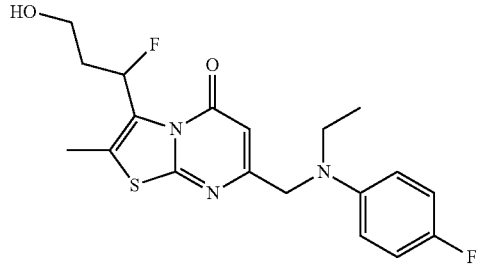 [SMILES: CCN(Cc1cc(=O)n2c(C(F)CCO)c(C)sc2n1)c1ccc(F)cc1]

To a solution of 3-[3-[(tert-butyldimethylsilyl)oxy]-1-fluoropropyl]-7-[[ethyl(4-fluorophenyl)amino]methyl]-2-methyl-5H-[1,3]thiazolo[3,2-a]pyrimidin-5-one (50 mg, 0.10 mmol) in tetrahydrofuran (15 mL) was added hydrogen chloride (1 M, 2.5 mL) dropwise with stirring. The resulting solution was stirred for 3 h at room temperature. The reaction was then quenched by a saturated aqueous sodium bicarbonate solution (20 mL), extracted with dichloromethane (3×30 mL), washed with brine, dried over sodium sulfate and concentrated in vacuo. The residue was purified by chromatography with dichloromethane/methanol (30/1) to afford 7-[[ethyl(4-fluorophenyl)amino]methyl]-3-(1-fluoro-3-hydroxypropyl)-2-methyl-5H-[1,3]thiazolo[3,2-a]pyrimidin-5-one as a light yellow solid (12.2 mg, 30%). LCMS (ESI): M+H+=394.1; $^1$H NMR (300 MHz, CD$_3$OD) δ 6.94-6.76 (m, 3H), 6.68-6.64 (m, 2H), 6.07 (s, 1H), 4.35 (s, 2H), 3.79-3.71 (m, 2H), 3.55-3.48 (m, 2H), 2.52 (s, 3H), 2.40-2.52 (m, 2H), 1.23-1.20 (m, 3H).

Examples 12.3 and 12.4: 3-(1,3-dihydroxypropyl)-7-[(N-ethyl-4-fluoro-anilino)methyl]-2-methyl-thiazolo[3,2-a]pyrimidin-5-one (enantiomers 1 and 2)

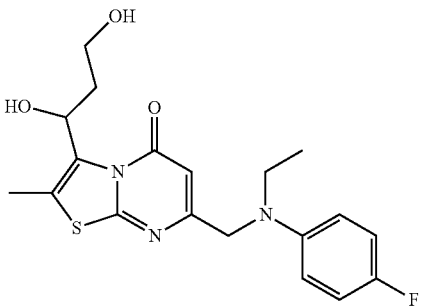 [SMILES: CCN(Cc1cc(=O)n2c(C(O)CCO)c(C)sc2n1)c1ccc(F)cc1]

The product of Example 12.1 was further purified by chiral SFC on a Chiralpak AD (2×15 cm) column eluting with 25% methanol (0.1% NH$_4$OH)/CO$_2$ at 100 bar at a flow rate of 70 mL/min. The peaks isolated were analyzed on Chiralpak AD (50×0.46 cm) column eluting with 25% methanol (0.1% NH$_4$OH)/CO$_2$, at 120 bar (flow rate 5 mL/min, 220 nm). From this separation two isomers were isolated.

Example 12.3: Peak 1; Enantiomer 1

Retention time=1.54 min; LCMS (ESI): M+H+=392.1; $^1$H NMR (300 MHz, CD$_3$OD) δ 6.95-6.88 (m, 2H), 6.70-6.65 (m, 2H), 6.22 (s, 1H), 5.32-5.27 (m, 1H), 4.40 (s, 2H), 3.75-3.67 (m, 1H), 3.57-3.49 (m, 3H), 2.51 (s, 3H), 2.22-2.10 (m, 1H), 2.00-1.94 (m, 1H), 1.24-1.22 (m, 3H).

Example 12.4: Peak 2, Enantiomer 2

Retention time=1.63 min; LCMS (ESI): M+H+=392.1; $^1$H NMR (300 MHz, CD$_3$OD) δ 6.95-6.88 (m, 2H), 6.70-6.65 (m, 2H), 6.22 (s, 1H), 5.32-5.27 (m, 1H), 4.40 (s, 2H), 3.75-3.67 (m, 1H), 3.57-3.49 (m, 3H), 2.51 (s, 3H), 2.22-2.10 (m, 1H), 2.00-1.94 (m, 1H), 1.24-1.22 (m, 3H).

The following example was prepared in a manner similar to Example 12.1:

| No. | Structure/Name | LCMS (M + H) | $^1$H NMR |
|---|---|---|---|
| 12.5 | 3-(1,2-dihydroxyethyl)-7-[(N-ethyl-4-fluoro-anilino)methyl]-2-methyl-thiazolo[3,2-a]pyrimidin-5-one | 378.0 | $^1$H NMR (300 MHz, CDCl$_3$) 6.94-6.88 (m, 2H), 6.60-6.54 (m, 2H), 6.32 (s, 1H), 6.02-5.97 (m, 1H) 4.34 (s, 2H), 4.02-3.96 (m, 1H), 3.74-3.68 (m, 1H), 3.48-3.46 (m, 2H), 2.47 (s, 3H), 1.25-1.20 (m, 3H) |

Method 13

Example 13.1: 7-[(N-ethyl-4-fluoro-anilino)methyl]-3-(3-hydroxypropyl)-2-methyl-thiazolo[3,2-a]pyrimidin-5-one

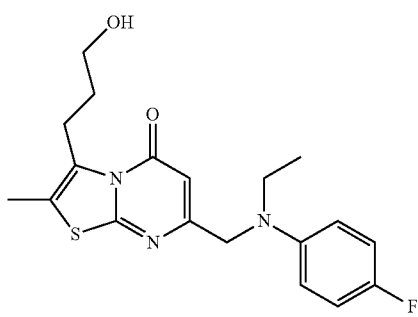 [SMILES: CCN(Cc1cc(=O)n2c(CCCO)c(C)sc2n1)c1ccc(F)cc1]

Step 1: (E)-Ethyl-3-(7-((ethyl(4-fluorophenyl)amino)methyl)-2-methyl-5-oxo-5H-thiazolo[3,2-a]pyrimidin-3-yl)acrylate

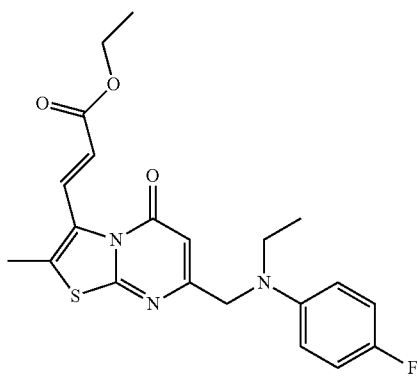 [SMILES: CCOC(=O)/C=C/c1c(C)sc2nc(CN(CC)c3ccc(F)cc3)cc(=O)n12]

To a solution of 3-bromo-7-((ethyl(4-fluorophenyl)amino)methyl)-2-methyl-5H-thiazolo[3,2-a]pyrimidin-5-one (from Example 5.1, Step 1) (400 mg, 1.01 mmol), tri(o-tolyl)phosphine (60 mg, 0.20 mmol), triethylamine (200 mg, 1.98 mmol) and tris(dibenzylideneacetone)dipalladium(0) (50 mg, 0.05 mmol) in acetonitrile (20 mL) was added ethyl acrylate (200 mg, 2.00 mmol). The reaction mixture was stirred for 3 h at 90° C. and then concentrated in vacuo. The residue was purified by chromatography with ethyl acetate/petroleum ether (1/2) to afford (E)-ethyl-3-(7-((ethyl(4-fluorophenyl)amino)methyl)-2-methyl-5-oxo-5H-thiazolo[3,2-a]pyrimidin-3-yl)acrylate as a light yellow solid (280 mg, 67%). LCMS (ESI): M+H$^+$=416.0; $^1$H NMR (300 MHz, CDCl$_3$) δ 8.26-8.20 (m, 1H), 6.94-6.90 (m, 2H), 6.62-6.59 (m, 2H), 6.20 (s, 1H), 6.02-5.98 (m, 1H), 4.31-4.27 (m, 4H), 3.50-3.47 (m, 2H), 2.48 (s, 3H), 1.37-1.22 (m, 6H).

Step 2: Ethyl-3-(7-((ethyl(4-fluorophenyl)amino)methyl)-2-methyl-5-oxo-5H-thiazolo[3,2-a]pyrimidin-3-yl)propanoate

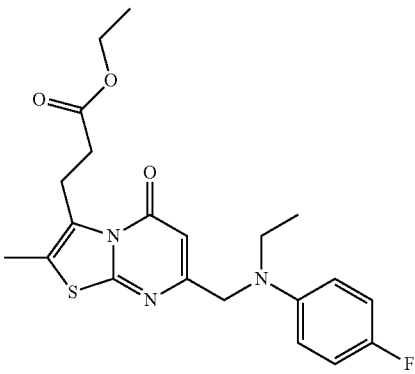 [SMILES: CCOC(=O)CCc1c(C)sc2nc(CN(CC)c3ccc(F)cc3)cc(=O)n12]

To a solution of (E)-ethyl-3-(7-((ethyl(4-fluorophenyl)amino)methyl)-2-methyl-5-oxo-5H-thiazolo[3,2-a]pyrimidin-3-yl)acrylate in methanol (10 mL) was added 10% palladium on carbon and the reaction solution was stirred 12 h at room temperature under a hydrogen atmosphere (1.5 atm). After filtration the resulting solution was concentrated in vacuo to afford ethyl-3-(7-((ethyl(4-fluorophenyl)amino)methyl)-2-methyl-5-oxo-5H-thiazolo[3,2-a]pyrimidin-3-yl)propanoate as a light yellow solid (180 mg, 90%). LCMS (ESI): M+H$^+$=418.0; $^1$H NMR (300 MHz, CDCl$_3$) δ 6.94-6.88 (m, 2H), 6.62-6.58 (m, 2H), 6.12 (s, 1H), 4.28 (s, 2H), 4.13-4.10 (m, 2H), 3.51-3.41 (m, 4H), 2.74-2.71 (m, 2H), 2.37 (s, 3H), 1.26-1.20 (m, 6H).

Step 3: 7-((Ethyl(4-fluorophenyl)amino)methyl)-3-(3-hydroxypropyl)-2-methyl-5H-thiazolo[3,2-a]pyrimidin-5-one

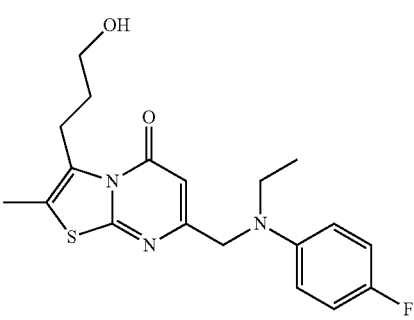 [SMILES: CCN(Cc1cc(=O)n2c(CCCO)c(C)sc2n1)c1ccc(F)cc1]

To a solution of ethyl-3-(7-((ethyl(4-fluorophenyl)amino)methyl)-2-methyl-5-oxo-5H-thiazolo[3,2-a]pyrimidin-3-yl)propanoate (180 mg, 0.43 mmol) in methanol (10 mL) was added lithiumborohydride (20 mg, 0.91 mmol) at 0° C. The resulting solution was stirred for 5 h at room temperature. The reaction was then quenched by a saturated aqueous ammonium chloride solution (20 mL), extracted with dichloromethane (3×50 mL), washed with brine, dried over anhydrous sodium sulfate, and then concentrated in vacuo. The residue was purified by silica gel chromatography with dichloromethane/methanol (30/1) to afford 7-((ethyl(4-fluorophenyl)amino)methyl)-3-(3-hydroxypropyl)-2-methyl-5H-thiazolo[3,2-a]pyrimidin-5-one as a light yellow solid (100 mg, 62%). LCMS (ESI): M+H⁺=376.0; ¹H NMR (400 MHz, CDCl₃) δ 6.94-6.90 (m, 2H), 6.63-6.59 (m, 2H), 6.15 (s, 1H), 4.31 (s, 2H), 3.68-3.66 (m, 2H), 3.50-3.47 (m, 2H), 3.35-3.32 (m, 2H), 2.36 (s, 3H), 1.95-1.90 (m, 2H), 1.22-1.19 (m, 3H).

Example 13.2: 7-((Ethyl(4-fluorophenyl)amino)methyl)-3-(3-methoxypropyl)-2-methyl-5H-thiazolo[3,2-a]pyrimidin-5-one

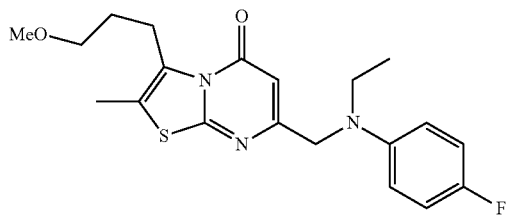 [SMILES: CCN(Cc1cc(=O)n2c(CCCOC)c(C)sc2n1)c1ccc(F)cc1]

To a solution of 7-((ethyl(4-fluorophenyl)amino)methyl)-3-(3-hydroxypropyl)-2-methyl-5H-thiazolo[3,2-a]pyrimidin-5-one (50 mg, 0.13 mmol) in tetrahydrofuran (5 mL) was added sodium hydride (7.0 mg, 60%, 0.29 mmol) and stirred for 1 h at room temperature. Then iodomethane (100 mg, 0.70 mmol) was added to the reaction and the resulting solution was stirred 12 h at room temperature. The reaction was quenched by water/ice (10 mL), extracted with dichloromethane (3×30 mL), washed with brine, dried over anhydrous sodium sulfate and concentrated in vacuo. The residue was purified by chromatography with ethyl acetate/petroleum ether (1/3) to afford 7-((ethyl(4-fluorophenyl)amino)methyl)-3-(3-methoxypropyl)-2-methyl-5H-thiazolo[3,2-a]pyrimidin-5-one as a light yellow semi-solid (7.9 mg, 15%). LCMS (ESI): M+H⁺=390.1; ¹H NMR (300 MHz, CDCl₃) δ 6.91-6.82 (m, 2H), 6.56-6.52 (m, 2H), 6.07 (s, 1H), 4.24 (s, 2H), 3.46-3.33 (m, 4H), 3.30 (s, 3H), 3.21-3.18 (m, 2H), 2.29 (s, 3H), 1.93-1.85 (m, 2H), 1.22-1.19 (m, 3H).

The following example was prepared in a manner similar to Example 13.1 and 13.2:

Example 13.4: 7-((Ethyl(4-fluorophenyl)amino)methyl)-3-(2-hydroxyethyl)-2-methyl-5H-thiazolo[3,2-a]pyrimidin-5-one

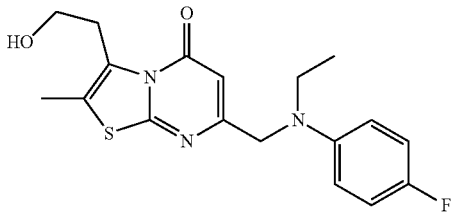 [SMILES: CCN(Cc1cc(=O)n2c(CCO)c(C)sc2n1)c1ccc(F)cc1]

Step 1: 3-[(E)-2-ethoxyvinyl]-7-[(N-ethyl-4-fluoroanilino)methyl]-2-methyl-thiazolo[3,2-a]pyrimidin-5-one

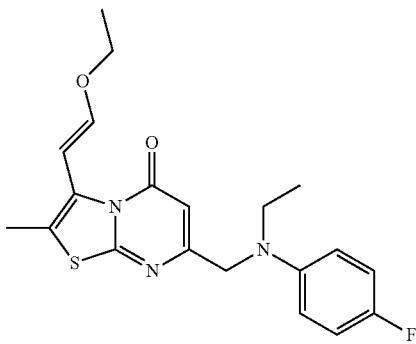 [SMILES: CCO/C=C/c1c(C)sc2nc(CN(CC)c3ccc(F)cc3)cc(=O)n12]

To a solution of 3-bromo-7-[[ethyl(4-fluorophenyl)amino]methyl]-2-methyl-5H-[1,3]thiazolo[3,2-a]pyrimidin-5-one (from Example 5.1, Step 1) (50 mg, 0.13 mmol) in 1,4-dioxane/water (0.6/0.2 mL) was added 2-[(E)-2-ethoxyethenyl]-4,4,5,5-tetramethyl-1,3,2-dioxaborolane (40 mg, 0.20 mmol), potassium phosphate (80 mg, 0.38 mmol) and tetrakis(triphenylphosphine)palladium (20 mg, 0.02 mmol). The resulting solution was stirred for 3 h at 90° C. under nitrogen. After cooling down to room temperature, the reaction mixture was concentrated in vacuo. The residue was purified by chromatography with ethyl acetate/petroleum

| No. | Structure/Name | LCMS (M + H) | ¹H NMR |
|---|---|---|---|
| 13.3 | 7-((Ethyl(4-fluorophenyl)amino)methyl)-3-(4-hydroxybutyl)-2-methyl-5H-thiazolo[3,2-a]pyrimidin-5-one | 390.1 | ¹H NMR (300 MHz, CDCl₃) δ 6.91-6.83 (m, 2H), 6.57-6.50 (m, 2H), 6.09 (s, 1H), 4.25 (s, 2H), 3.71-3.68 (m, 2H), 3.45-3.40 (m, 2H), 3.12-3.19 (m, 2H), 2.35 (s, 1H), 2.29 (s, 3H), 1.74-1.60 (m, 4H), 1.23-1.18 (m, 3H). | ether (1/5) to afford the title compound as a light yellow solid (16.9 mg, 35%). LCMS (ESI): M+H+=388.0; 1H NMR: (300 MHz, CDCl3): δ 6.93-6.85 (m, 2H), 6.60-6.51 (m, 2H), 6.52-5.48 (m, 1H), 6.34-6.19 (m, 1H), 6.10 (s, 1H), 4.27 (s, 2H), 3.99-3.92 (m, 2H), 3.53-3.42 (m, 2H), 2.38 (s, 3H), 1.38-1.35 (m, 3H), 2.23-2.19 (m, 3H).

Step 2: 2-(7-((Ethyl(4-fluorophenyl)amino)methyl)-2-methyl-5-oxo-5H-thiazolo[3,2-a]pyrimidin-3-yl)acetaldehyde

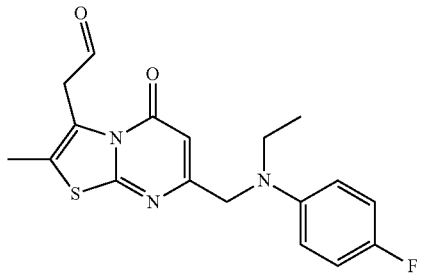 [SMILES: CCN(Cc1cc(=O)n2c(CC=O)c(C)sc2n1)c1ccc(F)cc1]

To a solution (E)-3-(2-ethoxyvinyl)-7-((ethyl(4-fluorophenyl)amino)methyl)-2-methyl-5H-thiazolo[3,2-a]pyrimidin-5-one in acetone was added 3 N hydrogen chloride (15 mL). The resulting solution was refluxed for 3 h in an oil bath. The pH value of the solution was adjusted to pH 8 with a saturated aqueous sodium bicarbonate solution. The mixture was extracted with dichloromethane (3×50 mL), washed with brine, dried over anhydrous sodium sulfate and concentrated in vacuo to afford 2-(7-((ethyl(4-fluorophenyl)amino)methyl)-2-methyl-5-oxo-5H-thiazolo[3,2-a]pyrimidin-3-yl)acetaldehyde was obtained as a light yellow oil (180 mg). The crude product was used in the next step without further purification.

Step 3: 7-((Ethyl(4-fluorophenyl)amino)methyl)-3-(2-hydroxyethyl)-2-methyl-5H-thiazolo[3,2-a]pyrimidin-5-one

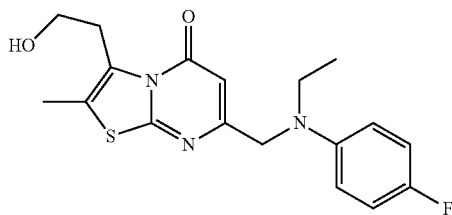 [SMILES: CCN(Cc1cc(=O)n2c(CCO)c(C)sc2n1)c1ccc(F)cc1]

To a solution of 2-(7-((ethyl(4-fluorophenyl)amino)methyl)-2-methyl-5-oxo-5H-thiazolo[3,2-a]pyrimidin-3-yl)acetaldehyde (180 mg, 0.50 mmol) in methanol (10 mL) was added sodium borohydride (40 mg, 1.06 mmol) at 0° C. After stirring overnight at room temperature, the reaction was quenched by saturated aqueous ammonium chloride (20 mL). The resulting solution was extracted with dichloromethane (3×50 mL), washed with brine, dried over anhydrous sodium sulfate and concentrated in vacuo. The residue was purified by chromatography with dichloromethane/methanol (30/1) to afford 7-((ethyl(4-fluorophenyl)amino)methyl)-3-(2-hydroxyethyl)-2-methyl-5H-thiazolo[3,2-a]pyrimidin-5-one as a white solid (90 mg, 50%). LCMS (ESI): M+H+=362.0; 1H NMR (300 MHz, CDCl3) δ 6.90-6.84 (m, 2H), 6.55-6.50 (m, 2H), 6.14 (s, 1H), 4.26 (s, 2H), 3.89-3.87 (m, 2H), 3.47-3.39 (m, 4H), 2.32 (s, 3H), 1.21-1.18 (m, 3H).

Example 13.5: 7-[[Ethyl(4-fluorophenyl)amino]methyl]-3-(2-methoxyethyl)-2-methyl-5H-[1,3]thiazolo[3,2-a]pyrimidin-5-one

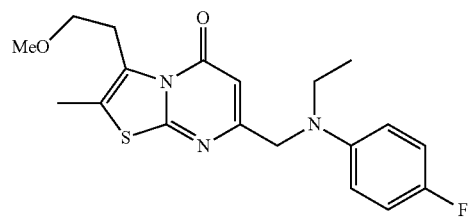 [SMILES: CCN(Cc1cc(=O)n2c(CCOC)c(C)sc2n1)c1ccc(F)cc1]

To a solution of 7-[[ethyl(4-fluorophenyl)amino]methyl]-3-(2-hydroxyethyl)-2-methyl-5H-[1,3]thiazolo[3,2-a]pyrimidin-5-one (50 mg, 0.14 mmol) in tetrahydrofuran (5 mL) was added sodium hydride (11 mg, 0.46 mmol) at 0° C. After stirred 0.5 h at room temperature, iodomethane (11 mg, 0.08 mmol) was added to the reaction. After stirring 3 h at room temperature, the reaction was quenched with water/ice (20 mL), extracted with dichloromethane (3×30 mL), washed with brine, dried over anhydrous sodium sulfate and concentrated in vacuo. The residue was purified by chromatography with ethyl acetate/petroleum ether (1/3) to afford 7-[[ethyl(4-fluorophenyl)amino]methyl]-3-(2-methoxyethyl)-2-methyl-5H-[1,3]thiazolo[3,2-a]pyrimidin-5-one as a gray semi-solid (11.5 mg, 22%). LCMS (ESI): M+H+=376.0; 1H NMR (300 MHz, CDCl3) δ 6.94-6.85 (m, 2H), 6.60-6.54 (m, 2H), 6.10 (s, 1H), 4.28 (s, 2H), 3.69-3.66 (m, 2H), 3.49-3.39 (m, 4H), 3.31 (s, 3H), 2.33 (s, 3H), 1.23-1.21 (m, 3H).

Example 13.6: 3-(7-[[ethyl(4-fluorophenyl)amino]methyl]-2-methyl-5-oxo-5H-[1,3]thiazolo[3,2-a]pyrimidin-3-yl)propanamide

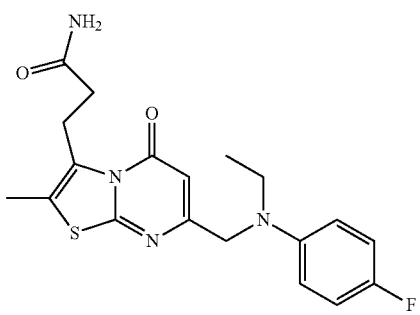 [SMILES: CCN(Cc1cc(=O)n2c(CCC(N)=O)c(C)sc2n1)c1ccc(F)cc1]

To a solution of ethyl 3-(7-[[ethyl(4-fluorophenyl)amino]methyl]-2-methyl-5-oxo-5H-[1,3]thiazolo[3,2-a]pyrimidin-3-yl)propanoate (from Example 13.1, Step 2) (50 mg, 0.12 mmol) in a 10 mL sealed tube was added 1 M ammonia in methanol (3 mL, 3 mmol). The reaction was sealed and stirred overnight at 80° C. and then concentrated in vacuo. The residue was purified by silica gel chromatography with dichloromethane/methanol (20/1) to afford 3-(7-[[ethyl(4-fluorophenyl)amino]methyl]-2-methyl-5-oxo-5H-[1,3]thiazolo[3,2-a]pyrimidin-3-yl)propanamide as an off-white solid (10 mg, 21%). LCMS (ESI): M+H$^+$=389.0; $^1$H NMR (300 MHz, CDCl$_3$) δ 6.97-6.92 (m, 2H), 6.74-6.72 (m, 2H), 6.19 (s, 1H), 4.32 (s, 2H), 3.54-3.43 (m, 4H), 2.60-2.57 (m, 2H), 2.38 (s, 3H), 1.27-1.24 (m, 3H).

Example 13.7: 3-[7-[(N-ethyl-4-fluoro-anilino) methyl]-2-methyl-5-oxo-thiazolo[3,2-a]pyrimidin-3-yl]propanenitrile

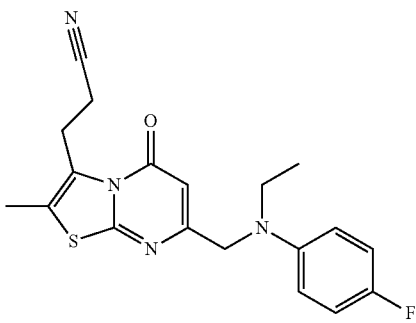 [SMILES: CCN(Cc1cc(=O)n2c(CCC#N)c(C)sc2n1)c1ccc(F)cc1]

To a solution of 3-(7-[[ethyl(4-fluorophenyl)amino] methyl]-2-methyl-5-oxo-5H-[1,3]thiazolo[3,2-a]pyrimidin-3-yl)propanamide (50 mg, 0.13 mmol) and triethylamine (30 mg, 0.30 mmol) in dichloromethane (10 mL) was added (trifluoromethane)sulfonyl trifluoromethanesulfonate (40 mg, 0.14 mmol) at 0° C. and then stirred at room temperature for 2 h. The reaction was quenched by saturated aqueous sodium bicarbonate, extracted with dichloromethane (3×30 mL), washed with brine, dried over anhydrous sodium sulfate and concentrated in vacuo. The residue was purified by chromatography with ethyl acetate/petroleum ether (1/1) to afford 3-(7-[[ethyl(4-fluorophenyl)amino]methyl]-2-methyl-5-oxo-5H-[1,3]thiazolo[3,2-a]pyrimidin-3-yl)propanenitrile as an off-white solid (14 mg, 29%). LCMS (ESI): M+H$^+$=370.9; $^1$H NMR (300 MHz, CDCl$_3$) δ 6.92-6.86 (m, 2H), 6.65-6.60 (m, 2H), 6.13 (s, 1H), 4.27 (s, 2H), 3.49-3.41 (m, 4H), 2.87-2.86 (m, 2H), 2.42 (s, 3H), 1.22-1.19 (m, 3H).

The following compound was prepared using methods analogous to those described above:

| No. | Structure/Name | LCMS (M + H) | $^1$H NMR |
|---|---|---|---|
| 13.8 | 3-[7-[(N-ethyl-4-fluoro-anilino)methyl]-2-methyl-5-oxo-thiazolo[3,2-a]pyrimidin-3-yl]-N,N-dimethyl-propanamide | 417.2 | $^1$H NMR (400 MHz, CDCl$_3$) δ 6.94-6.89 (m, 2H), 6.60-6.57 (m, 2H), 6.13 (s, 1H), 4.30 (s, 2H), 3.51-3.43 (m, 4H), 3.02 (s, 3H), 2.96 (s, 3H), 2.71-2.69 (m, 2H), 2.37 (s, 3H), 1.24-1.21 (m, 3H). |
| 13.9 | 7-[[Ethyl(4-fluorophenyl)amino]methyl]-3-(3-hydroxy-3-methylbutyl)-2-methyl-5H-[1,3]thiazolo[3,2-a]pyrimidin-5-one | 403.8 | $^1$H NMR (400 MHz, CD$_3$OD) δ 6.94-6.89 (m, 2H), 6.68-6.65 (m, 2H), 6.06 (s, 1H), 4.35 (s, 2H), 3.56-3.51 (m, 2H), 3.27-3.23 (m, 2H), 2.38 (s, 3H), 1.77-1.73 (m, 2H), 1.26 (s, 6H), 1.24-1.21 (m, 3H). |

Method 14

Example 14.1: 2-[7-[(N-ethyl-4-fluoro-anilino)methyl]-2-methyl-5-oxo-thiazolo[3,2-a]pyrimidin-3-yl]cyclopropanecarboxamide

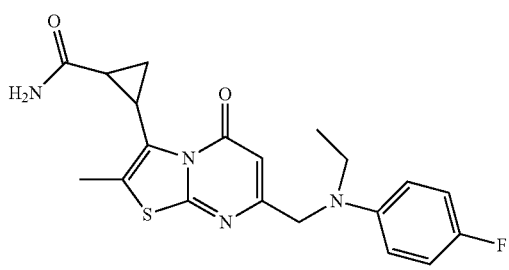 [SMILES: CCN(Cc1cc(=O)n2c(C3CC3C(N)=O)c(C)sc2n1)c1ccc(F)cc1]

Step 1: ethyl 2-(7-((ethyl(4-fluorophenyl)amino)methyl)-2-methyl-5-oxo-5H-thiazolo[3,2-a]pyrimidin-3-yl)cyclopropanecarboxylate

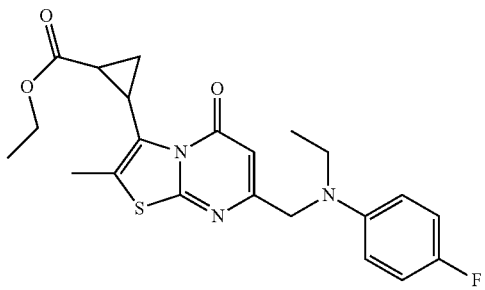 [SMILES: CCOC(=O)C1CC1c1c(C)sc2nc(CN(CC)c3ccc(F)cc3)cc(=O)n12]

To a microwave tube with a solution of 3-bromo-7-[[ethyl(4-fluorophenyl)amino]methyl]-2-methyl-5H-[1,3]thiazolo[3,2-a]pyrimidin-5-one (from Example 5.1, Step 1) (200 mg, 0.51 mmol) in acetonitrile/water (5/1 mL) was added ethyl 2-(4,4,5,5-tetramethyl-1,3-dioxolan-2-yl)cyclopropane-1-carboxylate (from Example 4.8, Step 1) (900 mg, 2.55 mmol), potassium carbonate (279 mg, 2.04 mmol) and [1,1'-bis(diphenylphosphino)ferrocene]palladium(II) dichloride (19 mg, 0.025 mmol). The resulting solution was stirred for 1 h at 120° C. The resulting mixture was concentrated in vacuo. The residue was purified by chromatography with ethyl acetate/petroleum ether (1/2) to afford ethyl 2-(7-[[ethyl(4-fluorophenyl)amino]methyl]-2-methyl-5-oxo-5H-[1,3]thiazolo[3,2-a]pyrimidin-3-yl)cyclopropane-1-carboxylate (80 mg, 37%) as a yellow oil. LCMS (ESI): M+H$^+$=430.1.

Step 2: 2-(7-((ethyl(4-fluorophenyl)amino)methyl)-2-methyl-5-oxo-5H-thiazolo[3,2-a]pyrimidin-3-yl)cyclopropanecarboxylic acid

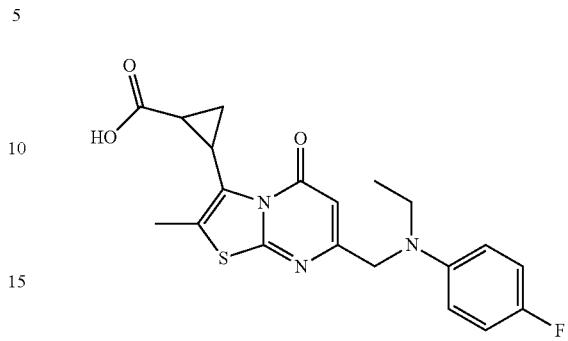

To a solution of ethyl 2-(7-[[ethyl(4-fluorophenyl)amino]methyl]-2-methyl-5-oxo-5H-[1,3]thiazolo[3,2-a]pyrimidin-3-yl)cyclopropane-1-carboxylate (80 mg, 0.18 mmol) in tetrahydrofuran/water (20/3 mL) was added lithium hydroxide (22 mg, 0.90 mmol). After stirring overnight at room temperature, the pH value of the solution was adjusted to oH 4-5 with 1 N HCl. The reaction mixture was extracted with ethyl acetate (200 mL), washed with brine, dried over anhydrous magnesium sulfate, concentrated in vacuo to afford 2-(7-[[ethyl(4-fluorophenyl)amino]methyl]-2-methyl-5-oxo-5H-[1,3]thiazolo[3,2-a]pyrimidin-3-yl)cyclopropane-1-carboxylic acid as a yellow oil (80 mg). The crude product was used in next step without further purification. LCMS (ESI): M+H$^+$=402.1.

Step 3: 2-[7-[(N-ethyl-4-fluoro-anilino)methyl]-2-methyl-5-oxo-thiazolo[3,2-a]pyrimidin-3-yl]cyclopropanecarboxamide

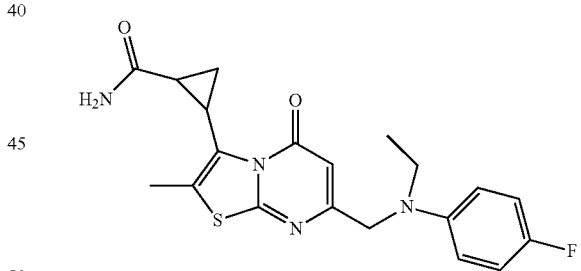

To a solution of 2-(7-[[ethyl(4-fluorophenyl)amino]methyl]-2-methyl-5-oxo-5H-[1,3]thiazolo[3,2-a]pyrimidin-3-yl)cyclopropane-1-carboxylic acid (50 mg, 0.12 mmol) in tetrahydrofuran (10 mL) was added triethylamine (25 mg, 0.24 mmol), chloro(propan-2-yloxy)methanone (22.8 mg, 0.19 mmol). The reaction solution was stirred for 10 min at room temperature. To the reaction was added 1 M ammonia in methanol (1 mL, 1 mmol). The reaction solution was stirred for an additional 20 min at room temperature. The resulting mixture was concentrated in vacuo. The residue was purified by chromatography with dichloromethane/methanol (20/1) to afford 2-(7-[[ethyl(4-fluorophenyl)amino]methyl]-2-methyl-5-oxo-5H-[1,3]thiazolo[3,2-a]pyrimidin-3-yl)cyclopropane-1-carboxamide as a yellow solid (35 mg, 70%). LCMS (ESI): M+H$^+$=400.9; $^1$H NMR (400 MHz, CD$_3$OD) δ 6.86-6.83 (m, 2H), 6.67-6.59 (m, 2H), 6.01

(s, 1H), 4.28 (s, 2H), 3.54-3.41 (m, 2H), 2.63-2.61 (m, 1H), 2.38 (s, 3H), 1.87-1.81 (m, 1H), 1.58-1.52 (m, 1H), 1.28-1.15 (m, 4H).

Example 14.2: 2-[7-[(N-ethyl-4-fluoro-anilino) methyl]-2-methyl-5-oxo-thiazolo[3,2-a]pyrimidin-3-yl]cyclopropanecarboxamide

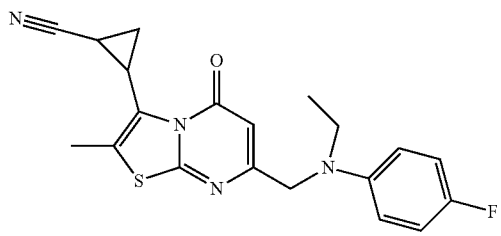 [SMILES: CCN(Cc1cc(=O)n2c(C3CC3C#N)c(C)sc2n1)c1ccc(F)cc1]

To a solution of 2-(7-[[ethyl(4-fluorophenyl)amino] methyl]-2-methyl-5-oxo-5H-[1,3]thiazolo[3,2-a]pyrimidin-3-yl)cyclopropane-1-carboxamide (40 mg, 0.10 mmol) in tetrahydrofuran (10 mL), trifluoracetic anhydride (105 mg, 0.50 mmol) and triethylamine (60.6 mg, 0.60 mmol) were added. The reaction solution was then stirred overnight at room temperature. The reaction was then quenched with water (20 mL) and extracted with ethyl acetate (100 ml). The combined organic layers were washed with brine, dried over anhydrous magnesium sulfate and concentrated in vacuo. The residue was purified by Prep-HPLC to afford 2-(7-[[ethyl(4-fluorophenyl)amino]methyl]-2-methyl-5-oxo-5H-[1,3]thiazolo[3,2-a]pyrimidin-3-yl)cyclopropane-1-carbonitrile as a off-white solid (5.4 mg, 14%). LCMS (ESI): M+H+=383.0; $^1$H NMR (400 MHz, CD$_3$OD) 6.94-6.90 (m, 2H), 6.69-6.56 (m, 2H), 6.11 (s, 1H), 4.34 (s, 2H), 3.56-3.51 (m, 2H), 2.94-2.90 (m, 1H), 1.99-1.94 (m, 1H), 1.80-1.76 (m, 1H), 1.60-1.55 (m, 1H), 1.25-1.21 (m, 3H)

Method 15

Example 15.1: 7-((5-ethyl-3-(trifluoromethyl)-1H-pyrazol-1-yl)methyl)-3-(2-(hydroxymethyl)cyclopropyl)-2-methyl-5H-thiazolo[3,2-a]pyrimidin-5-one

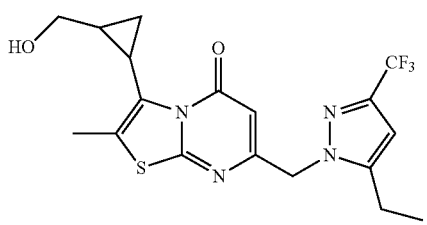 [SMILES: CCc1cc(C(F)(F)F)nn1Cc1cc(=O)n2c(C3CC3CO)c(C)sc2n1]

Step 1: 1,1,1-trifluorohexane-2,4-dione

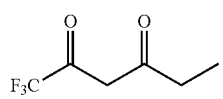

To a solution of ethyl 2,2,2-trifluoroacetate (4.20 g, 29.6 mmol) in tetrahydrofuran (120 mL) was added (tert-butoxy) potassium (2.70 g, 24.1 mmol), butan-2-one (1.44 g, 20.0 mmol). The resulting solution was stirred for 12 h at room temperature. The reaction was then quenched by water, extracted with ethyl acetate (3×100 mL), washed with brine, dried over anhydrous magnesium sulfate and concentrated under vacuum to afford 1,1,1-trifluorohexane-2,4-dione (600 mg, 18%) as a yellow solid. The crude product was used in next step without further purification.

Step 2: 5-ethyl-3-(trifluoromethyl)-1H-pyrazole

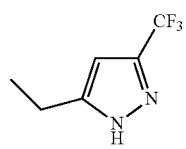

To a solution of 1,1,1-trifluorohexane-2,4-dione (350 mg, 2.08 mmol) in ethanol (20 mL) was added hydrazine monohydrate (135 mg, 2.19 mmol). The resulting solution was stirred for 12 h at 80° C. in an oil bath. The resulting mixture was concentrated under vacuum. The residue was purified by chromatography with dichloromethane/methanol (100:1) to afford 5-ethyl-3-(trifluoromethyl)-1H-pyrazole (140 mg, 41%) as an off-white solid.

Step 3: 3-bromo-7-((5-ethyl-3-(trifluoromethyl)-1H-pyrazol-1-yl)methyl)-2-methyl-5H-thiazolo[3,2-a]pyrimidin-5-one

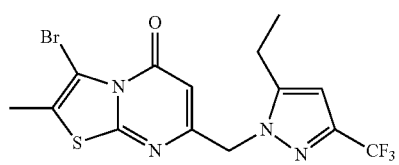 [SMILES: CCc1cc(C(F)(F)F)nn1Cc1cc(=O)n2c(Br)c(C)sc2n1]

To a solution of 3-bromo-7-(chloromethyl)-2-methyl-5H-[1,3]thiazolo[3,2-a]pyrimidin-5-one (from Example 4.1, Step 6) (165 mg, 0.56 mmol) in CH$_3$CN (20 mL) was added potassium iodide (46 mg, 0.28 mmol), potassium carbonate (155 mg, 1.12 mmol) and 5-ethyl-3-(trifluoromethyl)-1H-pyrazole (110 mg, 0.67 mmol). The resulting solution was stirred for 12 h at 80° C. in an oil bath. The resulting mixture was quenched with water (10 mL), extracted with dichloromethane (3×20 mL), washed with brine, dried over anhydrous sodium sulfate and concentrated under vacuum. The residue was purified by silica gel chromatography with ethyl acetate/petroleum ether (1:2.5) to afford 3-bromo-7-[[5-ethyl-3-(trifluoromethyl)-1H-pyrazol-1-yl]methyl]-2-methyl-5H-[1,3]thiazolo[3,2-a]pyrimidin-5-one (150 mg, 63%) as a light yellow solid.

Step 4: ethyl 2-(7-((5-ethyl-3-(trifluoromethyl)-1H-pyrazol-1-yl)methyl)-2-methyl-5-oxo-5H-thiazolo[3,2-a]pyrimidin-3-yl)cyclopropanecarboxylate

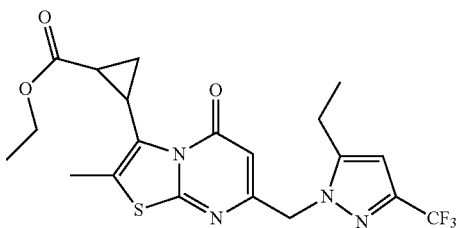 [SMILES: CCOC(=O)C1CC1c1c(C)sc2nc(Cn3nc(C(F)(F)F)cc3CC)cc(=O)n12]

To a solution of 3-bromo-7-[[5-ethyl-3-(trifluoromethyl)-1H-pyrazol-1-yl]methyl]-2-methyl-5H-[1,3]thiazolo[3,2-a]pyrimidin-5-one (from Example 4.8, Step 1) (160 mg, 0.38 mmol) in CH₃CN (2 mL) was added potassium carbonate (166 mg, 1.20 mmol), [1,1'-bis(diphenylphosphino)ferrocene]palladium (II) dichloride (30 mg, 0.04 mmol), ethyl 2-(4,4,5,5-tetramethyl-1,3-dioxolan-2-yl)cyclopropane-1-carboxylate (184 mg, 0.76 mmol) and water (0.6 mL). The reaction mixture was irradiated in a microwave for 1 h at 120° C. The resulting mixture was quenched with water (10 mL), extracted with dichloromethane (3×20 mL), washed with brine, dried over anhydrous sodium sulfate and concentrated under vacuum. The residue was purified by chromatography with ethyl acetate/petroleum ether (1:2) to afford 2-(7-[[5-ethyl-3-(trifluoromethyl)-1H-pyrazol-1-yl]methyl]-2-methyl-5-oxo-5H-[1,3]thiazolo[3,2-a]pyrimidin-3-yl)cyclopropane-1-carboxylate (50 mg, 29%) as an off-white solid.

Step 5: 2-(7-((5-ethyl-3-(trifluoromethyl)-1H-pyrazol-1-yl)methyl)-2-methyl-5-oxo-5H-thiazolo[3,2-a]pyrimidin-3-yl)cyclopropanecarboxylic acid

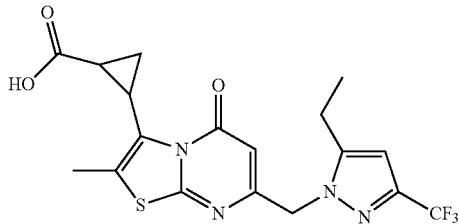 [SMILES: CCc1cc(C(F)(F)F)nn1Cc1cc(=O)n2c(C3CC3C(=O)O)c(C)sc2n1]

To a solution of 2-(7-[[5-ethyl-3-(trifluoromethyl)-1H-pyrazol-1-yl]methyl]-2-methyl-5-oxo-5H-[1,3]thiazolo[3,2-a]pyrimidin-3-yl)cyclopropane-1-carboxylate (50 mg, 0.11 mmol) in tetrahydrofuran (15 mL) was added a solution of lithium hydroxide (8 mg, 0.33 mmol) in water (1 mL). The resulting solution was stirred for 12 h at room temperature. The pH value of the solution was adjusted to pH 5 with aqueous hydrochloric acid. The resulting solution was extracted with 3×20 mL of ethyl acetate, washed with brine, dried over anhydrous magnesium sulfate, and concentrated under vacuum to afford 2-(7-[[5-ethyl-3-(trifluoromethyl)-1H-pyrazol-1-yl]methyl]-2-methyl-5-oxo-5H-[1,3]thiazolo[3,2-a]pyrimidin-3-yl)cyclopropane-1-carboxylic acid (40 mg, crude) as a reddish solid.

Step 6: 7-((5-ethyl-3-(trifluoromethyl)-1H-pyrazol-1-yl)methyl)-3-(2-(hydroxymethyl)cyclopropyl)-2-methyl-5H-thiazolo[3,2-a]pyrimidin-5-one

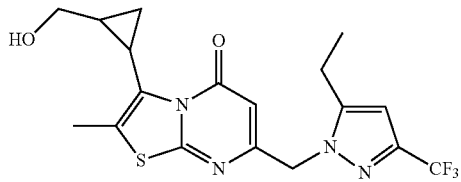 [SMILES: CCc1cc(C(F)(F)F)nn1Cc1cc(=O)n2c(C3CC3CO)c(C)sc2n1]

To a solution of 2-(7-[[5-ethyl-3-(trifluoromethyl)-1H-pyrazol-1-yl]methyl]-2-methyl-5-oxo-5H-[1,3]thiazolo[3,2-a]pyrimidin-3-yl)cyclopropane-1-carboxylic acid (30 mg, 0.07 mmol) in tetrahydrofuran (10 mL) was added triethylamine (14 mg, 0.14 mmol) and chloro(propan-2-yloxy)methanone (17 mg, 0.14 mmol). The resulting solution was stirred for 2 h at room temperature. Then a solution of sodium borohydride (8 mg, 0.21 mmol) in water (0.5 mL) was added. The resulting solution was stirred for 12 h at room temperature. The reaction was then quenched by the addition of saturated ammonium chloride aqueous solution, extracted with dichloromethane (3×20 mL), washed with brine, dried over anhydrous magnesium sulfate and concentrated under vacuum. The residue was purified by chromatography with ethyl acetate/petroleum ether (1:1.5) to afford 7-[[5-ethyl-3-(trifluoromethyl)-1H-pyrazol-1-yl]methyl]-3-[2-(hydroxymethyl)cyclopropyl]-2-methyl-5H-[1,3]thiazolo[3,2-a]pyrimidin-5-one (9.4 mg, 32%) as a light yellow solid. LCMS (ESI): [M+1]⁺413.1; ¹H NMR (300 MHz, CD₃OD) δ 6.51 (s, 1H), 5.67 (s, 1H), 5.25 (s, 2H), 3.64-3.54 (m, 2H), 2.77-2.69 (m, 2H), 2.42 (s, 3H), 2.15-2.11 (m, 1H), 1.45-1.29 (m, 4H), 1.27-1.12 (m, 2H).

The following examples were prepared in a manner similar to Example 15.1:

| No. | Structure/Name | LCMS (M + H) | ¹H NMR |
|---|---|---|---|
| 15.2 | 7-((3,5-bis(trifluoromethyl)-1H-pyrazol-1-yl)methyl)-3-(trans-2-(hydroxymethyl)cyclopropyl)-2-methyl-5H-thiazolo[3,2-a]pyrimidin-5-one | 453.20 | ¹H NMR (300 MHz, CD₃OD) δ 7.30 (s, 1H), 5.84 (s, 1H), 5.48 (s, 2H), 3.61-3.59 (m, 2H), 2.43 (s, 3H), 2.17-2.15 (m, 1H), 1.37-1.30 (m, 1H), 1.05-0.99 (m, 2H) |

| No. | Structure/Name | LCMS (M + H) | ¹H NMR |
|---|---|---|---|
| 15.3 | 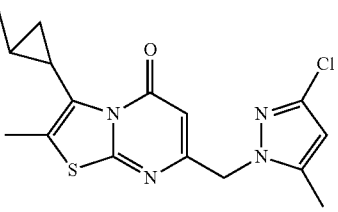<br>7-((3-chloro-5-methyl-1H-pyrazol-1-yl)methyl)-3-(trans-2-(hydroxymethyl)cyclopropyl)-2-methyl-5H-thiazolo[3,2-a]pyrimidin-5-one | 365.0 | ¹H NMR (300 MHz, CDCl₃) δ 6.04 (s, 1H), 5.67 (s, 1H), 5.06 (s, 2H), 4.06-4.01 (m, 1H), 3.14-3.06 (m, 1H), 2.39 (s, 3H), 2.25 (s, 4H), 1.30-1.20 (m, 1H), 1.05-0.97 (m, 2H) |
| 15.4 | 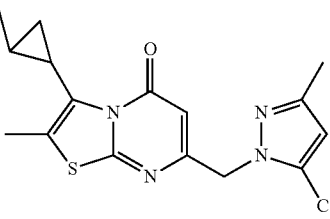<br>7-((5-chloro-3-methyl-1H-pyrazol-1-yl)methyl)-3-(trans-2-(hydroxymethyl)cyclopropyl)-2-methyl-5H-thiazolo[3,2-a]pyrimidin-5-one | 365.0 | ¹H NMR (300 MHz, CDCl₃) δ 6.10 (s, 1H), 5.61 (s, 1H), 5.15 (s, 2H), 4.07-4.02 (m, 2H), 3.12-3.05 (m, 1H), 2.38 (s, 3H), 2.27 (s, 3H), 2.23 (s, 1H), 1.30-1.26 (m, 1H), 1.05-0.94 (m, 2H) |
| 15.5 | 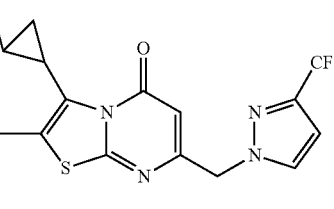<br>3-(trans-2-(hydroxymethyl)cyclopropyl)-2-methyl-7-((3-(trifluoromethyl)-1H-pyrazol-1-yl)methyl)-5H-thiazolo[3,2-a]pyrimidin-5-one | 385 | ¹H NMR (300 MHz, CDCl₃) δ 7.63-7.58 (m, 1H), 6.61-6.60 (m, 1H), 5.86 (s, 1H), 5.22 (s, 2H), 4.05-4.00 (m, 1H), 3.15-3.08 (m, 1H), 2.38 (s, 3H), 2.29-2.24 (m, 1H), 1.28-1.19 (m, 1H), 1.05-0.95 (m, 2H). |
| 15.6 | 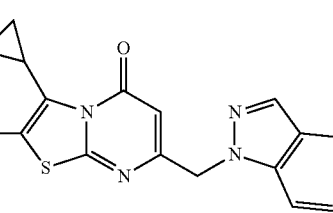<br>7-((1H-indazol-1-yl)methyl)-3-(trans-2-(hydroxymethyl)cyclopropyl)-2-methyl-5H-thiazolo[3,2-a]pyrimidin-5-one | 367.1 | ¹H NMR (300 MHz, CDCl₃): δ 8.09 (s, 1H), 7.79-7.76 (m, 1H), 7.42-7.37 (m, 2H), 7.22-7.17 (m, 1H), 5.57 (s, 1H), 5.47 (s, 2H), 4.35 (s, 2H), 3.07-3.04 (m, 1H), 2.37 (s, 3H), 2.23-2.21 (m, 1H), 1.25-1.21 (m, 1H), 1.02-0.92 (m 2H) |

Example 15.7 and 15.8: 7-((5-(2-hydroxyethyl)-3-(trifluoromethyl)-1H-pyrazol-1-yl)methyl)-3-(trans-2-(hydroxymethyl)cyclopropyl)-2-methyl-5H-thiazolo[3,2-a]pyrimidin-5-one and 7-((3-(2-hydroxyethyl)-5-(trifluoromethyl)-1H-pyrazol-1-yl)methyl)-3-(trans-2-(hydroxymethyl)cyclopropyl)-2-methyl-5H-thiazolo[3,2-a]pyrimidin-5-one

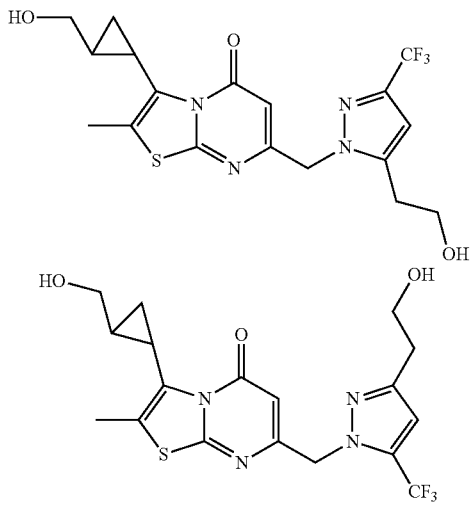

Step 1: ((but-3-ynyloxy)methyl)benzene

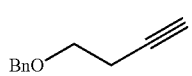

A mixture of but-3-yn-1-ol (3.0 g, 42.8 mmol), sodium hydride (3.0 g, 125.0 mmol), (bromomethyl)benzene (7.2 g, 42.1 mmol) in N,N-dimethylformamide (10 mL) was stirred at room temperature overnight. The resulting mixture was extracted with dichloromethane, washed with brine, washed with brine and concentrated under vacuum to afford crude [(but-3-yn-1-yloxy)methyl]benzene (2.6 g, 38%) as yellow oil. $^1$H NMR (300 MHz, CDCl$_3$) δ 7.30-7.27 (m, 5H), 4.81 (s, 2H), 3.64-3.59 (m, 2H), 2.55-2.49 (m, 2H), 2.02-2.00 (m, 1H).

Step 2: 6-(benzyloxy)-1,1,1-trifluorohex-3-yn-2-one

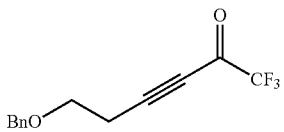 [SMILES: O=C(C#CCCOCc1ccccc1)C(F)(F)F]

To a solution of [(but-3-yn-1-yloxy)methyl]benzene (1.00 g, 6.24 mmol) in tetrahydrofuran (20 mL) was added butyllithium (2.5 M in hexanes; 3.0 mL, 7.50 mmol) dropwise at −78° C. The resulting solution was stirred for 0.5 h at −78° C. and 2,2,2-trifluoroethyl 2,2,2-trifluoroacetate (1.47 g, 7.50 mmol), trifluoroborane etherate (1.15 g, 7.50 mmol) was added to the reaction mixture and stirred for further 3 h at −78° C. The resulting mixture was washed with brine, extracted with dichloromethane (3×100 mL), washed with brine, dried over sodium sulfate and concentrated under vacuum. The residue was purified by column yridine raphy with ethyl acetate/petroleum ether (1:100) to afford 6-(benzyloxy)-1,1,1-trifluorohex-3-yn-2-one (0.6 g, 38%) as yellow oil. $^1$H NMR (300 MHz, CDCl$_3$) δ 7.40-7.27 (m, 5H), 4.58 (s, 2H), 3.72-3.68 (m, 2H), 2.83-2.79 (m, 2H).

Step 3: 5-(2-(benzyloxy)ethyl)-3-(trifluoromethyl)-1H-pyrazole

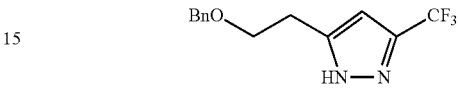

A mixture of 6-(benzyloxy)-1,1,1-trifluorohex-3-yn-2-one (0.6 g, 2.34 mmol) in hydrazine monohydrate (0.5 g, 10 mmol) and ethanol (10 mL) was stirred at 85° C. for 3 h. The resulting mixture was extracted with dichloromethane (3×100 mL), washed with brine, dried over sodium sulfate and concentrated under vacuum to afford 5-[2-(benzyloxy)ethyl]-3-(trifluoromethyl)-1H-pyrazole (0.6 g, 95%) as a yellow oil. $^1$H NMR (300 MHz, CDCl$_3$) δ 7.40-7.29 (m, 5H), 6.32 (s, 1H), 4.57 (s, 2H), 3.76-3.72 (m, 2H), 2.96-2.92 (m, 2H).

Step 4: 2-(3-(trifluoromethyl)-1H-pyrazol-5-yl)ethanol

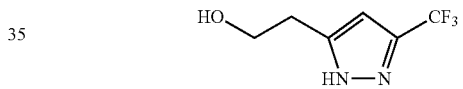

A mixture of 5-[2-(benzyloxy)ethyl]-3-(trifluoromethyl)-1H-pyrazole (400 mg, 1.48 mmol), palladium on carbon (150 mg), O-(hydroxychloryl)oxidanol (0.01 mL) in methanol (15 mL) and tetrahydrofuran (4 mL) was stirred at room temperature for 70 min under hydrogen. The solids were filtered off and the resulting mixture was concentrated under vacuum to afford 2-[3-(trifluoromethyl)-1H-pyrazol-5-yl]ethan-1-ol (250 mg, 95%) as a brown solid. LCMS [M+H]$^+$= 181.0.

Step 5: 3-bromo-7-((5-(2-hydroxyethyl)-3-(trifluoromethyl)-1H-pyrazol-1-yl)methyl)-2-methyl-5H-thiazolo[3,2-a]pyrimidin-5-one and 3-bromo-7-((3-(2-hydroxyethyl)-5-(trifluoromethyl)-1H-pyrazol-1-yl)methyl)-2-methyl-5H-thiazolo[3,2-a]pyrimidin-5-one

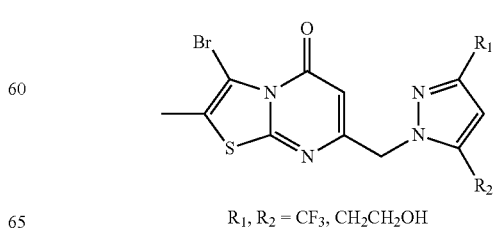

R$_1$, R$_2$ = CF$_3$, CH$_2$CH$_2$OH

A mixture of 2-(3-(trifluoromethyl)-1H-pyrazol-5-yl)ethan-1-ol (480 mg, 2.66 mmol), 3-bromo-7-(chloromethyl)-2-methyl-5H-[1,3]thiazolo[3,2-a]pyrimidin-5-one (from Example 4.1, Step 6) (300 mg, 1.02 mmol), potassium carbonate (690 mg, 4.99 mmol), and potassium iodide (0.28 g, 1.70 mmol) in CH$_3$CN (15 mL) was stirred at 85° C. for 2 h. The resulting mixture was extracted with dichloromethane (3×100 mL), washed with brine, dried over sodium sulfate and concentrated under vacuum. The residue was purified by silica gel column chromatography with ethyl acetate/petroleum ether (1:2) to afford a mixture of 3-bromo-7-[[5-(2-hydroxyethyl)-3-(trifluoromethyl)-1H-pyrazol-1-yl]methyl]-2-methyl-5H-[1,3]thiazolo[3,2-a]pyrimidin-5-one and 3-bromo-7-((3-(2-hydroxyethyl)-5-(trifluoromethyl)-1H-pyrazol-1-yl)methyl)-2-methyl-5H-thiazolo[3,2-a]pyrimidin-5-one (470 mg, 40%) as a light yellow solid. LCMS (ESI): [M+H]$^+$=437.0, 439.0.

Step 6: 7-((5-(2-hydroxyethyl)-3-(trifluoromethyl)-1H-pyrazol-1-yl)methyl)-3-(2-(hydroxymethyl)cyclopropyl)-2-methyl-5H-thiazolo[3,2-a]pyrimidin-5-one and 7-((3-(2-hydroxyethyl)-5-(trifluoromethyl)-1H-pyrazol-1-yl)methyl)-3-(2-(hydroxymethyl)cyclopropyl)-2-methyl-5H-thiazolo[3,2-a]pyrimidin-5-one

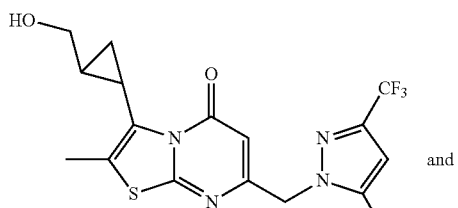

and

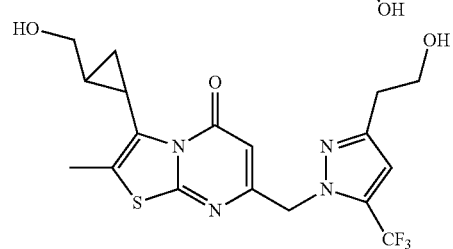

A mixture of 3-bromo-7-[[5-(2-hydroxyethyl)-3-(trifluoromethyl)-1H-pyrazol-1-yl]methyl]-2-methyl-5H-[1,3]thiazolo[3,2-a]pyrimidin-5-one (200 mg, 0.46 mmol), [1,1'-bis(diphenylphosphino)ferrocene]palladium(II) dichloride (35 mg, 0.05 mmol), sodium carbonate (100 mg, 0.94 mmol), potassium trans-2-(hydroxymethyl)cyclopropyltrifluoroborate (from Example 4.1, Step 2) (160 mg, 0.90 mmol) in CH$_3$CN (6 mL) and H$_2$O (2 mL) was irradiated with microwave radiation for 1.5 h at 120° C. in a sealed-tube. The resulting mixture was extracted with dichloromethane (3×20 mL), washed with brine, dried over sodium sulfate and concentrated under vacuum. The residue was purified by Prep-HPLC (Xselect CSH Prep C18 OBD Column, 5 um, 19×150 mm; mobile phase, water with 0.03% NH$_3$—H$_2$O and MeCN (23.0% MeCN up to 28.0% in 20 min)) to afford 7-[[5-(2-hydroxyethyl)-3-(trifluoromethyl)-1H-pyrazol-1-yl]methyl]-3-[trans-2-(hydroxymethyl)cyclopropyl]-2-methyl-5H-[1,3]thiazolo[3,2-a]pyrimidin-5-one (19.7 mg, 10.2%) as a white solid and 7-((3-(2-hydroxyethyl)-5-(trifluoromethyl)-1H-pyrazol-1-yl)methyl)-3-(trans-2-(hydroxymethyl)cyclopropyl)-2-methyl-5H-thiazolo[3,2-a]pyrimidin-5-one (4.3 mg, 2.2%).

Example 15.7: 7-[[5-(2-hydroxyethyl)-3-(trifluoromethyl)-1H-pyrazol-1-yl]methyl]-3-[trans-2-(hydroxymethyl)cyclopropyl]-2-methyl-5H-[1,3]thiazolo[3,2-a]pyrimidin-5-one LCMS (ESI): [M+H]$^+$=429.1; $^1$H NMR (300 MHz, CDCl$_3$) δ 6.46 (s, 1H), 5.81 (s, 1H), 5.24 (s, 2H), 4.04-3.93 (m, 1H), 3.91-3.89 (m, 2H), 3.13-3.06 (m, 1H), 2.94-2.90 (m, 4H), 2.38 (s, 3H), 2.27-2.21 (m, 1H), 1.27-1.16 (m, 1H), 1.01-0.90 (m, 2H).

Example 15.8: 7-((3-(2-hydroxyethyl)-5-(trifluoromethyl)-1H-pyrazol-1-yl)methyl)-3-(trans-2-(hydroxymethyl)cyclopropyl)-2-methyl-5H-thiazolo[3,2-a]pyrimidin-5-one LCMS (ESI): [M+H]$^+$=429.0; $^1$H NMR (300 MHz, CDCl$_3$) δ 6.91 (s, 1H), 5.56 (s, 1H), 5.26 (s, 2H), 4.06-4.01 (m, 1H), 3.96-3.92 (m, 2H), 3.12-3.06 (m, 1H), 2.94-2.89 (m, 2H), 2.38 (s, 3H), 2.21-2.15 (m, 1H), 1.27-1.16 (m, 1H), 1.03-0.90 (m, 2H).

Example 15.9 and 15.10: 7-((3-cyclopropyl-4-fluoro-5-(trifluoromethyl)-1H-pyrazol-1-yl)methyl)-3-(trans-2-(hydroxymethyl)cyclopropyl)-2-methyl-5H-thiazolo[3,2-a]pyrimidin-5-one and 7-((5-cyclopropyl-4-fluoro-3-(trifluoromethyl)-1H-pyrazol-1-yl)methyl)-3-(trans-2-(hydroxymethyl)cyclopropyl)-2-methyl-5H-thiazolo[3,2-a]pyrimidin-5-one

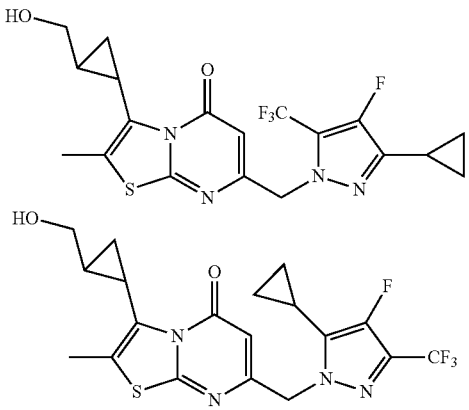

Step 1:
1-cyclopropyl-4,4,4-trifluorobutane-1,3-dione

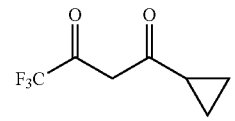 [SMILES: O=C(CC(=O)C(F)(F)F)C1CC1]

A mixture of sodium metal (276 mg, 12.0 mmol) and ethanol (20 mL) was stirred for 20 minutes at room temperature. To the reaction mixture was added 1-cyclopropylethan-1-one (1.42 mg, 0.0200 mmol) and ethyl 2,2,2-trifluoroacetate (840 mg, 5.91 mmol) and the resulting solution was stirred for 2 days at room temperature. The reaction was quenched with water (50 mL), extracted with dichloromethane (3×20 mL) washed with brine, and dried over anhydrous sodium sulfate and concentrated under vacuum to afford 1-cyclopropyl-4,4,4-trifluorobutane-1,3-dione (737 mg, 69%) as colorless oil. The crude product was used in next step without further purification.

Step 2:
3-cyclopropyl-5-(trifluoromethyl)-1H-pyrazole

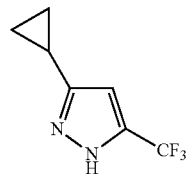 [SMILES: FC(F)(F)c1cc(C2CC2)n[nH]1]

To a solution of 1-cyclopropyl-4,4,4-trifluorobutane-1,3-dione (400 mg, 2.22 mmol) in ethanol (20 mL) was added hydrazine monohydrate (132 mg, excess) and the resulting solution was stirred for 2 days at 80° C. The resulting mixture was concentrated under vacuum. The residue was purified by chromatography with 2% methanol in dichloromethane to afford 3-cyclopropyl-5-(trifluoromethyl)-1H-pyrazole (258 mg, 66%) as an off-white solid. LCMS (ESI): [M+H]$^+$=177.0; $^1$H NMR (300 MHz, CDCl$_3$) δ 6.27 (s, 1H), 2.08-1.95 (m, 1H), 2.77-2.64 (m, 2H), 1.11-1.02 (m, 2H).

Step 3: 5-cyclopropyl-4-fluoro-3-(trifluoromethyl)-1H-pyrazole

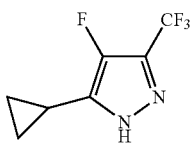 [SMILES: Fc1c(C(F)(F)F)n[nH]c1C1CC1]

To a solution of 5-cyclopropyl-3-(trifluoromethyl)-1H-pyrazole (500 mg, 2.84 mmol) in CH$_3$CN (10 mL) maintained with an inert atmosphere of nitrogen was added Selectfluor® (1.0 g, 2.84 mmol). The resulting solution was stirred for 12 h at 75° C. The resulting mixture was then concentrated under vacuum. The residue was purified by chromatography with 1% methanol in dichloromethane to afford 5-cyclopropyl-4-fluoro-3-(trifluoromethyl)-1H-pyrazole (280 mg, 51%) as a yellow solid. LCMS (ESI): [M+H]$^+$=195.0; $^1$H NMR (300 MHz, CDCl$_3$) δ 1.81 (m, 1H), 1.03 (m, 2H), 0.85 (m, 2H).

Step 4: 3-bromo-7-((3-cyclopropyl-4-fluoro-5-(trifluoromethyl)-1H-pyrazol-1-yl)methyl)-2-methyl-5H-thiazolo[3,2-a]pyrimidin-5-one and 3-bromo-7-((5-cyclopropyl-4-fluoro-3-(trifluoromethyl)-1H-pyrazol-1-yl)methyl)-2-methyl-5H-thiazolo[3,2-a]pyrimidin-5-one

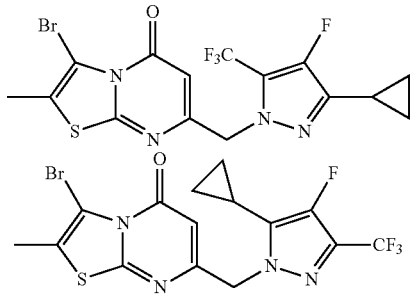

To a solution of 3-bromo-7-(chloromethyl)-2-methyl-5H-[1,3]thiazolo[3,2-a]pyrimidin-5-one (from Example 4.1, Step 6) (250 mg, 0.85 mmol) in CH$_3$CN (20 mL) was added 5-cyclopropyl-4-fluoro-3-(trifluoromethyl)-1H-pyrazole (200 mg, 1.03 mmol), potassium iodide (80 mg, 0.42 mmol), potassium carbonate (250 mg, 1.81 mmol). The resulting solution was stirred for 12 h at 80° C. The resulting mixture was concentrated under vacuum. The residue was purified by chromatography with ethyl acetate/petroleum ether (1:3) to afford 3-bromo-7-[[3-cyclopropyl-4-fluoro-5-(trifluoromethyl)-1H-pyrazol-1-yl]methyl]-2-methyl-5H-[1,3]thiazolo[3,2-a]pyrimidin-5-one (100 mg, 20%) as a light yellow solid (LCMS (ESI): [M+H]$^+$=452.2) and 3-bromo-7-[[5-cyclopropyl-4-fluoro-3-(trifluoromethyl)-1H-pyrazol-1-yl]methyl]-2-methyl-5H-[1,3]thiazolo[3,2-a]pyrimidin-5-one (200 mg, 50%) as a light yellow solid (LCMS (ESI): [M+1]$^+$=452.0).

Step 5: 7-((3-cyclopropyl-4-fluoro-5-(trifluoromethyl)-1H-pyrazol-1-yl)methyl)-3-(trans-2-(hydroxymethyl)cyclopropyl)-2-methyl-5H-thiazolo[3,2-a]pyrimidin-5-one (Example 15.9)

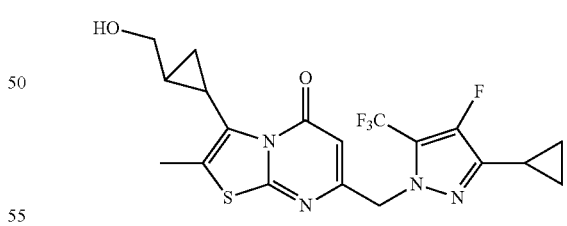

To a solution of 3-bromo-7-[[3-cyclopropyl-4-fluoro-5-(trifluoromethyl)-1H-pyrazol-1-yl]methyl]-2-methyl-5H-[1,3]thiazolo[3,2-a]pyrimidin-5-one (90 mg, 0.20 mmol) in CH$_3$CN (2 mL) under nitrogen, was added sodium carbonate (43 mg, 0.41 mmol), [1,1'-bis(diphenylphosphino)ferrocene]palladium(II) dichloride (30 mg, 0.04 mmol), potassium trans-2-(hydroxymethyl)cyclopropyltrifluoroborate (from Example 4.1, Step 2) (140 mg, 0.79 mmol) and water (0.6 mL). The reaction mixture was heated under microwave irradiation for 90 min at 120° C. The reaction mixture was then quenched with water (10 mL), extracted with ethyl acetate (3×20 mL), washed with brine, dried over anhydrous magnesium sulfate and concentrated under vacuum. The residue was purified on a silica gel column with ethyl acetate/petroleum ether (1:1), afford 7-[[3-cyclopropyl-4-fluoro-5-(trifluoromethyl)-1H-pyrazol-1-yl]methyl]-3-[trans-2-(hydroxymethyl)cyclopropyl]-2-methyl-5H-[1,3]thiazolo[3,2-a]pyrimidin-5-one (10.5 mg, 12%) as a light yellow solid. LCMS (ESI): [M+H]$^+$=442.9; $^1$H NMR (300 MHz, CD$_3$OD) δ 5.65 (s, 1H), 5.18 (s, 1H), 5.21 (s, 2H), 3.59 (m, 2H), 2.48 (s, 3H), 2.18 (m, 1H), 1.90 (m, 1H), 1.34 (m, 2H), 0.98 (m, 3H), 0.84 (m, 2H).

Step 6: 7-((5-cyclopropyl-4-fluoro-3-(trifluoromethyl)-1H-pyrazol-1-yl)methyl)-3-(trans-2-(hydroxymethyl)cyclopropyl)-2-methyl-5H-thiazolo[3,2-a]pyrimidin-5-one (Example 15.10)

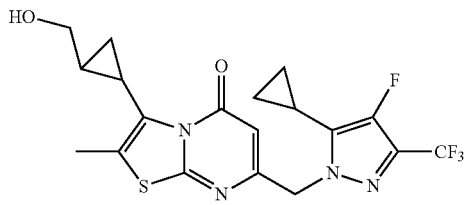 [SMILES: Cc1sc2nc(Cn3nc(C(F)(F)F)c(F)c3C3CC3)cc(=O)n2c1C1CC1CO]

Into a 10-mL sealed tube purged and maintained with an inert atmosphere of nitrogen, was placed 3-bromo-7-[[5-cyclopropyl-4-fluoro-3-(trifluoromethyl)-1H-pyrazol-1-yl]methyl]-2-methyl-5H-[1,3]thiazolo[3,2-a]pyrimidin-5-one (100 mg, 0.22 mmol), acetonitrile (2 mL), [1,1'-bis(diphenylphosphino)ferrocene]palladium(II) dichloride (34 mg, 0.05 mmol), sodium carbonate (48 mg, 0.45 mmol), potassium trans-2-(hydroxymethyl)cyclopropyltrifluoroborate (from Example 4.1, Step 2) (153 mg, 0.86 mmol) and water (0.6 mL). The reaction mixture was irradiated with microwave radiation for 90 min at 120° C. The resulting solution was extracted with ethyl acetate (3×20 mL), washed with brine, dried over anhydrous magnesium sulfate and concentrated in vacuo. The residue was purified by chromatography with ethyl acetate/petroleum ether (1:1), to afford 7-[[5-cyclopropyl-4-fluoro-3-(trifluoromethyl)-1H-pyrazol-1-yl]methyl]-3-[trans-2-(hydroxymethyl)cyclopropyl]-2-methyl-5H-[1,3]thiazolo[3,2-a]pyrimidin-5-one (18.5 mg, 19%) as a off-white solid. LCMS (ESI): [M+H]$^+$=443.0; $^1$H NMR (300 MHz, CD$_3$OD) δ 5.85 (s, 1H), 5.38 (s, 2H), 3.65 (m, 2H), 2.43 (s, 3H), 2.12 (m, 1H), 1.80 (m, 1H), 1.32 (m, 2H), 0.99 (m, 4H), 0.85 (m, 2H).

The following examples were prepared in a manner similar to Example 15.7-15.10:

| No. | Structure/Name | LCMS (M + H) | $^1$H NMR |
|---|---|---|---|
| 15.11 | 7-((5-cyclopropyl-3-(trifluoromethyl)-1H-pyrazol-1-yl)methyl)-3-(trans-2-(hydroxymethyl)cyclopropyl)-2-methyl-5H-thiazolo[3,2-a]pyrimidin-5-one | 425.25 | $^1$H NMR (300 MHz, CDCl$_3$) δ 6.35 (s, 1H), 5.54 (s, 1H), 5.22 (s, 2H), 4.06-4.02 (m, 2H), 3.12-3.05 (m, 1H), 2.38 (s, 3H), 2.26-2.22 (m, 1H), 2.00-1.91 (m, 1H), 1.32-1.21 (m, 1H), 1.05-0.92 (m, 4H), 0.83-0.74 (m, 2H) |
| 15.12 | 7-((3-cyclopropyl-5-(trifluoromethyl)-1H-pyrazol-1-yl)methyl)-3-(trans-2-(hydroxymethyl)cyclopropyl)-2-methyl-5H-thiazolo[3,2-a]pyrimidin-5-one | 425.0 | $^1$H NMR (300 MHz, CDCl$_3$) δ 6.19 (s, 1H), 5.67 (s, 1H), 5.32 (s, 2H), 4.06-4.01 (m, 1H), 3.14-3.07 (m, 1H), 2.41 (s, 3H), 2.29-2.23 (m, 1H), 1.74-1.66 (m, 1H), 1.28-1.23 (m, 1H), 1.06-0.95 (m, 4H), 0.78-0.69 (m, 2H) |

Examples 15.13, 15.14, 15.15, and 15.16: 7-[(5-cyclopropyl-3-methyl-pyrazol-1-yl)methyl]-3-[2-(hydroxymethyl)cyclopropyl]-2-methyl-thiazolo[3,2-a]pyrimidin-5-one (enantiomers 1 and 2) and 7-[(3-cyclopropyl-5-methyl-pyrazol-1-yl)methyl]-3-[2-(hydroxymethyl)cyclopropyl]-2-methyl-thiazolo[3,2-a]pyrimidin-5-one (enantiomers 1 and 2)

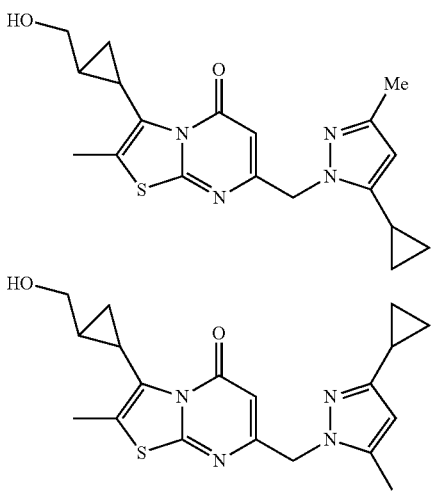

Examples 15.13, 15.14, 15.15 and 15.16 were prepared in a manner analogous to 15.7, where 2-[3-(trifluoromethyl)-1H-pyrazol-5-yl]ethan-1-ol was replaced by 5-cyclopropyl-3-methyl-1H-pyrazole in Step 5. Following the cross-coupling procedure in Step 6, the crude product was purified by Prep-HPLC (Column, XBridge Prep C18 OBD Column, 19*150 mm, 5 um; mobile phase, CH₃CN and water with 0.5% NH₃H₂O (35% CH₃CN up to 45% in 10 mins); Detector, UV 254/220 nm) to afford a mixture of racemic 7-[(5-cyclopropyl-3-methyl-pyrazol-1-yl)methyl]-3-[2-(hydroxymethyl)cyclopropyl]-2-methyl-thiazolo[3,2-a]pyrimidin-5-one and racemic 7-[(3-cyclopropyl-5-methyl-pyrazol-1-yl)methyl]-3-[2-(hydroxymethyl)cyclopropyl]-2-methyl-thiazolo[3,2-a]pyrimidin-5-one (60 mg, 70%) as a white solid. This material was purified by Chiral-HPLC (Column, CHIRALCEL, OJ-H (2×25 cm, 5 um); mobile phase, Hex:EtOH=85:15, 25 mins, flow rate, 20 ml/min; Detector, UV 254/220 nm) to afford four isomers:

Example 15.13: 7-[(5-cyclopropyl-3-methyl-pyrazol-1-yl)methyl]-3-[2-(hydroxymethyl)cyclopropyl]-2-methyl-thiazolo[3,2-a]pyrimidin-5-one (peak 1, enantiomer 1)

Retention time=8.2 min; Yield=4.2 mg, 5.0%; LCMS (ESI): M+H$^+$=271.1; $^1$H NMR (300 MHz, CDCl₃) δ 5.75 (s, 1H), 5.68 (s, 1H), 5.31 (s, 2H), 4.06-3.98 (m, 2H), 3.15-3.03 (m, 1H), 2.37 (s, 3H), 2.28-2.20 (m, 4H), 1.63-1.57 (m, 1H), 1.23-1.13 (m, 1H), 1.02-0.83 (m, 4H), 0.70-0.61 (m, 2H).

Example 15.14: 7-[(5-cyclopropyl-3-methyl-pyrazol-1-yl)methyl]-3-[2-(hydroxymethyl)cyclopropyl]-2-methyl-thiazolo[3,2-a]pyrimidin-5-one (peak 2, enantiomer 2)

Retention time=10 min; Yield=2.8 mg, 3.3%; LCMS (ESI): M+H$^+$=271.1; $^1$H NMR (300 MHz, CDCl₃) δ 5.75 (s, 1H), 5.68 (s, 1H), 5.31 (s, 2H), 4.06-3.98 (m, 2H), 3.15-3.03 (m, 1H), 2.37 (s, 3H), 2.28-2.20 (m, 4H), 1.63-1.57 (m, 1H), 1.23-1.13 (m, 1H), 1.02-0.83 (m, 4H), 0.70-0.61 (m, 2H).

Example 15.15: 7-[(3-cyclopropyl-5-methyl-pyrazol-1-yl)methyl]-3-[2-(hydroxymethyl)cyclopropyl]-2-methyl-thiazolo[3,2-a]pyrimidin-5-one (peak 3, enantiomer 1)

Retention time=14.8 min; Yield=6.9 mg, 8.2%; LCMS (ESI): M+H$^+$=271.1; $^1$H NMR (300 MHz, CDCl₃) δ 5.75 (s, 1H), 5.57 (s, 1H), 5.08 (s, 2H), 4.04-4.00 (m, 2H), 3.12-3.05 (m, 1H), 2.37 (s, 3H), 2.28-2.19 (m, 4H), 1.94-1.86 (m, 1H), 1.23-1.11 (m, 1H), 1.02-0.86 (m, 4H), 0.71-0.63 (m, 2H).

Example 15.16: 7-[(3-cyclopropyl-5-methyl-pyrazol-1-yl)methyl]-3-[2-(hydroxymethyl)cyclopropyl]-2-methyl-thiazolo[3,2-a]pyrimidin-5-one (peak 4, enantiomer 2)

Retention time=17.6 min; Yield=14.6 mg, 17.4%; LCMS (ESI): M+H$^+$=271.1; $^1$H NMR (300 MHz, CDCl₃) δ 5.75 (s, 1H), 5.57 (s, 1H), 5.08 (s, 2H), 4.04-4.00 (m, 2H), 3.12-3.05 (m, 1H), 2.37 (s, 3H), 2.28-2.19 (m, 4H), 1.94-1.86 (m, 1H), 1.23-1.11 (m, 1H), 1.02-0.86 (m, 4H), 0.71-0.63 (m, 2H).

The following examples were prepared in a manner similar to the preceding examples:

| No. | Structure/Name | LCMS (M + H) | $^1$H NMR |
|---|---|---|---|
| 15.17 | 7[(3,5-dicyclopropylpyrazol-1-yl)methyl]-3-[trans-2-(hydroxymethyl)cyclopropyl]-2-methyl-thiazolo[3,2-a]pyrimidin-5-one | 397.1 | $^1$H NMR (300 MHz, CDCl₃) δ 5.62 (s, 1H), 5.55 (s, 1H), 5.18 (s, 2H), 4.06-3.98 (m, 2H), 3.12-3.01 (m, 1H), 2.37 (s, 3H), 2.28-2.15 (m, 1H), 1.89-1.80 (m, 1H), 1.60-1.49 (m, 2H), 1.26-1.13 (m, 2H), 1.02-0.80 (m, 5H), 0.71-0.53 (m, 3H) |

-continued

| No. | Structure/Name | LCMS (M + H) | ¹H NMR |
|---|---|---|---|
| 15.18 | 7-((3,5-dimethyl-1H-pyrazol-1-yl)methyl)-6-fluoro-3-(trans-2-(hydroxymethyl)cyclopropyl)-2-methyl-5H-thiazolo[3,2-a]pyrimidin-5-one | 363.0 | ¹H NMR (300 MHz, CDCl₃) δ 5.85 (s, 1H), 5.22-5.19 (m, 2H), 4.09-4.00 (m, 1H), 3.77-3.74 (m, 1H), 3.25-3.18 (m, 1H), 2.38 (s, 3H), 2.31 (s, 3H), 2.29-2.27 (m, 1H), 2.23 (s, 3H), 1.32-1.28 (m, 1H), 1.08-1.01 (m, 2H). |
| 15.19 | 1-((3-(trans-2-(hydroxymethyl)cyclopropyl)-2-methyl-5-oxo-5H-thiazolo[3,2-a]pyrimidin-7-yl)methyl)-3-(trifluoromethyl)-1H-pyrazole-5-carbonitrile | 410.0 | ¹H NMR (300 MHz, CDCl₃) δ 7.12 (s, 2H), 5.93 (s, 1H), 5.39 (s, 2H), 4.06-4.01 (m, 1H), 3.15-3.08 (m, 1H), 2.39 (s, 3H), 2.39-2.23 (m, 1H), 1.33-1.22 (m, 1H), 1.05-1.02 (m, 2H) |
| 15.20 | 7-((5-cyclopropyl-3-(trifluoromethyl)-1H-pyrazol-1-yl)methyl)-6-fluoro-3-(trans-2-(hydroxymethyl)cyclopropyl)-2-methyl-5H-thiazolo[3,2-a]pyrimidin-5-one | 443.0 | ¹H NMR (300 MHz, CD₃OD) δ 6.29 (s, 1H), 5.53 (s, 2H), 3.71-3.57 (m, 2H), 2.41 (s, 3H), 2.17-2.15 (m, 1H), 2.01-1.94 (m, 1H), 1.46-1.41 (m, 1H), 1.09-1.01 (m, 4H), 0.77-0.72 (m, 2H). |
| 15.21 | 1-[[3-[trans-2-(hydroxymethyl)cyclopropyl]-2-methyl-5-oxo-thiazolo[3,2-a]pyrimidin-7-yl]methyl]-5-methyl-pyrazole-3-carbonitrile | 356.1 | ¹H NMR (400 MHz, DMSO-d₆) δ 6.81 (s, 1H), 5.70 (s, 1H), 5.29 (s, 2H), 4.53 (s, 1H), 3.46 (d, J = 5.9 Hz, 2H), 2.36 (d, J = 1.5 Hz, 3H), 2.32 (s, 3H), 2.00 (dtd, J = 7.1, 5.4, 1.7 Hz, 1H), 1.27 (dp, J = 8.5, 5.8 Hz, 1H), 0.85 (ddt, J = 16.0, 8.6, 5.1 Hz, 2H). |

-continued

| No. | Structure/Name | LCMS (M + H) | ¹H NMR |
|---|---|---|---|
| 15.22 | 7[[3-(difluoromethyl)-5-methyl-pyrazol-1-yl]methyl]-3-[trans-2-(hydroxymethyl)cyclopropyl]-2-methyl-thiazolo[3,2-a]pyrimidin-5-one | 381.1 | ¹H NMR (400 MHz, DMSO-$d_6$) δ 6.91 (t, J = 54.9 Hz, 1H), 6.38 (s, 1H), 5.52 (s, 1H), 5.19 (s, 2H), 4.52 (t, J = 5.7 Hz, 1H), 3.45 (t, J = 5.8 Hz, 2H), 2.36 (d, J = 1.5 Hz, 3H), 2.30 (s, 3H), 2.05-1.91 (m, 1H), 1.27 (dt, J = 8.7, 5.6 Hz, 1H), 0.97-0.66 (m, 3H). |
| 15.23 | 7-[(6-fluoroindazol-1-yl)methyl]-3-[trans-2-(hydroxymethyl)cyclopropyl]-2-methyl-thiazolo[3,2-a]pyrimidin-5-one | 385.1 | ¹H NMR (400 MHz, DMSO-$d_6$) δ 8.18 (s, 1H), 7.85 (dd, J = 8.9, 5.2 Hz, 1H), 7.59 (dd, J = 9.8, 2.2 Hz, 1H), 7.10-7.00 (m, 1H), 5.50 (s, 2H), 5.47 (s, 1H), 4.50 (t, J = 5.5 Hz, 1H), 3.43 (t, J = 5.7 Hz, 2H), 2.35 (d, J = 1.8 Hz, 3H), 2.04-1.89 (m, 1H), 1.25 (dp, J = 9.0, 5.9 Hz, 1H), 0.82 (ddt, J = 15.2, 8.6, 5.0 Hz, 2H). |
| 15.24 | 7-[[5-cyclopropyl-3-(trifluoromethyl)pyrazol-1-yl]methyl]-3[2-(hydroxymethyl)cyclopropyl]-2-isopropyl-thiazolo[3,2-a]pyrimidin-5-one | 453.2 | ¹HNMR (400 MHz, DMSO-$d_6$) δ 6.48 (s, 1H), 5.63 (s, 1H), 5.37 (s, 2H), 4.57 (t, J = 5.6 Hz, 1H), 3.65 (p, J = 6.7 Hz, 1H), 3.55-3.37 (m, 2H), 2.05-1.88 (m, 2H), 1.28 (dq, J = 8.8, 5.6 Hz, 1H), 1.22 (d, J = 6.8 Hz, 6H), 1.01-0.91 (m, 2H), 0.91-0.85 (m, 1H), 0.81 (dt, J = 8.8, 5.2 Hz, 1H), 0.73 (dt, J = 6.7, 4,0 Hz, 2H). |
| 15.25 | 7-[(3,5-dimethylpyrazol-1-yl)methyl]-3-[trans-2-(hydroxymethyl)cyclopropyl]-2-methyl-thiazolo[3,2-a]pyrimidin-5-one | 345.2 | ¹H NMR (400 MHz, DMSO-$d_6$) δ 5.89 (s, 1H), 5.35 (s, 1H), 5.02 (s, 2H), 4.52 (t, J = 5.6 Hz, 1H), 3.45 (t, J = 5.8 Hz, 2H), 2.36 (d, J = 1.6 Hz, 3H), 2.19 (s, 3H), 2.10 (s, 3H), 2.00 (qd, J = 7.4, 6.5, 2.6 Hz, 1H), 1.33-1.20 (m, 1H), 0.95-0.76 (m, 2H). |

| No. | Structure/Name | LCMS (M + H) | ¹H NMR |
|---|---|---|---|
| 15.26 | 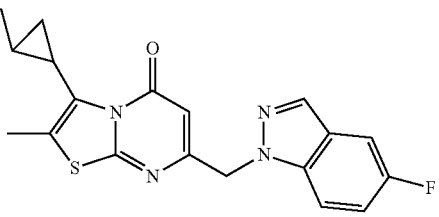<br>7-[(5-fluoroindazol-1-yl)methyl]-3-[trans-2-(hydroxymethyl)cyclopropyl]-2-methyl-thiazolo[3,2-a]pyrimidin-5-one | 385.1 | ¹H NMR (400 MHz, DMSO-$d_6$) δ 8.14 (s, 1H), 7.74 (dd, J = 9.1, 4.3 Hz, 1H), 7.58 (dd, J = 9.2, 2.4 Hz, 1H), 7.31 (td, J = 9.2, 2.5 Hz, 1H), 5.54 (s, 2H), 5.47 (s, 1H), 4.50 (t, J = 5.5 Hz, 1H), 3.43 (t, J = 5.5 Hz, 2H), 2.35 (s, 3H), 1.97 (ddd, J = 9.6, 6.7, 4.8 Hz, 1H), 1.31-1.15 (m, 1H), 0.82 (ddt, J = 16.2, 8.7, 5.1 Hz, 2H). |

Example 15.27: 5-ethyl-3-(trifluoromethyl)-1H-pyrazol-1-yl)methyl)-2-methyl-3-(pyrimidin-5-yl)-5H-thiazolo[3,2-a]pyrimidin-5-one

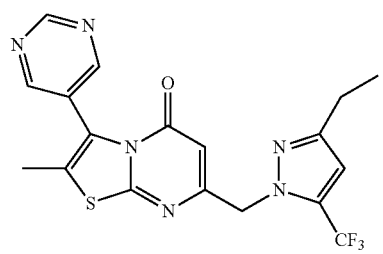 [SMILES: CCc1cc(C(F)(F)F)n(Cc2cc(=O)n3c(-c4cncnc4)c(C)sc3n2)n1]

To a solution of 3-bromo-7-[[5-ethyl-3-(trifluoromethyl)-1H-pyrazol-1-yl]methyl]-2-methyl-5H-[1,3]thiazolo[3,2-a]pyrimidin-5-one (from Example 15.1, Step 3) (80 mg, 0.19 mmol), 1,4-dioxane (2 mL), potassium phosphate (80 mg, 0.38 mmol), tetrakis(triphenylphosphine)palladium (22 mg, 0.02 mmol) and water (0.2 mL) in 1,4-dioxane (2 mL) under nitrogen, was added (pyrimidin-5-yl)boronic acid (47 mg, 0.38 mmol). The resulting solution was stirred for 3 h at 90° C. in an oil bath. The resulting mixture was quenched by water (10 mL), and extracted with dichloromethane (3×30 mL), washed with brine, dried over anhydrous sodium sulfate and concentrated under vacuum. The residue was purified by chromatography with ethyl acetate/petroleum ether (1:1) to afford 7-[[5-ethyl-3-(trifluoromethyl)-1H-pyrazol-1-yl]methyl]-2-methyl-3-(pyrimidin-5-yl)-5H-[1,3]thiazolo[3,2-a]pyrimidin-5-one (18.9 mg, 24%) as a yellow solid. LCMS (ESI): [M+H]⁺=462.0; ¹H NMR (300 MHz, CD$_3$OD) δ 9.18 (s, 1H), 8.82 (s, 2H), 6.52 (s, 1H), 5.70 (s, 1H), 5.31 (s, 2H), 2.80-2.72 (m, 2H), 2.30 (s, 3H), 1.34-1.29 (m, 3H).

Example 15.28 and 15.29: 7-((3-cyclopropyl-5-(trifluoromethyl)-1H-pyrazol-1-yl)methyl)-2-methyl-3-(pyrimidin-5-yl)-5H-thiazolo[3,2-a]pyrimidin-5-one and 7-((5-cyclopropyl-3-(trifluoromethyl)-1H-pyrazol-1-yl)methyl)-2-methyl-3-(pyrimidin-5-yl)-5H-thiazolo[3,2-a]pyrimidin-5-one

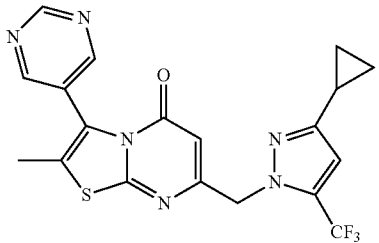

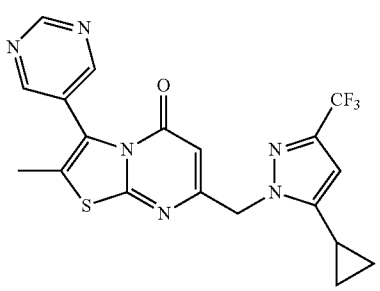

Step 1: 3-bromo-7-((3-cyclopropyl-5-(trifluoromethyl)-1H-pyrazol-1-yl)methyl)-2-methyl-5H-thiazolo[3,2-a]pyrimidin-5-one and 3-bromo-7-((5-cyclopropyl-3-(trifluoromethyl)-1H-pyrazol-1-yl)methyl)-2-methyl-5H-thiazolo[3,2-a]pyrimidin-5-one

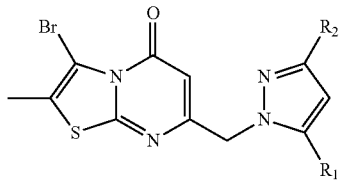

$R_1, R_2 = CF_3, cPr$

To a solution of 3-bromo-7-(chloromethyl)-2-methyl-5H-[1,3]thiazolo[3,2-a]pyrimidin-5-one (from Example 4.1, Step 6) (373 mg, 1.27 mmol) in CH$_3$CN (10 mL) was added 3-cyclopropyl-5-(trifluoromethyl)-1H-pyrazole (from Example 15.9, Step 2) (450 mg, 2.55 mmol), cesium carbonate (223 mg, 0.68 mmol) and potassium iodide (160 mg). The resulting solution was stirred overnight at 80° C. The solids were filtered off and the resulting mixture was concentrated under vacuum. The crude product was purified by Prep-HPLC (Xbridge Shield RP18 OBD Column, 5 um, 19×150 mm; mobile phase, water with 0.03% NH$_3$.H$_2$O and CH$_3$CN (10.0% CH$_3$CN up to 32.0% in 10 min, up to 100.0% in 1 min, hold 100.0% in 1 min, down to 10.0% in 2 min); Detector, uv 254 nm) to afford 3-bromo-7-[[3-cyclopropyl-5-(trifluoromethyl)-1H-pyrazol-1-yl]methyl]-2-methyl-5H-[1,3]thiazolo[3,2-a]pyrimidin-5-one (18 mg, 3%) as a white solid (LCMS (ESI): [M+H]$^+$=434.9; $^1$H NMR (300 MHz, CDCl$_3$) δ 6.36 (s, 1H), 5.54 (s, 1H), 5.21 (s, 2H), 2.35 (s, 3H), 1.90-2.01 (m, 1H), 0.94-1.00 (m, 2H), 0.71-0.79 (m, 2H)) and 3-bromo-7-[[5-cyclopropyl-3-(trifluoromethyl)-1H-pyrazol-1-yl]methyl]-2-methyl-5H-[1,3]thiazolo[3,2-a]pyrimidin-5-one (54 mg, 10%) as a white solid (LCMS (ESI): [M+H]$^+$=434.9; $^1$H NMR (300 MHz, CDCl$_3$) δ 6.18 (s, 1H), 5.66 (s, 1H), 5.30 (s, 2H), 2.36 (s, 3H), 1.72-1.65 (m, 1H), 1.03-0.98 (m, 2H), 0.76-0.71 (m, 2H)).

Step 4: 7-((3-cyclopropyl-5-(trifluoromethyl)-1H-pyrazol-1-yl)methyl)-2-methyl-3-(pyrimidin-5-yl)-5H-thiazolo[3,2-a]pyrimidin-5-one (Example 15.28)

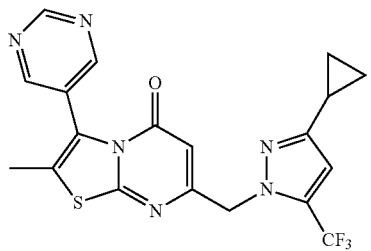 [SMILES: Cc1sc2nc(Cn3nc(C4CC4)cc3C(F)(F)F)cc(=O)n2c1-c1cncnc1]

To a solution of 3-bromo-7-[[3-cyclopropyl-5-(trifluoromethyl)-1H-pyrazol-1-yl]methyl]-2-methyl-5H-[1,3]thiazolo[3,2-a]pyrimidin-5-one (12 mg, 0.03 mmol) in CH$_3$CN (1.5 mL) and water (0.5 mL) was added (pyrimidin-5-yl) boronic acid (7 mg, 0.060 mmol), potassium phosphate (12 mg, 0.06 mmol) and tetrakis(triphenylphosphine)palladium (2.0 mg, 10 mmol %). After stirring 1 h at 100° C. under nitrogen atmosphere, the resulting mixture was concentrated under vacuum. The residue was purified by silica gel chromatography with 1% methanol in dichloromethane. The crude product was purified by Prep-HPLC (SunFire Prep C$_{18}$ OBD Column, 5 um, 19×150 mm; mobile phase, water with 10 mmol NH$_4$HCO$_3$ and CH$_3$CN (30.0% CH$_3$CN up to 60.0% in 8 min, up to 95.0% in 2 min, down to 30.0% in 2 min); Detector, UV 254/220 nm) to afford 7-[[3-cyclopropyl-5-(trifluoromethyl)-1H-pyrazol-1-yl]methyl]-2-methyl-3-(pyrimidin-5-yl)-5H-[1,3]thiazolo[3,2-a]pyrimidin-5-one (6.1 mg, 51%) as a white solid. LCMS (ESI): [M+H]$^+$=433.2; $^1$H NMR (300 MHz, CDCl$_3$) δ 9.26 (s, 1H), 8.70 (s, 2H), 6.35 (s, 1H), 5.49 (s, 1H), 5.26 (s, 2H), 2.29 (s, 3H), 1.98-1.88 (m, 1H), 0.99-0.93 (m, 2H), 0.76-0.74 (m, 2H).

Step 5: 7-((5-cyclopropyl-3-(trifluoromethyl)-1H-pyrazol-1-yl)methyl)-2-methyl-3-(pyrimidin-5-yl)-5H-thiazolo[3,2-a]pyrimidin-5-one (Example 15.29)

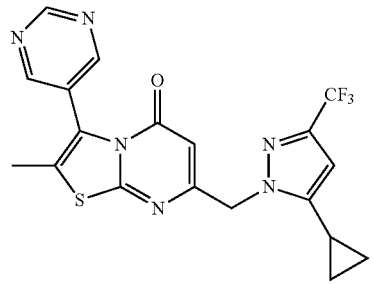 [SMILES: Cc1sc2nc(Cn3nc(C(F)(F)F)cc3C3CC3)cc(=O)n2c1-c1cncnc1]

To a solution of 3-bromo-7-[[5-cyclopropyl-3-(trifluoromethyl)-1H-pyrazol-1-yl]methyl]-2-methyl-5H-[1,3]thiazolo[3,2-a]pyrimidin-5-one (33 mg, 0.08 mmol) in CH$_3$CN (1.5 mL) and water (0.5 mL) was added (pyrimidin-5-yl) boronic acid (21 mg, 0.17 mmol), potassium phosphate (35 mg, 0.16 mmol) and tetrakis(triphenylphosphine)palladium (6 mg, 0.01 mmol). After stirring 1 h at 100° C. under nitrogen atmosphere, the resulting mixture was concentrated under vacuum. The residue was purified by chromatography with 1% methanol in dichloromethane. The crude product was purified by Prep-HPLC (SunFire Prep C$_{18}$ OBD Column, 5 um, 19×150 mm; mobile phase, water with 10 mmol NH$_4$HCO$_3$ and CH$_3$CN (30.0% CH$_3$CN up to 60.0% in 8 min, up to 95.0% in 2 min, down to 30.0% in 2 min); Detector, UV 254/220 nm) to afford 7-[[5-cyclopropyl-3-(trifluoromethyl)-1H-pyrazol-1-yl]methyl]-2-methyl-3-(pyrimidin-5-yl)-5H-[1,3]thiazolo[3,2-a]pyrimidin-5-one (29.2 mg, 89%) as a white solid. LCMS (ESI): [M+H]$^+$=433.2; $^1$H NMR (300 MHz, CDCl$_3$) δ 9.26 (s, 1H), 8.70 (s, 2H), 6.18 (s, 1H), 5.64 (s, 1H), 5.35 (s, 2H), 2.29 (s, 3H), 1.77-1.68 (m, 1H), 1.04-0.98 (m, 2H), 0.75-0.70 (m, 2H).

The following examples were prepared in a manner similar to Example 15.27, 15.28, and 15.29:

| No. | Structure/Name | LCMS (M + H) | ¹H NMR |
|---|---|---|---|
| 15.30 | 7-((3,5-bis(trifluoromethyl)-1H-pyrazol-1-yl)methyl)-2-methyl-3-(pyrimidin-5-yl)-5H-thiazolo[3,2-a]pyrimidin-5-one | 461.10 | ¹H NMR (300 MHz, DMSO-$d_6$) δ 9.19 (s, 1H), 8.85 (s, 2H), 7.69 (s, 1H), 5.88 (s, 1H), 5.56 (s, 2H), 2.21 (s, 3H) |
| 15.31 | 2-methyl-3-(pyrimidin-5-yl)-7-((5-(trifluoromethyl)-1H-pyrazol-1-yl)methyl)-5H-thiazolo[3,2-a]pyrimidin-5-one | 393 | ¹H NMR (300 MHz, CDCl$_3$) δ 9.27 (s, 1H), 8.70 (s, 2H), 7.61-7.60 (m, 1H), 6.61-6.60 (m, 1H), 5.84 (s, 1H), 5.25 (s, 2H), 2.28 (s, 3H) |
| 15.32 | 2-methyl-7-((5-methyl-3-(trifluoromethyl)-1H-pyrazol-1-yl)methyl)-3-(pyrimidin-5-yl)-5H-thiazolo[3,2-a]pyrimidin-5-one | 448.15 | ¹H NMR (300 MHz, CDCl$_3$) δ 9.25 (s, 1H), 8.69 (s, 2H), 6.37 (s, 1H), 5.61 (s, 1H), 5.20 (s, 2H), 2.33 (s, 3H), 2.29 (s, 3H) |

The following compounds were prepared using methods analogous to those described above:

| No. | Structure/Name | LCMS (M + H) | ¹H NMR |
|---|---|---|---|
| 15.33 | 7-((3,5-bis(trifluoromethyl)-1H-pyrazol-1-yl)methyl)-2-methyl-5H-thiazolo[3,2-a]pyrimidin-5-one | 382.95 | ¹H NMR (300 MHz, CDCl$_3$) δ 8.85 (s, 1H), 7.69 (s, 1H), 5.88 (s, 1H), 5.56 (s, 2H), 2.21 (s, 3H) |

| No. | Structure/Name | LCMS (M + H) | ¹H NMR |
|---|---|---|---|
| 15.34 | 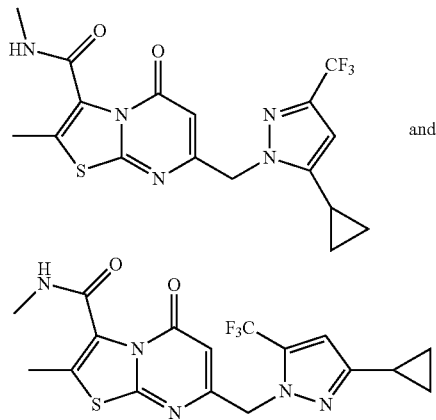<br>7-((1H-indazol-1-yl)methyl)-2-methyl-3-(pyrimidin-5-yl)-5H-thiazolo[3,2-a]pyrimidin-5-one | 375 | ¹H NMR (300 MHz, CDCl₃) δ 9.22 (s, 1H), 8.65 (s, 2H), 8.08 (s, 1H), 7.76 (m, 1H), 7.42-7.36 (m, 2H), 7.26-7.16 (m, 1H), 5.30 (s, 2H), 2.27 (s, 3H) |

Method 16

Example 16.1 and 16.2: 7-((5-cyclopropyl-3-(trifluoromethyl)-1H-pyrazol-1-yl)methyl)-N,2-dimethyl-5-oxo-5H-thiazolo[3,2-a]pyrimidine-3-carboxamide and 7-((3-cyclopropyl-5-(trifluoromethyl)-1H-pyrazol-1-yl)methyl)-N,2-dimethyl-5-oxo-5H-thiazolo[3,2-a]pyrimidine-3-carboxamide

Step 1: ethyl 2-oxobutanoate

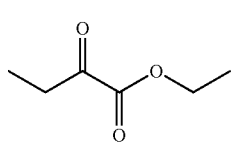

Into a 10 L 4-necked round-bottom flask purged and maintained with an inert atmosphere of nitrogen was placed diethyl oxalate (300 g, 2.05 mol, 1.00 equiv) and tetrahydrofuran (4.4 L), followed by ethyl magnesium bromide (740 mL, 1.08 equiv) dropwise with stirring at −10° C. over 2 h. The resulting solution was stirred at −10° C. for 30 min and quenched by the addition of 500 mL 3 M hydrogen chloride. The pH value of the solution was adjusted to pH 4 with hydrogen chloride (3 mol/L) and the resulting solution was extracted with 2×1 L of dichloromethane. The combined organic layers were washed with 1×2 L of sodium chloride, dried over anhydrous sodium sulfate and concentrated under vacuum to afford 200 g (crude) of ethyl 2-oxobutanoate as a yellow oil.

Step 2: ethyl 3-bromo-2-oxobutanoate

Into a 10-L 4-necked round-bottom flask was placed ethyl 2-oxobutanoate (265 g, 2.04 mol, 1.00 equiv), chloroform (5 L), a solution of HBr in AcOH (500 mL), and Br₂ (325 g, 2.03 mol, 1.00 equiv). The resulting solution was stirred at 70° C. for 2 h, cooled to room temperature and concentrated under vacuum to afford 392.9 g (92%) of ethyl 3-bromo-2-oxobutanoate as a brown oil.

Step 3: ethyl 2-amino-5-methyl-1,3-thiazole-4-carboxylate

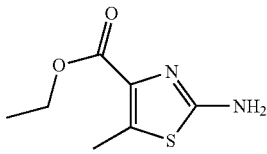

Into a 10-L round-bottom flask was placed ethyl 3-bromo-2-oxobutanoate (392.9 g, 1.88 mol, 1.00 equiv), 1,4-dioxane (3.5 L), and thiourea (143.8 g, 1.89 mol, 1.01 equiv). The resulting solution was stirred overnight at 100° C. and cooled to room temperature. The solids were then collected by filtration, washed with Et₂O and dried under vacuum to afford 310 g (89%) of ethyl 2-amino-5-methyl-1,3-thiazole-4-carboxylate as a light brown solid.

Step 4:
2-amino-N,5-dimethyl-1,3-thiazole-4-carboxamide

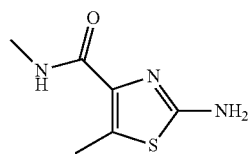

Into a 1-L pressure tank reactor was placed ethyl 2-amino-5-methyl-1,3-thiazole-4-carboxylate (140 g, 751.75 mmol, 1.00 equiv) and 30% methylamine in EtOH (500 mL). The resulting solution was stirred overnight at 85° C. and concentrated under vacuum. The residue was purified on a silica gel column eluting with dichloromethane/methanol (20/1) to afford 80 g (62%) of 2-amino-N,5-dimethyl-1,3-thiazole-4-carboxamide as a yellow solid.

Step 5: 7-(chloromethyl)-N,2-dimethyl-5-oxo-5H-[1,3]thiazolo[3,2-a]pyrimidine-3-carboxamide

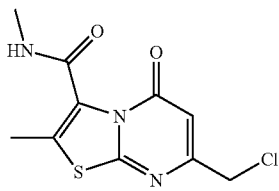 [SMILES: CNC(=O)c1c(C)sc2nc(CCl)cc(=O)n12]

Into a 3-L 3-necked round-bottom flask was placed 2-amino-N,5-dimethyl-1,3-thiazole-4-carboxamide (80 g, 467.24 mmol, 1.00 equiv), ethyl 4-chloro-3-oxobutanoate (154 g, 935.68 mmol, 2.00 equiv) and polyphosphoric acid (PPA) (800 g). The resulting solution was stirred at 110° C. for 2 h, cooled to 80° C. and quenched by the addition of 100 mL of water. The pH value of the solution was adjusted to pH 8 with sodium hydroxide (10% aq.). The solids were filtered off and the filtrate was extracted with dichloromethane (5 L×5). The combined organic layers were dried over anhydrous $Na_2SO_4$ and concentrated under vacuum. The residue was purified on a silica gel column eluting with dichloromethane/methanol (20/1) to give 80 g (63%) of 7-(chloromethyl)-N,2-dimethyl-5-oxo-5H-[1,3]thiazolo[3,2-a]pyrimidine-3-carboxamide as a tan solid. LCMS (ESI): $[M+H]^+$=272; $^1$H NMR (400 MHz, DMSO-$d_6$): δ 8.38 (q, J=4.8 Hz, 1H), 6.39 (s, 1H), 4.60 (s, 2H), 2.74 (d, J=4.8 Hz, 3H), 2.30 (s, 3H).

Step 6: 7-((5-cyclopropyl-3-(trifluoromethyl)-1H-pyrazol-1-yl)methyl)-N,2-dimethyl-5-oxo-5H-thiazolo[3,2-a]pyrimidine-3-carboxamide (Example 16.1) and 7-((3-cyclopropyl-5-(trifluoromethyl)-1H-pyrazol-1-yl)methyl)-N,2-dimethyl-5-oxo-5H-thiazolo[3,2-a]pyrimidine-3-carboxamide (Example 16.2)

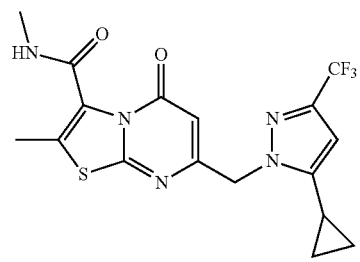

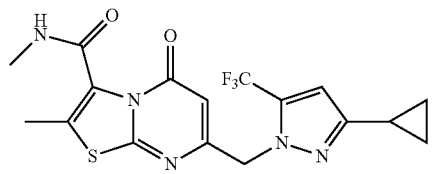

To a solution of 7-(chloromethyl)-N,2-dimethyl-5-oxo-5H-[1,3]thiazolo[3,2-a]pyrimidine-3-carboxamide (100 mg, 0.37 mmol), potassium iodide (30 mg, 0.19 mmol) and potassium carbonate (100 mg, 0.74 mmol) in $CH_3CN$ (10 mL) was added 5-cyclopropyl-3-(trifluoromethyl)-1H-pyrazole (from Example 15.9, Step 2) (80 mg, 0.45 mmol). The reaction mixture was stirred 3 h at 85° C. in an oil bath. After filtration to remove solids and concentration under vacuum, the residue was purified by silica gel chromatography with ethyl acetate/petroleum ether (2:1) to afford 7-[[5-cyclopropyl-3-(trifluoromethyl)-1H-pyrazol-1-yl]methyl]-N,2-dimethyl-5-oxo-5H-[1,3]thiazolo[3,2-a]pyrimidine-3-carboxamide (50.4 mg, 33%) as a white solid (LCMS (ESI): $[M+H]^+$=412.0; $^1$H NMR (300 MHz, $CDCl_3$) δ 6.27 (bs, 1H), 6.19 (s, 1H), 5.64 (s, 1H), 5.32 (s, 2H), 3.03 (m, 3H), 2.40 (s, 3H), 1.71-1.65 (m, 1H), 1.03-0.97 (m, 2H), 0.76-0.66 (m, 2H)) and 7-[[3-cyclopropyl-5-(trifluoromethyl)-1H-pyrazol-1-yl]methyl]-N,2-dimethyl-5-oxo-5H-[1,3]thiazolo[3,2-a]pyrimidine-3-carboxamide (20.7 mg, 14%) as a white solid (LCMS (ESI): $[M+H]^+$=411.9; $^1$H NMR (300 MHz, $CDCl_3$) δ 6.36 (s, 1H), 5.94 (br, 1H), 5.56 (s, 1H), 5.24 (s, 2H), 3.03 (m, 3H), 2.42 (s, 3H), 1.98-1.89 (m, 1H), 0.99-0.91 (m, 2H), 0.76-0.66 (m, 2H)).

Example 16.3 and 16.4: 7-((5-cyclopropyl-3-(trifluoromethyl)-1H-pyrazol-1-yl)methyl)-N-ethyl-5-oxo-2-(trifluoromethyl)-5H-thiazolo[3,2-a]pyrimidine-3-carboxamide and 7-((3-cyclopropyl-5-(trifluoromethyl)-1H-pyrazol-1-yl)methyl)-N-ethyl-5-oxo-2-(trifluoromethyl)-5H-thiazolo[3,2-a]pyrimidine-3-carboxamide

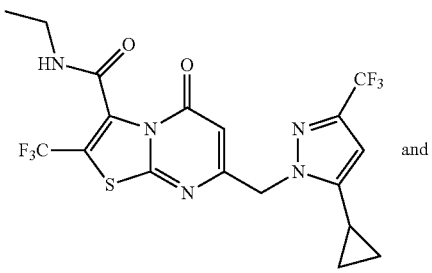

and

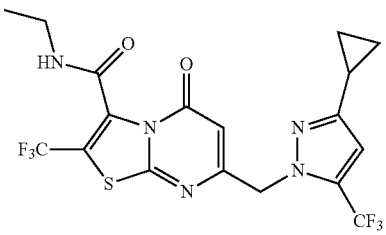

Step 1: methyl 2-amino-5-iodothiazole-4-carboxylate

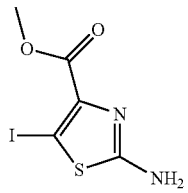

To a solution of methyl 2-amino-1,3-thiazole-4-carboxylate (20 g, 0.13 mol) in dichloromethane (300 mL) was added N-iodosuccinimide (34 g, 0.15 mol) in portions. The resulting solution was stirred overnight at room temperature. Then the reaction mixture was washed with saturated aqueous $Na_2SO_3$ (3×150 mL). The organic layer was dried over anhydrous sodium sulfate. After filtration, the filtrate was concentrated to afford methyl 2-amino-5-iodo-1,3-thiazole-4-carboxylate (21 g, 58%) as a reddish solid.

Step 2: methyl 5-iodothiazole-4-carboxylate

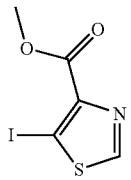

To a solution of methyl 2-amino-5-iodo-1,3-thiazole-4-carboxylate (21 g, 0.074 mol) in tetrahydrofuran (400 mL) was added t-butylnitrite (11.5 g, 0.11 mol). The resulting solution was stirred for 1 h at 50° C. in an oil bath. After cooled down to room temperature, the reaction mixture was concentrated under vacuum. The residue was purified by chromatography with ethyl acetate/petroleum ether (1:5) to afford methyl 5-iodo-1,3-thiazole-4-carboxylate (8 g, 40%) as a yellow solid. LCMS (ESI): $[M+H]^+$=269.9; $^1$H NMR (300 MHz, $CDCl_3$) δ 8.95 (s, 1H), 3.97 (s, 3H).

Step 3: methyl 5-(trifluoromethyl)thiazole-4-carboxylate

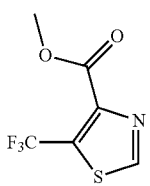

To a solution of methyl 5-iodo-1,3-thiazole-4-carboxylate (8.00 g, 29.7 mmol) and copper iodide (8.70 g, 45.7 mmol) in N,N-dimethylformamide (200 mL) was added methyl 2,2-difluoro-2-(fluorosulfonyl)acetate (8.70 g, 45.3 mmol). The resulting solution was stirred overnight at 80° C. in an oil bath. After filtration remove solids and concentration under vacuum, the residue was purified by chromatography with ethyl acetate/petroleum ether (1:5) to afford methyl 5-(trifluoromethyl)-1,3-thiazole-4-carboxylate (4 g, 64%) as a light yellow solid. LCMS (ESI): $[M+H]^+$=212.0; $^1$H NMR (300 MHz, $CDCl_3$) δ 8.91 (s, 1H), 4.00 (s, 3H).

Step 4: N-ethyl-5-(trifluoromethyl)thiazole-4-carboxamide

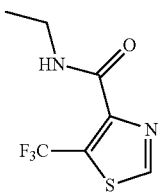

A mixture of methyl 5-(trifluoromethyl)-1,3-thiazole-4-carboxylate (1 g, 4.74 mmol) and ethylamine in ethanol (10 mL) was placed in a 30-mL sealed tube. The resulting solution was stirred overnight at 50° C. in an oil bath. After concentration under vacuum, the residue was purified by chromatography with ethyl acetate/petroleum ether (1:5) to afford N-ethyl-5-(trifluoromethyl)-1,3-thiazole-4-carboxamide (400 mg, 38%) as a light yellow oil. LCMS (ESI): $[M+H]^+$=225.0; $^1$H NMR (300 MHz, $CDCl_3$) δ 8.79 (s, 1H), 7.42 (br, 1H), 3.55-3.46 (m, 2H), 1.27 (m, 3H).

Step 5: 2-bromo-N-ethyl-5-(trifluoromethyl)thiazole-4-carboxamide

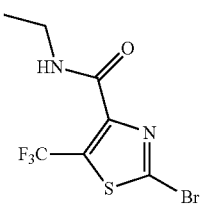

To a solution of N-ethyl-5-(trifluoromethyl)-1,3-thiazole-4-carboxamide (200 mg, 0.89 mmol) in tetrahydrofuran (3 mL) was added n-butyllithium (2.5 M in hexanes; 1.1 mL, 2.70 mmol) drop wise with stirring at −78° C. The resulting solution was stirred for 30 min at −78° C. Then carbon tetrabromide (900 mg, 2.70 mmol) in tetrahydrofuran (5 mL) was added drop wise with stirring at −78° C. After stirred 1 h at −78° C., the reaction was quenched with water/ice, extracted with dichloromethane (2×30 mL), washed with brine, dried over anhydrous sodium sulfate and concentrated in vacuo. The residue was purified by chromatography with ethyl acetate/petroleum ether (1:10) to afford 2-bromo-N-ethyl-5-(trifluoromethyl)-1,3-thiazole-4-carboxamide (40 mg, 15%) as a light yellow solid. LCMS (ESI): $[M+H]^+$=302.8, 304.8; $^1$H NMR (300 MHz, $CDCl_3$) δ 3.53-3.44 (m, 2H), 1.27 (m, 3H).

Step 6: 2-amino-N-ethyl-5-(trifluoromethyl)thiazole-4-carboxamide

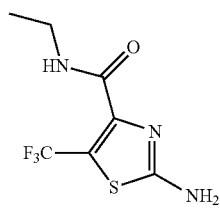

A mixture of 2-bromo-N-ethyl-5-(trifluoromethyl)-1,3-thiazole-4-carboxamide (500 mg, 1.65 mmol), 1,4-dioxane (5 mL) and ammonia (5 mL) was placed in a 30-mL sealed tube. The resulting solution was stirred overnight at 70° C. in an oil bath. The resulting mixture was extracted with $CH_2Cl_2$ (20 mL×2), washed with brine, dried over anhydrous sodium sulfate and concentrated in vacuo. The residue was purified by chromatography with ethyl acetate/petroleum ether (1:1) to afford 2-amino-N-ethyl-5-(trifluoromethyl)-1,3-thiazole-4-carboxamide (250 mg, 63%) as a light yellow semi-solid. LCMS (ESI): $[M+H]^+=240.0$; $^1$H NMR (300 MHz, $CDCl_3$) δ 7.15 (br, 1H), 5.24 (br, 2H), 3.48-3.39 (m, 2H), 1.22 (m, 3H).

Step 7: 7-(chloromethyl)-N-ethyl-5-oxo-2-(trifluoromethyl)-5H-thiazolo[3,2-a]pyrimidine-3-carboxamide

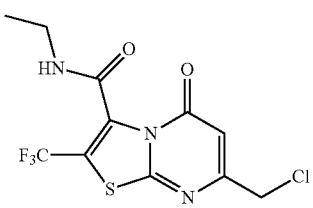 [SMILES: CCNC(=O)c1c(C(F)(F)F)sc2nc(CCl)cc(=O)n12]

To a mixture of 2-amino-N-ethyl-5-(trifluoromethyl)-1,3-thiazole-4-carboxamide (250 mg, 1.05 mmol) and ethyl 4-chloro-3-oxobutanoate (350 mg, 2.13 mmol) was added polyphosphoric acid (5 g, excess). The resulting mixture was stirred for 1.5 h at 110° C. in an oil bath. The reaction was then quenched by the addition of water and the pH value of the solution was adjusted to pH 8 with aqueous sodium hydroxide. The resulting mixture was extracted with dichloromethane (100 mL×2), washed with brine, dried over anhydrous sodium sulfate and concentrated in vacuo. The residue was purified by silica gel chromatography with dichloromethane/ethyl acetate (10:1) to afford 7-(chloromethyl)-N-ethyl-5-oxo-2-(trifluoromethyl)-5H-[1,3]thiazolo[3,2-a]pyrimidine-3-carboxamide (200 mg, 56%) as a white solid. LCMS (ESI): $[M+H]^+=339.9$; $^1$HNMR (300 MHz, $CDCl_3$) δ 6.49 (s, 1H), 5.90 (br, 1H), 4.41 (s, 2H), 3.60-3.51 (m, 2H), 1.22 (m, 3H).

Step 8: 7-((5-cyclopropyl-3-(trifluoromethyl)-1H-pyrazol-1-yl)methyl)-N-ethyl-5-oxo-2-(trifluoromethyl)-5H-thiazolo[3,2-a]pyrimidine-3-carboxamide (Example 16.3) and 7-((3-cyclopropyl-5-(trifluoromethyl)-1H-pyrazol-1-yl)methyl)-N-ethyl-5-oxo-2-(trifluoromethyl)-5H-thiazolo[3,2-a]pyrimidine-3-carboxamide (Example 16.4)

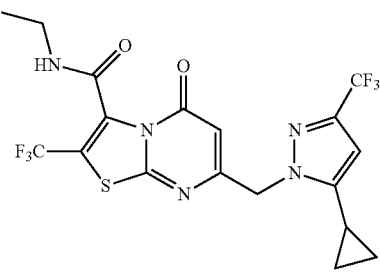

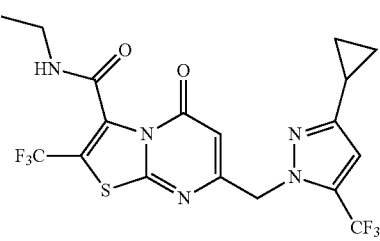

To a solution of 7-(chloromethyl)-N-ethyl-5-oxo-2-(trifluoromethyl)-5H-[1,3]thiazolo[3,2-a]pyrimidine-3-carboxamide (80 mg, 0.24 mmol) and potassium carbonate (80 mg, 2.00 equiv) in acetonitrile (8 mL) was added 5-cyclopropyl-3-(trifluoromethyl)-1H-pyrazole (from Example 15.9, Step 2) (50 mg, 0.28 mmol). The resulting solution was stirred for 3 h at 80° C. in an oil bath. After filtration to remove solids and concentration under vacuum, the residue was purified by chromatography with ethyl acetate/petroleum ether (1:2) to afford 7-[[5-cyclopropyl-3-(trifluoromethyl)-1H-pyrazol-1-yl]methyl]-N-ethyl-5-oxo-2-(trifluoromethyl)-5H-[1,3]thiazolo[3,2-a]pyrimidine-3-carboxamide (26.3 mg, 23%) as a white solid (LCMS (ESI): $[M+H]^+=480.0$; $^1$H NMR (300 MHz, $CDCl_3$) δ 6.20 (s, 1H), 5.89 (bs, 1H), 5.77 (s, 1H), 5.35 (s, 2H), 3.59-3.50 (m, 2H), 1.73-1.61 (m, 1H), 1.22 (m, 3H), 1.07-1.00 (m, 2H), 0.76-0.70 (m, 2H)) and 7-[[3-cyclopropyl-5-(trifluoromethyl)-1H-pyrazol-1-yl]methyl]-N-ethyl-5-oxo-2-(trifluoromethyl)-5H-[1,3]thiazolo[3,2-a]pyrimidine-3-carboxamide (16.5 mg, 15%) as a white solid (LCMS (ESI): $[M+H]^+=480.0$; $^1$H NMR (300 MHz, $CDCl_3$) δ 6.38 (s, 1H), 5.84 (bs, 1H), 5.67 (s, 1H), 5.25 (s, 2H), 3.59-3.50 (m, 2H), 1.98-1.89 (m, 1H), 1.22 (m, 3H), 0.99-0.91 (m, 2H), 0.78-0.73 (m, 2H)).

The following example was prepared in a manner similar to Examples 16.1, 16.2, 16.3, and 16.4:

| No. | Structure/Name | LCMS (M + H) | ¹H NMR |
|---|---|---|---|
| 16.5 | 7-((5-cyclopropyl-3-(trifluoromethyl)-1H-pyrazol-1-yl)methyl)-N-ethyl-5-oxo-5H-thiazolo[3,2-a]pyrimidine-3-carboxamide | 412.20 | ¹H NMR (300 MHz, CDCl₃) δ 9.36 (br, 1H), 7.97 (s, 1H), 6.19 (s, 1H), 5.80 (s, 1H), 5.37 (s, 2H), 3.49-3.40 (m, 2H), 1.75-1.66 (m, 1H), 1.26-1.20 (m, 3H), 1.02-0.95 (m, 2H), 0.74-0.65 (m, 2H) |

The following compounds were prepared using methods analogous to those described above:

| No. | Structure/Name | LCMS (M + H) | ¹H NMR |
|---|---|---|---|
| 16.6 | 2-cyclopropyl-7-((5-cyclopropyl-3-(trifluoromethyl)-1H-pyrazol-1-yl)methyl)-N-ethyl-5-oxo-5H-thiazolo[3,2-a]pyrimidine-3-carboxamide | 452.0 | ¹H NMR (300 MHz, CDCl₃) δ 6.17 (s, 1H), 5.98 (s, 1H), 5.65 (s, 1H), 5.31 (s, 2H), 3.57-3.48 (m, 2H), 2.18-2.11 (m, 1H), 1.69-1.62 (m, 1H), 1.30-1.22 (m, 3H), 1.19-1.13 (m, 2H), 1.01-0.92 (m, 2H), 0.87-0.81 (m, 2H), 0.72-0.67 (m, 2H) |
| 16.7 | 2-cyclopropyl-7-((3-cyclopropyl-5-(trifluoromethyl)-1H-pyrazol-1-yl)methyl)-N-ethyl-5-oxo-5H-thiazolo[3,2-a]pyrimidine-3-carboxamide | 452.0 | ¹H NMR (300 MHz, CDCl₃) δ 6.34 (s, 1H), 5.84 (s, 1H), 5.54 (s, 1H), 5.21 (s, 2H), 3.57-3.49 (m, 2H), 2.20-2.13 (m, 1H), 1.96-1.89 (m, 1H), 1.30-1.25 (m, 3H), 1.19-1.12 (m, 2H), 0.98-0.90 (m, 2H), 0.87-0.81 (m, 2H), 0.79-0.71 (m, 2H) |

Method 17

Example 17.1: 2-methyl-5-oxo-7-((3-(trifluoromethyl)-1H-pyrazol-1-yl)methyl)-5H-thiazolo[3,2-a]pyrimidine-3-carbonitrile

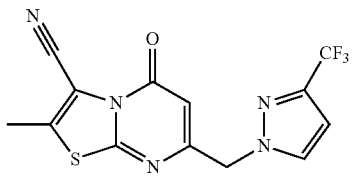 [SMILES: Cc1sc2nc(Cn3ccc(C(F)(F)F)n3)cc(=O)n2c1C#N]

Step 1: 3-bromo-2-methyl-7-((3-(trifluoromethyl)-1H-pyrazol-1-yl)methyl)-5H-thiazolo[3,2-a]pyrimidin-5-one

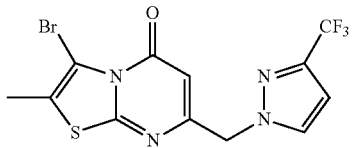 [SMILES: Cc1sc2nc(Cn3ccc(C(F)(F)F)n3)cc(=O)n2c1Br]

To a solution of 3-bromo-7-(chloromethyl)-2-methyl-5H-thiazolo[3,2-a]pyrimidin-5-one (from Example 4.1, Step 6) (300 mg, 0.76 mmol) in CH$_3$CN (5 mL) was added 3-(trifluoromethyl)-1H-pyrazole (125 mg, 0.92 mmol), potassium carbonate (316 mg, 2.29 mmol) and potassium iodide (63 mg, 0.38 mmol). The resulting solution was heated to reflux overnight. The solids were filtered out and the filtrate was concentrated under vacuum. The residue was purified by silica gel chromatography with dichloromethane/methanol (50/1) to afford 3-bromo-2-methyl-7-[[3-(trifluoromethyl)-1H-pyrazol-1-yl]methyl]-5H-[1,3]thiazolo[3,2-a]pyrimidin-5-one (200 mg, 67%) as a white solid.

Step 2: 2-methyl-5-oxo-7-((3-(trifluoromethyl)-1H-pyrazol-1-yl)methyl)-5H-thiazolo[3,2-a]pyrimidine-3-carbonitrile

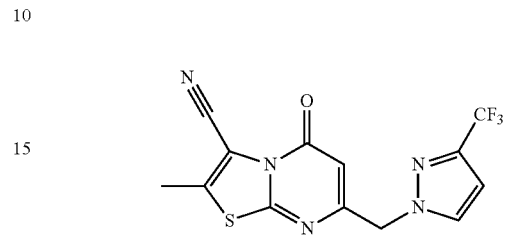

To a solution of 3-bromo-2-methyl-7-[[3-(trifluoromethyl)-1H-pyrazol-1-yl]methyl]-5H-[1,3]thiazolo[3,2-a]pyrimidin-5-one (120 mg, 0.31 mmol) in N,N-dimethylformamide (2 mL) was added copper (I) cyanide (32 mg, 0.36 mmol). The resulting solution was stirred for 1 h at 100° C. The reaction was then quenched by the addition of water. The solids were filtered off and the filtrate was extracted with ethyl acetate (3×10 mL), washed with brine, dried over anhydrous sodium sulfate and concentrated under vacuum. The residue was purified by chromatography with ethyl acetate/petroleum ether (1/5) to afford 2-methyl-5-oxo-7-[[3-(trifluoromethyl)-1H-pyrazol-1-yl]methyl]-5H-[1,3]thiazolo[3,2-a]pyrimidine-3-carbonitrile (10.2 mg, 10%) as a white solid. LCMS (ESI): [M+H]$^+$=340; $^1$H NMR (300 MHz, CDCl$_3$) δ 7.59 (m, 1H), 6.62 (m, 1H), 5.99 (s, 1H), 5.24 (s, 2H), 2.67 (s, 3H).

The following examples were prepared in a manner similar to Example 17.1:

| No. | Structure/Name | LCMS (M + H) | $^1$H NMR |
|---|---|---|---|
| 17.2 | 7-((5-cyclopropyl-3-(trifluoromethyl)-1H-pyrazol-1-yl)methyl)-2-methyl-5-oxo-5H-thiazolo[3,2-a]pyrimidine-3-carbonitrile | 380.0 | $^1$H NMR (300 MHz, CD$_3$OD) δ 6.34 (s, 1H), 5.89 (s, 1H), 5.44 (s, 2H), 2.66 (s, 3H), 1.91 (m, 1H), 1.04 (m, 2H), 0.77 (m, 2H) |
| 17.3 | 7-((3-cyclopropyl-5-(trifluoromethyl)-1H-pyrazol-1-yl)methyl)-2-methyl-5-oxo-5H-thiazolo[3,2-a]pyrimidine-3-carbonitrile | 379.90 | $^1$H NMR (300 MHz, CD$_3$OD) δ 6.57 (s, 1H), 5.71 (s, 1H), 5.30 (s, 2H), 2.64 (s, 3H), 1.95 (m, 1H), 0.96 (m, 2H), 0.75 (m, 2H) |

Method 18

Example 18.1: 3-(1-hydroxyethyl)-2-methyl-7-((3-(trifluoromethyl)-1H-pyrazol-1-yl)methyl)-5H-thiazolo[3,2-a]pyrimidin-5-one

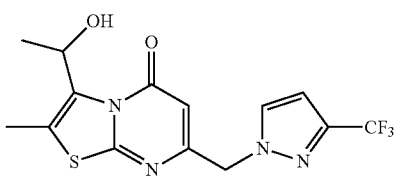 [SMILES: Cc1sc2nc(Cn3ccc(C(F)(F)F)n3)cc(=O)n2c1C(C)O]

Step 1: 4-bromopentane-2,3-dione

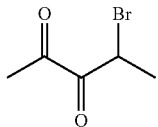

To a solution of pentane-2,3-dione (1.00 g, 9.99 mmol) in chloroform (30 mL) was added bromine (1.60 g, 10.01 mmol) and hydrogen bromide in acetic acid (33 wt %; 3 drops). The resulting solution was stirred for 3 h at 50° C. The resulting solution was concentrated to afford 4-bromopentane-2,3-dione as a solid (1.79 g). The crude product was used in next step without further purification.

Step 2: 1-(2-amino-5-methylthiazol-4-yl)ethanone

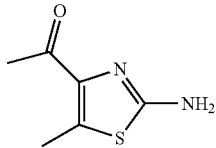

To a solution of 4-bromopentane-2,3-dione (1.79 g, 10.00 mmol) in ethanol (50 mL) was added thiourea (760 mg, 9.98 mmol). The resulting solution was stirred for 1 h at 100° C. and then cooled down room temperature. The mixture was filtered to afford 1-(2-amino-5-methyl-1,3-thiazol-4-yl)ethan-1-one as a off-white solid (1.2 g, 65%). LCMS (ESI): [M+H]$^+$=157.0.

Step 3: 3-acetyl-7-(chloromethyl)-2-methyl-5H-[1,3]thiazolo[3,2-a]pyrimidin-5-one

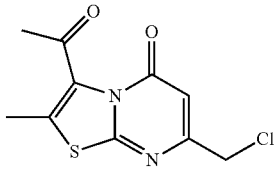 [SMILES: CC(=O)c1c(C)sc2nc(CCl)cc(=O)n12]

To a solution of 1-(2-amino-5-methyl-1,3-thiazol-4-yl)ethan-1-one (300 mg, 1.92 mmol) was added ethyl 4-chloro-3-oxobutanoate (474 mg, 2.88 mmol) and polyphosphoric acid (10 mL). The resulting solution was stirred for 1 h at 110° C. and then cooled down room temperature. The resulting solution was diluted with water (20 mL) and the pH value of the solution was adjusted to 8. The resulting solution was extracted and concentrated in vacuo. The residue was purified by chromatography with ethyl acetate/petroleum (1/1) to afford 3-acetyl-7-(chloromethyl)-2-methyl-5H-[1,3]thiazolo[3,2-a]pyrimidin-5-one as a light yellow solid (70.0 mg, 12%). LCMS (ESI): [M+H]$^+$=257.0; $^1$H NMR (300 MHz, CDCl$_3$) δ 6.46 (s, 1H), 4.42 (s, 2H), 2.52 (s, 3H), 2.39 (s, 3H).

Step 4: 3-acetyl-2-methyl-7-((3-(trifluoromethyl)-1H-pyrazol-1-yl)methyl)-5H-thiazolo[3,2-a]pyrimidin-5-one

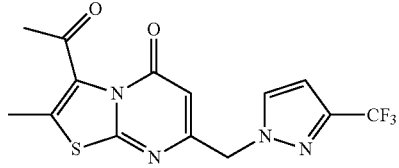 [SMILES: CC(=O)c1c(C)sc2nc(Cn3ccc(C(F)(F)F)n3)cc(=O)n12]

To a solution of 3-acetyl-7-(chloromethyl)-2-methyl-5H-[1,3]thiazolo[3,2-a]pyrimidin-5-one (200 mg, 0.78 mmol) in CH$_3$CN (25 mL) was added potassium iodide (68 mg, 0.39 mmol), potassium carbonate (220 mg, 1.59 mmol) and 3-(trifluoromethyl)-1H-pyrazole (160 mg, 1.18 mmol). The resulting solution was stirred for 12 h at 80° C. in an oil bath. The resulting mixture was quenched by water (10 mL), extracted with dichloromethane (3×20 mL), washed with brine, dried over anhydrous sodium sulfate and concentrated under vacuum. The residue was purified by chromatography with ethyl acetate/petroleum ether (1:2) to afford 3-acetyl-2-methyl-7-[[3-(trifluoromethyl)-1H-pyrazol-1-yl]methyl]-5H-[1,3]thiazolo[3,2-a]pyrimidin-5-one (195 mg, 70%) as a yellow solid. LCMS (ESI): [M+H]$^+$=357.1; $^1$H NMR (300 MHz, CDCl$_3$) δ 7.61 (m, 1H), 6.62 (m, 1H), 5.91 (s, 1H), 5.25 (s, 2H), 2.45 (s, 3H), 2.38 (s, 3H).

Step 5: 3-(1-hydroxyethyl)-2-methyl-7-((3-(trifluoromethyl)-1H-pyrazol-1-yl)methyl)-5H-thiazolo[3,2-a]pyrimidin-5-one

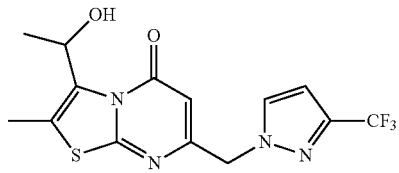 [SMILES: Cc1sc2nc(Cn3ccc(C(F)(F)F)n3)cc(=O)n2c1C(C)O]

To a solution of 3-acetyl-2-methyl-7-[[3-(trifluoromethyl)-1H-pyrazol-1-yl]methyl]-5H-[1,3]thiazolo[3,2-a]pyrimidin-5-one (30 mg, 0.08 mmol) in methanol (10 mL) was added sodium boronhydride (13 mg, 0.34 mmol). The resulting solution was stirred for 12 h at room temperature in an oil bath. The reaction was then quenched by aqueous ammonium chloride (10 ml), extracted with dichloromethane (3×20 mL), washed with brine, dried over anhydrous magnesium sulfate and concentrated under vacuum. The residue was purified by chromatography with ethyl acetate/petroleum ether (1:1) to afford 3-(1-hydroxyethyl)-2-methyl-7-[[3-(trifluoromethyl)-1H-pyrazol-1-yl]methyl]-5H-[1,3]thiazolo[3,2-a]pyrimidin-5-one (11.7 mg, 39%) as a light yellow solid. LCMS (ESI): [M+H]⁺=359.0; ¹H NMR (300 MHz, CD₃OD) δ 7.94-7.93 (m, 1H), 6.70 (m, 1H), 5.97 (s, 1H), 5.47-5.40 (m, 1H), 5.38 (m, 2H), 2.48 (s, 3H), 1.52 (m, 3H).

The following examples were prepared in a manner similar to Example 18.1

| No. | Structure/Name | LCMS (M + H) | ¹H NMR |
|---|---|---|---|
| 18.2 | 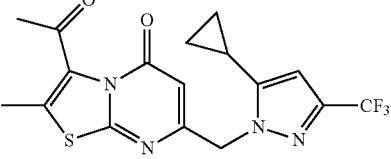<br>3-acetyl-7-((5-cyclopropyl-3-(trifluoromethyl)-1H-pyrazol-1-yl)methyl)-2-methyl-5H-thiazolo[3,2-a]pyrimidin-5-one | 397.0 | ¹H NMR (300 MHz, CD₃OD) δ 6.33 (s, 1H), 5.83 (s, 1H), 5.44 (s, 2H), 2.41 (s, 3H), 2.37 (s, 3H), 1.92 (m, 1H), 1.02 (m, 2H), 0.76 (m, 2H) |
| 18.3 | 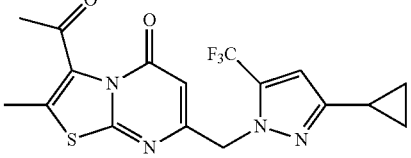<br>3-acetyl-7-((3-cyclopropyl-5-(trifluoromethyl)-1H-pyrazol-1-yl)methyl)-2-methyl-5H-thiazolo[3,2-a]pyrimidin-5-one | 397.0 | ¹HNMR (300 MHz, CD₃OD) δ 6.58 (s, 1H), 5.69 (s, 1H), 5.32 (s, 2H), 2.41 (s, 3H), 2.37 (s, 3H), 1.98 (m, 1H), 0.98 (m, 2H), 0.78 (m, 2H) |

The following compounds were prepared using methods analogous to those described above:

| No. | Structure/Name | LCMS (M + H) | ¹H NMR |
|---|---|---|---|
| 18.4 | 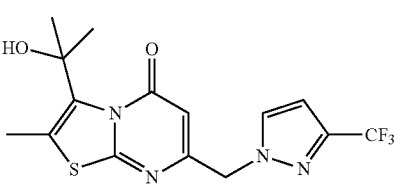 [SMILES: Cc1sc2nc(Cn3ccc(C(F)(F)F)n3)cc(=O)n2c1C(C)(C)O]<br>3-(2-hydroxypropan-2-yl)-2-methyl-7-((3-(trifluoromethyl)-1H-pyrazol-1-yl)methyl)-5H-thiazolo[3,2-a]pyrimidin-5-one | 373.10 | ¹H NMR (300 MHz, CDCl₃) δ 7.60 (m, 1H), 7.15 (m, 1H), 6.61 (m, 1H), 5.98 (s, 1H), 5.26 (s, 2H), 2.52 (s, 3H), 1.72 (s, 6H) |
| 18.5 | 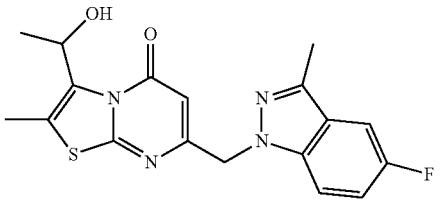 [SMILES: Cc1sc2nc(Cn3nc(C)c4cc(F)ccc43)cc(=O)n2c1C(C)O]<br>7-((5-fluoro-3-methyl-1H-indazol-1-yl)methyl)-3-(1-hydroxyethyl)-2-methyl-5H-thiazolo[3,2-a]pyrimidin-5-one | 373 | ¹H NMR (300 MHz, CDCl₃): δ 7.35-7.25 (m, 2H), 7.19-7.12 (m, 1H), 5.72 (s, 1H), 5.42 (s, 2H), 5.04 (m, 1H), 2.56 (s, 3H), 2.41 (s, 3H), 1.60 (m, 3H) |

Method 19

Example 19.1: 7-(1-(5-cyclopropyl-3-(trifluoromethyl)-1H-pyrazol-1-yl)ethyl)-3-(trans-2-(hydroxymethyl)cyclopropyl)-2-methyl-5H-thiazolo[3,2-a]pyrimidin-5-one

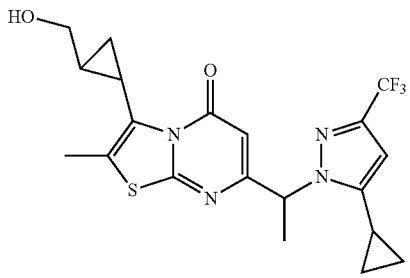 [SMILES: Cc1sc2nc(C(C)n3nc(C(F)(F)F)cc3C3CC3)cc(=O)n2c1C1CC1CO]

Step 1: 3-(trans-2-((tert-butyldimethylsilyloxy)methyl)cyclopropyl)-7-((5-cyclopropyl-3-(trifluoromethyl)-1H-pyrazol-1-yl)methyl)-2-methyl-5H-thiazolo[3,2-a]pyrimidin-5-one

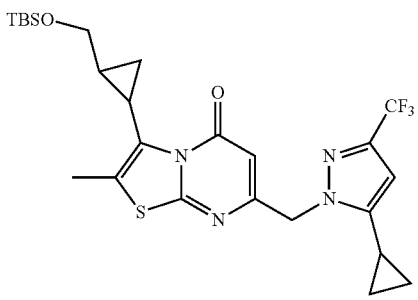 [SMILES: Cc1sc2nc(Cn3nc(C(F)(F)F)cc3C3CC3)cc(=O)n2c1C1CC1CO[Si](C)(C)C(C)(C)C]

To a solution of 7-[[5-cyclopropyl-3-(trifluoromethyl)-1H-pyrazol-1-yl]methyl]-3-[trans-2-(hydroxymethyl)cyclopropyl]-2-methyl-5H-[1,3]thiazolo[3,2-a]pyrimidin-5-one (from Example 15.11) (120 mg, 0.28 mmol) in dichloromethane (30 mL) was added tert-butyldimethylsilylchloride (177 mg, 1.18 mmol), imidazole (80 mg, 1.18 mmol) and 4-dimethylaminopyridine (5 mg, cat.). The resulting solution was stirred for overnight at 50° C. After cooling down to room temperature, the reaction mixture was concentrated under vacuum. The residue was purified by silica gel chromatography with ethyl acetate/petroleum ether (1:2) to afford 3-(2-[[(tert-butyldimethylsilyl)oxy]methyl]cyclopropyl)-7-[[5-cyclopropyl-3-(trifluoromethyl)-1H-pyrazol-1-yl]methyl]-2-methyl-5H-[1,3]thiazolo[3,2-a]pyrimidin-5-one (120 mg, 67%) as yellow oil. LCMS (ESI): [M+H]$^+$= 539.0. The crude product was used in next step without further purification.

Step 2: 3-(trans-2-((tert-butyldimethylsilyloxy)methyl)cyclopropyl)-7-(1-(5-cyclopropyl-3-(trifluoromethyl)-1H-pyrazol-1-yl)ethyl)-2-methyl-5H-thiazolo[3,2-a]pyrimidin-5-one

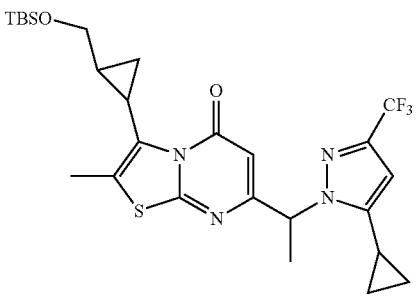 [SMILES: Cc1sc2nc(C(C)n3nc(C(F)(F)F)cc3C3CC3)cc(=O)n2c1C1CC1CO[Si](C)(C)C(C)(C)C]

To a solution of 3-(2-[[(tert-butyldimethylsilyl)oxy]methyl]cyclopropyl)-7-[[5-cyclopropyl-3-(trifluoromethyl)-1H-pyrazol-1-yl]methyl]-2-methyl-5H-[1,3]thiazolo[3,2-a]pyrimidin-5-one (120 mg, 0.22 mmol) in tetrahydrofuran (20 mL) was added n-butyllithium (1.5 mL, 85% in hexanes) and methyl iodide (158 mg, 1.11 mmol). The resulting solution was stirred overnight at room temperature. The reaction was then quenched with water (20 mL), extracted with dichloromethane (3×30 mL), washed with brine, dried over sodium sulfate and concentrated under vacuum. The residue was then purified by chromatography with ethyl acetate/petroleum ether (1:2) to afford 3-(trans-2-[[(tert-butyldimethylsilyl)oxy]methyl]cyclopropyl)-7-[1-[5-cyclopropyl-3-(trifluoromethyl)-1H-pyrazol-1-yl]ethyl]-2-methyl-5H-[1,3]thiazolo[3,2-a]pyrimidin-5-one (50 mg, 35%) as a light yellow solid. LCMS (ESI): [M+H]$^+$=553.0.

Step 3: 7-(1-(5-cyclopropyl-3-(trifluoromethyl)-1H-pyrazol-1-yl)ethyl)-3-(trans-2-(hydroxymethyl)cyclopropyl)-2-methyl-5H-thiazolo[3,2-a]pyrimidin-5-one

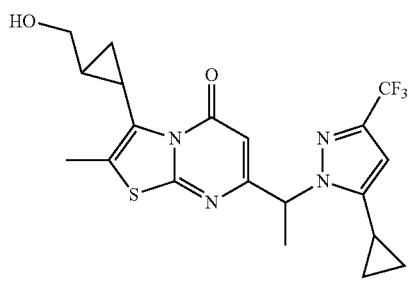 [SMILES: Cc1sc2nc(C(C)n3nc(C(F)(F)F)cc3C3CC3)cc(=O)n2c1C1CC1CO]

To a solution of 3-(trans-2-[[(tert-butyldimethylsilyl)oxy]methyl]cyclopropyl)-7-[1-[5-cyclopropyl-3-(trifluoromethyl)-1H-pyrazol-1-yl]ethyl]-2-methyl-5H-[1,3]thiazolo[3,2-a]pyrimidin-5-one (50 mg, 0.09 mmol) in ethanol (30 mL) was added 0.5% hydrogen chloride in ethanol (10 mL). The resulting solution was stirred for 2 h at room temperature. After cooling down to room temperature, the reaction mixture was concentrated under vacuum. The residue was purified by chromatography with dichloromethane/methanol (100:1) to afford 7-[1-[5-cyclopropyl-3-(trifluoromethyl)-1H-pyrazol-1-yl]ethyl]-3-[trans-2-(hydroxymethyl)cyclopropyl]-2-methyl-5H-[1,3]thiazolo[3,2-a]pyrimidin-5-one (14.3 mg, 34%) as a white solid. LCMS (ESI): [M+H]$^+$=439.0; $^1$H NMR (300 MHz, CD$_3$OD) δ 6.18 (s, 2H), 6.17 (s, 1H), 5.59-5.54 (m, 1H), 4.05-4.01 (m, 1H), 3.14-3.07 (m, 1H), 2.41 (s, 3H), 2.28-2.22 (m, 1H), 1.96-1.93 (m, 3H), 1.69-1.64 (m, 1H), 1.27-1.23 (m, 1H), 1.03-0.72 (m, 4H), 0.73-0.62 (m, 2H).

The following compound was prepared using methods analogous to those described above:

| No. | Structure/Name | LCMS (M + H) | $^1$H NMR |
|---|---|---|---|
| 19.2 | 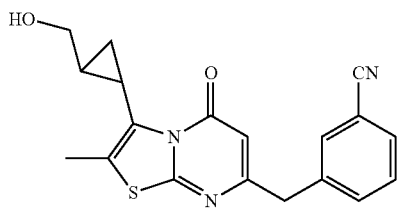<br>7-(1-(5-cyclopropyl-3-(trifluoromethyl)-1H-pyrazol-1-yl)ethyl)-3-(2-(hydroxymethyl)-1-methylcyclopropyl)-2-methyl-5H-thiazolo[3,2-a]pyrimidin-5-one | 439.0 | $^1$H NMR (300 MHz, CD$_3$OD) δ 6.18 (s, 1H), 5.73-5.70 (m, 1H), 5.60-5.57 (m, 1H), 4.03-3.96 (m, 1H), 3.42-3.35 (m, 1H), 2.41 (s, 3H), 1.98-1.92 (m, 4H), 1.71-1.63 (m, 1H), 2.52 (s, 3H), 1.45-1.40 (m, 1H), 1.06-0.92 (m, 3H), 0.73-0.65 (m, 3H) |

Method 20

Example 20.1: 3-((3-(trans-2-(hydroxymethyl)cyclopropyl)-2-methyl-5-oxo-5H-thiazolo[3,2-a]pyrimidin-7-yl)methyl)benzonitrile

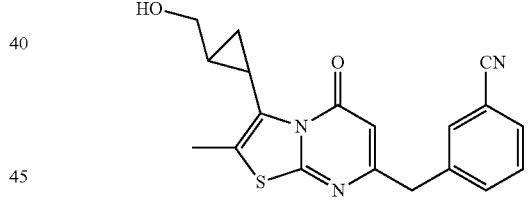

Step 1: 3-((3-bromo-2-methyl-5-oxo-5H-thiazolo[3,2-a]pyrimidin-7-yl)methyl)benzonitrile

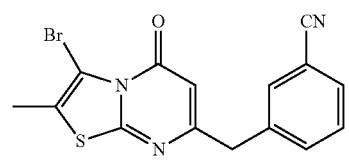

To a solution of 3-bromo-7-(chloromethyl)-2-methyl-5H-[1,3]thiazolo[3,2-a]pyrimidin-5-one (from Example 4.1, Step 6) (500 mg, 1.70 mmol) in 1,4-dioxane/H$_2$O (3/1 mL) was added tetrakis(triphenylphosphine)palladium (198 mg, 0.17 mmol), potassium phosphate (726 mg, 3.42 mmol) and (3-cyanophenyl)boronic acid (302 mg, 2.06 mmol). The resulting solution was stirred overnight at 80° C. After cooling down to room temperature, the resulting mixture was extracted with dichloromethane (3×30 mL), washed with brine (1×30 mL), dried over anhydrous sodium sulfate and concentrated in vacuo. The residue was purified by silica gel chromatography with ethyl acetate/petroleum ether (1:2) to afford 3-([3-bromo-2-methyl-5-oxo-5H-[1,3]thiazolo[3,2-a]pyrimidin-7-yl]methyl)benzonitrile (102 mg, 17%) as a brown solid. LCMS (ESI): [M+H]$^+$=360.0, 362.0; $^1$H NMR (300 MHz, CDCl$_3$) δ 7.65-7.41 (m, 4H), 6.04 (s, 1H), 3.91 (s, 2H), 2.35 (s, 3H).

Step 2: 3-((3-(trans-2-(hydroxymethyl)cyclopropyl)-2-methyl-5-oxo-5H-thiazolo[3,2-a]pyrimidin-7-yl)methyl)benzonitrile To a solution of 3-((3-bromo-2-methyl-5-oxo-5H-[1,3]thiazolo[3,2-a]pyrimidin-7-yl)methyl)benzonitrile (80 mg, 0.22 mmol) in CH$_3$CN/H$_2$O (3/1 ml) was added [1,1'-bis(diphenylphosphino)ferrocene]palladium(II) dichloride (16.7 mg, 0.02 mmol), sodium carbonate (47.2 mg, 0.45 mmol) and potassium trans-2-(hydroxymethyl)cyclopropyltrifluoroborate (from Example 4.1, Step 2) (79.3 mg, 0.45 mmol). The reaction mixture was irradiated in a microwave for 1.5 h at 120° C. The resulting mixture was extracted with dichloromethane (3×20 mL), washed with brine (10 mL), dried over sodium sulfate. After concentration under vacuum, the residue was purified on a silica gel column eluted with dichloromethane/methanol (50:1) to afford 3-([3-[trans-2-(hydroxymethyl)cyclopropyl]-2-methyl-5-oxo-5H-[1,3]thiazolo[3,2-a]pyrimidin-7-yl]methyl)benzonitrile (16.6 mg, 21%) as a white solid. LCMS (ESI): [M+H]$^+$=352.0; $^1$HNMR (300 MHz, CDCl$_3$) δ 7.62-7.58 (m, 3H), 7.50-7.44 (m, 1H), 6.02 (s, 1H), 4.04-4.00 (m, 1H), 3.99 (s, 2H), 3.20-3.13 (m, 1H), 2.42 (s, 3H), 2.26-2.25 (m, 1H), 1.28-1.25 (m, 1H), 1.05-1.00 (m, 2H).

Example 20.2: 3-((6-fluoro-3-(2-(hydroxymethyl)cyclopropyl)-2-methyl-5-oxo-5H-thiazolo[3,2-a]pyrimidin-7-yl)methyl)benzonitrile

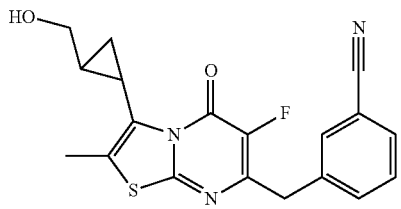 [SMILES: Cc1sc2nc(Cc3cccc(C#N)c3)c(F)c(=O)n2c1C1CC1CO]

Step 1: 3-((3-bromo-6-fluoro-2-methyl-5-oxo-5H-thiazolo[3,2-a]pyrimidin-7-yl)methyl)benzonitrile

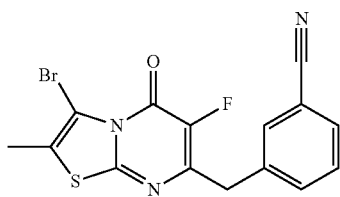 [SMILES: Cc1sc2nc(Cc3cccc(C#N)c3)c(F)c(=O)n2c1Br]

To a solution of 3-bromo-7-(chloromethyl)-6-fluoro-2-methyl-5H-[1,3]thiazolo[3,2-a]pyrimidin-5-one (from Example 4.29, Step 1) (130 mg, 0.42 mmol) in 1,4-dioxane/H₂O (3/1, 4 mL) added tetrakis(triphenylphosphine)palladium (48 mg, 0.04 mmol), potassium phosphate (179 mg, 0.84 mmol), and (3-cyanophenyl)boronic acid (74 mg, 0.50 mmol). The resulting solution was stirred overnight at 80° C., then the resulting mixture was concentrated under vacuum and the residue was purified by chromatography with ethyl acetate/petroleum ether (1:3) to afford 3-([3-bromo-6-fluoro-2-methyl-5-oxo-5H-[1,3]thiazolo[3,2-a]pyrimidin-7-yl]methyl)benzonitrile (36 mg, 23%) as a light yellow solid. LCMS (ESI): $[M+H]^+=377.9$.

Step 2: 3-((6-fluoro-3-(trans-2-(hydroxymethyl)cyclopropyl)-2-methyl-5-oxo-5H-thiazolo[3,2-a]pyrimidin-7-yl)methyl)benzonitrile

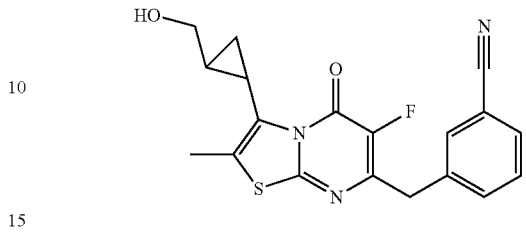

To a solution of 3-([3-bromo-2-methyl-5-oxo-5H-[1,3]thiazolo[3,2-a]pyrimidin-7-yl]methyl)-2-fluorobenzonitrile (100 mg, 0.26 mmol) in CH₃CN/H₂O (3/1 mL) under inert nitrogen atmosphere was added [1,1'-bis(diphenylphosphino)ferrocene]palladium(II) dichloride (20 mg, 0.03 mmol), sodium carbonate (56.2 mg, 0.53 mmol), and potassium trans-2-(hydroxymethyl)cyclopropyltrifluoroborate (from Example 4.1, Step 2) (94.4 mg, 0.53 mmol). The resulting solution was stirred for 90 min at 120° C. The mixture was concentrated under vacuum, and the residue was purified by chromatography with dichloromethane/methanol (50:1) to afford 2-fluoro-3-([3-[trans2-(hydroxymethyl)cyclopropyl]-2-methyl-5-oxo-5H-[1,3]thiazolo[3,2-a]pyrimidin-7-yl]methyl)benzonitrile as a off-white solid (9.9 mg, 10%). LCMS (ESI): $[M+H]^+=370.0$; ¹H NMR (300 MHz, CDCl₃) δ 7.57 (s, 1H), 7.55-7.52 (m, 2H), 7.41-7.40 (m, 1H), 4.06-3.96 (m, 3H), 3.22-3.17 (m, 1H), 2.37 (s, 3H), 2.30-2.10 (m, 1H), 1.34-1.25 (m, 1H), 1.06-0.98 (m, 2H).

The following examples were prepared in a manner similar to Example 20.1 and 20.2:

| No. | Structure/Name | LCMS (M + H) | ¹H NMR |
|---|---|---|---|
| 20.3 | ![structure] 2-fluoro-3-((3-(trans-2-(hydroxymethyl)cyclopropyl)-2-methyl-5-oxo-5H-thiazolo[3,2-a]pyrimidin-7-yl)methyl)benzonitrile | 370.0 | ¹H NMR (300 MHz, CDCl₃) δ 7.64-7.57 (m, 2H), 7.29-7.24 (m, 1H), 6.07 (s, 1H), 4.09-4.04 (m, 1H), 3.99 (s, 2H), 3.18-3.11 (m, 1H), 2.41 (s, 3H), 2.32-2.26 (m, 1H), 1.29-1.24 (m, 1H), 1.06-0.99 (m, 2H) |
| 20.4 | ![structure] 3-(trans-2-(hydroxymethyl)cyclopropyl)-7-(isoquinolin-4-ylmethyl)-2-methyl-5H-thiazolo[3,2-a]pyrimidin-5-one | 378.1 | ¹H NMR (300 MHz, CDCl₃) δ 9.28 (br, 1H), 8.48 (br, 1H), 8.11-8.09 (m, 1H), 8.02-7.99 (m, 1H), 7.86-7.81 (m, 1H), 7.75-7.70 (m, 1H), 5.99 (s, 1H), 4.36 (s, 2H), 4.08-4.00 (m, 2H), 3.09-3.02 (m, 1H), 2.36 (s, 3H), 2.26-2.21 (m, 1H), 1.28-1.20 (m, 1H), 1.03-0.97 (m, 2H) |

-continued

| No. | Structure/Name | LCMS (M + H) | ¹H NMR |
|---|---|---|---|
| 20.5 | 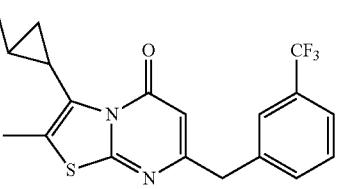<br>3-(trans-2-(hydroxymethyl)cyclopropyl)-2-methyl-7-(3-(trifluoromethyl)benzyl)-5H-thiazolo[3,2-a]pyrimidin-5-one | 395.0 | ¹H NMR (300 MHz, CDCl₃) δ 7.53-7.41 (m, 4H), 6.02 (s, 1H), 4.14-4.02 (m, 1H), 3.92 (s, 2H), 3.13-3.05 (m, 1H), 2.39 (s, 3H), 2.37-2.26 (m, 1H), 1.30-1.20 (m, 1H), 1.04-0.95 (m, 2H) |

The following compounds were prepared using methods analogous to those described above:

| No. | Structure/Name | LCMS (M + H) | ¹H NMR |
|---|---|---|---|
| 20.6 | 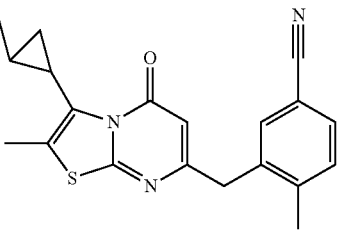<br>3-((3-(trans-2-(hydroxymethyl)cyclopropyl)-2-methyl-5-oxo-5H-thiazolo[3,2-a]pyrimidin-7-yl)methyl)-4-methylbenzonitrile | 366.00 | ¹H NMR (300 MHz, CD₃OD) δ 7.54 (m, 2H), 7.36 (m, 1H), 5.94 (s, 1H), 3.97 (s, 2H), 3.59 (m, 2H), 2.42 (s, 3H), 2.41 (s, 3H), 2.15 (m, 1H), 1.32 (m, 1H), 1.01 (m, 2H) |
| 20.7 | 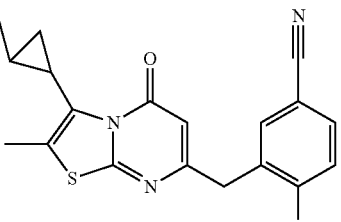<br>4-fluoro-3-((3-(trans-2-(hydroxymethyl)cyclopropyl)-2-methyl-5-oxo-5H-thiazolo[3,2-a]pyrimidin-7-yl)methyl)benzonitrile | 379.95 | ¹H NMR (300 MHz, CDCl₃) δ 7.62-7.57 (m, 2H), 7.19-7.15 (m, 1H), 6.05 (s, 1H), 4.17-4.05 (m, 2H), 3.90 (s, 2H), 3.12-3.07 (m, 1H), 2.38 (s, 3H), 2.28-2.26 (m, 1H), 1.30-1.24 (m, 1H), 1.04-0.98 (m, 2H) |
| 20.8 | 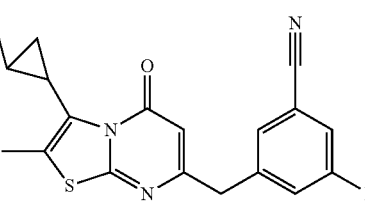<br>3-fluoro-5-((3-(trans-2-(hydroxymethyl)cyclopropyl)-2-methyl-5-oxo-5H-thiazolo[3,2-a]pyrimidin-7-yl)methyl)benzonitrile | 370.10 | ¹H NMR (300 MHz, CDCl₃) δ 7.42 (s, 1H), 7.30-7.28 (m, 2H), 6.10 (s, 1H), 4.10-4.05 (m, 1H), 3.91 (s, 2H), 3.18-3.11 (m, 1H), 2.41 (s, 3H), 2.35-2.25 (m, 1H), 1.35-1.25 (m, 1H), 1.07-1.00 (m, 2H) |

-continued

| No. | Structure/Name | LCMS (M + H) | ¹H NMR |
|---|---|---|---|
| 20.9 | 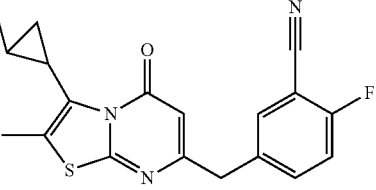<br>2-fluoro-5-((3-(trans-2-(hydroxymethyl)cyclopropyl)-2-methyl-5-oxo-5H-thiazolo[3,2-a]pyrimidin-7-yl)methyl)benzonitrile | 370.0 | ¹H NMR (300 MHz, CDCl₃) δ 7.59-7.48 (m, 2H), 7.20-7.14 (m, 1H), 6.06 (s, 1H), 4.14-4.03 (m, 1H), 3.85 (s, 2H), 3.10 (m, 1H), 2.39 (s, 3H), 2.31-2.24 (m, 1H), 1.26-1.23 (m, 1H), 1.06-1.01 (m, 2H) |
| 20.10 | 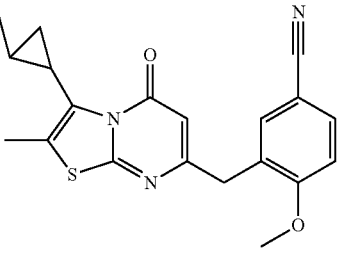<br>3-[[3-[trans-2-(hydroxymethyl)cyclopropyl]-2-methyl-5-oxo-thiazolo[3,2-a]pyrimidin-7-yl]methyl]-4-methoxy-benzonitrile | 382.0 | ¹H NMR (400 MHz, CDCl₃) δ 7.60-7.58 (m, 1H), 7.50 (s, 1H), 6.94-6.92 (m, 1H), 5.96 (s, 1H), 4.06-4.03 (m, 1H), 3.89-3.85 (m, 5H), 3.13-3.07 (m, 1H), 2.38 (s, 3H), 2.29-2.26 (m, 1H), 1.28-1.25 (m, 2H), 1.05-0.88 (m, 2H) |
| 20.11 | 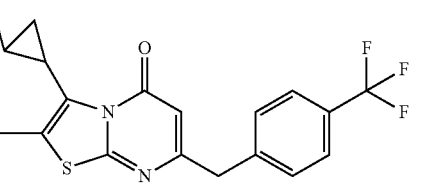<br>3-(2-(hydroxymethyl)cyclopropyl)-2-methyl-7-(4-(trifluoromethyl)benzyl)-5H-thiazolo[3,2-a]pyrimidin-5-one | 395.0 | ¹H NMR (300 MHz, CDCl₃) δ 7.60-7.59 (m, 2H), 7.40-7.37 (m, 2H), 6.04 (s, 1H), 4.21-4.18 (m, 1H), 4.07-4.01 (m, 1H), 3.91 (s, 2H), 3.11-3.04 (m, 1H), 2.39 (s, 3H), 2.36-2.24 (m, 1H), 1.25-1.19 (m, 1H), 1.04-0.99 (m, 2H) |
| 20.12 | 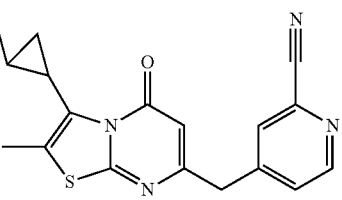<br>4-((3-(trans-2-(hydroxymethyl)cyclopropyl)-2-methyl-5-oxo-5H-thiazolo[3,2-a]pyrimidin-7-yl)methyl)picolinonitrile | 352.9 | ¹H NMR (300 MHz, CDCl₃) δ 8.62-8.61 (m, 1H), 7.86 (m, 1H), 7.64-7.62 (m, 1H), 6.21 (s, 1H), 3.99 (s, 2H), 3.63-3.57 (m, 2H), 2.41 (s, 3H), 2.20-2.11 (m, 1H), 1.40-1.28 (m, 1H), 1.05-0.99 (m, 2H) |

| No. | Structure/Name | LCMS (M + H) | ¹H NMR |
|---|---|---|---|
| 20.13 | 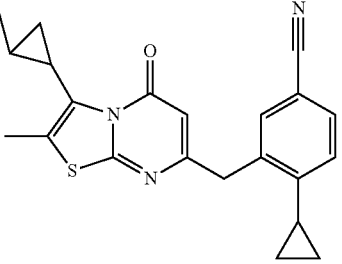

4-cyclopropyl-3-((3-(trans-2-(hydroxymethyl)cyclopropyl)-2-methyl-5-oxo-5H-thiazolo[3,2-a]pyrimidin-7-yl)methyl)benzonitrile | 392.0 | ¹H NMR (300 MHz, CDCl₃) δ 7.47-7.45 (m, 1H), 7.40-7.22 (m, 2H), 5.90 (s, 1H), 4.19 (s, 2H), 4.06-3.98 (m, 1H), 3.14-3.07 (m, 1H), 2.45 (s, 3H), 2.31-2.26 (m, 1H), 1.95-1.86 (m, 1H), 1.30-1.26 (m, 1H), 1.04-0.99 (m, 4H), 0.69-0.68 (m, 2H) |

Method 21

Example 21.1: 7-(3-cyanobenzyl)-N,2-dimethyl-5-oxo-5H-thiazolo[3,2-a]pyrimidine-3-carboxamide

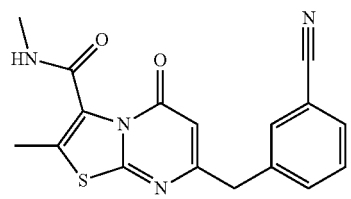 [SMILES: CNC(=O)c1c(C)sc2nc(Cc3cccc(C#N)c3)cc(=O)n12]

Step 1: 7-(3-cyanobenzyl)-N,2-dimethyl-5-oxo-5H-thiazolo[3,2-a]pyrimidine-3-carboxamide

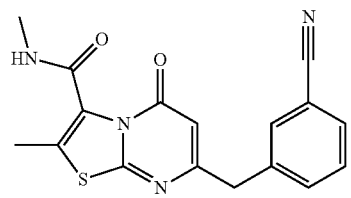 [SMILES: CNC(=O)c1c(C)sc2nc(Cc3cccc(C#N)c3)cc(=O)n12]

7-(Chloromethyl)-N,2-dimethyl-5-oxo-5H-[1,3]thiazolo[3,2-a]pyrimidine-3-carboxamide (from Example 16.1, Step 5) (50 mg, 0.18 mmol), (3-cyanophenyl)boronic acid (56 mg, 0.38 mmol), tetrakis(triphenylphosphine)palladium (20 mg, 0.019 mmol), potassium phosphate (80 mg, 0.38 mmol), 1,4-dioxane (1.5 mL) and water (0.5 mL) were placed in a 10-mL sealed tube. The resulting solution was stirred for 2 h at 80° C. in an oil bath. After cooling down to room temperature, the resulting mixture was extracted with CH₂Cl₂ (20 mL), washed with brine, dried over anhydrous sodium sulfate and concentrated in vacuo. The residue was purified by chromatography with dichloromethane/methanol (20:1) to afford 7-[(3-cyanophenyl)methyl]-N,2-dimethyl-5-oxo-5H-[1,3]thiazolo[3,2-a]pyrimidine-3-carboxamide (29.1 mg, 47%) as a white solid. LCMS (ESI): [M+H]⁺= 339.0; ¹H NMR (300 MHz, CDCl₃) δ 7.61-7.40 (m, 4H), 6.08 (s, 1H), 5.96 (br, 1H), 3.90 (s, 2H), 3.05 (m, 3H), 2.41 (s, 3H).

The following examples were prepared in a manner similar to Example 21.1:

| No. | Structure/Name | LCMS (M + H) | ¹H NMR |
|---|---|---|---|
| 21.2 | 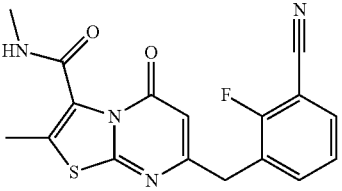 [SMILES: CNC(=O)c1c(C)sc2nc(Cc3cccc(C#N)c3F)cc(=O)n12]

7-(3-cyano-2-fluorobenzyl)-N,2-dimethyl-5-oxo-5H-thiazolo[3,2-a]pyrimidine-3-carboxamide | 356.9 | ¹H NMR (300 MHz, DMSO) δ 8.32 (m, 1H), 7.84 (m, 2H), 7.38 (m, 1H), 6.13 (s, 1H), 4.00 (s, 2H), 2.72 (s, 3H), 2.28 (s, 3H) |

| No. | Structure/Name | LCMS (M + H) | ¹H NMR |
|---|---|---|---|
| 21.3 | 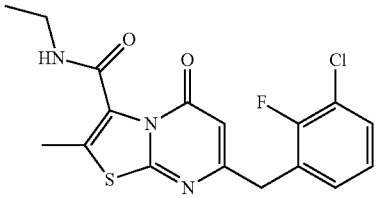 [SMILES: CCNC(=O)c1c(C)sc2nc(Cc3cccc(Cl)c3F)cc(=O)n12]<br>7-(3-chloro-2-fluorobenzyl)-N-ethyl-2-methyl-5-oxo-5H-thiazolo[3,2-a]pyrimidine-3-carboxamide | 380.10 | ¹H NMR (300 MHz, CDCl₃) δ 7.34-7.29 (m, 1H), 7.17-7.12 (m, 1H), 7.07-7.02 (m, 1H), 6.04 (s, 1H), 5.88 (br, 1H), 3.94 (s, 2H), 3.56-3.47 (m, 2H), 2.40 (s, 3H), 1.30-1.25 (m, 3H) |
| 21.4 | 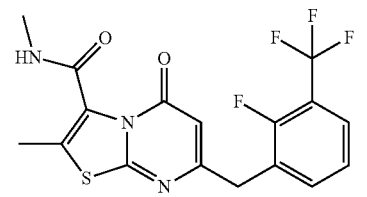 [SMILES: CNC(=O)c1c(C)sc2nc(Cc3cccc(C(F)(F)F)c3F)cc(=O)n12]<br>N-ethyl-7-(2-fluoro-3-(trifluoromethyl)benzyl)-2-methyl-5-oxo-5H-thiazolo[3,2-a]pyrimidine-3-carboxamide | 400.0 | ¹H NMR (300 MHz, CD₃OD) δ 7.63 (m, 2H), 7.32 (m, 1H), 6.14 (s, 1H), 4.05 (s, 2H), 3.92 (s, 3H), 2.38 (s, 3H) |
| 21.5 | 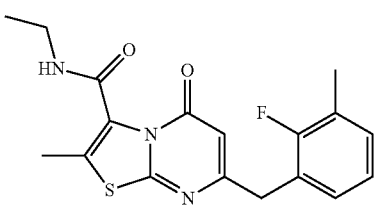 [SMILES: CCNC(=O)c1c(C)sc2nc(Cc3cccc(C)c3F)cc(=O)n12]<br>N-ethyl-7-(2-fluoro-3-methylbenzyl)-2-methyl-5-oxo-5H-thiazolo[3,2-a]pyrimidine-3-carboxamide | 360.0 | ¹H NMR (300 MHz, CDCl₃) δ 7.30-7.26 (m, 1H), 7.12-6.96 (m, 3H), 6.03 (s, 1H), 6.00 (s, 1H), 3.91 (s, 2H), 3.55-3.46 (m, 2H), 2.37 (s, 3H), 2.26 (s, 3H), 1.29-1.24 (m, 3H) |
| 21.6 | 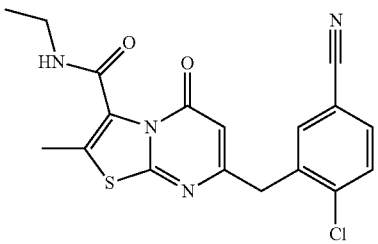 [SMILES: CCNC(=O)c1c(C)sc2nc(Cc3cc(C#N)ccc3Cl)cc(=O)n12]<br>7-(2-chloro-5-cyanobenzyl)-N-ethyl-2-methyl-5-oxo-5H-thiazolo[3,2-a]pyrimidine-3-carboxamide | 386.7 | ¹H NMR (300 MHz, CDCl₃) δ 7.59 (s, 1H), 7.50 (s, 2H), 6.05 (s, 1H), 5.82 (m, 1H), 4.27 (s, 2H), 3.55-3.51 (m, 3H), 2.44 (s, 3H), 1.30-1.26 (m, 3H) |
| 21.7 | 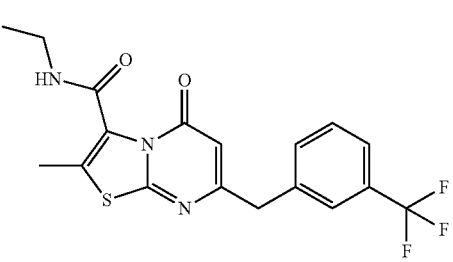 [SMILES: CCNC(=O)c1c(C)sc2nc(Cc3cccc(C(F)(F)F)c3)cc(=O)n12]<br>N-ethyl-2-methyl-5-oxo-7-(3-(trifluoromethyl)benzyl)-5H-thiazolo[3,2-a]pyrimidine-3-carboxamide | 396.0 | ¹H NMR (300 MHz, CDCl₃) δ 7.43-7.61 (m, 4H), 6.06 (s, 1H), 5.81 (br, 1H), 3.93 (s, 2H), 3.48-3.57 (m, 2H), 2.42 (s, 3H), 1.28 (m, 3H) |

| No. | Structure/Name | LCMS (M + H) | ¹H NMR |
|---|---|---|---|
| 21.8 | 7-(3-cyanobenzyl)-N-ethyl-2-methyl-5-oxo-5H-thiazolo[3,2-a]pyrimidine-3-carboxamide | 353.0 | ¹HNMR (300 MHz, CDCl₃) δ 7.56-7.40 (m, 4H), 6.08 (s, 1H), 5.83 (s, 1H), 3.90 (s, 2H), 3.53 (m, 2H), 2.42 (s, 3H), 1.28 (m, 3H) |
| 21.9 | 7-(3-cyano-2-fluorobenzyl)-2-cyclopropyl-N-ethyl-5-oxo-5H-thiazolo[3,2-a]pyrimidine-3-carboxamide | 397.0 | ¹H NMR (300 MHz, CDCl₃) δ 7.56-7.49 (m, 2H), 6.06 (s, 1H), 5.85 (s, 1H), 3.93 (s, 2H), 3.58-3.45 (m, 2H), 2.18-2.09 (m, 1H), 1.18-1.15 (m, 3H), 1.13-1.11 (m, 2H), 0.85-0.79 (m, 2H) |
| 21.10 | 7-(3-cyano-5-fluorobenzyl)-N-ethyl-2-methyl-5-oxo-5H-thiazolo[3,2-a]pyrimidine-3-carboxamide | 371.0 | ¹H NMR (300 MHz, CDCl₃) δ 7.37 (s, 1H), 7.23-7.22 (m, 2H), 6.10 (s, 1H), 5.82-5.73 (m, 1H), 3.89 (s, 2H), 3.58-3.50 (m, 2H), 2.43 (s, 3H), 1.31-1.26 (m, 3H) |
| 21.11 | 7-(3-cyanobenzyl)-N-ethyl-2-methyl-5-oxo-5H-thiazolo[3,2-a]pyrimidine-3-carboxamide | 339.0 | ¹H NMR (300 MHz, CD₃OD) δ 7.36-7.29 (m, 1H), 7.13-6.94 (m, 3H), 6.15 (s, 1H), 3.93 (s, 2H), 3.41 (m, 2H), 2.40 (s, 3H), 1.24 (m, 3H) |
| 21.12 | N-ethyl-7-(2-fluoro-3-(trifluoromethyl)benzyl)-2-methyl-5-oxo-5H-thiazolo[3,2-a]pyrimidine-3-carboxamide | 414.0 | ¹H NMR (300 MHz, CDCl₃) δ 7.53 (m, 2H), 7.23 (m, 1H), 6.05 (s, 1H), 5.88 (s, 1H), 3.96 (s, 2H), 3.52 (m, 2H), 2.40 (s, 3H), 1.27 (m, 3H) |

-continued

| No. | Structure/Name | LCMS (M + H) | ¹H NMR |
|---|---|---|---|
| 21.13 | 7-(3-cyano-2-fluorobenzyl)-N-ethyl-2-methyl-5-oxo-5H-thiazolo[3,2-a]pyrimidine-3-carboxamide | 371.0 | ¹H NMR (300 MHz, CDCl$_3$) δ 7.61-7.50 (m, 2H), 7.26-7.20 (m, 1H), 6.07 (s, 1H), 5.85 (s, 1H), 3.95 (s, 2H), 3.57-3.48 (m, 2H), 2.42 (s, 3H), 1.28 (m, 3H) |
| 21.14 | 7-[(3-chloro-2-fluoro-phenyl)methyl]-N,2-dimethyl-5-oxo-thiazolo[3,2-a]pyrimidine-3-carboxamide | 366.1 | ¹H NMR (400 MHz, DMSO-d$_6$) δ 8.30 (q, J = 4.6 Hz, 1H), 7.53-7.45 (m, 1H), 7.39-7.31 (m, 1H), 7.24-7.16 (m, 1H), 6.08 (s, 1H), 2.73 (dd, J = 4.7, 0.9 Hz, 3H), 2.29 (d, J = 0.9 Hz, 3H). |
| 21.15 | N,2-dimethyl-5-oxo-7-[[3-(trifluoromethyl)phenyl]methyl]thiazolo[3,2-a]pyrimidine-3-carboxamide | 382.1 | ¹H NMR (400 MHz, DMSO-d$_6$) δ 8.29 (d, J = 4.8 Hz, 1H), 7.68 (s, 1H), 7.65-7.52 (m, 3H), 6.19 (s, 1H), 3.98 (s, 2H), 2.73 (d, J = 4.6 Hz, 3H), 2.29 (s, 3H). |
| 21.16 | 7-[(3-chlorophenyl)methyl]-N,2-dimethyl-5-oxo-thiazolo[3,2-a]pyrimidine-3-carboxamide | 348.1 | ¹H NMR (400 MHz, DMSO-d$_6$) δ 8.29 (q, J = 4.6 Hz, 1H), 7.37 (t, J = 1.9 Hz, 1H), 7.34 (d, J = 7.4 Hz, 1H), 7.28 (ddt, J = 11.5, 7.4, 1.6 Hz, 2H), 6.16 (s, 1H), 3.88 (s, 2H), 2.73 (d, J = 4.7 Hz, 3H), 2.29 (s, 3H). |
| 21.17 | 7-[[2-cyclopropyl-5-(trifluoromethyl)phenyl]methyl]-N,2-dimethyl-5-oxo-thiazolo[3,2-a]pyrimidine-3-carboxamide | 422.1 | ¹H NMR (400 MHz, DMSO-d$_6$) δ 8.37-8.29 (m, 1H), 7.59 (d, J = 2.0 Hz, 1H), 7.56-7.49 (m, 1H), 7.17 (d, J = 8.1 Hz, 1H), 5.99 (d, J = 0.7 Hz, 1H), 4.18 (s, 2H), 2.73 (d, J = 4.7 Hz, 3H), 2.29 (s, 3H), 2.11-2.03 (m, 1H), 1.02-0.90 (m, 2H), 0.76-0.64 (m, 2H). |

Example 21.18: N-ethyl-2-methyl-5-oxo-7-((6-(trifluoromethyl)pyridine-2-yl)methyl)-5H-thiazolo[3,2-a]pyrimidine-3-carboxamide

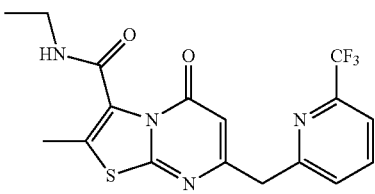 [SMILES: CCNC(=O)c1c(C)sc2nc(Cc3cccc(C(F)(F)F)n3)cc(=O)n12]

Step 1: Bis(pinacolato)diboron

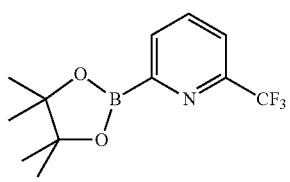 [SMILES: CC1(C)OB(c2cccc(C(F)(F)F)n2)OC1(C)C]

To a solution of 2-bromo-6-(trifluoromethyl)pyridine (500 mg, 2.21 mmol) in 1,4-dioxane (10 mL) under nitrogen, was added potassium acetate (862 mg, 8.78 mmol), [1,1′-bis(diphenylphosphino)ferrocene]palladium(II) dichloride (330 mg, 0.45 mmol), 4,4,5,5-tetramethyl-2-(tetramethyl-1,3,2-dioxaborolan-2-yl)-1,3,2-dioxaborolane (609 mg, 2.40 mmol). The resulting solution was stirred for 12 h at 90° C. The mixture was filtered to remove solids and concentrated under vacuum to afford [6-(trifluoromethyl)yridine-2-yl]boronic acid (500 mg, crude) as a black solid. The crude product was used in the next step without further purification. LCMS (ESI): [M+H]⁺=191.9.

Step 2: N-ethyl-2-methyl-5-oxo-7-((6-(trifluoromethyl)yridine-2-yl)methyl)-5H-thiazolo[3,2-a]pyrimidine-3-carboxamide

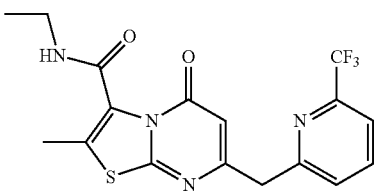 [SMILES: CCNC(=O)c1c(C)sc2nc(Cc3cccc(C(F)(F)F)n3)cc(=O)n12]

To a solution of 7-(chloromethyl)-N-ethyl-2-methyl-5-oxo-5H-[1,3]thiazolo[3,2-a]pyrimidine-3-carboxamide (prepared in a similar manner to Example 16.1, Step 5) (50 mg, 0.17 mmol) in 1,4-dioxane (2 mL) under nitrogen was added sodium carbonate (36 mg, 0.34 mmol), [6-(trifluoromethyl) yridine-2-yl]boronic acid (50 mg, 0.26 mmol), [1,1′-bis(diphenylphosphino)ferrocene]palladium(II) dichloride (13 mg, 0.02 mmol, and water (0.2 mL). The reaction mixture was irradiated with microwave radiation for 20 min at 120° C. The resulting solution was then extracted with ethyl acetate (3×20 mL), washed with brine, dried over anhydrous sodium sulfate, and concentrated under vacuum. The residue was purified by chromatography with dichloromethane/methanol (20:1) to afford N-ethyl-2-methyl-5-oxo-7-[[6-(trifluoromethyl) yridine-2-yl]methyl]-5H-[1,3]thiazolo[3,2-a]pyrimidine-3-carboxamide (22.8 mg, 33%) as a yellow solid. LCMS (ESI): [M+H]⁺=397.1; ¹H NMR (400 MHz, CDCl₃) δ 7.81 (m, 1H), 7.60 (m, 1H), 7.53 (m, 1H), 6.26 (s, 1H), 5.89 (s, 1H), 4.15 (s, 2H), 3.51 (m, 2H), 2.41 (s, 3H), 1.28 (m, 3H).

Example 21.19: N-ethyl-7-(2-ethyl-4,5-difluorobenzyl)-2-methyl-5-oxo-5H-thiazolo[3,2-a]pyrimidine-3-carboxamide

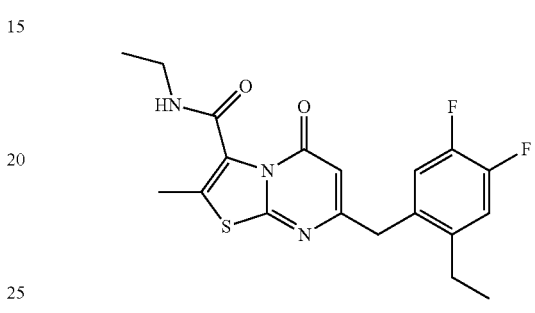

Step 1: 1-(benzyloxy)-2-bromo-4,5-difluorobenzene

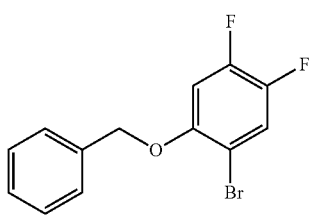 [SMILES: Fc1cc(Br)c(OCc2ccccc2)cc1F]

To a mixture of 2-bromo-4,5-difluorophenol (500 mg, 2.39 mmol, 1.00 equiv) and potassium carbonate (800 mg, 5.80 mmol) in CH₃CN (10 mL) was added (bromomethyl)benzene (610 mg, 3.57 mmol). The resulting solution was stirred for 3 h at 80° C. in an oil bath. After filtration to remove solids and concentration, the residue was purified by chromatography with ethyl acetate/petroleum ether (1:30) to afford 1-(benzyloxy)-2-bromo-4,5-difluorobenzene (600 mg, 84%) as colorless oil. ¹H NMR (300 MHz, CDCl₃) δ 7.46-7.32 (m, 5H), 6.82-6.76 (m, 1H), 5.10 (s, 2H).

Step 2: 1-(benzyloxy)-4,5-difluoro-2-vinylbenzene

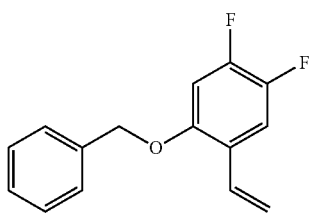 [SMILES: C=Cc1cc(F)c(F)cc1OCc1ccccc1]

1-(Benzyloxy)-2-bromo-4,5-difluorobenzene (560 mg, 1.87 mmol), tetrakis(triphenylphosphine)palladium (200 mg, 0.19 mmol), potassium phosphate (800 mg, 3.78 mmol), 1,4-dioxane (10 mL), water (1 mL) and 2-ethenyl-4,4,5,5-tetramethyl-1,3,2-dioxaborolane (580 mg, 3.77 mmol) were placed in a 30-mL sealed tube. The reaction mixture was stirred for 5 h at 80° C. in an oil bath. After filtration to remove solids and concentration, the residue was purified by chromatography with ethyl acetate/petroleum ether (1:10) to afford 1-(benzyloxy)-2-ethenyl-4,5-difluorobenzene (350 mg, 76%) as light yellow oil. $^1$H NMR (300 MHz, CDCl$_3$) δ 7.69-7.29 (m, 6H), 7.07-6.95 (m, 1H), 6.81-6.71 (m, 1H), 5.69-5.63 (m, 1H), 5.29-5.25 (m, 1H), 5.04 (s, 2H).

Step 3: 2-ethyl-4,5-difluorophenol

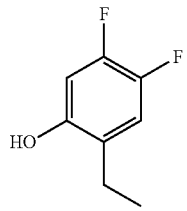

To a mixture of 1-(benzyloxy)-2-ethenyl-4,5-difluorobenzene (350 mg, 1.42 mmol) in methanol (10 mL) was added palladium on carbon (20 mg). The resulting reaction was stirred overnight at room temperature under hydrogen atmosphere (1 atm). After filtration to remove catalyst, the filtrate was concentrated under vacuum to afford 2-ethyl-4,5-difluorophenol (200 mg, 89%) as light yellow oil. The crude product was used in the next step without further purification.

Step 4: 2-ethyl-4,5-difluorophenyl trifluoromethanesulfonate

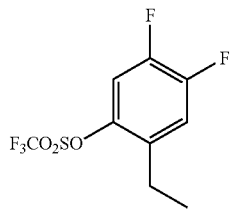

To a mixture of 2-ethyl-4,5-difluorophenol (200 mg, 1.26 mmol) and triethylamine (260 mg, 2.58 mmol) in dichloromethane (10 mL) was added trifluoroacetic anhydride (680 mg, 2.42 mmol) dropwise with stirring at 0° C. The resulting solution was stirred for 30 min at 0° C. The reaction was then quenched by the addition of water, extracted with dichloromethane (10 mL×2), washed with brine, dried over anhydrous sodium sulfate and concentrated in vacuo to afford 2-ethyl-4,5-difluorophenyl trifluoromethanesulfonate (180 mg, 50%) as a light yellow oil. The crude product was used in next step without further purification.

Step 5: 2-(2-ethyl-4,5-difluorophenyl)-4,4,5,5-tetramethyl-1,3,2-dioxaborolane

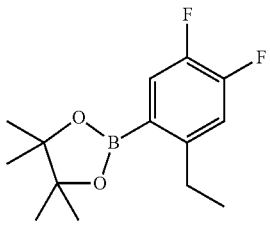 [SMILES: CCc1cc(F)c(F)cc1B1OC(C)(C)C(C)(C)O1]

To a mixture of 2-ethyl-4,5-difluorophenyl trifluoromethanesulfonate (180 mg, 0.62 mmol), [1,1'-bis(diphenylphosphino)ferrocene]palladium(II) dichloride (50 mg, 0.07 mmol), potassium acetate (120 mg, 1.23 mmol) in 1,4-dioxane (5 mL) was added 4,4,5,5-tetramethyl-2-(tetramethyl-1,3,2-dioxaborolan-2-yl)-1,3,2-dioxaborolane (240 mg, 0.93 mmol). The resulting mixture was stirred overnight at 90° C. in an oil bath under nitrogen atmosphere. After filtration to remove solids and concentration, the residue was purified by chromatography with ethyl acetate/petroleum ether (1:10) to afford 2-(2-ethyl-4,5-difluorophenyl)-4,4,5,5-tetramethyl-1,3,2-dioxaborolane (140 mg, 84%) as a light yellow oil. The crude product was used in next step without further purification.

Step 6: N-ethyl-7-(2-ethyl-4,5-difluorobenzyl)-2-methyl-5-oxo-5H-thiazolo[3,2-a]pyrimidine-3-carboxamide

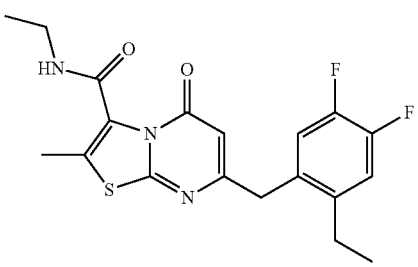 [SMILES: CCNC(=O)c1c(C)sc2nc(Cc3cc(F)c(F)cc3CC)cc(=O)n12]

7-(Chloromethyl)-N-ethyl-2-methyl-5-oxo-5H-[1,3]thiazolo[3,2-a]pyrimidine-3-carboxamide (prepared in a manner similar to Example 16.1, Step 5) (100 mg, 0.35 mmol, 1.00 equiv), 2-(2-ethyl-4,5-difluorophenyl)-4,4,5,5-tetramethyl-1,3,2-dioxaborolane (140 mg, 0.52 mmol, 1.50 equiv), [1,1'-bis(diphenylphosphino)ferrocene]palladium(II) dichloride (30 mg, 0.10 equiv), sodium carbonate (75 mg, 2.00 equiv), 1,4-dioxane (3 mL) and water (0.3 mL) were placed in a 10 mL sealed tube. The reaction mixture was irradiated with microwave radiation for 30 min at 120° C. The resulting solution was diluted with 30 mL of dichloromethane, washed with 2×10 mL of brine, dried over sodium sulfate and concentrated in vacuo. The residue was purified by silica gel chromatography with dichloromethane/methanol (40:1) to afford N-ethyl-7-[(2-ethyl-4,5-difluorophenyl)methyl]-2-methyl-5-oxo-5H-[1,3]thiazolo[3,2-a]pyrimidine-3-carboxamide (17.9 mg, 13%) as an off-white solid. LCMS (ESI): [M+H]$^+$=392.0; $^1$H NMR (300 MHz, CDCl$_3$) δ 7.04-6.91 (m, 2H), 5.88 (s, 1H), 5.82 (br, 1H), 3.84 (s, 2H), 3.58-3.48 (m, 2H), 2.59-2.52 (m, 2H), 2.42 (s, 3H), 1.28 (m, 3H), 1.17 (m, 3H).

Example 21.20: 7-[[3-(difluoromethyl)-2-fluoro-phenyl]methyl]-N-ethyl-2-methyl-5-oxo-thiazolo[3,2-a]pyrimidine-3-carboxamide

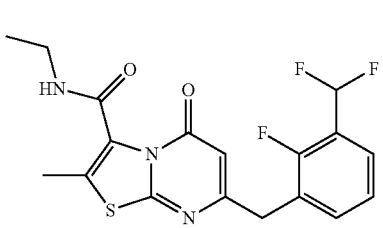 [SMILES: CCNC(=O)c1c(C)sc2nc(Cc3cccc(C(F)F)c3F)cc(=O)n12]

Step 1: 3-bromo-2-fluorobenzaldehyde

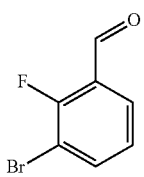

To a solution of (3-bromo-2-fluoro-phenyl)methanol (2.750 g, 13.413 mmol) in dichloromethane (50 mL) was added manganese dioxide (9.32 g, 107.31 mmol) and the resulting mixture was stirred at 45° C. overnight. Once complete, the reaction was filtered through diatomaceous earth and washed with dichloromethane to obtain 3-bromo-2-fluoro-benzaldehyde as a white solid (2.24 g, 83%). $^1$H NMR (400 MHz, DMSO-d$_6$) δ 10.19 (dt, J=1.3, 0.7 Hz, 1H), 8.05 (tdd, J=6.8, 3.1, 1.5 Hz, 1H), 7.85 (ddt, J=7.9, 6.4, 1.5 Hz, 1H), 7.37 (tdt, J=7.8, 1.6, 0.8 Hz, 1H).

Step 2: 1-bromo-3-(difluoromethyl)-2-fluorobenzene

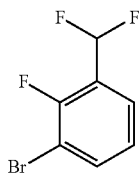 [SMILES: Fc1c(Br)cccc1C(F)F]

To a solution of 3-bromo-2-fluorobenzaldehyde (1980 mg, 9.5581 mmol) in dichloromethane (30 mL, 468.0 mmol) under inert atmosphere was added diethylaminosulfur trifluoride (2.53 mL, 19.116 mmol) at 0° C., and the mixture was stirred for 1 h at 0° C. The mixture was warmed to room temperature and stirred for 1 h. The reaction was carefully quenched with saturated sodium bicarbonate solution. The reaction mixture was then diluted with ethyl acetate (300 mL) and the organic layer was washed with saturated sodium bicarbonate solution and brine then concentrated to dryness and purified by chromatography (0-50% ethyl acetate in heptane over 20 minutes) to provide 1-bromo-3-(difluoromethyl)-2-fluorobenzene (1.35 g, 61%). $^1$H NMR (400 MHz, DMSO-d$_6$) δ 7.93 (ddq, J=7.9, 6.8, 1.2 Hz, 1H), 7.66 (ddq, J=7.6, 6.4, 1.2 Hz, 1H), 7.33 (td, J=7.9, 1.0 Hz, 1H), 7.24 (t, J=54.1 Hz, 1H).

Step 3: 2-[3-(difluoromethyl)-2-fluoro-phenyl]-4,4,5,5-tetramethyl-1,3,2-dioxaborolane

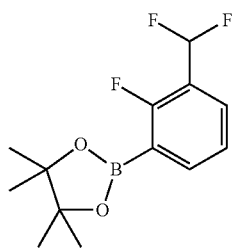 [SMILES: CC1(C)OB(c2cccc(C(F)F)c2F)OC1(C)C]

A mixture of 1-bromo-3-(difluoromethyl)-2-fluorobenzene (1.18 g, 5.09 mmol) and bis(pinacolato)diboron (2.59 g, 10.2 mmol) 1,1'-bis(diphenylphosphino)ferrocene palladium dichloride (280 mg, 0.382 mmol) and potassium acetate (1.50 g, 15.3 mmol) in 1,4-dioxane (15 mL) was heated at 100° C. overnight. The reaction mixture was filtered through diatomaceous earth and concentrated. The crude material was purified by chromatography (0-50% ethyl acetate in heptane) to obtain 2-[3-(difluoromethyl)-2-fluoro-phenyl]-4,4,5,5-tetramethyl-1,3,2-dioxaborolane as a light yellow solid (1.11 g, 80%). $^1$H NMR (400 MHz, DMSO-d$_6$) δ 7.86-7.73 (m, 2H), 7.36 (t, J=7.5 Hz, 1H), 7.18 (t, J=54.4 Hz, 1H), 1.31 (s, 12H).

Step 4: 7-[[3-(difluoromethyl)-2-fluoro-phenyl]methyl]-N-ethyl-2-methyl-5-oxo-thiazolo[3,2-a]pyrimidine-3-carboxamide

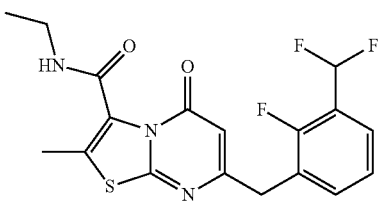 [SMILES: CCNC(=O)c1c(C)sc2nc(Cc3cccc(C(F)F)c3F)cc(=O)n12]

A mixture of 7-(chloromethyl)-N-ethyl-2-methyl-5-oxo-thiazolo[3,2-a]pyrimidine-3-carboxamide (prepared in a similar manner as Example 16.1, Step 5) (75 mg, 0.262 mmol), 2-[3-(difluoromethyl)-2-fluoro-phenyl]-4,4,4,55-tetramethyl-1,3,2-dioxaborolane (214 mg, 0.787 mmol), 1,1'-bis(diphenylphosphino)ferrocene palladium dichloride (14.4 mg, 0.0197 mmol) and potassium carbonate (110 mg, 0.787 mmol) in acetonitrile (3 mL) and water (0.75 mL) was heated at 120° C. in the microwave for 40 minutes. The reaction mixture was filtered through diatomaceous earth and concentrated. The crude material was purified by chromatography (0-100% ethyl acetate in heptane) to obtain 7-[[3-(difluoromethyl)-2-fluoro-phenyl]methyl]-N-ethyl-2-methyl-5-oxo-thiazolo[3,2-a]pyrimidine-3-carboxamide (49.6 mg, 47%). LCMS (ESI): [M+H]$^+$=396.1; $^1$H NMR (400 MHz, DMSO-d$_6$) δ 8.37 (t, J=5.7 Hz, 1H), 7.55 (q, J=8.0 Hz, 2H), 7.38-7.02 (m, 2H), 6.08 (s, 1H), 3.97 (s, 2H), 3.27-3.16 (m, 2H), 2.29 (s, 3H), 1.09 (t, J=7.2 Hz, 3H).

The following examples were prepared in a manner similar to Example 21.18, 21.19, and 21.20:

| No. | Structure/Name | LCMS (M + H) | ¹H NMR |
|---|---|---|---|
| 21.21 | N-ethyl-7-(2-ethyl-4,5-difluorobenzyl)-2-methyl-5-oxo-5H-thiazolo[3,2-a]pyrimidine-3-carboxamide | 374.0 | ¹H NMR (300 MHz, CDCl₃) δ 7.24-7.14 (m, 1H), 6.95-6.84 (m, 2H), 5.87 (s, 1H), 5.84 (s, 1H), 3.91 (s, 2H), 3.56-3.47 (m, 2H), 2.60-2.53 (m, 2H), 2.41 (s, 3H) 1.29-1.23 (m 3H) 1.19-1.14 (m, 3H) |
| 21.22 | 7-((6-cyanopyridin-2-yl)methyl)-N-ethyl-2-methyl-5-oxo-5H-thiazolo[3,2-a]pyrimidine-3-carboxamide | 354.05 | ¹H NMR (300 MHz, CDCl₃) δ 7.61-7.50 (m, 2H), 7.26-7.20 (m, 1H), 6.07 (s, 1H), 5.85 (s, 1H), 3.95 (s, 2H), 3.57-3.48 (m, 2H), 2.42 (s, 3H), 1.28 (m, 2H) |
| 21.23 | 7-[[3-(difluoromethyl)-2-fluoro-phenyl]methyl]-N,2-dimethyl-5-oxo-thiazolo[3,2-a]pyrimidine-3-carboxamide | 382.1 | ¹H NMR (400 MHz, DMSO-d₆) δ 8.31 (t, J = 5.3 Hz, 1H), 7.38-7.28 (m, 1H), 7.22 (t, J = 52 Hz, 2H), 6.08 (s, 1H), 4.06 (s, 2H), 2.73 (d, J = 4.6 Hz, 3H), 2.29 (s, 3H). |
| 21.24 | 7-[[2-fluoro-3-(hydroxymethyl)phenyl]methyl]-N,2-dimethyl-5-oxo-thiazolo[3,2-a]pyrimidine-3-carboxamide | 362.1 | ¹H NMR (400 MHz, DMSO-d₆) δ 8.31 (q, J = 4.7 Hz, 1H), 7.37 (td, J = 7.3, 1.8 Hz, 1H), 7.24 (td, J = 7.4, 1.8 Hz, 1H), 7.14 (t, J = 7.6 Hz, 1H), 6.00 (s, 1H), 5.20 (brs, 1H), 4.53 (s, 2H), 3.90 (s, 2H), 2.73 (d, J = 4.8 Hz, 3H), 2.29 (d, J = 1.0 Hz, 3H). |

Example 21.25: 7-(3-cyclopropyl-2-fluorobenzyl)-N-ethyl-2-methyl-5-oxo-5H-thiazolo[3,2-a]pyrimidine-3-carboxamide

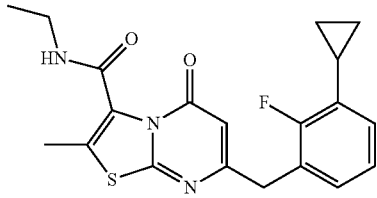 [SMILES: CCNC(=O)c1c(C)sc2nc(Cc3cccc(C4CC4)c3F)cc(=O)n12]

To a solution of 7-[(3-chloro-2-fluorophenyl)methyl]-N-ethyl-2-methyl-5-oxo-5H-[1,3]thiazolo[3,2-a]pyrimidine-3-carboxamide (prepared in a similar manner as Example 21.14) (70 mg, 0.18 mmol) in dioxane (2 mL) and water (0.5 mL) was added cyclopropylboronic acid (35 mg, 0.41 mmol), palladium acetate (28 mg, 0.12 mmol) and tricyclohexylphosphine (21 mg). After stirring overnight at 90° C. under nitrogen atmosphere, the resulting mixture was concentrated under vacuum. The residue was purified by chromatography with 2% methanol in dichloromethane. The crude product was purified by Prep-HPLC (SunFire Prep $C_{18}$ OBD Column, 5 um, 19×150 mm; mobile phase A, water with 10 mmol $NH_4HCO_3$ and mobile phase B, $CH_3CN$; 50.0% $CH_3CN$ up to 82.0% in 10 min, down to 50.0% in 2 min; Detector, UV 254/220 nm) to afford 7-[(3-cyclopropyl-2-fluorophenyl)methyl]-N-ethyl-2-methyl-5-oxo-5H-[1,3]thiazolo[3,2-a]pyrimidine-3-carboxamide (16.8 mg, 24%) as a white solid. LCMS (ESI): [M+H]$^+$=386.10; $^1$H NMR (300 MHz, CDCl$_3$) δ 7.26-6.96 (m, 2H), 6.96-6.78 (m, 1H), 6.05 (s, 1H), 5.85 (br, 1H), 3.95 (s, 2H), 3.58-3.42 (m, 2H), 2.42 (s, 3H), 2.10-2.02 (m, 1H), 1.28 (m, 3H), 1.00-0.94 (m, 2H), 0.73-0.68 (m, 2H).

Example 21.26: 7-(3-cyano-2-fluorobenzyl)-N-ethyl-6-fluoro-5-oxo-5H-thiazolo[3,2-a]pyrimidine-3-carboxamide

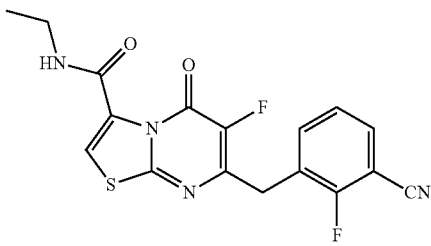 [SMILES: CCNC(=O)c1csc2nc(Cc3cccc(C#N)c3F)c(F)c(=O)n12]

Step 1: 7-(3-cyano-2-fluorobenzyl)-N-ethyl-5-oxo-5H-thiazolo[3,2-a]pyrimidine-3-carboxamide

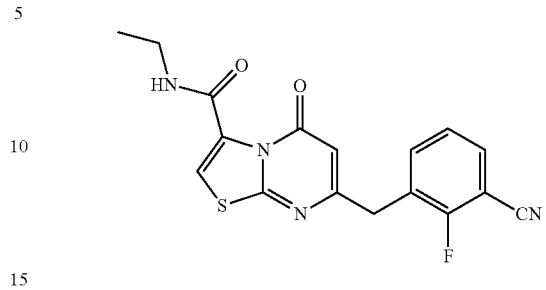

To a solution of 7-(chloromethyl)-N-ethyl-5-oxo-5H-[1,3]thiazolo[3,2-a]pyrimidine-3-carboxamide (prepared in a similar manner as Example 16.1, Step 5) (100 mg, 0.37 mmol) in 1,4-dioxane/water (2 mL/0.5 mL) was added (3-cyano-2-fluorophenyl)boronic acid (121 mg, 0.73 mmol), [1,1'-bis(diphenylphosphino)ferrocene]palladium(II) dichloride (28 mg, 0.04 mmol), and sodium carbonate (78 mg, 0.74 mmol). The reaction mixture was irradiated with microwave radiation for 45 min at 100° C. The resulting mixture was concentrated under vacuum and purified by chromatography with dichloromethane/methanol (30:1) to afford 7-[(3-cyano-2-fluorophenyl)methyl]-N-ethyl-5-oxo-5H-[1,3]thiazolo[3,2-a]pyrimidine-3-carboxamide (69 mg, 53%) as a yellow solid. LCMS (ESI): [M+H]$^+$=357.0.

Step 2: 7-(3-cyano-2-fluorobenzyl)-N-ethyl-6-fluoro-5-oxo-5H-thiazolo[3,2-a]pyrimidine-3-carboxamide

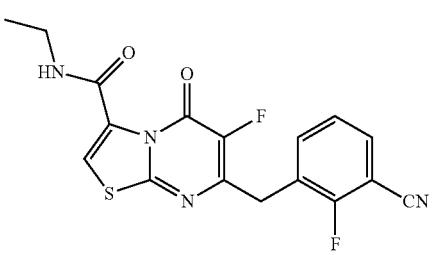 [SMILES: CCNC(=O)c1csc2nc(Cc3cccc(C#N)c3F)c(F)c(=O)n12]

To a solution of 7-[(3-cyano-2-fluorophenyl)methyl]-N-ethyl-5-oxo-5H-[1,3]thiazolo[3,2-a]pyrimidine-3-carboxamide (30 mg, 0.08 mmol) in $CH_3CN$ (3 mL) was added Selectfluor® (30 mg, 0.24 mmol). The resulting solution was stirred for 1.5 h at 75° C. The resulting mixture was cooled to room temperature and concentrated under vacuum, and the residue was purified by chromatography with dichloromethane/methanol (30:1) to afford 7-[(3-cyano-2-fluorophenyl)methyl]-N-ethyl-6-fluoro-5-oxo-5H-[1,3]thiazolo[3,2-a]pyrimidine-3-carboxamide (8 mg, 25%) as a white solid. LCMS (ESI): [M+H]$^+$=375.0; $^1$H NMR (300 MHz, CDCl$_3$) δ 7.73-7.65 (m, 2H), 7.58 (s, 1H), 7.36-7.31 (m, 1H), 4.20 (s, 2H), 3.33-3.31 (m, 2H), 1.29-1.10 (m, 3H).

Example 21.27: 7-(3-cyano-2-fluorobenzyl)-6-fluoro-N,N-dimethyl-5-oxo-5H-thiazolo[3,2-a]pyrimidine-3-carboxamide

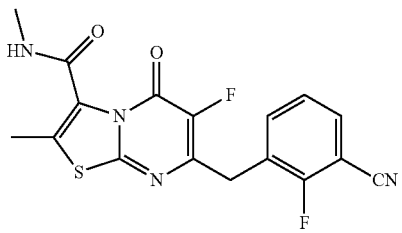 [SMILES: CNC(=O)c1c(C)sc2nc(Cc3cccc(C#N)c3F)c(F)c(=O)n12]

Step 1: 7-(chloromethyl)-6-fluoro-N,N-dimethyl-5-oxo-5H-thiazolo[3,2-a]pyrimidine-3-carboxamide.

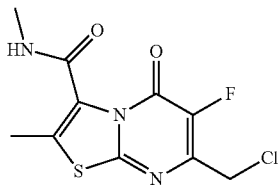 [SMILES: CNC(=O)c1c(C)sc2nc(CCl)c(F)c(=O)n12]

To a solution of 7-(chloromethyl)-N,2-dimethyl-5-oxo-5H-[1,3]thiazolo[3,2-a]pyrimidine-3-carboxamide (from Example 16.1, Step 5) (500 mg, 1.84 mmol) in CH₃CN (10 mL) was added Selectfluor® (980 mg, 2.76 mmol) and the resulting solution was stirred for 4 h at 75° C. The resulting mixture was concentrated under vacuum. The residue was purified by chromatography with dichloromethane/ethyl acetate (5:1) to afford 7-(chloromethyl)-6-fluoro-N,2-dimethyl-5-oxo-5H-[1,3]thiazolo[3,2-a]pyrimidine-3-carboxamide (110 mg, 21%) as a light yellow solid. LCMS (ESI): [M+H]⁺=290.0.

Step 2: 7-(3-cyano-2-fluorobenzyl)-6-fluoro-N,N-dimethyl-5-oxo-5H-thiazolo[3,2-a]pyrimidine-3-carboxamide

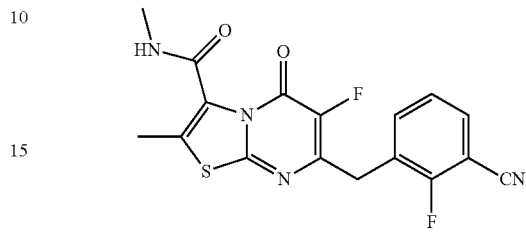

To a solution of 7-(chloromethyl)-6-fluoro-N,2-dimethyl-5-oxo-5H-[1,3]thiazolo[3,2-a]pyrimidine-3-carboxamide (100 mg, 0.35 mmol) in 1,4-dioxane (2 mL) under nitrogen was added (3-cyano-2-fluorophenyl)boronic acid (86 mg, 0.52 mmol), sodium carbonate (74 mg, 0.70 mmol), [1,1'-bis(diphenylphosphino)ferrocene]palladium(II) dichloride (26 mg, 0.04 mmol), and water (0.2 mL). The reaction mixture was irradiated with microwave radiation for 20 min at 120° C. The resulting solution was extracted with ethyl acetate (3×20 mL), washed with brine, dried over anhydrous sodium sulfate, and concentrated under vacuum. The residue was purified by chromatography with dichloromethane/ethyl acetate (2:3), to afford 7-[(3-cyano-2-fluorophenyl)methyl]-6-fluoro-N,N-dimethyl-5-oxo-5H-[1,3]thiazolo[3,2-a]pyrimidine-3-carboxamide (18 mg, 14%) as a off-white solid. LCMS (ESI): [M+H]⁺=374.9; ¹H NMR (300 MHz, CDCl₃) δ 7.56 (m, 2H), 7.21 (m, 1H), 5.97 (s, 1H), 4.09 (m, 2H), 3.05 (m, 3H), 2.41 (s, 3H).

The following examples were prepared in a manner similar to Example 21.26 and 21.27:

| No. | Structure/Name | LCMS (M + H) | ¹H NMR |
|---|---|---|---|
| 21.28 | 7-(3-cyano-2-fluorobenzyl)-N-ethyl-6-fluoro-2-methyl-5-oxo-5H-thiazolo[3,2-a]pyrimidine-3-carboxamide | 388.9 | ¹H NMR (300 MHz, CDCl₃) δ 7.56-7.50 (m, 2H), 7.23-7.19 (m, 1H), 5.86 (s, 1H), 4.09 (s, 2H), 3.58-3.51 (m, 2H), 2.40 (s, 3H), 1.32-1.28 (m, 3H) |
| 21.29 | 6-fluoro-7-(2-fluoro-3-(trifluoromethyl)benzyl)-N,2-dimethyl-5-oxo-5H-thiazolo[3,2-a]pyrimidine-3-carboxamide | 418.0 | ¹H NMR (300 MHz, CDCl₃) δ 7.51 (m, 2H), 7.21 (m, 1H), 5.91 (s, 1H), 4.10 (s, 2H), 3.05 (m, 3H), 2.41 (s, 3H) |

The following compounds were prepared using methods analogous to those described above:

| No. | Structure/Name | LCMS (M + H) | $^1$H NMR |
|---|---|---|---|
| 21.30 | 7-(5-cyano-2-methylbenzyl)-N-ethyl-2-methyl-5-oxo-5H-thiazolo[3,2-a]pyrimidine-3-carboxamide | 367.0 | $^1$H NMR (300 MHz, CD$_3$OD) δ 7.54 (m, 2H), 7.39 (m, 1H), 6.03 (s, 1H), 4.09 (s, 2H), 3.39 (m, 2H), 2.39 (s, 6H), 1.22 (m, 3H) |
| 21.31 | 7-(5-cyano-2-fluorobenzyl)-N-ethyl-2-methyl-5-oxo-5H-thiazolo[3,2-a]pyrimidine-3-carboxamide | 371.0 | $^1$H NMR (300 MHz, CDCl$_3$) δ 7.66-7.58 (m, 2H), 7.25-7.20 (m, 1H), 6.12 (s, 1H), 5.90-5.80 (m, 1H), 3.96 (s, 2H), 3.60-3.50 (m, 2H), 2.45 (s, 3H), 1.33-1.29 (m, 3H) |
| 21.32 | 7-(2-chloro-5-fluorobenzyl)-N-ethyl-2-methyl-5-oxo-5H-thiazolo[3,2-a]pyrimidine-3-carboxamide | 379.95 | $^1$H NMR (300 MHz, CDCl$_3$) δ 7.36-7.32 (m, 1H), 7.03-6.91 (m, 2H), 5.99 (s, 1H), 5.87 (br, 1H), 3.99 (s, 2H), 3.57-3.48 (m, 2H), 2.41 (s, 3H), 1.28 (m, 3H) |
| 21.33 | 7-(3-cyano-2-fluorobenzyl)-N-ethyl-5-oxo-5H-thiazolo[3,2-a]pyrimidine-3-carboxamide | 357.0 | $^1$H NMR (300 MHz, CDCl$_3$) δ 9.66 (br, 1H), 8.02 (s, 1H), 7.58-7.55 (m, 2H), 7.27 (s, 1H), 6.19 (s, 1H), 4.00 (s, 2H), 3.50-3.41 (m, 2H), 1.27-1.17 (m, 3H) |
| 21.34 | | 421.20 | $^1$H NMR (300 MHz, CDCl$_3$) δ 7.70-7.66 (m, 1H), 7.09-7.04 (m, 2H), 5.95-5.92 (m, 2H), 4.08 (s, 2H), 3.56-3.47 (m, 2H), 2.41 (s, 3H), 1.30-1.18 (m, 3H) |

| No. | Structure/Name | LCMS (M + H) | ¹H NMR |
|---|---|---|---|
| 21.35 | 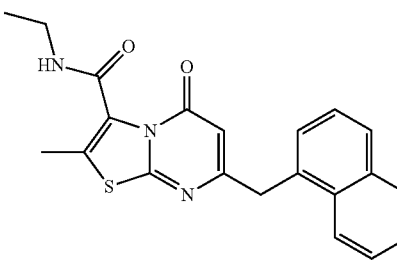<br>N-ethyl-2-methyl-7-(naphthalen-1-ylmethyl)-5-oxo-5H-thiazolo[3,2-a]pyrimidine-3-carboxamide | 378.0 | ¹H NMR (300 MHz, CDCl₃) δ 7.87-7.79 (m, 3H), 7.52-7.40 (m, 4H), 5.95-5.84 (m, 1H), 5.81 (s, 1H), 4.36 (s, 2H), 3.66-3.47 (m, 2H), 2.37 (s, 3H), 1.25-1.16 (t, 3H) |
| 21.36 | 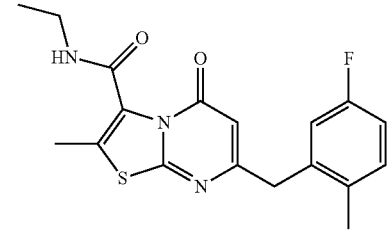 [SMILES: CCNC(=O)c1c(C)sc2nc(Cc3cc(F)ccc3C)cc(=O)n12]<br>N-ethyl-7-(5-fluoro-2-methylbenzyl)-2-methyl-5-oxo-5H-thiazolo[3,2-a]pyrimidine-3-carboxamide | 360.0 | ¹H NMR (300 MHz, CD₃OD) δ 7.19 (m, 1H), 6.94 (m, 2H), 5.95 (s, 1H), 3.95 (s, 2H), 3.40 (m, 2H), 2.40 (s, 3H), 2.26 (s, 3H), 1.23 (m, 3H) |
| 21.37 | 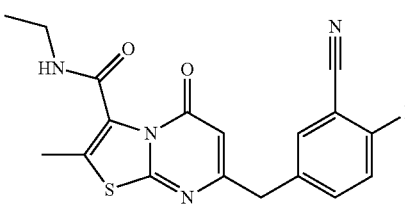<br>7-(3-cyano-4-fluorobenzyl)-N-ethyl-2-methyl-5-oxo-5H-thiazolo[3,2-a]pyrimidine-3-carboxamide | 371.0 | ¹H NMR (400 MHz, CDCl₃) δ 7.54-7.47 (m, 2H), 7.19-7.14 (m, 1H), 6.09 (s, 1H), 5.84 (br, 1H), 3.86 (s, 2H), 3.57-3.50 (m, 2H), 2.42 (s, 3H), 1.27 (m, 3H) |
| 21.38 | 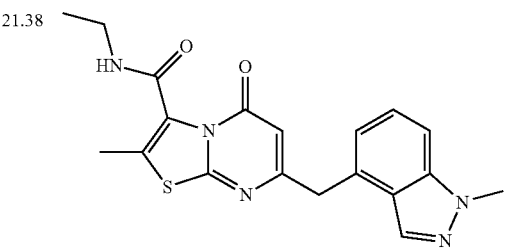<br>N-ethyl-2-methyl-7-((1-methyl-1H-indazol-4-yl)methyl)-5-oxo-5H-thiazolo[3,2-a]pyrimidine-3-carboxamide | 382.20 | ¹H NMR (400 MHz, CDCl₃) δ 7.98 (s, 1H), 7.37-7.30 (m, 2H), 7.02-7.01 (m, 1H), 6.01 (s, 1H), 5.83 (s, 1H), 4.25 (s, 2H), 4.12 (s, 3H), 3.51-3.50 (m, 2H), 2.45-2.35 (m, 3H), 1.27-1.15 (m, 3H) |

N-ethyl-7-(5-fluoro-2-(trifluoromethyl)benzyl)-2-methyl-5-oxo-5H-thiazolo[3,2-a]pyrimidine-3-carboxamide

| No. | Structure/Name | LCMS (M + H) | ¹H NMR |
|---|---|---|---|
| 21.39 | 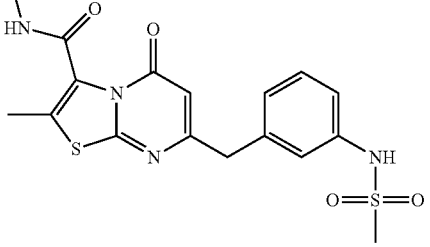<br>N-ethyl-2-methyl-7-(3-(methylsulfonamido)benzyl)-5-oxo-5H-thiazolo[3,2-a]pyrimidine-3-carboxamide | 421.0 | ¹H NMR (300 MHz, CD₃OD) δ 7.29 (m, 2H), 7.09 (m, 2H), 6.13 (s, 1H), 3.91 (s, 2H), 3.40 (m, 2H), 2.94 (s, 3H), 2.39 (s, 3H), 1.23 (m, 3H) |
| 21.40 | 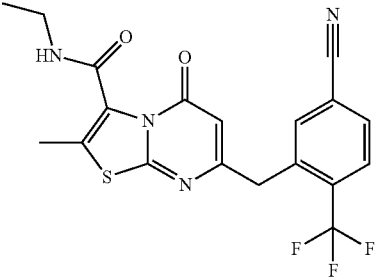 [SMILES: CCNC(=O)c1c(C)sc2nc(Cc3cc(C#N)ccc3C(F)(F)F)cc(=O)n12]<br>7-(5-cyano-2-(trifluoromethyl)benzyl)-N-ethyl-2-methyl-5-oxo-5H-thiazolo[3,2-a]pyrimidine-3-carboxamide | 421.20 | ¹H NMR (300 MHz, CDCl₃) δ 7.81-7.78 (m, 1H), 7.69-7.67 (m, 1H), 5.60 (s, 1H), 5.82 (s, 1H), 4.11 (s, 2H), 3.58-3.52 (m, 2H), 2.44 (s, 3H), 1.31-1.26 (m, 3H) |
| 21.41 | 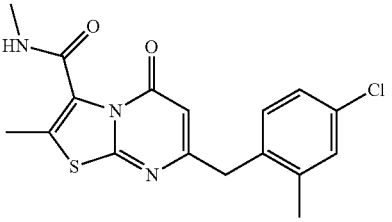 [SMILES: CNC(=O)c1c(C)sc2nc(Cc3ccc(Cl)cc3C)cc(=O)n12]<br>7-(4-chloro-2-methylbenzyl)-N,2-dimethyl-5-oxo-5H-thiazolo[3,2-a]pyrimidine-3-carboxamide | 362.0 | ¹H NMR (300 MHz, CDCl₃) δ 7.13 (m, 3H), 5.99 (s, 1H), 5.87 (s, 1H), 4.10 (s, 2H), 3.03 (s, 3H), 2.30 (s, 3H), 2.24 (s, 3H) |
| 21.42 | 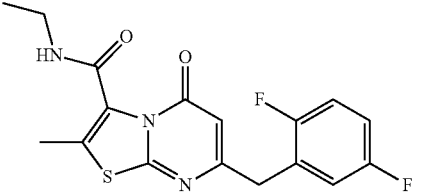 [SMILES: CCNC(=O)c1c(C)sc2nc(Cc3cc(F)ccc3F)cc(=O)n12]<br>7-(2,5-difluorobenzyl)-N-ethyl-2-methyl-5-oxo-5H-thiazolo[3,2-a]pyrimidine-3-carboxamide | 364.0 | ¹H NMR (300 MHz, CDCl₃) δ 7.05-6.89 (m, 3H), 6.10 (s, 1H), 6.04 (s, 1H), 3.88 (s, 2H), 3.55-3.46 (m, 2H), 2.36 (s, 3H), 1.29-1.27 (m, 3H) |
| 21.43 | 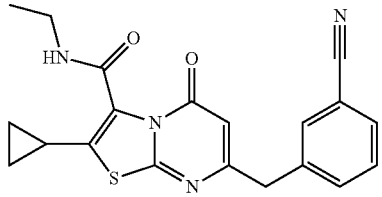 [SMILES: CCNC(=O)c1c(C2CC2)sc2nc(Cc3cccc(C#N)c3)cc(=O)n12] | 379.0 | ¹H NMR (300 MHz, CDCl₃) δ 7.54-7.53 (m, 2H), 7.49-7.38 (m, 2H), 6.06 (s, 1H), 5.89 (s, 1H), 3.88 (s, 2H), 3.56-3.49 (m, 2H), 2.19-2.09 (m, 1H), 1.31-1.21 (m, 3H), 1.18-1.11 (m, 2H), 0.88-0.78 (m, 2H) |

| No. | Structure/Name | LCMS (M + H) | ¹H NMR |
|---|---|---|---|
| | 7-(3-cyanobenzyl)-2-cyclopropyl-N-ethyl-5-oxo-5H-thiazolo[3,2-a]pyrimidine-3-carboxamide | | |
| 21.44 | N-ethyl-7-(2-fluorobenzyl)-2-methyl-5-oxo-5H-thiazolo[3,2-a]pyrimidine-3-carboxamide | 346.0 | ¹H NMR (400 MHz, CDCl₃) δ 7.48-7.46 (m, 1H), 7.30-7.21 (m, 1H), 7.14-7.03 (m, 2H), 6.06 (s, 1H), 6.01 (s, 1H), 3.93 (s, 2H), 3.56-3.46 (m, 2H), 2.38 (s, 3H), 1.30-1.25 (m, 3H) |
| 21.45 | 7-(2,3-difluorobenzyl)-N-ethyl-2-methyl-5-oxo-5H-thiazolo[3,2-a]pyrimidine-3-carboxamide | 364.0 | ¹H NMR (400 MHz, CDCl₃) δ 7.11-6.99 (m, 3H), 6.04 (s, 1H), 5.90 (s, 1H), 3.95 (s, 2H), 3.55-3.48 (m, 2H), 2.40 (s, 3H) 1.29-1.16 (m 3H) |
| 21.46 | N-ethyl-7-(3-fluorobenzyl)-2-methyl-5-oxo-5H-thiazolo[3,2-a]pyrimidine-3-carboxamide | 346.0 | ¹H NMR (300 MHz, CD₃OD) δ 7.36-7.29 (m, 1H), 7.13-6.94 (m, 3H), 6.15 (s, 1H), 3.93 (s, 2H), 3.41 (m, 2H), 2.40 (s, 3H), 1.24 (m, 3H) |
| 21.47 | 7-[(3-chloro-4-fluoro-phenyl)methyl]-N,2-dimethyl-5-oxo-thiazolo[3,2-a]pyrimidine-3-carboxamide | 366.1 | ¹H NMR (400 MHz, DMSO-d₆) δ 8.29 (t, J = 4.8 Hz, 1H), 7.52 (dd, J = 7.2, 2.0 Hz, 1H), 7.39-7.28 (m, 2H), 6.17 (s, 1H), 2.73 (d, J = 4.7 Hz, 3H), 2.29 (s, 3H). |
| 21.48 | 7-[(2,5-dichlorophenyl)methyl]-N,2-dimethyl-5-oxo-thiazolo[3,2-a]pyrimidine-3-carboxamide | 382.0 | ¹H NMR (400 MHz, DMSO-d₆) δ 8.32 (q, J = 4.7 Hz, 1H), 7.52-7.48 (m, 2H), 7.39 (dd, J = 8.6, 2.6 Hz, 1H), 5.97 (s, 1H), 4.02 (s, 2H), 2.73 (d, J = 4.8 Hz, 3H), 2.29 (s, 3H). |

| No. | Structure/Name | LCMS (M + H) | ¹H NMR |
|---|---|---|---|
| 21.49 | N,2-dimethyl-5-oxo-7-[[3-(trifluoromethoxy)phenyl]methyl]thiazolo[3,2-a]pyrimidine-3-carboxamide | 398.1 | ¹H NMR (400 MHz, DMSO-$d_6$) δ 8.35-8.25 (m, 1H), 7.45 (t, J = 7.9 Hz, 1H), 7.33 (dd, J = 9.9, 2.4 Hz, 2H), 7.27-7.19 (m, 1H), 6.16 (d, J = 1.2 Hz, 1H), 3.93 (s, 2H), 2.73 (d, J = 4.6 Hz, 3H), 2.29 (s, 3H). |
| 21.50 | 7-[(5-cyano-2-fluoro-phenyl)methyl]-N,2-dimethyl-5-oxo-thiazolo[3,2-a]pyrimidine-3-carboxamide | 357.1 | ¹H NMR (400 MHz, DMSO-$d_6$) δ 8.30 (d, J = 4.9 Hz, 1H), 7.92 (dd, J = 6.9, 2.2 Hz, 1H), 7.85 (ddd, J = 8.5, 4.8, 2.2 Hz, 1H), 7.44 (dd, J = 9.7, 8.6 Hz, 1H), 6.11 (s, 1H), 3.97 (s, 2H), 2.73 (d, J = 4.7 Hz, 3H), 2.29 (s, 3H). |
| 21.51 | 7-[(3-chloro-5-cyano-phenyl)methyl]-N,2-dimethyl-5-oxo-thiazolo[3,2-a]pyrimidine-3-carboxamide | 373.0 | ¹H NMR (400 MHz, DMSO-$d_6$) δ 8.31-8.25 (m, 1H), 7.91 (t, J = 1.8 Hz, 1H), 7.76 (dt, J = 7.0, 1.6 Hz, 2H), 6.22 (s, 1H), 3.94 (s, 2H), 2.74 (d, J = 4.7 Hz, 3H), 2.29 (s, 3H). |
| 21.52 | 7-[(3-cyclopropylphenyl)methyl]-N,2-dimethyl-5-oxo-thiazolo[3,2-a]pyrimidine-3-carboxamide | 354.1 | ¹H NMR (400 MHz, DMSO-$d_6$) δ 8.30 (q, J = 4.7 Hz, 1H), 7.20-7.14 (m, 1H), 7.03 (dd, J = 6.8, 1.4 Hz, 2H), 6.91 (dt, J = 7.9, 1.5 Hz, 1H), 6.08 (s, 1H), 3.80 (s, 2H), 2.73 (d, J = 4.7 Hz, 3H), 2.28 (s, 3H), 1.88 (tt, J = 8.4, 5.1 Hz, 1H), 0.97-0.88 (m, 2H), 0.68-0.61 (m, 2H). |
| 21.53 | 7-[(2,5-difluorophenyl)methyl]-N,2-dimethyl-5-oxo-thiazolo[3,2-a]pyrimidine-3-carboxamide | 350.1 | ¹H NMR (400 MHz, DMSO-$d_6$) δ 8.31 (q, J = 4.7 Hz, 1H), 7.24 (tt, J = 8.8, 4.1 Hz, 2H), 7.15 (tt, J = 8.8, 3.6 Hz, 1H), 6.06 (s, 1H), 3.91 (s, 2H), 2.73 (d, J = 4.7 Hz, 3H), 2.29 (s, 3H). |

| No. | Structure/Name | LCMS (M + H) | ¹H NMR |
|---|---|---|---|
| 21.54 | 7-[(3,4-difluorophenyl)methyl]-N,2-dimethyl-5-oxo-thiazolo[3,2-a]pyrimidine-3-carboxamide | 350.1 | ¹H NMR (400 MHz, DMSO-$d_6$) δ 8.30 (q, J = 4.7 Hz, 1H), 7.43-7.29 (m, 2H), 7.15 (dd, J = 4.6, 2.2 Hz, 1H), 6.15 (s, 1H), 3.86 (s, 2H), 2.78-2.68 (m, 3H), 2.34 (s, 3H). |
| 21.55 | 7-[(2,3-difluorophenyl)methyl]-N,2-dimethyl-5-oxo-thiazolo[3,2-a]pyrimidine-3-carboxamide | 350.1 | ¹H NMR (400 MHz, DMSO-$d_6$) δ 8.31 (t, J = 5.3 Hz, 1H), 7.38-7.28 (m, 1H), 7.22-7.13 (m, 2H), 6.08 (s, 1H), 4.06 (s, 2H), 2.73 (d, J = 4.6 Hz, 3H), 2.29 (s, 3H). |
| 21.56 | 7-[(4-chloro-2-fluoro-phenyl)methyl]-N,2-dimethyl-5-oxo-thiazolo[3,2-a]pyrimidine-3-carboxamide | 366.1 | ¹H NMR (400 MHz, DMSO-$d_6$) δ 8.32 (q, J = 4.7 Hz, 1H), 7.46-7.41 (m, 1H), 7.41-7.36 (m, 1H), 7.26 (dd, J = 8.3, 2.1 Hz, 1H), 6.06 (s, 1H), 3.91 (s, 2H), 2.73 (d, J = 4.7 Hz, 3H), 2.29 (s, 3H). |
| 21.57 | 7-[(2,4-dichlorophenyl)methyl]-N,2-dimethyl-5-oxo-thiazolo[3,2-a]pyrimidine-3-carboxamide | 382.0 | ¹H NMR (400 MHz, DMSO-$d_6$) δ 8.29 (d, J = 5.4 Hz, 1H), 7.61-7.55 (m, 2H), 7.30 (dd, J = 8.3, 2.1 Hz, 1H), 6.19 (s, 1H), 3.88 (s, 2H), 2.73 (d, J = 4.7 Hz, 3H), 2.29 (s, 3H). |
| 21.58 | 7-[(3-fluoro-4-methyl-phenyl)methyl]-N,2-dimethyl-5-oxo-thiazolo[3,2-a]pyrimidine-3-carboxamide | 346.1 | ¹H NMR (400 MHz, DMSO-$d_6$) δ 8.29 (d, J = 5.2 Hz, 1H), 7.21 (t, J = 8.0 Hz, 1H), 7.09-6.99 (m, 2H), 6.12 (s, 1H), 3.83 (s, 2H), 2.73 (dt, J = 4.8, 0.8 Hz, 3H), 2.29 (s, 3H), 2.23 (s, 3H). |

-continued

| No. | Structure/Name | LCMS (M + H) | ¹H NMR |
|---|---|---|---|
| 21.59 | 7-[[4-fluoro-2-(trifluoromethyl)phenyl]methyl]-N,2-dimethyl-5-oxo-thiazolo[3,2-a]pyrimidine-3-carboxamide | 400.1 | ¹H NMR (400 MHz, DMSO-$d_6$) δ 8.32-8.26 (m, 1H), 7.73 (dd, J = 7.1, 2.2 Hz, 1H), 7.67 (ddd, J = 7.8, 4.9, 2.3 Hz, 1H), 7.45 (dd, J = 11.0, 8.4 Hz, 1H), 6.19 (s, 1H), 3.96 (s, 2H), 2.73 (d, J = 4.6 Hz, 3H), 2.29 (s, 3H). |
| 21.60 | 7-[(2-cyclopropyl-4-fluoro-phenyl)methyl]-N,2-dimethyl-5-oxo-thiazolo[3,2-a]pyrimidine-3-carboxamide | 372.1 | ¹H NMR (400 MHz, DMSO-$d_6$) δ 8.36 (q, J = 4.7 Hz, 1H), 7.24 (dd, J = 8.5, 6.2 Hz, 1H), 6.96 (td, J = 8.5, 2.8 Hz, 1H), 6.78 (dd, J = 10.7, 2.7 Hz, 1H), 5.92 (d, J = 0.7 Hz, 1H), 4.04 (s, 2H), 2.73 (d, J = 4.7 Hz, 3H), 2.29 (s, 3H), 1.98 (ddd, J = 13.7, 8.6, 5.3 Hz, 1H), 0.94-0.85 (m 2H) 0.69-0.60 (m, 2H). |
| 21.61 | 7-(5-cyano-2-(2-fluoroethyl)benzyl)-N-ethyl-2-methyl-5-oxo-5H-thiazolo[3,2-a]pyrimidine-3-carboxamide | 425.0 | ¹H NMR (300 MHz, CDCl₃) δ 7.65 (m, 3H), 5.93 (s, 1H), 5.85 (s, 1H), 4.72 (m, 1H), 4.57 (m, 1H), 3.96 (s, 2H), 3.52 (m, 2H), 3.13 (m, 1H), 3.05 (m, 1H), 2.42 (s, 3H), 1.25 (m, 3H) |
| 21.62 | 7-(2-chloro-3-cyanobenzyl)-N-ethyl-2-methyl-5-oxo-5H-thiazolo[3,2-a]pyrimidine-3-carboxamide | 386.9 | ¹H NMR (300 MHz, DMSO-$d_6$) δ 8.42-8.39 (m, 1H), 7.93-7.90 (m, 1H), 7.78-7.76 (m, 1H), 7.57-7.52 (m, 1H), 6.02 (s, 1H), 4.11 (s, 2H), 3.31-3.18 (m, 2H), 2.30 (s, 3H), 1.12-1.07 (m, 3H) |

| No. | Structure/Name | LCMS (M + H) | ¹H NMR |
|---|---|---|---|
| 21.63 | 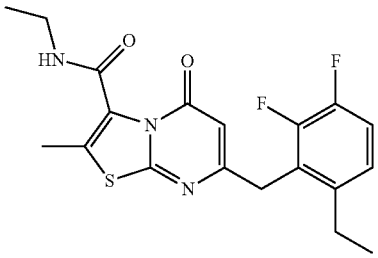 [SMILES: CCNC(=O)c1c(C)sc2nc(Cc3c(CC)ccc(F)c3F)cc(=O)n12]<br>N-ethyl-7-(6-ethyl-2,3-difluorobenzyl)-2-methyl-5-oxo-5H-thiazolo[3,2-a]pyrimidine-3-carboxamide | 392.0 | $^1$H NMR (300 MHz, CDCl$_3$) δ 7.04 (m, 2H), 5.94 (s, 1H), 5.82 (s, 1H), 4.01 (s, 2H), 3.51 (m, 2H), 2.58 (m, 2H), 2.41 (s, 3H), 1.26 (m, 3H), 1.15 (m, 3H) |
| 21.64 | 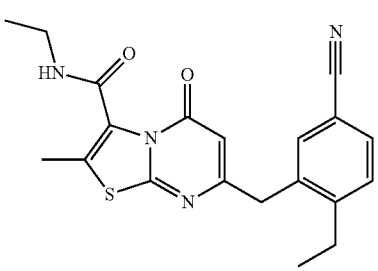 [SMILES: CCNC(=O)c1c(C)sc2nc(Cc3cc(C#N)ccc3CC)cc(=O)n12]<br>7-(5-cyano-2-ethylbenzyl)-N-ethyl-2-methyl-5-oxo-5H-thiazolo[3,2-a]pyrimidine-3-carboxamide | 381.0 | $^1$H NMR (300 MHz, CDCl$_3$) δ 7.53-7.51 (m, 1H), 7.44 (s, 1H), 7.33-7.26 (m, 1H), 5.89-5.87 (m, 2H), 3.94(s, 2H), 3.56-3.49 (m, 2H), 2.71-2.65 (m, 2H), 2.41 (s, 3H), 1.29-1.23 (m, 3H), 1.21-1.17 (m, 3H) |
| 21.65 | 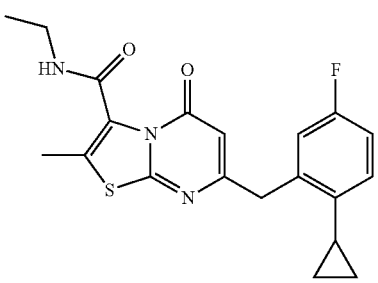 [SMILES: CCNC(=O)c1c(C)sc2nc(Cc3cc(F)ccc3C3CC3)cc(=O)n12]<br>7-(2-cyclopropyl-5-fluorobenzyl)-N-ethyl-2-methyl-5-oxo-5H-thiazolo[3,2-a]pyrimidine-3-carboxamide | 386.10 | $^1$H NMR (300 MHz, CDCl$_3$) δ 7.27-7.00 (m, 1H), 6.92-6.68 (m, 2H), 5.95 (s, 1H), 5.86 (br, 1H), 4.10 (s, 2H), 3.58-3.49 (m, 2H), 2.43 (s, 3H), 1.84-1.75 (m, 1H), 1.31-1.19 (m, 3H), 0.92-0.88 (m, 2H), 0.67-0.55 (m, 2H) |
| 21.66 | 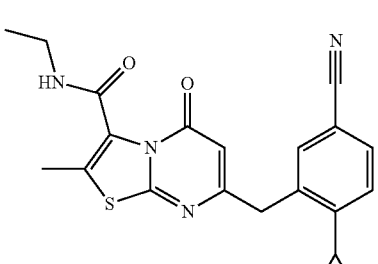<br>7-(5-cyano-2-cyclopropylbenzyl)-N-ethyl-2-methyl-5-oxo-5H-thiazolo[3,2-a]pyrimidine-3-carboxamide | 393.0 | $^1$H NMR (300 MHz, CDCl$_3$) δ 7.47-7.44 (m, 1H), 7.32-7.19 (m, 2H), 5.94 (s, 1H), 5.83-5.81 (m, 1H), 4.16 (s, 2H), 3.56-3.52 (m, 2H), 2.41 (s, 3H), 1.92-1.82 (m, 1H), 1.32-1.23 (m, 3H), 1.02-0.96 (m, 2H), 0.70-0.65 (m, 2H) |

-continued

| No. | Structure/Name | LCMS (M + H) | ¹H NMR |
|---|---|---|---|
| 21.67 | 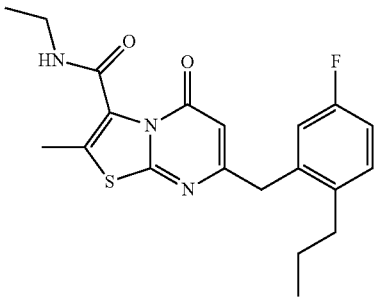 [SMILES: CCCc1ccc(F)cc1Cc1cc(=O)n2c(C(=O)NCC)c(C)sc2n1]<br>N-ethyl-7-(5-fluoro-2-propylbenzyl)-2-methyl-5-oxo-5H-thiazolo[3,2-a]pyrimidine-3-carboxamide | 388.0 | ¹H NMR (300 MHz, CDCl₃) δ 7.16-7.11 (m, 1H), 6.93-6.83 (m, 2H), 5.86 (s, 1H), 5.86 (s, 1H), 3.90 (s, 2H), 3.53-3.51 (m, 2H), 2.54-2.49 (m, 2H), 2.42 (s, 3H), 1.59-1.51 (m, 2H) 1.29-1.24 (m 3H) 0.96-0.91 (m, 3H) |
| 21.68 | 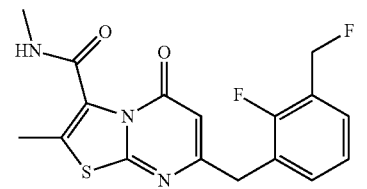 [SMILES: CNC(=O)c1c(C)sc2nc(Cc3cccc(CF)c3F)cc(=O)n12]<br>7-[[2-fluoro-3-(fluoromethyl)phenyl]methyl]-N,2-dimethyl-5-oxo-thiazolo[3,2-a]pyrimidine-3-carboxamide | 364.1 | ¹H NMR (400 MHz, DMSO-d₆) δ 8.31 (q, J = 4.6 Hz, 1H), 7.43 (tq, J = 7.4, 2.2 Hz, 2H), 7.26-7.18 (m, 1H), 6.04 (s, 1H), 5.48 (dd, J = 47.6, 1.2 Hz, 2H) 3.95 (s, 2H) 2.73 (d, J = 4.7 Hz, 3H), 2.29 (s, 3H). |

Method 22

Example 22.1: N-ethyl-7-(1-(2-fluoro-3-(trifluoromethyl)phenyl)ethyl)-2-methyl-5-oxo-5H-thiazolo[3,2-a]pyrimidine-3-carboxamide

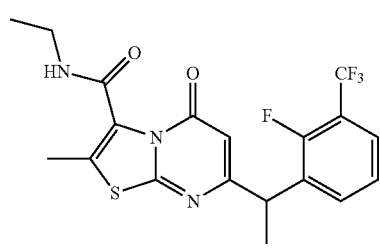 [SMILES: CCNC(=O)c1c(C)sc2nc(C(C)c3cccc(C(F)(F)F)c3F)cc(=O)n12]

Step 1: N-ethyl-7-(1-(2-fluoro-3-(trifluoromethyl)phenyl)ethyl)-2-methyl-5-oxo-5H-thiazolo[3,2-a]pyrimidine-3-carboxamide

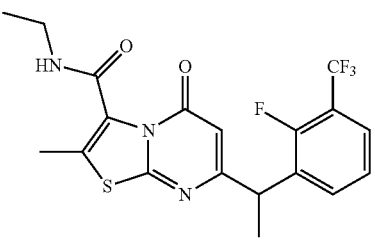 [SMILES: CCNC(=O)c1c(C)sc2nc(C(C)c3cccc(C(F)(F)F)c3F)cc(=O)n12]

To a −78° C. solution of N-ethyl-7-[[2-fluoro-3-(trifluoromethyl)phenyl]methyl]-2-methyl-5-oxo-5H-[1,3]thiazolo[3,2-a]pyrimidine-3-carboxamide (from Example 21.12) (200 mg, 0.48 mmol) in tetrahydrofuran (20 mL) was added n-butyllithium (2.5 M in hexanes; 1 mL). After 30 min at −78° C., iodomethane (235 mg, 1.66 mmol) was added. The resulting solution was stirred for 3 h at room temperature. The reaction was then quenched by water (20 mL), extracted with dichloromethane (3×30 mL), washed with brine, dried over sodium sulfate and concentrated in vacuo. The residue was purified by chromatography with dichloromethane/methanol (50:1) to afford N-ethyl-7-[1-[2-fluoro-3-(trifluoromethyl)phenyl]ethyl]-2-methyl-5-oxo-5H-[1,3]thiazolo[3,2-a]pyrimidine-3-carboxamide (52.7 mg, 25%) as a white solid. LCMS (ESI): [M+H]$^+$=428.0; $^1$H NMR (300 MHz, CDCl$_3$) δ 7.60-7.48 (m, 2H), 7.20-7.19 (m, 1H), 6.13 (s, 1H), 5.92 (m, 1H), 4.42-4.34 (m, 2H), 3.56-3.48 (m, 2H), 2.40 (s, 3H), 1.64-1.62 (m, 3H), 1.30-1.25 (m, 3H).

The following compound was prepared using methods analogous to those described above:

To a solution of 3-bromo-7-(chloromethyl)-2-methyl-5H-[1,3]thiazolo[3,2-a]pyrimidin-5-one (from Example 4.1, Step 6) (500 mg, 1.70 mmol) in 1,4-dioxane/H$_2$O (3/1 mL) was added (3-cyanophenyl)boronic acid (300 mg, 2.04 mmol), tetrakis(triphenylphosphine)palladium (197 mg, 0.17 mmol) and potassium phosphate (730 mg, 3.44 mmo). The resulting solution was stirred overnight at 80° C. After cooling down to room temperature, the resulting mixture was washed with brine (30 mL), extracted with dichloromethane (3×20 mL), dried over anhydrous sodium sulfate and concentrated under vacuum. The residue was purified by silica gel chromatography with ethyl acetate/petroleum ether (1:2) to afford of 3-([3-bromo-2-methyl-5-oxo-5H-[1,3]thiazolo[3,2-a]pyrimidin-7-yl]methyl)benzonitrile as a light brown solid (522 mg, 85%). LCMS [M+H]$^+$=360.0, 362.0.

| No. | Structure/Name | LCMS (M + H) | $^1$H NMR |
|---|---|---|---|
| 22.2 | 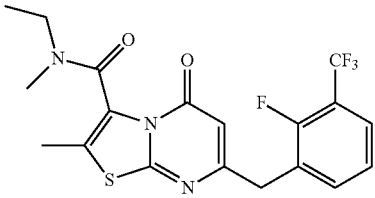 [SMILES: CCN(C)C(=O)c1c(C)sc2nc(Cc3cccc(C(F)(F)F)c3F)cc(=O)n12]<br>N-ethyl-7-(2-fluoro-3-(trifluoromethyl)benzyl)-N,2-dimethyl-5-oxo-5H-thiazolo[3,2-a]pyrimidine-3-carboxamide | 428.0 | $^1$H NMR (300 MHz, CDCl$_3$) δ 7.55-7.48 (m, 2H), 7.26-7.18 (m, 1H), 6.05 (s, 1H), 3.97 (s, 2H), 3.77-3.68 (m, 0.5H), 3.54-3.45 (m, 0.5H), 3.26-3.18 (m, 1H), 3.11 (s, 1H), 2.86 (s, 2H), 2.34 (s, 3H), 1.30-1.25 (m, 2H), 1.17-1.12 (m, 1H). |

Method 23

Example 23.1: 3-((3-(2-cyanocyclopropyl)-2-methyl-5-oxo-5H-thiazolo[3,2-a]pyrimidin-7-yl)methyl)benzonitrile

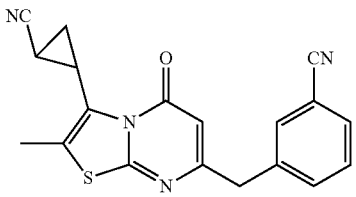 [SMILES: Cc1sc2nc(Cc3cccc(C#N)c3)cc(=O)n2c1C1CC1C#N]

Step 1: 3-((3-bromo-2-methyl-5-oxo-5H-thiazolo[3,2-a]pyrimidin-7-yl)methyl)benzonitrile

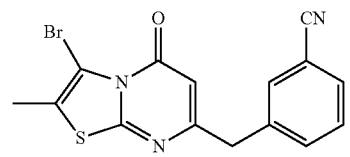 [SMILES: Cc1sc2nc(Cc3cccc(C#N)c3)cc(=O)n2c1Br]

Step 2: ethyl 2-(7-(3-cyanobenzyl)-2-methyl-5-oxo-5H-thiazolo[3,2-a]pyrimidin-3-yl)cyclopropanecarboxylate

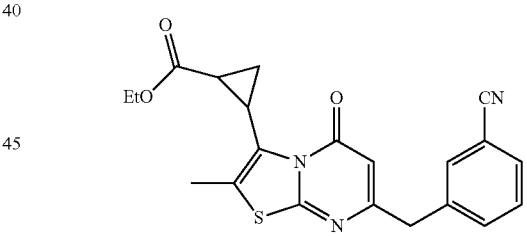

To a solution of 3-([3-bromo-2-methyl-5-oxo-5H-[1,3]thiazolo[3,2-a]pyrimidin-7-yl]methyl)benzonitrile (200 mg, 0.56 mmol) in CH$_3$CN/H$_2$O (3/1 mL) was added ethyl 2-(tetramethyl-1,3,2-dioxaborolan-2-yl)cyclopropane-1-carboxylate (from Example 4.18, Step 1) (267 mg, 1.11 mmol), [1,1'-bis(diphenylphosphino)ferrocene]palladium (II) dichloride (42 mg, 0.06 mmol) and potassium carbonate (154 mg, 1.11 mmol). The reaction mixture was heated under microwave irradiation for 1.5 h at 120° C. The resulting mixture was washed with brine (20 mL), extracted with dichloromethane (3×20 mL), dried over anhydrous sodium sulfate and concentrated under vacuum. The residue was purified by chromatography with dichloromethane/methanol (50:1) to afford ethyl 7-[(3-cyanophenyl)methyl]-2-methyl-5-oxo-5H-[1,3]thiazolo[3,2-a]pyrimidine-3-carboxylate (68 mg 35%) as a brown solid. LCMS (ESI): [M+H]$^+$=394.0.

Step 3: 2-(7-(3-cyanobenzyl)-2-methyl-5-oxo-5H-thiazolo[3,2-a]pyrimidin-3-yl)cyclopropanecarboxylic acid

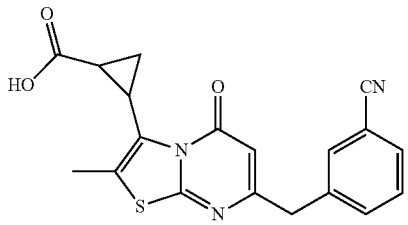 [SMILES: Cc1sc2nc(Cc3cccc(C#N)c3)cc(=O)n2c1C1CC1C(=O)O]

To a solution of 7-[(3-cyanophenyl)methyl]-2-methyl-5-oxo-5H-[1,3]thiazolo[3,2-a]pyrimidin-3-yl]cyclopropane-1-carboxylate (68 mg, 0.17 mmol) in THF/H$_2$O (2/1 mL) was added lithium hydroxide (73 mg, 1.7 mmol). The resulting solution was stirred overnight at room temperature. The pH of the solution was adjusted to pH 7 with hydrochloric acid solution (aq.) and the resulting mixture was extracted with ethyl acetate (3×20 mL), washed with brine, dried over sodium sulfate and concentrated under vacuum to afford 2-[7-[(3-cyanophenyl)methyl]-2-methyl-5-oxo-5H-[1,3]thiazolo[3,2-a]pyrimidin-3-yl]cyclopropane-1-carboxylic acid (80 mg, crude) as a brown solid. The crude product was used in next step without further purification. LCMS (ESI): [M+H]$^+$=366.0.

Step 4: 2-(7-(3-cyanobenzyl)-2-methyl-5-oxo-5H-thiazolo[3,2-a]pyrimidin-3-yl)cyclopropanecarboxamide

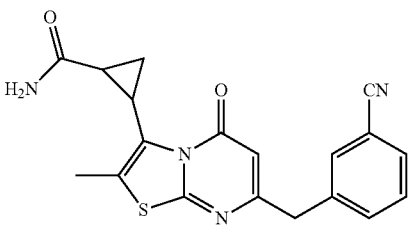 [SMILES: Cc1sc2nc(Cc3cccc(C#N)c3)cc(=O)n2c1C1CC1C(N)=O]

To a solution of 2-[7-[(3-cyanophenyl)methyl]-2-methyl-5-oxo-5H-[1,3]thiazolo[3,2-a]pyrimidin-3-yl]cyclopropane-1-carboxylic acid (80 mg, 0.22 mmol) in tetrahydrofuran (5 mL) was added propan-2-yl chloroformate (40.4 mg, 0.33 mmol), triethylamine (44 mg, 0.43 mmol) and ammonia (2 mL, 25 weight % in water). The resulting solution was stirred for 1 h at room temperature and concentrated under vacuum, and the residue was purified by chromatography with dichloromethane/methanol (30:1) to afford 2-[7-[(3-cyanophenyl)methyl]-2-methyl-5-oxo-5H-[1,3]thiazolo[3,2-a]pyrimidin-3-yl]cyclopropane-1-carboxamide (21 mg, 26%) as a brown solid. LCMS (ESI): [M+H]$^+$=364.9.

Step 5: 3-((3-(2-cyanocyclopropyl)-2-methyl-5-oxo-5H-thiazolo[3,2-a]pyrimidin-7-yl)methyl)benzonitrile

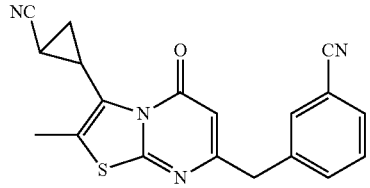 [SMILES: Cc1sc2nc(Cc3cccc(C#N)c3)cc(=O)n2c1C1CC1C#N]

To a solution of 2-[7-[(3-cyanophenyl)methyl]-2-methyl-5-oxo-5H-[1,3]thiazolo[3,2-a]pyrimidin-3-yl]cyclopropane-1-carboxamide (17 mg, 0.05 mmol) in methylene chloride (10 mL) was added 1,8-diazabicyclo[5.4.0]undec-7-ene (0.25 mL) and ethoxyphosphonoyl dichloride (0.25 mL). The resulting solution was stirred for 1 h at room temperature. The reaction was then quenched by water (30 mL), extracted with dichloromethane (3×20 mL), washed with brine, and concentrated under vacuum. The residue was purified on a silica gel column eluted with dichloromethane/methanol (50:1) to afford 3-[[3-(2-cyanocyclopropyl)-2-methyl-5-oxo-5H-[1,3]thiazolo[3,2-a]pyrimidin-7-yl]methyl]benzonitrile (12.6 mg, 78%) as a off-white solid. LCMS (ESI): [M+H]$^+$=347.0; $^1$H NMR (300 MHz, CDCl$_3$) δ 7.69-7.60 (m, 3H), 7.53-7.47 (m, 1H), 6.16 (s, 1H), 3.94 (s, 2H), 2.92-2.88 (m, 1H), 2.39 (s, 3H), 1.96-1.92 (m, 1H), 1.81-1.74 (m, 1H), 1.59-1.52 (m, 1H).

Example 23.2: 3-((3-(2-cyanocyclopropyl)-2-methyl-5-oxo-5H-thiazolo[3,2-a]pyrimidin-7-yl)methyl)-2-fluorobenzonitrile

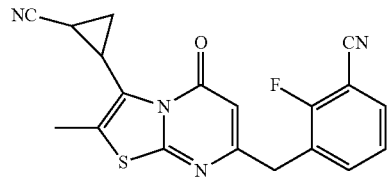 [SMILES: Cc1sc2nc(Cc3cccc(C#N)c3F)cc(=O)n2c1C1CC1C#N]

Step 1: 3-((3-bromo-2-methyl-5-oxo-5H-thiazolo[3,2-a]pyrimidin-7-yl)methyl)-2-fluorobenzonitrile

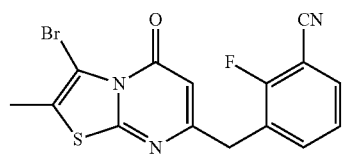 [SMILES: Cc1sc2nc(Cc3cccc(C#N)c3F)cc(=O)n2c1Br]

A mixture of 3-bromo-7-(chloromethyl)-2-methyl-5H-[1,3]thiazolo[3,2-a]pyrimidin-5-one (from Example 4.1, Step 6) (500 mg, 1.70 mmol), potassium phosphate (733 mg, 3.45 mmol), tetrakis(triphenylphosphine)palladium (198 mg, 0.17 mmol), (3-cyano-2-fluorophenyl)boronic acid (339 mg, 2.06 mmol), 1,4-dioxane (6 mL) and water (1 mL) was stirred overnight at 80° C. in a 30-mL sealed tube. The resulting mixture was diluted with brine and extracted with 3×30 mL of dichloromethane, and the combined organic layers were washed with brine, dried over anhydrous sodium sulfate, and concentrated under vacuum. The residue was purified by silica gel chromatography with dichloromethane/methanol (80:1) to afford 3-([3-bromo-2-methyl-5-oxo-5H-[1,3]thiazolo[3,2-a]pyrimidin-7-yl]methyl)-2-fluorobenzonitrile (70 mg, 11%) as a yellow solid. LCMS (ESI): [M+H]$^+$=378.

Step 2: 3-((3-(2-cyanocyclopropyl)-2-methyl-5-oxo-5H-thiazolo[3,2-a]pyrimidin-7-yl)methyl)-2-fluorobenzonitrile

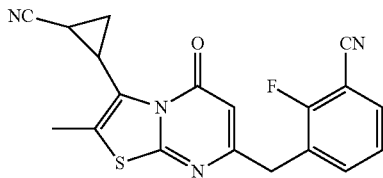 [SMILES: Cc1sc2nc(Cc3cccc(C#N)c3F)cc(=O)n2c1C1CC1C#N]

To a solution of 3-([3-bromo-2-methyl-5-oxo-5H-[1,3]thiazolo[3,2-a]pyrimidin-7-yl]methyl)-2-fluorobenzonitrile (100 mg, 0.26 mmol) in 1,4-dioxane/H$_2$O (2 mL/0.5 mL) added tetrakis(triphenylphosphine)palladium (31 mg, 0.03 mmol,), potassium phosphate (112 mg, 0.53 mmol), and potassium trans-2-cyanocyclopropyltrifluoroborate (prepared in a manner similar to Example 4.1, Step 2) (92 mg, 0.53 mmol). The resulting solution was stirred for 3 h at 80° C. After filtration to remove solids, the filtrate was concentrated under vacuum and purified by chromatography with dichloromethane/methanol (100:1) to afford 3-[[3-(2-cyanocyclopropyl)-2-methyl-5-oxo-5H-[1,3]thiazolo[3,2-a]pyrimidin-7-yl]methyl]-2-fluorobenzonitrile (16 mg, 17%) as a white solid. LCMS (ESI): [M+H]$^+$=364.9; $^1$H NMR (300 MHz, CDCl$_3$) δ 7.60-7.54 (m, 2H), 7.28-7.21 (m, 1H), 6.03 (s, 1H), 3.94 (s, 2H), 3.00-2.94 (m, 1H), 2.43 (s, 3H), 1.90-1.80 (m, 1H), 1.79-1.70 (m, 1H), 1.45-1.35 (m, 1H).

The following example was prepared in a manner similar to Example 23.1 and 23.2:

| No. | Structure/Name | LCMS (M + H) | $^1$H NMR |
|---|---|---|---|
| 23.3 | 6-((3-(2-cyanocyclopropyl)-2-methyl-5-oxo-5H-thiazolo[3,2-a]pyrimidin-7-yl)methyl)picolinonitrile | 348.05 | $^1$H NMR (300 MHz, CDCl$_3$) δ 7.95-7.92 (m, 1H), 7.77-7.69 (m, 2H), 6.21 (s, 1H), 4.86 (s, 2H), 2.86-2.98 (m, 1H), 2.39 (s, 3H), 1.28-2.02 (m, 3H) |

The following compound was prepared using methods analogous to those described above:

| No. | Structure/Name | LCMS (M + H) | $^1$H NMR |
|---|---|---|---|
| 23.4 | 3-((3-(2-cyanocyclopropyl)-2-methyl-5-oxo-5H-thiazolo[3,2-a]pyrimidin-7-yl)methyl)-4-methoxybenzonitrile | 753.15 | $^1$H NMR (300 MHz, CDCl$_3$) δ 7.62 (m, 1H), 7.50 (s, 1H), 6.96 (m, 1H), 6.01 (s, 1H), 3.91 (s, 3H), 3.88 (s, 2H), 3.01 (m, 1H), 2.41 (s, 3H), 1.81 (m, 1H), 1.74 (m, 1H), 1.41 (m, 1H) |

Method 24

Example 24.1: 2-methyl-3-(pyrimidin-5-yl)-7-(3-(trifluoromethyl)benzyl)-5H-thiazolo[3,2-a]pyrimidin-5-one

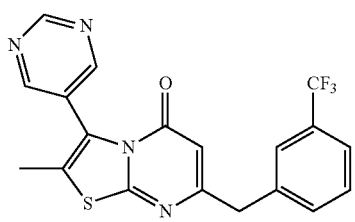 [SMILES: Cc1sc2nc(Cc3cccc(C(F)(F)F)c3)cc(=O)n2c1-c1cncnc1]

To a solution of 3-bromo-2-methyl-7-[[3-(trifluoromethyl)phenyl]methyl]-5H-[1,3]thiazolo[3,2-a]pyrimidin-5-one (prepared in a manner similar to Example 21.1, Step 1) (60 mg, 0.15 mmol) in 1,4-dioxane (2 mL) was added (pyrimidin-5-yl)boronic acid (37 mg, 0.30 mmol), potassium phosphate (64 mg, 0.30 mmol), tetrakis(triphenylphosphine)palladium (17 mg, 0.01 mmol) and water (0.2 mL). The resulting solution was stirred for 3 h at 90° C. in an oil bath. The resulting solution was quenched with water (10 mL), extracted with dichloromethane (3×20 mL), washed with brine, dried over anhydrous sodium sulfate and concentrated under vacuum. The residue was then purified by chromatography with ethyl acetate/petroleum ether (1:2.5) to afford 2-methyl-3-(pyrimidin-5-yl)-7-[[3-(trifluoromethyl)phenyl]methyl]-5H-[1,3]thiazolo[3,2-a]pyrimidin-5-one (27.7 mg, 46%) as a off-white solid. LCMS (ESI): [M+H+41]⁺444.1; $^1$H NMR (300 MHz, CD$_3$OD) δ 9.18 (s, 1H), 8.82 (s, 2H), 7.65-7.55 (m, 4H), 6.11 (s, 1H), 4.03 (s, 2H), 2.28 (s, 3H).

The following examples were prepared in a manner similar to Example 24.1:

| No. | Structure/Name | LCMS (M + H) | $^1$H NMR |
|---|---|---|---|
| 24.2 | 7-(2-fluoro-3-(trifluoromethyl)benzyl)-2-methyl-3-(pyrimidin-5-yl)-5H-thiazolo[3,2-a]pyrimidin-5-one | 421.0 | $^1$H NMR (300 MHz, CDCl$_3$) δ 9.25 (s, 1H), 8.70 (s, 2H), 7.56-7.50 (m, 2H), 7.22-7.19 (m, 1H), 5.99 (s, 1H), 3.99 (s, 2H), 2.27 (s, 3H) |
| 24.3 | 2-fluoro-3-((2-methyl-5-oxo-3-(pyrimidin-5-yl)-5H-thiazolo[3,2-a]pyrimidin-7-yl)methyl)benzonitrile | 378.0 | $^1$H NMR (300 MHz, CDCl$_3$) δ 9.25 (s, 1H), 8.69 (s, 2H), 7.60-7.53 (m, 2H), 7.23-7.21 (m, 1H), 6.00 (s, 1H), 3.96 (s, 2H), 2.26 (s, 3H) |
| 24.4 | 3-((3-cyclopropyl-2-methyl-5-oxo-5H-thiazolo[3,2-a]pyrimidin-7-yl)methyl)-2-fluorobenzonitrile | 340.0 | $^1$H NMR (300 MHz, CDCl$_3$) δ 7.60-7.51 (m, 2H), 7.24-7.18 (m, 1H), 5.96 (s, 1H), 3.90 (s, 2H), 2.36 (s, 3H), 2.26-2.25 (m, 1H), 1.10-1.03 (m, 2H), 0.69-0.65 (m, 2H) |

The following compounds were prepared using methods analogous to those described above:

| No. | Structure/Name | LCMS (M + H) | ¹H NMR |
|---|---|---|---|
| 24.5 | 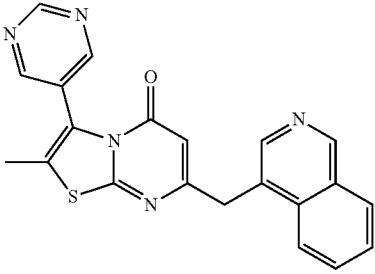 [SMILES: Cc1sc2nc(Cc3cncc4ccccc34)cc(=O)n2c1-c1cncnc1]<br>7-(isoquinolin-4-ylmethyl)-2-methyl-3-(pyrimidin-5-yl)-5H-thiazolo[3,2-a]pyrimidin-5-one | 386.0 | ¹H NMR (300 MHz, CDCl₃) δ 9.22 (s, 2H), 8.66 (s, 2H), 8.49 (s, 1H), 8.03 (m, 1H), 7.95 (m, 1H), 7.76-7.62 (m, 2H), 5.87 (s, 1H), 4.32 (s, 2H), 2.26 (s, 3H) |
| 24.6 | 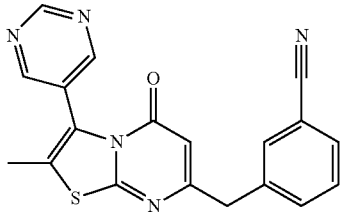 [SMILES: Cc1sc2nc(Cc3cccc(C#N)c3)cc(=O)n2c1-c1cncnc1]<br>3-((2-methyl-5-oxo-3-(pyrimidin-5-yl)-5H-thiazolo[3,2-a]pyrimidin-7-yl)methyl)benzonitrile | 401.15 | ¹H NMR (300 MHz, CDCl₃) δ 9.26 (s, 1H), 8.76 (s, 2H), 7.68-7.41 (m, 3H), 7.29-7.26 (m, 1H), 6.02 (s, 1H), 3.92 (s, 2H), 2.27 (s, 3H) |
| 24.7 | 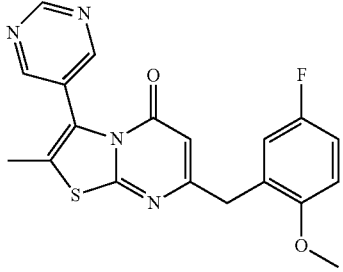 [SMILES: COc1ccc(F)cc1Cc1cc(=O)n2c(-c3cncnc3)c(C)sc2n1]<br>7-(5-fluoro-2-methoxybenzyl)-2-methyl-3-(pyrimidin-5-yl)-5H-thiazolo[3,2-a]pyrimidin-5-one | 382.95 | ¹H NMR (300 MHz, CD₃OD) δ 9.21 (s, 1H), 8.81 (s, 2H), 7.07-6.95 (m, 3H), 5.92 (s, 1H), 3.91 (s, 2H), 3.79 (s, 3H), 2.17 (s, 3H) |
| 24.8 | 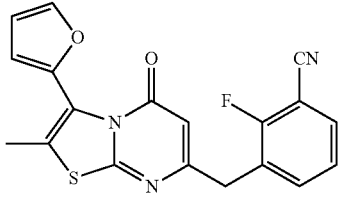 [SMILES: Cc1sc2nc(Cc3cccc(C#N)c3F)cc(=O)n2c1-c1ccco1]<br>2-fluoro-3-((3-(furan-2-yl)-2-methyl-5-oxo-5H-thiazolo[3,2-a]pyrimidin-7-yl)methyl)benzonitrile | 366.0 | ¹H NMR (300 MHz, CDCl₃) δ 7.58-7.52 (m, 3H), 7.24-7.19 (m, 1H), 6.52-6.50 (m, 2H), 6.01 (s, 1H), 3.95 (s, 2H), 2.30 (s, 3H) |

| No. | Structure/Name | LCMS (M + H) | ¹H NMR |
|---|---|---|---|
| 24.9 | 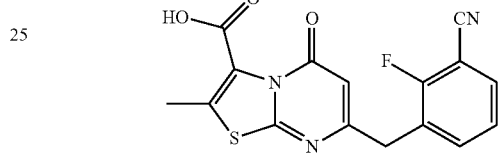<br>3-bromo-2-methyl-7-(3-(methylsulfonyl)benzyl)-5H-thiazolo[3,2-a]pyrimidin-5-one | 415 | ¹H NMR (300 MHz, CDCl₃) δ 7.87-7.84 (m, 3H), 7.56-7.53 (m, 1H), 6.04 (s, 1H), 3.95 (s, 2H), 3.06 (s, 3H), 2.35 (s, 3H) |

Method 25

Example 25.1: 7-(3-cyano-2-fluorobenzyl)-2-methyl-5-oxo-N-(2,2,2-trifluoroethyl)-5H-thiazolo[3,2-a]pyrimidine-3-carboxamide

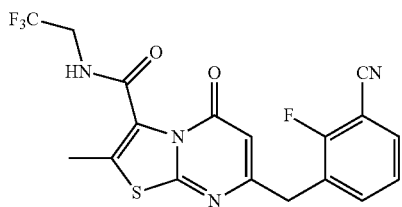 [SMILES: Cc1sc2nc(Cc3cccc(C#N)c3F)cc(=O)n2c1C(=O)NCC(F)(F)F]

Step 1: ethyl 7-(3-cyano-2-fluorobenzyl)-2-methyl-5-oxo-5H-thiazolo[3,2-a]pyrimidine-3-carboxylate

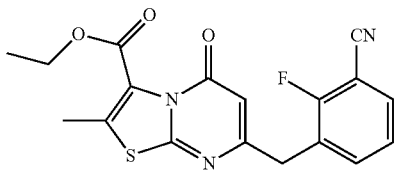 [SMILES: CCOC(=O)c1c(C)sc2nc(Cc3cccc(C#N)c3F)cc(=O)n12]

To a solution of ethyl 7-(chloromethyl)-2-methyl-5-oxo-5H-[1,3]thiazolo[3,2-a]pyrimidine-3-carboxylate (500 mg, 1.74 mmol) in dioxane (2 mL) and water (0.5 mL) was added (3-cyano-2-fluorophenyl)boronic acid (375 mg, 2.27 mmol), sodium carbonate (370 mg, 3.49 mmol) and [1,1'-bis(diphenylphosphino)ferrocene]palladium(II) dichloride (77 mg, 0.11 mmol). After stirring 20 minutes at 120° C. under nitrogen atmosphere, the resulting mixture was concentrated under vacuum. The residue was purified by chromatography with 10% ethyl acetate in dichloromethane to afford ethyl 7-[(3-cyano-2-fluorophenyl)methyl]-2-methyl-5-oxo-5H-[1,3]thiazolo[3,2-a]pyrimidine-3-carboxylate (23.1 mg, 18%) as a white solid. LCMS (ESI): [M+H]⁺=372.0; ¹H NMR (300 MHz, CDCl₃) δ 7.72-7.66 (m, 2H), 7.36-7.31 (m, 1H), 6.19 (s, 1H), 4.44-4.37 (m, 2H), 4.06 (s, 2H), 2.43 (s, 3H), 1.36 (m, 3H).

Step 2: 7-(3-cyano-2-fluorobenzyl)-2-methyl-5-oxo-5H-thiazolo[3,2-a]pyrimidine-3-carboxylic acid

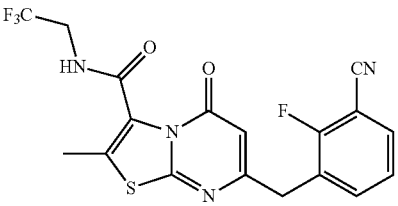 [SMILES: Cc1sc2nc(Cc3cccc(C#N)c3F)cc(=O)n2c1C(=O)NCC(F)(F)F]

To a solution of ethyl 7-[(3-cyano-2-fluorophenyl)methyl]-2-methyl-5-oxo-5H-[1,3]thiazolo[3,2-a]pyrimidine-3-carboxylate (prepared in a manner similar to Example 21.1) (100 mg, 0.27 mmol) in tetrahydrofuran (3 mL) was added lithium hydroxide (64 mg, 2.67 mmol) in water (3 mL). The resulting solution stirred for 3 days at room temperature. The reaction mixture was diluted with dichloromethane (20 mL) and water (5 mL). The pH value of the water layer was adjusted to pH 6 with hydrogen chloride. The resulting solution was extracted with dichloromethane (3×10 mL), washed with brine, dried over anhydrous sodium sulfate and concentrated under vacuum to afford 7-[(3-cyano-2-fluorophenyl)methyl]-2-methyl-5-oxo-5H-[1,3]thiazolo[3,2-a]pyrimidine-3-carboxylic acid (22 mg, 24%) as a brown solid. The crude product was used in next step without further purification. LCMS (ESI): [M+H]⁺=344.0.

Step 3: 7-(3-cyano-2-fluorobenzyl)-2-methyl-5-oxo-N-(2,2,2-trifluoroethyl)-5H-thiazolo[3,2-a]pyrimidine-3-carboxamide To a solution of 7-[(3-cyano-2-fluorophenyl)methyl]-2-methyl-5-oxo-5H-[1,3]thiazolo[3,2-a]pyrimidine-3-carboxylic acid (60 mg, 0.17 mmol) in N,N-dimethylformamide (9 mL) was added 2,2,2-trifluoroethan-1-amine (36 mg, 0.36 mmol), N-hydroxybenzotriazole (36 mg, 0.27 mmol), N,N-diisopropylethylamine (66 mg, 0.51 mmol) and 1,1'-thiocarbonyldiimidazole (48 mg, 0.27 mmol). After stirred for 5 h at room temperature, the mixture was diluted with water (5 mL). The resulting solution was extracted with dichloromethane (20 mL×3), washed with brine, dried over anhydrous sodium sulfate and concentrated under vacuum. The residue was purified by chromatography with 1% methanol in dichloromethane. The crude product was purified by Prep-HPLC (SunFire Prep $C_{18}$ OBD Column, 5 um, 19×150 mm; mobile phase, water with 10 mmol $NH_4HCO_3$ and $CH_3CN$ (50.0% $CH_3CN$ up to 82.0% in 10 min, down to 50.0% in 2 min); Detector, UV 254/220 nm) to afford 7-[(3-cyano-2-fluorophenyl)methyl]-2-methyl-5-oxo-N-(2,2,2-trifluoroethyl)-5H-[1,3]thiazolo[3,2-a]pyrimidine-3-carboxamide (20.8 mg, 28%) as a white solid. LCMS (ESI): [M+H]$^+$ 424.95; $^1$H NMR (300 MHz, CD$_3$OD) δ 7.72-7.66 (m, 2H), 7.36-7.31 (m, 1H), 6.19 (s, 1H), 4.15-4.06 (m, 4H), 2.40 (s, 3H).

The following example was prepared in a manner similar to Example 25.1:

Step 1: 7-(3-cyanobenzyl)-2-methyl-5-oxo-5H-thiazolo[3,2-a]pyrimidine-3-carbonitrile

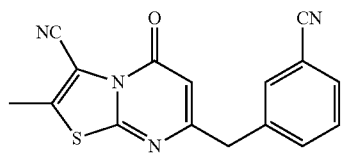

To a solution of 3-([3-bromo-2-methyl-5-oxo-5H-[1,3]thiazolo[3,2-a]pyrimidin-7-yl]methyl)benzonitrile (from Example 21.1, Step 1) (100 mg, 0.28 mmol) in N,N-dimethylformamide (10 mL) under inert atmosphere was added copper cyanide (49 mg, 0.55 mmol). The resulting solution was stirred for 1 h at 100° C. After cooling to room temperature, the reaction mixture was concentrated under vacuum. The residue was purified by chromatography with dichloromethane/methanol (50:1) to afford 7-[(3-cyanophenyl)methyl]-2-methyl-5-oxo-5H-[1,3]thiazolo[3,2-a]pyrimidine-3-carbonitrile (8.4 mg, 10%) as a off-white solid. LCMS (ESI): [M+H]$^+$=306.9; $^1$H NMR (300 MHz, CDCl$_3$) δ 7.60-7.56 (m, 2H), 7.51-7.41 (m, 2H), 6.17 (s, 1H), 3.91 (s, 2H), 2.65 (s, 3H).

| No. | Structure/Name | LCMS (M + H) | $^1$H NMR |
|---|---|---|---|
| 25.2 | N-(cyanomethyl)-7-(2-fluoro-3-(trifluoromethyl)benzyl)-2-methyl-5-oxo-5H-thiazolo[3,2-a]pyrimidine-3-carboxamide | 424.95 | (300 MHz, DMSO-d$_6$) δ 9.15 (m, 1H), 7.75-7.68 (m, 2H), 7.42-7.37 (m, 1H), 6.16 (s, 1H), 4.32 (m, 2H), 4.03 (s, 2H), 2.31 (s, 3H) |

Method 26

Example 26.1: 7-(3-cyanobenzyl)-2-methyl-5-oxo-5H-thiazolo[3,2-a]pyrimidine-3-carbonitrile

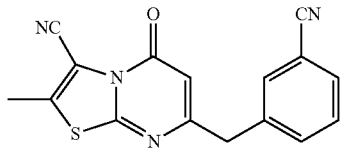

The following example was prepared in a manner similar to Example 26.1:

| No. | Structure/Name | LCMS (M + H) | $^1$H NMR |
|---|---|---|---|
| 26.2 | 7-(2-fluoro-3-(trifluoromethyl)benzyl)-2-methyl-5-oxo-5H-thiazolo[3,2-a]pyrimidine-3-carbonitrile | 368.0 | $^1$H NMR (300 MHz, CDCl$_3$) δ 7.57-7.48 (m, 2H), 7.23-7.21 (m, 1H), 6.16 (s, 1H), 3.98 (s, 2H), 2.65 (s, 3H) |

The following compounds were prepared using methods analogous to those described herein.

| No. | Structure/Name | LCMS (M + H) | ¹H NMR |
|---|---|---|---|
| 27.1 | 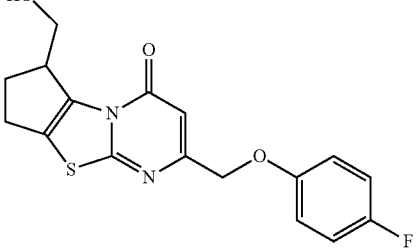  10-(4-fluorophenoxymethyl)-3-(hydroxymethyl)-7-thia-1,9-diazatricyclo[6.4.0.0^[2,6]]dodeca-2(6),8,10-trien-12-one | 347 | ¹H NMR (300 MHz, CDCl₃) δ 7.01-6.87 (m, 4H), 6.52 (s, 1H), 4.95 (s, 2H), 3.96-3.91 (m, 2H), 3.77-3.66 (m, 1H), 2.98-2.64 (m, 3H), 2.28-2.11 (m, 1H) |
| 27.2 | 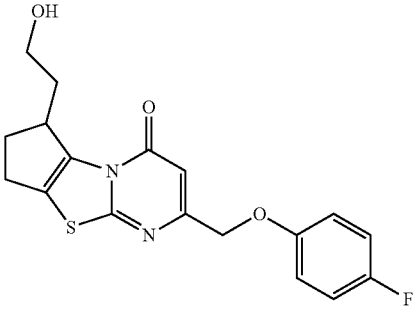 [SMILES: O=c1cc(COc2ccc(F)cc2)nc2sc3c(n12)C(CCO)CC3]  10-(4-Fluorophenoxymethyl)-3-(2-hydroxyethyl)-7-thia-1,9-diazatricyclo[6.4.0.0^[2,6]]dodeca-2(6),8,10-trien-12-one | 361.10 | ¹H NMR (300 MHz, CDCl₃) δ 7.02-6.88 (m, 4H), 6.48 (s, 1H), 4.94 (s, 2H), 3.95-3.91 (m, 1H), 3.68-3.62 (m, 2H), 2.99-2.91 (m, 1H), 2.85-2.69 (m, 2H), 2.30-2.24 (m, 1H), 2.00-1.89 (m, 2H) |
| 27.3 | 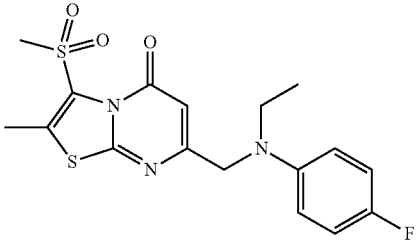 [SMILES: CCN(Cc1cc(=O)n2c(S(C)(=O)=O)c(C)sc2n1)c1ccc(F)cc1]  7-[(N-ethyl-4-fluoro-anilino)methyl]-2-methyl-3-methylsulfonyl-thiazolo[3,2-a]pyrimidin-5-one | 396.1 | |
| 27.4 | 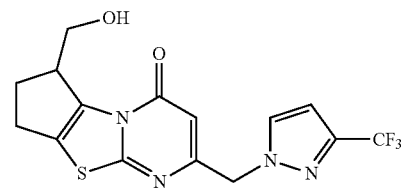 [SMILES: O=c1cc(Cn2ccc(C(F)(F)F)n2)nc2sc3c(n12)C(CO)CC3]  3-(hydroxymethyl)-10-[[3-(trifluoromethyl)-1H-pyrazol-1-yl]methyl]-7-thia-1,9-diazatricyclo[6.4.0.0^[2,6]]dodeca-2(6),8,10-trien-12-one | 388.15 | ¹H NMR (400 MHz, CD₃OD) δ 7.94 (s, 1H), 6.70 (s, 1H), 5.93 (s, 1H), 5.36 (s, 2H), 3.88-3.76 (m, 3H), 3.02-2.40 (m, 4H) |

| No. | Structure/Name | LCMS (M + H) | ¹H NMR |
|---|---|---|---|
| 27.5 | 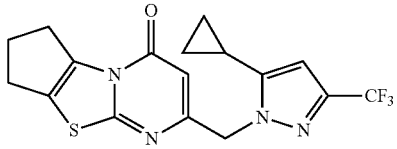 [SMILES: O=c1cc(Cn2nc(C(F)(F)F)cc2C2CC2)nc2sc3c(n12)CCC3]<br>10-{[5-cyclopropyl-3-(trifluoromethyl)-1H-pyrazol-1-yl]methyl}-7-thia-1,9-diazatricyclo[6.4.0.0^{2,6}]dodeca-2(6),8,10-trien-12-one | 381.00 | ¹H NMR (300 MHz, CD₃OD) δ 6.32 (s, 1H), 5.72 (s, 1H), 5.41 (m, 2H), 3.54-3.28 (m, 2H), 2.93-2.87 (m, 2H), 2.54-2.45 (m, 2H), 1.95-1.86 (m, 1H), 1.05-0.99 (m, 2H), 0.77-0.72 (m, 2H) |
| 27.6 | 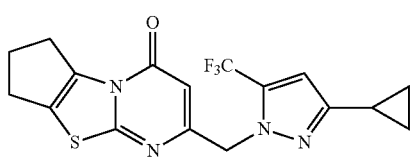 [SMILES: O=c1cc(Cn2nc(C3CC3)cc2C(F)(F)F)nc2sc3c(n12)CCC3]<br>10-{[3-cyclopropyl-5-(trifluoromethyl)-1H-pyrazol-1-yl]methyl}-7-thia-1,9-diazatricyclo[6.4.0.0^{2,6}]dodeca-2(6),8,10-trien-12-one | 381.00 | ¹H NMR (300 MHz, CD₃OD) δ 6.58 (s, 1H), 5.58 (s, 1H), 5.21 (m, 2H), 3.54-3.28 (m, 2H), 2.93-2.87 (m, 2H), 2.59-2.41 (m, 2H), 2.01-1.93 (m, 1H), 0.98-0.96 (m, 2H), 0.79-0.77 (m, 2H) |
| 27.7 | 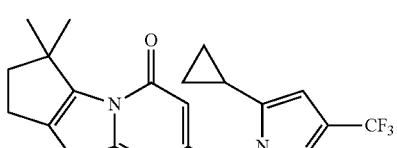<br>10-{[5-cyclopropyl-3-(trifluoromethyl)-1H-pyrazol-1-yl]methyl}-3,3-dimethyl-7-thia-1,9-diazatricyclo[6.4.0.0^{2,6}]dodeca-2(6),8,10-trien-12-one | 409.1 | ¹H NMR (300 MHz, CDCl₃) δ 6.17 (s, 1H), 5.65 (s, 1H), 5.33 (s, 2H), 2.85 (m, 2H), 2.38 (m, 2H), 1.75 (m, 1H), 1.50 (s, 6H), 1.01 (m, 2H), 0.75 (m, 2H) |
| 27.8 | 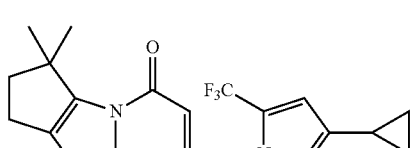<br>10-{[3-cyclopropyl-5-(trifluoromethyl)-1H-pyrazol-1-yl]methyl}-3,3-dimethyl-7-thia-1,9-diazatricyclo[6.4.0.0^{2,6}]dodeca-2(6),8,10-trien-12-one | 409.0 | ¹H NMR (300 MHz, CDCl₃) δ 6.34 (s, 1H), 5.51 (s, 1H), 5.23 (s, 2H), 2.85 (m, 2H), 2.36 (m, 2H), 1.94 (m 1H) 1.49 (s, 6H) 0.98 (m, 2H), 0.77 (m, 2H) |
| 27.9 | 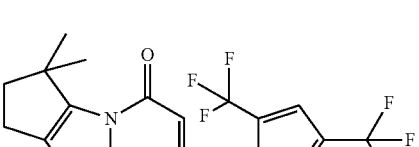<br>10-{[3,5-bis(trifluoromethyl)-1H-pyrazol-1-yl]methyl}-3,3-dimethyl-7-thia-1,9-diazatricyclo[6.4.0.0^{2,6}]dodeca-2(6),8,10-trien-12-one | 437.0 | ¹H NMR (300 MHz, CD₃OD) δ 7.30 (s, 1H), 5.88 (s, 1H), 5.50 (s, 2H), 2.90 (m, 2H), 2.39 (m, 2H), 1.50 (s, 6H) |

| No. | Structure/Name | LCMS (M + H) | ¹H NMR |
|---|---|---|---|
| 27.10 | 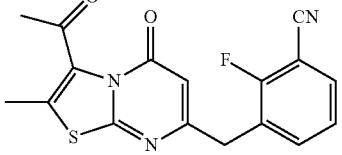<br>3-((3-acetyl-2-methyl-5-oxo-5H-thiazolo[3,2-a]pyrimidin-7-yl)methyl)-2-fluorobenzonitrile | 341.9 | ¹H NMR (400 MHz, CDCl$_3$) δ 7.58-7.54 (m, 2H), 7.26-7.22 (m, 1H), 6.10 (s, 1H), 3.97 (s, 2H), 2.46 (s, 3H), 2.36 (s, 3H) |
| 27.11 | 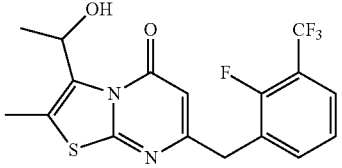 [SMILES: Cc1sc2nc(Cc3cccc(C(F)(F)F)c3F)cc(=O)n2c1C(C)O]<br>7-(2-fluoro-3-(trifluoromethyl)benzyl)-3-(1-hydroxyethyl)-2-methyl-5H-thiazolo[3,2-a]pyrimidin-5-one (enantiomer 1) | 387.0 | ¹H NMR (300 MHz, CDCl$_3$) δ 7.60-7.48 (m, 2H), 7.28-7.19 (m, 1H), 6.17 (s, 1H), 5.83 (m, 1H), 5.08-5.03 (m, 1H), 4.00 (s, 2H), 2.40 (s, 3H), 1.56-1.49 (m, 3H) |
| 27.12 | 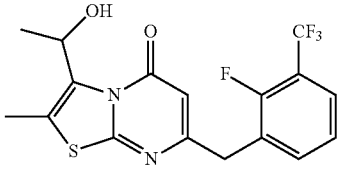 [SMILES: Cc1sc2nc(Cc3cccc(C(F)(F)F)c3F)cc(=O)n2c1C(C)O]<br>7-(2-fluoro-3-(trifluoromethyl)benzyl)-3-(1-hydroxyethyl)-2-methyl-5H-thiazolo[3,2-a]pyrimidin-5-one (enantiomer 2) | 387.0 | ¹H NMR (300 MHz, CDCl$_3$) δ 7.60-7.48 (m, 2H), 7.22-7.19 (m, 1H), 6.16 (s, 1H), 5.84 (m, 1H), 5.08-5.02 (m, 1H), 4.00 (s, 2H), 2.42 (s, 3H), 1.56-1.49 (m, 3H) |
| 27.13 | 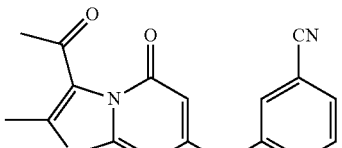<br>3-((3-acetyl-2-methyl-5-oxo-5H-thiazolo[3,2-a]pyrimidin-7-yl)methyl)benzonitrile | 323.95 | ¹H NMR (300 MHz, CDCl$_3$) δ 7.59-7.51 (m, 3H), 7.46-7.41 (m, 1H), 6.10 (s, 1H), 3.93 (s, 2H), 2.47 (s, 3H), 2.37 (s, 3H) |
| 27.14 | 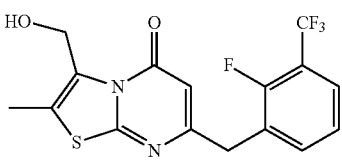 [SMILES: Cc1sc2nc(Cc3cccc(C(F)(F)F)c3F)cc(=O)n2c1CO]<br>7-(2-fluoro-3-(trifluoromethyl)benzyl)-3-(hydroxymethyl)-2-methyl-5H-thiazolo[3,2-a]pyrimidin-5-one | 273.10 | ¹H NMR (300 MHz, CDCl$_3$) δ 7.57-7.48 (m, 2H), 7.26-7.19 (m, 1H), 6.12 (s, 1H), 4.74 (s, 2H), 4.42 (br, 1H), 3.99 (s, 2H), 2.42 (s, 3H) |
| 27.15 | 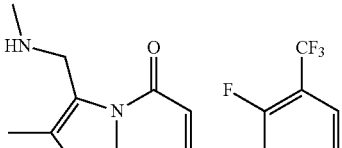 | 386.0 | ¹H NMR (300 MHz, CDCl$_3$) δ 7.61-7.47 (m, 2H), 7.26-7.19 (m, 1H), 6.04 (s, 1H), 4.06 (s, 2H), 3.96 (s, 2H), 2.46 (s, 3H), 2.43 (s, 3H) |

| No. | Structure/Name | LCMS (M + H) | ¹H NMR |
|---|---|---|---|
| | 7-(2-fluoro-3-(trifluoromethyl)benzyl)-2-methyl-3-((methylamino)methyl)-5H-thiazolo[3,2-a]pyrimidin-5-one | | |

Example 12: 3-[2-(Hydroxymethyl)cyclopropyl]-2-methyl-7-[3-(trifluoromethyl)phenoxy]thiazolo[3,2-a]pyrimidin-5-one

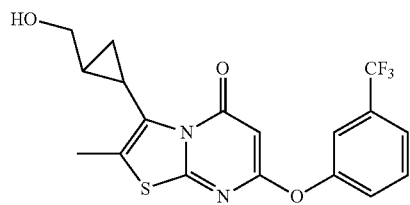

Step 1: 7-Hydroxy-2-methyl-5H-thiazolo[3,2-a]pyrimidin-5-one

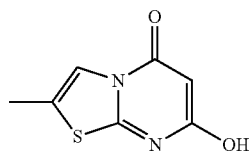

To a solution of 5-methyl-1,3-thiazol-2-amine (10 g, 87.6 mmol) in xylene (300 mL) was added 1,3-dimethyl propanedioate (23 g, 174 mmol), and stirred overnight at 150° C. The resulting mixture was concentrated in vacuo to afford 7-hydroxy-2-methyl-5H-[1,3]thiazolo[3,2-a]pyrimidin-5-one (14.6 g, 91%) as a light brown solid. LCMS (ESI): M+H$^+$=183.0;

Step 2: 7-Chloro-2-methyl-5H-thiazolo[3,2-a]pyrimidin-5-one

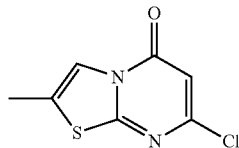

To a solution of 7-hydroxy-2-methyl-5H-[1,3]thiazolo[3,2-a]pyrimidin-5-one (30 g, 165 mmol) in phosphorus oxychloride (250 mL, 2.68 mol) was stirred for 5 h at 110° C. The resulting solution was concentrated in vacuo. The residue was purified by chromatography on silica gel eluting with dichloromethane/ethyl acetate (30/1) to afford 7-chloro-2-methyl-5H-[1,3]thiazolo[3,2-a]pyrimidin-5-one (2.34 g, 7%) as a yellow solid. LCMS (ESI): M+H$^+$=201.0.

Step 3: 2-Methyl-7-(3-(trifluoromethyl)phenoxy)-5H-thiazolo[3,2-a]pyrimidin-5-one

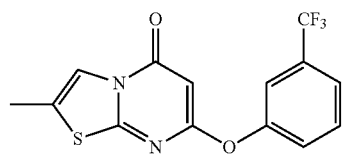 [SMILES: Cc1cn2c(=O)cc(Oc3cccc(C(F)(F)F)c3)nc2s1]

To a solution of 7-chloro-2-methyl-5H-thiazolo[3,2-a]pyrimidin-5-one (500 mg, 2.50 mmol) in N,N-dimethylformamide (50 mL) was added 3-(trifluoromethyl)phenol (808 mg, 5 mmol) and potassium carbonate (1.03 g, 7.5 mmol). The resulting solution was stirred overnight at 100° C. and then concentrated in vacuo. The residue was purified by flash chromatography on silica gel eluting with dichloromethane/methanol (50/1) to afford 2-methyl-7-(3-(trifluoromethyl)phenoxy)-5H-thiazolo[3,2-a]pyrimidin-5-one (500 mg, 61%) as a yellow solid. LCMS (ESI): M+H$^+$=327.0.

Step 4: 3-Bromo-2-methyl-7-[3-(trifluoromethyl)phenoxy]-5H-[1,3]thiazolo[3,2-a]pyrimidin-5-one

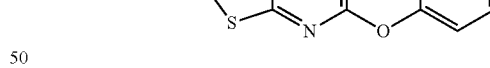

To a solution of 2-methyl-7-[3-(trifluoromethyl)phenoxy]-5H-[1,3]thiazolo[3,2-a]pyrimidin-5-one (500 mg, 1.53 mmol) in tetrahydrofuran (30 mL) was dropwise added n-butyllithium (1.5 mL, 2.5 mol/L) at −78° C. under an inert atmosphere of nitrogen, and the reaction was stirred for 30 mins at −78° C. 1-Bromopyrrolidine-2,5-dione (300 mg, 1.69 mmol) was added at −78° C. and the resulting solution was raised slowly to room temperature. The reaction was quenched by 30 mL of water, then extracted and concentrated in vacuo. The residue was purified by chromatography on silica gel eluting with dichloromethane/petroleum ether (10/1) to afford 3-bromo-2-methyl-7-[3-(trifluoromethyl)phenoxy]-5H-[1,3]thiazolo[3,2-a]pyrimidin-5-one (100 mg, 13%) as an off-white solid. LCMS (ESI): M+H$^+$=405.0.

Step 5: 3-[2-(Hydroxymethyl)cyclopropyl]-2-methyl-7-[3-(trifluoromethyl)phenoxy]-5H-[1,3]thiazolo[3,2-a]pyrimidin-5-one

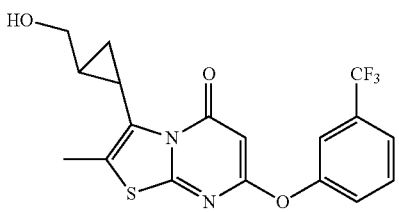

To a solution of 3-bromo-2-methyl-7-[3-(trifluoromethyl)phenoxy]-5H-[1,3]thiazolo[3,2-a]pyrimidin-5-one (30 mg, 0.07 mmol) in acetonitrile/water (2 mL/0.5 mL) was added bis(diphenylphosphino)ferrocene]palladium(II) dichloride (6 mg, 0.01 mmol), sodium carbonate (16 mg, 0.15 mmol), and potassium trans-2-(hydroxymethyl)cyclopropyltrifluoroborate (26 mg, 0.15 mmol). The reaction mixture was irradiated with microwave radiation for 90 min at 120° C. and then concentrated in vacuo. The residue was purified by flash chromatography on silica gel eluting with dichloromethane/methanol (50/1) to afford 3-[2-(hydroxymethyl)cyclopropyl]-2-methyl-7-[3-(trifluoromethyl)phenoxy]-5H-[1,3]thiazolo[3,2-a]pyrimidin-5-one (1.2 mg, 4%) as an off-white solid. LCMS (ESI): M+H$^+$=396.9; $^1$H NMR (300 MHz, CDCl$_3$) δ 7.57-7.52 (m, 2H), 7.40 (s, 1H), 7.35-7.31 (m, 1H), 5.58 (s, 1H), 4.08-4.05 (m, 1H), 3.12-3.07 (m, 1H), 2.38 (s, 3H), 2.29-2.26 (m, 1H), 1.28-1.26 (m, 1H), 1.06-0.99 (m, 2H).

Example 24: 3-[2-(Hydroxymethyl)cyclopropyl]-2-methyl-7-[[4-(trifluoromethyl)thiazol-2-yl]methyl]thiazolo[3,2-a]pyrimidin-5-one

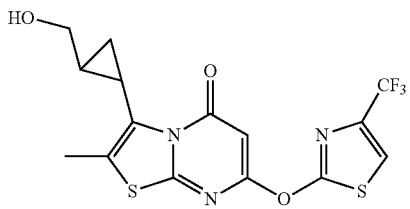

Step 1: Methyl 2-[3-bromo-2-methyl-5-oxo-5H-[1,3]thiazolo[3,2-a]pyrimidin-7-yl]acetate

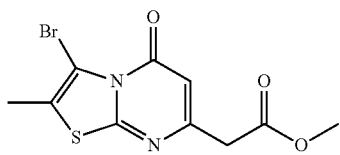

To a solution of 3-bromo-7-(chloromethyl)-2-methyl-5H-[1,3]thiazolo[3,2-a]pyrimidin-5-one (19.4 g, 66.1 mmol) in methanol (200 mL) was added [1,1"-bis(diphenylphosphino)ferrocene]palladium(II) dichloride (5.0 g, 6.83 mmol) and triethylamine (20 g, 197 mmol), and the reaction was placed under an atmosphere of CO (g) at 5 atm. The resulting solution was stirred for 12 h at room temperature and concentrated in vacuo. The residue was purified by flash chromatography on silica gel eluting with ethyl acetate/petroleum ether (1/3) to afford methyl 2-[3-bromo-2-methyl-5-oxo-5H-[1,3]thiazolo[3,2-a]pyrimidin-7-yl]acetate (12.4 g, 59%) as a yellow solid. LCMS (ESI): M+H$^+$=317.0.

Step 2: 2-[3-Bromo-2-methyl-5-oxo-5H-[1,3]thiazolo[3,2-a]pyrimidin-7-yl]acetamide

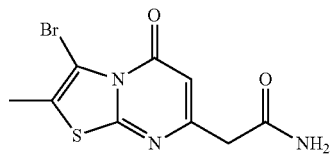 [SMILES: Cc1sc2nc(CC(N)=O)cc(=O)n2c1Br]

To a solution of methyl 2-[3-bromo-2-methyl-5-oxo-5H-[1,3]thiazolo[3,2-a]pyrimidin-7-yl]acetate (3 g, 9.46 mmol) in methanol (20 mL) was added NH$_3$ in methanol (40 mL, 5 mol/L). The reaction tube was sealed and the resulting solution was stirred for 6 h at 60° C. and then concentrated in vacuo. The residue was purified by flash chromatography on silica gel eluting with dichloromethane/methanol (5/1) to afford 2-[3-bromo-2-methyl-5-oxo-5H-[1,3]thiazolo[3,2-a]pyrimidin-7-yl]acetamide (689 mg, 24%) as a brown solid. LCMS (ESI): M+H$^+$=302.0.

Step 3: 2-[3-Bromo-2-methyl-5-oxo-5H-[1,3]thiazolo[3,2-a]pyrimidin-7-yl]ethanethioamide

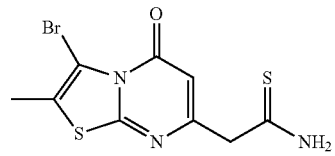

To a solution of 2-[3-bromo-2-methyl-5-oxo-5H-[1,3]thiazolo[3,2-a]pyrimidin-7-yl]acetamide (689 mg, 2.28 mmol) in tetrahydrofuran (20 mL) was added 2,4-bis(4-methoxyphenyl)-1,3-dithia-2,4-diphosphetane-2,4-disulfide (2.8 g, 6.92 mmol). The resulting solution was stirred for 1 h at 65° C. and then concentrated in vacuo. The residue was purified by flash chromatography on silica gel eluting with dichloromethane/ethyl acetate (3/1) to afford 2-[3-bromo-2-methyl-5-oxo-5H-[1,3]thiazolo[3,2-a]pyrimidin-7-yl]ethanethioamide (334 mg, 46%) as a yellow solid. LCMS (ESI): M+H$^+$=318.0.

Step 4: 3-Bromo-2-methyl-7-[[4-(trifluoromethyl)-1,3-thiazol-2-yl]methyl]-5H-[1,3]thiazolo[3,2-a]pyrimidin-5-one

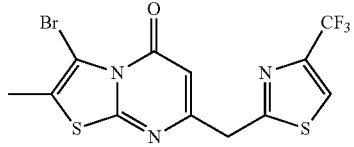 [SMILES: Cc1sc2nc(Cc3nc(C(F)(F)F)cs3)cc(=O)n2c1Br]

To a solution of 2-[3-bromo-2-methyl-5-oxo-5H-[1,3]thiazolo[3,2-a]pyrimidin-7-yl]ethanethioamide (200 mg, 0.63 mmol) in ethanol (10 mL) was added 3-bromo-1,1,1-trifluoropropan-2-one (180 mg, 0.94 mmol). The resulting solution was stirred for 1 h at 100° C., and the resulting mixture was concentrated in vacuo. The residue was purified by flash chromatography on silica gel eluting with dichloromethane/ethyl acetate (40/1) to afford 3-bromo-2-methyl-7-[[4-(trifluoromethyl)-1,3-thiazol-2-yl]methyl]-5H-[1,3]thiazolo[3,2-a]pyrimidin-5-one (164 mg, 64%) as a yellow solid. LCMS (ESI): M+H$^+$=410.0.

Step 5: 3-[2-(Hydroxymethyl)cyclopropyl]-2-methyl-7-[[4-(trifluoromethyl)-1,3-thiazol-2-yl]methyl]-5H-[1,3]thiazolo[3,2-a]pyrimidin-5-one

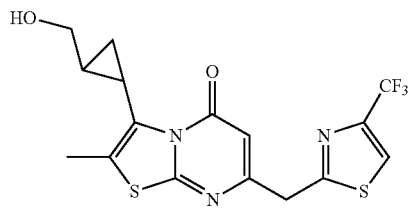

To a solution of 3-bromo-2-methyl-7-[[4-(trifluoromethyl)-1,3-thiazol-2-yl]methyl]-5H-[1,3]thiazolo[3,2-a]pyrimidin-5-one (164 mg, 0.40 mmol) in acetonitrile/water (2 mL/0.5 mL) was added potassium trans-2-(hydroxymethyl)cyclopropyltrifluoroborate (143 mg, 0.80 mmol), [1,1"-bis(diphenylphosphino)ferrocene]palladium(II) dichloride (30 mg, 0.04 mmol), and sodium carbonate (85 mg, 0.80 mmol). The reaction mixture was irradiated with microwave radiation for 1.5 h at 120° C., and the resulting mixture was concentrated in vacuo. The residue was purified by flash chromatography on silica gel eluting with dichloromethane/methanol (50/1) to afford 3-[2-(hydroxymethyl)cyclopropyl]-2-methyl-7-[[4-(trifluoromethyl)-1,3-thiazol-2-yl]methyl]-5H-[1,3]thiazolo[3,2-a]pyrimidin-5-one (7.7 mg, 5%) as an off-white solid. LCMS (ESI): M+H$^+$=402.0; $^1$H NMR (300 MHz, CDCl$_3$) δ 7.71 (s, 1H), 6.22 (s, 1H), 4.30 (s, 2H), 4.08-4.04 (m, 1H), 3.16-3.09 (m, 1H), 2.39 (s, 3H), 2.30-2.22 (m, 1H), 1.28-1.07 (m, 1H), 1.05-1.03 (m, 2H).

Example 28: 7-[[5-Chloro-3-(trifluoromethyl)-1H-pyrazol-1-yl]methyl]-N-ethyl-2-methyl-5-oxo-5H-[1,3]thiazolo[3,2-a]pyrimidine-3-carboxamide

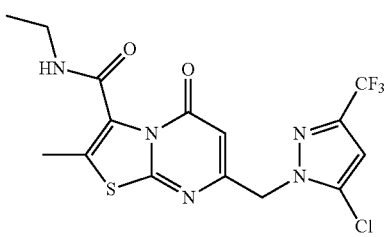 [SMILES: CCNC(=O)c1c(C)sc2nc(Cn3nc(C(F)(F)F)cc3Cl)cc(=O)n12]

Step 1: Ethyl 3-bromo-2-oxobutanoate

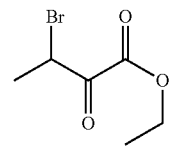

Into each of two 3000-mL 3-necked round-bottom flasks purged and maintained with an inert atmosphere of nitrogen was placed dichloromethane (1500 mL) and ethyl 2-oxobutanoate (286 g, 2.20 mol, 1.00 equiv) followed by the addition of dibromane (352 g, 2.20 mol, 1.00 equiv) dropwise with stirring at 0-5° C. The resulting solutions were stirred at 25° C. overnight. The combined reactions were quenched by the addition of 3000 mL of saturated aqueous sodium bicarbonate. The resulting solution was extracted with 2×500 mL of dichloromethane and the combined organic layers were dried over anhydrous Na$_2$SO$_4$ and concentrated under vacuum to afford 780 g (85%) of ethyl 3-bromo-2-oxobutanoate as yellow oil.

Step 2: Ethyl 2-amino-5-methylthiazole-4-carboxylate hydrobromide

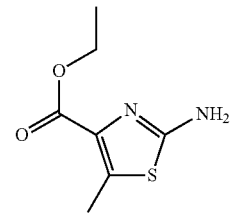

Into each of three 3000-mL round-bottom flasks was placed ethanol (2100 mL), thiourea (101.5 g, 1.33 mol, 1.03 equiv), and ethyl 3-bromo-2-oxobutanoate (270 g, 1.29 mol, 1.00 equiv). The resulting solutions were stirred at 85° C. in an oil bath overnight. The combined reaction mixtures were cooled to room temperature and filtered to afford 840 g (crude) of ethyl 2-amino-5-methylthiazole-4-carboxylate hydrobromide as a light yellow solid.

Step 3: 2-Amino-N-ethyl-5-methyl-1,3-thiazole-4-carboxamide

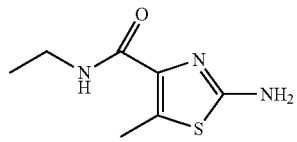

Into a 50000-mL pressure tank reactor was placed a solution of ethanamine in ethanol (3500 mL) and ethyl 2-amino-5-methylthiazole-4-carboxylate hydrobromide (400 g, 2.15 mol, 1.00 equiv). The resulting solution was stirred at 120° C. for 64 h. This reaction was repeated once. The combined resulting mixtures were concentrated under vacuum. The residue was applied onto a silica gel column eluting with dichloromethane/methanol (20:1) to afford 300 g (38%) of 2-amino-N-ethyl-5-methyl-1,3-thiazole-4-carboxamide as a yellow solid.

Step 4: 7-(Chloromethyl)-N-ethyl-2-methyl-5-oxo-5H-[1,3]thiazolo[3,2-a]pyrimidine-3-carboxamide

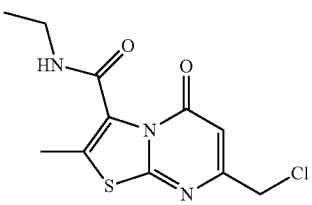

Into each of two 3000-mL 3-necked round-bottom flasks was placed PPA (1500 g), ethyl 4-chloro-3-oxobutanoate (603 g, 3.66 mol, 4.50 equiv), and 2-amino-N-ethyl-5-methyl-1,3-thiazole-4-carboxamide (150 g, 809.73 mmol, 1.00 equiv). The resulting solutions were stirred at 110° C. for 2 h. The combined reaction mixtures were cooled to 80° C. and quenched carefully by the addition of 450 mL of water. The pH of the solution was adjusted to 8 with saturated aqueous sodium carbonate. The solids were collected by filtration and washed with DCM to afford 260 g (56%) of 7-(chloromethyl)-N-ethyl-2-methyl-5-oxo-5H-[1,3]thiazolo[3,2-a]pyrimidine-3-carboxamide as a yellow solid.

Step 5: 7-[[5-Chloro-3-(trifluoromethyl)-1H-pyrazol-1-yl]methyl]-N-ethyl-2-methyl-5-oxo-5H-[1,3]thiazolo[3,2-a]pyrimidine-3-carboxamide

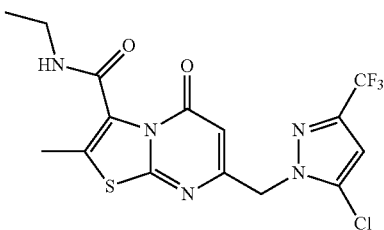 [SMILES: CCNC(=O)c1c(C)sc2nc(Cn3nc(C(F)(F)F)cc3Cl)cc(=O)n12]

Into each of two 3000-mL round-bottom flasks purged and maintained with an inert atmosphere of nitrogen was placed $CH_3CN$ (1500 mL), potassium carbonate (126 g, 911.66 mmol, 2.00 equiv), KI (38 g, 0.50 equiv), 5-chloro-3-(trifluoromethyl)-1H-pyrazole (160 g, 938.31 mmol, 2.00 equiv), and 7-(chloromethyl)-N-ethyl-2-methyl-5-oxo-5H-[1,3]thiazolo[3,2-a]pyrimidine-3-carboxamide (130 g, 454.94 mmol, 1.00 equiv). The resulting solutions were stirred at 80° C. for 4 h. The combined reaction mixtures were cooled to room temperature, concentrated under vacuum, and dissolved in 8 L of ethyl acetate. The solids were filtered out. The resulting filtrate was concentrated under vacuum. The crude product was re-crystallized from EtOAc. The residue was applied onto a silica gel column eluted with petroleum ether/EtOAc/DCM (1:1:1). The crude product was purified by HPLC (Column: SO230330-2, C18, 330 g, 20-45 um, 100 A; 254 nm, 220 nm; $CH_3CN$:0.05% $TFA/H_2O$=40%-65%, 20 min) to give 50 g (13%) of 7-[[5-chloro-3-(trifluoromethyl)-1H-pyrazol-1-yl]methyl]-N-ethyl-2-methyl-5-oxo-5H-[1,3]thiazolo[3,2-a]pyrimidine-3-carboxamide as a white solid. LCMS (ESI): $M+H^+$=420; $^1H$ NMR (300 MHz, $CDCl_3$) δ 6.58 (s, 1H), 5.93 (s, 1H), 5.72 (s, 1H), 3.47-3.56 (m, 2H), 2.42 (s, 3H), 1.25-1.30 (t, J=7.2 Hz, 3H).

Example 39: 3-[[3-(2,2-Difluorocyclopropyl)-2-methyl-5-oxo-thiazolo[3,2-a]pyrimidin-7-yl]methyl]-2-fluorobenzonitrile

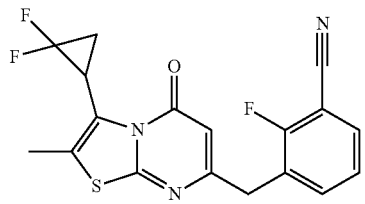 [SMILES: Cc1sc2nc(Cc3cccc(C#N)c3F)cc(=O)n2c1C1CC1(F)F]

Step 1: 3-((3-Bromo-2-methyl-5-oxo-5H-thiazolo[3,2-a]pyrimidin-7-yl)methyl)-2-fluorobenzonitrile

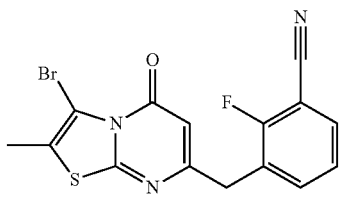 [SMILES: Cc1sc2nc(Cc3cccc(C#N)c3F)cc(=O)n2c1Br]

To a solution of 3-bromo-7-(chloromethyl)-2-methyl-5H-thiazolo[3,2-a]pyrimidin-5-one (500 mg, 1.70 mmol) in 1,4-dioxane/water (10 mL/1 mL) in a sealed tube was added (3-cyano-2-fluorophenyl)boronic acid (420 mg, 2.55 mmol), bis(diphenylphosphino)ferrocene]palladium(II) dichloride (125 mg, 0.17 mmol), and sodium carbonate (370 mg, 3.49 mmol). The resulting solution was stirred for 12 h at 80° C., and then concentrated in vacuo. The residue was purified by flash chromatography on silica gel eluting with dichloromethane/ethyl acetate (80/1) to afford 3-((3-bromo-2-methyl-5-oxo-5H-thiazolo[3,2-a]pyrimidin-7-yl)methyl)-2-fluorobenzonitrile (150 mg, 23%) as a light yellow solid. LCMS (ESI): [M+H]=378.0.

Step 2: 3-([3-Ethenyl-2-methyl-5-oxo-5H-[1,3]thiazolo[3,2-a]pyrimidin-7-yl]methyl)-2-fluorobenzonitrile

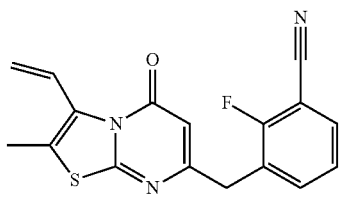 [SMILES: C=Cc1c(C)sc2nc(Cc3cccc(C#N)c3F)cc(=O)n12]

To a solution of 2-ethenyl-4,4,5,5-tetramethyl-1,3,2-dioxaborolane (244 mg, 1.58 mmol) in 1,4-dioxane/water (1.5 mL/0.5 mL) was added 3-([3-bromo-2-methyl-5-oxo-5H-[1,3]thiazolo[3,2-a]pyrimidin-7-yl]methyl)-2-fluorobenzonitrile (300 mg, 0.79 mmol), sodium carbonate (168 mg, 1.59 mmol), and 1,1'-bis(diphenylphosphino)ferrocenepalladiumdichloride (50 mg, 0.07 mmol). The resulting solution was stirred for 2 h at 90° C. The reaction was quenched by water, then extracted with dichloromethane and concentrated in vacuo. The residue was purified by flash chromatography on silica gel eluting with dichloromethane/methanol (40/1) to afford of 2-fluoro-3-([2-methyl-5-oxo-3-[2-(trifluoromethyl)cyclopropyl]-5H-[1,3]thiazolo[3,2-a]pyrimidin-7-yl]methyl)benzonitrile (178 mg, 69%) as a white solid. LCMS (ESI): M+H$^+$=326.0.

Step 3: 3-[[3-(2,2-Difluorocyclopropyl)-2-methyl-5-oxo-5H-[1,3]thiazolo[3,2-a]pyrimidin-7-yl]methyl]-2-fluorobenzonitrile

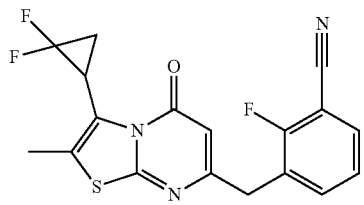 [SMILES: Cc1sc2nc(Cc3cccc(C#N)c3F)cc(=O)n2c1C1CC1(F)F]

To a solution of 3-([3-ethenyl-2-methyl-5-oxo-5H-[1,3]thiazolo[3,2-a]pyrimidin-7-yl]methyl)-2-fluorobenzonitrile (80 mg, 0.25 mmol) in tetrahydrofuran (8 mL) was added sodium iodide (72 mg, 0.48 mmol) and trimethyl(trifluoromethyl)silane (176 mg, 1.29 mmol). The resulting solution was stirred for 2 h at 65° C. The reaction was quenched by water, then extracted with dichloromethane and concentrated in vacuo. The residue was purified by preparative HPLC (Column, XBridge Prep C$_{18}$ OBD Column, 5 um, 19×150 mm; mobile phase, water with 10 mmol monosodium hydrogen carbonate and acetonitrile (24.0% acetonitrile up to 46.0% in 10 min); Detector, UV 254/220 nm) to afford 3-[[3-(2,2-difluorocyclopropyl)-2-methyl-5-oxo-5H-[1,3]thiazolo[3,2-a]pyrimidin-7-yl]methyl]-2-fluorobenzonitrile as a white solid (15.4 mg, 17%). LCMS (ESI): M+H$^+$=376.0; $^1$H NMR (300 MHz, CDCl$_3$) δ 7.61-7.53 (m, 2H), 7.26-7.20 (m, 1H), 5.99 (s, 1H), 3.93 (s, 2H), 2.80-2.74 (m, 1H), 2.40 (s, 3H), 1.98-1.84 (m, 1H), 1.60-1.46 (m, 1H).

Example 47: 7-[[2-Fluoro-3-(trifluoromethyl)phenyl]methyl]-3-(1H-imidazol-2-yl)-2-methyl-thiazolo[3,2-a]pyrimidin-5-one hydrate)

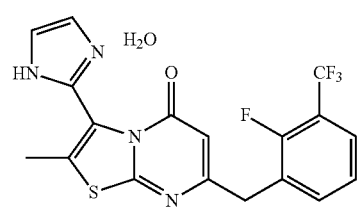

Step 1: Methyl 7-(chloromethyl)-2-methyl-5-oxo-5H-thiazolo[3,2-a]pyrimidine-3-carboxylate

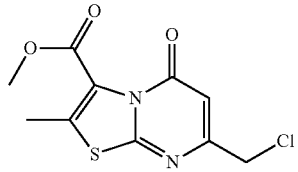 [SMILES: COC(=O)c1c(C)sc2nc(CCl)cc(=O)n12]

To a solution of methyl 2-amino-5-methylthiazole-4-carboxylate (5 g, 26.8 mmol) in PPA (30 mL) was added ethyl 4-chloro-3-oxobutanoate (8.82 g, 53.6 mmol), and stirred for 1 h at 110° C. The mixture was quenched by water, and the pH value of the solution was adjusted to 7 with sodium hydroxide (1 mol/L). The resulting solution was extracted with dichloromethane and concentrated in vacuo. The residue was purified by flash chromatography on silica gel eluting with dichloromethane/ethyl acetate (10/1) to afford methyl 7-(chloromethyl)-2-methyl-5-oxo-5H-thiazolo[3,2-a]pyrimidine-3-carboxylate (3.2 g, 45%) as a yellow solid. LCMS (ESI): M+H$^+$=273.0.

Step 2: Methyl 7-(2-fluoro-3-(trifluoromethyl)benzyl)-2-methyl-5-oxo-5H-thiazolo[3,2-a]pyrimidine-3-carboxylate

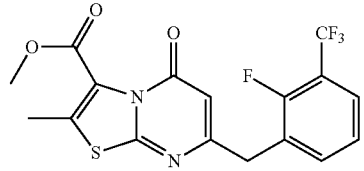 [SMILES: COC(=O)c1c(C)sc2nc(Cc3cccc(C(F)(F)F)c3F)cc(=O)n12]

To a solution of methyl 7-(chloromethyl)-2-methyl-5-oxo-5H-thiazolo[3,2-a]pyrimidine-3-carboxylate (900 mg, 3.14 mmol) in 1,4-dioxane/water (10 mL/0.5 mL) was added 2-fluoro-3-(trifluoromethyl)phenylboronic acid (982 mg, 4.72 mmol), bis(diphenylphosphino)ferrocene]palladium(II) dichloride (150 mg, 0.21 mmol), and potassium carbonate (869 mg, 6.29 mmol). The resulting solution was stirred for 14 h at 90° C. and then concentrated in vacuo. The residue was purified by flash chromatography on silica gel eluting with ethyl acetate/petroleum ether (1/1) to afford methyl 7-(2-fluoro-3-(trifluoromethyl)benzyl)-2-methyl-5-oxo-5H-thiazolo[3,2-a]pyrimidine-3-carboxylate (800 mg, 62%) as a yellow solid. LCMS (ESI): M+H$^+$=401.0.

Step 3: 7-(2-Fluoro-3-(trifluoromethyl)benzyl)-3-(hydroxymethyl)-2-methyl-5H-thiazolo[3,2-a]pyrimidin-5-one

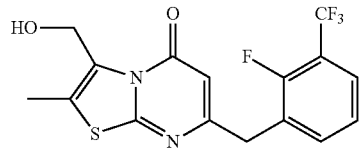 [SMILES: Cc1sc2nc(Cc3cccc(C(F)(F)F)c3F)cc(=O)n2c1CO]

To a solution of methyl 7-(2-fluoro-3-(trifluoromethyl)benzyl)-2-methyl-5-oxo-5H-thiazolo[3,2-a]pyrimidine-3-carboxylate (300 mg, 0.72 mmol) in dichloromethane (10 ml) was added DIBAL-H (2 mL, 1 mol/L in toluene) at −78° C. The reaction solution was stirred for 2 h at room temperature, and then quenched by water. The resulting solution was extracted with dichloromethane and concentrated in vacuo. The residue was purified by flash chromatography on silica gel eluting with dichloromethane/ethyl acetate (2/1) to afford 7-(2-fluoro-3-(trifluoromethyl)benzyl)-2-methyl-5-oxo-5H-thiazolo[3,2-a]pyrimidine-3-carbaldehyde (136 mg, 50%) as a white solid. LCMS (ESI): M+H$^+$=373.0.

Step 4: 7-(2-Fluoro-3-(trifluoromethyl)benzyl)-2-methyl-5-oxo-5H-thiazolo[3,2-a]pyrimidine-3-carbaldehyde

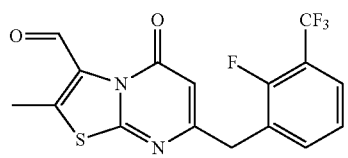 [SMILES: Cc1sc2nc(Cc3cccc(C(F)(F)F)c3F)cc(=O)n2c1C=O]

To a solution of 7-[[2-fluoro-3-(trifluoromethyl)phenyl]methyl]-3-(hydroxymethyl)-2-methyl-5H-[1,3]thiazolo[3,2-a]pyrimidin-5-one (50 mg, 0.13 mmol) in dichloromethane (5 mL) was added 1,1-bis(acetyloxy)-3-oxo-3H-11^[5],2-benziodaoxol-1-yl acetate (85 mg, 0.20 mmol). The resulting solution was stirred overnight at room temperature. After the reaction was quenched with water, then extracted with dichloromethane and concentrated in vacuo. The residue was purified by flash chromatography on silica gel eluting with dichloromethane/methanol (40/1) to afford 7-[[2-fluoro-3-(trifluoromethyl)phenyl]methyl]-2-methyl-5-oxo-5H-[1,3]thiazolo[3,2-a]pyrimidine-3-carbaldehyde (38 mg, 76%) as an off-white solid. LCMS (ESI): M+H$^+$=326.0.

Step 5: 7-[[2-Fluoro-3-(trifluoromethyl)phenyl]methyl]-3-(1H-imidazol-2-yl)-2-methyl-thiazolo[3,2-a]pyrimidin-5-one hydrate

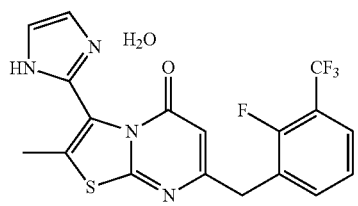

To a solution of 7-[[2-fluoro-3-(trifluoromethyl)phenyl]methyl]-2-methyl-5-oxo-5H-[1,3]thiazolo[3,2-a]pyrimidine-3-carbaldehyde (38 mg, 0.10 mmol) in ethanol (2 mL) was added ammonia (0.2 mL, 5.71 mmol) and oxalaldehyde (200 mg, 3.45 mmol). The resulting solution was stirred overnight at room temperature. After the reaction was quenched with water, then extracted with dichloromethane and concentrated in vacuo. The residue was purified by preparative HPLC (Column, XBridge Prep C$_{18}$ OBD Column, 5 um, 19×150 mm; mobile phase, water with 10 mmol monosodium hydrogen carbonate and acetonitrile (24.0% acetonitrile up to 46.0% in 10 min); Detector, UV 254/220 nm) to afford 7-[[2-fluoro-3-(trifluoromethyl)phenyl]methyl]-3-(1H-imidazol-2-yl)-2-methyl-5H-[1,3]thiazolo[3,2-a]pyrimidin-5-one monohydrate as an off-white solid (4.5 mg, 10%). LCMS [M+H]$^+$ 371.0; $^1$H NMR (300 MHz, CDCl$_3$) δ 10.82 (br, 1H), 7.56-7.48 (m, 2H), 7.25-7.17 (m, 3H), 6.03 (s, 1H), 5.02 (br, 2H), 3.98 (s, 2H), 2.56 (s, 3H).

Example 91: N-Ethyl-7-[[2-fluoro-3-(trifluoromethyl)phenyl]methyl]-2-methoxy-5-oxo-thiazolo[3,2-a]pyrimidine-3-carboxamide

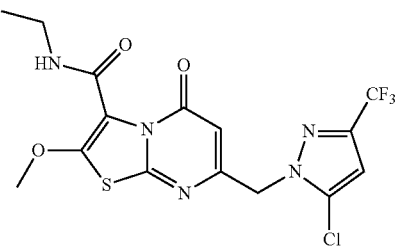 [SMILES: CCNC(=O)c1c(OC)sc2nc(Cn3nc(C(F)(F)F)cc3Cl)cc(=O)n12]

Step 1: 2-Amino-N-ethyl-5-methoxy-1,3-thiazole-4-carboxamide

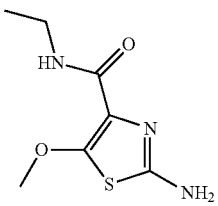

To a solution of 2-amino-5-chloro-N-ethyl-1,3-thiazole-4-carboxamide (1.00 g, 4.86 mmol) in methanol (5 mL) was added sodium methoxide (1.05 g, 19.4 mmol). The resulting solution was stirred for 2 h at 50° C. and then quenched with water. The resulting solution was extracted with dichloromethane and concentrated in vacuo. The residue was purified by flash chromatography on silica gel eluting with dichloromethane/methanol (20/1) to afford of 2-amino-N-ethyl-5-methoxy-1,3-thiazole-4-carboxamide (300 mg, 31%) as an off-white solid. LCMS (ESI): M+H$^+$=202.0.

Step 2: 7-(Chloromethyl)-N-ethyl-2-methoxy-5-oxo-5H-thiazolo[3,2-a]pyrimidine-3-carboxamide

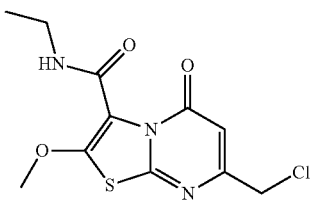 [SMILES: CCNC(=O)c1c(OC)sc2nc(CCl)cc(=O)n12]

To a solution of 2-amino-N-ethyl-5-methoxy-1,3-thiazole-4-carboxamide (2.50 g, 12.4 mmol) in polyphosphoric acid (30 mL) was added ethyl 4-chloro-3-oxobutanoate (4.09 g, 24.8 mmol). The resulting solution was stirred for 3 h at 60° C. The reaction mixture was diluted with methanol (50 mL) and the pH value of the solution was adjusted to 7 with triethylamine. The mixture was added water (200 mL), and the resulting solution was extracted with dichloromethane and concentrated in vacuo. The residue was purified by flash chromatography on silica gel eluting with dichloromethane/methanol (50/1) to afford 7-(chloromethyl)-N-ethyl-2-methoxy-5-oxo-5H-[1,3]thiazolo[3,2-a]pyrimidine-3-carboxamide (190 mg, 5%) as an off-white solid. LCMS (ESI): M+H$^+$=302.0.

Step 3: N-Ethyl-7-[[2-fluoro-3-(trifluoromethyl)phenyl]methyl]-2-methoxy-5-oxo-5H-[1,3]thiazolo[3,2-a]pyrimidine-3-carboxamide

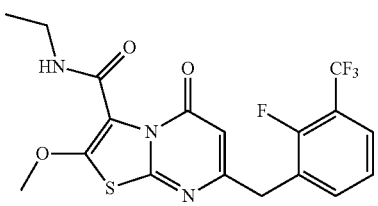 [SMILES: CCNC(=O)c1c(OC)sc2nc(Cc3cccc(C(F)(F)F)c3F)cc(=O)n12]

To a solution of 7-(chloromethyl)-N-ethyl-2-methoxy-5-oxo-5H-[1,3]thiazolo[3,2-a]pyrimidine-3-carboxamide (280 mg, 0.93 mmol) in 1,4-dioxane/water (1.5 mL/0.5 mL) was added [2-fluoro-3-(trifluoromethyl)phenyl]boronic acid (400 mg, 1.92 mmol), tricyclohexylphosphane (260 mg, 0.93 mmol), diacetoxypalladium (100 mg, 0.45 mmol), and potassium phosphate (400 mg, 1.88 mmol). The resulting solution was stirred overnight at 90° C. and then concentrated invacuo. The residue was purified by preparative HPLC with the following conditions (1#-Pre-HPLC-005 (Waters)): Column, SunFire Prep C$_{18}$ OBD Column, 5 um, 19*150 mm; mobile phase, water with 10 mmol monosodium hydrogen carbonate and acetonitrile (50.0% acetonitrile up to 82.0% in 10 min, down to 50.0% in 2 min); Detector, UV 254/220 nm to afford N-ethyl-7-[[2-fluoro-3-(trifluoromethyl)phenyl]methyl]-2-methoxy-5-oxo-5H-[1,3]thiazolo[3,2-a]pyrimidine-3-carboxamide (31.6 mg, 8%) as an off-white solid. LCMS (ESI): M+H$^+$=430.1; $^1$H NMR (400 MHz, CD$_3$OD) δ 7.68-7.61 (m, 2H), 7.36-7.32 (m, 1H), 6.19 (s, 1H), 4.08 (s, 5H), 3.41-3.32 (m, 2H), 1.25-1.21 (m, 3H).

Example 105: 2-Cyano-N-ethyl-7-[[2-fluoro-3-(trifluoromethyl)phenyl]methyl]-5-oxo-thiazolo[3,2-a]pyrimidine-3-carboxamide

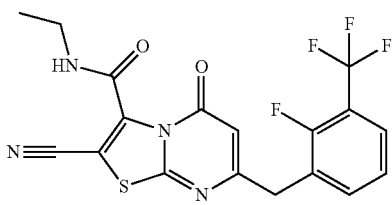 [SMILES: CCNC(=O)c1c(C#N)sc2nc(Cc3cccc(C(F)(F)F)c3F)cc(=O)n12]

Step 1: 2-Amino-N-ethylthiazole-4-carboxamide

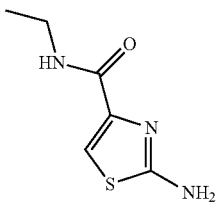

A solution of ethyl 2-aminothiazole-4-carboxylate (11.5 g, 72.7 mmol) in ethanamine/ethanol (100 mL, 30%) was stirred for 2 h at 110° C. in a sealed tube, and the resulting solution was concentrated in vacuo to afford 2-amino-N-ethylthiazole-4-carboxamide (12.3 g, 99%). LCMS (ESI): M+H$^+$=172.0.

Step 2: 2-Amino-5-chloro-N-ethylthiazole-4-carboxamide

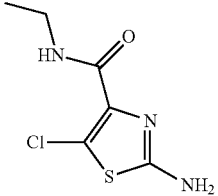

To a solution of 2-amino-N-ethylthiazole-4-carboxamide (12.3 g, 71.8 mmol) in N,N-dimethyformaide (100 ml) was added N-chlorosuccinimide (10.5 g, 79.0 mmol). The resulting solution was stirred overnight at 50° C. and concentrated in vacuo. The residue was purified by flash chromatography on silica gel eluting with dichloromethane/ethyl acetate (8/1) to afford 2-amino-5-chloro-N-ethylthiazole-4-carboxamide (7.6 g, 51%) as a brown solid. LCMS (ESI): M+H$^+$=206.0.

Step 3: 2-Chloro-7-(chloromethyl)-N-ethyl-5-oxo-5H-thiazolo[3,2-a]pyrimidine-3-carboxamide

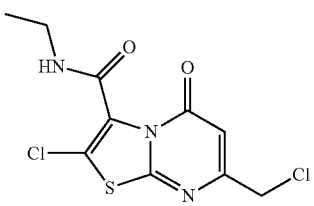 [SMILES: CCNC(=O)c1c(Cl)sc2nc(CCl)cc(=O)n12]

To a solution of 2-amino-5-chloro-N-ethylthiazole-4-carboxamide (12.4 g, 60.3 mmol) in polyphosphoric acid (30 mL) was added ethyl-4-chloro-3-oxobutanoate (20 g, 121 mmol). The reaction mixture was stirred for 1 h at 110° C. The reaction was quenched by water/ice, and the pH of the solution was adjusted to 7 with sodium hydroxide (1 mol/L). The resulting solution was extracted with dichloromethane and concentrated in vacuo. The residue was purified by flash chromatography on silica gel eluting with dichloromethane/methanol (50/1) to afford 2-chloro-7-(chloromethyl)-N- ethyl-5-oxo-5H-thiazolo[3,2-a]pyrimidine-3-carboxamide (4.7 g, 25%) as a brown solid. LCMS (ESI): M+H⁺=305.0, 307.0.

Step 4: 2-Chloro-N-ethyl-7-[[2-fluoro-3-(trifluoromethyl)phenyl]methyl-5-oxo-5H-[1,3]thiazolo[3,2-a]pyrimidine-3-carboxamide

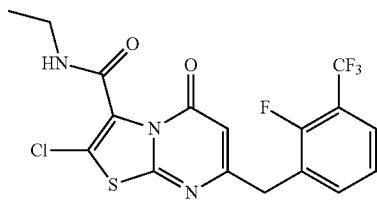

To a solution of 2-chloro-7-(chloromethyl)-N-ethyl-5-oxo-5H-[1,3]thiazolo[3,2-a]pyrimidine-3-carboxamide (100 mg, 0.33 mmol) in 1,4-dioxane/water (1.5 mL/0.5 mL) was added 2-fluoro-3-(trifluoromethyl)phenyl]boronic acid (100 mg, 0.48 mmol), potassium carbonate (90 mg, 0.65 mmol), and [1,1'-bis(diphenylphosphino)ferrocene]palladium(II) dichloride (50 mg, 0.07 mmol). The resulting solution was stirred overnight at 90° C. and then concentrated in vacuo. The residue was purified by preparative HPLC (Column, XBridge Prep $C_{18}$ OBD Column, 5 um, 19×150 mm; mobile phase, water with 10 mmol monosodium hydrogen carbonate and acetonitrile (24.0% acetonitrile up to 46.0% in 10 min); Detector, UV 254/220 nm) to afford 2-chloro-N-ethyl-7-[[2-fluoro-3-(trifluoromethyl)phenyl]methyl]-5-oxo-5H-[1,3]thiazolo[3,2-a]pyrimidine-3-carboxamide (13.4 mg, 9%) as a white solid. LCMS (ESI): M+H⁺=434.0; ¹H NMR (300 MHz, CDCl₃) δ 7.61-7.44 (m, 2H), 7.31-7.19 (m, 1H), 6.10 (s, 1H), 5.84 (br, 1H), 3.96 (s, 2H), 3.59-3.50 (m, 2H), 1.32-1.20 (m, 3H).

Step 5: Methyl 3-(ethylcarbamoyl)-7-[[2-fluoro-3-(trifluoromethyl)phenyl]methyl]-5-oxo-5H-[1,3]thiazolo[3,2-a]pyrimidine-2-carboxylate

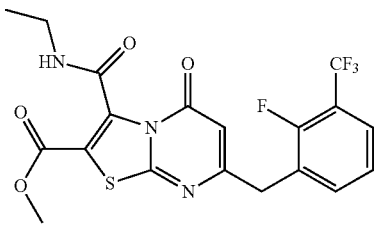 [SMILES: CCNC(=O)c1c(C(=O)OC)sc2nc(Cc3cccc(C(F)(F)F)c3F)cc(=O)n12]

To a solution of 2-chloro-N-ethyl-7-[[2-fluoro-3-(trifluoromethyl)phenyl]methyl]-5-oxo-5H-[1,3]thiazolo[3,2-a]pyrimidine-3-carboxamide (500 mg, 1.15 mmol) in methanol (10 mL) was added triethylamine (233 mg, 2.30 mmol) and [1,1'-bis(diphenylphosphino)ferrocene]palladium(II) dichloride (85 mg, 0.12 mmol). The resulting solution was stirred for 6 h at 50° C. under carbon monoxide atmosphere about 10 atm and then concentrated in vacuo. The residue was purified by flash chromatography on silica gel eluting with dichloromethane/methanol (20/1) to afford methyl 3-(ethylcarbamoyl)-7-[[2-fluoro-3-(trifluoromethyl)phenyl] methyl]-5-oxo-5H-[1,3]thiazolo[3,2-a]pyrimidine-2-carboxylate (350 mg, 66%) as a brown solid. LCMS (ESI): M+H⁺=458.0.

Step 6: 3-(Ethylcarbamoyl)-7-[[2-fluoro-3-(trifluoromethyl)phenyl]methyl]-5-oxo-5H-[1,3]thiazolo[3,2-a]pyrimidine-2-carboxylic acid

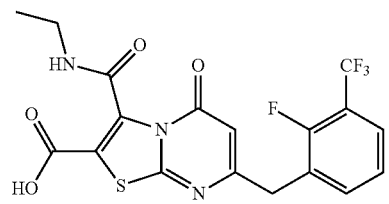 [SMILES: CCNC(=O)c1c(C(=O)O)sc2nc(Cc3cccc(C(F)(F)F)c3F)cc(=O)n12]

To a solution of methyl 3-(ethylcarbamoyl)-7-[[2-fluoro-3-(trifluoromethyl)phenyl]methyl]-5-oxo-5H-[1,3]thiazolo[3,2-a]pyrimidine-2-carboxylate (170 mg, 0.37 mmol) in tetrahydrofuran/water (6 mL/2 mL) was added lithium hydroxide (110 mg, 4.59 mmol). The reaction mixture was stirred for 1 h at room temperature. The pH of the solution was adjusted to 6 with aqueous HCl solution (1 mol/L). The resulting solution was extracted with dichloromethane and concentrated in vacuo to afford 3-(ethylcarbamoyl)-7-[[2-fluoro-3-(trifluoromethyl)phenyl]methyl]-5-oxo-5H-[1,3]thiazolo[3,2-a]pyrimidine-2-carboxylic acid (110 mg, 67%) as a brown solid. LCMS (ESI): M−H⁻=442.0.

Step 7: 3-N-Ethyl-7-[[2-fluoro-3-(trifluoromethyl)phenyl]methyl]-5-oxo-5H-[1,3]thiazolo[3,2-a]pyrimidine-2,3-dicarboxamide

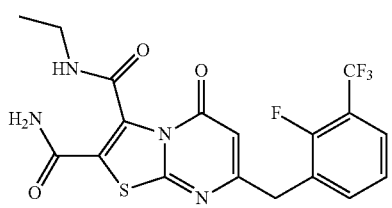 [SMILES: CCNC(=O)c1c(C(N)=O)sc2nc(Cc3cccc(C(F)(F)F)c3F)cc(=O)n12]

To a solution of 3-(ethylcarbamoyl)-7-[[2-fluoro-3-(trifluoromethyl)phenyl]methyl]-5-oxo-5H-[1,3]thiazolo[3,2-a]pyrimidine-2-carboxylic acid (300 mg, 0.68 mmol) in dichloromethane (5 mL) was added triethylamine (200 mg, 1.98 mmol) and chloro(propan-2-yloxy)methanone (166 mg, 1.35 mmol) at 0° C. The mixture was stirred for 20 min at room temperature, and then ammonium hydroxide (0.5 mL, 30%) was added. The resulting solution was stirred for 2 h at room temperature and then concentrated in vacuo. The residue was purified by flash chromatography on silica gel eluting with dichloromethane/methanol (50/1) to afford 3-N-ethyl-7-[[2-fluoro-3-(trifluoromethyl)phenyl]methyl]-5-oxo-5H-[1,3]thiazolo[3,2-a]pyrimidine-2,3-dicarboxamide (152 mg, 51%) as a brown solid. LCMS (ESI): M+H⁺=443.0.

Step 8: 2-Cyano-N-ethyl-7-[[2-fluoro-3-(trifluoromethyl)phenyl]methyl]-5-oxo-5H-[1,3]thiazolo[3,2-a]pyrimidine-3-carboxamide

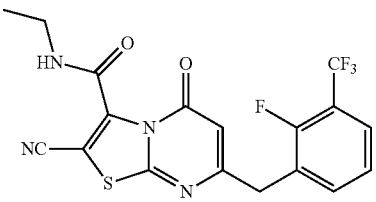 [SMILES: CCNC(=O)c1c(C#N)sc2nc(Cc3cccc(C(F)(F)F)c3F)cc(=O)n12]

To a solution of 3-N-ethyl-7-[[2-fluoro-3-(trifluoromethyl)phenyl]methyl]-5-oxo-5H-[1,3]thiazolo[3,2-a]pyrimidine-2,3-dicarboxamide (152 mg) in dichloromethane (5 mL) was added triethylamine (0.5 mL) and trifluoroacetic anhydride (0.2 mL, 0.93 mmol). The resulting solution was stirred for 30 min at room temperature and concentrated in vacuo. The residue was purified by preparative HPLC (Column, SunFire Prep $C_{18}$ OBD Column, 5 um, 19*150 mm; mobile phase, Water with 10 mmol monosodium hydrogen carbonate and acetonitrile (50.0% acetonitrile up to 82.0% in 10 min, down to 50.0% in 2 min); Detector, UV 254/220 nm) to afford 2-cyano-N-ethyl-7-[[2-fluoro-3-(trifluoromethyl)phenyl]methyl]-5-oxo-5H-[1,3]thiazolo[3,2-a]pyrimidine-3-carboxamide (7.4 mg, 5%) as an off-white solid. LCMS (ESI): M+H$^+$=424.9; $^1$H NMR (300 MHz, CDCl$_3$) δ 7.61-7.54 (m, 1H), 7.50-7.46 (m, 1H), 7.26-7.21 (m, 1H), 6.55 (br, 1H), 6.18 (s, 1H), 3.99 (s, 2H), 3.61-3.52 (m, 2H), 1.33-1.26 (m, 3H).

Example 153: 7-[(5-Cyclopropyltriazol-1-yl)methyl]-3-[2-(hydroxymethyl)cyclopropyl]-2-methyl-thiazolo[3,2-a]pyrimidin-5-one

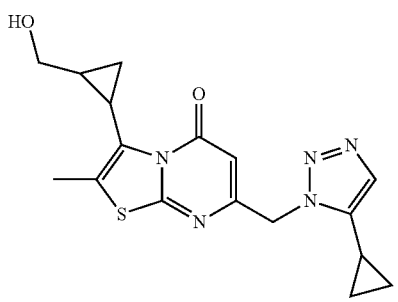 [SMILES: Cc1sc2nc(Cn3nncc3C3CC3)cc(=O)n2c1C1CC1CO]

Step 1: 7-(Azidomethyl)-3-bromo-2-methyl-thiazolo[3,2-a]pyrimidin-5-one

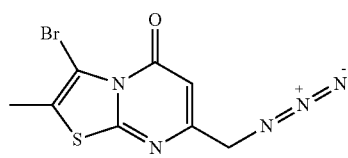

Sodium azide (134 mg, 2.04 mmol) in water (0.85 mL) was added to a solution of 3-bromo-7-(chloromethyl)-2-methyl-thiazolo[3,2-a]pyrimidin-5-one (200 mg, 0.68 mmol) in acetonitrile (3.4 mL, 0.2 M). The mixture was stirred at room temperature for 20 h and at 50° C. for another 20 h. Water (10 mL) was added and the product was recovered by filtration. The solid was washed with cold water and heptane and was dried under vacuum to afford 7-(azidomethyl)-3-bromo-2-methyl-thiazolo[3,2-a]pyrimidin-5-one as a beige solid (167 mg, 82%). LCMS (ESI): M+H$^+$=300.1, 302.1; $^1$H NMR (400 MHz, DMSO-d$_6$) δ 6.21 (d, J=0.8 Hz, 1H), 4.35 (s, 2H), 2.33 (s, 3H).

Step 2: 3-Bromo-7-[(5-cyclopropyltriazol-1-yl)methyl]-2-methyl-thiazolo[3,2-a]pyrimidin-5-one

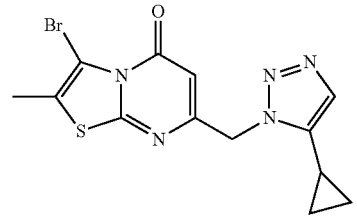 [SMILES: Cc1sc2nc(Cn3nncc3C3CC3)cc(=O)n2c1Br]

A degassed solution of chloro(pentamethylcyclopentadienyl)bis(triphenylphosphine)ruthenium(II) (12 mg, 0.01 mmol) in 1,4-dioxane (1.5 mL) with N$_2$ was added to a solution of 7-(azidomethyl)-3-bromo-2-methyl-thiazolo[3,2-a]pyrimidin-5-one (89 mg, 0.29 mmol) and ethynylcyclopropane (59 mg, 0.89 mmol) in 1,4-dioxane (1.5 mL) under N$_2$. The mixture was capped and stirred at 60° C. for 20 h. The crude mixture was adsorbed on diatomaceous earth and purified by flash chromatography (0-5% MeOH/DCM gradient) to yield 3-bromo-7-[(5-cyclopropyltriazol-1-yl)methyl]-2-methyl-thiazolo[3,2-a]pyrimidin-5-one as a beige solid (90 mg, 83%). LCMS (ESI): M+H$^+$=366.1, 368.1; $^1$H NMR (400 MHz, Chloroform-d) δ 7.35 (s, 1H), 5.78 (s, 1H), 5.45 (s, 2H), 2.36 (s, 3H), 1.71-1.65 (m, 1H), 1.07-0.97 (m, 2H), 0.76-0.67 (m, 2H).

Step 3: 7-[(5-Cyclopropyltriazol-1-yl)methyl]-3-[2-(hydroxymethyl)cyclopropyl]-2-methyl-thiazolo[3,2-a]pyrimidin-5-one

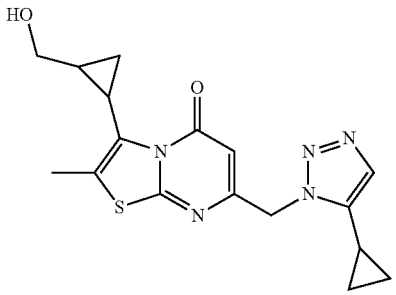 [SMILES: Cc1sc2nc(Cn3nncc3C3CC3)cc(=O)n2c1C1CC1CO]

Pd[dppf]Cl$_2$ (18 mg, 0.02 mmol) was added to a solution of 3-bromo-7-[(5-cyclopropyltriazol-1-yl)methyl]-2-methyl-thiazolo[3,2-a]pyrimidin-5-one (90 mg, 0.24 mmol), potassium trifluoro-[2-(hydroxymethyl)cyclopropyl]borane (65 mg, 0.37 mmol), and K$_2$CO$_3$ (68 mg, 0.49 mmol) in 1,4-dioxane/water (1.5 mL, 10:1) under N$_2$ in a microwave vessel. The vial was capped and heated at 120° C. for 45 min in the microwave. The crude reaction was filtered through a pad of diatomaceous earth and the filtrate was concentrated to dryness. The crude product was purified by flash chromatography (0-10% MeOH/DCM gradient) to give 7-[(5-cyclopropyltriazol-1-yl)methyl]-3-[2-(hydroxymethyl)cyclopropyl]-2-methyl-thiazolo[3,2-a]pyrimidin-5-one as a white solid (16 mg, 18%). LCMS (ESI): M+H$^+$=358.2; $^1$H NMR (400 MHz, DMSO-d$_6$) δ 7.44 (s, 1H), 5.73 (s, 1H), 5.51 (s, 2H), 4.54 (t, J=5.5 Hz, 1H), 3.46 (t, J=5.7 Hz, 2H), 2.37 (s, 3H), 2.06-1.95 (m, 1H), 1.93-1.82 (m, 1H), 1.34-1.21 (m, 1H), 0.99-0.91 (m, 2H), 0.90-0.78 (m, 2H), 0.71-0.60 (m, 2H).

Example 206: 3-(Azetidin-1-yl)-7-[[5-chloro-3-(trifluoromethyl)pyrazol-1-yl]methyl]-2-(trifluoromethyl)thiazolo[3,2-a]pyrimidin-5-one

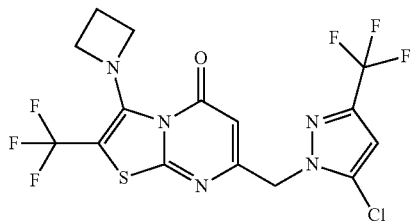 [SMILES: O=c1cc(Cn2nc(C(F)(F)F)cc2Cl)nc2sc(C(F)(F)F)c(N3CCC3)n12]

A mixture of 3-bromo-7-[[5-chloro-3-(trifluoromethyl)pyrazol-1-yl]methyl]-2-(trifluoromethyl)thiazolo[3,2-a]pyrimidin-5-one (50 mg, 0.10 mmol), azetidine hydrochloride (12 mg, 0.12 mmol), and K$_2$CO$_3$ (36 mg, 0.26 mmol) in acetonitrile (0.5 mL) was stirred at 80° C. for 3 h and at room temperature for 20 h. The mixture was filtered to remove the salts and adsorbed on diatomaceous earth. The crude product was purified by flash chromatography (10% EtOAc/heptane) followed by a second purification by preparative HPLC to provide 3-(azetidin-1-yl)-7-[[5-chloro-3-(trifluoromethyl)pyrazol-1-yl]methyl]-2-(trifluoromethyl)thiazolo[3,2-a]pyrimidin-5-one s a yellow lyophilized solid (11 mg, 24%). LCMS (ESI): M+H$^+$=458.0; $^1$H NMR (400 MHz, DMSO-d$_6$) δ 7.14 (s, 1H), 5.86 (s, 1H), 5.37 (s, 2H), 4.20 (td, J=7.6, 7.1, 1.8 Hz, 4H), 2.24 (p, J=7.7 Hz, 2H).

Examples 207 and 208: 2-(7-((5-Chloro-3-(trifluoromethyl)-1H-pyrazol-1-yl)methyl)-2-(trifluoromethyl)-5-oxo-5H-thiazolo[3,2-a]pyrimidin-3-yl)cyclopropanecarbonitrile (enantiomers)

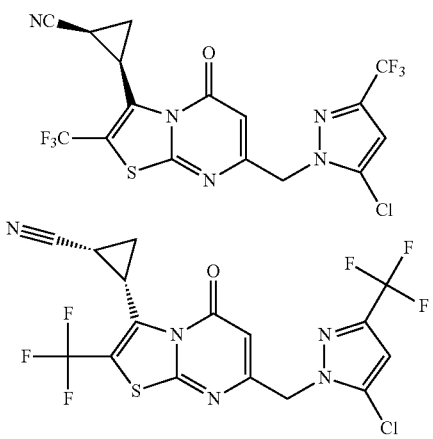

Step 1: N,N-Dimethyl-3-(trifluoromethyl)-1H-pyrazole-1-sulfonamide

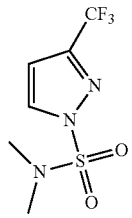

Into a 20-L 4-necked round-bottom flask purged and maintained with an inert atmosphere of nitrogen was placed 3-(trifluoromethyl)-1H-pyrazole (1000 g, 7.35 mol, 1.00 equiv), CH$_3$CN (10 L), and 1,4-diazabicyclo[2.2.2]octane (990 g, 8.83 mol, 1.20 equiv) followed by the addition of N,N-dimethylsulfamoyl chloride (1156 g, 8.05 mol, 1.10 equiv) dropwise with stirring at 0° C. The resulting solution was stirred at room temperature for 3 h, concentrated under vacuum, diluted with 10 L of H$_2$O, and extracted with 3×5 L of ethyl acetate. The combined organic layers were washed with 2×5 L of brine, dried over anhydrous sodium sulfate and concentrated under vacuum. The residue was applied onto a silica gel column eluted with dichloromethane to afford 1700 g (95%) of N,N-dimethyl-3-(trifluoromethyl)-1H-pyrazole-1-sulfonamide as colorless oil.

Step 2: 5-Chloro-N,N-dimethyl-3-(trifluoromethyl)-1H-pyrazole-1-sulfonamide

Into a 20-L 4-necked round-bottom flask purged and maintained with an inert atmosphere of nitrogen was placed N,N-dimethyl-3-(trifluoromethyl)-1H-pyrazole-1-sulfonamide (1200 g, 4.93 mol, 1.00 equiv) and tetrahydrofuran (10 L) followed by the addition of n-BuLi (2.5 M in hexane) (2.37 L, 1.20 equiv) dropwise with stirring at −78° C. The mixture was stirred at −70 to −80° C. for 1 h. To this was added a solution of C$_2$Cl$_6$ (1605 g, 1.40 equiv) in tetrahydrofuran (2.5 L) dropwise with stirring at −70° C. The resulting solution was stirred at −70° C. for 3 h, quenched by the addition of 1000 mL of saturated aqueous NH$_4$Cl, and extracted with 2×1 L of ethyl acetate. The combined organic layers were washed with 2×3 L of brine, dried over anhydrous sodium sulfate and concentrated under vacuum. The residue was applied onto a silica gel column eluted with ethyl acetate/petroleum ether (1:30) to afford 1120 g (82%) of 5-chloro-N,N-dimethyl-3-(trifluoromethyl)-1H-pyrazole-1-sulfonamide as light yellow oil.

Step 3: 5-Chloro-3-(trifluoromethyl)-1H-pyrazole

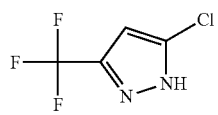

Into a 10-L 4-necked round-bottom flask was placed 5-chloro-N,N-dimethyl-3-(trifluoromethyl)-1H-pyrazole-1-sulfonamide (2200 g, 7.92 mol, 1.00 equiv) and dichloromethane (2000 mL) followed by the addition of trifluoroacetic acid (1500 mL, 3.00 equiv) dropwise with stirring at 0° C. The resulting solution was stirred at room temperature for 5 h, concentrated under vacuum, and diluted with 6 L of H$_2$O. The pH of the solution was adjusted to 8-9 with sodium bicarbonate. The resulting solution was extracted with 3×4 L of ethyl acetate. The combined organic layers were dried over anhydrous sodium sulfate and concentrated under vacuum. The crude product was purified by distillation under reduced pressure (15 mm Hg) and the fraction was collected at 52-65° C. The crude product was re-crystallized from DCM/n-hexane (1:50) to afford 520 g (38%) of 5-chloro-3-(trifluoromethyl)-1H-pyrazole as a white solid. LCMS (ESI): M+H$^+$=171.

Step 4: 2-(Tetramethyl-1,3,2-dioxaborolan-2-yl)cyclopropane-1-carbonitrile

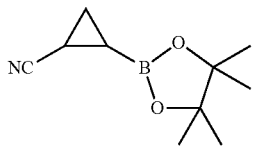

Into a 30-mL sealed tube purged and maintained with an inert atmosphere of nitrogen a solution of cyclopropanecarbonitrile (1.0 g, 14.9 mmol) in tetrahydrofuran (12.2 mL) was added [Ir(COD)OMe]$_2$ (320 mg, 0.25 mmol), bis(pinacolato) diboron (1.59 g, 12.5 mmol) and 2,9-dimethylphenanthroline (50.5 mg, 0.49 mmol). The reaction mixture was stirred at 90° C. for 18 h and concentrated in vacuo. The residue was purified by chromatography with ethyl acetate/petroleum ether (1:4) to afford 2-(tetramethyl-1,3,2-dioxaborolan-2-yl)cyclopropane-1-carbonitrile as a light yellow oil (1 g, crude).

Step 5: Potassium 2-(cyano)cyclopropyltrifluoroborate

To a solution of 2-(tetramethyl-1,3,2-dioxaborolan-2-yl)cyclopropane-1-carbonitrile (180 g, crude) in methanol (4.5 L) was added difluorane potassium (9.98 g, 129 mmol) in H$_2$O (2 L). The resulting reaction mixture stirred at room temperature for 12 h and concentrated in vacuo. The residue was washed with propan-2-one (6×1.5 L). The filtrate was concentrated in vacuo, dissolved with water (5 L), and washed with DCM (3×3 L) and EtOAc (3×3 L). The water layer was freeze-dry to afford 2-(trifluoro-lambda4-boranyl)cyclopropane-1-carbonitrile potassium as a white solid (151.9 g, about 30% in two steps).

Step 6: 5-Bromo-1,3-thiazol-2-amine

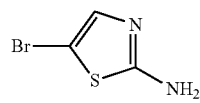

To a mixture of sodium bicarbonate (5.8 kg, 69.04 mol, 3.00 equiv) in water (30 L) and dichloromethane (20 L) was added 5-bromo-1,3-thiazol-2-amine hydrobromide (6 kg, 23.08 mol, 1.00 equiv) in batches. The resulting mixture was stirred at room temperature for 4 h and extracted with dichloromethane. The combined organic layers were dried over anhydrous sodium sulfate and concentrated under vacuum to afford 5-bromo-1,3-thiazol-2-amine as a gray solid (2.9 kg, 70%).

Step 7: 5-Bromo-2-chloro-1,3-thiazole

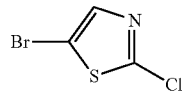

To a solution of 5-bromo-1,3-thiazol-2-amine (1 kg, 5.59 mol, 1.00 equiv) in CH$_3$CN (7 L) was added CuCl (0.83 kg, 8.4 mol, 1.5 equiv) followed by the addition of t-BuONO (1.15 kg, 11.2 mol, 2.00 equiv) dropwise with stirring. The reaction mixture was stirred at 70° C. overnight, cooled to room temperature, quenched with water, and extracted with dichloromethane. The combined organic layers were dried over anhydrous sodium sulfate and concentrated. The residue was purified by chromatography eluted with diethyl ether/petroleum ether (1/20) to afford 5-bromo-2-chloro-1,3-thiazole as a yellow solid (0.4 kg, 36%).

Step 8: 4-Bromo-2-chloro-5-iodo-1,3-thiazole

To a solution of 5-bromo-2-chloro-1,3-thiazole (500 g, 2.52 mol, 1.00 equiv) in tetrahydrofuran (8 L) was added LDA (1517 mL, 2 mol/L, 3 mmol, 1.20 equiv) dropwise with stirring at −70° C. under nitrogen atmosphere. The resulting solution was stirred at −70° C. for 2 h. To this reaction mixture was added a solution of I$_2$ (967 g, 3.81 mol, 1.50 equiv) in tetrahydrofuran (3 L) dropwise with stirring at −70° C. The reaction mixture was stirred at room temperature overnight, quenched with water, and extracted with dichloromethane. The combined organic layers were dried over anhydrous sodium sulfate and concentrated under vacuum to give a residue, which was purified by chromatography eluted with ethyl acetate/petroleum ether (1:50) to afford 4-bromo-2-chloro-5-iodo-1,3-thiazole (500 g, 61%) as a gray solid.

Step 9:
4-Bromo-2-chloro-5-(trifluoromethyl)-1,3-thiazole

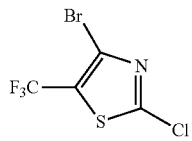 [SMILES: FC(F)(F)c1sc(Cl)nc1Br]

To a mixture of 4-bromo-2-chloro-5-iodo-1,3-thiazole (500 g, 1.54 mol, 1.00 equiv) in N,N-dimethylformamide (5 L) was added CuI (440 g, 2.31 mol, 1.50 equiv) and methyl 2,2-difluoro-2-(fluorosulfonyl)acetate (593 g, 3.09 mol, 2.00 equiv). The reaction mixture was stirred at 80° C. overnight under nitrogen atmosphere, cooled to room temperature, and filtered. The filtrate was diluted with water and extracted with ether. The combined organic layers were washed with brine, dried over anhydrous sodium sulfate and concentrated under vacuum to give a residue, which was purified by chromatography eluting with diethyl ether/petroleum ether (1/20) to afford 4-bromo-2-chloro-5-(trifluoromethyl)-1,3-thiazole as a light yellow oil (300 g, crude), which was used in next step without further purification.

Step 10:
4-Bromo-5-(trifluoromethyl)-1,3-thiazol-2-amine

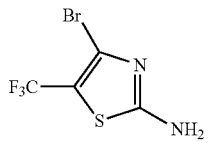 [SMILES: Nc1nc(Br)c(C(F)(F)F)s1]

To a solution of 4-bromo-2-chloro-5-(trifluoromethyl)-1,3-thiazole (300 g, 1.13 mol, 1.00 equiv) in 1,4-dioxane (2 L) was added NH$_3$/H$_2$O (28%, 2 L). The resulting solution was stirred at 50° C. overnight. The resulting solution was extracted with ethyl acetate. The combined organic layers were dried over anhydrous sodium sulfate and concentrated under vacuum to give a residue, which was purified by chromatography eluted with ethyl acetate/petroleum ether (1:8) to afford 4-bromo-5-(trifluoromethyl)-1,3-thiazol-2-amine as a light yellow solid (160 g, 42% in 2 steps).

Step 11: 3-Bromo-7-(chloromethyl)-2-(trifluoromethyl)-5H-[1,3]thiazolo[3,2-a]pyrimidin-5-one

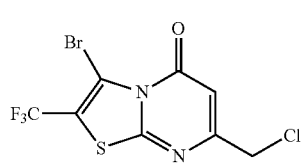 [SMILES: O=c1cc(CCl)nc2sc(C(F)(F)F)c(Br)n12]

To a mixture of 4-bromo-5-(trifluoromethyl)-1,3-thiazol-2-amine (320 g, 1.30 mol, 1.00 equiv) in PPA (3200 g) was added ethyl 4-chloro-3-oxobutanoate (1068 g, 6.49 mol, 5.00 equiv). The resulting mixture was stirred at 130° C. for 2 h, quenched by the addition of water, and extracted with ethyl acetate. The combined organic layers were dried over anhydrous sodium sulfate and concentrated under vacuum to give a residue, which was purified by chromatography eluted with ethyl acetate/petroleum ether (1/10) to afford 3-bromo-7-(chloromethyl)-2-(trifluoromethyl)-5H-[1,3]thiazolo[3,2-a]pyrimidin-5-one as a light yellow solid (306 g, 68%). LCMS (ESI): M+H$^+$=348.9.

Step 12: 3-Bromo-7-((5-chloro-3-(trifluoromethyl)-1H-pyrazol-1-yl)methyl)-2-(trifluoromethyl)-5H-thiazolo[3,2-a]pyrimidin-5-one

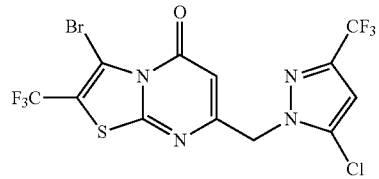

To a mixture of 3-bromo-7-(chloromethyl)-2-(trifluoromethyl)-5H-thiazolo[3,2-a]pyrimidin-5-one (1 g, 2.88 mmol) in acetonitrile (10 mL) was added sodium carbonate (610 mg, 5.75 mmol) and 5-chloro-3-(trifluoromethyl)-1H-pyrazole (590 mg, 3.45 mmol). The resulting mixture was stirred overnight at 80° C. After 30 iterations on the same scale, the mixtures were combined, then filtered and concentrated in vacuo. The residue was purified by flash chromatography on silica gel eluting with ethyl acetate/petroleum ether (1:20) to afford 3-(trifluoromethyl)-1H-pyrazol-1-yl)methy)-2-(trifluoromethylethyl)-5H-thiazolo[3,2-a]pyrimidin-5-one (13.5 g, 40%) as a light yellow solid and 3-bromo-7-((3-chloro-5-(trifluoromethyl)-1H-pyrazol-1-yl)methyl)-2-(trifluoromethyl)-5H-thiazolo[3,2-a]pyrimidin-5-one (6.0 g, 15%) a light yellow solid. LCMS (ESI): M+H$^+$=480.9.

Step 13: 2-(7-[[5-Chloro-3-(trifluoromethyl)-1H-pyrazol-1-yl]methyl]-5-oxo-2-(trifluoromethyl)-5H-[1,3]thiazolo[3,2-a]pyrimidin-3-yl)cyclopropane-1-carbonitrile (cis enantiomers)

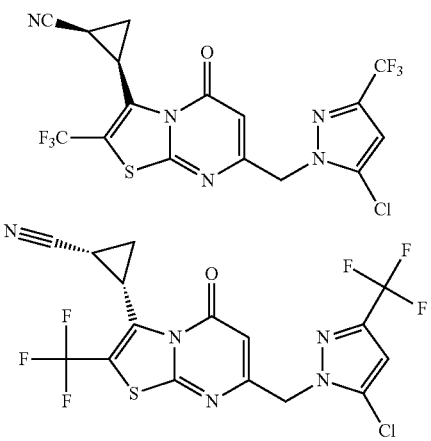

To a mixture of 3-bromo-7-[[5-chloro-3-(trifluoromethyl)-1H-pyrazol-1-yl]methyl]-2-(trifluoromethyl)-5H-[1,3]thiazolo[3,2-a]pyrimidin-5-one (500 mg, 1.03 mmol) in 1,4-dioxane/water (10 mL/1 mL) was added [bis(diphenylphosphino)ferrocene]palladium(II) dichloride (171 mg, 0.23 mmol), sodium carbonate (500 mg, 4.68 mmol), and 2-(trifluoro-lambda4-boranyl)cyclopropane-1-carbonitrile potassium (500 mg, 2.87 mmol). The resulting mixture was stirred overnight at 85° C. The reaction was repeated 20 times on the same scale and combined. The resulting mixture was extracted with dichloromethane and concentrated in vacuo. The residue was purified by flash chromatography on silica gel eluting with ethyl acetate/petroleum ether (1/2) to afford the racemic product (4.5 g, 46%). Then the racemic product was separated with supercritical fluid chromatography (Column: Phenomenex Lux 5u Cellulose-4,250*50 mm; Mobile Phase: $CO_2$:MeOH=50:50; Flow rate: 160 mL/min; detector: 220 nm) to afford two enantiomers. Enantiomer 1 (Peak 1, 1.88 g, 20%, white solid): Retention Time: 4.43 min; LCMS (ESI): M+H$^+$=468.0; $^1$H NMR (400 MHz, CDCl$_3$) δ 6.60 (s, 1H), 5.81 (s, 1H), 5.27 (s, 2H), 3.11-3.00 (m, 1H), 1.91-1.80 (m, 2H), 1.65-1.62 (m, 1H). Peak 2 (Enantiomer 2, 1.89 g, 20%, white solid): Retention Time: 5.59 min; LCMS (ESI): M+H$^+$=468.0; $^1$H NMR (400 MHz, CDCl$_3$) δ 6.63 (s, 1H), 5.84 (s, 1H), 5.29 (s, 2H), 3.15-3.07 (m, 1H), 1.95-1.86 (m, 2H), 1.68-1.59 (m, 1H).

Example 220: 2-[7-[(N-Ethyl-4-fluoro-anilino)methyl]-5-oxo-thiazolo[3,2-a]pyrimidin-3-yl]-1-(hydroxymethyl)cyclopropanecarbonitrile

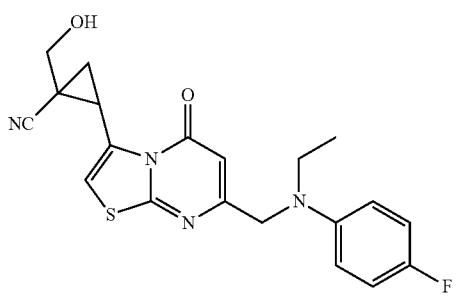 [SMILES: CCN(Cc1cc(=O)n2c(C3CC3(C#N)CO)csc2n1)c1ccc(F)cc1]

Step 1: 7-(Chloromethyl)-3-(hydroxymethyl)thiazolo[3,2-a]pyrimidin-5-one

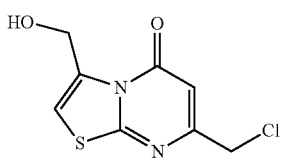 [SMILES: O=c1cc(CCl)nc2scc(CO)n12]

To methyl 7-(chloromethyl)-5-oxo-thiazolo[3,2-a]pyrimidine-3-carboxylate (0.2 g, 0.77 mmol) in 4 mL methanol at rt was added sodium borohydride (0.11 g, 2.9 mmol) over 1 min resulting in exotherm. After 5 min, additional NaBH$_4$ (50 mg) was added, resulting in gas evolution. After 1 h, the mixture was partitioned between CH$_2$Cl$_2$ and 1 N HCl (aq). The phases were separated and the aqueous phase was extracted with CH$_2$Cl$_2$. The combined organic phases were dried with Na$_2$SO$_4$ and concentrated onto silica gel for purification using CombiFlash® (12 g column, 0 to 80% EtOAc in CH$_2$Cl$_2$, 15 min) to afford 36 mg (20%) of 7-(chloromethyl)-3-(hydroxymethyl)thiazolo[3,2-a]pyrimidin-5-one as a tan solid.

Step 2: 7-(Chloromethyl)-5-oxo-thiazolo[3,2-a]pyrimidine-3-carbaldehyde

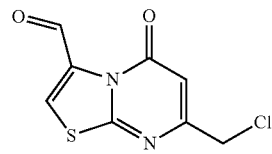 [SMILES: O=Cc1csc2nc(CCl)cc(=O)n12]

To 7-(chloromethyl)-3-(hydroxymethyl)thiazolo[3,2-a]pyrimidin-5-one (36 mg, 0.16 mmol) in 5 mL CH$_2$Cl$_2$ was added alumina (0.34 g, 3.3 mmol), then pyridinium chlorochromate (0.17 g, 0.78 mmol). The mixture was stirred overnight, then filtered through diatomaceous earth and concentrated onto silica gel for purification using CombiFlash® (4 g column, 0 to 80% EtOAc in CH$_2$Cl$_2$, 15 min) to afford 28 mg (78%) of 7-(chloromethyl)-5-oxo-thiazolo[3,2-a]pyrimidine-3-carbaldehyde as a colorless solid.

Step 3: (E)-3-[7-(Chloromethyl)-5-oxo-thiazolo[3,2-a]pyrimidin-3-yl]-2-cyano-prop-2-enoate

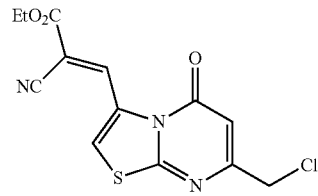 [SMILES: CCOC(=O)/C(C#N)=C/c1csc2nc(CCl)cc(=O)n12]

To a solution of 7-(chloromethyl)-5-oxo-thiazolo[3,2-a]pyrimidine-3-carbaldehyde (80 mg, 0.35 mmol) and ethyl cyanoacetate (40 mg, 0.35 mmol) in 5 mL CH$_2$Cl$_2$ was added 1 drop of piperidine resulting in a bright yellow color. After 2 h, the mixture was concentrated onto silica gel for purification using CombiFlash® (4 g column, 0 to 40% EtOAc in CH$_2$Cl$_2$, 15 min) to afford 66 mg (58%) of ethyl (E)-3-[7-(chloromethyl)-5-oxo-thiazolo[3,2-a]pyrimidin-3-yl]-2-cyano-prop-2-enoate as a yellow solid.

Step 4: Ethyl 2-[7-(chloromethyl)-5-oxo-thiazolo[3,2-a]pyrimidin-3-yl]-1-cyano-cyclopropanecarboxylate

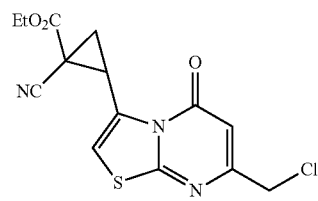 [SMILES: CCOC(=O)C1(C#N)CC1c1csc2nc(CCl)cc(=O)n12]

To a solution of trimethylsulfoxonium iodide (69 mg, 0.31 mmol) in 1 mL DMSO at rt was added sodium hydride (60% dispersion in paraffin liquid, 12 mg, 0.31 mmol). The mixture was stirred 5 min at which time ethyl (E)-3-[7-(chloromethyl)-5-oxo-thiazolo[3,2-a]pyrimidin-3-yl]-2-cyano-prop-2-enoate (66 mg, 0.20 mmol) in 1 mL DMSO was added quickly dropwise resulting in a dark orange color. The mixture was stirred 1 h, then partitioned between EtOAc and water. The phases were separated and the aqueous phase extracted with EtOAc. The combined organic phases were washed with brine, dried with $Na_2SO_4$, and concentrated onto silica for purification using CombiFlash® (12 g column, 0 to 80% EtOAc in $CH_2Cl_2$, 15 min) to afford 14 mg (20%) of ethyl 2-[7-(chloromethyl)-5-oxo-thiazolo[3,2-a]pyrimidin-3-yl]-1-cyano-cyclopropanecarboxylate as a single diastereomer.

Step 5: 2-[7-(Chloromethyl)-5-oxo-thiazolo[3,2-a]pyrimidin-3-yl]-1-(hydroxymethyl)cyclopropanecarbonitrile

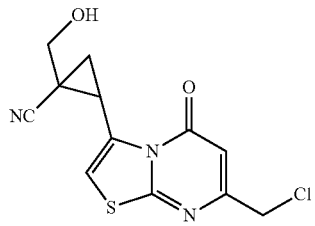 [SMILES: N#CC1(CO)CC1c1csc2nc(CCl)cc(=O)n12]

To a solution of ethyl 2-[7-(chloromethyl)-5-oxo-thiazolo[3,2-a]pyrimidin-3-yl]-1-cyano-cyclopropanecarboxylate (14 mg, 0.04 mmol) in 2 mL MeOH at 0° C. was added sodium borohydride (22 mg, 0.58 mmol) in one portion. The mixture was warmed to room temperature and stirred overnight. The mixture was concentrated, then partitioned between $CH_2Cl_2$ and 1N HCl (aq). The phases were separated, and the aqueous phase extracted with $CH_2Cl_2$. The combined organic phases were dried with $Na_2SO_4$ and concentrated. The above process was repeated (3 mL MeOH and 40 mg $NaBH_4$ added at room temperature) to effect complete conversion. Workup as before and concentration onto silica gel for purification using CombiFlash® (4 g column, 0 to 100% EtOAc in $CH_2Cl_2$, 15 min) afforded 11 mg (90%) of 2-[7-(chloromethyl)-5-oxo-thiazolo[3,2-a]pyrimidin-3-yl]-1-(hydroxymethyl)cyclopropanecarbonitrile as a colorless solid.

Step 6: 2-[7-[(N-Ethyl-4-fluoro-anilino)methyl]-5-oxo-thiazolo[3,2-a]pyrimidin-3-yl]-1-(hydroxymethyl)cyclopropanecarbonitrile

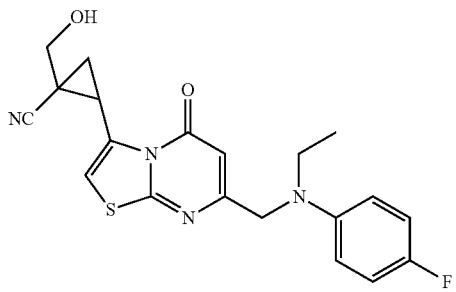 [SMILES: CCN(Cc1cc(=O)n2c(C3CC3(C#N)CO)csc2n1)c1ccc(F)cc1]

A mixture of N-ethyl-4-fluoro-aniline (8 mg, 0.06 mmol) and 2-[7-(chloromethyl)-5-oxo-thiazolo[3,2-a]pyrimidin-3-yl]-1-(hydroxymethyl)cyclopropanecarbonitrile (11 mg, 0.04 mmol) in 2 mL acetonitrile was stirred for 3 d. The mixture was concentrated onto silica for purification using CombiFlash® (4 g column, 0 to 100% EtOAc in $CH_2Cl_2$, 15 min) to afford 7 mg (47%) of 2-[7-[(N-ethyl-4-fluoro-anilino)methyl]-5-oxo-thiazolo[3,2-a]pyrimidin-3-yl]-1-(hydroxymethyl)cyclopropanecarbonitrile as a colorless solid. $^1$H NMR (400 MHz, Chloroform-d) δ 6.93 (m, 2H), 6.7 (s, 1H), 6.61 (m, 2H), 6.25 (s, 1H), 4.33 (s, 2H), 4.16 (m, 2H), 3.48 (m, 2H), 3.32 (d, J=11.2 Hz, 1H), 3.25 (ddd, J=8.5, 7.1, 1.5 Hz, 1H), 1.76 (m, 1H), 1.55 (dd, J=8.3, 6.3 Hz, 1H), 1.24 (t, J=7.1 Hz, 3H). MS m/z 399.13 (M+H).

Example 222: 7-[[5-Chloro-3-(trifluoromethyl)pyrazol-1-yl]methyl]-3-(2-hydroxy-1-methyl-ethyl)-2-methyl-thiazolo[3,2-a]pyrimidin-5-one

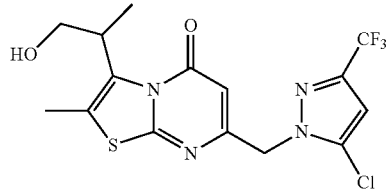

Step 1: Methyl 2-methyl-3-oxopentanoate

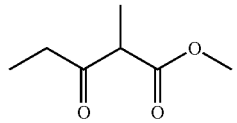

To a solution of methyl 3-oxopentanoate (10 g, 76.8 mmol) in tetrahydrofuran (20 mL) was added potassium carbonate (21 g, 152 mmol) and iodomethane (12 g, 84.5 mmol). The resulting mixture was stirred for 5 h at 70° C., and then cooled to room temperature. The mixture was concentrated in vacuo to afford methyl 2-methyl-3-oxopentanoate as yellow oil (12 g, crude).

Step 2: Methyl 4-bromo-2-methyl-3-oxopentanoate

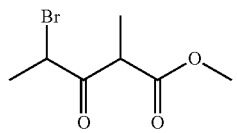

To a solution of methyl 2-methyl-3-oxopentanoate (9.00 g, 62.4 mmol) in chloroform (25 mL, 310 mmol) was added $Br_2$ (12 g, 75.1 mmol). The resulting solution was stirred for 12 h at 25° C., and then concentrated in vacuo to afford methyl 4-bromo-2-methyl-3-oxopentanoate (13 g, 93%) as yellow oil.

Step 3: Ethyl 2-(2-amino-5-methyl-1,3-thiazol-4-yl)propanoate

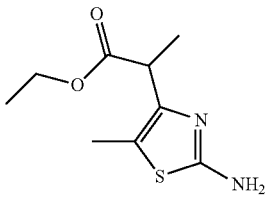

To a solution of methyl 4-bromo-2-methyl-3-oxopentanoate (10 g, 44.8 mmol) in ethanol (100 mL, 1.72 mol) was added thiourea (4.8 g, 63.1 mmol). The resulting solution was stirred for 12 h at 110° C. The reaction mixture was cooled to room temperature and then concentrated in vacuo. The residue was purified by flash chromatography on silica gel eluting with ethyl acetate/petroleum ether (1/3) to afford ethyl 2-(2-amino-5-methyl-1,3-thiazol-4-yl)propanoate (8 g, 83%) as a yellow oil. LCMS (ESI): M+H$^+$=215.1.

Step 4: Ethyl 2-[7-(chloromethyl)-2-methyl-5-oxo-5H-[1,3]thiazolo[3,2-a]pyrimidin-3-yl]propanoate

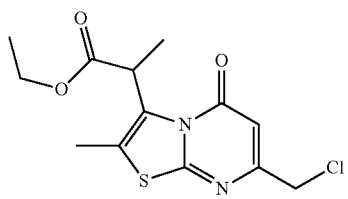 [SMILES: CCOC(=O)C(C)c1c(C)sc2nc(CCl)cc(=O)n12]

To a solution of ethyl 2-(2-amino-5-methyl-1,3-thiazol-4-yl)propanoate (10 g, 46.7 mmol) in polyphosphoric acid (54 g, 469 mmol) was added ethyl 4-chloro-3-oxobutanoate (6.6 g, 40.1 mmol). The resulting solution was stirred for 1 h at 110° C. and then cooled to room temperature. The pH of the solution was adjusted to 7 with sodium carbonate (5%). The resulting solution was extracted with ethyl acetate and concentrated in vacuo. The residue was purified by flash chromatography on silica gel eluting with ethyl acetate/petroleum ether (1/3) to afford ethyl 2-[7-(chloromethyl)-2-methyl-5-oxo-5H-[1,3]thiazolo[3,2-a]pyrimidin-3-yl]propanoate as a brown solid (13 g, 88%). LCMS (ESI): M+H$^+$=315.0.

Step 5: Ethyl 2-(7-[[5-chloro-3-(trifluoromethyl)-1H-pyrazol-1-yl]methyl]-2-methyl-5-oxo-5H [1,3]thiazolo[3,2-a]pyrimidin-3-yl)propanoate

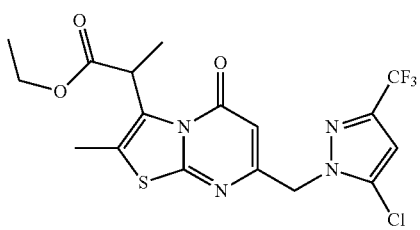 [SMILES: CCOC(=O)C(C)c1c(C)sc2nc(Cn3nc(C(F)(F)F)cc3Cl)cc(=O)n12]

To a solution of ethyl 2-[7-(chloromethyl)-2-methyl-5-oxo-5H-[1,3]thiazolo[3,2-a]pyrimidin-3-yl]propanoate (2 g, 6.35 mmol) in acetonitrile (30 mL) was added 5-chloro-3-(trifluoromethyl)-1H-pyrazole (1.1 g, 6.45 mmol), potassium iodide (1.06 g, 6.39 mmol), and potassium carbonate (2.2 g, 15.9 mmol). The resulting mixture was stirred for 2 h at 90° C., cooled to room temperature and concentrated in vacuo. The residue was purified by flash chromatography on silica gel eluting with ethyl acetate/petroleum ether (1/4) to afford ethyl 2-(7-[[5-chloro-3-(trifluoromethyl)-1H-pyrazol-1-yl]methyl]-2-methyl-5-oxo-5H-[1,3]thiazolo[3,2-a]pyrimidin-3-yl)propanoate (2.9 g, crude) as a brown solid. LCMS (ESI): M+H$^+$=449.0.

Step 6: 7-[[5-Chloro-3-(trifluoromethyl)-1H-pyrazol-1-yl]methyl]-3-(1-hydroxypropan-2-yl)-2-methyl-5H-[1,3]thiazolo[3,2-a]pyrimidin-5-one

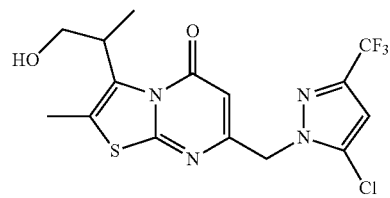 [SMILES: Cc1sc2nc(Cn3nc(C(F)(F)F)cc3Cl)cc(=O)n2c1C(C)CO]

To a solution of methyl 2-(7-[[5-chloro-3-(trifluoromethyl)-1H-pyrazol-1-yl]methyl]-2-methyl-5-oxo-5H-[1,3]thiazolo[3,2-a]pyrimidin-3-yl)propanoate (60 mg, 0.14 mmol) in dichloromethane (6 mL) was added DIBAL-H (40 mg, 0.28 mmol) at 0° C. The resulting solution was stirred for 12 h at 25° C., and the reaction was then quenched by water. The resulting solution was extracted with ethyl acetate and concentrated in vacuo. The residue was purified by flash chromatography on silica gel eluting with dichloromethane/ethyl acetate (2/1) to afford 7-[[5-chloro-3-(trifluoromethyl)-1H-pyrazol-1-yl]methyl]-3-(1-hydroxypropan-2-yl)-2-methyl-5H-[1,3]thiazolo[3,2-a]pyrimidin-5-one (28.7 mg, 51%) as a light yellow oil. LCMS (ESI): M+H$^+$=407.1; $^1$H NMR (400 MHz, CDCl$_3$) δ 6.60 (s, 1H), 5.68 (s, 1H), 5.27 (s, 2H), 3.94-3.90 (m, 2H), 2.43 (s, 3H), 1.74 (m, 1H), 1.38-1.37 (m, 3H).

Example 240: 7-[[2-Fluoro-3-(trifluoromethyl)phenyl]methyl]-2-methyl-3-(1H-1,2,4-triazol-5-yl)thiazolo[3,2-a]pyrimidin-5-one

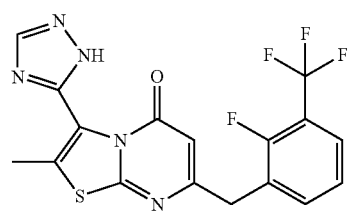 [SMILES: Cc1sc2nc(Cc3cccc(C(F)(F)F)c3F)cc(=O)n2c1-c1ncn[nH]1]

Step 1. Methyl 7-[[2-fluoro-3-(trifluoromethyl)phenyl]methyl]-2-methyl-5-oxo-thiazolo[3,2-a]pyrimidine-3-carboxylate

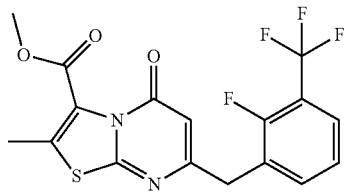 [SMILES: COC(=O)c1c(C)sc2nc(Cc3cccc(C(F)(F)F)c3F)cc(=O)n12]

Pd[dppf]Cl$_2$ (108 mg, 0.15 mmol) was added to a solution of methyl 7-(chloromethyl)-2-methyl-5-oxo-thiazolo[3,2-a]pyrimidine-3-carboxylate (400 mg, 1.47 mmol), [2-fluoro-3-(trifluoromethyl)phenyl]boronic acid (457 mg, 2.20 mmol), and K$_2$CO$_3$ (405 mg, 2.93 mmol) in 1,4-dioxane/water (9 mL, 10:1) under N$_2$. The mixture was stirred at 90° C. for 20 h. The reaction mixture was filtered through diatomaceous earth and washed with EtOAc. The crude product was adsorbed on diatomaceous earth and purified by flash chromatography (0-60% EtOAc/heptane gradient) to afford methyl 7-[[2-fluoro-3-(trifluoromethyl)phenyl]methyl]-2-methyl-5-oxo-thiazolo[3,2-a]pyrimidine-3-carboxylate as an orange solid (409 mg, 70%). LCMS (ESI): M+H$^+$=401.0; $^1$H NMR (400 MHz, DMSO-d$_6$) δ 7.70 (q, J=8.1 Hz, 2H), 7.38 (t, J=7.8 Hz, 1H), 6.18 (s, 1H), 4.03 (s, 2H), 3.84 (s, 3H), 2.38 (s, 3H).

Step 2. 7-[[2-Fluoro-3-(trifluoromethyl)phenyl]methyl]-2-methyl-5-oxo-thiazolo[3,2-a]pyrimidine-3-carboxylic acid

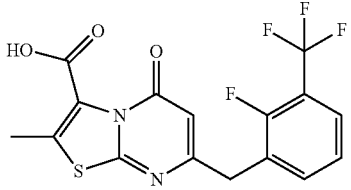

Methyl 7-[[2-fluoro-3-(trifluoromethyl)phenyl]methyl]-2-methyl-5-oxo-thiazolo[3,2-a]pyrimidine-3-carboxylate (365 mg, 0.91 mmol) was dissolved in THF (9 mL) and LiOH 2 M (4.5 mL, 9.12 mmol) was added. The mixture was stirred at 60° C. for 6 h. The mixture was extracted with DCM (3×20 mL). The aqueous layer was acidified with 1 N HCl and extracted with DCM (4×20 mL). The organics were dried with MgSO$_4$, filtered and concentrated to give 7-[[2-fluoro-3-(trifluoromethyl)phenyl]methyl]-2-methyl-5-oxo-thiazolo[3,2-a]pyrimidine-3-carboxylic acid as a crude beige solid (186 mg, 53%). LCMS (ESI): M+H$^+$=387.1.

Step 3. 7-[[2-Fluoro-3-(trifluoromethyl)phenyl]methyl]-2-methyl-5-oxo-thiazolo[3,2-a]pyrimidine-3-carboxamide

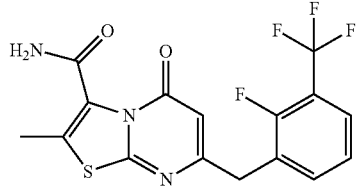 [SMILES: Cc1sc2nc(Cc3cccc(C(F)(F)F)c3F)cc(=O)n2c1C(N)=O]

Oxalyl chloride (42 µL, 0.47 mmol) was added to a solution of 7-[[2-fluoro-3-(trifluoromethyl)phenyl]methyl]-2-methyl-5-oxo-thiazolo[3,2-a]pyrimidine-3-carboxylic acid (90 mg, 0.23 mmol,) and DMF (2 µL, 0.02 mmol) in DCM (1.5 mL) at 0° C. The mixture was stirred at room temperature for 30 min and then the reaction mixture was concentrated to dryness. The solvent was switched for THF (0.6 mL) and a solution of ammonia in 1,4-dioxane (0.5 mol/L, 4 mL, 1.86 mmol) was added at 0° C. The mixture was stirred at room temperature for 30 min. The reaction was partitioned in water/DCM and extracted with DCM (3×10 mL). The organics were washed with brine, dried with MgSO$_4$, filtered and concentrated to obtain 7-[[2-fluoro-3-(trifluoromethyl)phenyl]methyl]-2-methyl-5-oxo-thiazolo[3,2-a]pyrimidine-3-carboxamide as a crude pale yellow solid (73 mg, 81%). LCMS (ESI): M+H$^+$=386.2.

Step 4. 7-[[2-Fluoro-3-(trifluoromethyl)phenyl]methyl]-2-methyl-3-(1H-1,2,4-triazol-5-yl)thiazolo[3,2-a]pyrimidin-5-one

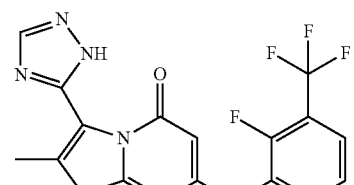

7-[[2-Fluoro-3-(trifluoromethyl)phenyl]methyl]-2-methyl-5-oxo-thiazolo[3,2-a]pyrimidine-3-carboxamide (73 mg, 0.19 mmol) in N,N-dimethylformamide dimethyl acetal (1.9 mL, 14.2 mmol) was stirred at 100° C. for 4 h. The mixture was concentrated, treated with acetic acid (1.9 mL, 32.7 mmol) and hydrazine (120 µL, 3.78 mmol), and stirred at 100° C. for 2 h. The reaction mixture was concentrated and purified by preparative HPLC and lyophilization to provide 7-[[2-fluoro-3-(trifluoromethyl)phenyl]methyl]-2-methyl-3-(1H-1,2,4-triazol-5-yl)thiazolo[3,2-a]pyrimidin-5-one as a beige solid (19 mg, 25%). LCMS (ESI): M+H$^+$=410.1; $^1$H NMR (~2:1 triazole tautomer ratio, * denotes minor tautomer peaks, 400 MHz, DMSO-d$_6$) δ 14.19 (s, 1H), 8.52 (s, 1H), 7.79-7.65 (m, 2H), 7.39 (t, J=7.8 Hz, 1H), 6.13* (s, 0.3H), 6.04 (s, 0.7H), 4.02 (s, 2H), 2.33* (s, 1H), 2.18 (s, 2H).

Example 244: 3-Acetyl-7-[[5-chloro-3-(trifluoromethyl)pyrazol-1-yl]methyl]-2-methoxy-thiazolo[3,2-a]pyrimidin-5-one

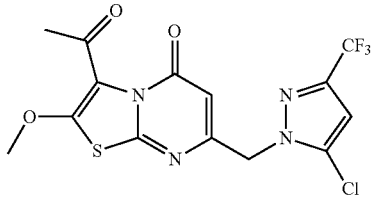 [SMILES: COc1sc2nc(Cn3nc(C(F)(F)F)cc3Cl)cc(=O)n2c1C(C)=O]

Step 1: 5-Methoxythiazole-2-amine

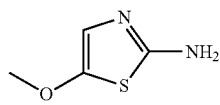

To a solution of 5-bromo-1,3-thiazol-2-amine hydrobromide (26 g, 100 mmol) in methanol (100 mL) was added dropwise sodium methoxide (12 g, 222 mmol) in 40 mL methanol at 0° C. The resulting solution was stirred for 1 h at room temperature and the reaction was diluted with ethyl acetate. The solids were filtered out and the filtrate was concentrated in vacuo to afford 5-methoxy-1,3-thiazol-2-amine (6.5 g, crude) as a tan solid. LCMS (ESI): M+H$^+$= 131.0.

Step 2: 2-(5-Methoxythiazol-2-yl)isoindoline-1,3-dione

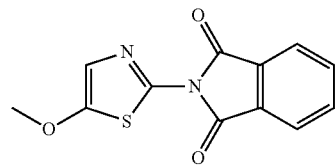 [SMILES: COc1cnc(N2C(=O)c3ccccc3C2=O)s1]

To a solution of 5-methoxy-1,3-thiazol-2-amine (6.50 g, crude) in acetonitrile (100 mL) was added ethyl 1,3-dioxo-2,3-dihydro-1H-isoindole-2-carboxylate (10.9 g, 49.9 mmol). The resulting solution was stirred overnight at 50° C. and then concentrated in vacuo. The residue was purified by flash chromatography on silica gel eluting with dichloromethane/petroleum ether (3/1) to afford 2-(5-methoxy-1,3-thiazol-2-yl)-2,3-dihydro-1H-isoindole-1,3-dione (5 g, 38%) as a light brown solid. LCMS (ESI): M+H$^+$=261.0.

Step 3: 2-(4-Chloro-5-methoxythiazol-2-yl)isoindoline-1,3-dione

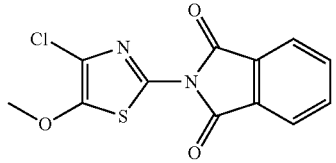 [SMILES: COc1sc(N2C(=O)c3ccccc3C2=O)nc1Cl]

A solution of 2-(5-methoxy-1,3-thiazol-2-yl)-2,3-dihydro-1H-isoindole-1,3-dione (4.00 g, 15.4 mmol) in acetonitrile (100 mL) was treated with N-chlorosuccinimide (2.16 g, 16.2 mmol) and then stirred for 2 h at 90° C. The resulting mixture was concentrated in vacuo to afford 2-(4-chloro-5-methoxy-1,3-thiazol-2-yl)-2,3-dihydro-1H-isoindole-1,3-dione (4.6 g, crude) as an orange solid. LCMS (ESI): M+H$^+$=295.0.

Step 4: 4-Chloro-5-methoxythiazol-2-amine

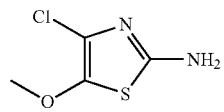

To a solution of 2-(4-chloro-5-methoxy-1,3-thiazol-2-yl)-2,3-dihydro-1H-isoindole-1,3-dione (4.6 g, 15.6 mmol) in methanol (50 mL) was added NH$_2$NH$_2$.H$_2$O (15 mL, 308 mmol). The resulting solution was stirred for 4 h at room temperature. The solids were filtered out and the filtrate was concentrated in vacuo to afford 4-chloro-5-methoxy-1,3-thiazol-2-amine (2 g, 78%) as a light brown solid. LCMS (ESI): M+H$^+$=165.0.

Step 5: 3-Chloro-7-(chloromethyl)-2-methoxy-5H-thiazolo[3,2-a]pyrimidin-5-one

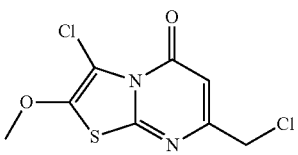

To a solution of 4-chloro-5-methoxy-1,3-thiazol-2-amine (2.00 g, 12.1 mmol) in PPA (30 g, 260 mmol) was added ethyl 4-chloro-3-oxobutanoate (6.00 g, 36.4 mmol). The resulting solution was stirred for 2 h at 60° C. and then quenched with water/ice. The resulting solution was extracted with dichloromethane and concentrated in vacuo. The residue was purified by flash chromatography on silica gel eluting with ethyl acetate/petroleum ether (1/3) to afford 3-chloro-7-(chloromethyl)-2-methoxy-5H-thiazolo[3,2-a]pyrimidin-5-one (1.5 g, 47%) as a light brown solid. LCMS (ESI): M+H$^+$=265.0.

Step 6: 3-Chloro-7-((5-chloro-3-(trifluoromethyl)-1H-pyrazol-1-yl)methyl)-2-methoxy-5H-thiazolo[3,2-a]pyrimidin-5-one

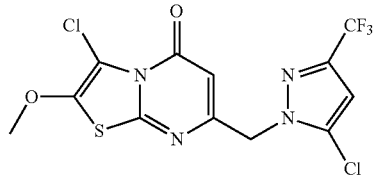 [SMILES: COc1sc2nc(Cn3nc(C(F)(F)F)cc3Cl)cc(=O)n2c1Cl]

To a solution of 3-chloro-7-(chloromethyl)-2-methoxy-5H-thiazolo[3,2-a]pyrimidin-5-one (100 mg, 0.38 mmol) in acetonitrile (2 mL) was added 5-chloro-3-(trifluoromethyl)-1H-pyrazole (78 mg, 0.46 mmol) and potassium carbonate (104 mg, 0.75 mmol). The resulting solution was stirred for 2 h at 80° C. and then concentrated in vacuo. The residue was purified by preparative TLC with ethyl acetate/petroleum ether (1/2) to afford 3-chloro-7-[[5-chloro-3-(trifluoromethyl)-1H-pyrazol-1-yl]methyl]-2-methoxy-5H-thiazolo[3,2-a]pyrimidin-5-one (24.4 mg, 16%) as a white solid. LCMS (ESI): M+H$^+$=399.9; $^1$H NMR (300 MHz, CDCl$_3$) δ 6.58 (s, 1H), 5.73 (s, 1H), 5.23 (s, 2H), 4.02 (s, 3H).

Step 7: 7-((5-Chloro-3-(trifluoromethyl)-1H-pyrazol-1-yl)methyl)-3-(1-ethoxyvinyl)-2-methoxy-5H-thiazolo[3,2-a]pyrimidin-5-one

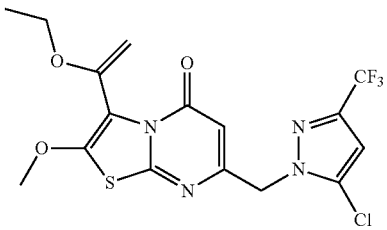 [SMILES: C=C(OCC)c1c(OC)sc2nc(Cn3nc(C(F)(F)F)cc3Cl)cc(=O)n12]

To a solution of 3-chloro-7-[[5-chloro-3-(trifluoromethyl)-1H-pyrazol-1-yl]methyl]-2-methoxy-5H-thiazolo[3,2-a]pyrimidin-5-one (300 mg, 0.752 mmol) in 1,4-dioxane (8 mL) was added tributyl(1-ethoxyethenyl)stannane (543 mg, 1.504 mmol), DIEA (194 mg, 1.50 mmol), and bis(diphenylphosphino)ferrocene]palladium(II) dichloride (106 mg, 0.151 mmol). The resulting solution was stirred overnight at 80° C. and then concentrated invacuo. The residue was purified by preparative TLC with ethyl acetate/petroleum ether (1:2) to afford 7-((5-chloro-3-(trifluoromethyl)-1H-pyrazol-1-yl)methyl)-3-(1-ethoxyvinyl)-2-methoxy-5H-thiazolo[3,2-a]pyrimidin-5-one (180 mg, 55%) as light yellow oil. LCMS (ESI): M+H$^+$=435.0.

Step 8: 3-Acetyl-7-((5-chloro-3-(trifluoromethyl)-1H-pyrazol-1-yl)methyl)-2-methoxy-5H-thiazolo[3,2-a]pyrimidin-5-one

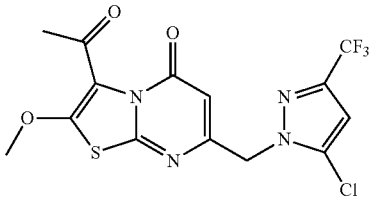 [SMILES: COc1sc2nc(Cn3nc(C(F)(F)F)cc3Cl)cc(=O)n2c1C(C)=O]

To a solution of 7-((5-chloro-3-(trifluoromethyl)-1H-pyrazol-1-yl)methyl)-3-(1-ethoxyvinyl)-2-methoxy-5H-thiazolo[3,2-a]pyrimidin-5-one (180 mg, 0.414 mmol) in dichloromethane (10 mL) was added a solution of hydrogen chloride in 1,4-dioxane (0.5 mL, saturated). The resulting solution was stirred for 30 min at room temperature and then concentrated in vacuo. The residue was purified by preparative TLC with ethyl acetate/petroleum ether (1/1) to afford 3-acetyl-7-((5-chloro-3-(trifluoromethyl)-1H-pyrazol-1-yl)methyl)-2-methoxy-5H-thiazolo[3,2-a]pyrimidin-5-one (64.7 mg, 38%) as a white solid. LCMS (ESI): M+H$^+$= 407.0; $^1$H NMR (300 MHz, CDCl$_3$) δ 6.58 (s, 1H), 5.81 (s, 1H), 5.27 (s, 2H), 4.05 (s, 3H), 2.50 (s, 3H).

Example 250: 7-[[5-Chloro-3-(trifluoromethyl)pyrazol-1-yl]methyl]-3-propanoyl-2-(trifluoromethyl)thiazolo[3,2-a]pyrimidin-5-one

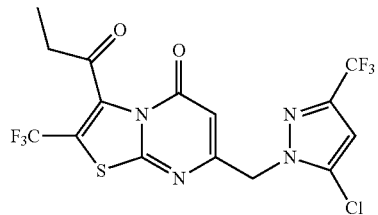 [SMILES: CCC(=O)c1c(C(F)(F)F)sc2nc(Cn3nc(C(F)(F)F)cc3Cl)cc(=O)n12]

Step 1: Methyl 2-[[(tert-butoxy)carbonyl]amino]-1,3-thiazole-4-carboxylate

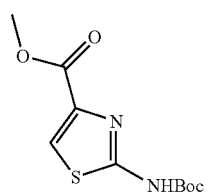 [SMILES: COC(=O)c1csc(NC(=O)OC(C)(C)C)n1]

To a solution of 2-amino-1,3-thiazole-4-carboxylate (20 g, 126 mmol) and 4-dimethylaminopyridine (1.54 g, 12.6 mmol) in dichloromethane/tetrahydrofuran (200 mL/200 mL) was added di-tert-butyl dicarbonate (33 g, 151 mmol). The resulting solution was stirred for 12 h at room temperature and then concentrated in vacuo. The residue was purified by chromatography with ethyl acetate/petroleum ether (1/2) to afford methyl 2-[[(tert-butoxy)carbonyl]

amino]-1,3-thiazole-4-carboxylate (28 g, 86%) as an off-white solid. LCMS (ESI): M+H$^+$=259.0.

Step 2: 2-[[(tert-Butoxy)carbonyl]amino]-1,3-thiazole-4-carboxylic acid

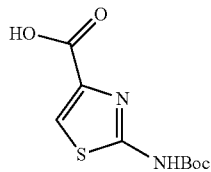

To a solution of methyl 2-[[(tert-butoxy)carbonyl]amino]-1,3-thiazole-4-carboxylate (28 g, 108 mmol) in tetrahydrofuran (300 mL) was added a solution of lithium hydroxide (10.4 g, 433 mmol) in water (150 mL). The resulting mixture was stirred for 12 h at room temperature. The pH of the solution was adjusted to 4 with hydrochloric acid (2 mol/L). The solids were collected by filtration to afford 2-[[(tert-butoxy)carbonyl]amino]-1,3-thiazole-4-carboxylic acid (20 g, 76%) as an off-white solid. LCMS (ESI): M+H$^+$=245.0.

Step 3: tert-Butyl N-[4-[methoxy(methyl)carbamoyl]-1,3-thiazol-2-yl]carbamate

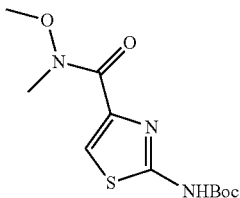 [SMILES: CON(C)C(=O)c1csc(NC(=O)OC(C)(C)C)n1]

To a mixture of 2-[[(tert-butoxy)carbonyl]amino]-1,3-thiazole-4-carboxylic acid (20.0 g, 81.9 mmol) in dichloromethane (400 mL) was added methoxy(methyl)amine hydrochloride (16.0 g, 164 mmol), HATU (37.4 g, 98.3 mmol), and triethylamine (16.6 g, 164 mmol). The resulting mixture was stirred for 4 h at room temperature. The reaction was then quenched by water, then extracted with ethyl acetate and concentrated in vacuo to afford tert-butyl N-[4-[methoxy(methyl)carbamoyl]-1,3-thiazol-2-yl]carbamate (20 g, 85%) as a light red solid. LCMS (ESI): M+H$^+$=288.0.

Step 4: tert-Butyl N-(4-propanoyl-1,3-thiazol-2-yl)carbamate

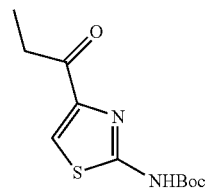 [SMILES: CCC(=O)c1csc(NC(=O)OC(C)(C)C)n1]

To a solution of tert-butyl N-[4-[methoxy(methyl)carbamoyl]-1,3-thiazol-2-yl]carbamate (5.00 g, 17.4 mmol) in tetrahydrofuran (100 mL, 1.23 mol) was added bromo(ethyl)magnesium (4.59 mL, 34.8 mmol) at −70° C. The resulting solution was stirred for 12 h at room temperature. The reaction was diluted with saturated aqueous NH$_4$Cl (30 mL), extracted with ethyl acetate, and concentrated in vacuo. The residue was purified by flash chromatography on silica gel eluting with ethyl acetate/petroleum ether (1/3) to afford tert-butyl N-(4-propanoyl-1,3-thiazol-2-yl)carbamate (1.3 g, 29%) as a light yellow solid. LCMS (ESI): M+H$^+$=257.0.

Step 5: 1-(2-Amino-1,3-thiazol-4-yl)propan-1-one

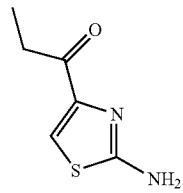

To a solution of tert-butyl N-(4-propanoyl-1,3-thiazol-2-yl)carbamate (1.3 g, 5.07 mmol) in dichloromethane (15 mL) was added trifluoroacetic acid (24 mL). The resulting solution was stirred for 2 h at 0° C. and then concentrated in vacuo. The residue was dissolved in dichloromethane and then washed with sodium bicarbonate (1 mol/L). The organic layers were concentrated in vacuo to afford 1-(2-amino-1,3-thiazol-4-yl)propan-1-one (750 mg, 90%) as a light yellow solid. LCMS (ESI): M+H$^+$=157.0.

Step 6: 1-(2-Amino-5-iodo-1,3-thiazol-4-yl)propan-1-one

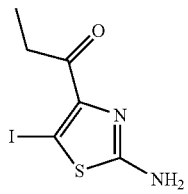

To a solution of 1-(2-amino-1,3-thiazol-4-yl)propan-1-one (850 mg, 5.44 mmol) in dichloromethane (20 mL) was added N-iodo-succinimide (1.35 g, 5.99 mmol). The resulting mixture was stirred for 12 h at room temperature and then concentrated in vacuo. The residue was purified by flash chromatography on silica gel eluting with ethyl acetate/petroleum ether (1/3) to afford 1-(2-amino-5-iodo-1,3-thiazol-4-yl)propan-1-one (1 g, 65%) as a brown solid. LCMS (ESI): M+H$^+$=283.0.

Step 7: 2-(5-Iodo-4-propanoyl-1,3-thiazol-2-yl)-2,3-dihydro-1H-isoindole-1,3-dione

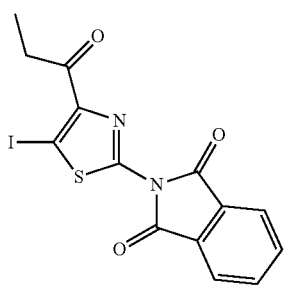 [SMILES: CCC(=O)c1nc(N2C(=O)c3ccccc3C2=O)sc1I]

To a solution of 1-(2-amino-5-iodo-1,3-thiazol-4-yl)propan-1-one (500 mg, 1.77 mmol) and triethylamine (89.7 mg, 0.89 mmol) in dichloromethane (30 mL) was added ethyl 1,3-dioxo-2,3-dihydro-1H-isoindole-2-carboxylate (777 mg, 3.54 mmol). The resulting mixture was stirred for 12 h at 40° C., and concentrated in vacuo. The residue was purified by flash chromatography on silica gel eluting with ethyl acetate/petroleum ether (1/2) to afford 2-(5-iodo-4-propanoyl-1,3-thiazol-2-yl)-2,3-dihydro-1H-isoindole-1,3-dione (450 mg, 62%) as a light red solid. LCMS (ESI): M+H$^+$=413.0.

Step 8: 2-(5-Iodo-4-propanoyl-1,3-thiazol-2-yl)-2,3-dihydro-1H-isoindole-1,3-dione

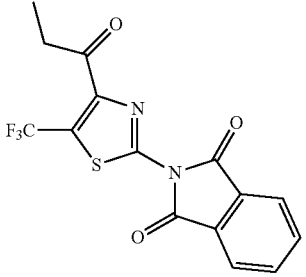 [SMILES: CCC(=O)c1nc(N2C(=O)c3ccccc3C2=O)sc1C(F)(F)F]

To a solution of 2-(5-iodo-4-propanoyl-1,3-thiazol-2-yl)-2,3-dihydro-1H-isoindole-1,3-dione (450 mg, 1.09 mmol) in N,N-dimethylformamide (10 mL) was added ethyl 2,2-difluoro-2-(fluorosulfonyl)acetate (450 mg, 2.18 mmol) and copper(I) iodide (416 mg, 2.18 mmol). The resulting mixture was stirred for 2 h at 80° C. and then concentrated in vacuo. The residue was dissolved in dichloromethane (20 mL), and the solids were filtered out. The resulting solution was concentrated in vacuo to afford 2-[4-propanoyl-5-(trifluoromethyl)-1,3-thiazol-2-yl]-2,3-dihydro-1H-isoindole-1,3-dione (230 mg, 59%) as a yellow solid. LCMS (ESI): M+H$^+$=355.0.

Step 9: 1-[2-Amino-5-(trifluoromethyl)-1,3-thiazol-4-yl]propan-1-one

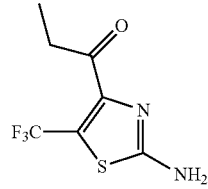

To a solution of 2-[4-propanoyl-5-(trifluoromethyl)-1,3-thiazol-2-yl]-2,3-dihydro-1H-isoindole-1,3-dione (230 mg, 0.65 mmol) in acetonitrile (10 mL) was added hydrazine monohydrate (0.31 mL, 6.38 mmol). The resulting solution was stirred for 30 min at room temperature. After concentration, the residue was purified by flash chromatography on silica gel eluting with ethyl acetate/petroleum ether (1/1) to afford 1-[2-amino-5-(trifluoromethyl)-1,3-thiazol-4-yl]propan-1-one (60 mg, 41%) as a light yellow oil. LCMS (ESI): M+H$^+$=225.0.

Step 10: 7-(Chloromethyl)-3-propanoyl-2-(trifluoromethyl)-5H-[1,3]thiazolo[3,2-a]pyrimidin-5-one

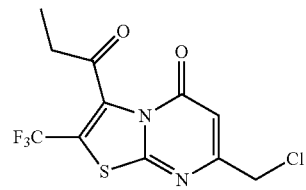 [SMILES: CCC(=O)c1c(C(F)(F)F)sc2nc(CCl)cc(=O)n12]

To a mixture of 1-[2-amino-5-(trifluoromethyl)-1,3-thiazol-4-yl]propan-1-one (60 mg, 0.27 mmol) in polyphosphoric acid (1 g, 8.69 mmol) was added ethyl 4-chloro-3-oxobutanoate (220 mg, 1.34 mmol). The resulting mixture was stirred for 12 h at 130° C. The reaction was then quenched by water (25 mL), extracted with ethyl acetate and concentrated in vacuo. The residue was purified by flash chromatography on silica gel eluting with ethyl acetate/petroleum ether (1/2) to afford 7-(chloromethyl)-3-propanoyl-2-(trifluoromethyl)-5H-[1,3]thiazolo[3,2-a]pyrimidin-5-one (15 mg, 17%) as a yellow solid. LCMS (ESI): M+H$^+$=325.0.

Step 11: 7-[[5-Chloro-3-(trifluoromethyl)-1H-pyrazol-1-yl]methyl]-3-propanol-2-(trifluoromethyl)-5H-[1,3]thiazolo[3,2-a]pyrimidin-5-one

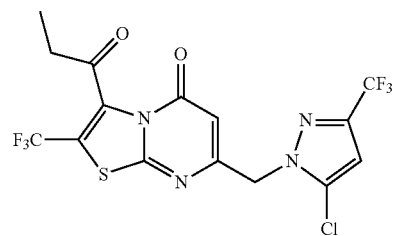 [SMILES: CCC(=O)c1c(C(F)(F)F)sc2nc(Cn3nc(C(F)(F)F)cc3Cl)cc(=O)n12]

353

To a mixture of 7-(chloromethyl)-3-propanoyl-2-(trifluoromethyl)-5H-[1,3]thiazolo[3,2-a]pyrimidin-5-one (15 mg, 0.05 mmol) in acetonitrile (3 mL, 57.1 mmol) was added potassium carbonate (13 mg, 0.09 mmol) and 5-chloro-3-(trifluoromethyl)-1H-pyrazole (10 mg, 0.06 mmol). The resulting mixture was stirred for 2 h at 80° C. After filtration and concentration, the residue was purified by chromatography with ethyl acetate/petroleum ether (1/3) to afford 7-[[5-chloro-3-(trifluoromethyl)-1H-pyrazol-1-yl]methyl]-3-propanoyl-2-(trifluoromethyl)-5H-[1,3]thiazolo[3,2-a]pyrimidin-5-one (4.5 mg, 21%) as a light brown solid. LCMS (ESI): M+H$^+$=459.0; $^1$H NMR (400 MHz, CDCl$_3$) δ 6.60 (s, 1H), 5.83 (s, 1H), 5.31 (s, 2H), 2.97-2.83 (m, 2H), 1.29-1.25 (m, 3H).

Example 251: 2-[7-[(3,5-Dichloropyrazol-1-yl) methyl]-2-oxo-thiazolo[3,2-a]pyrimidin-3-yl]cyclopropanecarbonitrile

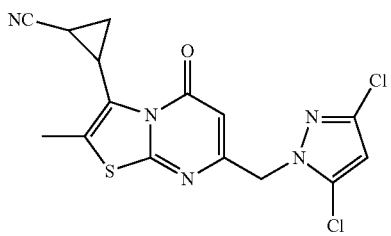 [SMILES: Cc1sc2nc(Cn3nc(Cl)cc3Cl)cc(=O)n2c1C1CC1C#N]

Step 1: N,N-Dimethyl-1H-pyrazole-1-sulfonamide

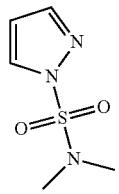

A solution of 1H-pyrazole (30 g, 440 mmol) in tetrahydrofuran (500 mL) was treated with sodium hydride (26 g, 648 mmol, 60%) at 0° C., and then stirred for 1 h at 0° C. N,N-Dimethylsulfamoyl chloride (95 g, 661 mmol) was added dropwise at 0° C. The resulting solution was stirred for additional 2 h at room temperature and then quenched by water. The resulting solution was extracted with dichloromethane and concentrated in vacuo. The residue was purified by flash chromatography on silica gel eluting with ethyl acetate/petroleum ether (1/6) to afford to N,N-dimethyl-1H-pyrazole-1-sulfonamide (58 g, 75%) as colorless oil. LCMS (ESI): M+H$^+$=175.0.

354

Step 2: 5-Chloro-N,N-dimethyl-1H-pyrazole-1-sulfonamide

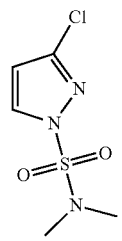

To a solution of N,N-dimethyl-1H-pyrazole-1-sulfonamide (37.2 g, 212 mmol) in tetrahydrofuran (600 mL) was added dropwise n-BuLi (127 mL, 2.5 mmol/L) at −78° C. The resulting solution was stirred for 1 h at −78° C. Hexachloroethane (75.4 g, 318 mmol) in tetrahydrofuran (400 mL) was added dropwise at −78° C. The reaction mixture was allowed to warm to room temperature and was stirred overnight at room temperature. The reaction was then quenched by water, then extracted with dichloromethane and concentrated in vacuo. The residue was purified by flash chromatography on silica gel eluting with ethyl acetate/petroleum ether (1/6) to afford 5-chloro-N,N-dimethyl-1H-pyrazole-1-sulfonamide as a red oil (39.5 g, 89%). LCMS (ESI): M+H$^+$=209.0.

Step 3: 5-Chloro-1H-pyrazole

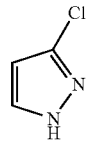

To a solution of 5-chloro-N,N-dimethyl-1H-pyrazole-1-sulfonamide (30 g, 143 mmol) in dichloromethane (500 mL) was added trifluoroacetic acid (45.7 g, 401 mmol). The reaction mixture was stirred for 2 h at room temperature and quenched by water. The pH of the solution was adjusted to 8 with saturated sodium bicarbonate. The resulting solution was extracted with dichloromethane and concentrated in vacuo to afford 5-chloro-1H-pyrazole as a reddish solid (14 g, 95%). LCMS (ESI): M+H$^+$=103.0.

Step 4: 5-Chloro-1-nitro-1H-pyrazole

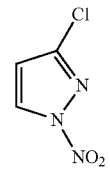

To a solution of 5-chloro-1H-pyrazole (14 g, 136 mmol) in acetic acid/acetic anhydride (36 mL/92 mL) was added fuming nitric acid (36 mL). The resulting solution was stirred overnight at room temperature, and then diluted with water (500 mL). The solids were collected by filtration to afford 5-chloro-1-nitro-1H-pyrazole as a yellow solid (7 g, 35%).

Step 5: 5-Chloro-3-nitro-1H-pyrazole

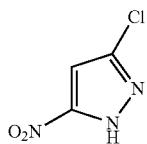

A solution of 5-chloro-1-nitro-1H-pyrazole (3 g, 20.3 mmol) in anisole (53.6 mL) was stirred overnight at 130° C. The resulting solution was diluted with of H₂O:petroleum ether (1:1), then extracted with sodium hydroxide (10%) and the aqueous layers combined. The pH of the solution was adjusted to 2 with hydrochloric acid (3 mol/L). The resulting solution was extracted with ethyl acetate and concentrated in vacuo to afford 5-chloro-3-nitro-1H-pyrazole as a yellow solid (2.7 g, 90%).

Step 6: 3-Bromo-7-[(5-chloro-3-nitro-1H-pyrazol-1-yl)methyl]-2-methyl-5H-[1,3]thiazolo[3,2-a]pyrimidin-5-one

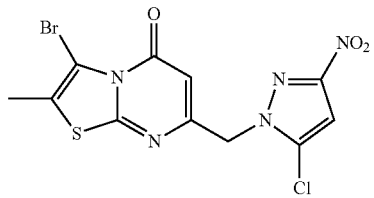 [SMILES: Cc1sc2nc(Cn3nc([N+](=O)[O-])cc3Cl)cc(=O)n2c1Br]

To a solution of 3-bromo-7-(chloromethyl)-2-methyl-5H-[1,3]thiazolo[3,2-a]pyrimidin-5-one (400 mg, 1.36 mmol) in acetonitrile (50 mL) was added 5-chloro-3-nitro-1H-pyrazole (211 mg, 1.43 mmol), KI (113 mg, 0.68 mmol), and potassium carbonate (565 mg, 4.09 mmol). The resulting solution was stirred for 2 h at 80° C., cooled, extracted with dichloromethane, and then concentrated in vacuo to afford 3-bromo-7-[(5-chloro-3-nitro-1H-pyrazol-1-yl)methyl]-2-methyl-5H-[1,3]thiazolo[3,2-a]pyrimidin-5-one as a gray solid (20 mg, 4%). LCMS (ESI): M+H$^+$=405.0.

Step 7: 7-((3-Amino-5-chloro-1H-pyrazol-1-yl)methyl)-3-bromo-2-methyl-5H-thiazolo[3,2-a]pyrimidin-5-one

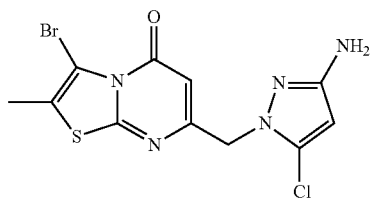 [SMILES: Cc1sc2nc(Cn3nc(N)cc3Cl)cc(=O)n2c1Br]

To a solution of 3-bromo-7-((5-chloro-3-nitro-1H-pyrazol-1-yl)methyl)-2-methyl-5H-thiazolo[3,2-a]pyrimidin-5-one (30 mg, 0.066 mmol) in ethanol/water (5 mL/1 mL) was added iron powder (29 mg, 0.52 mmol) and ammonium chloride (35 mg, 0.660 mmol). The reaction mixture was stirred for 2 h at 80° C., cooled and extracted with dichloromethane. The combined organic phase was concentrated in vacuo to afford 7-((3-amino-5-chloro-1H-pyrazol-1-yl)methyl)-3-bromo-2-methyl-5H-thiazolo[3,2-a]pyrimidin-5-one as a gray solid (10 mg, 4%). LCMS (ESI): M+H$^+$=375.0.

Step 8: 3-Bromo-7-[(3,5-dichloro-1H-pyrazol-1-yl)methyl]-2-methyl-5H-[1,3]thiazolo[3,2-a]pyrimidin-5-one

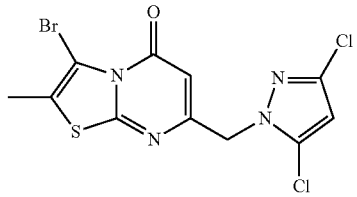 [SMILES: Cc1sc2nc(Cn3nc(Cl)cc3Cl)cc(=O)n2c1Br]

To a solution of 7-[(5-amino-3-chloro-1H-pyrazol-1-yl)methyl]-3-bromo-2-methyl-5H-[1,3]thiazolo[3,2-a]pyrimidin-5-one (1 g, 2.67 mmol) in acetonitrile (10 mL) was added tert-butyl nitrite (495 mg, 4.80 mmol) and copper(I) chloride (715 mg, 5.32 mmol). The resulting mixture was stirred for 1 h at 25° C. and then concentrated in vacuo. The residue was purified by flash chromatography on silica gel eluting with ethyl acetate/petroleum ether (1/1) to afford 3-bromo-7-[(3,5-dichloro-1H-pyrazol-1-yl)methyl]-2-methyl-5H-[1,3]thiazolo[3,2-a]pyrimidin-5-one (200 mg, 19%) as a yellow solid. LCMS (ESI): M+H$^+$=395.0.

Step 9: 2-[7-[(3,5-Dichloro-1H-pyrazol-1-yl)methyl]-2-methyl-5-oxo-5H-[1,3]thiazolo[3,2-a]pyrimidin-3-yl]cyclopropane-1-carbonitrile

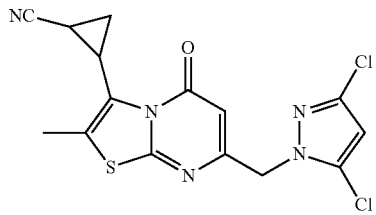 [SMILES: Cc1sc2nc(Cn3nc(Cl)cc3Cl)cc(=O)n2c1C1CC1C#N]

To a solution of 3-bromo-7-[(3,5-dichloro-1H-pyrazol-1-yl)methyl]-2-methyl-5H-[1,3]thiazolo[3,2-a]pyrimidin-5-one (150 mg, 0.38 mmol) in acetonitrile/water (4 ml/0.4 ml) was added 2-(trifluoro-lambda4-boranyl)cyclopropane-1-carbonitrile potassium (263 mg, 1.52 mmol), sodium carbonate (80 mg, 0.75 mmol), and [bis(diphenylphosphino)ferrocene]palladium(II) dichloride (27 mg, 0.037 mmol). The resulting solution was stirred for 14 h at 90° C. and then concentrated in vacuo. The residue was purified by flash chromatography on silica gel eluting with ethyl acetate/petroleum ether (1/1) to afford the racemic product (45 mg, 31%). The racemic product was separated by chiral HPLC with the following conditions (Column: Chiralpak ic 0.46*25 cm, 5 um; Mobile Phase: 100% MeOH-HPLC; Flow rate: 1 mL/min; detector: 254 nm) to afford the title compound as a white solid (13.3 mg, 9%). Retention Time: 9.18 min; LCMS (ESI): M+H⁺=381.0; ¹H NMR (300 MHz, CDCl₃) δ 6.25 (s, 1H), 5.71 (s, 1H), 5.14 (s, 2H), 2.99-2.94 (m, 1H), 2.39 (s, 3H), 1.84-1.79 (m, 1H), 1.69-1.66 (m, 1H), 1.45-1.35 (m 1H).

Example 258: 7-[[5-Chloro-3-(trifluoromethyl)pyrazol-1-yl]methyl]-2-(difluoromethyl)-N-ethyl-5-oxo-thiazolo[3,2-a]pyrimidine-3-carboxamide

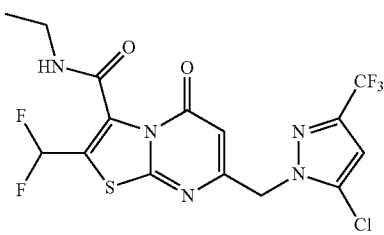 [SMILES: CCNC(=O)c1c(C(F)F)sc2nc(Cn3nc(C(F)(F)F)cc3Cl)cc(=O)n12]

Step 1: 2-Chloro-7-[[5-chloro-3-(trifluoromethyl)-1H-pyrazol-1-yl]methyl]-N-ethyl-5-oxo-5H-[1,3]thiazolo[3,2-a]pyrimidine-3-carboxamide

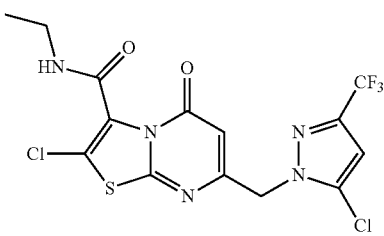 [SMILES: CCNC(=O)c1c(Cl)sc2nc(Cn3nc(C(F)(F)F)cc3Cl)cc(=O)n12]

To a solution of 2-chloro-7-(chloromethyl)-N-ethyl-5-oxo-5H-[1,3]thiazolo[3,2-a]pyrimidine-3-carboxamide (2 g, 6.53 mmol) in acetonitrile (10 mL) was added 5-chloro-3-(trifluoromethyl)-1H-pyrazole (872 mg, 5.11 mmol), potassium iodide (542 mg, 3.26 mmol), and potassium carbonate (1.8 g, 13 mmol). The resulting mixture was stirred for 1 h at 80° C. and concentrated in vacuo. The residue was purified by flash chromatography on silica gel eluting with ethyl acetate/petroleum ether (1/1) to afford of 2-chloro-7-[[5-chloro-3-(trifluoromethyl)-1H-pyrazol-1-yl]methyl]-N-ethyl-5-oxo-5H-[1,3]thiazolo[3,2-a]pyrimidine-3-carboxamide (1.1 g, 38%) as a yellow solid. LCMS (ESI): M+H⁺=441.0.

Step 2: 7-[[5-Chloro-3-(trifluoromethyl)-1H-pyrazol-1-yl]methyl]-2-ethenyl-N-ethyl-5-oxo-5H-[1,3]thiazolo[3,2-a]pyrimidine-3-carboxamide

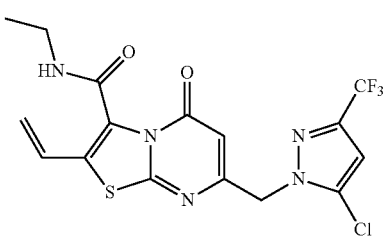 [SMILES: C=Cc1sc2nc(Cn3nc(C(F)(F)F)cc3Cl)cc(=O)n2c1C(=O)NCC]

To a solution of 2-chloro-7-[[5-chloro-3-(trifluoromethyl)-1H-pyrazol-1-yl]methyl]-N-ethyl-5-oxo-5H-[1,3]thiazolo[3,2-a]pyrimidine-3-carboxamide (500 mg, 1.14 mmol) in 1,4-dioxane/water (15 mL/1 mL) was added 2-ethenyl-4,4,5,5-tetramethyl-1,3,2-dioxaborolane (349 mg, 2.27 mmol), sodium carbonate, (238 mg, 2.25 mmol) and [bis(diphenylphosphino)ferrocene]palladium(II) dichloride (83 mg, 0.11 mmol). The resulting solution was stirred for 14 h at 90° C. and then concentrated in vacuo. The residue was purified by flash chromatography on silica gel eluting with ethyl acetate/petroleum ether (1/1) to afford 7-[[5-chloro-3-(trifluoromethyl)-1H-pyrazol-1-yl]methyl]-2-ethenyl-N-ethyl-5-oxo-5H-[1,3]thiazolo[3,2-a]pyrimidine-3-carboxamide as a yellow solid (200 mg, 41%). LCMS (ESI): M+H⁺=432.0.

Step 3: 7-[[5-Chloro-3-(trifluoromethyl)-1H-pyrazol-1-yl]methyl]-N-ethyl-2-formyl-5-oxo-5H-[1,3]thiazolo[3,2-a]pyrimidine-3-carboxamide

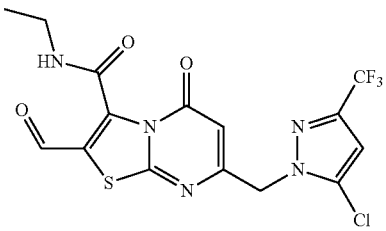 [SMILES: CCNC(=O)c1c(C=O)sc2nc(Cn3nc(C(F)(F)F)cc3Cl)cc(=O)n12]

To a solution of 7-[[5-chloro-3-(trifluoromethyl)-1H-pyrazol-1-yl]methyl]-2-ethenyl-N-ethyl-5-oxo-5H-[1,3]thiazolo[3,2-a]pyrimidine-3-carboxamide (175 mg, 0.41 mmol) in 1,4-dioxane/water (5 mL/3 mL) was added osmium tetraoxide (1.03 mg, 0.004 mmol), N-methylmorpholine-N-oxide (94.83 mg, 0.811 mmol), and sodium periodate (173 mg, 0.81 mmol). The resulting solution was stirred for 14 h at 25° C. and concentrated. The residue was purified by flash chromatography on silica gel eluting with ethyl acetate/petroleum ether (1/2) to afford 7-[[5-chloro-3-(trifluoromethyl)-1H-pyrazol-1-yl]methyl]-N-ethyl-2-formyl-5-oxo-5H-[1,3]thiazolo[3,2-a]pyrimidine-3-carboxamide (50 mg 28%) as a light yellow solid. LCMS (ESI): M+H⁺=456.0.

Step 4: 7-((5-Chloro-3-(trifluoromethyl)-1H-pyrazol-1-yl)methyl)-2-(difluoromethyl)-N-ethyl-5-oxo-5H-thiazolo[3,2-a]pyrimidine-3-carboxamide

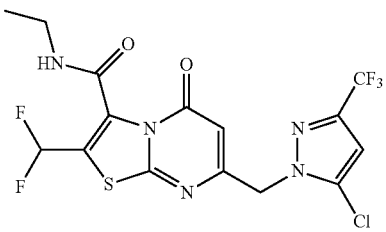 [SMILES: CCNC(=O)c1c(C(F)F)sc2nc(Cn3nc(C(F)(F)F)cc3Cl)cc(=O)n12]

To a solution of 7-[[5-chloro-3-(trifluoromethyl)-1H-pyrazol-1-yl]methyl]-N-ethyl-2-formyl-5-oxo-5H-[1,3]thiazolo[3,2-a]pyrimidine-3-carboxamide (100 mg, 0.23 mmol) in dichloromethane (20 mL) was added bis(2- methoxyethyl)amino]sulfur trifluoride (510 mg, 2.31 mmol) at 0° C. The resulting solution was stirred for 14 h at 25° C., and then quenched by water. The resulting solution was extracted with ethyl acetate and concentrated in vacuo to afford 7-[[5-chloro-3-(trifluoromethyl)-1H-pyrazol-1-yl]methyl]-2-(difluoromethyl)-N-ethyl-5-oxo-5H-[1,3]thiazolo[3,2-a]pyrimidine-3-carboxamide as a white solid (21.2 mg, 20%). LCMS (ESI): M+H$^+$=456.0; $^1$H NMR (400 MHz, CDCl$_3$) δ 7.10-6.83 (m, 1H), 6.59 (s, 1H), 6.37 (s, 1H), 5.80 (s, 1H), 5.30 (s, 2H), 3.54-3.47 (m, 2H), 1.28-1.25 (m, 3H).

Examples 266 and 267: 2-[2-Chloro-7-[[5-chloro-3-(trifluoromethyl)pyrazol-1-yl]methyl]-5-oxo-thiazolo[3,2-a]pyrimidin-3-yl]cyclopropanecarbonitrile (cis enantiomers)

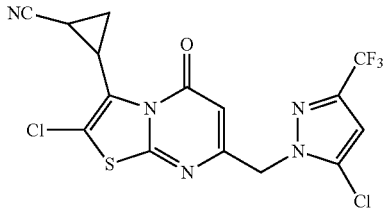 [SMILES: N#CC1CC1c1c(Cl)sc2nc(Cn3nc(C(F)(F)F)cc3Cl)cc(=O)n12]

Step 1: tert-Butyl N-(4-bromo-5-chloro-1,3-thiazol-2-yl)carbamate

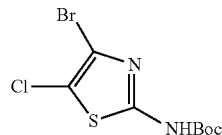 [SMILES: CC(C)(C)OC(=O)Nc1nc(Br)c(Cl)s1]

To a solution of tert-butyl N-(5-bromo-1,3-thiazol-2-yl)carbamate (5 g, 17.9 mmol) in tetrahydrofuran (100 ml) was added dropwise LDA (29.4 ml, 2 mol/L) at −78° C., and the resulting mixture was stirred for 1 h at −78° C. Then the mixture was added a solution of hexachloroethane (14 g, 59.1 mmol) in tetrahydrofuran (50 ml) at −78° C. The reaction was stirred for additional 15 h at room temperature. The reaction was quenched by water, then extracted with dichloromethane and concentrated in vacuo. The residue was purified by flash chromatography on silica gel eluting with ethyl acetate/petroleum ether (1/9) to afford tert-butyl N-(4-bromo-5-chloro-1,3-thiazol-2-yl)carbamate (4.07 g, 72%) as brown oil. LCMS (ESI): M+H$^+$=313.0.

Step 2: 4-Bromo-5-chloro-1,3-thiazol-2-amine

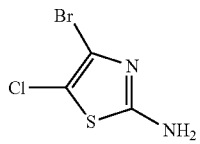

To a solution of tert-butyl N-(4-bromo-5-chloro-1,3-thiazol-2-yl)carbamate (4.07 g, 13.0 mmol) in dichloromethane (20 mL) was added trifluoroacetic acid (29.7 g, 260 mmol), and the reaction was stirred for 15 h at room temperature. The pH of the solution was adjusted to 7 with saturated sodium bicarbonate, then extracted with dichloromethane and concentrated in vacuo. The residue was purified by flash chromatography on silica gel eluting with ethyl acetate/petroleum ether (1/5) to afford 4-bromo-5-chloro-1,3-thiazol-2-amine (1.02 g, 37%) as a brown solid. LCMS (ESI): M+H$^+$=213.0.

Step 3: 3-Bromo-2-chloro-7-(chloromethyl)-5H-[1,3]thiazolo[3,2-a]pyrimidin-5-one

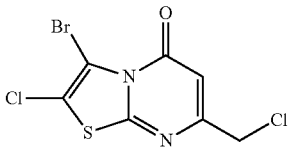 [SMILES: O=c1cc(CCl)nc2sc(Cl)c(Br)n12]

To a solution of 4-bromo-5-chloro-1,3-thiazol-2-amine (700 mg, 3.28 mmol) in polyphosphoric acid (2.81 g, 24.4 mmol) was added ethyl 4-chloro-3-oxobutanoate (1.08 g, 6.56 mmol). The reaction mixture was stirred for 1 h at 110° C. and cooled to room temperature. The reaction was then quenched by water and the pH of the solution was adjusted to 7 with sodium hydroxide (1 mol/L). The resulting solution was extracted with dichloromethane and concentrated in vacuo. The residue was purified by flash chromatography on silica gel eluting with ethyl acetate/petroleum ether (1/3) to afford 3-bromo-2-chloro-7-(chloromethyl)-5H-[1,3]thiazolo[3,2-a]pyrimidin-5-one (900 mg, 87%) as a brown solid. LCMS (ESI): M+H$^+$=313.0.

Step 4: 3-Bromo-2-chloro-7-((5-chloro-3-(trifluoromethyl)-1H-pyrazol-1-yl)methyl)-5H-thiazolo[3,2-a]pyrimidin-5-one

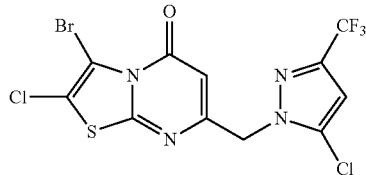 [SMILES: O=c1cc(Cn2nc(C(F)(F)F)cc2Cl)nc2sc(Cl)c(Br)n12]

To a solution of 3-bromo-2-chloro-7-(chloromethyl)-5H-[1,3]thiazolo[3,2-a]pyrimidin-5-one (500 mg, 1.59 mmol) in acetonitrile (10 mL) was added 5-chloro-3-(trifluoromethyl)-1H-pyrazole (327 mg, 1.92 mmol), potassium iodide (133 mg, 0.80 mmol), and potassium carbonate (442 mg, 3.20 mmol). The resulting solution was stirred for 2 h at 80° C. and cooled. The solid was filtered off and the filtrate was concentrated in vacuo. The residue was purified by flash chromatography on silica gel eluting with ethyl acetate/petroleum ether (1/9) to afford 3-bromo-2-chloro-7-(chloromethyl)-5H-[1,3]thiazolo[3,2-a]pyrimidin-5-one as a brown solid (300 mg, 60%). LCMS (ESI): M+H$^+$=448.0.

Step 5: 2-(2-Chloro-7-[[5-chloro-3-(trifluoromethyl)-1H-pyrazol-1-yl]methyl]-5-oxo-5H-[1,3]thiazolo[3,2-a]pyrimidin-3-yl)cyclopropane-1-carbonitrile (enantiomer 1)

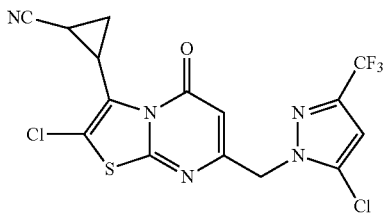

To a solution of 3-bromo-2-chloro-7-[[5-chloro-3-(trifluoromethyl)-1H-pyrazol-1-yl]methyl]-5H-[1,3]thiazolo[3,2-a]pyrimidin-5-one (100 mg, 0.22 mmol) in 1,4-dioxane/water (3 mL/0.3 mL) was added potassium 2-(cyano)cyclopropyltrifluoroborate (77.2 mg, 0.45 mmol), [bis(diphenylphosphino)ferrocene]palladium(II) dichloride (16.3 mg, 0.022 mmol), and potassium phosphate (94.8 mg, 0.45 mmol). The resulting solution was stirred for 14 h at 85° C. and concentrated in vacuo. The residue was purified by flash chromatography on silica gel eluting with ethyl acetate/petroleum ether (1/1) to afford the racemic product (40 mg, 41%). Then the racemic product was separated with chiral HPLC with the following conditions (Column: Phenomenex Lux 5u Cellulose-4, AXIA Packed 250*21.2 mm, 5 um; Mobile Phase: 100% MeOH; Flow rate: 20 mL/min; detector: 254 nm/220 nm) to afford two enantiomers. Enantiomer 1 (Peak 1, white solid, 7.5 mg, 8%): Retention Time: 1.54 min; LCMS (ESI): M+H$^+$=434.0; $^1$H NMR (400 MHz, CDCl$_3$) δ 6.59 (s, 1H), 5.74 (s, 1H), 5.24 (s, 2H), 2.98-2.93 (m, 1H), 1.88-1.82 (m, 2H), 1.66-1.61 (m, 1H). Enantiomer 2 (Peak 2, 6.1 mg, 6%): Retention Time: 2.06 min; LCMS (ESI): M+H$^+$=434.0; $^1$H NMR (400 MHz, CDCl$_3$) δ 6.59 (s, 1H), 5.75 (s, 1H), 5.24 (s, 2H), 2.99-2.89 (m, 1H), 1.88-1.82 (m, 2H), 1.66-1.61 (m, 1H).

The following examples were prepared using methods analogous to those described in the appropriate Reference Method or Example (Ref. Method or Ex.) column. Satisfactory analytical data was obtained for each compound.

| Ex. | Structure/Name | Chemical Name | Ref. Method or Ex. |
|---|---|---|---|
| 1 | | 7-[(3-cyclopropyl-2-fluorophenyl)methyl]-N,2-dimethyl-5-oxo-thiazolo[3,2-a]pyrimidine-3-carboxamide | Method 21 |
| 2 | | N-ethyl-2-methyl-5-oxo-7-[(2,3,6-trifluorophenyl)methyl]thiazolo[3,2-a]pyrimidine-3-carboxamide | Method 21 |
| 3 | | 2-fluoro-3-[(2-methyl-3-oxazol-2-yl-5-oxo-thiazolo[3,2-a]pyrimidin-7-yl)methyl]benzonitrile | Method 24 |
| 4 | | 7-[(5-cyano-3-cyclopropyl-2-fluorophenyl)methyl]-N-ethyl-2-methyl-5-oxo-thiazolo[3,2-a]pyrimidine-3-carboxamide | Method 21 |

| Ex. | Structure/Name | Chemical Name | Ref. Method or Ex. |
|---|---|---|---|
| 5 | | N-ethyl-7-[(2-fluoro-3-methoxy-phenyl)methyl]-2-methyl-5-oxo-thiazolo[3,2-a]pyrimidine-3-carboxamide | Method 21 |
| 6 | | 7-[(3-cyclopropyl-2-fluoro-phenyl)methyl]-6-fluoro-N,2-dimethyl-5-oxo-thiazolo[3,2-a]pyrimidine-3-carboxamide | Method 21 |
| 7 | | 2-[7-[(3-chloro-2-fluoro-phenyl)methyl]-2-methyl-5-oxo-thiazolo[3,2-a]pyrimidin-3-yl]-N-methyl-acetamide | Method 2 |
| 8 | | 7-[(3-chloro-2-fluoro-phenyl)methyl]-N-ethyl-6-fluoro-2-methyl-5-oxo-thiazolo[3,2-a]pyrimidine-3-carboxamide | Method 21 |
| 9 | | 7-[(4,5-difluoro-2-methoxy-phenyl)methyl]-N,2-dimethyl-5-oxo-thiazolo[3,2-a]pyrimidine-3-carboxamide | Method 21 |
| 10 | | 2-fluoro-3-[[2-methyl-3-(2-methylcyclopropyl)-5-oxo-thiazolo[3,2-a]pyrimidin-7-yl]methyl]benzonitrile | Method 20 |
| 11 | | 2-[7-[(3-cyclopropyl-2-fluoro-phenyl)methyl]-2-methyl-5-oxo-thiazolo[3,2-a]pyrimidin-3-yl]-N-methyl-acetamide | Method 2 |

-continued

| Ex. | Structure/Name | Chemical Name | Ref. Method or Ex. |
|---|---|---|---|
| 13 | | N-ethyl-6-fluoro-7-[[2-fluoro-3-(trifluoromethyl)phenyl]methyl]-2-methyl-5-oxo-thiazolo[3,2-a]pyrimidine-3-carboxamide | Method 21 |
| 14 | | 7-[[2-chloro-5-(trifluoromethyl)phenyl]methyl]-N,2-dimethyl-5-oxo-thiazolo[3,2-a]pyrimidine-3-carboxamide | Method 21 |
| 15 | | 7-[(3-cyano-2-fluoro-phenyl)methyl]-6-fluoro-2-methyl-5-oxo-N-(2,2,2-trifluoroethyl)thiazolo[3,2-a]pyrimidine-3-carboxamide | Method 21 |
| 16 | | 7-[(2-chloro-4,5-difluoro-phenyl)methyl]-N,2-dimethyl-5-oxo-thiazolo[3,2-a]pyrimidine-3-carboxamide | Method 21 |
| 17 | | 7-[[4,5-difluoro-2-(2-fluoroethyl)phenyl]methyl]-N-ethyl-2-methyl-5-oxo-thiazolo[3,2-a]pyrimidine-3-carboxamide | Method 21 |

| Ex. | Structure/Name | Chemical Name | Ref. Method or Ex. |
|---|---|---|---|
| 18 | | 2-[7-[[5-cyclopropyl-3-(trifluoromethyl)pyrazol-1-yl]methyl]-2-methyl-5-oxo-thiazolo[3,2-a]pyrimidin-3-yl]-N-methyl-acetamide | Method 2 |
| 19 | | 2-[7-[[2-fluoro-3-(trifluoromethyl)phenyl]methyl]-2-methyl-5-oxo-thiazolo[3,2-a]pyrimidin-3-yl]-N-methyl-acetamide | Method 2 |
| 20 | | 7-[(5-chloro-3-methyl-pyrazol-1-yl)methyl]-N-ethyl-2-methyl-5-oxo-thiazolo[3,2-a]pyrimidine-3-carboxamide | Ex. 28 |
| 21 | | 7-[(3-chloro-5-methyl-pyrazol-1-yl)methyl]-N-ethyl-2-methyl-5-oxo-thiazolo[3,2-a]pyrimidine-3-carboxamide | Ex. 28 |
| 22 | | 7-[(3-chloro-5-cyclopropyl-pyrazol-1-yl)methyl]-N-ethyl-2-methyl-5-oxo-thiazolo[3,2-a]pyrimidine-3-carboxamide | Ex. 28 |
| 23 | | 7-[(5-chloro-3-cyclopropyl-pyrazol-1-yl)methyl]-N-ethyl-2-methyl-5-oxo-thiazolo[3,2-a]pyrimidine-3-carboxamide | Ex. 28 |

-continued

| Ex. | Structure/Name | Chemical Name | Ref. Method or Ex. |
|---|---|---|---|
| 25 | 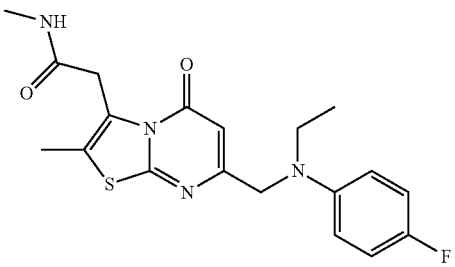 [SMILES: CCN(Cc1cc(=O)n2c(CC(=O)NC)c(C)sc2n1)c1ccc(F)cc1] | 2-[7-[(N-ethyl-4-fluoro-anilino)methyl]-2-methyl-5-oxo-thiazolo[3,2-a]pyrimidin-3-yl]-N-methyl-acetamide | Method 2 |
| 26 | 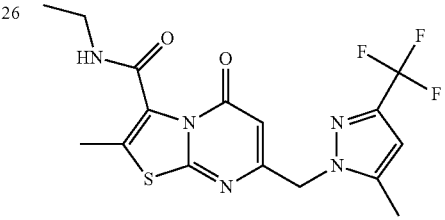 | N-ethyl-2-methyl-7-[[5-methyl-3-(trifluoromethyl)pyrazol-1-yl]methyl]-5-oxo-thiazolo[3,2-a]pyrimidine-3-carboxamide | Ex. 28 |
| 27 | 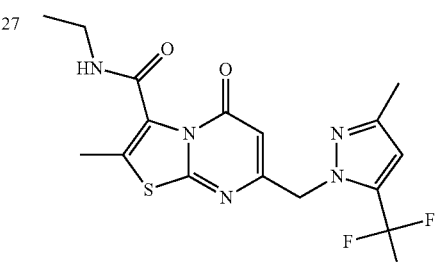 | N-ethyl-2-methyl-7-[[3-methyl-5-(trifluoromethyl)pyrazol-1-yl]methyl]-5-oxo-thiazolo[3,2-a]pyrimidine-3-carboxamide | Ex. 28 |
| 29 | 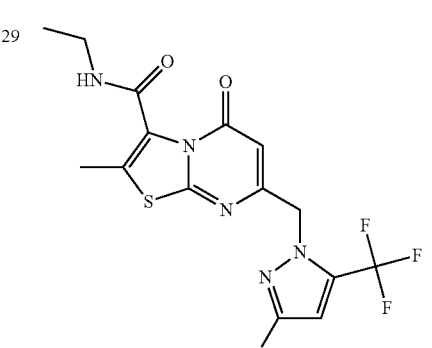 | 7-[[3-chloro-5-(trifluoromethyl)pyrazol-1-yl]methyl]-N-ethyl-2-methyl-5-oxo-thiazolo[3,2-a]pyrimidine-3-carboxamide | Ex. 28 |
| 30 | 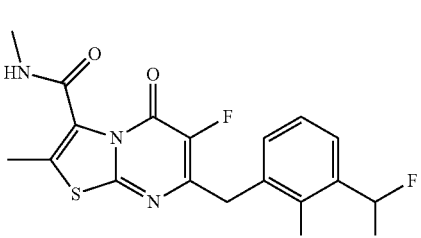 | 7-[[3-(difluoromethyl)-2-fluoro-phenyl]methyl]-6-fluoro-N,2-dimethyl-5-oxo-thiazolo[3,2-a]pyrimidine-3-carboxamide | Method 21 |

| Ex. | Structure/Name | Chemical Name | Ref. Method or Ex. |
|---|---|---|---|
| 31 | | 7-[[3-(difluoromethyl)-2-fluoro-phenyl]methyl]-N-ethyl-6-fluoro-2-methyl-5-oxo-thiazolo[3,2-a]pyrimidine-3-carboxamide | Method 21 |
| 32 | | 7-(4-bicyclo[4.2.0]octa-1,3,5-trienylmethyl)-N,2-dimethyl-5-oxo-thiazolo[3,2-a]pyrimidine-3-carboxamide | Method 21 |
| 33 | | N-ethyl-7-[[2-fluoro-3-(1-hydroxycyclopropyl)phenyl]methyl]-2-methyl-5-oxo-thiazolo[3,2-a]pyrimidine-3-carboxamide | Method 21 |
| 34 | | 6-fluoro-3-[2-(hydroxymethyl)cyclopropyl]-2-methyl-7-[3-(trifluoromethyl)phenoxy]thiazolo[3,2-a]pyrimidin-5-one | Ex. 12 |
| 35 | | N-ethyl-7-[[2-fluoro-3-(1-fluorocyclopropyl)phenyl]methyl]-2-methyl-5-oxo-thiazolo[3,2-a]pyrimidine-3-carboxamide | Method 21 |
| 36 | | N-ethyl-7-[[2-fluoro-3-[1-(fluoromethyl)vinyl]phenyl]methyl]-2-methyl-5-oxo-thiazolo[3,2-a]pyrimidine-3-carboxamide | Method 21 |
| 37 | | 7-[(2-ethynyl-4,5-difluoro-phenyl)methyl]-N,2-dimethyl-5-oxo-thiazolo[3,2-a]pyrimidine-3-carboxamide | Method 21 |

| Ex. | Structure/Name | Chemical Name | Ref. Method or Ex. |
|---|---|---|---|
| 38 | | 2-fluoro-3-[[2-methyl-5-oxo-3-[2-(trifluoromethyl)cyclopropyl]thiazolo[3,2-a]pyrimidin-7-yl]methyl]benzonitrile | Method 20 |
| 40 | | N-ethyl-7-[[2-fluoro-3-(trifluoromethyl)phenyl]methyl]-5-oxo-2-(trifluoromethyl)thiazolo[3,2-a]pyrimidine-3-carboxamide | Ex. 28 |
| 41 | | 7-[(3-cyano-2-fluoro-phenyl)methyl]-N-ethyl-5-oxo-2-(trifluoromethyl)thiazolo[3,2-a]pyrimidine-3-carboxamide | Ex. 28 |
| 42 | | 7-[[3-(difluoromethyl)-2-fluoro-phenyl]methyl]-N-ethyl-5-oxo-2-(trifluoromethyl)thiazolo[3,2-a]pyrimidine-3-carboxamide | Ex. 28 |
| 43 | | 7-[[5-chloro-3-(trifluoromethyl)pyrazol-1-yl]methyl]-N-ethyl-5-oxo-2-(trifluoromethyl)thiazolo[3,2-a]pyrimidine-3-carboxamide | Ex. 28 |
| 44 | | 7-[[3-chloro-5-(trifluoromethyl)pyrazol-1-yl]methyl]-N-ethyl-5-oxo-2-(trifluoromethyl)thiazolo[3,2-a]pyrimidine-3-carboxamide | Ex. 28 |

| Ex. | Structure/Name | Chemical Name | Ref. Method or Ex. |
|---|---|---|---|
| 45 | | N-ethyl-7-[[5-methyl-3-(trifluoromethyl)pyrazol-1-yl]methyl]-5-oxo-2-(trifluoromethyl)thiazolo[3,2-a]pyrimidine-3-carboxamide | Ex. 28 |
| 46 | | N-ethyl-7-[[3-methyl-5-(trifluoromethyl)pyrazol-1-yl]methyl]-5-oxo-2-(trifluoromethyl)thiazolo[3,2-a]pyrimidine-3-carboxamide | Ex. 28 |
| 48 | | N-ethyl-7-[2-fluoro-3-(trifluoromethyl)phenoxy]-2-methyl-5-oxo-thiazolo[3,2-a]pyrimidine-3-carboxamide | Ex. 12 |
| 49 | | 7-[(3-cyano-2-fluoro-5-methyl-phenyl)methyl]-N-ethyl-2-methyl-5-oxo-thiazolo[3,2-a]pyrimidine-3-carboxamide | Method 21 |
| 50 | | 7-[(3-chloro-2-fluoro-phenyl)methyl]-N-ethyl-5-oxo-2-(trifluoromethyl)thiazolo[3,2-a]pyrimidine-3-carboxamide | Ex. 28 |
| 51 | | 7-[[2-fluoro-3-(trifluoromethyl)phenyl]methyl]-2-methyl-5-oxo-N-(2,2,2-trifluoroethyl)thiazolo[3,2-a]pyrimidine-3-carboxamide | Method 25 |

-continued

| Ex. | Structure/Name | Chemical Name | Ref. Method or Ex. |
|---|---|---|---|
| 52 | | 2-methyl-7-[[5-methyl-3-(trifluoromethyl)pyrazol-1-yl]methyl]-5-oxo-N-(2,2,2-trifluoroethyl)thiazolo[3,2-a]pyrimidine-3-carboxamide | Method 25 |
| 53 | | 7-[[5-cyclopropyl-3-(trifluoromethyl)pyrazol-1-yl]methyl]-N-methyl-5-oxo-2-(trifluoromethyl)thiazolo[3,2-a]pyrimidine-3-carboxamide | Ex. 28 |
| 54 | | 7-[[3-cyclopropyl-5-(trifluoromethyl)pyrazol-1-yl]methyl]-N-methyl-5-oxo-2-(trifluoromethyl)thiazolo[3,2-a]pyrimidine-3-carboxamide | Ex. 28 |
| 55 | | 7-[[5-chloro-3-(trifluoromethyl)pyrazol-1-yl]methyl]-N-methyl-5-oxo-2-(trifluoromethyl)thiazolo[3,2-a]pyrimidine-3-carboxamide | Ex. 28 |
| 56 | | 7-[[3-chloro-5-(trifluoromethyl)pyrazol-1-yl]methyl]-N-methyl-5-oxo-2-(trifluoromethyl)thiazolo[3,2-a]pyrimidine-3-carboxamide | Ex. 28 |

| Ex. | Structure/Name | Chemical Name | Ref. Method or Ex. |
|---|---|---|---|
| 57 | | 7-[[5-cyclopropyl-3-(trifluoromethyl)pyrazol-1-yl]methyl]-2-methyl-5-oxo-N-(2,2,2-trifluoroethyl)thiazolo[3,2-a]pyrimidine-3-carboxamide | Method 25 |
| 58 | | 7-[[3-cyclopropyl-5-(trifluoromethyl)pyrazol-1-yl]methyl]-2-methyl-5-oxo-N-(2,2,2-trifluoroethyl)thiazolo[3,2-a]pyrimidine-3-carboxamide | Method 25 |
| 59 | | 7-[2-fluoro-3-(trifluoromethyl)phenoxy]-N,2-dimethyl-5-oxo-thiazolo[3,2-a]pyrimidine-3-carboxamide | Ex. 12 |
| 60 | | 2-chloro-N-ethyl-7-[[2-fluoro-3-(trifluoromethyl)phenyl]methyl]-5-oxo-thiazolo[3,2-a]pyrimidine-3-carboxamide | Ex. 258 |
| 61 | | N-methyl-7-[[5-methyl-3-(trifluoromethyl)pyrazol-1-yl]methyl]-5-oxo-2-(trifluoromethyl)thiazolo[3,2-a]pyrimidine-3-carboxamide | Ex. 28 |
| 62 | | N-methyl-7-[[3-methyl-5-(trifluoromethyl)pyrazol-1-yl]methyl]-5-oxo-2-(trifluoromethyl)thiazolo[3,2-a]pyrimidine-3-carboxamide | Ex. 28 |

| Ex. | Structure/Name | Chemical Name | Ref. Method or Ex. |
|---|---|---|---|
| 63 | | 7-[[2-fluoro-3-(trifluoromethyl)phenyl]methyl]-N-methyl-5-oxo-2-(trifluoromethyl)thiazolo[3,2-a]pyrimidine-3-carboxamide | Ex. 28 |
| 64 | | 7-[(3-chloro-2-fluoro-phenyl)methyl]-N-methyl-5-oxo-2-(trifluoromethyl)thiazolo[3,2-a]pyrimidine-3-carboxamide | Ex. 28 |
| 65 | | 7-[[5-chloro-3-(trifluoromethyl)pyrazol-1-yl]methyl]-2-methyl-5-oxo-N-(2,2,2-trifluoroethyl)thiazolo[3,2-a]pyrimidine-3-carboxamide | Method 25 |
| 66 | | 7-[[3-chloro-5-(trifluoromethyl)pyrazol-1-yl]methyl]-2-methyl-5-oxo-N-(2,2,2-trifluoroethyl)thiazolo[3,2-a]pyrimidine-3-carboxamide | Method 25 |
| 67 | | 2-methyl-7-[[3-methyl-5-(trifluoromethyl)pyrazol-1-yl]methyl]-5-oxo-N-(2,2,2-trifluoroethyl)thiazolo[3,2-a]pyrimidine-3-carboxamide | Method 25 |
| 68 | | 7-(3-cyano-2-fluoro-phenoxy)-N-ethyl-2-methyl-5-oxo-thiazolo[3,2-a]pyrimidine-3-carboxamide | Ex. 12 |

-continued

| Ex. | Structure/Name | Chemical Name | Ref. Method or Ex. |
|---|---|---|---|
| 69 | | 2-chloro-7-[(3-cyano-2-fluoro-phenyl)methyl]-N-ethyl-5-oxo-thiazolo[3,2-a]pyrimidine-3-carboxamide | Ex. 258 |
| 70 | | 7-[(3-cyano-2-fluoro-phenyl)methyl]-N-methyl-5-oxo-2-(trifluoromethyl)thiazolo[3,2-a]pyrimidine-3-carboxamide | Ex. 28 |
| 71 | | N-ethyl-2-[7-[[2-fluoro-3-(trifluoromethyl)phenyl]methyl]-2-methyl-5-oxo-thiazolo[3,2-a]pyrimidin-3-yl]acetamide | Method 2 |
| 72 | | N,2-dimethyl-5-oxo-7-[[4-(trifluoromethyl)pyrazol-1-yl]methyl]thiazolo[3,2-a]pyrimidine-3-carboxamide | Ex. 28 |
| 73 | | 3-cyclopropyl-7-[2-fluoro-3-(trifluoromethyl)phenoxy]-2-methyl-thiazolo[3,2-a]pyrimidin-5-one | Ex. 12 |
| 74 | | 3-[[2-chloro-5-oxo-3-[2-(trifluoromethyl)cyclopropyl]thiazolo[3,2-a]pyrimidin-7-yl]methyl]-2-fluoro-benzonitrile | Ex. 267 |
| 75 | | 2-[7-[[2-fluoro-3-(trifluoromethyl)phenyl]methyl]-5-oxo-2-(trifluoromethyl)thiazolo[3,2-a]pyrimidin-3-yl]-N-methyl-acetamide | Method 2 |

| Ex. | Structure/Name | Chemical Name | Ref. Method or Ex. |
|---|---|---|---|
| 76 | | 7-[[5-cyclopropyl-3-(trifluoromethyl)pyrazol-1-yl]methyl]-N-ethyl-2-methyl-5-oxo-thiazolo[3,2-a]pyrimidine-3-carboxamide | Ex. 28 |
| 77 | | 2-fluoro-3-[2-methyl-5-oxo-3-[2-(trifluoromethyl)cyclopropyl]thiazolo[3,2-a]pyrimidin-7-yl]oxy-benzonitrile | Ex. 12 |
| 78 | | 2-[7-[[5-cyclopropyl-3-(trifluoromethyl)pyrazol-1-yl]methyl]-5-oxo-2-(trifluoromethyl)thiazolo[3,2-a]pyrimidin-3-yl]-N-methyl-acetamide | Method 2 |
| 79 | | 2-[7-[[3-cyclopropyl-5-(trifluoromethyl)pyrazol-1-yl]methyl]-5-oxo-2-(trifluoromethyl)thiazolo[3,2-a]pyrimidin-3-yl]-N-methyl-acetamide | Method 2 |
| 80 | | 7-[[2-fluoro-3-(trifluoromethyl)phenyl]methyl]-2-methyl-3-(methylsulfonylmethyl)thiazolo[3,2-a]pyrimidin-5-one | Method 10 |
| 81 | | 7-[[2-fluoro-3-(trifluoromethyl)phenyl]methyl]-3-(1H-imidazol-2-ylmethyl)-2-methyl-thiazolo[3,2-a]pyrimidin-5-one | Method 10 |

| Ex. | Structure/Name | Chemical Name | Ref. Method or Ex. |
|---|---|---|---|
| 82 | | N-ethyl-7-[(N-ethyl-4-fluoro-anilino)methyl]-2-methyl-5-oxo-thiazolo[3,2-a]pyrimidine-3-carboxamide | Ex. 28 |
| 83 | | N-ethyl-7-[(N-ethyl-4-fluoro-anilino)methyl]-5-oxo-2-(trifluoromethyl)thiazolo[3,2-a]pyrimidine-3-carboxamide | Ex. 28 |
| 84 | | 2-fluoro-3-[[3-(2-methylcyclopropyl)-5-oxo-2-(trifluoromethyl)thiazolo[3,2-a]pyrimidin-7-yl]methyl]benzonitrile | Ex. 207 |
| 85 | | 3-[[2-chloro-3-(2-methylcyclopropyl)-5-oxo-thiazolo[3,2-a]pyrimidin-7-yl]methyl]-2-fluoro-benzonitrile | Ex. 267 |
| 86 | | 7-[2-fluoro-3-(trifluoromethyl)phenoxy]-2-methyl-3-(2-methylcyclopropyl)thiazolo[3,2-a]pyrimidin-5-one | Ex. 12 |
| 87 | | N-ethyl-7-[[2-fluoro-3-(trifluoromethyl)phenyl]methyl]-2-isopropyl-5-oxo-thiazolo[3,2-a]pyrimidine-3-carboxamide | Method 21 |

-continued

| Ex. | Structure/Name | Chemical Name | Ref. Method or Ex. |
|---|---|---|---|
| 88 | | 2-fluoro-3-[[5-oxo-2-(trifluoromethyl)-3-[2-(trifluoromethyl)cyclopropyl]thiazolo[3,2-a]pyrimidin-7-yl]methyl]benzonitrile | Ex. 207 |
| 89 | | 6-[[5-chloro-3-(trifluoromethyl)pyrazol-1-yl]methyl]-2,3-dihydro-1H-cyclopenta[3,4]thiazolo[1,4-a]pyrimidin-8-one | Method 27 |
| 90 | | 6-[[3-chloro-5-(trifluoromethyl)pyrazol-1-yl]methyl]-2,3-dihydro-1H-cyclopenta[3,4]thiazolo[1,4-a]pyrimidin-8-one | Method 27 |
| 92 | | 6-[[2-fluoro-3-(trifluoromethyl)phenyl]methyl]-1-(hydroxymethyl)-2,3-dihydro-1H-cyclopenta[3,4]thiazolo[1,4-a]pyrimidin-8-one | Method 27 |
| 93 | | 2-ethyl-7-[[2-fluoro-3-(trifluoromethyl)phenyl]methyl]-N-methyl-5-oxo-thiazolo[3,2-a]pyrimidine-3-carboxamide | Method 21 |
| 94 | | 2-[7-[[2-fluoro-3-(trifluoromethyl)phenyl]methyl]-5-oxo-2-(trifluoromethyl)thiazolo[3,2-a]pyrimidine-3-yl]cyclopropanecarbonitrile | Ex. 207 |
| 95 | | 6-[[5-cyclopropyl-3-(trifluoromethyl)pyrazol-1-yl]methyl]-1-(hydroxymethyl)-2,3-dihydro-1H-cyclopenta[3,4]thiazolo[1,4-a]pyrimidin-8-one | Method 27 |

| Ex. | Structure/Name | Chemical Name | Ref. Method or Ex. |
|---|---|---|---|
| 96 | | 7-[[5-chloro-3-(trifluoromethyl)pyrazol-1-yl]methyl]-N,2-dimethyl-5-oxo-thiazolo[3,2-a]pyrimidine-3-carboxamide | Ex. 28 |
| 97 | | 7-[[3-chloro-5-(trifluoromethyl)pyrazol-1-yl]methyl]-N,2-dimethyl-5-oxo-thiazolo[3,2-a]pyrimidine-3-carboxamide | Ex. 28 |
| 98 | | 2-[7-[[5-chloro-3-(trifluoromethyl)pyrazol-1-yl]methyl]-2-methyl-5-oxo-thiazolo[3,2-a]pyrimidin-3-yl]-N-methyl-acetamide | Method 2 |
| 99 | | 2-[7-[[3-chloro-5-(trifluoromethyl)pyrazol-1-yl]methyl]-2-methyl-5-oxo-thiazolo[3,2-a]pyrimidin-3-yl]-N-methyl-acetamide | Method 2 |
| 100 | | 7-[[2-fluoro-3-(trifluoromethyl)phenyl]methyl]-3-(2-hydroxycyclopropyl)-2-methyl-thiazolo[3,2-a]pyrimidin-5-one | Method 20 |
| 101 | | 2-[7-[2-fluoro-3-(trifluoromethyl)phenoxy]-2-methyl-5-oxo-thiazolo[3,2-a]pyrimidin-3-yl]cyclopropanecarbonitrile | Ex. 12 |

| Ex. | Structure/Name | Chemical Name | Ref. Method or Ex. |
|---|---|---|---|
| 102 | | 7-[[5-chloro-3-(trifluoromethyl)pyrazol-1-yl]methyl]-3-[2-(hydroxymethyl)cyclopropyl]-2-methyl-thiazolo[3,2-a]pyrimidin-5-one | Method 15 |
| 103 | | 7-[[3-chloro-5-(trifluoromethyl)pyrazol-1-yl]methyl]-3-[2-(hydroxymethyl)cyclopropyl]-2-methyl-thiazolo[3,2-a]pyrimidin-5-one | Method 15 |
| 104 | | 2-[7-[[5-chloro-3-(trifluoromethyl)pyrazol-1-yl]methyl]-2-methyl-5-oxo-thiazolo[3,2-a]pyrimidin-3-yl]cyclopropanecarbonitrile | Method 15 |
| 106 | | 7-[[2-fluoro-3-(trifluoromethyl)phenyl]methyl]-N-isopropyl-2-methyl-5-oxo-thiazolo[3,2-a]pyrimidine-3-carboxamide | Method 21 |
| 107 | | 2-fluoro-3-[2-methyl-3-(2-methylcyclopropyl)-5-oxo-thiazolo[3,2-a]pyrimidin-7-yl]oxy-benzonitrile | Ex. 12 |
| 108 | | 7-[[5-chloro-3-(trifluoromethyl)pyrazol-1-yl]methyl]-3-(1-hydroxy-1-methyl-ethyl)-2-methyl-thiazolo[3,2-a]pyrimidin-5-one | Method 18 |

| Ex. | Structure/Name | Chemical Name | Ref. Method or Ex. |
|---|---|---|---|
| 109 | | 7-[[3-chloro-5-(trifluoromethyl)pyrazol-1-yl]methyl]-3-(1-hydroxy-1-methyl-ethyl)-2-methyl-thiazolo[3,2-a]pyrimidin-5-one | Method 18 |
| 110 | | 7-[[5-chloro-3-(trifluoromethyl)pyrazol-1-yl]methyl]-3-(1-hydroxyethyl)-2-methyl-thiazolo[3,2-a]pyrimidin-5-one | Method 18 |
| 111 | | 7-[[3-chloro-5-(trifluoromethyl)pyrazol-1-yl]methyl]-3-(1-hydroxyethyl)-2-methyl-thiazolo[3,2-a]pyrimidin-5-one | Method 18 |
| 112 | | 7-[[2-fluoro-3-(trifluoromethyl)phenyl]methyl]-2-methyl-5-oxo-N-sec-butyl-thiazolo[3,2-a]pyrimidine-3-carboxamide | Method 21 |
| 113 | | 3-[[3-(azetidin-1-yl)-2-methyl-5-oxo-thiazolo[3,2-a]pyrimidin-7-yl]methyl]-2-fluoro-benzonitrile | Method 6 |
| 114 | | 7-[[5-chloro-3-(trifluoromethyl)pyrazol-1-yl]methyl]-2-methyl-5-oxo-thiazolo[3,2-a]pyrimidine-3-carbonitrile | Method 17 |

| Ex. | Structure/Name | Chemical Name | Ref. Method or Ex. |
|---|---|---|---|
| 115 | | 7-[[3-chloro-5-(trifluoromethyl)pyrazol-1-yl]methyl]-2-methyl-5-oxo-thiazolo[3,2-a]pyrimidine-3-carbonitrile | Method 17 |
| 116 | | 7-[[5-chloro-3-(trifluoromethyl)pyrazol-1-yl]methyl]-3-cyclopropyl-2-methyl-thiazolo[3,2-a]pyrimidin-5-one | Method 15 |
| 117 | | 7-[[3-chloro-5-(trifluoromethyl)pyrazol-1-yl]methyl]-3-cyclopropyl-2-methyl-thiazolo[3,2-a]pyrimidin-5-one | Method 15 |
| 118 | | 7-[[5-chloro-3-(trifluoromethyl)pyrazol-1-yl]methyl]-2-methyl-3-(2-methylcyclopropyl)thiazolo[3,2-a]pyrimidin-5-one | Method 15 |
| 119 | | 3-acetyl-7-[[5-chloro-3-(trifluoromethyl)pyrazol-1-yl]methyl]-2-methyl-thiazolo[3,2-a]pyrimidin-5-one | Method 18 |
| 120 | | 3-acetyl-7-[[3-chloro-5-(trifluoromethyl)pyrazol-1-yl]methyl]-2-methyl-thiazolo[3,2-a]pyrimidin-5-one | Method 18 |

| Ex. | Structure/Name | Chemical Name | Ref. Method or Ex. |
|---|---|---|---|
| 121 | | 2-chloro-7-[[2-fluoro-3-(trifluoromethyl)phenyl]methyl]-3-(2-methylcyclopropyl)thiazolo[3,2-a]pyrimidin-5-one | Method 33 |
| 122 | | 7-[[3-chloro-5-(trifluoromethyl)pyrazol-1-yl]methyl]-2-methyl-3-pyrimidin-5-yl-thiazolo[3,2-a]pyrimidin-5-one | Method 15 |
| 123 | | 7-[[3-cyclopropyl-5-(trifluoromethyl)pyrazol-1-yl]methyl]-N-ethyl-2-methyl-5-oxo-thiazolo[3,2-a]pyrimidine-3-carboxamide | Ex. 28 |
| 124 | | 7-[[[(5-chloro-2-pyridyl)-methyl-amino]methyl]-N-ethyl-2-methyl-5-oxo-thiazolo[3,2-a]pyrimidine-3-carboxamide | Ex. 28 |
| 125 | | 2-[7-[[5-chloro-3-(trifluoromethyl)pyrazol-1-yl]methyl]-2-methyl-5-oxo-thiazolo[3,2-a]pyrimidin-3-yl]cyclopropanecarbonitrile (cis enantiomer 1) | Method 15 |
| 126 | | 2-[7-[[5-chloro-3-(trifluoromethyl)pyrazol-1-yl]methyl]-2-methyl-5-oxo-thiazolo[3,2-a]pyrimidin-3-yl]cyclopropanecarbonitrile (cis enantiomer 2) | Method 15 |

-continued

| Ex. | Structure/Name | Chemical Name | Ref. Method or Ex. |
|---|---|---|---|
| 127 | | 7-[[3-chloro-5-(trifluoromethyl)pyrazol-1-yl]methyl]-N-ethyl-2-methoxy-5-oxo-thiazolo[3,2-a]pyrimidine-3-carboxamide | Ex. 91 |
| 128 | | 7-[[5-chloro-3-(trifluoromethyl)pyrazol-1-yl]methyl]-N-ethyl-2-methoxy-5-oxo-thiazolo[3,2-a]pyrimidine-3-carboxamide | Ex. 91 |
| 129 | | 7-[[5-cyclopropyl-3-(trifluoromethyl)pyrazol-1-yl]methyl]-N-ethyl-2-methoxy-5-oxo-thiazolo[3,2-a]pyrimidine-3-carboxamide | Ex. 91 |
| 130 | | 7-[[3-cyclopropyl-5-(trifluoromethyl)pyrazol-1-yl]methyl]-N-ethyl-2-methoxy-5-oxo-thiazolo[3,2-a]pyrimidine-3-carboxamide | Ex. 91 |
| 131 | | 2-[7-[[2-fluoro-3-(trifluoromethyl)phenyl]methyl]-2-methyl-5-oxo-thiazolo[3,2-a]pyrimidin-3-yl]cyclopropanecarbonitrile | Method 20 |
| 132 | | 7-[[5-chloro-3-(trifluoromethyl)pyrazol-1-yl]methyl]-2-methyl-3-(1H-pyrazol-yl)thiazolo[3,2-a]pyrimidin-5-one | Method 15 |

-continued

| Ex. | Structure/Name | Chemical Name | Ref. Method or Ex. |
|---|---|---|---|
| 133 | | 7-[[3-chloro-5-(trifluoromethyl)pyrazol-1-yl]methyl]-2-methyl-3-(1H-pyrazol-5-yl)thiazolo[3,2-a]pyrimidin-5-one | Method 15 |
| 134 | | 7-[[5-chloro-3-(trifluoromethyl)pyrazol-1-yl]methyl]-2-methyl-3-(3-pyridyl)thiazolo[3,2-a]pyrimidin-5-one | Method 15 |
| 135 | | 7-[[5-chloro-3-(trifluoromethyl)pyrazol-1-yl]methyl]-3-isopropenyl-2-methyl-thiazolo[3,2-a]pyrimidin-5-one | Method 15 |
| 136 | | 7-[[5-chloro-3-(trifluoromethyl)pyrazol-1-yl]methyl]-3-[2-(hydroxymethyl)cyclopropyl]-2-methyl-thiazolo[3,2-a]pyrimidin-5-one (trans enantiomer 1) | Method 15 |
| 137 | | 7-[[5-chloro-3-(trifluoromethyl)pyrazol-1-yl]methyl]-3-[2-(hydroxymethyl)cyclopropyl]-2-methyl-thiazolo[3,2-a]pyrimidin-5-one (trans enantiomer 2) | Method 15 |
| 138 | | 7-[[5-chloro-3-(trifluoromethyl)pyrazol-1-yl]methyl]-3-(5-fluoro-3-pyridyl)-2-methyl-thiazolo[3,2-a]pyrimidin-5-one | Method 15 |

-continued

| Ex. | Structure/Name | Chemical Name | Ref. Method or Ex. |
|---|---|---|---|
| 139 | | 7-[[3-chloro-5-(trifluoromethyl)pyrazol-1-yl]methyl]-3-(5-fluoro-3-pyridyl)-2-methyl-thiazolo[3,2-a]pyrimidin-5-one | Method 15 |
| 140 | | 7-[[5-chloro-3-(trifluoromethyl)pyrazol-1-yl]methyl]-2-methyl-3-propanoyl-thiazolo[3,2-a]pyrimidin-5-one | Method 18 |
| 141 | | 7-[[3-chloro-5-(trifluoromethyl)pyrazol-1-yl]methyl]-2-methyl-3-propanoyl-thiazolo[3,2-a]pyrimidin-5-one | Method 18 |
| 142 | | 7-[[5-chloro-3-(trifluoromethyl)pyrazol-1-yl]methyl]-2-methyl-3-thiazol-2-yl-thiazolo[3,2-a]pyrimidin-5-one | Method 15 |
| 143 | | N-ethyl-7-[[(5-fluoro-2-pyridyl)-methyl-amino]methyl]-2-methyl-5-oxo-thiazolo[3,2-a]pyrimidine-3-carboxamide | Ex. 28 |

| Ex. | Structure/Name | Chemical Name | Ref. Method or Ex. |
|---|---|---|---|
| 144 | 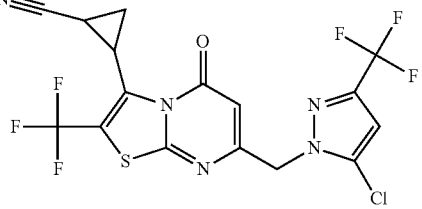 | 2-[7-[[5-chloro-3-(trifluoromethyl)pyrazol-1-yl]methyl]-5-oxo-2-(trifluoromethyl)thiazolo[3,2-a]pyrimidin-3-yl]cyclopropanecarbonitrile | Ex. 207 |
| 145 | 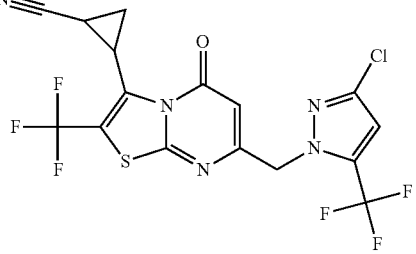 | 2-[7-[[3-chloro-5-(trifluoromethyl)pyrazol-1-yl]methyl]-5-oxo-2-(trifluoromethyl)thiazolo[3,2-a]pyrimidin-3-yl]cyclopropanecarbonitrile | Ex. 207 |
| 146 | 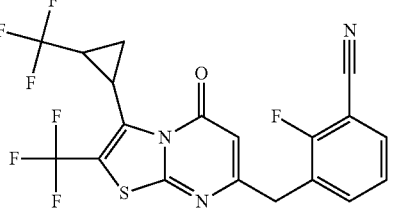 | 2-fluoro-3-[[5-oxo-2-(trifluoromethyl)-3-[2-(trifluoromethyl)cyclopropyl]thiazolo[3,2-a]pyrimidin-7-yl]methyl]benzonitrile | 207 |
| 147 | 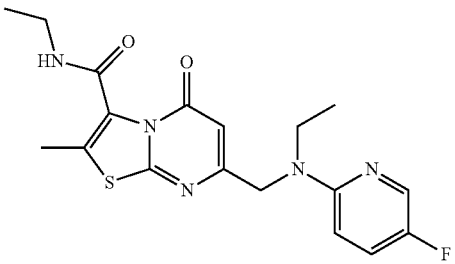 [SMILES: CCNC(=O)c1c(C)sc2nc(CN(CC)c3ccc(F)cn3)cc(=O)n12] | N-ethyl-7-[[ethyl-(5-fluoro-2-pyridyl)amino]methyl]-2-methyl-5-oxo-thiazolo[3,2-a]pyrimidine-3-carboxamide | Ex. 28 |
| 148 | 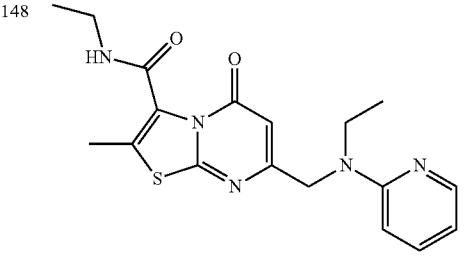 | N-ethyl-7-[[ethyl(2-pyridyl)amino]methyl]-2-methyl-5-oxo-thiazolo[3,2-a]pyrimidine-3-carboxamide | Ex. 28 |
| 149 | 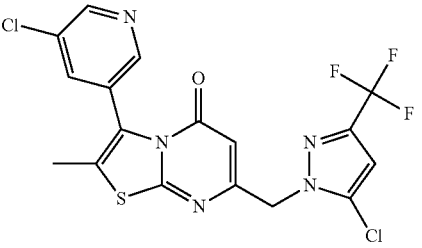 [SMILES: Cc1sc2nc(Cn3nc(C(F)(F)F)cc3Cl)cc(=O)n2c1-c1cncc(Cl)c1] | 3-(5-chloro-3-pyridyl)-7-[[5-chloro-3-(trifluoromethyl)pyrazol-1-yl]methyl]-2-methyl-thiazolo[3,2-a]pyrimidin-5-one | Method 15 |

| Ex. | Structure/Name | Chemical Name | Ref. Method or Ex. |
|---|---|---|---|
| 150 | | 3-(5-chloro-3-pyridyl)-7-[[3-chloro-5-(trifluoromethyl)pyrazol-1-yl]methyl]-2-methyl-thiazolo[3,2-a]pyrimidin-5-one | Method 15 |
| 151 | | 7-[[5-chloro-3-(trifluoromethyl)pyrazol-1-yl]methyl]-2-methyl-3-thiazol-4-yl-thiazolo[3,2-a]pyrimidin-5-one | Method 15 |
| 152 | | 7-[[(5-chloro-2-pyridyl)-ethyl-amino]methyl]-N-ethyl-2-methyl-5-oxo-thiazolo[3,2-a]pyrimidine-3-carboxamide | Ex. 28 |
| 154 | | 7-[[5-chloro-3-(trifluoromethyl)pyrazol-1-yl]methyl]-2-methyl-3-[2-methylcyclopropyl]thiazolo[3,2-a]pyrimidin-5-one (trans enantiomer 1) | Method 15 |
| 155 | | 7-[[5-chloro-3-(trifluoromethyl)pyrazol-1-yl]methyl]-2-methyl-3-[2-methylcyclopropyl]thiazolo[3,2-a]pyrimidin-5-one (trans enantiomer 2) | Method 15 |
| 156 | | 2-ethoxy-N-ethyl-7-[[2-fluoro-3-(trifluoromethyl)phenyl]methyl]-5-oxo-thiazolo[3,2-a]pyrimidine-3-carboxamide | Ex. 91 |

-continued

| Ex. | Structure/Name | Chemical Name | Ref. Method or Ex. |
|---|---|---|---|
| 157 | | 7-[[5-chloro-3-(trifluoromethyl)pyrazol-1-yl]methyl]-3-(2-fluoro-3-pyridyl)-2-methyl-thiazolo[3,2-a]pyrimidin-5-one | Method 15 |
| 158 | | 7-[[5-chloro-3-(trifluoromethyl)pyrazol-1-yl]methyl]-2-methyl-3-oxazol-2-yl-thiazolo[3,2-a]pyrimidin-5-one | Method 15 |
| 159 | | 7-[[3-chloro-5-(trifluoromethyl)pyrazol-1-yl]methyl]-2-methyl-3-oxazol-2-yl-thiazolo[3,2-a]pyrimidin-5-one | Method 15 |
| 160 | | 7-[[5-chloro-3-(trifluoromethyl)pyrazol-1-yl]methyl]-2-methyl-3-(trifluoromethyl)thiazolo[3,2-a]pyrimidin-5-one | Method 15 |
| 161 | | 7-[[3-chloro-5-(trifluoromethyl)pyrazol-1-yl]methyl]-2-methyl-3-(trifluoromethyl)thiazolo[3,2-a]pyrimidin-5-one | Method 15 |
| 162 | | 2-[7-[[2-fluoro-3-(trifluoromethyl)phenyl]methyl]-5-oxo-2-(trifluoromethyl)thiazolo[3,2-a]pyrimidin-3-yl]cyclopropanecarbonitrile | Ex. 207 |

-continued

| Ex. | Structure/Name | Chemical Name | Ref. Method or Ex. |
|---|---|---|---|
| 163 | | 7-[[(5-chloro-2-pyridyl)-methyl-amino]methyl]-3-[2-(hydroxymethyl)cyclopropyl]-2-methyl-thiazolo[3,2-a]pyrimidin-5-one | Method 14 |
| 164 | | 7-[(3,5-dichloropyrazol-1-yl)methyl]-N-ethyl-2-methyl-5-oxo-thiazolo[3,2-a]pyrimidine-3-carboxamide | Ex. 28 |
| 165 | | N-ethyl-7-[[2-fluoro-3-(trifluoromethyl)phenyl]methyl]-5-oxo-2-(2,2,2-trifluoroethoxy)thiazolo[3,2-a]pyrimidine-3-carboxamide | Ex. 91 |
| 166 | | 3-acetyl-7-[[5-chloro-3-(trifluoromethyl)pyrazol-1-yl]methyl]-2-(trifluoromethyl)thiazolo[3,2-a]pyrimidin-5-one | Ex. 207 |
| 167 | | 3-acetyl-7-[[3-chloro-5-(trifluoromethyl)pyrazol-1-yl]methyl]-2-(trifluoromethyl)thiazolo[3,2-a]pyrimidin-5-one | Ex. 207 |
| 168 | | 3-[(4-chloropyrazol-1-yl)methyl]-7-[[5-chloro-3-(trifluoromethyl)pyrazol-1-yl]methyl]-2-methyl-thiazolo[3,2-a]pyrimidin-5-one | Method 10 |

-continued

| Ex. | Structure/Name | Chemical Name | Ref. Method or Ex. |
|---|---|---|---|
| 169 | | 7-[[5-chloro-3-(trifluoromethyl)pyrazol-1-yl]methyl]-3-isopropenyl-2-(trifluoromethyl)thiazolo[3,2-a]pyrimidin-5-one | Ex. 207 |
| 170 | | 7-[[5-chloro-3-(trifluoromethyl)pyrazol-1-yl]methyl]-3-(1H-imidazol-2-yl)-2-methyl-thiazolo[3,2-a]pyrimidin-5-one | Ex. 258 |
| 171 | | 7-[[5-chloro-3-(trifluoromethyl)pyrazol-1-yl]methyl]-3-pyrimidin-5-yl-2-(trifluoromethyl)thiazolo[3,2-a]pyrimidin-5-one | Ex. 207 |
| 172 | | 7-[[3-chloro-5-(trifluoromethyl)pyrazol-1-yl]methyl]-3-pyrimidin-5-yl-2-(trifluoromethyl)thiazolo[3,2-a]pyrimidin-5-one | Ex. 207 |
| 173 | | 7-[[3-chloro-5-(trifluoromethyl)pyrazol-1-yl]methyl]-3-(3-pyridyl)-2-(trifluoromethyl)thiazolo[3,2-a]pyrimidin-5-one | Ex. 207 |
| 174 | | 7-[[5-chloro-3-(trifluoromethyl)pyrazol-1-yl]methyl]-N-ethyl-5-oxo-2-(2,2,2-trifluoroethoxy)thiazolo[3,2-a]pyrimidine-3-carboxamide | Ex. 91 |

| Ex. | Structure/Name | Chemical Name | Ref. Method or Ex. |
|---|---|---|---|
| 175 | | 7-[[5-chloro-3-(trifluoromethyl)pyrazol-1-yl]methyl]-2-ethoxy-N-ethyl-5-oxo-thiazolo[3,2-a]pyrimidine-3-carboxamide | Ex. 91 |
| 176 | | 7-[[3-chloro-5-(trifluoromethyl)pyrazol-1-yl]methyl]-2-ethoxy-N-ethyl-5-oxo-thiazolo[3,2-a]pyrimidine-3-carboxamide | Ex. 91 |
| 177 | | 7-[[5-chloro-3-(trifluoromethyl)pyrazol-1-yl]methyl]-2-methyl-3-(2-methylpropoyl)thiazolo[3,2-a]pyrimidin-5-one | Method 18 |
| 178 | | 7-[[3-chloro-5-(trifluoromethyl)pyrazol-1-yl]methyl]-2-methyl-3-(2-methylpropanoyl)thiazolo[3,2-a]pyrimidin-5-one | Method 18 |
| 179 | | 7-[[2-fluoro-3-(trifluoromethyl)phenyl]methyl]-2-methyl-N-[(1R)-1-methylpropyl]-5-oxo-thiazolo[3,2-a]pyrimidine-3-carboxamide | Method 21 |
| 180 | | 7-[[2-fluoro-3-(trifluoromethyl)phenyl]methyl]-2-methyl-N-[(1S)-1-methylpropyl]-5-oxo-thiazolo[3,2-a]pyrimidine-3-carboxamide | Method 21 |

-continued

| Ex. | Structure/Name | Chemical Name | Ref. Method or Ex. |
|---|---|---|---|
| 191 | | 7-[[(4-chloro-2-pyridyl)-ethyl-amino]methyl]-N-ethyl-2-methyl-5-oxo-thiazolo[3,2-a]pyrimidine-3-carboxamide | Ex. 28 |
| 182 | | 7-[[(5-fluoro-2-pyridyl)-methyl-amino]methyl]-3-[2-(hydroxymethyl)cyclopropyl]-2-methyl-thiazolo[3,2-a]pyrimidin-5-one | Method 15 |
| 183 | | 7-[[5-chloro-3-(trifluoromethyl)pyrazol-1-yl]methyl]-3-(methoxymethyl)-2-methyl-thiazolo[3,2-a]pyrimidin-5-one | Method 10 |
| 184 | | 7-[[5-chloro-3-(trifluoromethyl)pyrazol-1-yl]methyl]-3-cyclopropyl-2-(trifluoromethyl)thiazolo[3,2-a]pyrimidin-5-one | Ex. 91 |
| 185 | | 7-[[5-chloro-3-(trifluoromethyl)pyrazol-1-yl]methyl]-2-methyl-3-(methylsulfonylmethyl)thiazolo[3,2-a]pyrimidin-5-one | Method 10 |
| 186 | | 7-[[5-chloro-3-(trifluoromethyl)pyrazol-1-yl]methyl]-2-methyl-3-(pyrazol-1-ylmethyl)thiazolo[3,2-a]pyrimidin-5-one | Method 10 |

-continued

| Ex. | Structure/Name | Chemical Name | Ref. Method or Ex. |
|---|---|---|---|
| 187 |  | 2-[7-[[2-chloro-5-(trifluoromethyl)phenyl]methyl]-2-methyl-5-oxo-thiazolo[3,2-a]pyrimidin-3-yl]cyclopropanecarbonitrile | Method 20 |
| 188 |  | 7-[[5-chloro-3-(trifluoromethyl)pyrazol-1-yl]methyl]-3-cyclobutyl-2-methyl-thiazolo[3,2-a]pyrimidin-5-one | Ex. 28 |
| 189 |  | 7-[[3-chloro-5-(trifluoromethyl)pyrazol-1-yl]methyl]-3-cyclobutyl-2-methyl-thiazolo[3,2-a]pyrimidin-5-one | Ex. 28 |
| 190 |  | 2-[7-[[(5-chloro-2-pyridyl)-methyl-amino]methyl]-2-methyl-5-oxo-thiazolo[3,2-a]pyrimidin-3-yl]cyclopropanecarbonitrile | Method 14 |
| 191 |  | 7-[[ethyl-(5-fluoro-2-pyridyl)amino]methyl]-3-[2-(hydroxymethyl)cyclopropyl]-2-methyl-thiazolo[3,2-a]pyrimidin-5-one | Method 14 |
| 192 |  | 3-chloro-7-[[5-chloro-3-(trifluoromethyl)pyrazol-1-yl]methyl]-2-methyl-thiazolo[3,2-a]pyrimidin-5-one | Method 15 |

-continued

| Ex. | Structure/Name | Chemical Name | Ref. Method or Ex. |
|---|---|---|---|
| 193 | | 3-chloro-7-[[3-chloro-5-(trifluoromethyl)pyrazol-1-yl]methyl]-2-methyl-thiazolo[3,2-a]pyrimidin-5-one | Method 15 |
| 194 | | 2-[7-[(4,5-difluoro-2-methoxy-phenyl)methyl]-2-methyl-5-oxo-thiazolo[3,2-a]pyrimidin-3-yl]cyclopropanecarbonitrile | Method 23 |
| 195 | | 2-[7-[[ethyl-(5-fluoro-2-pyridyl)amino]methyl]-2-methyl-5-oxo-thiazolo[3,2-a]pyrimidin-3-yl]cyclopropanecarbonitrile | Method 14 |
| 196 | | 7-[[(5-chloro-2-pyridyl)-ethyl-amino]methyl]-3-[2-(hydroxymethyl)cyclopropyl]-2-methyl-thiazolo[3,2-a]pyrimidin-5-one | Method 14 |
| 197 | | 5-[7-[[5-chloro-3-(trifluoromethyl)pyrazol-1-yl]methyl]-2-methyl-5-oxo-thiazolo[3,2-a]pyrimidin-3-yl]pyridine-3-carbonitrile | Method 15 |
| 198 | | 7-[[5-chloro-3-(trifluoromethyl)pyrazol-1-yl]methyl]-2-methyl-3-(2,2,2-trifluoroacetyl)thiazolo[3,2-a]pyrimidin-5-one | Method 10 |

-continued

| Ex. | Structure/Name | Chemical Name | Ref. Method or Ex. |
|---|---|---|---|
| 199 | | 7-[[5-chloro-3-(trifluoromethyl)pyrazol-1-yl]methyl]-3-(2-methylcyclopropyl)-2-(trifluoromethyl)thiazolo[3,2-a]pyrimidin-5-one | Ex. 207 |
| 200 | | 7-[[3-chloro-5-(trifluoromethyl)pyrazol-1-yl]methyl]-3-(2-methylcyclopropyl)-2-(trifluoromethyl)thiazolo[3,2-a]pyrimidin-5-one | Method 15 |
| 201 | | 7-[[5-chloro-3-(trifluoromethyl)pyrazol-1-yl]methyl]-2-methyl-3-pyrimidin-5-yl-thiazolo[3,2-a]pyrimidin-5-one | Method 15 |
| 202 | | 7-[[5-chloro-3-(trifluoromethyl)pyrazol-1-yl]methyl]-2-ethyl-3-(3-pyridyl)thiazolo[3,2-a]pyrimidin-5-one | Method 23 |
| 203 | | 7-[[5-chloro-3-(trifluoromethyl)pyrazol-1-yl]methyl]-2-methyl-3-(2,2,2-trifluoro-1-hydroxy-ethyl)thiazolo[3,2-a]pyrimidin-5-one | Method 14 |
| 204 | | 7-[[(5-bromo-2-pyridyl)-ethyl-amino]methyl]-N-ethyl-2-methyl-5-oxo-thiazolo[3,2-a]pyrimidine-3-carboxamide | Method 14 |

| Ex. | Structure/Name | Chemical Name | Ref. Method or Ex. |
|---|---|---|---|
| 205 | | N-ethyl-7-[[ethyl-(5-fluoro-2-pyridyl)amino]methyl]-5-oxo-2-(trifluoromethyl)thiazolo[3,2-a]pyrimidine-3-carboxamide | Method 15 |
| 209 | | 2-[7-[[5-methoxy-3-(trifluoromethyl)pyrazol-1-yl]methyl]-2-methyl-5-oxo-thiazolo[3,2-a]pyrimidin-3-yl]cyclopropanecarbonitrile | Method 15 |
| 210 | | 2-[7-[[3-methoxy-5-(trifluoromethyl)pyrazol-1-yl]methyl]-2-methyl-5-oxo-thiazolo[3,2-a]pyrimidin-3-yl]cyclopropanecarbonitrile | Method 15 |
| 211 | | 3-acetyl-7-[[5-chloro-3-(trifluoromethyl)pyrazol-1-yl]methyl]-2-ethyl-thiazolo[3,2-a]pyrimidin-5-one | Method 18 |
| 212 | | 3-acetyl-7-[[3-chloro-5-(trifluoromethyl)pyrazol-1-yl]methyl]-2-ethyl-thiazolo[3,2-a]pyrimidin-5-one | Method 18 |
| 213 | | 2-[7-[[5-chloro-3-(trifluoromethyl)pyrazol-1-yl]methyl]-2-ethyl-5-oxo-thiazolo[3,2-a]pyrimidin-3-yl]cyclopropanecarbonitrile | Method 15 |

-continued

| Ex. | Structure/Name | Chemical Name | Ref. Method or Ex. |
|---|---|---|---|
| 214 | 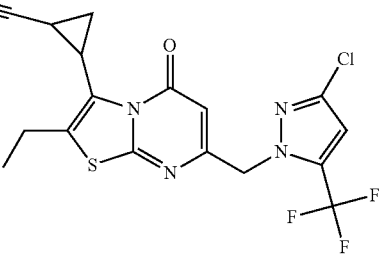 | 2-[7-[[3-chloro-5-(trifluoromethyl)pyrazol-1-yl]methyl]-2-ethyl-5-oxo-thiazolo[3,2-a]pyrimidin-3-yl]cyclopropanecarbonitrile | Method 15 |
| 215 | 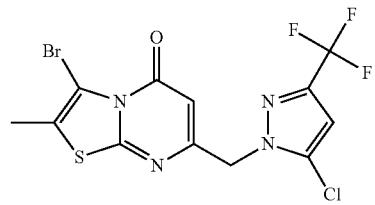 | 3-bromo-7-[[5-chloro-3-(trifluoromethyl)pyrazol-1-yl]methyl]-2-methyl-thiazolo[3,2-a]pyrimidin-5-one | Method 15 |
| 216 | 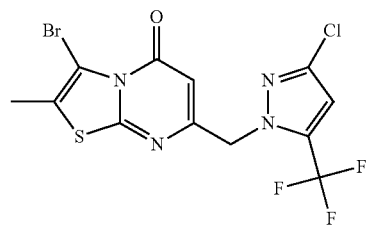 [SMILES: Cc1sc2nc(Cn3nc(Cl)cc3C(F)(F)F)cc(=O)n2c1Cl] | 3-bromo-7-[[3-chloro-5-(trifluoromethyl)pyrazol-1-yl]methyl]-2-methyl-thiazolo[3,2-a]pyrimidin-5-one | Method 15 |
| 217 | 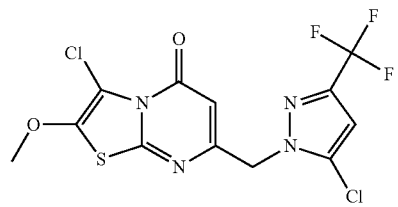 [SMILES: COc1sc2nc(Cn3nc(C(F)(F)F)cc3Cl)cc(=O)n2c1Cl] | 3-chloro-7-[[5-chloro-3-(trifluoromethyl)pyrazol-1-yl]methyl]-2-methoxy-thiazolo[3,2-a]pyrimidin-5-one | Ex. 244 |
| 218 | 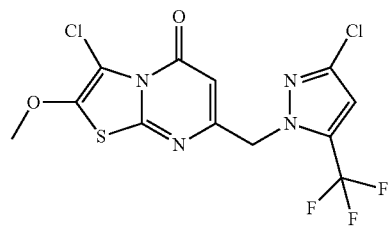 [SMILES: COc1sc2nc(Cn3nc(Cl)cc3C(F)(F)F)cc(=O)n2c1Cl] | 3-chloro-7-[[3-chloro-5-(trifluoromethyl)pyrazol-1-yl]methyl]-2-methoxy-thiazolo[3,2-a]pyrimidin-5-one | Ex. 244 |
| 219 | 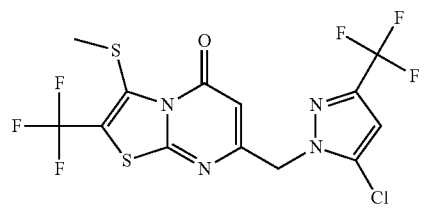 [SMILES: CSc1c(C(F)(F)F)sc2nc(Cn3nc(C(F)(F)F)cc3Cl)cc(=O)n12] | 7-[[5-chloro-3-(trifluoromethyl)pyrazol-1-yl]methyl]-3-methylsulfanyl-2-(trifluoromethyl)thiazolo[3,2-a]pyrimidin-5-one | Ex. 206 |

| Ex. | Structure/Name | Chemical Name | Ref. Method or Ex. |
|---|---|---|---|
| 221 | | 7-[[5-chloro-3-(trifluoromethyl)pyrazol-1-yl]methyl]-3-(cyclopropylmethyl)-2-methyl-thiazolo[3,2-a]pyrimidin-5-one | Method 15 |
| 223 | | 7-[[3-chloro-5-(trifluoromethyl)pyrazol-1-yl]methyl]-3-(2-hydroxy-1-methyl-ethyl)-2-methyl-thiazolo[3,2-a]pyrimidin-5-one | Ex. 222 |
| 224 | | 7-[[5-chloro-3-(trifluoromethyl)pyrazol-1-yl]methyl]-3-(cyclopropanecarbonyl)-2-methyl-thiazolo[3,2-a]pyrimidin-5-one | Method 10 |
| 225 | | 3-bromo-7-[[5-chloro-3-(trifluoromethyl)pyrazol-1-yl]methyl]thiazolo[3,2-a]pyrimidin-5-one | Method 15 |
| 226 | | 3-bromo-7-[[3-chloro-5-(trifluoromethyl)pyrazol-1-yl]methyl]thiazolo[3,2-a]pyrimidin-5-one | Method 15 |
| 227 | | 7-[(3-amino-5-chloro-pyrazol-1-yl)methyl]-3-bromo-2-methyl-thiazolo[3,2-a]pyrimidin-5-one | Method 15 |
| 228 | | 7-[(5-amino-3-chloro-pyrazol-1-yl)methyl]-3-bromo-2-methyl-thiazolo[3,2-a]pyrimidin-5-one | Method 15 |

| Ex. | Structure/Name | Chemical Name | Ref. Method or Ex. |
|---|---|---|---|
| 229 | | 2-[7-[[5-chloro-3-(trifluoromethyl)pyrazol-1-yl]methyl]-2-methyl-5-oxo-thiazolo[3,2-a]pyrimidin-3-yl]acetonitrile | Method 10 |
| 230 | | N-ethyl-7-[[(5-fluoro-2-pyridyl)-methyl-amino]methyl]-5-oxo-2-(trifluoromethyl)thiazolo[3,2-a]pyrimidine-3-carboxamide | Ex. 28 |
| 231 | | 7-[[5-chloro-3-(trifluoromethyl)pyrazol-1-yl]methyl]-3-(3,3-difluoroazetidin-1-yl)-2-(trifluoromethyl)thiazolo[3,2-a]pyrimidin-5-one | Ex. 206 |
| 233 | | 7-[[5-chloro-3-(trifluoromethyl)pyrazol-1-yl]methyl]-2-methoxy-3-(3-pyridyl)thiazolo[3,2-a]pyrimidin-5-one | Ex. 244 |
| 234 | | 2-[7-[[5-bromo-3-(trifluoromethyl)pyrazol-1-yl]methyl]-2-methyl-5-oxo-thiazolo[3,2-a]pyrimidin-3-yl]cyclopropanecarbonitrile | Method 15 |
| 235 | | 3-chloro-7-[[5-chloro-3-(trifluoromethyl)pyrazol-1-yl]methyl]thiazolo[3,2-a]pyrimidin-5-one | Method 15 |

-continued

| Ex. | Structure/Name | Chemical Name | Ref. Method or Ex. |
|---|---|---|---|
| 236 | | 3-chloro-7-[[3-chloro-5-(trifluoromethyl)pyrazol-1-yl]methyl]thiazolo[3,2-a]pyrimidin-5-one | Method 15 |
| 237 | | 2-acetyl-7-[[5-chloro-3-(trifluoromethyl)pyrazol-1-yl]methyl]-N-ethyl-5-oxo-thiazolo[3,2-a]pyrimidine-3-carboxamide | Ex. 258 |
| 238 | | 2-acetyl-7-[[3-chloro-5-(trifluoromethyl)pyrazol-1-yl]methyl]-N-ethyl-5-oxo-thiazolo[3,2-a]pyrimidine-3-carboxamide | Ex. 258 |
| 239 | | 7-[[5-chloro-3-(trifluoromethyl)pyrazol-1-yl]methyl]-3-(trifluoromethyl)thiazolo[3,2-a]pyrimidin-5-one | Method 15 |
| 241 | | 2-[7-[[5-chloro-3-(trifluoromethyl)pyrazol-1-yl]methyl]-5-oxo-thiazolo[3,2-a]pyrimidin-3-yl]cyclopropanecarbonitrile | Method 15 |
| 242 | | 3-acetyl-7-[[5-chloro-3-(trifluoromethyl)pyrazol-1-yl]methyl]thiazolo[3,2-a]pyrimidin-5-one | Method 18 |

-continued

| Ex. | Structure/Name | Chemical Name | Ref. Method or Ex. |
|---|---|---|---|
| 243 | | 7-[[5-chloro-3-(trifluoromethyl)pyrazol-1-yl]methyl]-3-(2,2,2-trifluoroethoxy)-2-(trifluoromethyl)thiazolo[3,2-a]pyrimidin-5-one | Ex. 206 |
| 245 | | 3-acetyl-7-[3-chloro-5-(trifluoromethyl)pyrazol-1-yl]methyl]-2-methoxy-thiazolo[3,2-a]pyrimidin-5-one | Ex. 244 |
| 246 | | 3-bromo-7-[(5-chloro-3-nitro-pyrazol-1-yl)methyl]-2-methyl-thiazolo[3,2-a]pyrimidin-5-one | Method 15 |
| 247 | | 7-[[5-chloro-3-(trifluoromethyl)pyrazol-1-yl]methyl]-3-(1H-pyrazol-5-yl)-2-(trifluoromethyl)thiazolo[3,2-a]pyrimidin-5-one | Ex. 207 |
| 248 | | 7-[[5-chloro-3-(trifluoromethy)pyrazol-1-yl]methyl]-3-thiazol-4-yl-2-(trifluoromethyl)thiazolo[3,2-a]pyrimidin-5-one | Ex. 207 |
| 249 | | 7-[[5-chloro-3-(trifluoromethyl)pyrazol-1-yl]methyl]-3-(5-fluoro-3-pyridyl)-2-(trifluoromethyl)thiazolo[3,2-a]pyrimidin-5-one | Ex. 207 |

-continued

| Ex. | Structure/Name | Chemical Name | Ref. Method or Ex. |
|---|---|---|---|
| 251A | | 2-[7-[[5-chloro-3-(trifluoromethyl)pyrazol-1-yl]methyl]-2-methyl-5-oxo-thiazolo[3,2-a]pyrimidin-3-yl]propanenitrile | Ex. 222 |
| 252 | | 2-[7-[[3-chloro-5-(trifluoromethyl)pyrazol-1-yl]methyl]-2-methyl-5-oxo-thiazolo[3,2-a]pyrimidin-3-yl]propanenitrile | Ex. 222 |
| 253 | | 2-fluoro-3-[[3-[2-methylcyclopropyl]-5-oxo-2-(trifluoromethyl)thiazolo[3,2-a]pyrimidin-7-yl]methyl]benzonitrile | Ex. 207 |
| 254 | | 7-[[5-chloro-3-(trifluoromethyl)pyrazol-1-yl]methyl]-3-(3-fluoroazetidin-1-yl)-2-(trifluoromethyl)thiazolo[3,2-a]pyrimidin-5-one | Ex. 206 |
| 255 | | 3-(5-chloro-3-pyridyl)-7-[[5-chloro-3-(trifluoromethyl)pyrazol-1-yl]methyl]-2-(trifluoromethyl)thiazolo[3,2-a]pyrimidin-5-one | Ex. 207 |
| 256 | | 7-[(3,5-dichloropyrazol-1-yl)methyl]-N-ethyl-5-oxo-2-(trifluoromethyl)thiazolo[3,2-a]pyrimidine-3-carboxamide | Ex. 28 |

-continued

| Ex. | Structure/Name | Chemical Name | Ref. Method or Ex. |
|---|---|---|---|
| 257 | 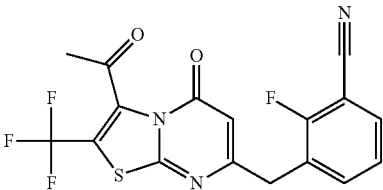 [SMILES: CC(=O)c1c(C(F)(F)F)sc2nc(Cc3cccc(C#N)c3F)cc(=O)n12] | 3-[[3-acetyl-5-oxo-2-(trifluoromethyl)thiazolo[3,2-a]pyrimidin-7-yl]methyl]-2-fluoro-benzonitrile | Ex. 207 |
| 259 | 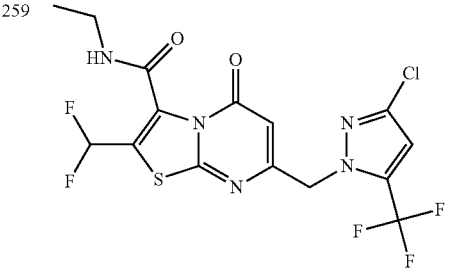 | 7-[[3-chloro-5-(trifluoromethyl)pyrazol-1-yl]methyl]-2-(difluoromethyl)-N-ethyl-5-oxo-thiazolo[3,2-a]pyrimidine-3-carboxamide | Ex. 258 |
| 260 | 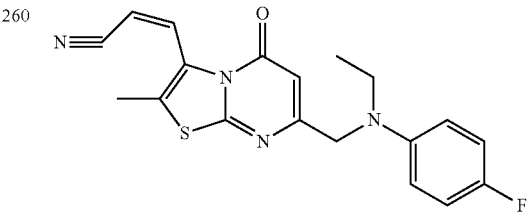 | (Z)-3-[7-[(N-ethyl-4-fluoro-anilino)methyl]-2-methyl-5-oxo-thiazolo[3,2-a]pyrimidin-3-yl]prop-2-enenitrile | Method 5 |
| 261 | 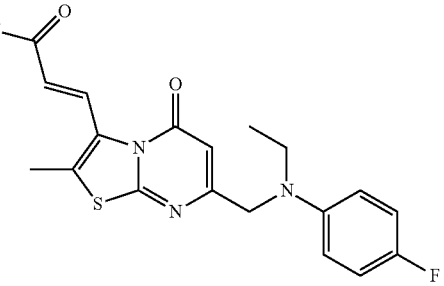 | (E)-3-[7-[(N-ethyl-4-fluoro-anilino)methyl]-2-methyl-5-oxo-thiazolo[3,2-a]pyrimidin-3-yl]prop-2-enamide | Method 5 |
| 262 | 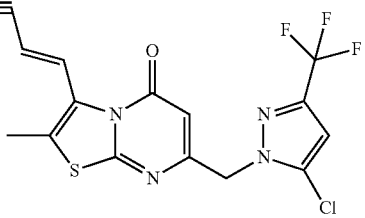 | (E)-3-[7-[[5-chloro-3-(trifluoromethyl)pyrazol-1-yl]methyl]-2-methyl-5-oxo-thiazolo[3,2-a]pyrimidin-3-yl]prop-2-enenitrile | Method 5 |
| 263 | 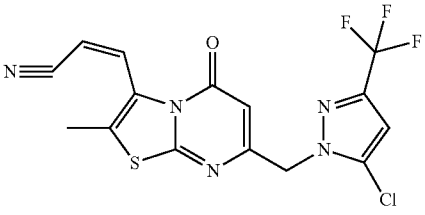 [SMILES: Cc1sc2nc(Cn3nc(C(F)(F)F)cc3Cl)cc(=O)n2c1/C=C\C#N] | (Z)-3-[7-[[5-chloro-3-(trifluoromethyl)pyrazol-1-yl]methyl]-2-methyl-5-oxo-thiazolo[3,2-a]pyrimidin-3-yl]prop-2-enenitrile | Method 5 |

| Ex. | Structure/Name | Chemical Name | Ref. Method or Ex. |
|---|---|---|---|
| 264 | | (E)-3-[7-[[5-chloro-3-(trifluoromethyl)pyrazol-1-yl]methyl]-2-methyl-5-oxo-thiazolo[3,2-a]pyrimidin-3-yl]prop-2-enamide | Method 5 |
| 265 | | N-ethyl-7-[[5-isobutyl-3-(trifluoromethyl)pyrazol-1-yl]methyl]-2-methyl-5-oxo-thiazolo[3,2-a]pyrimidine-3-carboxamide | Ex. 28 |
| 268 | | 2-[2-chloro-7-[[3-chloro-5-(trifluoromethyl)pyrazol-1-yl]methyl]-5-oxo-thiazolo[3,2-a]pyrimidin-3-yl]cyclopropanecarbonitrile | Ex. 267 |
| 269 | | 7-[[5-chloro-3-(trifluoromethyl)pyrazol-1-yl]methyl]-3-[2-(hydroxymethyl)cyclopropyl]-2-(trifluoromethyl)thiazolo[3,2-a]pyrimidin-5-one (trans enantiomer 1) | Ex. 207 |
| 270 | | 7-[[5-chloro-3-(trifluoromethyl)pyrazol-1-yl]methyl]-3-[2-(hydroxymethyl)cyclopropyl]-2-(trifluoromethyl)thiazolo[3,2-a]pyrimidin-5-one (trans enantiomer 2) | Ex. 207 |

-continued

| Ex. | Structure/Name | Chemical Name | Ref. Method or Ex. |
|---|---|---|---|
| 271 | | 2-[7-[(4-chloro-1-methyl-pyrazol-3-yl)methyl]-2-methyl-5-oxo-thiazolo[3,2-a]pyrimidin-3-yl]cyclopropanecarbonitrile | Method 20 |
| 272 | | 2-[2-methyl-5-oxo-7-[[3-(trifluoromethyl)pyrazol-1-yl]methyl]thiazolo[3,2-a]pyrimidin-3-yl]cyclopropanecarbonitrile (cis enantiomer 1) | Method 15 |
| 273 | | 2-[2-methyl-5-oxo-7-[[3-(trifluoromethyl)pyrazol-1-yl]methyl]thiazolo[3,2-a]pyrimidin-3-yl]cyclopropanecarbonitrile (cis enantiomer 2) | Method 15 |
| 274 | | 2-[7-[[5-bromo-3-(trifluoromethyl)pyrazol-1-yl]methyl]-2-methyl-5-oxo-thiazolo[3,2-a]pyrimidin-3-yl]cyclopropanecarbonitrile (cis enantiomer 1) | Method 15 |
| 275 | | 2-[7-[[5-bromo-3-(trifluoromethyl)pyrazol-1-yl]methyl]-2-methyl-5-oxo-thiazolo[3,2-a]pyrimidin-3-yl]cyclopropanecarbonitrile (cis enantiomer 2) | Method 15 |
| 276 | | 2-[7-[[5-chloro-3-(trifluoromethyl)pyrazol-1-yl]methyl]-6-fluoro-5-oxo-2-(trifluoromethyl)thiazolo[3,2-a]pyrimidin-3-yl]cyclopropanecarbonitrile (cis enantiomer 1) | Ex. 207 |
| 277 | | 2-[7-[[5-chloro-3-(trifluoromethyl)pyrazol-1-yl]methyl]-6-fluoro-5-oxo-2-(trifluoromethyl)thiazolo[3,2-a]pyrimidin-3-yl]cyclopropanecarbonitrile (cis enantiomer 2) | Ex. 207 |

-continued

| Ex. | Structure/Name | Chemical Name | Ref. Method or Ex. |
|---|---|---|---|
| 278 | | 2-[2-methyl-7-[[1-methyl-4-(trifluoromethyl)imidazol-2-yl]methyl]-5-oxo-thiazolo[3,2-a]pyrimidin-3-yl]cyclopropanecarbonitrile | Ex. 24 |
| 279 | | (E)-3-[7-[(N-ethyl-4-fluoro-anilino)methyl]-2-methyl-5-oxo-thiazolo[3,2-a]pyrimidin-3-yl]prop-2-enenitrile | Method 5 |

The following compounds were prepared using methods analogous to those described herein. Satisfactory analytical data was obtained for each compound.

| Ex. | Structure | Name |
|---|---|---|
| 280 | 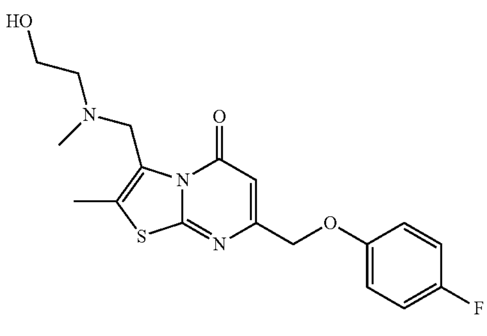 [SMILES: Cc1sc2nc(COc3ccc(F)cc3)cc(=O)n2c1CN(C)CCO] | 7-[(4-fluorophenoxy)methyl]-3-[[2-hydroxyethyl(methyl)amino]methyl]-2-methyl-thiazolo[3,2-a]pyrimidin-5-one |
| 281 | 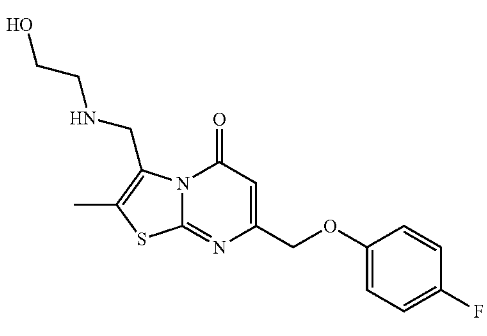 [SMILES: Cc1sc2nc(COc3ccc(F)cc3)cc(=O)n2c1CNCCO] | 7-[(4-fluorophenoxy)methyl]-3-[(2-hydroxyethylamino)methyl]-2-methyl-thiazolo[3,2-a]pyrimidin-5-one |

| Ex. | Structure | Name |
|---|---|---|
| 282 | 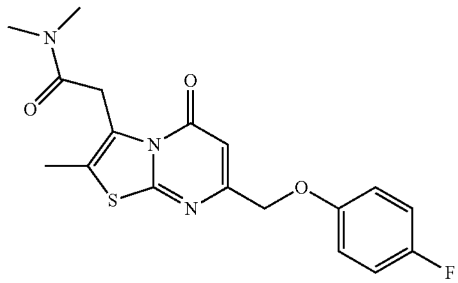 [SMILES: Cc1sc2nc(COc3ccc(F)cc3)cc(=O)n2c1CC(=O)N(C)C] | 2-[7-[(4-fluorophenoxy)methyl]-2-methyl-5-oxo-thiazolo[3,2-a]pyrimidin-3-yl]-N,N-dimethyl-acetamide |
| 283 | 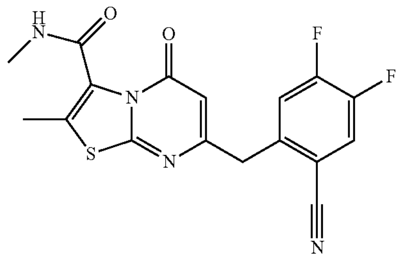 [SMILES: CNC(=O)c1c(C)sc2nc(Cc3cc(F)c(F)cc3C#N)cc(=O)n12] | 7-[(2-cyano-4,5-difluoro-phenyl)methyl]-N,2-dimethyl-5-oxo-thiazolo[3,2-a]pyrimidine-3-carboxamide |
| 284 | 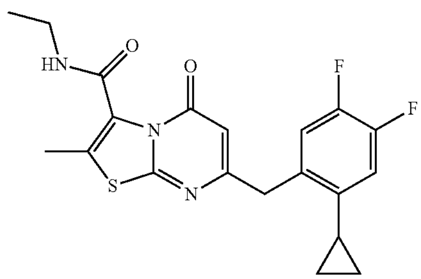 [SMILES: CCNC(=O)c1c(C)sc2nc(Cc3cc(F)c(F)cc3C3CC3)cc(=O)n12] | 7-[(2-cyclopropyl-4,5-difluoro-phenyl)methyl]-N-ethyl-2-methyl-5-oxo-thiazolo[3,2-a]pyrimidine-3-carboxamide |
| 285 | 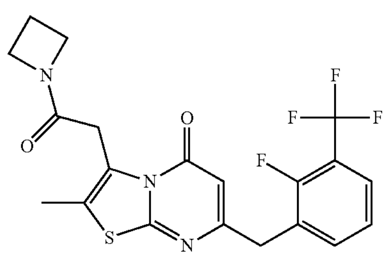 [SMILES: Cc1sc2nc(Cc3cccc(C(F)(F)F)c3F)cc(=O)n2c1CC(=O)N1CCC1] | 3-[2-(azetidin-1-yl)-2-oxo-ethyl]-7-[[2-fluoro-3-(trifluoromethyl)phenyl]methyl]-2-methyl-thiazolo[3,2-a]pyrimidin-5-one |
| 286 | 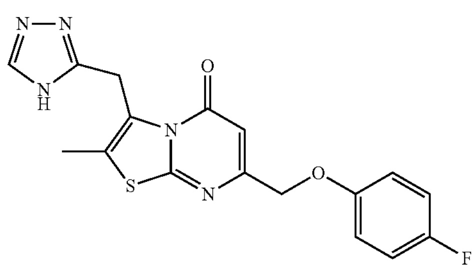 [SMILES: Cc1sc2nc(COc3ccc(F)cc3)cc(=O)n2c1Cc1nnc[nH]1] | 7-[(4-fluorophenoxy)methyl]-2-methyl-3-(4H-1,2,4-triazol-3-ylmethyl)thiazolo[3,2-a]pyrimidin-5-one |
| 287 | 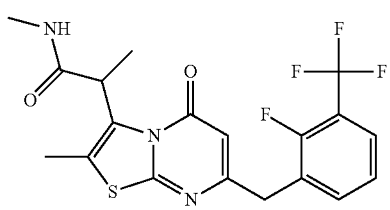 [SMILES: CNC(=O)C(C)c1c(C)sc2nc(Cc3cccc(C(F)(F)F)c3F)cc(=O)n12] | 2-[7-[[2-fluoro-3-(trifluoromethyl)phenyl]methyl]-2-methyl-5-oxo-thiazolo[3,2-a]pyrimidin-3-yl]-N-methyl-propanamide |

| Ex. | Structure | Name |
|---|---|---|
| 288 | 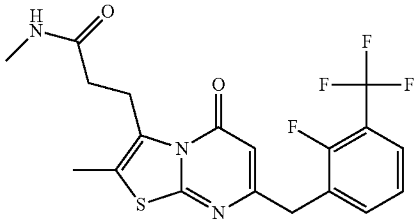 [SMILES: CNC(=O)CCc1c(C)sc2nc(Cc3cccc(C(F)(F)F)c3F)cc(=O)n12] | 3-[7-[[2-fluoro-3-(trifluoromethyl)phenyl]methyl]-2-methyl-5-oxo-thiazolo[3,2-a]pyrimidin-3-yl]-N-methyl-propanamide |
| 289 | 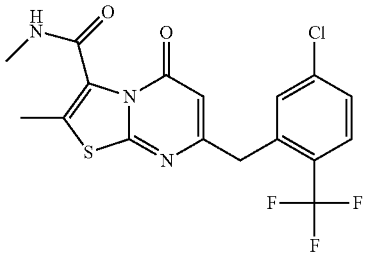 [SMILES: CNC(=O)c1c(C)sc2nc(Cc3cc(Cl)ccc3C(F)(F)F)cc(=O)n12] | 7-[[5-chloro-2-(trifluoromethyl)phenyl]methyl]-N,2-dimethyl-5-oxo-thiazolo[3,2-a]pyrimidine-3-carboxamide |
| 290 | 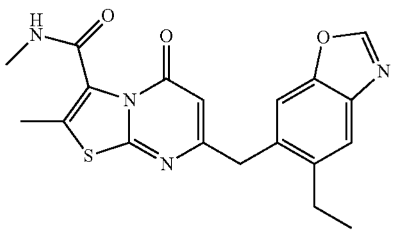 [SMILES: CCc1cc2ncoc2cc1Cc1cc(=O)n2c(C(=O)NC)c(C)sc2n1] | 7-[(5-ethyl-1,3-benzoxazol-6-yl)methyl]-N,2-dimethyl-5-oxo-thiazolo[3,2-a]pyrimidine-3-carboxamide |
| 291 | 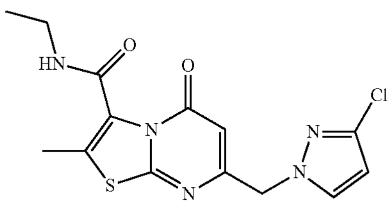 [SMILES: CCNC(=O)c1c(C)sc2nc(Cn3ccc(Cl)n3)cc(=O)n12] | 7-[(3-chloropyrazol-1-yl)methyl]-N-ethyl-2-methyl-5-oxo-thiazolo[3,2-a]pyrimidine-3-carboxamide |
| 292 | 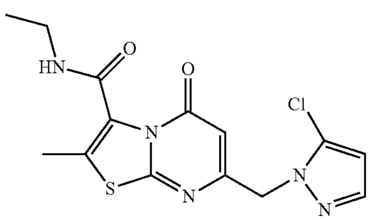 [SMILES: CCNC(=O)c1c(C)sc2nc(Cn3nccc3Cl)cc(=O)n12] | 7-[(5-chloropyrazol-1-yl)methyl]-N-ethyl-2-methyl-5-oxo-thiazolo[3,2-a]pyrimidine-3-carboxamide |
| 293 | 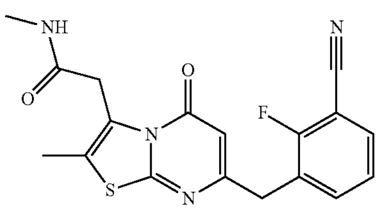 [SMILES: CNC(=O)Cc1c(C)sc2nc(Cc3cccc(C#N)c3F)cc(=O)n12] | 2-[7-[(3-cyano-2-fluoro-phenyl)methyl]-2-methyl-5-oxo-thiazolo[3,2-a]pyrimidin-3-yl]-N-methyl-acetamide |
| 294 | 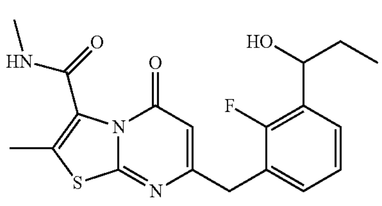 [SMILES: CCC(O)c1cccc(Cc2cc(=O)n3c(C(=O)NC)c(C)sc3n2)c1F] | N-ethyl-7-[[2-fluoro-3-(1-hydroxypropyl)phenyl]methyl]-2-methyl-5-oxo-thiazolo[3,2-a]pyrimidine-3-carboxamide |

| Ex. | Structure | Name |
|---|---|---|
| 295 | 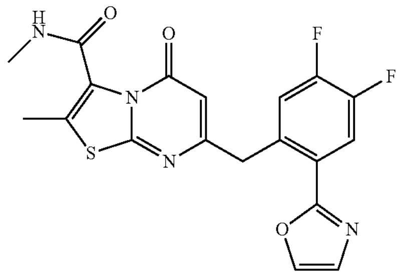 [SMILES: CNC(=O)c1c(C)sc2nc(Cc3cc(F)c(F)cc3-c3ncco3)cc(=O)n12] | 7-[(4,5-difluoro-2-oxazol-2-yl-phenyl)methyl]-N,2-dimethyl-5-oxo-thiazolo[3,2-a]pyrimidine-3-carboxamide |
| 296 | 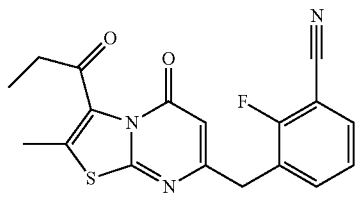 [SMILES: CCC(=O)c1c(C)sc2nc(Cc3cccc(C#N)c3F)cc(=O)n12] | 2-fluoro-3-[(2-methyl-5-oxo-3-propanoyl-thiazolo[3,2-a]pyrimidin-7-yl)methyl]benzonitrile |
| 297 | 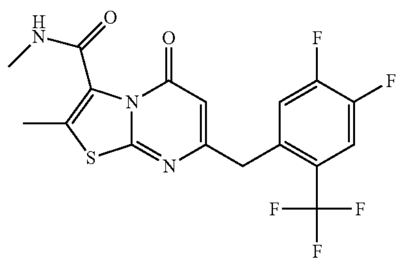 [SMILES: CNC(=O)c1c(C)sc2nc(Cc3cc(F)c(F)cc3C(F)(F)F)cc(=O)n12] | 7-[[4,5-difluoro-2-(trifluoromethyl)phenyl]methyl]-N,2-dimethyl-5-oxo-thiazolo[3,2-a]pyrimidine-3-carboxamide |
| 298 | 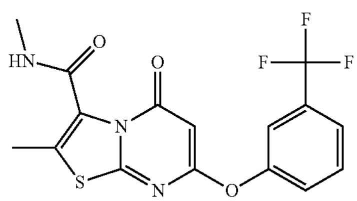 [SMILES: CNC(=O)c1c(C)sc2nc(Oc3cccc(C(F)(F)F)c3)cc(=O)n12] | N,2-dimethyl-5-oxo-7-[3-(trifluoromethyl)phenoxy]thiazolo[3,2-a]pyrimidine-3-carboxamide |
| 299 | 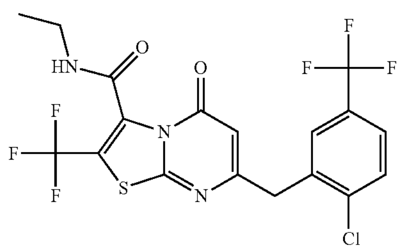 [SMILES: CCNC(=O)c1c(C(F)(F)F)sc2nc(Cc3cc(C(F)(F)F)ccc3Cl)cc(=O)n12] | 7-[[2-chloro-5-(trifluoromethyl)phenyl]methyl]-N-ethyl-5-oxo-2-(trifluoromethyl)thiazolo[3,2-a]pyrimidine-3-carboxamide |
| 300 | 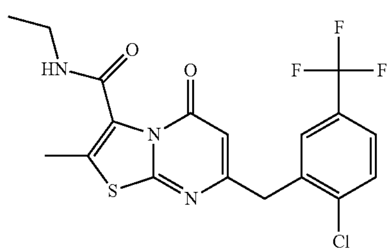 [SMILES: CCNC(=O)c1c(C)sc2nc(Cc3cc(C(F)(F)F)ccc3Cl)cc(=O)n12] | 7-[[2-chloro-5-(trifluoromethyl)phenyl]methyl]-N-ethyl-2-methyl-5-oxo-thiazolo[3,2-a]pyrimidine-3-carboxamide |

| Ex. | Structure | Name |
|---|---|---|
| 301 | 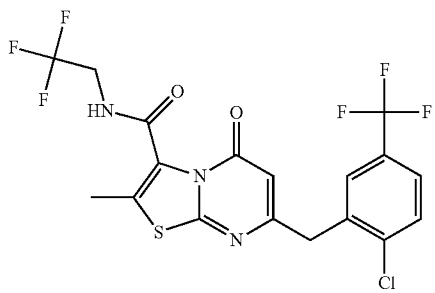 [SMILES: Cc1sc2nc(Cc3cc(C(F)(F)F)ccc3Cl)cc(=O)n2c1C(=O)NCC(F)(F)F] | 7-[[2-chloro-5-(trifluoromethyl)phenyl]methyl]-2-methyl-5-oxo-N-(2,2,2-trifluoroethyl)thiazolo[3,2-a]pyrimidine-3-carboxamide |
| 302 | 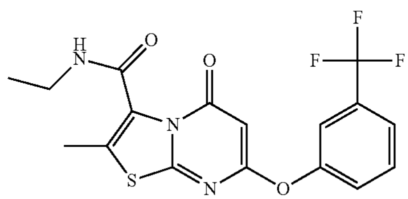 [SMILES: CCNC(=O)c1c(C)sc2nc(Oc3cccc(C(F)(F)F)c3)cc(=O)n12] | N-ethyl-2-methyl-5-oxo-7-[3-(trifluoromethyl)phenoxy]thiazolo[3,2-a]pyrimidine-3-carboxamide |
| 303 | 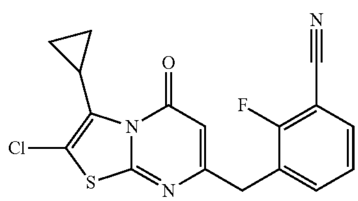 [SMILES: N#Cc1cccc(Cc2cc(=O)n3c(C4CC4)c(Cl)sc3n2)c1F] | 3-[(2-chloro-3-cyclopropyl-5-oxo-thiazolo[3,2-a]pyrimidin-7-yl)methyl]-2-fluoro-benzonitrile |
| 304 | 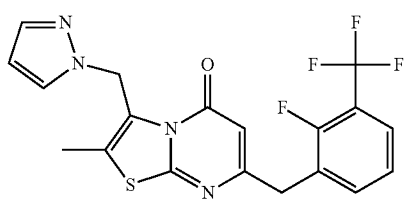 [SMILES: Cc1sc2nc(Cc3cccc(C(F)(F)F)c3F)cc(=O)n2c1Cn1cccn1] | 7-[[2-fluoro-3-(trifluoromethyl)phenyl]methyl]-2-methyl-3-(pyrazol-1-ylmethyl)thiazolo[3,2-a]pyrimidin-5-one |
| 305 | 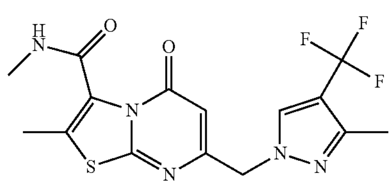 | N,2-dimethyl-7-[[3-methyl-4-(trifluoromethyl)pyrazol-1-yl]methyl]-5-oxo-thiazolo[3,2-a]pyrimidine-3-carboxamide |
| 306 | 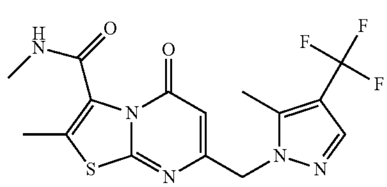 [SMILES: CNC(=O)c1c(C)sc2nc(Cn3ncc(C(F)(F)F)c3C)cc(=O)n12] | N,2-dimethyl-7-[[5-methyl-4-(trifluoromethyl)pyrazol-1-yl]methyl]-5-oxo-thiazolo[3,2-a]pyrimidine-3-carboxamide |
| 307 | 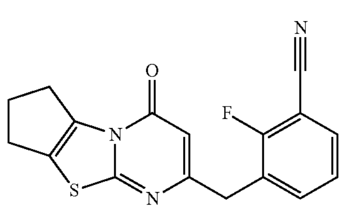 [SMILES: N#Cc1cccc(Cc2cc(=O)n3c4c(sc3n2)CCC4)c1F] | 2-fluoro-3-[(8-oxo-2,3-dihydro-1H-cyclopenta[3,4]thiazolo[1,4-a]pyrimidin-6-yl)methyl]benzonitrile |

-continued

| Ex. | Structure | Name |
|---|---|---|
| 308 | 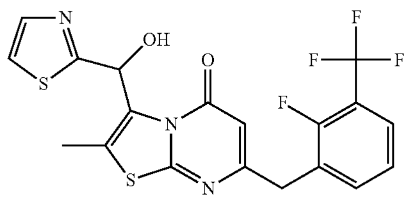 [SMILES: Cc1sc2nc(Cc3cccc(C(F)(F)F)c3F)cc(=O)n2c1C(O)c1nccs1] | 7-[[2-fluoro-3-(trifluoromethyl)phenyl]methyl]-3-[hydroxy(thiazol-2-yl)methyl]-2-methyl-thiazolo[3,2-a]pyrimidin-5-one |
| 309 | 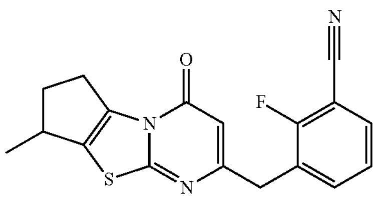 [SMILES: CC1CCc2c1sc1nc(Cc3cccc(C#N)c3F)cc(=O)n21] | 2-fluoro-3-[(3-methyl-8-oxo-2,3-dihydro-1H-cyclopenta[3,4]thiazolo[1,4-a]pyrimidin-6-yl)methyl]benzonitrile |
| 310 | 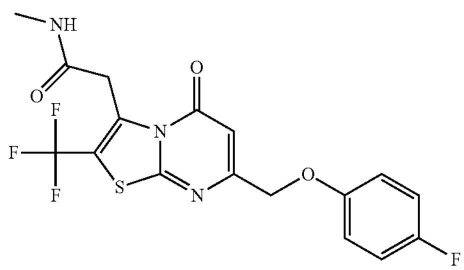 [SMILES: CNC(=O)Cc1c(C(F)(F)F)sc2nc(COc3ccc(F)cc3)cc(=O)n12] | 2-[7-[(4-fluorophenoxy)methyl]-5-oxo-2-(trifluoromethyl)thiazolo[3,2-a]pyrimidin-3-yl]-N-methyl-acetamide |
| 311 | 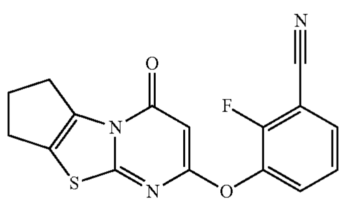 [SMILES: N#Cc1cccc(Oc2cc(=O)n3c4c(sc3n2)CCC4)c1F] | 2-fluoro-3-[(8-oxo-2,3-dihydro-1H-cyclopenta[3,4]thiazolo[1,4-a]pyrimidin-6-yl)oxy]benzonitrile |
| 312 | 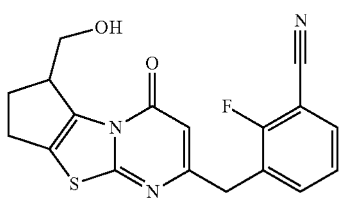 [SMILES: N#Cc1cccc(Cc2cc(=O)n3c4c(sc3n2)CCC4CO)c1F] | 2-fluoro-3-[[1-(hydroxymethyl)-8-oxo-2,3-dihydro-1H-cyclopenta[3,4]thiazolo[1,4-a]pyrimidin-6-yl]methyl]benzonitrile |
| 313 | 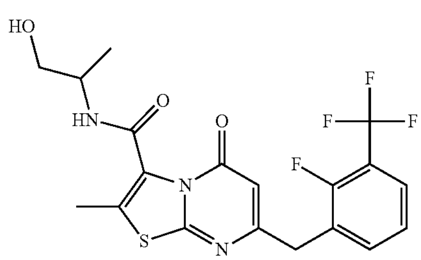 [SMILES: Cc1sc2nc(Cc3cccc(C(F)(F)F)c3F)cc(=O)n2c1C(=O)NC(C)CO] | 7-[[2-fluoro-3-(trifluoromethyl)phenyl]methyl]-N-(2-hydroxy-1-methyl-ethyl)-2-methyl-5-oxo-thiazolo[3,2-a]pyrimidine-3-carboxamide |
| 314 | 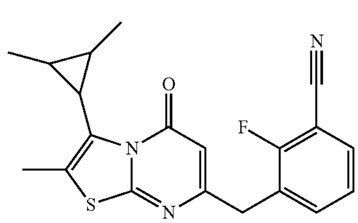 [SMILES: Cc1sc2nc(Cc3cccc(C#N)c3F)cc(=O)n2c1C1C(C)C1C] | 3-[[3-(2,3-dimethylcyclopropyl)-2-methyl-5-oxo-thiazolo[3,2-a]pyrimidin-7-yl]methyl]-2-fluoro-benzonitrile |

-continued

| Ex. | Structure | Name |
|---|---|---|
| 315 | 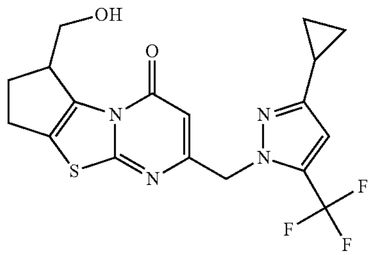 [SMILES: O=c1cc(Cn2nc(C3CC3)cc2C(F)(F)F)nc2sc3c(n12)C(CO)CC3] | 6-[[3-cyclopropyl-5-(trifluoromethyl)pyrazol-1-yl]methyl]-1-(hydroxymethyl)-2,3-dihydro-1H-cyclopenta[3,4]thiazolo[1,4-a]pyrimidin-8-one |
| 316 | 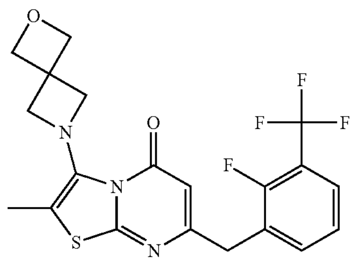 [SMILES: Cc1sc2nc(Cc3cccc(C(F)(F)F)c3F)cc(=O)n2c1N1CC2(COC2)C1] | 7-[[2-fluoro-3-(trifluoromethyl)phenyl]methyl]-2-methyl-3-(2-oxa-6-azaspiro[3.3]heptan-6-yl)thiazolo[3,2-a]pyrimidin-5-one |
| 317 | 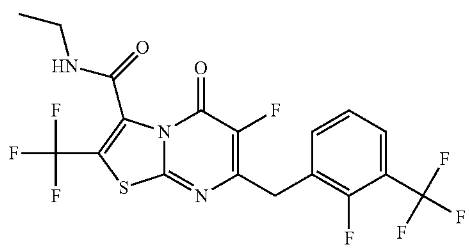 [SMILES: CCNC(=O)c1c(C(F)(F)F)sc2nc(Cc3cccc(C(F)(F)F)c3F)c(F)c(=O)n12] | N-ethyl-6-fluoro-7-[[2-fluoro-3-(trifluoromethyl)phenyl]methyl]-5-oxo-2-(trifluoromethyl)thiazolo[3,2-a]pyrimidine-3-carboxamide |
| 318 | 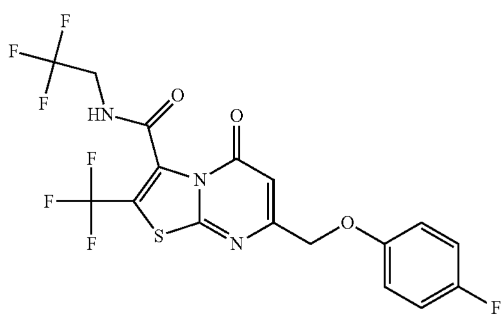 [SMILES: O=C(NCC(F)(F)F)c1c(C(F)(F)F)sc2nc(COc3ccc(F)cc3)cc(=O)n12] | 7-[(4-fluorophenoxy)methyl]-5-oxo-N-(2,2,2-trifluoroethyl)-2-(trifluoromethyl)thiazolo[3,2-a]pyrimidine-3-carboxamide |
| 319 | 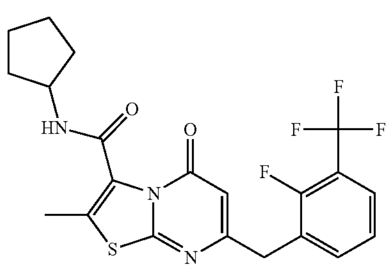 [SMILES: Cc1sc2nc(Cc3cccc(C(F)(F)F)c3F)cc(=O)n2c1C(=O)NC1CCCC1] | N-cyclopentyl-7-[[2-fluoro-3-(trifluoromethyl)phenyl]methyl]-2-methyl-5-oxo-thiazolo[3,2-a]pyrimidine-3-carboxamide |
| 320 | 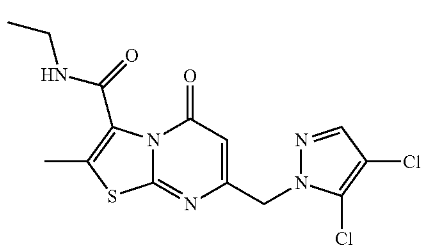 [SMILES: CCNC(=O)c1c(C)sc2nc(Cn3ncc(Cl)c3Cl)cc(=O)n12] | 7-[(4,5-dichloropyrazol-1-yl)methyl]-N-ethyl-2-methyl-5-oxo-thiazolo[3,2-a]pyrimidine-3-carboxamide |

| Ex. | Structure | Name |
|---|---|---|
| 321 | 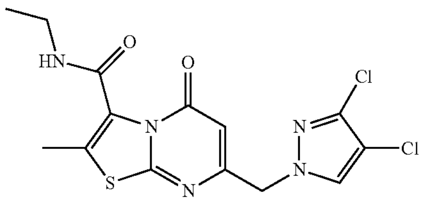 [SMILES: CCNC(=O)c1c(C)sc2nc(Cn3cc(Cl)c(Cl)n3)cc(=O)n12] | 7-[(3,4-dichloropyrazol-1-yl)methyl]-N-ethyl-2-methyl-5-oxo-thiazolo[3,2-a]pyrimidine-3-carboxamide |
| 322 | 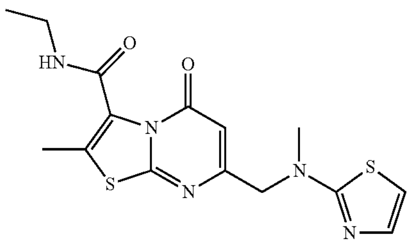 [SMILES: CCNC(=O)c1c(C)sc2nc(CN(C)c3nccs3)cc(=O)n12] | N-ethyl-2-methyl-7-[[methyl(thiazol-2-yl)amino]methyl]-5-oxo-thiazolo[3,2-a]pyrimidine-3-carboxamide |
| 323 | 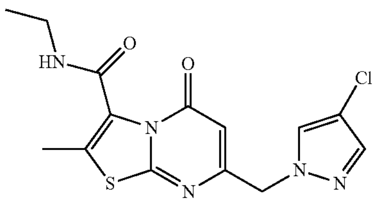 [SMILES: CCNC(=O)c1c(C)sc2nc(Cn3cc(Cl)cn3)cc(=O)n12] | 7-[(4-chloropyrazol-1-yl)methyl]-N-ethyl-2-methyl-5-oxo-thiazolo[3,2-a]pyrimidine-3-carboxamide |
| 324 | 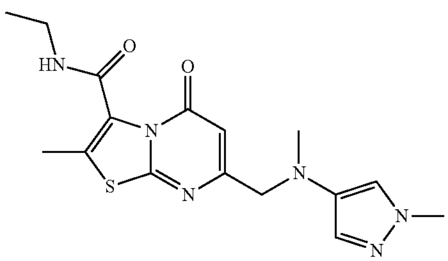 [SMILES: CCNC(=O)c1c(C)sc2nc(CN(C)c3cnn(C)c3)cc(=O)n12] | N-ethyl-2-methyl-7-[[methyl-(1-methylpyrazol-4-yl)amino]methyl]-5-oxo-thiazolo[3,2-a]pyrimidine-3-carboxamide |
| 325 | 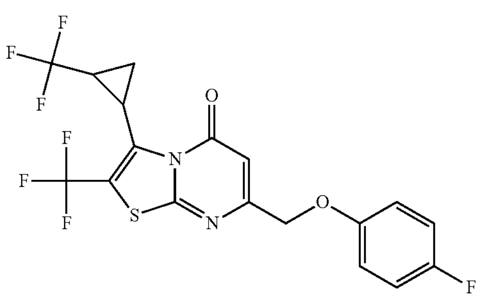 [SMILES: O=c1cc(COc2ccc(F)cc2)nc2sc(C(F)(F)F)c(C3CC3C(F)(F)F)n12] | 7-[(4-fluorophenoxy)methyl]-2-(trifluoromethyl)-3-[2-(trifluoromethyl)cyclopropyl]thiazolo[3,2-a]pyrimidin-5-one |
| 326 | 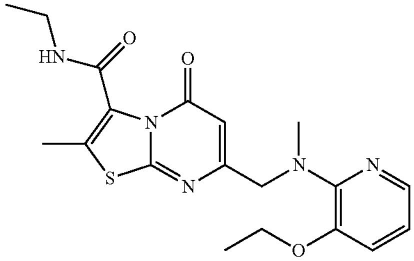 [SMILES: CCNC(=O)c1c(C)sc2nc(CN(C)c3ncccc3OCC)cc(=O)n12] | 7-[[[(3-ethoxy-2-pyridyl)-methyl-amino]methyl]-N-ethyl-2-methyl-5-oxo-thiazolo[3,2-a]pyrimidine-3-carboxamide |

| Ex. | Structure | Name |
|---|---|---|
| 327 | 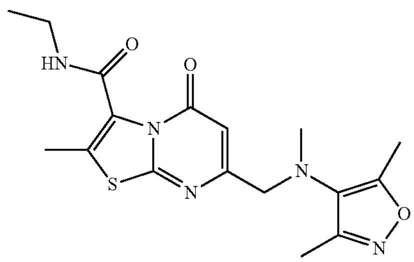 [SMILES: CCNC(=O)c1c(C)sc2nc(CN(C)c3c(C)noc3C)cc(=O)n12] | 7-[[(3,5-dimethylisoxazol-4-yl)-methyl-amino]methyl]-N-ethyl-2-methyl-5-oxo-thiazolo[3,2-a]pyrimidine-3-carboxamide |
| 328 | 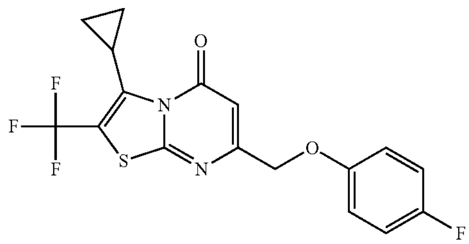 [SMILES: O=c1cc(COc2ccc(F)cc2)nc2sc(C(F)(F)F)c(C3CC3)n12] | 3-cyclopropyl-7-[(4-fluorophenoxy)methyl]-2-(trifluoromethyl)thiazolo[3,2-a]pyrimidin-5-one |
| 329 | 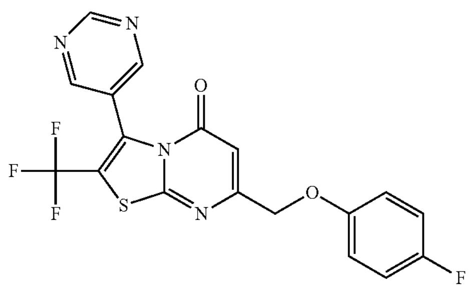 [SMILES: O=c1cc(COc2ccc(F)cc2)nc2sc(C(F)(F)F)c(-c3cncnc3)n12] | 7-[(4-fluorophenoxy)methyl]-3-pyrimidin-5-yl-2-(trifluoromethyl)thiazolo[3,2-a]pyrimidin-5-one |
| 330 | 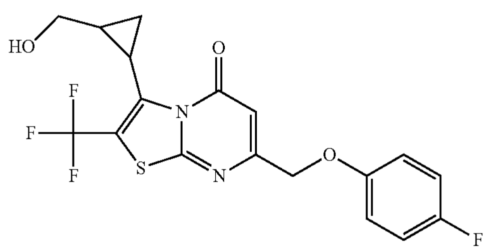 [SMILES: O=c1cc(COc2ccc(F)cc2)nc2sc(C(F)(F)F)c(C3CC3CO)n12] | 7-[(4-fluorophenoxy)methyl]-3-[2-(hydroxymethyl)cyclopropyl]-2-(trifluoromethyl)thiazolo[3,2-a]pyrimidin-5-one |
| 331 | 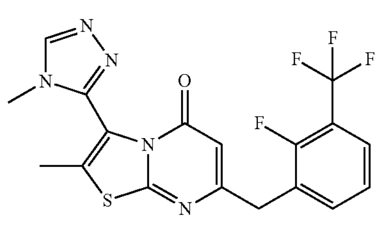 [SMILES: Cc1sc2nc(Cc3cccc(C(F)(F)F)c3F)cc(=O)n2c1-c1nncn1C] | 7-[[2-fluoro-3-(trifluoromethyl)phenyl]methyl]-2-methyl-3-(4-methyl-1,2,4-triazol-3-yl)thiazolo[3,2-a]pyrimidin-5-one |
| 332 | 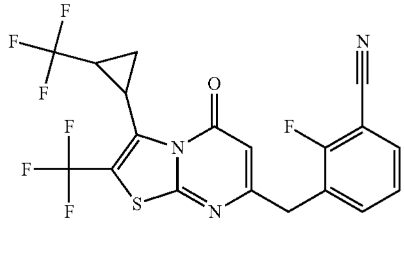 [SMILES: N#Cc1cccc(Cc2cc(=O)n3c(C4CC4C(F)(F)F)c(C(F)(F)F)sc3n2)c1F] | 2-fluoro-3-[[5-oxo-2-(trifluoromethyl)-3-[2-(trifluoromethyl)cyclopropyl]thiazolo[3,2-a]pyrimidin-7-yl]methyl]benzonitrile |

-continued

| Ex. | Structure | Name |
|---|---|---|
| 333 | 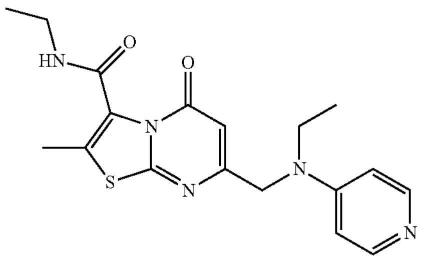 [SMILES: CCNC(=O)c1c(C)sc2nc(CN(CC)c3ccncc3)cc(=O)n12] | N-ethyl-7-[[ethyl(4-pyridyl)amino]methyl]-2-methyl-5-oxo-thiazolo[3,2-a]pyrimidine-3-carboxamide |
| 334 | 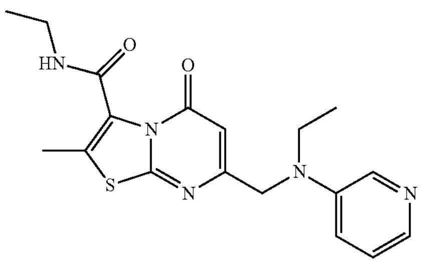 [SMILES: CCNC(=O)c1c(C)sc2nc(CN(CC)c3cccnc3)cc(=O)n12] | N-ethyl-7-[[ethyl(3-pyridyl)amino]methyl]-2-methyl-5-oxo-thiazolo[3,2-a]pyrimidine-3-carboxamide |
| 335 | 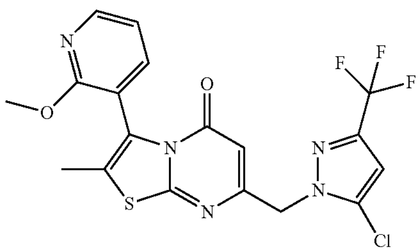 [SMILES: COc1ncccc1-c1c(C)sc2nc(Cn3nc(C(F)(F)F)cc3Cl)cc(=O)n12] | 7-[[5-chloro-3-(trifluoromethyl)pyrazol-1-yl]methyl]-3-(2-methoxy-3-pyridyl)-2-methyl-thiazolo[3,2-a]pyrimidin-5-one |
| 336 | 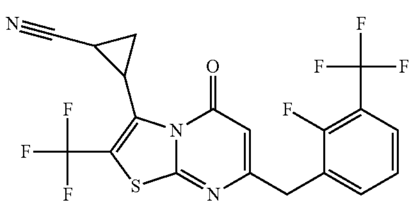 [SMILES: N#CC1CC1c1c(C(F)(F)F)sc2nc(Cc3cccc(C(F)(F)F)c3F)cc(=O)n12] | 2-[7-[[2-fluoro-3-(trifluoromethyl)phenyl]methyl]-5-oxo-2-(trifluoromethyl)thiazolo[3,2-a]pyrimidin-3-yl]cyclopropanecarbonitrile |
| 337 | 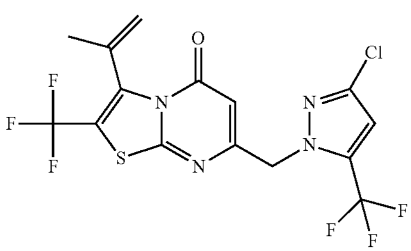 [SMILES: C=C(C)c1c(C(F)(F)F)sc2nc(Cn3nc(Cl)cc3C(F)(F)F)cc(=O)n12] | 7-[[3-chloro-5-(trifluoromethyl)pyrazol-1-yl]methyl]-3-isopropenyl-2-(trifluoromethyl)thiazolo[3,2-a]pyrimidin-5-one |
| 338 | 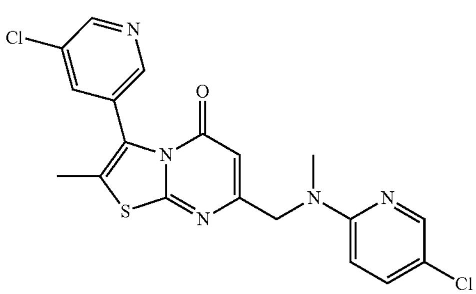 [SMILES: Cc1sc2nc(CN(C)c3ccc(Cl)cn3)cc(=O)n2c1-c1cncc(Cl)c1] | 3-(5-chloro-3-pyridyl)-7-[[(5-chloro-2-pyridyl)-methyl-amino]methyl]-2-methyl-thiazolo[3,2-a]pyrimidin-5-one |

-continued

| Ex. | Structure | Name |
|---|---|---|
| 339 | 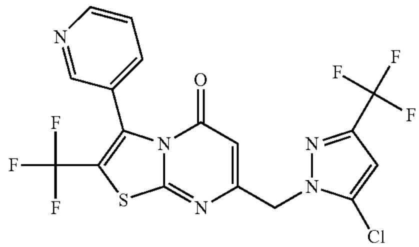 [SMILES: O=c1cc(Cn2nc(C(F)(F)F)cc2Cl)nc2sc(C(F)(F)F)c(-c3cccnc3)n12] | 7-[[5-chloro-3-(trifluoromethyl)pyrazol-1-yl]methyl]-3-(3-pyridyl)-2-(trifluoromethyl)thiazolo[3,2-a]pyrimidin-5-one |
| 340 | 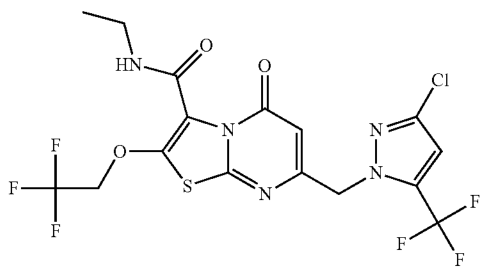 [SMILES: CCNC(=O)c1c(OCC(F)(F)F)sc2nc(Cn3nc(Cl)cc3C(F)(F)F)cc(=O)n12] | 7-[[3-chloro-5-(trifluoromethyl)pyrazol-1-yl]methyl]-N-ethyl-5-oxo-2-(2,2,2-trifluoroethoxy)thiazolo[3,2-a]pyrimidine-3-carboxamide |
| 341 | 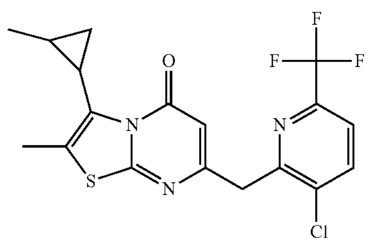 [SMILES: Cc1sc2nc(Cc3nc(C(F)(F)F)ccc3Cl)cc(=O)n2c1C1CC1C] | 7-[[3-chloro-6-(trifluoromethyl)-2-pyridyl]methyl]-2-methyl-3-(2-methylcyclopropyl)thiazolo[3,2-a]pyrimidin-5-one |
| 342 | 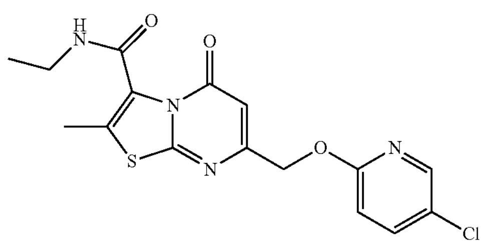 [SMILES: CCNC(=O)c1c(C)sc2nc(COc3ccc(Cl)cn3)cc(=O)n12] | 7-[(5-chloro-2-pyridyl)oxymethyl]-N-ethyl-2-methyl-5-oxo-thiazolo[3,2-a]pyrimidine-3-carboxamide |
| 343 | 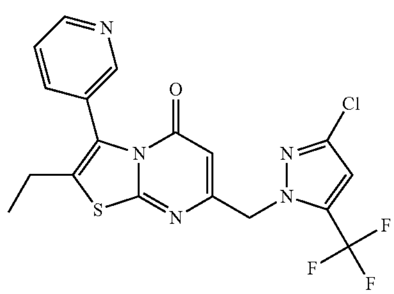 [SMILES: CCc1sc2nc(Cn3nc(Cl)cc3C(F)(F)F)cc(=O)n2c1-c1cccnc1] | 7-[[3-chloro-5-(trifluoromethyl)pyrazol-1-yl]methyl]-2-ethyl-3-(3-pyridyl)thiazolo[3,2-a]pyrimidin-5-one |
| 344 | 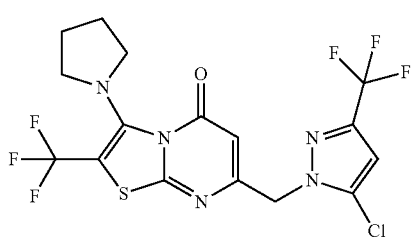 [SMILES: O=c1cc(Cn2nc(C(F)(F)F)cc2Cl)nc2sc(C(F)(F)F)c(N3CCCC3)n12] | 7-[[5-chloro-3-(trifluoromethyl)pyrazol-1-yl]methyl]-3-pyrrolidin-1-yl-2-(trifluoromethyl)thiazolo[3,2-a]pyrimidin-5-one |

| Ex. | Structure | Name |
|---|---|---|
| 345 | 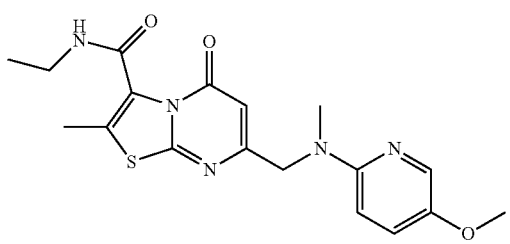 [SMILES: CCNC(=O)c1c(C)sc2nc(CN(C)c3ccc(OC)cn3)cc(=O)n12] | N-ethyl-7-[[(5-methoxy-2-pyridyl)-methyl-amino]methyl]-2-methyl-5-oxo-thiazolo[3,2-a]pyrimidine-3-carboxamide |
| 346 | 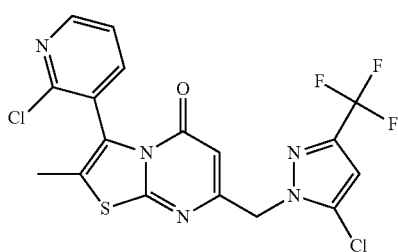 [SMILES: Cc1sc2nc(Cn3nc(C(F)(F)F)cc3Cl)cc(=O)n2c1-c1cccnc1Cl] | 3-(2-chloro-3-pyridyl)-7-[[5-chloro-3-(trifluoromethyl)pyrazol-1-yl]methyl]-2-methyl-thiazolo[3,2-a]pyrimidin-5-one |
| 347 | 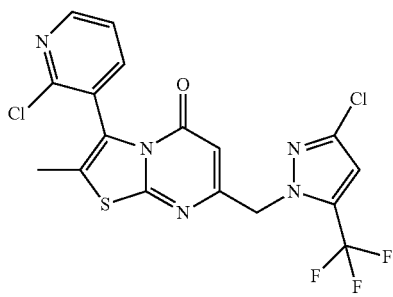 [SMILES: Cc1sc2nc(Cn3nc(Cl)cc3C(F)(F)F)cc(=O)n2c1-c1cccnc1Cl] | 3-(2-chloro-3-pyridyl)-7-[[3-chloro-5-(trifluoromethyl)pyrazol-1-yl]methyl]-2-methyl-thiazolo[3,2-a]pyrimidin-5-one |
| 348 | 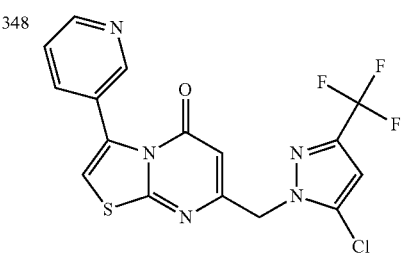 | 7-[[5-chloro-3-(trifluoromethyl)pyrazol-1-yl]methyl]-3-(3-pyridyl)thiazolo[3,2-a]pyrimidin-5-one |
| 349 | 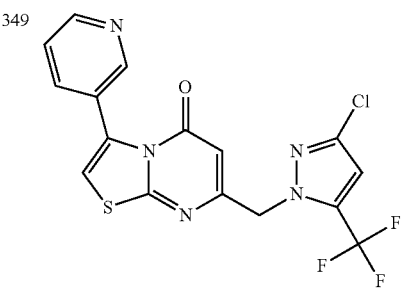 | 7-[[3-chloro-5-(trifluoromethyl)pyrazol-1-yl]methyl]-3-(3-pyridyl)thiazolo[3,2-a]pyrimidin-5-one |

-continued

| Ex. | Structure | Name |
|---|---|---|
| 350 | 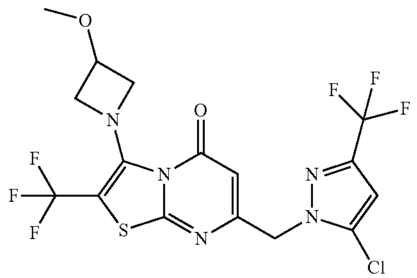 [SMILES: COC1CN(c2c(C(F)(F)F)sc3nc(Cn4nc(C(F)(F)F)cc4Cl)cc(=O)n23)C1] | 7-[[5-chloro-3-(trifluoromethyl)pyrazol-1-yl]methyl]-3-(3-methoxyazetidin-1-yl)-2-(trifluoromethyl)thiazolo[3,2-a]pyrimidin-5-one |
| 351 | 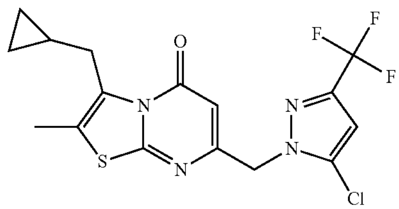 [SMILES: Cc1sc2nc(Cn3nc(C(F)(F)F)cc3Cl)cc(=O)n2c1CC1CC1] | 7-[[5-chloro-3-(trifluoromethyl)pyrazol-1-yl]methyl]-3-(cyclopropylmethyl)-2-methyl-thiazolo[3,2-a]pyrimidin-5-one |
| 352 | 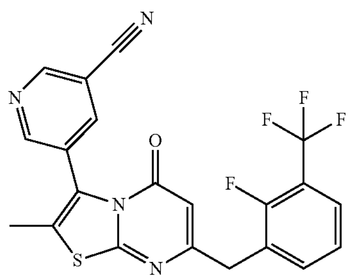 [SMILES: Cc1sc2nc(Cc3cccc(C(F)(F)F)c3F)cc(=O)n2c1-c1cncc(C#N)c1] | 5-[7-[[2-fluoro-3-(trifluoromethyl)phenyl]methyl]-2-methyl-5-oxo-thiazolo[3,2-a]pyrimidin-3-yl]pyridine-3-carbonitrile |
| 353 | 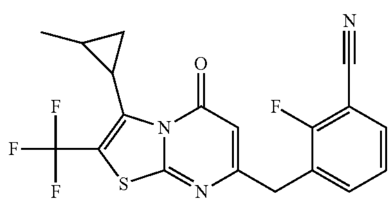 [SMILES: CC1CC1c1c(C(F)(F)F)sc2nc(Cc3cccc(C#N)c3F)cc(=O)n12] | 2-fluoro-3-[[3-[2-methylcyclopropyl]-5-oxo-2-(trifluoromethyl)thiazolo[3,2-a]pyrimidin-7-yl]methyl]benzonitrile |
| 354 | 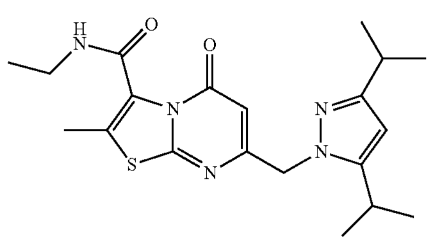 [SMILES: CCNC(=O)c1c(C)sc2nc(Cn3nc(C(C)C)cc3C(C)C)cc(=O)n12] | 7-[(3,5-diisopropylpyrazol-1-yl)methyl]-N-ethyl-2-methyl-5-oxo-thiazolo[3,2-a]pyrimidine-3-carboxamide |
| 355 | 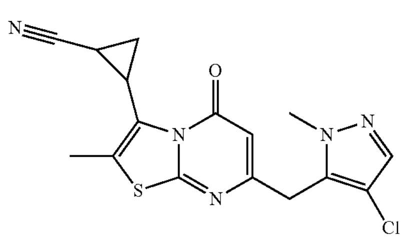 [SMILES: Cc1sc2nc(Cc3c(Cl)cnn3C)cc(=O)n2c1C1CC1C#N] | 2-[7-[(4-chloro-2-methyl-pyrazol-3-yl)methyl]-2-methyl-5-oxo-thiazolo[3,2-a]pyrimidin-3-yl]cyclopropanecarbonitrile |

-continued

| Ex. | Structure | Name |
|---|---|---|
| 356 | 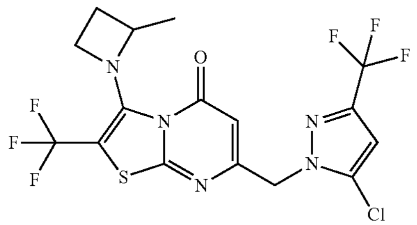 [SMILES: CC1CCN1c1c(C(F)(F)F)sc2nc(Cn3nc(C(F)(F)F)cc3Cl)cc(=O)n12] | 7-[[5-chloro-3-(trifluoromethyl)pyrazol-1-yl]methyl]-3-(2-methylazetidin-1-yl)-2-(trifluoromethyl)thiazolo[3,2-a]pyrimidin-5-one |
| 357 | 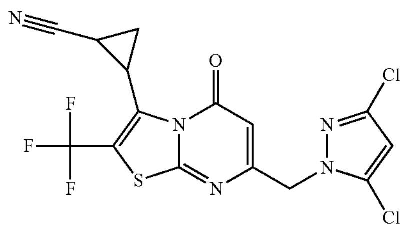 [SMILES: N#CC1CC1c1c(C(F)(F)F)sc2nc(Cn3nc(Cl)cc3Cl)cc(=O)n12] | 2-[7-[(3,5-dichloropyrazol-1-yl)methyl]-5-oxo-2-(trifluoromethyl)thiazolo[3,2-a]pyrimidin-3-yl]cyclopropanecarbonitrile (cis enantiomer 1) |
| 358 | 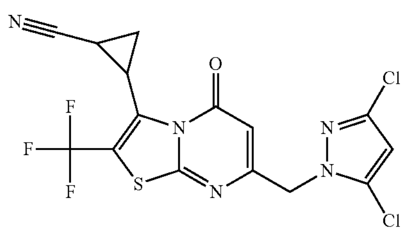 [SMILES: N#CC1CC1c1c(C(F)(F)F)sc2nc(Cn3nc(Cl)cc3Cl)cc(=O)n12] | 2-[7-[(3,5-dichloropyrazol-1-yl)methyl]-5-oxo-2-(trifluoromethyl)thiazolo[3,2-a]pyrimidin-3-yl]cyclopropanecarbonitrile (cis enantiomer 2) |
| 359 | 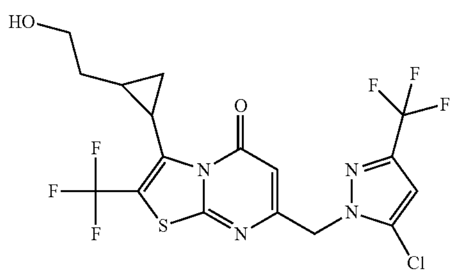 [SMILES: O=c1cc(Cn2nc(C(F)(F)F)cc2Cl)nc2sc(C(F)(F)F)c(C3CC3CCO)n12] | 7-[[5-chloro-3-(trifluoromethyl)pyrazol-1-yl]methyl]-3-[2-(2-hydroxyethyl)cyclopropyl]-2-(trifluoromethyl)thiazolo[3,2-a]pyrimidin-5-one (trans enantiomer 1) |
| 360 | 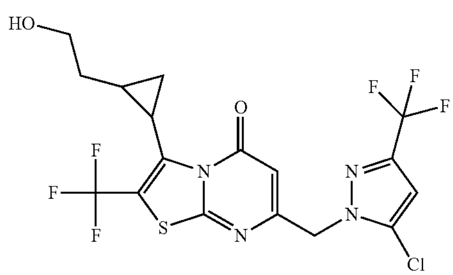 [SMILES: O=c1cc(Cn2nc(C(F)(F)F)cc2Cl)nc2sc(C(F)(F)F)c(C3CC3CCO)n12] | 7-[[5-chloro-3-(trifluoromethyl)pyrazol-1-yl]methyl]-3-[2-(2-hydroxyethyl)cyclopropyl]-2-(trifluoromethyl)thiazolo[3,2-a]pyrimidin-5-one (trans enantiomer 2) |
| 361 | 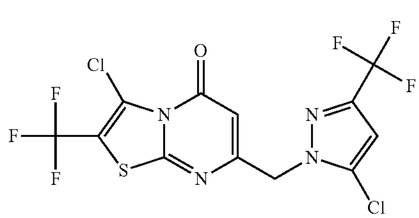 [SMILES: O=c1cc(Cn2nc(C(F)(F)F)cc2Cl)nc2sc(C(F)(F)F)c(Cl)n12] | 3-chloro-7-[[5-chloro-3-(trifluoromethyl)pyrazol-1-yl]methyl]-2-(trifluoromethyl)thiazolo[3,2-a]pyrimidin-5-one |

-continued

| Ex. | Structure | Name |
|---|---|---|
| 362 | 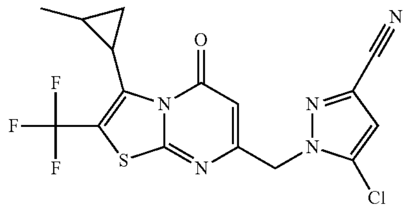 [SMILES: CC1CC1c1c(C(F)(F)F)sc2nc(Cn3nc(C#N)cc3Cl)cc(=O)n12] | 5-chloro-1-[[3-[2-methylcyclopropyl]-5-oxo-2-(trifluoromethyl)thiazolo[3,2-a]pyrimidin-7-yl]methyl]pyrazole-3-carbonitrile (cis enantiomer 1) |
| 363 | 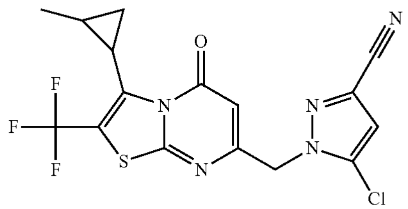 [SMILES: CC1CC1c1c(C(F)(F)F)sc2nc(Cn3nc(C#N)cc3Cl)cc(=O)n12] | 5-chloro-1-[[3-[2-methylcyclopropyl]-5-oxo-2-(trifluoromethyl)thiazolo[3,2-a]pyrimidin-7-yl]methyl]pyrazole-3-carbonitrile (cis enantiomer 2) |
| 364 | 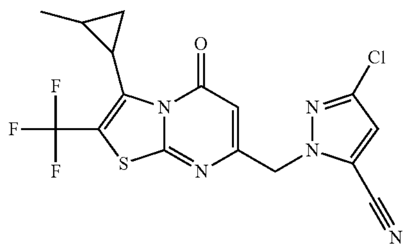 [SMILES: CC1CC1c1c(C(F)(F)F)sc2nc(Cn3nc(Cl)cc3C#N)cc(=O)n12] | 5-chloro-2-[[3-[2-methylcyclopropyl]-5-oxo-2-(trifluoromethyl)thiazolo[3,2-a]pyrimidin-7-yl]methyl]pyrazole-3-carbonitrile |
| 365 | 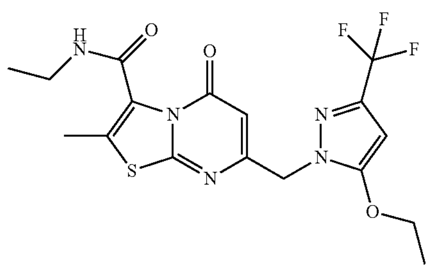 [SMILES: CCNC(=O)c1c(C)sc2nc(Cn3nc(C(F)(F)F)cc3OCC)cc(=O)n12] | 7-[[5-ethoxy-3-(trifluoromethyl)pyrazol-1-yl]methyl]-N-ethyl-2-methyl-5-oxo-thiazolo[3,2-a]pyrimidine-3-carboxamide |
| 366 | 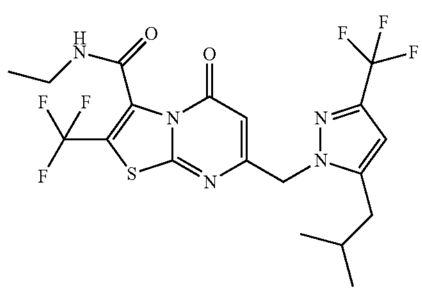 [SMILES: CCNC(=O)c1c(C(F)(F)F)sc2nc(Cn3nc(C(F)(F)F)cc3CC(C)C)cc(=O)n12] | N-ethyl-7-[[5-isobutyl-3-(trifluoromethyl)pyrazol-1-yl]methyl]-5-oxo-2-(trifluoromethyl)thiazolo[3,2-a]pyrimidine-3-carboxamide |
| 367 | 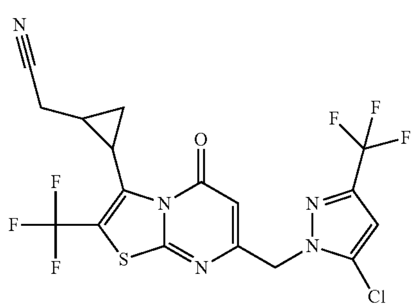 [SMILES: N#CCC1CC1c1c(C(F)(F)F)sc2nc(Cn3nc(C(F)(F)F)cc3Cl)cc(=O)n12] | 2-[2-[7-[[5-chloro-3-(trifluoromethyl)pyrazol-1-yl]methyl]-5-oxo-2-(trifluoromethyl)thiazolo[3,2-a]pyrimidin-3-yl]cyclopropyl]acetonitrile (trans enantiomer 1) |

| Ex. | Structure | Name |
|---|---|---|
| 368 | 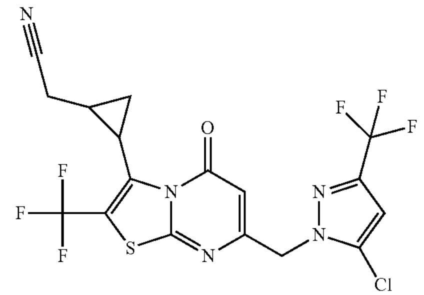 [SMILES: N#CCC1CC1c1c(C(F)(F)F)sc2nc(Cn3nc(C(F)(F)F)cc3Cl)cc(=O)n12] | 2-[2-[7-[[5-chloro-3-(trifluoromethyl)pyrazol-1-yl]methyl]-5-oxo-2-(trifluoromethyl)thiazolo[3,2-a]pyrimidin-3-yl]cyclopropyl]acetonitrile (trans enantiomer 2) |

It is understood that the person skilled in the art will be able to prepare the compounds of the present invention using methods known in the art along with the general method of synthesis described herein.

Assay 1: Cell-Based Assay

HEK cells stably transfected with tetracycline inducible hNR1 and hNR2A were seeded into clear bottom 384 well poly-D-lysine coated plates ($2.5 \times 10^4$ cells per well) in Minimum Essential Media (MEM; without L-) including 7.5 µg mL$^{-1}$ doxycycline and 500 µM (+)-ketamine. The cells were incubated at 37° C. in 5% CO$_2$ for 24 h. For measurement of changes in cytosolic calcium, the seeding media was removed and the cells incubated at 37° C. for 60 min with 1× Becton Dickinson Calcium Assay Kit reagent in Hanks Balanced Salt Solution (HBSS; w/o magnesium, including 1.8 mM calcium, 0.65 mg ml$^{-1}$ probenecid and 10 µM (+)-ketamine, pH 7.15) then allowed to equilibrate to rt for 30 min. Concentration-effect curves to Positive Allosteric Modulators (PAMs) were constructed by adding different concentrations (with 30 µM glycine and 300 nM L-glutamate (EC$_{30}$)) to different wells in HBSS. Compounds were added after a 10 second baseline read and maximum level of relative fluorescence units (RFU) was measured over a 5 min period. Responses were scaled relative to 100 µM L-glutamate maximal response (100%) and 0 µM L-glutamate (0%). EC$_{50}$ values are provided for compounds reaching maximal response plateaus, and the max % (EC$_{50}$ (- -)) only if no plateau was reached.

A four-parameter Hill equation was fitted to individual concentration-effect curves:

$$Y = S_0 + \frac{S_{inf} - S_0}{1 + \left(\frac{10^{logAC50}}{10^c}\right)^n}$$

in which Y, $S_0$, $S_{inf}$, $AC_{50}$, n and c were effect, lower-asymptote, upper-asymptote, mid-point location, slope parameter, and concentration respectively.

Data for compounds tested in this assay are shown below in Table 2.

TABLE 2

| No. | EC$_{50}$ (uM) | Max % |
|---|---|---|
| 1.1 | 9.6 | 63% |
| 1.2 | — | 92% |

TABLE 2-continued

| No. | EC$_{50}$ (uM) | Max % |
|---|---|---|
| 1.3 | — | 45% |
| 1.4 | 11.2 | 59.5% |
| 1.5 | 23 | 51.4% |
| 1.6 | 31.6 | 64% |
| 1.7 | 27 | 44.8% |
| 1.8 | 26.3 | 47.4% |
| 1.9 | — | 99.5% |
| 1.10 | — | 44% |
| 1.11 | — | 73% |
| 1.12 | — | 45.5% |
| 1.13 | — | 41.6% |
| 1.14 | — | 42.7% |
| 1.15 | — | 55.1% |
| 1.16 | — | 56.5% |
| 1.17 | 4 | 68.6% |
| 2.1 | 5.2 | 51.3% |
| 2.2 | — | 96.5% |
| 2.3 | 12.6 | 49.8% |
| 2.4 | 3.0 | 44.6% |
| 2.5 | 32.9 | 115% |
| 2.6 | 19.6 | 59.9% |
| 2.7 | 26 | 61.3% |
| 2.8 | — | 137% |
| 2.9 | — | 56.4% |
| 2.10 | — | 119% |
| 2.11 | — | 87.4% |
| 3.1 | 41 | 56.2% |
| 3.2 | 10.1 | 42.7% |
| 3.3 | — | 61.8% |
| 3.4 | — | 44.6% |
| 3.5 | — | 65.6% |
| 3.6 | — | 68% |
| 4.1 | 5.1 | 141% |
| 4.2 | 1.3 | 137% |
| 4.3 | 20.5 | 71.6% |
| 4.4 | 2.5 | 138% |
| 4.5 | 5.7 | 42.2% |
| 4.6 | 7.7 | 128% |
| 4.7 | 5.8 | 134% |
| 4.8 | 4.4 | 99.3% |
| 4.9 | 4.4 | 123% |
| 4.10 | 4.3 | 108% |
| 4.11 | 4.8 | 40.8% |
| 4.12 | 30.6 | 127% |
| 4.13 | 31.1 | 72.8% |
| 4.14 | 7.8 | 93% |
| 4.15 | 13.9 | 50% |
| 4.16 | — | 46.2% |
| 4.17 | — | 40.3% |
| 4.18 | 5.0 | 102% |
| 4.19 | 9.0 | 46.9% |
| 4.20 | 2.4 | 93.9% |
| 4.21 | 16.3 | 47.4 |
| 4.22 | — | 84.2 |
| 4.23 | 26.5 | 62.9% |

TABLE 2-continued

| No. | EC$_{50}$ (uM) | Max % |
|---|---|---|
| 4.24 | 2.1 | 80% |
| 4.25 | 2.8 | 109% |
| 4.26 | — | 98.8 |
| 4.27 | — | 103% |
| 4.28 | 3.4 | 89% |
| 4.29 | 17.5 | 134% |
| 4.30 | 15.5 | 75.4% |
| 4.31 | — | 43.3% |
| 4.32 | — | 50.2% |
| 4.33 | 13.8 | 121% |
| 4.34 | — | 49.2% |
| 5.1 | 0.560 | 145.1 |
| 5.2 | 5.7 | 148% |
| 5.3 | 2.2 | 177% |
| 5.4 | 0.956 | 172% |
| 5.5 | 2.4 | 168% |
| 5.6 | 0.766 | 164% |
| 5.7 | 0.867 | 160% |
| 5.8 | 0.669 | 156% |
| 5.9 | 1.3 | 143% |
| 5.10 | 18 | 133% |
| 5.11 | 2.9 | 118% |
| 5.12 | — | 106% |
| 5.13 | — | 87.9% |
| 5.14 | 7.5 | 111% |
| 5.15 | 7 | 144% |
| 5.16 | 2.5 | 157% |
| 5.17 | 0.108 | 176% |
| 5.18 | 0.091 | 164% |
| 5.19 | 1.7 | 141% |
| 5.20 | 0.815 | 157% |
| 5.21 | 0.584 | 141% |
| 5.22 | 1.6 | 142% |
| 5.23 | 2.6 | 135% |
| 5.24 | 0.731 | 142% |
| 5.25 | 0.7 | 141 |
| 5.26 | 0.563 | 149% |
| 5.27 | 1.1 | 139% |
| 5.28 | .0952 | 176% |
| 5.29 | 0.445 | 147% |
| 5.30 | 4.3 | 132% |
| 5.31 | 2.7 | 132% |
| 5.32 | 4.3 | 123% |
| 5.33 | 4.2 | 120 |
| 5.34 | 2.8 | 118% |
| 5.35 | 2.7 | 136% |
| 5.36 | — | 61.3% |
| 5.37 | 0.515 | 152% |
| 5.38 | 1.1 | 147% |
| 5.39 | 0.952 | 167% |
| 5.40 | 1.9 | 149% |
| 5.41 | 2 | 125% |
| 5.42 | 0.0329 | 162% |
| 5.43 | 0.821 | 145% |
| 5.44 | 1.1 | 158% |
| 5.45 | 0.214 | 139% |
| 5.46 | 3.8 | 155% |
| 5.47 | 0.976 | 151% |
| 5.48 | 6.2 | 136% |
| 5.49 | 12.9 | 127% |
| 5.50 | — | 96.8% |
| 5.51 | 40.7 | 80.3% |
| 5.52 | 1.6 | 58% |
| 5.53 | 1.3 | 153% |
| 5.54 | 51.5 | 129% |
| 5.55 | 4.7 | 111% |
| 5.56 | — | 110% |
| 5.57 | 6.4 | 120% |
| 5.58 | 5.1 | 120% |
| 6.1 | 10 | 123% |
| 6.2 | 5 | 121% |
| 6.3 | 10.1 | 91.9% |
| 7.1 | 0.853 | 184% |
| 7.2 | 0.612 | 134% |
| 7.3 | 0.376 | 156% |
| 7.4 | 5.7 | 166% |
| 7.5 | 2.1 | 162% |
| 7.6 | 3.7 | 151% |
| 7.7 | 21 | 148% |
| 7.8 | 2.5 | 126% |
| 7.9 | 1.3 | 121% |
| 8.1 | 5.2 | 146% |
| 8.2 | 7.2 | 122% |
| 8.3 | 1.3 | 150% |
| 8.4 | 0.569 | 164% |
| 8.5 | 16.9 | 114% |
| 8.6 | — | 60.5% |
| 8.7 | — | 81.4% |
| 8.8 | 8.7 | 108% |
| 8.9 | 11.1 | 124% |
| 8.10 | 12.5 | 127% |
| 8.11 | 2.7 | 154% |
| 8.12 | 0.385 | 161% |
| 8.13 | 2.2 | 162% |
| 8.14 | 1.1 | 154% |
| 8.15 | 2.3 | 138% |
| 8.16 | 13 | 137% |
| 9.1 | — | 48.1% |
| 9.2 | 2.9 | 117% |
| 9.3 | 7.0 | 108% |
| 9.4 | 9.2 | 114% |
| 10.1 | 4.4 | 130% |
| 10.2 | 5.3 | 110% |
| 10.3 | 0.535 | 177% |
| 10.4 | 0.593 | 186% |
| 10.5 | 0.495 | 158% |
| 10.6 | 0.548 | 176% |
| 10.7 | 23.4 | 127% |
| 10.8 | — | 63.5% |
| 10.9 | — | 72.1% |
| 10.10 | 18.8 | 132% |
| 10.11 | 1.2 | 167% |
| 10.12 | 2.1 | 149% |
| 10.13 | 0.345 | 165% |
| 10.14 | 1.5 | 172% |
| 10.15 | 1.3 | 156% |
| 10.16 | 2.7 | 147% |
| 10.17 | 1.2 | 174% |
| 10.18 | 16.9 | 88.2% |
| 10.19 | 0.837 | 165% |
| 10.20 | 2.2 | 178% |
| 10.21 | — | 117% |
| 10.22 | 7.5 | 156% |
| 10.23 | 22.9 | 169% |
| 10.24 | 8.9 | 160% |
| 10.25 | 0.345 | 165% |
| 11.1 | 2 | 159% |
| 11.2 | — | 107% |
| 11.3 | 3.2 | 132% |
| 11.4 | — | 103% |
| 11.5 | 4.6 | 167% |
| 11.6 | 5.0 | 133% |
| 12.1 | 0.723 | 166% |
| 12.2 | 0.27 | 192% |
| 12.3 | 1.6 | 183% |
| 12.4 | 0.591 | 176% |
| 12.5 | 0.974 | 153% |
| 13.1 | 0.434 | 161% |
| 13.2 | 0.913 | 130% |
| 13.3 | 0.783 | 137% |
| 13.4 | 0.777 | 185% |
| 13.5 | 1 | 152% |
| 13.6 | 1.4 | 125% |
| 13.7 | 0.547 | 137% |
| 13.8 | — | 61.2% |
| 13.9 | 5.0 | 166% |
| 14.1 | 2.6 | 163% |
| 14.2 | 0.122 | 205% |
| 15.1 | 2.2 | 144% |
| 15.2 | 1 | 167% |
| 15.3 | 0.489 | 144% |
| 15.4 | 0.782 | 137% |
| 15.5 | 1.7 | 131% |
| 15.6 | 9.2 | 138% |
| 15.7 | 0.826 | 158% |
| 15.8 | 30.8 | 122% |

TABLE 2-continued

| No. | EC$_{50}$ (uM) | Max % |
|---|---|---|
| 15.9 | 18.6 | 117% |
| 15.10 | 3.1 | 133% |
| 15.11 | 0.151 | 159% |
| 15.12 | 2.5 | 143% |
| 15.13 | — | 67.6% |
| 15.14 | 3.1 | 159% |
| 15.15 | — | 61.9% |
| 15.16 | 17.7 | 115% |
| 15.17 | 3.4 | 137% |
| 15.18 | 10.5 | 143% |
| 15.19 | 0.512 | 126% |
| 15.20 | 0.314 | 153% |
| 15.21 | 1.6 | 161% |
| 15.22 | 0.704 | 149% |
| 15.23 | 1.9 | 143% |
| 15.24 | 1.4 | 138% |
| 15.25 | 16.5 | 137% |
| 15.26 | 3.8 | 123% |
| 15.27 | 12.3 | 137% |
| 15.28 | — | 80.8% |
| 15.29 | 7 | 135% |
| 15.30 | 22 | 116% |
| 15.31 | — | 57.8% |
| 15.32 | — | 94.8% |
| 15.33 | 18.8 | 51.8% |
| 15.34 | — | 48.2% |
| 16.1 | 2.3 | 140% |
| 16.2 | 11.7 | 110% |
| 16.3 | 1.4 | 160% |
| 16.4 | 9.2 | 130% |
| 16.5 | 10.6 | 149% |
| 16.6 | 5.5 | 140% |
| 16.7 | 36.2 | 67.5% |
| 17.1 | — | 107% |
| 17.2 | 2 | 119% |
| 17.3 | — | 104% |
| 18.1 | — | 94.8% |
| 18.2 | 2.2 | 144% |
| 18.3 | 25.4 | 129% |
| 18.4 | — | 127% |
| 18.5 | — | 40.7% |
| 19.1 | 12.2 | 116% |
| 19.2 | — | 64.2% |
| 20.1 | 3.1 | 137% |
| 20.2 | 7.4 | 145% |
| 20.3 | 1.8 | 148% |
| 20.4 | 8.5 | 147% |
| 20.5 | 24 | 124% |
| 20.6 | 7.2 | 137% |
| 20.7 | 10.8 | 137% |
| 20.8 | 19 | 134% |
| 20.9 | 13.9 | 133% |
| 20.10 | 9.1 | 127% |
| 20.11 | 31.2 | 78.7% |
| 20.12 | — | 74% |
| 20.13 | 5.8 | 146% |
| 21.1 | — | 96.6% |
| 21.2 | 21.6 | 133% |
| 21.3 | 7.6 | 131% |
| 21.4 | 7.4 | 129% |
| 21.5 | 18.9 | 124% |
| 21.6 | 45.3 | 114% |
| 21.7 | — | 100% |
| 21.8 | — | 99.3% |
| 21.9 | — | 90.1% |
| 21.10 | — | 70.3% |
| 21.11 | — | 47% |
| 21.12 | 6.7 | 112% |
| 21.13 | 12.3 | 131% |
| 21.14 | 11 | 112% |
| 21.15 | — | 112% |
| 21.16 | 14.3 | 107% |
| 21.17 | 23.7 | 107% |
| 21.18 | — | 58.5 |
| 21.19 | 7.4 | 145% |
| 21.20 | 5.2 | 114% |
| 21.21 | 33.6 | 134% |
| 21.22 | — | 60.1% |
| 21.23 | 6.5 | 107% |
| 21.24 | 34.5 | 102% |
| 21.25 | 3.9 | 105% |
| 21.26 | — | 76.5% |
| 21.27 | 16 | 122% |
| 21.28 | 11.4 | 126% |
| 21.29 | 4.7 | 98.2% |
| 21.30 | — | 100% |
| 21.31 | — | 88.8% |
| 21.32 | — | 84.3% |
| 21.33 | — | 82.5% |
| 21.34 | — | 79.9% |
| 21.35 | — | 77.8% |
| 21.36 | — | 71.8% |
| 21.37 | — | 68.4% |
| 21.38 | — | 66.5% |
| 21.39 | — | 62.6% |
| 21.40 | — | 61.6% |
| 21.41 | — | 59.7% |
| 21.42 | — | 54.5% |
| 21.43 | — | 53.5% |
| 21.44 | — | 51.9% |
| 21.45 | — | 49.1% |
| 21.46 | — | 43.2% |
| 21.47 | — | 103% |
| 21.48 | 8.2 | 100% |
| 21.49 | — | 82.3% |
| 21.50 | — | 76.1 |
| 21.51 | — | 75.0 |
| 21.52 | — | 72.9% |
| 21.53 | — | 49% |
| 21.54 | — | 46% |
| 21.55 | — | 43.8 |
| 21.56 | — | 41% |
| 21.57 | — | 64.1% |
| 21.58 | — | 46.1 |
| 21.59 | — | 42.5% |
| 21.60 | — | 78% |
| 21.61 | 33.1 | 131% |
| 21.62 | — | 45.6% |
| 21.63 | — | 124% |
| 21.64 | — | 120% |
| 21.65 | — | 96.3% |
| 21.66 | — | 92.4% |
| 21.67 | — | 75% |
| 21.68 | 4.2 | 111% |
| 22.1 | — | 96.9% |
| 22.2 | — | 41.4% |
| 23.1 | 18.1 | 124% |
| 23.2 | 2.6 | 134% |
| 23.3 | 14.8 | 133% |
| 23.4 | 6.5 | 124% |
| 24.1 | — | 78.5% |
| 24.2 | — | 116% |
| 24.3 | — | 87.7% |
| 24.4 | 15.3 | 103% |
| 24.5 | — | 59.3% |
| 24.6 | — | 50.5 |
| 24.7 | — | 47.4% |
| 24.8 | 8.9 | 94.8% |
| 24.9 | — | 48.5% |
| 25.1 | 18.7 | 86.2% |
| 25.2 | 15.2 | 140% |
| 26.1 | — | 80.6% |
| 26.2 | 9 | 71% |
| 27.1 | — | 45.6% |
| 27.2 | — | 83.2% |
| 27.3 | — | 93.3% |
| 27.4 | — | 58.4% |
| 27.5 | 30.4 | 53.2% |
| 27.6 | — | 91.6% |
| 27.7 | 26.5 | 68.5% |
| 27.8 | 30.4 | 53.2% |
| 27.9 | — | 47.8% |
| 27.10 | 29.1 | 131% |
| 27.11 | 25.3 | 93.8% |
| 27.12 | 40.8 | 41.4% |
| 27.13 | — | 48.8% |

TABLE 2-continued

| No. | EC$_{50}$ (uM) | Max % |
| --- | --- | --- |
| 27.14 | 44.5 | 93% |
| 27.15 | — | 65.3% |

Additional data for compounds tested in this assay are shown in Table 3.

TABLE 3

| Ex. | EC$_{50}$ (uM) | Max % |
| --- | --- | --- |
| 1 | 0.932 | 84.0 |
| 2 | 33.7 | 50.6 |
| 3 | 10.9 | 55.9 |
| 4 | 3.88 | 47.5 |
| 5 | 15.1 | 105 |
| 6 | 0.753 | 66.8 |
| 7 | 9.73 | 77.9 |
| 8 | 2.55 | 86.5 |
| 9 | 8.04 | 86.4 |
| 10 | 0.471 | 138 |
| 11 | 1.14 | 78.9 |
| 12 | 2.05 | 113 |
| 13 | 0.858 | 89.9 |
| 14 | 1.56 | 56.2 |
| 15 | 9.02 | 91.5 |
| 16 | 15.5 | 88.0 |
| 17 | 7.04 | 176 |
| 18 | 2.25 | 192 |
| 19 | 5.45 | 99.5 |
| 20 | 10.2 | 136 |
| 21 | 7.88 | 112 |
| 22 | 4.13 | 172 |
| 23 | 3.48 | 90.0 |
| 24 | 1.33 | 129 |
| 25 | 0.292 | 204 |
| 26 | 4.82 | 130 |
| 27 | 10.6 | 126 |
| 28 | 0.388 | 125 |
| 29 | 1.76 | 165 |
| 30 | 2.57 | 106 |
| 31 | 4.17 | 111 |
| 32 | 5.95 | 110 |
| 33 | 6.43 | 75.8 |
| 34 | 24.5 | 78.4 |
| 35 | 3.99 | 70.7 |
| 36 | 1.72 | 80.5 |
| 37 | 9.02 | 69.4 |
| 38 | 0.533 | 129 |
| 39 | 6.1 | 101 |
| 40 | 1.32 | 61.4 |
| 41 | 4.78 | 101 |
| 42 | 1.57 | 105 |
| 43 | 0.362 | 131 |
| 44 | 0.685 | 114 |
| 45 | 1.25 | 130 |
| 46 | 7.04 | 123 |
| 47 | 5.14 | 89.3 |
| 48 | 7.66 | 92.3 |
| 49 | 17.5 | 85.2 |
| 50 | 6.4 | 95.2 |
| 51 | 3.16 | 62.5 |
| 52 | 8.76 | 129 |
| 53 | 0.635 | 162 |
| 54 | 2.2 | 96.2 |
| 55 | 1.16 | 136 |
| 56 | 2.27 | 139 |
| 57 | 0.627 | 174 |
| 58 | 6.53 | 126 |
| 59 | 8.22 | 96.7 |
| 60 | 3.22 | 106 |
| 61 | 8.06 | 127 |
| 62 | 24.6 | 108 |
| 63 | 3.71 | 94.5 |
| 64 | 12.1 | 114 |
| 65 | 0.551 | 128 |
| 66 | 1.69 | 149 |
| 67 | 36.6 | 119 |
| 68 | 30.4 | 105 |
| 69 | 11.2 | 114 |
| 70 | 2.92 | 68.7 |
| 71 | 1.37 | 61.6 |
| 72 | 62.6 | 41.0 |
| 73 | 40.1 | 53.9 |
| 74 | 0.507 | 148 |
| 75 | 28.9 | 71.9 |
| 76 | 0.436 | 145 |
| 77 | 0.271 | 129 |
| 78 | 2.96 | 174 |
| 79 | 14.3 | 56.5 |
| 80 | 12.2 | 43.1 |
| 81 | 52.0 | 53.8 |
| 82 | 0.0787 | 192 |
| 83 | 0.154 | 185 |
| 84 | 11.2 | 109 |
| 85 | 2.39 | 128 |
| 86 | 10.5 | 114 |
| 87 | 42.0 | 92.4 |
| 88 | 3.7 | 118 |
| 89 | 9.04 | 79.2 |
| 90 | 1.22 | 45.7 |
| 91 | 1.03 | 89.4 |
| 92 | 47.1 | 94.5 |
| 93 | 1.83 | 120 |
| 94 | 2.08 | 125 |
| 95 | 9.2 | 135 |
| 96 | 1.21 | 119 |
| 97 | 5.11 | 154 |
| 98 | 1.57 | 130 |
| 99 | 3.69 | 148 |
| 100 | 11.6 | 94.1 |
| 101 | 3.71 | 107 |
| 102 | 0.0547 | 129 |
| 103 | 0.251 | 151 |
| 104 | 0.0341 | 137 |
| 105 | 3.9 | 96.1 |
| 106 | 3.4 | 69.7 |
| 107 | 0.994 | 121 |
| 108 | 0.247 | 111 |
| 109 | 0.734 | 121 |
| 110 | 1.88 | 126 |
| 111 | 6.0 | 143 |
| 112 | 0.825 | 55.7 |
| 113 | 2.37 | 69.3 |
| 114 | 1.34 | 116 |
| 115 | 2.75 | 128 |
| 116 | 0.351 | 101 |
| 117 | 1.03 | 107 |
| 118 | 0.169 | 128 |
| 119 | 0.325 | 131 |
| 120 | 0.995 | 151 |
| 121 | 17.6 | 38.0 |
| 122 | 9.14 | 109 |
| 123 | 2.59 | 110 |
| 124 | 5.9 | 108 |
| 125 | 0.0278 | 154 |
| 126 | 0.249 | 125 |
| 127 | 4.87 | 155 |
| 128 | 0.682 | 108 |
| 129 | 0.774 | 149 |
| 130 | 6.86 | 102 |
| 131 | 0.681 | 113 |
| 132 | 2.04 | 119 |
| 133 | 10.1 | 135 |
| 134 | 0.501 | 76.6 |
| 135 | 0.397 | 115 |
| 136 | 0.0391 | 142 |
| 137 | 0.42 | 129 |
| 138 | 0.775 | 104 |
| 139 | 6.36 | 124 |
| 140 | 0.147 | 129 |
| 141 | 0.328 | 131 |
| 142 | 2.09 | 126 |
| 143 | 12.0 | 137 |
| 144 | 0.0411 | 151 |

TABLE 3-continued

| Ex. | EC$_{50}$ (uM) | Max % |
|---|---|---|
| 145 | 0.132 | 175 |
| 146 | 0.156 | 140 |
| 147 | 1.98 | 179 |
| 148 | 20.8 | 159 |
| 149 | 0.729 | 107 |
| 150 | 17.3 | 114 |
| 151 | 0.538 | 115 |
| 152 | 2.85 | 140 |
| 153 | 73.5 | 100 |
| 154 | 0.504 | 126 |
| 155 | 0.0616 | 136 |
| 156 | 1.47 | 74.2 |
| 157 | 13.0 | 99.8 |
| 158 | 1.42 | 130 |
| 159 | 7.59 | 149 |
| 160 | 0.753 | 133 |
| 161 | 1.49 | 141 |
| 162 | 0.199 | 130 |
| 163 | 0.359 | 143 |
| 164 | 0.562 | 131 |
| 165 | 1.37 | 46.3 |
| 166 | 2.69 | 126 |
| 167 | 5.26 | 132 |
| 168 | 34.1 | 73.3 |
| 169 | 7.46 | 108 |
| 170 | 0.814 | 135 |
| 171 | 1.21 | 67.5 |
| 172 | 27.6 | 83.3 |
| 173 | 24.7 | 78.6 |
| 174 | 1.67 | 90.5 |
| 175 | 0.864 | 90.6 |
| 176 | 8.92 | 131 |
| 177 | 0.123 | 133 |
| 178 | 0.354 | 163 |
| 179 | 0.698 | 54.1 |
| 180 | 2.94 | 59.1 |
| 191 | 7.34 | 120 |
| 182 | 0.175 | 169 |
| 183 | 5.29 | 129 |
| 184 | 9.99 | 118 |
| 185 | 17.8 | 97.9 |
| 186 | 3.85 | 94.1 |
| 187 | 11.1 | 104 |
| 188 | 3.14 | 129 |
| 189 | 7.45 | 121 |
| 190 | 0.779 | 136 |
| 191 | 0.172 | 187 |
| 192 | 0.198 | 96.3 |
| 193 | 0.243 | 80.9 |
| 194 | 1.28 | 117 |
| 195 | 0.0742 | 177 |
| 196 | 0.0642 | 171 |
| 197 | 0.327 | 89.8 |
| 198 | 0.201 | 108 |
| 199 | 1.39 | 119 |
| 200 | 3.13 | 124 |
| 201 | 1.4 | 88.4 |
| 202 | 23.9 | 100 |
| 203 | 5.85 | 135 |
| 204 | 5.12 | 137 |
| 205 | 1.12 | 163 |
| 206 | 7.19 | 121 |
| 207 | 0.0074 | 150 |
| 208 | 0.37 | 120 |
| 209 | 0.0666 | 157 |
| 210 | 8.92 | 161 |
| 211 | 0.31 | 123 |
| 212 | 5.84 | 133 |
| 213 | 0.066 | 152 |
| 214 | 0.18 | 154 |
| 215 | 0.0911 | 95.6 |
| 216 | 0.0594 | 64.9 |
| 217 | 4.74 | 125 |
| 218 | 83.0 | 112 |
| 219 | 10.5 | 118 |
| 220 | 47.0 | 95.6 |
| 221 | 3.76 | 96.5 |
| 222 | 2.92 | 115 |

TABLE 3-continued

| Ex. | EC$_{50}$ (uM) | Max % |
|---|---|---|
| 223 | 10.9 | 128 |
| 224 | 0.366 | 115 |
| 225 | 8.69 | 99.6 |
| 226 | 1.42 | 48.4 |
| 227 | 13.0 | 59.3 |
| 228 | 32.2 | 66.5 |
| 229 | 6.46 | 107 |
| 230 | 6.86 | 130 |
| 231 | 61.3 | 116 |
| 233 | 6.14 | 98.6 |
| 234 | 0.0342 | 163 |
| 235 | 21.2 | 127 |
| 236 | 44.5 | 103 |
| 237 | 0.889 | 98.7 |
| 238 | 2.32 | 123 |
| 239 | 14.2 | 131 |
| 240 | 37.1 | 120 |
| 241 | 0.313 | 134 |
| 242 | 11.4 | 134 |
| 243 | 0.864 | 122 |
| 244 | 0.392 | 134 |
| 245 | 0.409 | 139 |
| 246 | 0.0999 | 148 |
| 247 | 7.7 | 108 |
| 248 | 1.45 | 124 |
| 249 | 6.33 | 99.2 |
| 250 | 13.8 | 111 |
| 251 | 0.42 | 133 |
| 251A | 2.62 | 106 |
| 252 | 5.76 | 140 |
| 253 | 9.95 | 111 |
| 254 | 1.37 | 104 |
| 255 | 7.86 | 66.2 |
| 256 | 0.611 | 145 |
| 257 | 20.5 | 93.5 |
| 258 | 0.227 | 133 |
| 259 | 0.749 | 159 |
| 260 | 2.45 | 138 |
| 261 | 1.54 | 126 |
| 262 | 1.11 | 112 |
| 263 | 0.501 | 117 |
| 264 | 5.09 | 82 |
| 265 | 4.84 | 101 |
| 266 | 0.0249 | 158 |
| 267 | 0.157 | 141 |
| 268 | 0.182 | 166 |
| 269 | 0.0831 | 144 |
| 270 | 0.518 | 120 |
| 271 | 3.57 | 136 |
| 272 | 0.252 | 143 |
| 273 | 2.08 | 124 |
| 274 | 0.012 | |
| 275 | 0.0737 | |
| 276 | 0.0364 | 156 |
| 277 | 0.155 | 140 |
| 278 | 10.6 | 129 |
| 279 | 1.82 | 141 |
| 280 | — | 28.3 |
| 281 | — | 30.9 |
| 282 | — | 41.2 |
| 283 | — | 56.2 |
| 284 | — | 149 |
| 285 | — | 38.0 |
| 286 | — | 59.0 |
| 287 | — | 123 |
| 288 | — | 121 |
| 289 | — | 129 |
| 290 | — | 50.5 |
| 291 | — | 86.6 |
| 292 | — | 46.3 |
| 293 | — | 96.3 |
| 294 | — | 82.8 |
| 295 | — | 49.4 |
| 296 | — | 111 |
| 297 | — | 93.1 |
| 298 | — | 82.3 |
| 299 | — | 53.1 |
| 300 | — | 72.1 |

TABLE 3-continued

| Ex. | EC$_{50}$ (uM) | Max % |
|---|---|---|
| 301 | — | 35.8 |
| 302 | — | 85.4 |
| 303 | — | 116 |
| 304 | — | 34.8 |
| 305 | — | 32.9 |
| 306 | — | 32.2 |
| 307 | — | 41.7 |
| 308 | — | 35.3 |
| 309 | — | 47.5 |
| 310 | — | 32.5 |
| 311 | — | 28.9 |
| 312 | — | 67.0 |
| 313 | — | 88.2 |
| 314 | — | 98.4 |
| 315 | — | 54.4 |
| 316 | — | 49.0 |
| 317 | — | 51.1 |
| 318 | — | 27.0 |
| 319 | — | 28.2 |
| 320 | — | 26.9 |
| 321 | — | 26.6 |
| 322 | — | 36.1 |
| 323 | — | 53.7 |
| 324 | — | 62.2 |
| 325 | — | 30.9 |
| 326 | — | 36.2 |
| 327 | — | 35.5 |
| 328 | — | 39.3 |
| 329 | — | 29.3 |
| 330 | — | 38.3 |
| 331 | — | 47.5 |
| 332 | — | 75.4 |
| 333 | — | 42.3 |
| 334 | — | 48.0 |
| 335 | — | 53.8 |
| 336 | — | 81.5 |
| 337 | — | 103 |
| 338 | — | 65.5 |
| 339 | — | 71.5 |
| 340 | — | 131 |
| 341 | — | 95.2 |
| 342 | — | 66.1 |
| 343 | — | 103 |
| 344 | — | 38.4 |
| 345 | — | 32.3 |
| 346 | — | 51.1 |
| 347 | — | 41.1 |
| 348 | — | 82.1 |
| 349 | — | 35.4 |
| 350 | — | 87.9 |
| 351 | 3.76 | 96.5 |
| 352 | — | 83.7 |
| 353 | — | 34.9 |
| 354 | — | NT |
| 355 | — | 46.9 |

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

The invention claimed is:
1. A compound of Formula (II):

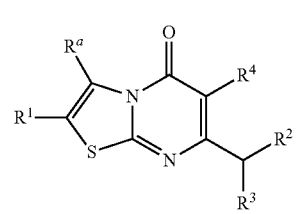

(II)

wherein
R$^a$ is C$_{1-6}$alkyl or C$_{2-6}$alkenyl, each optionally substituted with one or more R$^b$ substituents; C$_{2-6}$alkynyl; halo; —C(O)R$^c$; —NR$^d$R$^e$; —C(O)NR$^d$R$^e$; —C(S)NR$^d$R$^e$; —C(=N—OH)—C$_{1-4}$alkyl; —OC$_{1-4}$alkyl; —OC$_{1-4}$haloalkyl; —SC$_{1-4}$alkyl; SO$_2$C$_{1-4}$alkyl; cyano; C$_{3-6}$cycloalkyl optionally substituted with one or more R$^f$ substituents; or a phenyl, monocyclic heteroaryl, or heterocycloalkyl ring, each ring optionally substituted with one or more R$^g$ substituents;
wherein each R$^b$ substituent is independently selected from the group consisting of —OH, —C$_{1-4}$alkoxy, —NR$^d$R$^e$, —C(O)NR$^d$R$^e$, —SC$_{1-4}$alkyl, —SO$_2$C$_{1-4}$alkyl, cyano, halo, C$_{3-6}$cycloalkyl, and monocyclic heteroaryl;
R$^c$ is C$_{1-4}$alkyl, —C$_{1-4}$haloalkyl, C$_{3-6}$cycloalkyl, or a monocyclic, carbon-linked heterocycloalkyl;
R$^d$ is H or C$_{1-4}$alkyl;
R$^e$ is H; C$_{1-4}$alkyl optionally substituted with —CN, —CF$_3$, —OH, or a monocyclic heterocycloalkyl; C$_{3-6}$cycloalkyl; —OH; or —OC$_{1-4}$alkoxy;
or R$^d$ and R$^e$ taken together with the nitrogen to which they are attached form a heterocycloalkyl, optionally substituted with C$_{1-4}$alkyl or OH;
each R$^f$ substituent is independently selected from the group consisting of: C$_{1-4}$alkyl optionally substituted with —OH, cyano, or C$_{1-4}$alkoxy; —OH; halo; C$_{1-4}$haloalkyl; —CONH$_2$; and cyano; and
each R$^g$ substituent is independently selected from the group consisting of C$_{1-4}$alkyl, CF$_3$, halo, —NH$_2$, —OCH$_3$, cyano, and —OH;
R$^1$ is selected from the group consisting of H, C$_{1-6}$alkyl, C$_{1-4}$haloalkyl, C$_{3-6}$cycloalkyl, halo, —OC$_{1-4}$alkyl, —OC$_{1-4}$haloalkyl, cyano, and —C(O)C$_{1-4}$alkyl; or R$^a$ and R$^1$ taken together with the carbons to which they are attached form a 5- to 7-membered ring, optionally containing an O or NH, and optionally substituted with one or more R$^h$ substituents;
wherein each R$^h$ substituent is independently —C(O)NR$^i$R$^j$, cyano, or is C$_{1-4}$alkyl optionally substituted with —OH, OCH$_3$, cyano, or —C(O)NR$^i$R$^j$; or two R$^h$ groups attached to the same carbon and taken together with the carbon to which they are attached form a carbonyl or a C$_{3-6}$cycloalkyl;
wherein R$^i$ and R$^j$ are each independently H or C$_{1-4}$alkyl;
R$^2$ is —R$^m$, —OR$^m$, or —NR$^m$R$^n$;
wherein R$^m$ is phenyl, naphthyl, pyridyl, pyrazinyl, pyridazinyl, pyrrolyl, pyrazolyl, triazolyl, imidazolyl, furanyl, oxazolyl, isoxazolyl, thiophenyl, thiazolyl, isothiazolyl, indolyl, indazolyl, quinolinyl, or isoquinolinyl, each optionally substituted with one or more $R^s$ substituents;

wherein each $R^s$ substituent is independently selected from the group consisting of $C_{1-4}$alkyl, $C_{2-4}$alkenyl (optionally substituted with halo), $C_{2-4}$alkynyl, $C_{1-4}$haloalkyl, $C_{1-4}$alkoxy, $C_{1-4}$alkyl-OH, $C_{1-4}$haloalkoxy, halo, cyano, $C_{3-6}$cycloalkyl (optionally substituted with —OH or halo), monocyclic heteroaryl, —$NH_2$, —$NO_2$, $NHSO_2C_{1-4}$alkyl, and —$SO_2C_{1-4}$alkyl;

$R'''$ is H, $C_{1-4}$haloalkyl, or $C_{1-4}$alkyl optionally substituted with —OH or $C_{1-4}$alkoxy;

or $R'''$ and $R''$ taken together with the nitrogen to which they are attached form a pyrrolidine or piperidine ring, optionally substituted with $C_{1-4}$alkyl and optionally fused to phenyl, wherein said phenyl is optionally substituted with halo;

$R^3$ is H or methyl; and $R^4$ is H or fluoro;

or a pharmaceutically acceptable salt thereof.

2. A compound of claim 1 of Formula (I):

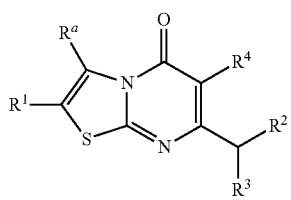

(I)

wherein
$R^a$ is $C_{1-6}$alkyl optionally substituted with one or more $R^b$ substituents; $C_{2-6}$alkenyl; $C_{2-6}$alkynyl; halo; —C(O)$R^c$; —$NR^dR^e$; —C(O)$NR^dR^e$; —C(S)$NR^dR^e$; —C(=N—OH)—$C_{1-4}$alkyl; $SO_2C_{1-4}$alkyl; cyano; $C_{3-6}$cycloalkyl optionally substituted with one or more $R^f$ substituents; or a phenyl, monocyclic heteroaryl, or heterocycloalkyl ring, each ring optionally substituted with one or more $R^g$ substituents;

wherein each $R^b$ substituent is independently selected from the group consisting of —OH, —$C_{1-4}$alkoxy, —$NR^dR^e$, —C(O)$NR^dR^e$, —$SC_{1-4}$alkyl, —$SO_2C_{1-4}$alkyl, cyano, halo, and monocyclic heteroaryl;

$R^c$ is $C_{1-4}$alkyl, —$C_{1-4}$haloalkyl, $C_{3-6}$cycloalkyl, or a monocyclic, carbon-linked heterocycloalkyl;

$R^d$ is H or $C_{1-4}$alkyl;

$R^e$ is H; $C_{1-4}$alkyl optionally substituted with —CN, —$CF_3$, —OH, or a monocyclic heterocycloalkyl; $C_{3-6}$cycloalkyl; —OH; or —$OC_{1-4}$alkoxy;

or $R^d$ and $R^e$ taken together with the nitrogen to which they are attached form a heterocycloalkyl, optionally substituted with $C_{1-4}$alkyl or OH;

each $R^f$ substituent is independently selected from the group consisting of: $C_{1-4}$alkyl optionally substituted with —OH, cyano, or $C_{1-4}$alkoxy; $C_{1-4}$haloalkyl; —$CONH_2$; and cyano; and each $R^g$ substituent is independently selected from the group consisting of $C_{1-4}$alkyl, $CF_3$, halo, —$NH_2$, —$OCH_3$, cyano, and —OH;

$R^1$ is selected from the group consisting of H, $C_{1-6}$alkyl, $C_{1-4}$haloalkyl, and $C_{3-6}$cycloalkyl; or $R^a$ and $R^1$ taken together with the carbons to which they are attached form a 5- to 7-membered ring, optionally containing an O or NH, and optionally substituted with one or more $R^h$ substituents;

wherein each $R^h$ substituent is independently —C(O)$NR^iR^j$, cyano, or is $C_{1-4}$alkyl optionally substituted with —OH, $OCH_3$, cyano, or —C(O)$NR^iR^j$; or two $R^h$ groups attached to the same carbon and taken together with the carbon to which they are attached form a carbonyl or a $C_{3-6}$cycloalkyl;

wherein $R^i$ and $R^j$ are each independently H or $C_{1-4}$alkyl;

$R^2$ is —$R'''$, —$OR'''$, or —$NR'''R''$;

wherein $R'''$ is phenyl, naphthyl, pyridyl, pyrazinyl, pyridazinyl, pyrrolyl, pyrazolyl, triazolyl, imidazolyl, furanyl, oxazolyl, isoxazolyl, thiophenyl, thiazolyl, isothiazolyl, indolyl, indazolyl, quinolinyl, or isoquinolinyl, each optionally substituted with one or more $R^s$ substituents;

wherein each $R^s$ substituent is independently selected from the group consisting of $C_{1-4}$alkyl, $C_{1-4}$haloalkyl, $C_{1-4}$alkoxy, $C_{1-4}$alkyl-OH, $C_{1-4}$haloalkoxy, halo, cyano, $C_{3-6}$cycloalkyl, $NHSO_2C_{1-4}$alkyl, and —$SO_2C_{1-4}$alkyl;

$R''$ is H, $C_{1-4}$haloalkyl, or $C_{1-4}$alkyl optionally substituted with —OH or $C_{1-4}$alkoxy;

or $R'''$ and $R''$ taken together with the nitrogen to which they are attached form a pyrrolidine or piperidine ring, optionally substituted with $C_{1-4}$alkyl and optionally fused to phenyl, wherein said phenyl is optionally substituted with halo;

$R^3$ is H or methyl; and $R^4$ is H or fluoro;

or a pharmaceutically acceptable salt thereof.

3. The compound of claim 1, or a pharmaceutically acceptable salt thereof, wherein $R^a$ is $C_{1-6}$alkyl optionally substituted with one or more $R^b$ substituents.

4. The compound of claim 1, or a pharmaceutically acceptable salt thereof, wherein $R^a$ is $C_{1-6}$alkyl optionally substituted with one or two $R^b$ substituents.

5. The compound of claim 1, or a pharmaceutically acceptable salt thereof, wherein $R^a$ is methyl, ethyl, propyl, isopropyl, butyl, isobutyl, sec-butyl, tert-butyl, pentyl, or isopentyl, each optionally substituted with one or more $R^b$ substituents.

6. The compound of claim 1, or a pharmaceutically acceptable salt thereof, wherein each $R^b$ is independently —OH, methoxy, ethoxy, —$NR^dR^e$, —C(O)$NR^dR^e$, thiomethyl, thioethyl, methanesulfonyl, ethanesulfonyl, cyano, fluoro, chloro, bromo, pyrrolyl, pyrazolyl, imidazolyl, furanyl, thiophenyl, triazolyl, tetrazolyl, oxazolyl, or thiazolyl.

7. The compound of claim 1, or a pharmaceutically acceptable salt thereof, wherein each $R^b$ is independently —OH, —C(O)$NHCH_3$, —$CF_3$, methoxy, ethoxy, fluoro, —C(O)$NH_2$, —C(O)N$(CH_3)_2$, —N$(CH_3)_2$, methanesulfonyl, thiomethyl, cyano, pyrazolyl, 6-oxa-1-azaspiro[3.3]heptan-1-yl, azetidinyl, 3-hydroxyazetidinyl, pyrrolidinyl, or hydroxyethylamino.

8. The compound of claim 1, or a pharmaceutically acceptable salt thereof, wherein $R^a$ is $C_{1-6}$alkenyl or $C_{1-6}$alkynyl.

9. The compound of claim 1, or a pharmaceutically acceptable salt thereof, wherein $R^a$ is ethenyl, isopropenyl, or propynyl.

10. The compound of claim 1, or a pharmaceutically acceptable salt thereof, wherein $R^a$ is halo.

11. The compound of claim 1, or a pharmaceutically acceptable salt thereof, wherein $R^a$ is bromo, chloro, fluoro, or iodo.

12. The compound of claim 1, or a pharmaceutically acceptable salt thereof, wherein $R^a$ is —C(O)$R^c$; —N$R^d R^e$; —C(O)N$R^d R^e$; C(S)N$R^d R^e$; —C(=N—OH)—$C_{1-4}$alkyl; or $SO_2 C_{1-4}$alkyl.

13. The compound of claim 1, or a pharmaceutically acceptable salt thereof, wherein $R^c$ is methyl, ethyl, propyl, isopropyl, butyl, fluoromethyl, difluoromethyl, trifluoromethyl, cyclopropyl, cyclobutyl, cyclopentyl, cyclohexyl, azetidinyl, pyrrolidinyl, piperidinyl, morpholinyl, thiomorpholinyl, oxetanyl, tetrahydrofuranyl, or tetrahydropyranyl.

14. The compound of claim 1, or a pharmaceutically acceptable salt thereof, wherein $R^c$ is ethyl, cyclopropyl, methyl, oxetanyl, or trifluoromethyl.

15. The compound of claim 1, or a pharmaceutically acceptable salt thereof, wherein $R^d$ is H, methyl, ethyl, propyl, isopropyl, butyl, isobutyl, or tert-butyl.

16. The compound of claim 1, or a pharmaceutically acceptable salt thereof, wherein $R^e$ is H, methyl, ethyl, propyl, isopropyl, butyl, isobutyl, tert-butyl, cyanomethyl, trifluoroethyl, hydroxyethyl, 2-hydroxy-1-methylethyl, hydroxypropyl, cyclopropyl, hydroxy, methoxy, or oxetanylmethyl.

17. The compound of claim 1, or a pharmaceutically acceptable salt thereof, wherein $R^d$ and $R^e$ taken together with the nitrogen to which they are attached form azetidinyl, pyrrolidinyl, piperidinyl, morpholinyl, thiomorpholinyl, oxetanyl, tetrahydrofuranyl, tetrahydropyranyl, or 6-oxa-1-azaspiro[3.3]heptan-1-yl, each optionally substituted with $C_{1-4}$alkyl or —OH.

18. The compound of claim 1, or a pharmaceutically acceptable salt thereof, wherein $R^a$ is cyano.

19. The compound of claim 1, or a pharmaceutically acceptable salt thereof, wherein $R^a$ is $C_{3-6}$cycloalkyl optionally substituted with one or more $R^f$ substituents.

20. The compound of claim 1, or a pharmaceutically acceptable salt thereof, wherein $R^a$ is cyclopropyl, cyclobutyl, cyclopentyl, or cyclohexyl, each optionally substituted with one or more $R^f$ substituents.

21. The compound of claim 1, or a pharmaceutically acceptable salt thereof, wherein $R^a$ is cyclopropyl, optionally substituted with one or more $R^f$ substituents.

22. The compound of claim 1, or a pharmaceutically acceptable salt thereof, wherein each $R^f$ is independently: methyl, ethyl, propyl, or isopropyl, each optionally substituted with —OH, cyano, methoxy, or ethoxy; $C_{1-4}$fluoroalkyl; —CONH$_2$; or cyano.

23. The compound of claim 1, or a pharmaceutically acceptable salt thereof, wherein each $R^f$ is independently hydroxymethyl, methyl, cyano, trifluoromethyl, cyanomethyl, methoxymethyl, fluoromethyl, hydroxymethyl, 1-hydroxy-1-methyl-ethyl, or —CONH$_2$.

24. The compound of claim 1, or a pharmaceutically acceptable salt thereof, wherein $R^a$ is a phenyl, monocyclic heteroaryl, or heterocycloalkyl ring, each ring optionally substituted with one or more $R^g$ substituents.

25. The compound of claim 1, or a pharmaceutically acceptable salt thereof, wherein $R^a$ is a phenyl, pyrrolyl, furanyl, thiophenyl, pyrazolyl, imidazolyl, oxazolyl, thiazolyl, triazolyl, pyridyl, pyrimidinyl, pyridazinyl, pyrazinyl, or pyrimidinyl, each optionally substituted with one or more $R^g$ substituents.

26. The compound of claim 1, or a pharmaceutically acceptable salt thereof, wherein $R^a$ is optionally substituted with one or two $R^g$ substituents.

27. The compound of claim 1, or a pharmaceutically acceptable salt thereof, wherein each $R^g$ is independently methyl, ethyl, propyl, isopropyl, —CF$_3$, fluoro, chloro, —NH$_2$, —OCH$_3$, cyano, or —OH.

28. The compound of claim 1, or a pharmaceutically acceptable salt thereof, wherein each $R^g$ is independently fluoro, methyl, —NH$_2$, —CF$_3$, chloro, methoxy, or cyano.

29. The compound of claim 1, or a pharmaceutically acceptable salt thereof, wherein $R^a$ and $R^1$ taken together with the carbons to which they are attached form a 5- to 7-membered ring, optionally containing an O or NH, and optionally substituted with one or more $R^h$ substituents.

30. The compound of claim 1, or a pharmaceutically acceptable salt thereof, wherein $R^a$ and $R^1$ taken together with the carbons to which they are attached form cyclopentenyl, cyclohexenyl, dihydrofuranyl, dihydropyranyl, dihydropyrrolyl, or tetrahydropyridine, each optionally substituted with one or more $R^h$ substituents.

31. The compound of claim 1, or a pharmaceutically acceptable salt thereof, wherein each $R^h$ is independently: methyl, ethyl, or propyl, each optionally substituted with hydroxy, cyano, methoxy, or —C(O)N(CH$_3$)$_2$; C(O)N$R^i R^j$; or cyano.

32. The compound of claim 1, or a pharmaceutically acceptable salt thereof, wherein each $R^h$ is independently hydroxypropyl, hydroxyethyl, hydroxymethyl, methyl, cyano, methoxymethyl, —C(O)NH$_2$, or CH$_2$C(O)N(CH$_3$)$_2$.

33. The compound of claim 1, or a pharmaceutically acceptable salt thereof, wherein two $R^h$ groups attached to the same carbon are taken together with the carbon to which they are attached to form cyclopentyl or a carbonyl.

34. The compound of claim 1, or a pharmaceutically acceptable salt thereof, wherein $R^1$ is H, methyl, ethyl, propyl, isopropyl, butyl, isobutyl, sec-butyl, tert-butyl, pentyl, fluoromethyl, fluoromethyl, trifluoromethyl, fluoroethyl, trifluoroethyl, cyclopropyl, cyclobutyl, cyclopentyl, or cyclohexyl.

35. The compound of claim 1, or a pharmaceutically acceptable salt thereof, wherein $R^1$ is H, methyl, isopropyl, trifluoromethyl, or cyclopropyl.

36. The compound of claim 1, or a pharmaceutically acceptable salt thereof, wherein $R^2$ is $R^m$.

37. The compound of claim 1, or a pharmaceutically acceptable salt thereof, wherein $R^2$ is —O$R^m$.

38. The compound of claim 1, or a pharmaceutically acceptable salt thereof, wherein $R^2$ is —N$R^m R^n$.

39. The compound of claim 1, or a pharmaceutically acceptable salt thereof, wherein $R^m$ is phenyl, naphthyl, pyridyl, indazolyl, or isoquinolinyl, each optionally substituted with one or more $R^s$ substituents.

40. The compound of claim 1, or a pharmaceutically acceptable salt thereof, wherein $R^m$ is pyrazolyl, optionally substituted with one or more $R^s$ substituents.

41. The compound of claim 1, or a pharmaceutically acceptable salt thereof, wherein $R^m$ is phenyl, optionally substituted with one or more $R^s$ substituents.

42. The compound of claim 1, or a pharmaceutically acceptable salt thereof, wherein $R^m$ is optionally substituted with one or two $R^s$ substituents.

43. The compound of claim 1, or a pharmaceutically acceptable salt thereof, wherein each $R^s$ is independently methyl, ethyl, propyl, isopropyl, butyl, fluoromethyl, difluoromethyl, trifluoromethyl, fluoroethyl, trifluoroethyl, methoxy, ethoxy, isopropoxy, hydroxymethyl, hydroxyethyl, trifluoromethoxy, fluoro, chloro, bromo, iodo, cyano, cyclopropyl, cyclobutyl, cyclopentyl, cyclohexyl, NHSO$_2 C_{1-2}$alkyl, or —SO$_2 C_{1-2}$alkyl.

44. The compound of claim 1, or a pharmaceutically acceptable salt thereof, wherein each $R^s$ is independently fluoro, chloro, trifluoromethyl, cyano, methyl, methoxy, cyclopropyl, —$NHSO_2CH_3$, fluoroethyl, ethyl, propyl, difluoromethyl, hydroxymethyl, fluoromethyl, or methanesulfonyl.

45. The compound of claim 1, wherein $R^2$ is $R^m$ and $R^m$ is

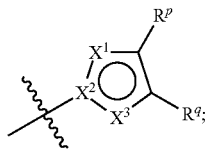

wherein at least one of $X^1$, $X^2$, and $X^3$ is N, and the other two are independently N, $NR^r$, O, S, or C—$R^r$;

$R^p$ and $R^r$ are each independently H; $C_{1-4}$haloalkyl; $C_{1-4}$alkyl optionally substituted with OH; halo; cyano; or $C_{3-6}$cycloalkyl; and $R^q$ is H or fluoro;

or $R^q$ and $R^r$ taken together with the carbons to which they are attached form phenyl, optionally substituted with halo;

or a pharmaceutically acceptable salt thereof.

46. The compound of claim 45, or a pharmaceutically acceptable salt thereof, wherein $X^1$ and $X^2$ are each N and $X^3$ is C—$R^r$.

47. The compound of claim 45, or a pharmaceutically acceptable salt thereof, wherein $X^2$ is N and $X^1$ and $X^3$ are each independently C—$R^r$.

48. The compound of claim 45, or a pharmaceutically acceptable salt thereof, wherein $X^1$, $X^2$, and $X^3$ are each N.

49. The compound of claim 45, or a pharmaceutically acceptable salt thereof, wherein $R^p$ and $R^r$ are each independently H, fluoromethyl, difluoromethyl, trifluoromethyl, fluoroethyl, trifluoroethyl, methyl, ethyl, hydroxymethyl, hydroxyethyl, chloro, cyano, cyclopropyl, cyclobutyl, or cyclopentyl.

50. The compound of claim 45, or a pharmaceutically acceptable salt thereof, wherein $R^p$ is trifluoromethyl, chloro, methyl, hydroxyethyl, cyclopropyl, cyano, difluoromethyl, or ethyl.

51. The compound of claim 45, or a pharmaceutically acceptable salt thereof, wherein $R^r$ is ethyl, trifluoromethyl, methyl, chloro, H, hydroxyethyl, cyclopropyl, or cyano.

52. The compound of claim 45, or a pharmaceutically acceptable salt thereof, wherein $R^q$ is H or fluoro.

53. The compound of claim 45, or a pharmaceutically acceptable salt thereof, wherein $R^q$ and $R^r$ taken together with the carbons to which they are attached form phenyl, optionally substituted with fluoro.

54. The compound of claim 1, or a pharmaceutically acceptable salt thereof, wherein $R^n$ is H, fluoromethyl, difluoromethyl, trifluoromethyl, fluoroethyl, difluoroethyl, or trifluoroethyl, or is methyl or ethyl optionally substituted with —OH, methoxy, or ethoxy.

55. The compound of claim 1, or a pharmaceutically acceptable salt thereof, wherein $R^n$ is H, methyl, ethyl, fluoroethyl, difluoroethyl, or trifluoroethyl.

56. The compound of claim 1, or a pharmaceutically acceptable salt thereof, wherein $R^m$ and $R^n$ taken together with the nitrogen to which they are attached form dihydroindole, optionally substituted with methyl or fluoro.

57. The compound of claim 1, wherein $R^3$ is H.

58. The compound of claim 1, or a pharmaceutically acceptable salt thereof, wherein $R^3$ is methyl.

59. The compound of claim 1, or a pharmaceutically acceptable salt thereof, wherein $R^4$ is H.

60. The compound of claim 1, or a pharmaceutically acceptable salt thereof, wherein $R^4$ is fluoro.

61. A compound selected from the group consisting of the following compounds:

N-(cyanomethyl)-7-((4-fluorophenoxy)methyl)-2-methyl-5-oxo-5H-thiazolo[3,2-a]pyrimidine-3-carboxamide;

7-(4-Fluorophenoxymethyl)-N,2-dimethyl-5-oxo-5H-[1,3]thiazolo[3,2-a]pyrimidine-3-carboxamide;

3-[(Azetidin-1-yl)carbonyl]-7-(4-fluorophenoxymethyl)-2-methyl-5H-[1,3]thiazolo[3,2-a]pyrimidin-5-one;

N-ethyl-7-(4-fluorophenoxymethyl)-2-methyl-5-oxo-5H-[1,3]thiazolo[3,2-a]pyrimidine-3-carboxamide;

7-(4-Fluorophenoxymethyl)-2-methyl-5-oxo-N-(2,2,2-trifluoroethyl)-5H-[1,3]thiazolo[3,2-a]pyrimidine-3-carboxamide;

7-(3,4-Difluorophenoxymethyl)-N,2-dimethyl-5-oxo-5H-[1,3]thiazolo[3,2-a]pyrimidine-3-carboxamide;

N-ethyl-7-(4-fluorophenoxymethyl)-5-oxo-5H-[1,3]thiazolo[3,2-a]pyrimidine-3-carboxamide;

7-((4-fluorophenoxy)methyl)-2-methyl-5-oxo-5H-thiazolo[3,2-a]pyrimidine-3-carboxamide;

7-((4-fluorophenoxy)methyl)-N-hydroxy-2-methyl-5-oxo-5H-thiazolo[3,2-a]pyrimidine-3-carboxamide;

7-(4-Fluorophenoxymethyl)-2-methyl-5-oxo-N-(propan-2-yl)-5H-[1,3]thiazolo[3,2-a]pyrimidine-3-carboxamide;

7-(4-Fluorophenoxymethyl)-N-(2-hydroxyethyl)-2-methyl-5-oxo-5H-[1,3]thiazolo[3,2-a]pyrimidine-3-carboxamide;

7-(4-Fluorophenoxymethyl)-N-(1-hydroxypropan-2-yl)-2-methyl-5-oxo-5H-[1,3]thiazolo[3,2-a]pyrimidine-3-carboxamide;

7-((4-fluorophenoxy)methyl)-2-methyl-N-(oxetan-3-ylmethyl)-5-oxo-5H-thiazolo[3,2-a]pyrimidine-3-carboxamide;

7-((4-fluorophenoxy)methyl)-N-(3-hydroxypropyl)-2-methyl-5-oxo-5H-thiazolo[3,2-a]pyrimidine-3-carboxamide;

N-cyclopropyl-7-((4-fluorophenoxy)methyl)-2-methyl-5-oxo-5H-thiazolo[3,2-a]pyrimidine-3-carboxamide;

7-((4-fluorophenoxy)methyl)-N-methoxy-2-methyl-5-oxo-5H-thiazolo[3,2-a]pyrimidine-3-carboxamide;

7-(4-Fluorophenoxymethyl)-N,2-dimethyl-5-oxo-5H-[1,3]thiazolo[3,2-a]pyrimidine-3-carbothioamide;

7-((4-fluorophenoxy)methyl)-2-methyl-3-propionyl-5H-thiazolo[3,2-a]pyrimidin-5-one;

7-((4-fluorophenoxy)methyl)-3-(1-hydroxypropyl)-2-methyl-5H-thiazolo[3,2-a]pyrimidin-5-one;

7-(4-Fluorophenoxymethyl)-3-(1-hydroxyethyl)-2-methyl-5H-[1,3]thiazolo[3,2-a]pyrimidin-5-one;

7-(4-Fluorophenoxymethyl)-3-(2-hydroxypropan-2-yl)-2-methyl-5H-[1,3]thiazolo[3,2-a]pyrimidin-5-one;

3-acetyl-7-((4-fluorophenoxy)methyl)-2-methyl-5H-thiazolo[3,2-a]pyrimidin-5-one;

2-(7-((4-fluorophenoxymethyl)-2-methyl-5-oxo-5H-thiazolo[3,2-a]pyrimidin-3-yl)-N-methylacetamide;

3-Cyclopropanecarbonyl-7-(4-fluorophenoxymethyl)-2-methyl-5H-[1,3]thiazolo[3,2-a]pyrimidin-5-one;

7-(4-Fluorophenoxymethyl)-3-[1-(hydroxyimino)ethyl]-2-methyl-5H-[1,3]thiazolo[3,2-a]pyrimidin-5-one;

7-((4-fluorophenoxy)methyl)-2-methyl-3-(oxetane-3-carbonyl)-5H-thiazolo[3,2-a]pyrimidin-5-one;
7-((4-fluorophenoxy)methyl)-2-methyl-3-(2,2,2-trifluoro-1-hydroxyethyl)-5H-thiazolo[3,2-a]pyrimidin-5-one;
7-(4-Fluorophenoxymethyl)-2-methyl-3-(trifluoroacetyl)-5H-[1,3]thiazolo[3,2-a]pyrimidin-5-one;
2-cyclopropyl-N-ethyl-7-((4-fluorophenoxy)methyl)-5-oxo-5H-thiazolo[3,2-a]pyrimidine-3-carboxamide;
7-(4-Fluorophenoxymethyl)-N-methyl-5-oxo-2-(trifluoromethyl)-5H-[1,3]thiazolo[3,2-a]pyrimidine-3-carboxamide;
2-Cyclopropyl-7-(4-fluorophenoxymethyl)-N-methyl-5-oxo-5H-[1,3]thiazolo[3,2-a]pyrimidine-3-carboxamide;
N-Ethyl-7-(4-fluorophenoxymethyl)-5-oxo-2-(trifluoromethyl)-5H-[1,3]thiazolo[3,2-a]pyrimidine-3-carboxamide;
7-((4-fluorophenoxy)methyl)-N-methyl-5-oxo-5H-thiazolo[3,2-a]pyrimidine-3-carboxamide;
N-ethyl-7-[[(5-fluoropyridin-2-yl)oxy]methyl]-2-methyl-5-oxo-5H-[1,3]thiazolo[3,2-a]pyrimidine-3-carboxamide;
7-(4-Fluorophenoxymethyl)-3-[trans-2-(hydroxymethyl)cyclopropyl]-2-methyl-5H-[1,3]thiazolo[3,2-a]pyrimidin-5-one;
7-((3-fluorophenoxy)methyl)-3-(trans-2-(hydroxymethyl)cyclopropyl)-2-methyl-5H-thiazolo[3,2-a]pyrimidin-5-one;
7-((4-fluorophenoxy)methyl)-2-methyl-3-(pyrimidin-5-yl)-5H-thiazolo[3,2-a]pyrimidin-5-one;
7-(2,4-Difluorophenoxymethyl)-3-[trans-2-(hydroxymethyl)cyclopropyl]-2-methyl-5H-[1,3]thiazolo[3,2-a]pyrimidin-5-one;
7-(3,4-Difluorophenoxymethyl)-3-[trans-2-(hydroxymethyl)cyclopropyl]-2-methyl-5H-[1,3]thiazolo[3,2-a]pyrimidin-5-one;
7-(4-Chlorophenoxymethyl)-3-[trans-2-(hydroxymethyl)cyclopropyl]-2-methyl-5H-[1,3]thiazolo[3,2-a]pyrimidin-5-one;
7-[[(5-Fluoropyridin-2-yl)oxy]methyl]-3-[trans-2-(hydroxymethyl)cyclopropyl]-2-methyl-5H-[1,3]thiazolo[3,2-a]pyrimidin-5-one;
3-(trans-2-(hydroxymethyl)cyclopropyl)-2-methyl-7-((4-(trifluoromethyl)phenoxy)methyl)-5H-thiazolo[3,2-a]pyrimidin-5-one;
7-((4-fluorophenoxy)methyl)-2-methyl-3-(oxazol-2-yl)-5H-thiazolo[3,2-a]pyrimidin-5-one;
7-((2-fluorophenoxy)methyl)-3-(trans-2-(hydroxymethyl)cyclopropyl)-2-methyl-5H-thiazolo[3,2-a]pyrimidin-5-one;
4-((3-(trans-2-(hydroxymethyl)cyclopropyl)-2-methyl-5-oxo-5H-thiazolo[3,2-a]pyrimidin-7-yl)methoxy)benzonitrile;
7-((4-fluorophenoxy)methyl)-3-(trans-2-(hydroxymethyl)cyclopropyl)-5H-thiazolo[3,2-a]pyrimidin-5-one;
7-((4-fluorophenoxy)methyl)-2-methyl-3-(1H-pyrazol-5-yl)-5H-thiazolo[3,2-a]pyrimidin-5-one;
7-((4-fluorophenoxy)methyl)-2-methyl-3-(4H-1,2,4-triazol-3-yl)-5H-thiazolo[3,2-a]pyrimidin-5-one;
3-cyclopropyl-7-[(4-fluorophenoxy)methyl]-2-methyl-thiazolo[3,2-a]pyrimidin-5-one;
cis-2-[7-(4-Fluorophenoxymethyl)-2-methyl-5-oxo-5H-[1,3]thiazolo[3,2-a]pyrimidin-3-yl]cyclopropane-1-carbonitrile;
trans-2-[7-(4-Fluorophenoxymethyl)-2-methyl-5-oxo-5H-[1,3]thiazolo[3,2-a]pyrimidin-3-yl]cyclopropane-1-carbonitrile;
7-(4-Fluorophenoxymethyl)-3-[cis-2-(hydroxymethyl)cyclopropl]-2-methyl-5H-[1,3]thiazolo[3,2-a]pyrimidin-5-one;
trans-7-(4-Fluorophenoxymethyl)-2-methyl-3-[2-(trifluoromethyl)cyclopropyl]-5H-[1,3]thiazolo[3,2-a]pyrimidin-5-one;
7-(4-Fluorophenoxymethyl)-2-methyl-3-(2-methylcyclopropyl)-5H-[1,2]thiazolo[3,2-a]pyrimidin-5-one;
trans-2-[2-[7-(4-Fluorophenoxymethyl)-2-methyl-5-oxo-5H-[1,3]thiazolo[3,2-a]pyrimidin-3-yl]cyclopropyl]acetonitrile;
7-(4-Fluorophenoxymethyl)-3-[2-(methoxymethyl)cyclopropyl]-2-methyl-5H-[1,3]thiazolo[3,2-a]pyrimidin-5-one;
3-(2-(fluoromethyl)cyclopropyl)-7-((4-fluorophenoxy)methyl)-2-methyl-5H-thiazolo[3,2-a]pyrimidin-5-one;
6-fluoro-7-((4-fluorophenoxy)methyl)-3-(trans-2-(hydroxymethyl)cyclopropyl)-2-methyl-5H-thiazolo[3,2-a]pyrimidin-5-one;
7-(4-Fluorophenoxymethyl)-3-(3-hydroxypropyl)-2-methyl-5H-[1,3]thiazolo[3,2-a]pyrimidin-5-one;
7-(4-Fluorophenoxymethyl)-3-(methoxymethyl)-2-methyl-5H-[1,3]thiazolo[3,2-a]pyrimidin-5-one;
7-((4-fluorophenoxy)methyl)-3-(3-hydroxyoxetan-3-yl)-2-methyl-5H-thiazolo[3,2-a]pyrimidin-5-one;
7-(4-Fluorophenoxymethyl)-3-(4-hydroxybutan-2-yl)-2-methyl-5H-[1,3]thiazolo[3,2-a]pyrimidin-5-one;
7-(4-Fluorophenoxymethyl)-3-[2-(2-hydroxypropan-2-yl)cyclopropyl]-2-methyl-5H-[1,3]thiazolo[3,2-a]pyrimidin-5-one;
7-[(N-ethyl-4-fluoro-anilino)methyl]-2-methyl-3-pyrimidin-5-yl-thiazolo[3,2-a]pyrimidin-5-one;
7-(((4-fluorophenyl)(methyl)amino)methyl)-2-methyl-3-pyrimidin-5-yl)-5H-thiazolo[3,2-a]pyrimidin-5-one;
7-(((4-fluorophenyl)(2,2,2-trifluoroethyl)amino)methyl)-2-methyl-3-pyrimidin-5-yl)-5H-thiazolo[3,2-a]pyrimidin-5-one;
7-(((3,4-difluorophenyl)(ethyl)amino)methyl)-2-methyl-3-(pyrimidin-5-yl)-5H-thiazolo[3,2-a]pyrimidin-5-one;
7-((ethyl(3-fluorophenyl)amino)methyl)-2-methyl-3-(pyrimidin-5-yl)-5H-thiazolo[3,2-a]pyrimidin-5-one;
7-(((2,2-difluoroethyl)(4-fluorophenyl)amino)methyl)-2-methyl-3-(pyrimidin-5-yl)-5H-thiazolo[3,2-a]pyrimidin-5-one;
7-((ethyl(pyridine-2-yl)amino)methyl)-3-(trans-2-(hydroxymethyl)cyclopropyl)-2-methyl-5H-thiazolo[3,2-a]pyrimidin-5-one;
7-((ethyl(4-fluorophenyl)amino)methyl)-2-methyl-3-(thiazol-2-yl)-5H thiazolo[3,2-a]pyrimidin-5-one;
7-((ethyl(4-fluorophenyl)amino)methyl)-2-methyl-3-(thiophen-2-yl)-5H-thiazolo[3,2-a]pyrimidin-5-one;
3-(ethyl((2-methyl-5-oxo-3-(pyrimidin-5-yl)-5H-thiazolo[3,2-a]pyrimidin-7-yl)methyl)amino)benzonitrile;
3-(2-aminopyridin-3-yl)-7-((ethyl(4-fluorophenyl)amino)methyl)-2-methyl-5H thiazolo[3,2-a]pyrimidin-5-one;
7-((ethyl(pyridine-2-yl)amino)methyl)-2-methyl-3-pyrimidin-5-yl)-5H thiazolo[3,2-a]pyrimidin-5-one;
7-((4-fluorophenylamino)methyl)-2-methyl-3-(pyrimidin-5-yl)-5H-thiazolo[3,2-a]pyrimidin-5-one;
3-butyl-7-((ethyl(4-fluorophenyl)amino)methyl)-2-methyl-5H-thiazolo[3,2-a]pyrimidin-5-one;
2-cyclopropyl-7-[(N-ethyl-4-fluoro-anilino)methyl]-3-pyrimidin-5-yl-thiazolo[3,2-a]pyrimidin-5-one;

2-ethyl-7-((ethyl(4-fluorophenyl)amino)methyl)-3-(pyrimidin-5-yl)-5H-thiazolo[3,2-a]pyrimidin-5-one;
7-((ethyl(4-fluorophenyl)amino)methyl)-3-(trans-2-(hydroxymethyl)cyclopropyl)-2-methyl-5H-thiazolo[3,2-a]pyrimidin-5-one;
7-[(N-ethyl-4-fluoro-anilino)methyl]-2-methyl-3-thiazol-4-yl-thiazolo[3,2-a]pyrimidin-5-one;
7-[(N-ethyl-4-fluoro-anilino)methyl]-2-methyl-3-(3-pyridyl)thiazolo[3,2-a]pyrimidin-5-one;
7-[(N-ethyl-4-fluoro-anilino)methyl]-2-methyl-phenyl-thiazolo[3,2-a]pyrimidin-5-one;
7-[(N-ethyl-4-fluoro-anilino)methyl]-2,3-dimethyl-thiazolo[3,2-a]pyrimidin-5-one;
7-[(N-ethyl-4-fluoro-anilino)methyl]-3-(5-fluoro-3-pyridyl)-2-methyl-thiazolo[3,2-a]pyrimidin-5-one;
7-[(N-ethyl-4-fluoro-anilino)methyl]-3-(2-fluoro-3-pyridyl)-2-methyl-thiazolo[3,2-a]pyrimidin-5-one;
3-cyclopropyl-7-[(N-ethyl-4-fluoro-anilino)methyl]-2-methyl-thiazolo[3,2-a]pyrimidin-5-one;
7-[(N-ethyl-4-fluoro-anilino)methyl]-2-methyl-3-pyrazin-2-yl-thiazolo[3,2-a]pyrimidin-5-one;
7-[(N-ethyl-4-fluoro-anilino)methyl]-3-[trans-2-(hydroxymethyl)cyclopropyl]thiazolo[3,2-a]pyrimidin-5-one;
7-[(N-ethyl-4-fluoro-anilino)methyl]-3-isopropenyl-2-methyl-thiazolo[3,2-a]pyrimidin-5-one;
7-[(N-ethyl-4-fluoro-anilino)methyl]-2-methyl-3-pyridazin-4-yl-thiazolo[3,2-a]pyrimidin-5-one;
3-(5-chloro-3-pyridyl)-7-[(N-ethyl-4-fluoro-anilino)methyl]-2-methyl-thiazolo[3,2-a]pyrimidin-5-one;
7-[(N-ethyl-4-fluoro-anilino)methyl]-2-methyl-3-(4-pyridyl)thiazolo[3,2-a]pyrimidin-5-one;
7-[(N-ethyl-4-fluoro-anilino)methyl]-2-methyl-3-(1-methylpyrazol-4-yl)thiazolo[3,2-a]pyrimidin-5-one;
7-[(N-ethyl-4-fluoro-anilino)methyl]-2-methyl-3-(1H-pyrazol-4-yl)thiazolo[3,2-a]pyrimidin-5-one;
5-[7-[(N-ethyl-4-fluoro-anilino)methyl]-2-methyl-5-oxo-thiazolo[3,2-a]pyrimidin-3-yl]pyridine-3-carbonitrile;
7-[(N-ethyl-4-fluoro-anilino)methyl]-2-methyl-3-[5-(trifluoromethyl)-3-pyridyl]thiazolo[3,2-a]pyrimidin-5-one;
7-[(N-ethyl-4-fluoro-anilino)methyl]-2-methyl-3-oxazol-2-yl-thiazolo[3,2-a]pyrimidin-5-one;
7-((ethyl(4-fluorophenyl)amino)methyl)-2-methyl-3-(trifluoromethyl)-5H-thiazolo[3,2-a]pyrimidin-5-one;
7-((ethyl(4-fluorophenyl)amino)methyl)-3-(trans-2-(fluoromethyl)cyclopropyl)-2-methyl-5H-thiazolo[3,2-a]pyrimidin-5-one;
3-ethyl-7-((ethyl(4-fluorophenyl)amino)methyl)-2-methyl-5H-thiazolo[3,2-a]pyrimidin-5-one;
7-((ethyl(4-fluorophenyl)amino)methyl)-2-methyl-3-propyl-5H-thiazolo[3,2-a]pyrimidin-5-one;
7-[[4-fluoro-N-(2-fluoroethyl)anilino]methyl]-3-[trans-2-(hydroxymethyl)cyclopropyl]-2-methyl-thiazolo[3,2-a]pyrimidin-5-one;
7-((ethyl(4-fluorophenyl)amino)methyl)-3-(furan-3-yl)-2-methyl-5H-thiazolo[3,2-a]pyrimidin-5-one;
7-((ethyl(4-fluorophenyl)amino)methyl)-3-(furan-2-yl)-2-methyl-5H-thiazolo[3,2-a]pyrimidin-5-one;
7-((5-fluoro-2-methylindolin-1-yl)methyl)-3-(furan-2-yl)-2-methyl-5H-thiazolo[3,2-a]pyrimidin-5-one;
7-((ethyl(4-fluorophenyl)amino)methyl)-2-methyl-3-(thiophen-3-yl)-5H-thiazolo[3,2-a]pyrimidin-5-one;
7-((5-fluoro-2-methylindolin-1-yl)methyl)-2-methyl-3-(pyrimidin-5-yl)-5H-thiazolo[3,2-a]pyrimidin-5-one;
7-((ethyl(4-fluorophenyl)amino)methyl)-2-methyl-3-(4-methylthiazol-2-yl)-5H-thiazolo[3,2-a]pyrimidin-5-one;
7-((ethyl(4-fluorophenyl)amino)methyl)-2-methyl-3-(6-oxo-1,6-dihydropyridin-3-yl)-5H-thiazolo[3,2-a]pyrimidin-5-one;
3-(6-aminopyridin-3-yl)-7-((ethyl(4-fluorophenyl)amino)methyl)-2-methyl-5H-thiazolo[3,2-a]pyrimidin-5-one;
7-((ethyl(4-fluorophenyl)amino)methyl)-2-methyl-3-(prop-1-ynyl)-5H-thiazolo[3,2-a]pyrimidin-5-one;
7-((ethyl(4-fluorophenyl)amino)methyl)-2-methyl-3-vinyl-5H-thiazolo[3,2-a]pyrimidin-5-one;
3-bromo-2-cyclopropyl-7-[(N-ethyl-4-fluoro-anilino)methyl]thiazolo[3,2-a]pyrimidin-5-one;
3-(3,5-difluorophenyl)-7-[(N-ethyl-4-fluoro-anilino)methyl]-2-methyl-thiazolo[3,2-a]pyrimidin-5-one;
7-[(N-ethyl-4-fluoro-anilino)methyl]-2-methyl-3-(1-methylpyrazol-3-yl)thiazolo[3,2-a]pyrimidin-5-one;
3-(2-amino-4-pyridyl)-7-[(N-ethyl-4-fluoro-anilino)methyl]-2-methyl-thiazolo[3,2-a]pyrimidin-5-one;
7-[(N-ethyl-4-fluoro-anilino)methyl]-3-(5-methoxy-3-pyridyl)-2-methyl-thiazolo[3,2-a]pyrimidin-5-one;
7-((ethyl(4-fluorophenyl)amino)methyl)-2-methyl-3-morpholino-5H-thiazolo[3,2-a]pyrimidin-5-one;
3-(dimethylamino)-7-((ethyl(4-fluorophenyl)amino)methyl)-2-methyl-5H-thiazolo[3,2-a]pyrimidin-5-one;
7-((ethyl(4-fluorophenyl)amino)methyl)-2-methyl-3-(pyrrolidin-1-yl)-5H-thiazolo[3,2-a]pyrimidin-5-one;
7-(((3,4-difluorophenyl)(ethyl)amino)methyl)-2-methyl-5-oxo-5H-thiazolo[3,2-a]pyrimidine-3-carbonitrile;
7-((ethyl(3-fluorophenyl)amino)methyl)-2-methyl-5-oxo-5H-thiazolo[3,2-a]pyrimidine-3-carbonitrile;
7-[(N-ethyl-4-fluoro-anilino)methyl]-2-methyl-5-oxo-thiazolo[3,2-a]pyrimidine-3-carbonitrile;
7-[(N-ethyl-4-fluoro-anilino)methyl]-5-oxo-thiazolo[3,2-a]pyrimidine-3-carbonitrile;
7-((5-fluoro-2-methylindolin-1-yl)methyl)-2-methyl-5-oxo-5H-thiazolo[3,2-a]pyrimidine-3-carbonitrile;
7-(((3-cyanophenyl)(ethyl)amino)methyl)-2-methyl-5-oxo-5H-thiazolo[3,2-a]pyrimidine-3-carbonitrile;
7-((ethyl(pyridin-2-yl)amino)methyl)-2-methyl-5-oxo-5H-thiazolo[3,2-a]pyrimidine-3-carbonitrile;
2-methyl-7-((2-methylindolin-1-yl)methyl)-5-oxo-5H-thiazolo[3,2-a]pyrimidine-3-carbonitrile;
7-(((3,5-difluorophenyl)(ethyl)amino)methyl)-2-methyl-5-oxo-5H-thiazolo[3,2-a]pyrimidine-3-carbonitrile;
6-[(N-ethyl-4-fluoro-anilino)methyl]-2,3-dihydro-1H-cyclopenta[3,4]thiazolo[1,4-a]pyrimidin-8-one;
2-[(N-ethyl-4-fluoro-anilino)methyl]-6,7,8,9-tetrahydro-pyrimido[2,1-b][1,3]benzothiazol-4-one;
6-[(N-ethyl-4-fluoro-anilino)methyl]-1-(hydroxymethyl)-2,3-dihydro-1H-cyclopenta[3,4]thiazolo[1,4-a]pyrimidin-8-one;
6-[(N-ethyl-4-fluoro-anilino)methyl]spiro[2,3-dihydrocyclopenta[3,4]thiazolo[1,4-a]pyrimidine-1,1'-cyclopentane]-8-one;
6-[(N-ethyl-4-fluoro-anilino)methyl]-2,3-dihydrocyclopenta[3,4]thiazolo[1,4-a]pyrimidine-1,8-dione;
6-[(N-ethyl-4-fluoro-anilino)methyl]-1,1-dimethyl-2,3-dihydrocyclopenta[3,4]thiazolo[1,4-a]pyrimidin-8-one;
2-[(N-ethyl-4-fluoro-anilino)methyl]-8,9-dihydro-6H-pyrano[3,4]thiazolo[1,4-a]pyrimidin-4-one;
2-[(N-ethyl-4-fluoro-anilino)methyl]-7-methyl-8,9-dihydro-6H-pyrido[3,4]thiazolo[1,4-a]pyrimidin-4-one;

6-[(N-ethyl-4-fluoro-anilino)methyl-8-oxo-2,3-dihydro-1H-cyclopenta[3,4]thiazolo[1,4-a]pyrimidine-1-carboxamide;

6-[(N-ethyl-4-fluoro-anilino)methyl]-8-oxo-2,3-dihydro-1H-cyclopenta[3,4]thiazolo[1,4-a]pyrimidine-1-carbonitrile;

2-[6-[(N-ethyl-4-fluoro-anilino)methyl]-8-oxo-2,3-dihydro-1H-cyclopenta[3,4]thiazolo[1,4-a]pyrimidin-1-yl]acetonitrile;

6-[(N-ethyl-4-fluoro-anilino)methyl]-1-(2-hydroxyethyl)-2,3-dihydro-1H-cyclopenta[3,4]thiazolo[1,4-a]pyrimidin-8-one;

2-((ethyl(4-fluorophenyl)amino)methyl)-6-(methoxymethyl)-7,8-dihydrocyclopenta[4,5]thiazolo[3,2-a]pyrimidin-4(6H)-one;

2-[6-[(N-ethyl-4-fluoro-anilino)methyl]-8-oxo-2,3-dihydro-1H-cyclopenta[3,4]thiazolo[1,4-a]pyrimidin-1-yl]acetamide;

3-cyclohexyl-7-[[ethyl(4-fluorophenyl)amino]methyl]-2-methyl-5H-[1,3]thiazolo[3,2-a]pyrimidin-5-one;

7-[(N-ethyl-4-fluoro-anilino)methyl]-3-isopropyl-2-methyl-thiazolo[3,2-a]pyrimidin-5-one;

3-cyclopentyl-7-[(N-ethyl-4-fluoro-anilino)methyl]-2-methyl-thiazolo[3,2-a]pyrimidin-5-one;

7-[(N-ethyl-4-fluoro-anilino)methyl]-2-methyl-3-tetrahydropyran-4-yl-thiazolo[3,2-a]pyrimidin-5-one;

3-cyclobutyl-7-[(N-ethyl-4-fluoro-anilino)methyl]-2-methyl-thiazolo[3,2-a]pyrimidin-5-one;

3-tert-butyl-7-[(N-ethyl-4-fluoro-anilino)methyl]-2-methyl-thiazolo[3,2-a]pyrimidin-5-one;

3-acetyl-7-((ethyl(4-fluorophenyl)amino)methyl)-2-methyl-5H-thiazolo[3,2-a]pyrimidin-5-one;

7-[(N-ethyl-4-fluoro-anilino)methyl]-N,2-dimethyl-5-oxo-thiazolo[3,2-a]pyrimidine-3-carboxamide;

7-[(N-ethyl-4-fluoro-anilino)methyl]-3-(1-hydroxy-1-methyl-ethyl)-2-methyl-thiazolo[3,2-a]pyrimidin-5-one;

7-[(N-ethyl-4-fluoro-anilino)methyl]-3-(1-hydroxyethyl)-2-methyl-thiazolo[3,2-a]pyrimidin-5-one;

3-[(dimethylamino)methyl]-7-[[ethyl(4-fluorophenyl)amino]methyl-2-methyl-5H-[1,3]thiazolo[3,2-a]pyrimidin-5-one;

3-(azetidin-1-ylmethyl)-7-[(N-ethyl-4-fluoro-anilino)methyl]-2-methyl-thiazolo[3,2-a]pyrimidin-5-one;

7-[(N-ethyl-4-fluoro-anilino)methyl]-2-methyl-3-(pyrrolidin-1-ylmethyl)thiazolo[3,2-a]pyrimidin-5-one;

7-[(N-ethyl-4-fluoro-anilino)methyl]-3-[(3-hydroxyazetidin-1-yl)methyl]-2-methyl-thiazolo[3,2-a]pyrimidin-5-one;

7-[(N-ethyl-4-fluoro-anilino)methyl]-2-methyl-3-(2,2,2-trifluoro-1-hydroxy-ethyl)thiazolo[3,2-a]pyrimidin-5-one;

7-((ethyl(4-fluorophenyl)amino)methyl)-3-(hydroxymethyl)-2-methyl-5H-thiazolo[3,2-a]pyrimidin-5-one;

7-[[ethyl(4-fluorophenyl)amino]methyl]-3-(methoxymethyl)-2-methyl-5H-[1,3]thiazolo[3,2-a]pyrimidin-5-one;

7-[[Ethyl(4-fluorophenyl)amino]methyl]-2-methyl-3-(1H-pyrazol-1-ylmethyl)-5H-[1,3]thiazolo[3,2-a]pyrimidin-5-one;

7-[(N-ethyl-4-fluoro-anilino)methyl]-2-methyl-3-(methylsulfonylmethyl)thiazolo[3,2-a]pyrimidin-5-one;

3-(ethoxymethyl)-7-[(N-ethyl-4-fluoro-anilino)methyl]-2-methyl-thiazolo[3,2-a]pyrimidin-5-one;

2-[7-[(N-ethyl-4-fluoro-anilino)methyl]-2-methyl-5-oxo-thiazolo[3,2-a]pyrimidin-3-yl]acetonitrile;

3-tert-butyl-7-[(N-ethyl-4-fluoro-anilino)methyl]thiazolo[3,2-a]pyrimidin-5-one;

7-[(N-ethyl-4-fluoro-anilino)methyl]-3-(1-hydroxy-1-methyl-ethyl)thiazolo[3,2-a]pyrimidin-5-one;

7-[(N-ethyl-4-fluoro-anilino)methyl]-3-(1-hydroxyethyl)thiazolo[3,2-a]pyrimidin-5-one;

7-[(N-ethyl-4-fluoro-anilino)methyl]-2-methyl-3-(6-oxa-1-azaspiro[3.3]heptan-1-ylmethyl)thiazolo[3,2-a]pyrimidin-5-one;

7-[(N-ethyl-4-fluoro-anilino)methyl]-3-[(2-hydroxyethylamino)methyl]-2-methyl-thiazolo[3,2-a]pyrimidin-5-one;

3-(ethyl((3-(hydroxymethyl)-2-methyl-5-oxo-5H-thiazolo[3,2-a]pyrimidin-7-yl)methyl)amino)benzonitrile;

3-[ethyl-[[3-(methoxymethyl)-2-methyl-5-oxo-thiazolo[3,2-a]pyrimidin-7-yl]methyl]amino]benzonitrile;

7-((ethyl(4-fluorophenyl)amino)methyl)-2-methyl-3-((methylthio)methyl)-5H-thiazolo[3,2-a]pyrimidin-5-one;

3-chloro-7-[[ethyl(4-fluorophenyl)amino]methyl]-2-methyl-5H-[1,3]thiazolo[3,2-a]pyrimidin-5-one;

7-[(N-ethyl-4-fluoro-anilino)methyl]-3-fluoro-2-methyl-thiazolo[3,2-a]pyrimidin-5-one;

7-[(N-ethyl-4-fluoro-anilino)methyl]-2-methyl-thiazolo[3,2-a]pyrimidin-5-one;

7-[(N-ethyl-4-fluoro-anilino)methyl]-3-iodo-2-methyl-thiazolo[3,2-a]pyrimidin-5-one;

3-chloro-7-[(N-ethyl-4-fluoro-anilino)methyl]thiazolo[3,2-a]pyrimidin-5-one;

7-[(N-ethylanilino)methyl]-2-methyl-thiazolo[3,2-a]pyrimidin-5-one;

3-(1,3-dihydroxypropyl)-7-[(N-ethyl-4-fluoro-anilino)methyl]-2-methyl-thiazolo[3,2-a]pyrimidin-5-one;

7-[(N-ethyl-4-fluoro-anilino)methyl]-3-(1-fluoro-3-hydroxy-propyl)-2-methyl-thiazolo[3,2-a]pyrimidin-5-one;

3-(1,2-dihydroxyethyl)-7-[(N-ethyl-4-fluoro-anilino)methyl]-2-methyl-thiazolo[3,2-a]pyrimidin-5-one;

7-[(N-ethyl-4-fluoro-anilino)methyl]-3-(3-hydroxypropyl)-2-methyl-thiazolo[3,2-a]pyrimidin-5-one;

7-((Ethyl(4-fluorophenyl)amino)methyl)-3-(3-methoxypropyl)-2-methyl-5H-thiazolo[3,2-a]pyrimidin-5-one;

7-((Ethyl(4-fluorophenyl)amino)methyl)-3-(4-hydroxybutyl)-2-methyl-5H-thiazolo[3,2-a]pyrimidin-5-one;

7-((Ethyl(4-fluorophenyl)amino)methyl)-3-(2-hydroxyethyl)-2-methyl-5H-thiazolo[3,2-a]pyrimidin-5-one;

7-[[Ethyl(4-fluorophenyl)amino]methyl]-3-(2-methoxyethyl)-2-methyl-5H-[1,3]thiazolo[3,2-a]pyrimidin-5-one;

3-(7-[[ethyl(4-fluorophenyl)amino]methyl]-2-methyl-5-oxo-5H-[1,3]thiazolo[3,2-a]pyrimidin-3-yl)propanamide;

3-[7-[(N-ethyl-4-fluoro-anilino)methyl]-2-methyl-5-oxo-thiazolo[3,2-a]pyrimidin-3-yl]propanenitrile;

3-[7-[(N-ethyl-4-fluoro-anilino)methyl]-2-methyl-5-oxo-thiazolo[3,2-a]pyrimidin-3-yl]-N,N-dimethyl-propanamide;

7-[[Ethyl(4-fluorophenyl)amino]methyl]-3-(3-hydroxy-3-methylbutyl)-2-methyl-5H-[1,3]thiazolo[3,2-a]pyrimidin-5-one;

2-[7-[(N-ethyl-4-fluoro-anilino)methyl]-2-methyl-5-oxo-thiazolo[3,2-a]pyrimidin-3-yl]cyclopropanecarboxamide;

7-((5-ethyl-3-(trifluoromethyl)-1H-pyrazol-1-yl)methyl)-3-(2-(hydroxymethyl)cyclopropyl)-2-methyl-5H-thiazolo[3,2-a]pyrimidin-5-one;

7-((3,5-bis(trifluoromethyl)-1H-pyrazol-1-yl)methyl)-3-(trans-2-(hydroxymethyl)cyclopropyl)-2-methyl-5H-thiazolo[3,2-a]pyrimidin-5-one;

7-((3-chloro-5-methyl-1H-pyrazol-1-yl)methyl)-3-(trans-2-(hydroxymethyl)cyclopropyl)-2-methyl-5H-thiazolo[3,2-a]pyrimidin-5-one;

7-((5-chloro-3-methyl-1H-pyrazol-1-yl)methyl)-3-(trans-2-(hydroxymethyl)cyclopropyl)-2-methyl-5H-thiazolo[3,2-a]pyrimidin-5-one;

3-(trans-2-(hydroxymethyl)cyclopropyl)-2-methyl-7-((3-(trifluoromethyl)-1H-pyrazol-1-yl)methyl)-5H-thiazolo[3,2-a]pyrimidin-5-one;

7-((1H-indazol-1-yl)methyl)-3-(trans-2-(hydroxymethyl)cyclopropyl)-2-methyl-5H-thiazolo[3,2-a]pyrimidin-5-one;

7-((5-(2-hydroxyethyl)-3-(trifluoromethyl)-1H-pyrazol-1-yl)methyl)-3-(trans-2-(hydroxymethyl)cyclopropyl)-2-methyl-5H-thiazolo[3,2-a]pyrimidin-5-one;

7-((3-(2-hydroxyethyl)-5-(trifluoromethyl)-1H-pyrazol-1-yl)methyl)-3-(trans-2-(hydroxymethyl)cyclopropyl)-2-methyl-5H-thiazolo[3,2-a]pyrimidin-5-one;

7-((3-cyclopropyl-4-fluoro-5-(trifluoromethyl)-1H-pyrazol-1-yl)methyl)-3-(trans-2-(hydroxymethyl)cyclopropyl)-2-methyl-5H-thiazolo[3,2-a]pyrimidin-5-one;

7-((5-cyclopropyl-4-fluoro-3-(trifluoromethyl)-1H-pyrazol-1-yl)methyl)-3-(trans-2-(hydroxymethyl)cyclopropyl)-2-methyl-5H-thiazolo[3,2-a]pyrimidin-5-one;

7-((5-cyclopropyl-3-(trifluoromethyl)-1H-pyrazol-1-yl)methyl)-3-(trans-2-(hydroxymethyl)cyclopropyl)-2-methyl-5H-thiazolo[3,2-a]pyrimidin-5-one;

7-((3-cyclopropyl-5-(trifluoromethyl)-1H-pyrazol-1-yl)methyl)-3-(trans-2-(hydroxymethyl)cyclopropyl)-2-methyl-5H-thiazolo[3,2-a]pyrimidin-5-one;

7-[(5-cyclopropyl-3-methyl-pyrazol-1-yl)methyl]-3-[trans-2-(hydroxymethyl)cyclopropyl]-2-methyl-thiazolo[3,2-a]pyrimidin-5-one;

7-[(3-cyclopropyl-5-methyl-pyrazol-1-yl)methyl]-3-[trans-2-(hydroxymethyl)cyclopropyl]-2-methyl-thiazolo[3,2-a]pyrimidin-5-one;

7-[(3,5-dicyclopropylpyrazol-1-yl)methyl]-3-[trans-2-(hydroxymethyl)cyclopropyl]-2-methyl-thiazolo[3,2-a]pyrimidin-5-one;

7-((3,5-dimethyl-1H-pyrazol-1-yl)methyl)-6-fluoro-3-(trans-2-(hydroxymethyl)cyclopropyl)-2-methyl-5H-thiazolo[3,2-a]pyrimidin-5-one;

1-((3-(trans-2-(hydroxymethyl)cyclopropyl)-2-methyl-5-oxo-5H-thiazolo[3,2-a]pyrimidin-7-yl)methyl)-3-(trifluoromethyl)-1H-pyrazole-5-carbonitrile;

7-((5-cyclopropyl-3-(trifluoromethyl)-1H-pyrazol-1-yl)methyl)-6-fluoro-3-(trans-2-(hydroxymethyl)cyclopropyl)-2-methyl-5H-thiazolo[3,2-a]pyrimidin-5-one;

1-[[3-[trans-2-(hydroxymethyl)cyclopropyl]-2-methyl-5-oxo-thiazolo[3,2-a]pyrimidin-7-yl]methyl]-5-methyl-pyrazole-3-carbonitrile;

7-[[3-(difluoromethyl)-5-methyl-pyrazol-1-yl]methyl]-3-[trans-2-(hydroxymethyl)cyclopropyl]-2-methyl-thiazolo[3,2-a]pyrimidin-5-one;

7-[(6-fluoroindazol-1-yl)methyl]-3-[trans-2-(hydroxymethyl)cyclopropyl]-2-methyl-thiazolo[3,2-a]pyrimidin-5-one;

7-[[5-cyclopropyl-3-(trifluoromethyl)pyrazol-1-yl]methyl]-3-[2-(hydroxymethyl)cyclopropyl]-2-isopropyl-thiazolo[3,2-a]pyrimidin-5-one;

7-[(3,5-dimethylpyrazol-1-yl)methyl]-3-[trans-2-(hydroxymethyl)cyclopropyl]-2-methyl-thiazolo[3,2-a]pyrimidin-5-one;

7-[(5-fluoroindazol-1-yl)methyl]-3-[trans-2-(hydroxymethyl)cyclopropyl]-2-methyl-thiazolo[3,2-a]pyrimidin-5-one;

5-ethyl-3-(trifluoromethyl)-1H-pyrazol-1-yl)methyl)-2-methyl-3-(pyrimidin-5-yl)-5H-thiazolo[3,2-a]pyrimidin-5-one;

7-((3-cyclopropyl-5-(trifluoromethyl)-1H-pyrazol-1-yl)methyl)-2-methyl-3-(pyrimidin-5-yl)-5H-thiazolo[3,2-a]pyrimidin-5-one;

7-((5-cyclopropyl-3-(trifluoromethyl)-1H-pyrazol-1-yl)methyl)-2-methyl-3-(pyrimidin-5-yl)-5H-thiazolo[3,2-a]pyrimidin-5-one;

7-((3, 5-bis(trifluoromethyl)-1H-pyrazol-1-yl)methyl)-2-methyl-3-(pyrimidin-5-yl)-5H-thiazolo[3,2-a]pyrimidin-5-one;

2-methyl-3-(pyrimidin-5-yl)-7-((5-(trifluoromethyl)-1H-pyrazol-1-yl)methyol)-5H-thiazolo[3,2-a]pyrimidin-5-one;

2-methyl-7-((5-methyl-3-(trifluoromethyl)-1H-pyrazol-1-yl)methyl)-3-pyrimidin-5-yl)-5H-thiazolo[3,2-a]pyrimidin-5-one;

7-((3,5-bis(trifluoromethyl)-1H-pyrazol-1-yl)methyl)-2-methyl-5H-thiazolo[3,2-a]pyrimidin-5-one;

7-((1H-indazol-1-yl)methyl)-2-methyl-3-(pyrimidin-5-yl)-5H-thiazolo[3,2-a]pyrimidin-5-one;

7-((5-cyclopropyl-3-(trifluoromethyl)-1H-pyrazol-1-yl)methyl)-N,2-dimethyl-5-oxo-5H-thiazolo[3,2-a]pyrimidine-3-carboxamide;

7-((3-cyclopropyl-5-(trifluoromethyl)-1H-pyrazol-1-yl)methyl)-N,2-dimethyl-5-oxo-5H-thiazolo[3,2-a]pyrimidine-3-carboxamide;

7-((5-cyclopropyl-3-(trifluoromethyl)-1H-pyrazol-1-yl)methyl)-N-ethyl-5-oxo-2-(trifluoromethyl)-5H-thiazolo[3,2-a]pyrimidine-3-carboxamide;

7-((3-cyclopropyl-5-(trifluoromethyl)-1H-pyrazol-1-yl)methyl)-N-ethyl-5-oxo-2-(trifluoromethyl)-5H-thiazolo[3,2-a]pyrimidine-3-carboxamide;

7-((5-cyclopropyl-3-(trifluoromethyl)-1H-pyrazol-1-yl)methyl)-N-ethyl-5-oxo-5H-thiazolo[3,2-a]pyrimidine-3-carboxamide;

2-cyclopropyl-7-((5-cyclopropyl-3-(trifluoromethyl)-1H-pyrazol-1-yl)methyl)-N-ethyl-5-oxo-5H-thiazolo[3,2-a]pyrimidine-3-carboxamide;

2-cyclopropyl-7-((3-cyclopropyl-5-(trifluoromethyl)-1H-pyrazol-1-yl)methyl)-N-ethyl-5-oxo-5H-thiazolo[3,2-a]pyrimidine-3-carboxamide;

2-methyl-5-oxo-7-((3-(trifluoromethyl)-1H-pyrazol-1-yl)methyl)-5H-thiazolo[3,2-a]pyrimidine-3-carbonitrile;

7-((5-cyclopropyl-3-(trifluoromethyl)-1H-pyrazol-1-yl)methyl)-2-methyl-5-oxo-5H-thiazolo[3,2-a]pyrimidine-3-carbonitrile;

7-((3-cyclopropyl-5-(trifluoromethyl)-1H-pyrazol-1-yl)methyl)-2-methyl-5-oxo-5H-thiazolo[3,2-a]pyrimidine-3-carbonitrile;

3-(1-hydroxyethyl)-2-methyl-7-((3-(trifluoromethyl)-1H-pyrazol-1-yl)methyl)-5H-thiazolo[3,2-a]pyrimidin-5-one;

3-acetyl-7-((5-cyclopropyl-3-(trifluoromethyl)-1H-pyrazol-1-yl)methyl)-2-methyl-5H-thiazolo[3,2-a]pyrimidin-5-one;

3-acetyl-7-((3-cyclopropyl-5-(trifluoromethyl)-1H-pyrazol-1-yl)methyl)-2-methyl-5H thiazolo[3,2-a]pyrimidin-5-one;

3-(2-hydroxypropan-2-yl)-2-methyl-7-((3-(trifluoromethyl)-1H-pyrazol-1-yl)methyl)-5H-thiazolo[3,2-a]pyrimidin-5-one;

7-((5-fluoro-3-methyl-1H-indazol-1-yl)methyl)-3-(1-hydroxyethyl)-2-methyl-H thiazolo[3,2-a]pyrimidin-5-one;
7-(1-(5-cyclopropyl-3-(trifluoromethyl)-1H-pyrazol-1-yl)ethyl)-3-(trans-2-(hydroxymethyl)cyclopropyl)-2-methyl-5H-thiazolo[3,2-a]pyrimidin-5-one;
7-(1-(5-cyclopropyl-3-(trifluoromethyl)-1H-pyrazol-1-yl)ethyl)-3-(2-(hydroxymethyl)-1-methylcyclopropyl)-2-methyl-5H-thiazolo[3,2-a]pyrimidin-5-one;
3-((3-(trans-2-(hydroxymethyl)cyclopropyl)-2-methyl-5-oxo-5H-thiazolo[3,2-a]pyrimidin-7-yl)methyl)benzonitrile;
3-((6-fluoro-3-(2-(hydroxymethyl)cyclopropyl)-2-methyl-5-oxo-5H-thiazolo[3,2-a]pyrimidin-7-yl)methyl)benzonitrile;
2-fluoro-3-((3-(trans-2-(hydroxymethyl)cyclopropyl)-2-methyl-5-oxo-5H-thiazolo[3,2-a]pyrimidin-7-yl)methyl)benzonitrile;
3-(trans-2-(hydroxymethyl)cyclopropyl)-7-(isoquinolin-4-ylmethyl)-2-methyl-5H-thiazolo[3,2-a]pyrimidin-5-one;
3-(trans-2-(hydroxymethyl)cyclopropyl)-2-methyl-7-(3-(trifluoromethyl)benzyl)-5H-thiazolo[3,2-a]pyrimidin-5-one;
3-((3-(trans-2-(hydroxymethyl)cyclopropyl)-2-methyl-5-oxo-5H-thiazolo[3,2-a]pyrimidin-7-yl)methy)-4-methylbenzonitrile;
4-fluoro-3-((3-(trans-2-(hydroxymethyl)cyclopropyl)-2-methyl-5-oxo-5H-thiazolo[3,2-a]pyrimidin-7-yl)methyl)benzonitrile;
3-fluoro-5-((3-(trans-2-(hydroxymethyl)cyclopropyl)-2-methyl-5-oxo-5H-thiazolo[3,2-a]pyrimidin-7-yl)methyl)benzonitrile;
2-fluoro-5-((3-(trans-2-(hydroxymethyl)cyclopropyl)-2-methyl-5-oxo-5H-thiazolo[3,2-a]pyrimidin-7-yl)methyl)benzonitrile;
3-[[3-trans-2-(hydroxymethyl)cyclopropyl]-2-methyl-5-oxo-thiazolo[3,2-a]pyrimidin-7-yl]methyl]-4-methoxy-benzonitrile;
3-(2-(hydroxymethyl)cyclopropyl)-2-methyl-7-(4-(trifluoromethyl)benzyl)-5H-thiazolo[3,2-a]pyrimidin-5-one;
4-((3-(trans-2-(hydroxymethyl)cyclopropyl)-2-methyl-5-oxo-5H-thiazolo[3,2-a]pyrimidin-7-yl)methyl)picolinonitrile;
4-cyclopropyl-3-((3-(trans-2-(hydroxymethyl)cyclopropyl)-2-methyl-5-oxo-5H-thiazolo[3,2-a]pyrimidin-7-yl)methy)benzonitrile;
7-(3-cyanobenzyl)-N,2-dimethyl-5-oxo-5H-thiazolo[3,2-a]pyrimidine-3-carboxamide;
7-(3-cyano-2-fluorobenzyl)-N,2-dimethyl-5-oxo-5H-thiazolo[3,2-a]pyrimidine-3-carboxamide;
7-(3-chloro-2-fluorobenzyl)-N-ethyl-2-methyl-5-oxo-5H-thiazolo[3,2-a]pyrimidine-3-carboxamide;
N-ethyl-7-(2-fluoro-3-(trifluoromethyl)benzyl)-2-methyl-5-oxo-5H-thiazolo[3,2-a]pyrimidine-3-carboxamide;
N-ethyl-7-(2-fluoro-3-methylbenzyl)-2-methyl-5-oxo-5H-thiazolo[3,2-a]pyrimidine-3-carboxamide;
7-(2-chloro-5-cyanobenzyl)-N-ethyl-2-methyl-5-oxo-5H-thiazolo[3,2-a]pyrimidine-3-carboxamide;
N-ethyl-2-methyl-5-oxo-7-(3-(trifluoromethyl)benzyl)-5H-thiazolo[3,2-a]pyrimidine-3-carboxamide;
7-(3-cyanobenzyl)-N-ethyl-2-methyl-5-oxo-5H-thiazolo[3,2-a]pyrimidine-3-carboxamide;
7-(3-cyano-2-fluorobenzyl)-2-cyclopropyl-N-ethyl-5-oxo-5H-thiazolo[3,2-a]pyrimidine-3-carboxamide;
7-(3-cyano-5-fluorobenzyl)-N-ethyl-2-methyl-5-oxo-5H-thiazolo[3,2-a]pyrimidine-3-carboxamide;
7-(3-cyano-2-fluorobenzyl)-N-ethyl-2-methyl-5-oxo-5H-thiazolo[3,2-a]pyrimidine-3-carboxamide;
7-[(3-chloro-2-fluoro-phenyl)methyl]-N,2-dimethyl-5-oxo-thiazolo[3,2-a]pyrimidine-3-carboxamide;
N,2-dimethyl-5-oxo-7-[[3-(trifluoromethyl)phenyl]methyl]thiazolo[3,2-a]pyrimidine-3-carboxamide;
7-[(3-chlorophenyl)methyl]-N,2-dimethyl-5-oxo-thiazolo[3,2-a]pyrimidine-3-carboxamide;
7-[[2-cyclopropyl-5-(trifluoromethyl)phenyl]methyl]-N,2-dimethyl-5-oxo-thiazolo[3,2-a]pyrimidine-3-carboxamide;
N-ethyl-2-methyl-5-oxo-7-((6-(trifluoromethyl)pyridine-2-yl)methyl)-5H-thiazolo[3,2-a]pyrimidine-3-carboxamide;
N-ethyl-7-(2-ethyl-4,5-difluorobenzyl)-2-methyl-5-oxo-5H-thiazolo[3,2-a]pyrimidine-3-carboxamide;
7-[[3-(difluoromethyl)-2-fluoro-phenyl]methyl]-N-ethyl-2-methyl-5-oxo-thiazolo[3,2-a]pyrimidine-3-carboxamide;
7-((6-cyanopyridin-2-yl)methyl)-N-ethyl-2-methyl-5-oxo-5H-thiazolo[3,2-a]pyrimidine-3-carboxamide;
7-[[3-(difluoromethyl)-2-fluoro-phenyl]methyl]-N,2-dimethyl-5-oxo-thiazolo[3,2-a]pyrimidine-3-carboxamide;
7-[[2-fluoro-3-(hydroxymethyl)phenyl]methyl]-N,2-dimethyl-5-oxo-thiazolo[3,2-a]pyrimidine-3-carboxamide;
7-(3-cyclopropyl-2-fluorobenzyl)-N-ethyl-2-methyl-5-oxo-5H-thiazolo[3,2-a]pyrimidine-3-carboxamide;
7-(3-cyano-2-fluorobenzyl)-N-ethyl-6-fluoro-5-oxo-5H-thiazolo[3,2-a]pyrimidine-3-carboxamide;
7-(3-cyano-2-fluorobenzyl)-6-fluoro-N,N-dimethyl-5-oxo-5H-thiazolo[3,2-a]pyrimidine-3-carboxamide;
7-(3-cyano-2-fluorobenzyl)-N-ethyl-6-fluoro-2-methyl-5-oxo-5H-thiazolo[3,2-a]pyrimidine-3-carboxamide;
6-fluoro-7-(2-fluoro-3-(trifluoromethyl)benzyl)-N,2-dimethyl-5-oxo-5H-thiazolo[3,2-a]pyrimidine-3-carboxamide;
7-(5-cyano-2-methylbenzyl)-N-ethyl-2-methyl-5-oxo-5H-thiazolo[3,2-a]pyrimidine-3-carboxamide;
7-(5-cyano-2-fluorobenzyl)-N-ethyl-2-methyl-5-oxo-5H-thiazolo[3,2-a]pyrimidine-3-carboxamide;
7-(2-chloro-5-fluorobenzyl)-N-ethyl-2-methyl-5-oxo-5H-thiazolo[3,2-a]pyrimidine-3-carboxamide;
7-(3-cyano-2-fluorobenzyl)-N-ethyl-5-oxo-5H-thiazolo[3,2-a]pyrimidine-3-carboxamide;
N-ethyl-7-(5-fluoro-2-(trifluoromethyl)benzyl)-2-methyl-5-oxo-5H-thiazolo[3,2-a]pyrimidine-3-carboxamide;
N-ethyl-2-methyl-7-(naphthalen-1-ylmethyl)-5-oxo-5H-thiazolo[3,2-a]pyrimidine-3-carboxamide;
N-ethyl-7-(5-fluoro-2-methylbenzyl)-2-methyl-5-oxo-5H-thiazolo[3,2-a]pyrimidine-3-carboxamide;
7-(3-cyano-4-fluorobenzyl)-N-ethyl-2-methyl-5-oxo-5H-thiazolo[3,2-a]pyrimidine-3-carboxamide;
N-ethyl-2-methyl-7-((1-methyl-1H-indazol-4-yl)methyl)-5-oxo-5H-thiazolo[3,2-a]pyrimidine-3-carboxamide;
N-ethyl-2-methyl-7-(3-(methylsulfonamido)benzyl)-5-oxo-5H-thiazolo[3,2-a]pyrimidine-3-carboxamide;
7-(5-cyano-2-(trifluoromethyl)benzyl)-N-ethyl-2-methyl-5-oxo-5H-thiazolo[3,2-a]pyrimidine-3-carboxamide;
7-(4-chloro-2-methylbenzyl)-N,2-dimethyl-5-oxo-5H-thiazolo[3,2-a]pyrimidine-3-carboxamide;
7-(2,5-difluorobenzyl)-N-ethyl-2-methyl-5-oxo-5H-thiazolo[3,2-a]pyrimidine-3-carboxamide;

7-(3-cyanobenzyl)-2-cyclopropyl-N-ethyl-5-oxo-5H-thiazolo[3,2-a]pyrimidine-3-carboxamide;
N-ethyl-7-(2-fluorobenzyl)-2-methyl-5-oxo-5H-thiazolo[3,2-a]pyrimidine-3-carboxamide;
7-(2,3-difluorobenzyl)-N-ethyl-2-methyl-5-oxo-5H-thiazolo[3,2-a]pyrimidine-3-carboxamide;
N-ethyl-7-(3-fluorobenzyl)-2-methyl-5-oxo-5H-thiazolo[3,2-a]pyrimidine-3-carboxamide;
7-[(3-chloro-4-fluoro-phenyl)methyl]-N,2-dimethyl-5-oxo-thiazolo[3,2-a]pyrimidine-3-carboxamide;
7-[(2,5-dichlorophenyl)methyl]-N,2-dimethyl-5-oxo-thiazolo[3,2-a]pyrimidine-3-carboxamide;
N,2-dimethyl-5-oxo-7-[[3-(trifluoromethoxy)phenyl]methyl]thiazolo[3,2-a]pyrimidine-3-carboxamide;
7-[(5-cyano-2-fluoro-phenyl)methyl]-N,2-dimethyl-5-oxo-thiazolo[3,2-a]pyrimidine-3-carboxamide;
7-[(3-chloro-5-cyano-phenyl)methyl]-N,2-dimethyl-5-oxo-thiazolo[3,2-a]pyrimidine-3-carboxamide;
7-[(3-cyclopropylphenyl)methyl]-N,2-dimethyl-5-oxo-thiazolo[3,2-a]pyrimidine-3-carboxamide;
7-[(2,5-difluorophenyl)methyl]-N,2-dimethyl-5-oxo-thiazolo[3,2-a]pyrimidine-3-carboxamide;
7-[(3,4-difluorophenyl)methyl]-N,2-dimethyl-5-oxo-thiazolo[3,2-a]pyrimidine-3-carboxamide;
7-[(2,3-difluorophenyl)methyl]-N,2-dimethyl-5-oxo-thiazolo[3,2-a]pyrimidine-3-carboxamide;
7-[(4-chloro-2-fluoro-phenyl)methyl]-N,2-dimethyl-5-oxo-thiazolo[3,2-a]pyrimidine-3-carboxamide;
7-[(2,4-dichlorophenyl)methyl]-N,2-dimethyl-5-oxo-thiazolo[3,2-a]pyrimidine-3-carboxamide,
7-[(3-fluoro-4-methyl-phenyl)methyl]-N,2-dimethyl-5-oxo-thiazolo[3,2-a]pyrimidine-3-carboxamide;
7-[[4-fluoro-2-(trifluoromethyl)phenyl]methyl]-N,2-dimethyl-5-oxo-thiazolo[3,2-a]pyrimidine-3-carboxamide;
7-[(2-cyclopropyl-4-fluoro-phenyl)methyl]-N,2-dimethyl-5-oxo-thiazolo[3,2-a]pyrimidine-3-carboxamide;
7-(5-cyano-2-(2-fluoroethyl)benzyl)-N-ethyl-2-methyl-5-oxo-5H-thiazolo[3,2,2-a]pyrimidine-3-carboxamide;
7-(2-chloro-3-cyanobenzyl)-N-ethyl-2-methyl-5-oxo-5H-thiazolo[3,2-a]pyrimidine-3-carboxamide;
N-ethyl-7-(6-ethyl-2,3-difluorobenzyl)-2-methyl-5-oxo-5H-thiazolo[3,2-a]pyrimidine-3-carboxamide;
7-(5-cyano-2-ethylbenzyl)-N-ethyl-2-methyl-5-oxo-5H-thiazolo[3,2-a]pyrimidine-3-carboxamide;
7-(2-cyclopropyl-5-fluorobenzyl)-N-ethyl-2-methyl-5-oxo-5H-thiazolo[3,2-a]pyrimidine-3-carboxamide;
7-(5-cyano-2-cyclopropylbenzyl)-N-ethyl-2-methyl-5-oxo-5H-thiazolo[3,2-a]pyrimidine-3-carboxamide;
N-ethyl-7-(5-fluoro-2-propylbenzyl)-2-methyl-5-oxo-5H-thiazolo[3,2-a]pyrimidine-3-carboxamide;
7-[[2-fluoro-3-(fluoromethyl)phenyl]ethyl]-N,2-dimethyl-5-oxo-thiazolo[3,2-a]pyrimidine-3-carboxamide;
N-ethyl-7-(1-(2-fluoro-3-(trifluoromethyl)phenyl)ethyl)-2-methyl-5-oxo-5H-thiazolo[3,2-a]pyrimidine-3-carboxamide;
N-ethyl-7-(2-fluoro-3-(trifluoromethyl)benzyl)-N,2-dimethyl-5-oxo-5H-thiazolo[3,2-a]pyrimidine-3-carboxamide;
3-((3-(2-cyanocyclopropyl)-2-methyl-5-oxo-5H-thiazolo[3,2-a]pyrimidin-7-yl)methy)benzonitrile;
3-((3-(2-cyanocyclopropyl)-2-methyl-5-oxo-5H-thiazolo[3,2-a]pyrimidin-7-yl)methyl)-2-fluorobenzonitrile;
6-((3-(2-cyanocyclopropyl)-2-methyl-5-oxo-5H-thiazolo[3,2-a]pyrimidin-7-yl)methyl)picolinonitrile;
3-((3-(2-cyanocyclopropyl)-2-methyl-5-oxo-5H-thiazolo[3,2-a]pyrimidin-7-yl)methyl)-4-methoxybenzonitrile;
2-methyl-3-(pyrimidin-5-yl)-7-(3-(trifluoromethyl)benzyl)-5H-thiazolo[3,2-a]pyrimidin-5-one;
7-(2-fluoro-3-(trifluoromethyl)benzyl)-2-methyl-3-(pyrimidin-5-yl)-5H-thiazolo[3,2-a]pyrimidin-5-one;
2-fluoro-3-((2-methyl-5-oxo-3-(pyrimidin-5-yl)-5H-thiazolo[3,2-a]pyrimidin-7-yl)methy)benzonitrile;
3-((3-cyclopropyl-2-methyl-5-oxo-5H-thiazolo[3,2-a]pyrimidin-7-yl)methyl)-2-fluorobenzonitrile;
7-(isoquinolin-4-ylmethyl)-2-methyl-3-pyrimidin-5-yl)-5H-thiazolo[3,2-a]pyrimidin-5-one;
3-((2-methyl-5-oxo-3-(pyrimidin-5-yl)-5H-thiazolo[3,2-a]pyrimidin-7-yl)methyl)benzonitrile;
7-(5-fluoro-2-methoxybenzyl)-2-methyl-3-(pyrimidin-5-yl)-5H-thiazolo[3,2-a]pyrimidin-5-one;
2-fluoro-3-((3-(furan-2-yl)-2-methyl-5-oxo-5H-thiazolo[3,2-a]pyrimidin-7-yl)methyl)benzonitrile;
3-bromo-2-methyl-7-(3-(methylsulfonyl)benzyl)-5H-thiazolo[3,2-a]pyrimidin-5-one;
7-(3-cyano-2-fluorobenzyl)-2-methyl-5-oxo-N-(2,22-trifluoroethyl)-5H-thiazolo[3,2-a]pyrimidine-3-carboxamide;
N-(cyanomethyl)-7-(2-fluoro-3-(trifluoromethyl)benzyl)-2-methyl-5-oxo-5H-thiazolo[3,2-a]pyrimidine-3-carboxamide;
7-(3-cyanobenzyl)-2-methyl-5-oxo-5H-thiazolo[3,2-a]pyrimidine-3-carbonitrile;
7-(2-fluoro-3-(trifluoromethyl)benzyl)-2-methyl-5-oxo-5H-thiazolo[3,2-a]pyrimidine-3-carbonitrile;
10-(4-fluorophenoxymethyl)-3-(hydroxymethyl)-7-thia-1,9-diazatricyclo[6,4,0,0^[2,6]]dodeca-2(6),8,10-trien-12-one;
10-(4-Fluorophenoxymethyl)-3-(2-hydroxyethyl)-7-thia-1,9-diazatricyclo[6,4,0,0^[2,6]]dodeca-2(6),8,10-trien-12-one;
7-[(N-ethyl-4-fluoro-anilino)methyl]-2-methyl-3-methylsulfonyl-thiazolo[3,2-a]pyrimidin-5-one;
3-(hydroxymethyl)-10-[[3-(trifluoromethyl)-1H-pyrazol-1-yl]methyl]-7-thia-1,9-diazatricyclo[6,4,0,0^[2,6]]dodeca-2(6),8,10-trien-12-one;
10-{[5-cyclopropyl-3-(trifluoromethyl)-1H-pyrazol-1-yl]methyl}-7-thia-1,9-diazatricyclo[6,4,0,0^{2,6}]dodeca-2(6),8,10-trien-12-one;
10-{[3-cyclopropyl-5-(trifluoromethyl)-1H-pyrazol-1-yl]methyl}-7-thia-1,9-diazatricyclo[6,4,0,0^2,6}]dodeca-2(6),8, 10-trien-12-one;
10-{[5-cyclopropyl-3-(trifluoromethyl)-1H-pyrazol-1-yl]methyl}-3,3-dimethyl-7-thia-1,9-diazatricyclo[6,4,0,0^{2,6}]dodeca-2(6),8,10-trien-12-one;
10-{[3-cyclopropyl-5-(trifluoromethyl)-1H-pyrazol-1-yl]methyl}-3,3-dimethyl-7-thia-1,9-diazatricyclo[6,4,0,0^{2,6}]dodeca-2(6),8,1-trien-12-one;
10-{[3,5-bis(trifluoromethyl)-1H-pyrazol-1-yl]methyl}-3,3-dimethyl-7-thia-1,9-diazatricyclo[6,4,0,0^{2,6}]dodeca-2(6),8,10-trien-12-one;
3-((3-acetyl-2-methyl-5-oxo-5H-thiazolo[3,2-a]pyrimidin-7-yl)methyl)-2-fluorobenzonitrile;
7-(2-fluoro-3-(trifluoromethyl)benzyl)-3-(1-hydroxyethyl)-2-methyl-5H-thiazolo[3,2-a]pyrimidin-5-one;
3-((3-acetyl-2-methyl-5-oxo-5H-thiazolo[3,2-a]pyrimidin-7-yl)methyl)benzonitrile;
7-(2-fluoro-3-(trifluoromethyl)benzyl)-3-(hydroxymethyl)-2-methyl-5H-thiazolo[3,2-a]pyrimidin-5-one;
7-(2-fluoro-3-(trifluoromethyl)benzyl)-2-methyl-3-((methylamino)methyl)-5H-thiazolo[3,2-a]pyrimidin-5-one;
7-[(3-cyclopropyl-2-fluoro-phenyl)methyl]-N,2-dimethyl-5-oxo-thiazolo[3,2-a]pyrimidine-3-carboxamide;

N-ethyl-2-methyl-5-oxo-7-[(2,3,6-trifluorophenyl)methyl]thiazolo[3,2-a]pyrimidine-3-carboxamide;

2-fluoro-3[(2-methyl-3-oxazol-2-yl-5-oxo-thiazolo[3,2-a]pyrimidin-7-yl)methyl]benzonitrile;

7-[(5-cyano-3-cyclopropyl-2-fluoro-phenyl)methyl]-N-ethyl-2-methyl-5-oxo-thiazolo[3,2-a]pyrimidine-3-carboxamide;

N-ethyl-7-[(2-fluoro-3-methoxy-phenyl)methyl]-2-methyl-5-oxo-thiazolo[3,2-a]pyrimidine-3-carboxamide;

7-[(3-cyclopropyl-2-fluoro-phenyl)methyl]-6-fluoro-N,2-dimethyl-5-oxo-thiazolo[3,2-a]pyrimidine-3-carboxamide;

2-[7-[(3-chloro-2-fluoro-phenyl)methyl]-2-methyl-5-oxo-thiazolo[3,2-a]pyrimidin-3-yl]-N-methyl-acetamide;

7-[(3-chloro-2-fluoro-phenyl)methyl]-N-ethyl-6-fluoro-2-methyl-5-oxo-thiazolo[3,2-a]pyrimidine-3-carboxamide;

7-[(4,5-difluoro-2-methoxy-phenyl)methyl]-N,2-dimethyl-5-oxo-thiazolo[3,2-a]pyrimidine-3-carboxamide;

2-fluoro-3[[2-methyl-3-(2-methylcyclopropyl)-5-oxo-thiazolo[3,2-a]pyrimidin-7-yl]methyl]benzonitrile;

2-[7-[(3-cyclopropyl-2-fluoro-phenyl)methyl]-2-methyl-5-oxo-thiazolo[3,2-a]pyrimidin-3-yl]-N-methyl-acetamide;

N-ethyl-6-fluoro-7-[[2-fluoro-3-(trifluoromethyl)phenyl]methyl]-2-methyl-5-oxo-thiazolo[3,2-a]pyrimidine-3-carboxamide;

7-[[2-chloro-5-(trifluoromethyl)phenyl]methyl]-N,2-dimethyl-5-oxo-thiazolo[3,2-a]pyrimidine-3-carboxamide;

7-[(3-cyano-2-fluoro-phenyl)methyl]-6-fluoro-2-methyl-5-oxo-N-(2,2,2-trifluoroethyl)thiazolo[3,2-a]pyrimidine-3-carboxamide;

7-[(2-chloro-4,5-difluoro-phenyl)methyl]-N,2-dimethyl-5-oxo-thiazolo[3,2-a]pyrimidine-3-carboxamide;

7-[[4,5-difluoro-2-(2-fluoroethyl)phenyl]methyl]-N-ethyl-2-methyl-5-oxo-thiazolo[3,2-a]pyrimidine-3-carboxamide;

2-[7-[[5-cyclopropyl-3-(trifluoromethyl)pyrazol-1-yl]methyl]-2-methyl-5-oxo-thiazolo[3,2-a]pyrimidin-3-yl]-N-methyl-acetamide;

2-[7-[[2-fluoro-3-(trifluoromethyl)phenyl]methyl]-2-methyl-5-oxo-thiazolo[3,2-a]pyrimidin-3-yl]-N-methyl-acetamide;

7-[(5-chloro-3-methyl-pyrazol-1-yl)methyl]-N-ethyl-2-methyl-5-oxo-thiazolo[3,2-a]pyrimidine-3-carboxamide;

7-[(3-chloro-5-methyl-pyrazol-1-yl)methyl]-N-ethyl-2-methyl-5-oxo-thiazolo[3,2-a]pyrimidine-3-carboxamide;

7-[(3-chloro-5-cyclopropyl-pyrazol-1-yl)methyl]-N-ethyl-2-methyl-5-oxo-thiazolo[3,2-a]pyrimidine-3-carboxamide;

7-[(5-chloro-3-cyclopropyl-pyrazol-1-yl)methyl]-N-ethyl-2-methyl-5-oxo-thiazolo[3,2-a]pyrimidine-3-carboxamide;

3-[2-(hydroxymethyl)cyclopropyl]-2-methyl-7-[[4-(trifluoromethyl)thiazol-2-yl]methyl]thiazolo[3,2-a]pyrimidin-5-one;

2-[7-[(N-ethyl-4-fluoro-anilino)methyl]-2-methyl-5-oxo-thiazolo[3,2-a]pyrimidin-3-yl]-N-methyl-acetamide;

N-ethyl-2-methyl-7-[[5-methyl-3-(trifluoromethyl)pyrazol-1-yl]methyl]-5-oxo-thiazolo[3,2-a]pyrimidine-3-carboxamide;

N-ethyl-2-methyl-7-[[3-methyl-5-(trifluoromethyl)pyrazol-1-yl]methyl]-5-oxo-thiazolo[3,2-a]pyrimidine-3-carboxamide;

7-[[5-chloro-3-(trifluoromethyl)pyrazol-1-yl]methyl]-N-ethyl-2-methyl-5-oxo-thiazolo[3,2-a]pyrimidine-3-carboxamide;

7-[[3-chloro-5-(trifluoromethyl)pyrazol-1-yl]methyl]-N-ethyl-2-methyl-5-oxo-thiazolo[3,2-a]pyrimidine-3-carboxamide;

7-[[3-(difluoromethyl)-2-fluoro-phenyl]methyl]-6-fluoro-N,2-dimethyl-5-oxo-thiazolo[3,2-a]pyrimidine-3-carboxamide;

7-[[3-(difluoromethyl)-2-fluoro-phenyl]methyl]-N-ethyl-6-fluoro-2-methyl-5-oxo-thiazolo[3,2-a]pyrimidine-3-carboxamide;

7-(4-bicyclo[4,2,0]octa-1,3, 5-trienylmethyl)-N,2-dimethyl-5-oxo-thiazolo[3,2-a]pyrimidine-3-carboxamide;

N-ethyl-7-[[2-fluoro-3-(1-hydroxycyclopropyl)phenyl]methyl]-2-methyl-5-oxo-thiazolo[3,2-a]pyrimidine-3-carboxamide;

N-ethyl-7-[[2-fluoro-3-(1-fluorocyclopropyl)phenyl]methyl]-2-methyl-5-oxo-thiazolo[3,2-a]pyrimidine-3-carboxamide;

N-ethyl-7-[[2-fluoro-3-[1-(fluoromethyl)vinyl]phenyl]methyl]-2-methyl-5-oxo-thiazolo[3,2-a]pyrimidine-3-carboxamide;

7-[(2-ethynyl-4,5-difluoro-phenyl)methyl]-N,2-dimethyl-5-oxo-thiazolo[3,2-a]pyrimidine-3-carboxamide;

2-fluoro-3-[[2-methyl-5-oxo-3-[2-(trifluoromethyl)cyclopropyl]thiazolo[3,2-a]pyrimidin-7-yl]methyl]benzonitrile;

3-[[3-(2,2-difluorocyclopropyl)-2-methyl-5-oxo-thiazolo[3,2-a]pyrimidin-7-yl]methyl]-2-fluoro-benzonitrile;

N-ethyl-7-[[2-fluoro-3-(trifluoromethyl)phenyl]methyl]-5-oxo-2-(trifluoromethyl)thiazolo[3,2-a]pyrimidine-3-carboxamide;

7-[(3-cyano-2-fluoro-phenyl)methyl]-N-ethyl-5-oxo-2-(trifluoromethyl)thiazolo[3,2-a]pyrimidine-3-carboxamide;

7-[[3-(difluoromethyl)-2-fluoro-phenyl]methyl]-N-ethyl-5-oxo-2-(trifluoromethyl)thiazolo[3,2-a]pyrimidine-3-carboxamide;

7-[[5-chloro-3-(trifluoromethyl)pyrazol-1-yl]methyl]-N-ethyl-5-oxo-2-(trifluoromethyl)thiazolo[3,2-a]pyrimidine-3-carboxamide;

7-[[3-chloro-5-(trifluoromethyl)pyrazol-1-yl]methyl]-N-ethyl-5-oxo-2-(trifluoromethyl)thiazolo[3,2-a]pyrimidine-3-carboxamide;

N-ethyl-7-[[5-methyl-3-(trifluoromethyl)pyrazol-1-yl]methyl]-5-oxo-2-(trifluoromethyl)thiazolo[3,2-a]pyrimidine-3-carboxamide;

N-ethyl-7-[[3-methyl-5-(trifluoromethyl)pyrazol-1-yl]methyl]-5-oxo-2-(trifluoromethyl)thiazolo[3,2-a]pyrimidine-3-carboxamide;

7-[[2-fluoro-3-(trifluoromethyl)phenyl]methyl]-3-(1H-imidazol-2-yl)-2-methyl-thiazolo[3,2-a]pyrimidin-5-one;

7-[(3-cyano-2-fluoro-5-methyl-phenyl)methyl]-N-ethyl-2-methyl-5-oxo-thiazolo[3,2-a]pyrimidine-3-carboxamide;

7-[(3-chloro-2-fluoro-phenyl)methyl]-N-ethyl-5-oxo-2-(trifluoromethyl)thiazolo[3,2-a]pyrimidine-3-carboxamide;

7-[[2-fluoro-3-(trifluoromethyl)phenyl]methyl]-2-methyl-5-oxo-N-(2,2,2-trifluoroethyl)thiazolo[3,2-a]pyrimidine-3-carboxamide;

2-methyl-7-[[5-methyl-3-(trifluoromethyl)pyrazol-1-yl]
methyl]-5-oxo-N-(2,2,2-trifluoroethyl)thiazolo[3,2-a]
pyrimidine-3-carboxamide;
7-[[5-cyclopropyl-3-(trifluoromethyl)pyrazol-1-yl]
methyl]-N-methyl-5-oxo-2-(trifluoromethyl)thiazolo
[3,2-a]pyrimidine-3-carboxamide;
7-[[3-cyclopropyl-5-(trifluoromethyl)pyrazol-1-yl]
methyl]-N-methyl-5-oxo-2-(trifluoromethyl)thiazolo
[3,2-a]pyrimidine-3-carboxamide;
7-[[5-chloro-3-(trifluoromethyl)pyrazol-1-yl]methyl]-N-
methyl-5-oxo-2-(trifluoromethyl)thiazolo[3,2-a]py-
rimidine-3-carboxamide;
7-[[3-chloro-5-(trifluoromethyl)pyrazol-1-yl]methyl]-N-
methyl-5-oxo-2-(trifluoromethyl)thiazolo[3,2-a]py-
rimidine-3-carboxamide;
7-[[5-cyclopropyl-3-(trifluoromethyl)pyrazol-1-yl]
methyl]-2-methyl-5-oxo-N-(2,2,2-trifluoroethyl)thi-
azolo[3,2-a]pyrimidine-3-carboxamide;
7-[[3-cyclopropyl-5-(trifluoromethyl)pyrazol-1-yl]
methyl]-2-methyl-5-oxo-N-(2,2,2-trifluoroethyl)thi-
azolo[3,2-a]pyrimidine-3-carboxamide;
2-chloro-N-ethyl-7-[[2-fluoro-3-(trifluoromethyl)phenyl]
methyl]-5-oxo-thiazolo[3,2-a]pyrimidine-3-carboxam-
ide;
N-methyl-7-[[5-methyl-3-(trifluoromethyl)pyrazol-1-yl]
methyl]-5-oxo-2-(trifluoromethyl)thiazolo[3,2-a]py-
rimidine-3-carboxamide;
N-methyl-7-[[3-methyl-5-(trifluoromethyl)pyrazol-1-yl]
methyl]-5-oxo-2-(trifluoromethyl)thiazolo[3,2-a]py-
rimidine-3-carboxamide;
7-[[2-fluoro-3-(trifluoromethyl)phenyl]methyl]-N-
methyl-5-oxo-2-(trifluoromethyl)thiazolo[3,2-a]py-
rimidine-3-carboxamide;
7-[(3-chloro-2-fluoro-phenyl)methyl]-N-methyl-5-oxo-2-
(trifluoromethyl)thiazolo[3,2-a]pyrimidine-3-carbox-
amide;
7-[[5-chloro-3-(trifluoromethyl)pyrazol-1-yl]methyl]-2-
methyl-5-oxo-N-(2,2,2-trifluoroethyl)thiazolo[3,2-a]
pyrimidine-3-carboxamide;
7-[[3-chloro-5-(trifluoromethyl)pyrazol-1-yl]methyl]-2-
methyl-5-oxo-N-(2,2,2-trifluoroethyl)thiazolo[3,2-a]
pyrimidine-3-carboxamide;
2-methyl-7-[[3-methyl-5-(trifluoromethyl)pyrazol-1-yl]
methyl]-5-oxo-N-(2,2,2-trifluoroethyl)thiazolo[3,2-a]
pyrimidine-3-carboxamide;
2-chloro-7-[(3-cyano-2-fluoro-phenyl)methyl]-N-ethyl-
5-oxo-thiazolo[3,2-a]pyrimidine-3-carboxamide;
7-[(3-cyano-2-fluoro-phenyl)methyl]-N-methyl-5-oxo-2-
(trifluoromethyl)thiazolo[3,2-a]pyrimidine-3-carbox-
amide;
N-ethyl-2-[7-[[2-fluoro-3-(trifluoromethyl)phenyl]
methyl]-2-methyl-5-oxo-thiazolo[3,2-a]pyrimidin-3-
yl]acetamide;
N,2-dimethyl-5-oxo-7-[[4-(trifluoromethyl)pyrazol-1-yl]
methyl]thiazolo[3,2-a]pyrimidine-3-carboxamide;
3-[[2-chloro-5-oxo-3-[2-(trifluoromethyl)cyclopropyl]
thiazolo[3,2-a]pyrimidin-7-yl]methyl]-2-fluoro-benzo-
nitrile;
2-[7-[[2-fluoro-3-(trifluoromethyl)phenyl]methyl]-5-
oxo-2-(trifluoromethyl)thiazolo[3,2-a]pyrimidin-3-yl]-
N-methyl-acetamide;
7-[[5-cyclopropyl-3-(trifluoromethyl)pyrazol-1-yl]
methyl]-N-ethyl-2-methyl-5-oxo-thiazolo[3,2-a]py-
rimidine-3-carboxamide;
2-[7-[[5-cyclopropyl-3-(trifluoromethyl)pyrazol-1-yl]
methyl]-5-oxo-2-(trifluoromethyl)thiazolo[3,2-a]py-
rimidin-3-yl]-N-methyl-acetamide;

2-[7-[[3-cyclopropyl-5-(trifluoromethyl)pyrazol-1-yl]
methyl]-5-oxo-2-(trifluoromethyl)thiazolo[3,2-a]py-
rimidin-3-yl]-N-methyl-acetamide;
7-[[2-fluoro-3-(trifluoromethyl)phenyl]methyl]-2-
methyl-3-(methylsulfonylmethyl)thiazolo[3,2-a]py-
rimidin-5-one;
7-[[2-fluoro-3-(trifluoromethyl)phenyl]methyl]-3-(1H-
imidazol-2-ylmethyl)-2-methyl-thiazolo[3,2-a]pyrimi-
din-5-one;
N-ethyl-7-[(N-ethyl-4-fluoro-anilino)methyl]-2-methyl-
5-oxo-thiazolo[3,2-a]pyrimidine-3-carboxamide;
N-ethyl-7-[(N-ethyl-4-fluoro-anilino)methyl]-5-oxo-2-
(trifluoromethyl)thiazolo[3,2-a]pyrimidine-3-carbox-
amide;
2-fluoro-3-[[3-(2-methylcyclopropyl)-5-oxo-2-(trifluo-
romethyl)thiazolo[3,2-a]pyrimidin-7-yl]methyl]benzo-
nitrile;
3-[[2-chloro-3-(2-methylcyclopropyl)-5-oxo-thiazolo[3,
2-a]pyrimidin-7-yl]methyl]-2-fluoro-benzonitrile;
N-ethyl-7-[[2-fluoro-3-(trifluoromethyl)phenyl]methyl]-
2-isopropyl-5-oxo-thiazolo[3,2-a]pyrimidine-3-car-
boxamide;
6-[[5-chloro-3-(trifluoromethyl)pyrazol-1-yl]methyl]-2,
3-dihydro-1H-cyclopenta[3,4]thiazolo[1,4-a]pyrimi-
din-8-one;
6-[[3-chloro-5-(trifluoromethyl)pyrazol-1-yl]methyl]-2,
3-dihydro-1H-cyclopenta[3, 4]thiazolo[1,4-a]pyrimi-
din-8-one;
N-ethyl-7-[[2-fluoro-3-(trifluoromethyl)phenyl]methyl]-
2-methoxy-5-oxo-thiazolo[3,2-a]pyrimidine-3-carbox-
amide;
6-[[2-fluoro-3-(trifluoromethyl)phenyl]methyl]-1-(hy-
droxymethyl)-2,3-dihydro-1H-cyclopenta[3,4]thiazolo
[1,4-a]pyrimidin-8-one;
2-ethyl-7-[[2-fluoro-3-(trifluoromethyl)phenyl]methyl]-
N-methyl-5-oxo-thiazolo[3,2-a]pyrimidine-3-carbox-
amide;
6-[[5-cyclopropyl-3-(trifluoromethyl)pyrazol-1-yl]
methyl]-1-(hydroxymethyl)-2,3-dihydro-1H-cyclo-
penta[3,4]thiazolo[1,4-a]pyrimidin-8-one;
7-[[5-chloro-3-(trifluoromethyl)pyrazol-1-yl]methyl]-N,
2-dimethyl-5-oxo-thiazolo[3,2-a]pyrimidine-3-carbox-
amide;
7-[[3-chloro-5-(trifluoromethyl)pyrazol-1-yl]methyl]-N,
2-dimethyl-5-oxo-thiazolo[3,2-a]pyrimidine-3-carbox-
amide;
2-[7-[[5-chloro-3-(trifluoromethyl)pyrazol-1-yl]methyl]-
2-methyl-5-oxo-thiazolo[3,2-a]pyrimidin-3-yl]-N-
methyl-acetamide;
2-[7-[[3-chloro-5-(trifluoromethyl)pyrazol-1-yl]methyl]-
2-methyl-5-oxo-thiazolo[3,2-a]pyrimidin-3-yl]-N-
methyl-acetamide;
7-[[2-fluoro-3-(trifluoromethyl)phenyl]methyl]-3-(2-hy-
droxycyclopropyl)-2-methyl-thiazolo[3,2-a]pyrimidin-
5-one;
7-[[5-chloro-3-(trifluoromethyl)pyrazol-1-yl]methyl]-3-
[2-(hydroxymethyl)cyclopropyl]-2-methyl-thiazolo[3,
2-a]pyrimidin-5-one;
7-[[3-chloro-5-(trifluoromethyl)pyrazol-1-yl]methyl]-3-
[2-(hydroxymethyl)cyclopropyl]-2-methyl-thiazolo[3,
2-a]pyrimidin-5-one;
2-[7-[[5-chloro-3-(trifluoromethyl)pyrazol-1-yl]methyl]-
2-methyl-5-oxo-thiazolo[3,2-a]pyrimidin-3-yl]cyclo-
propanecarbonitrile;
2-cyano-N-ethyl-7-[[2-fluoro-3-(trifluoromethyl)phenyl]
methyl]-5-oxo-thiazolo[3,2-a]pyrimidine-3-carboxam-
ide;

7-[[2-fluoro-3-(trifluoromethyl)phenyl]methyl]-N-isopropyl-2-methyl-5-oxo-thiazolo[3,2-a]pyrimidine-3-carboxamide;
7-[[5-chloro-3-(trifluoromethyl)pyrazol-1-yl]methyl]-3-(1-hydroxy-1-methyl-ethyl)-2-methyl-thiazolo[3,2-a]pyrimidin-5-one;
7-[[3-chloro-5-(trifluoromethyl)pyrazol-1-yl]methyl]-3-(1-hydroxy-1-methyl-ethyl)-2-methyl-thiazolo[3,2-a]pyrimidin-5-one;
7-[[5-chloro-3-(trifluoromethyl)pyrazol-1-yl]methyl]-3-(1-hydroxyethyl)-2-methyl-thiazolo[3,2-a]pyrimidin-5-one;
7-[[3-chloro-5-(trifluoromethyl)pyrazol-1-yl]methyl]-3-(1-hydroxyethyl)-2-methyl-thiazolo[3,2-a]pyrimidin-5-one;
7-[[2-fluoro-3-(trifluoromethyl)phenyl]ethyl]-2-methyl-5-oxo-N-sec-butyl-thiazolo[3,2-a]pyrimidine-3-carboxamide;
3-[[3-(azetidin-1-yl)-2-methyl-5-oxo-thiazolo[3,2-a]pyrimidin-7-yl]methyl]-2-fluoro-benzonitrile;
7-[[5-chloro-3-(trifluoromethyl)pyrazol-1-yl]methyl]-2-methyl-5-oxo-thiazolo[3,2-a]pyrimidine-3-carbonitrile;
7-[[3-chloro-5-(trifluoromethyl)pyrazol-1-yl]methyl]-2-methyl-5-oxo-thiazolo[3,2-a]pyrimidine-3-carbonitrile;
7-[[5-chloro-3-(trifluoromethyl)pyrazol-1-yl]methyl]-3-cyclopropyl-2-methyl-thiazolo[3,2-a]pyrimidin-5-one;
7-[[3-chloro-5-(trifluoromethyl)pyrazol-1-yl]methyl]-3-cyclopropyl-2-methyl-thiazolo[3,2-a]pyrimidin-5-one;
7-[[5-chloro-3-(trifluoromethyl)pyrazol-1-yl]methyl]-2-methyl-3-2 methylcyclopropyl)thiazolo[3,2-a]pyrimidin-5-one;
3-acetyl-7-[[5-chloro-3-(trifluoromethylpyrazol-1-yl]methyl]-2-methyl-thiazolo[3,2-a]pyrimidin-5-one;
3-acetyl-7-[[3-chloro-5-(trifluoromethyl)pyrazol-1-yl]methyl]-2-methyl-thiazolo[3,2-a]pyrimidin-5-one;
2-chloro-7-[[2-fluoro-3-(trifluoromethyl)phenyl]methyl]-3-(2-methylcyclopropyl)thiazolo[3,2-a]pyrimidin-5-one;
7-[[3-chloro-5-(trifluoromethyl)pyrazol-1-yl]methyl]-2-methyl-3-pyrimidin-5-yl-thiazolo[3,2-a]pyrimidin-5-one;
7-[[3-cyclopropyl-5-(trifluoromethyl)pyrazol-1-yl]methyl]-N-ethyl-2-methyl-5-oxo-thiazolo[3,2-a]pyrimidine-3-carboxamide;
7-[[(5-chloro-2-pyridyl)-methyl-amino]methyl]-N-ethyl-2-methyl-5-oxo-thiazolo[3,2-a]pyrimidine-3-carboxamide;
cis-2-[7-[[5-chloro-3-(trifluoromethyl)pyrazol-1-yl]methyl]-2-methyl-5-oxo-thiazolo[3,2-a]pyrimidin-3-yl]cyclopropanecarbonitrile;
7-[[3-chloro-5-(trifluoromethyl)pyrazol-1-yl]methyl]-N-ethyl-2-methoxy-5-oxo thiazolo[3,2-a]pyrimidine-3-carboxamide;
7-[[5-chloro-3-(trifluoromethyl)pyrazol-1-yl]methyl]-N-ethyl-2-methoxy-5-oxo thiazolo[3,2-a]pyrimidine-3-carboxamide;
7-[[5-cyclopropyl-3-(trifluoromethyl)pyrazol-1-yl]methyl]-N-ethyl-2-methoxy-5-oxo thiazolo[3,2-a]pyrimidine-3-carboxamide;
7-[[3-cyclopropyl-5-(trifluoromethyl)pyrazol-1-yl]methyl]-N-ethyl-2-methoxy-5-oxo thiazolo[3,2-a]pyrimidine-3-carboxamide;
2-[7-[[2-fluoro-3-(trifluoromethyl)phenyl]methyl]-2-methyl-5-oxo-thiazolo[3,2-a]pyrimidin-3-yl]cyclopropanecarbonitrile;
7-[[5-chloro-3-(trifluoromethyl)pyrazol-1-yl]methyl]-2-methyl-3-(1H-pyrazol-5-yl)thiazolo[3,2-a]pyrimidin-5-one;
7-[[3-chloro-5-(trifluoromethyl)pyrazol-1-yl]methyl]-2-methyl-3-(1H-pyrazol-5-yl)thiazolo[3,2-a]pyrimidin-5-one;
7-[[5-chloro-3-(trifluoromethyl)pyrazol-1-yl]methyl]-2-methyl-3-(3-pyridyl)thiazolo[3,2-a]pyrimidin-5-one;
7-[[5-chloro-3-(trifluoromethyl)pyrazol-1-yl]methyl]-3-isopropenyl-2-methyl-thiazolo[3,2-a]pyrimidin-5-one;
trans-7-[[5-chloro-3-(trifluoromethyl)pyrazol-1-yl]methyl]-3-[2-(hydroxymethyl)cyclopropyl]-2-methyl-thiazolo[3,2-a]pyrimidin-5-one;
7-[[5-chloro-3-(trifluoromethyl)pyrazol-1-yl]methyl]-3-(5-fluoro-3-pyridyl)-2-methyl-thiazolo[3,2-a]pyrimidin-5-one;
7-[[3-chloro-5-(trifluoromethyl)pyrazol-1-yl]methyl]-3-(5-fluoro-3-pyridyl)-2-methyl-thiazolo[3,2-a]pyrimidin-5-one;
7-[[5-chloro-3-(trifluoromethyl)pyrazol-1-yl]methyl]-2-methyl-3-propanoyl-thiazolo[3,2-a]pyrimidin-5-one;
7-[[3-chloro-5-(trifluoromethyl)pyrazol-1-yl]methyl]-2-methyl-3-propanoyl-thiazolo[3,2-a]pyrimidin-5-one;
7-[[5-chloro-3-(trifluoromethyl)pyrazol-1-yl]methyl]-2-methyl-3-thiazol-2-yl-thiazolo[3,2-a]pyrimidin-5-one;
N-ethyl-7-[[(5-fluoro-2-pyridyl)-methyl-amino]methyl]-2-methyl-5-oxo-thiazolo[3,2-a]pyrimidine-3-carboxamide;
2-[7-[[5-chloro-3-(trifluoromethyl)pyrazol-1-yl]methyl]-5-oxo-2-(trifluoromethyl)thiazolo[3,2-a]pyrimidin-3-yl]cyclopropanecarbonitrile;
2[7-[[3-chloro-5-(trifluoromethyl)pyrazol-1-yl]methyl]-5-oxo-2-(trifluoromethyl)thiazolo[3,2-a]pyrimidin-3-yl]cyclopropanecarbonitrile;
N-ethyl-7-[[ethyl-(5-fluoro-2-pyridyl)amino]methyl]-2-methyl-5-oxo-thiazolo[3,2-a]pyrimidine-3-carboxamide;
N-ethyl-7-[[ethyl(pyridyl)amino]methyl]-2-methyl-5-oxo-thiazolo[3,2-a]pyrimidine-3-carboxamide;
3-(5-chloro-3-pyridyl)-7-[[5-chloro-3-(trifluoromethyl)pyrazol-1-yl]methyl]-2-methyl-thiazolo[3,2-a]pyrimidin-5-one;
3-(5-chloro-3-pyridyl)-7-[[3-chloro-5-(trifluoromethyl)pyrazol-1-yl]methyl]-2-methyl-thiazolo[3,2-a]pyrimidin-5-one;
7-[[5-chloro-3-(trifluoromethyl)pyrazol-1-yl]methyl]-2-methyl-3-thiazol-4-yl-thiazolo[3,2-a]pyrimidin-5-one;
7-[[(5-chloro-2-pyridyl)-ethyl-amino]methyl]-N-ethyl-2-methyl-5-oxo-thiazolo[3,2-a]pyrimidine-3-carboxamide;
7-[(5-cyclopropyltriazol-1-yl)methyl]-3-[2-(hydroxymethyl)cyclopropyl]-2-methyl-thiazolo[3,2-a]pyrimidin-5-one;
trans-7-[[5-chloro-3-(trifluoromethyl)pyrazol-1-yl]methyl]-2-methyl-3-[2-methylcyclopropyl]thiazolo[3,2-a]pyrimidin-5-one;
2-ethoxy-N-ethyl-7-[[2-fluoro-3-(trifluoromethyl)phenyl]methyl]-5-oxo-thiazolo[3,2-a]pyrimidine-3-carboxamide;
7-[[5-chloro-3-(trifluoromethyl)pyrazol-1-yl]methyl]-3-(2-fluoro-3-pyridyl)-2-methyl-thiazolo[3,2-a]pyrimidin-5-one;
7-[[5-chloro-3-(trifluoromethyl)pyrazol-1-yl]methyl]-2-methyl-3-oxazol-2-yl-thiazolo[3,2-a]pyrimidin-5-one;
7-[[3-chloro-5-(trifluoromethyl)pyrazol-1-yl]methyl]-2-methyl-3-oxazol-2-yl-thiazolo[3,2-a]pyrimidin-5-one;

7-[[5-chloro-3-(trifluoromethyl)pyrazol-1-yl]methyl]-2-methyl-3-(trifluoromethyl)thiazolo[3,2-a]pyrimidin-5-one;

7-[[3-chloro-5-(trifluoromethyl)pyrazol-1-yl]methyl]-2-methyl-3-(trifluoromethyl)thiazolo[3,2-a]pyrimidin-5-one;

7-[[(5-chloro-2-pyridyl)-methyl-amino]methyl]-3-[2-(hydroxymethyl)cyclopropl]-2-methyl-thiazolo[3,2-a]pyrimidin-5-one;

7-[(3,5-dichloropyrazol-1-yl)methyl]-N-ethyl-2-methyl-5-oxo-thiazolo[3,2-a]pyrimidine-3-carboxamide;

N-ethyl-7-[[2-fluoro-3-(trifluoromethyl)phenyl]methyl]-5-oxo-2-(2,2,2-trifluoroethoxy)thiazolo[3,2-a]pyrimidine-3-carboxamide;

3-acetyl-7-[[5-chloro-3-(trifluoromethyl)pyrazol-1-yl]methyl]-2-(trifluoromethyl)thiazolo[3,2-a]pyrimidin-5-one;

3-acetyl-7-[[3-chloro-5-(trifluoromethyl)pyrazol-1-yl]methyl]-2-(trifluoromethyl)thiazolo[3,2-a]pyrimidin-5-one;

3-[(4-chloropyrazol-1-yl)methyl]-7-[[5-chloro-3-(trifluoromethyl)pyrazol-1-yl]methyl]-2-methyl-thiazolo[3,2-a]pyrimidin-5-one;

7-[[5-chloro-3-(trifluoromethyl)pyrazol-1-yl]methyl]-3-isopropenyl-2-(trifluoromethyl)thiazolo[3,2-a]pyrimidin-5-one;

7-[[5-chloro-3-(trifluoromethyl)pyrazol-1-yl]methyl]-3-(1H-imidazol-2-yl)-2-methyl-thiazolo[3,2-a]pyrimidin-5-one;

7-[[5-chloro-3-(trifluoromethyl)pyrazol-1-yl]methyl]-3-pyrimidin-5-yl-2-(trifluoromethyl)thiazolo[3,2-a]pyrimidin-5-one;

7-[[3-chloro-5-(trifluoromethyl)pyrazol-1-yl]methyl]-3-pyrimidin-5-yl-2-(trifluoromethyl)thiazolo[3,2-a]pyrimidin-5-one;

7-[[3-chloro-5-(trifluoromethyl)pyrazol-1-yl]methyl]-3-(3-pyridyl)-2-(trifluoromethyl)thiazolo[3,2-a]pyrimidin-5-one;

7-[[5-chloro-3-(trifluoromethyl)pyrazol-1-yl]methyl]-N-ethyl-5-oxo-2-(2,2,2-trifluoroethoxy)thiazolo[3,2-a]pyrimidine-3-carboxamide;

7-[[5-chloro-3-(trifluoromethyl)pyrazol-1-yl]methyl]-2-ethoxy-N-ethyl-5-oxo-thiazolo[3,2-a]pyrimidine-3-carboxamide;

7-[[3-chloro-5-(trifluoromethyl)pyrazol-1-yl]methyl]-2-ethoxy-N-ethyl-5-oxo-thiazolo[3,2-a]pyrimidine-3-carboxamide;

7-[[5-chloro-3-(trifluoromethyl)pyrazol-1-yl]methyl]-2-methyl-3-(2-methylpropanoyl)thiazolo[3,2-a]pyrimidin-5-one;

7-[[3-chloro-5-(trifluoromethyl)pyrazol-1-yl]methyl]-2-methyl-3-(2-methylpropanoyl)thiazolo[3,2-a]pyrimidin-5-one;

7-[[2-fluoro-3-(trifluoromethyl)phenyl]methyl]-2-methyl-N-[(1R)-1-methylethpropyl]-5-oxo-thiazolo[3,2-a]pyrimidine-3-carboxamide;

7-[[2-fluoro-3-(trifluoromethyl)phenyl]methyl]-2-methyl-N-[(1S)-1-methylpropyl]-5-oxo-thiazolo[3,2-a]pyrimidine-3-carboxamide;

7-[[(4-chloro-2-pyridyl)-ethyl-amino]methyl]-N-ethyl-2-methyl-5-oxo-thiazolo[3,2-a]pyrimidine-3-carboxamide;

7-[[(5-fluoro-2-pyridyl)-methyl-amino]methyl]-3-[2-(hydroxymethyl)cyclopropl]-2-methyl-thiazolo[3,2-a]pyrimidin-5-one;

7-[[5-chloro-3-(trifluoromethyl)pyrazol-1-yl]methyl]-3-(methoxymethyl)-2-methyl-thiazolo[3,2-a]pyrimidin-5-one;

7-[[5-chloro-3-(trifluoromethyl)pyrazol-1-yl]methyl]-3-cyclopropyl-2-(trifluoromethyl)thiazolo[3,2-a]pyrimidin-5-one;

7-[[5-chloro-3-(trifluoromethyl)pyrazol-1-yl]methyl]-2-methyl-3-(methylsulfonylmethyl)thiazolo[3,2-a]pyrimidin-5-one;

7-[[5-chloro-3-(trifluoromethyl)pyrazol-1-yl]methyl]-2-methyl-3-(pyrazol-1-ylmethyl)thiazolo[3,2-a]pyrimidin-5-one;

2-[7-[[2-chloro-5-(trifluoromethyl)phenyl]methyl]-2-methyl-5-oxo-thiazolo[3,2-a]pyrimidin-3-yl]cyclopropanecarbonitrile;

7-[[5-chloro-3-(trifluoromethyl)pyrazol-1-yl]methyl]-3-cyclobutyl-2-methyl-thiazolo[3,2-a]pyrimidin-5-one;

7-[[3-chloro-5-(trifluoromethyl)pyrazol-1-yl]methyl]-3-cyclobutyl-2-methyl-thiazolo[3,2-a]pyrimidin-5-one;

2-[7-[[(5-chloro-2-pyridyl)-methyl-amino]methyl]-2-methyl-5-oxo-thiazolo[3,2-a]pyrimidin-3-yl]cyclopropanecarbonitrile;

7-[[ethyl-(5-fluoro-2-pyridyl)amino]methyl]-3-[2-(hydroxymethyl)cyclopropyl]-2-methyl-thiazolo[3,2-a]pyrimidin-5-one;

3-chloro-7-[[5-chloro-3-(trifluoromethyl)pyrazol-1-yl]methyl]-2-methyl-thiazolo[3,2-a]pyrimidin-5-one;

3-chloro-7-[[3-chloro-5-(trifluoromethyl)pyrazol-1-yl]methyl]-2-methyl-thiazolo[3,2-a]pyrimidin-5-one;

2-[7-[(4,5-difluoro-2-methoxy-phenyl)methyl]-2-methyl-5-oxo-thiazolo[3,2-a]pyrimidin-3-yl]cyclopropanecarbonitrile;

2-[7-[[ethyl-(5-fluoro-2-pyridyl)amino]methyl]-2-methyl-5-oxo-thiazolo[3,2-a]pyrimidin-3-yl]cyclopropanecarbonitrile;

7-[[5-chloro-2-pyridyl)-ethyl-amino]methyl]-3-[2-(hydromethyl)cyclopropyl]-2-methyl-thiazolo[3,2-a]pyrimidin-5-one;

5-[7-[[5-chloro-3-(trifluoromethyl)pyrazol-1-yl]methyl]-2-methyl-5-oxo-thiazolo[3,2-a]pyrimidin-3-yl]pyridine-3-carbonitrile;

7-[[5-chloro-3-(trifluoromethyl)pyrazol-1-yl]methyl]-2-methyl-3-(2,2,2-trifluoroacetyl)thiazolo[3,2-a]pyrimidin-5-one;

7-[[5-chloro-3-(trifluoromethyl)pyrazol-1-yl]methyl]-3-(2-methylcyclopropyl)-2-(trifluoromethyl)thiazolo[3,2-a]pyrimidin-5-one;

7-[[3-chloro-5-(trifluoromethyl)pyrazol-1-yl]methyl]-3-(2-methylcyclopropyl)-2-(trifluoromethyl)thiazolo[3,2-a]pyrimidin-5-one;

7-[[5-chloro-3-(trifluoromethyl)pyrazol-1-yl]methyl]-2-methyl-3-pyrimidin-5-yl-thiazolo[3,2-a]pyrimidin-5-one;

7-[[5-chloro-3-(trifluoromethyl)pyrazol-1-yl]methyl]-2-ethyl-3-(3-pyridyl)thiazolo[3,2-a]pyrimidin-5-one;

7-[[5-chloro-3-(trifluoromethyl)pyrazol-1-yl]methyl]-2-methyl-3-(2,2,2-trifluoro-1-hydroxy-ethyl)thiazolo[3,2-a]pyrimidin-5-one;

7-[[(5-bromo-2-pyridyl)-ethyl-amino]methyl-N-ethyl-2-methyl]-5-oxo-thiazolo[3,2-a]pyrimidine-3-carboxamide;

N-ethyl-7-[[ethyl-(5-fluoro-2-pyridyl)amino]methyl]-5-oxo-2-(trifluoromethyl)thiazolo[3,2-a]pyrimidine-3-carboxamide;

3-(azetidin-1-yl)-7-[[5-chloro-3-(trifluoromethyl)pyrazol-1-yl]methyl]-2-(trifluoromethyl)thiazolo[3,2-a]pyrimidin-5-one;

cis-2-[7-[[5-chloro-3-(trifluoromethyl)pyrazol-1-yl]
methyl]-5-oxo-2-(trifluoromethyl)thiazolo[3,2-a]pyrimidin-3-yl]cyclopropanecarbonitrile;
2-[7-[[5-methoxy-3-(trifluoromethyl)pyrazol-1-yl]
methyl]-2-methyl-5-oxo-thiazolo[3,2-a]pyrimidin-3-yl]cyclopropanecarbonitrile;
2-[7-[[3-methoxy-5-(trifluoromethyl)pyrazol-1-yl]
methyl]-2-methyl-5-oxo-thiazolo[3,2-a]pyrimidin-3-yl]cyclopropanecarbonitrile;
3-acetyl-7-[[5-chloro-3-(trifluoromethyl)pyrazol-1-yl]
methyl]-2-ethyl-thiazolo[3,2-a]pyrimidin-5-one;
3-acetyl-7-[[3-chloro-5-(trifluoromethyl)pyrazol-1-yl]
methyl]-2-ethyl-thiazolo[3,2-a]pyrimidin-5-one;
2-[7-[[5-chloro-3-(trifluoromethyl)pyrazol-1-yl]methyl]-2-ethyl-5-oxo-thiazolo[3,2-a]pyrimidin-3-yl]cyclopropanecarbonitrile;
2-[7-[[3-chloro-5-(trifluoromethyl)pyrazol-1-yl]methyl]-2-ethyl-5-oxo-thiazolo[3,2-a]pyrimidin-3-yl]cyclopropane carbonitrile;
3-bromo-7-[[5-chloro-3-(trifluoromethyl)pyrazol-1-yl]
methyl]-2-methyl-thiazolo[3,2-a]pyrimidin-5-one;
3-bromo-7-[[3-chloro-5-(trifluoromethyl)pyrazol-1-yl]
methyl]-2-methyl-thiazolo[3,2-a]pyrimidin-5-one;
3-chloro-7-[[5-chloro-3-(trifluoromethyl)pyrazol-1-yl]
methyl]-2-methoxy-thiazolo[3,2-a]pyrimidin-5-one;
3-chloro-7-[[3-chloro-5-(trifluoromethyl)pyrazol-1-yl]
methyl]-2-methoxy-thiazolo[3,2-a]pyrimidin-5-one;
7-[[5-chloro-3-(trifluoromethyl)pyrazol-1-yl]methyl]-3-methylsulfanyl-2-(trifluoromethyl)thiazolo[3,2-a]pyrimidin-5-one;
2-[7-[(N-ethyl-4-fluoro-anilino)methyl]-S-oxo-thiazolo[3,2-a]pyrimidin-3-yl]-1-(hydroxymethyl)cyclopropane carbonitrile;
7-[[5-chloro-3-(trifluoromethyl)pyrazol-1-yl]methyl]-3-(2-hydroxy-1-methyl-ethyl)-2-methyl-thiazolo[3,2-a]pyrimidin-5-one;
7-[[3-chloro-5-(trifluoromethyl)pyrazol-1-yl]methyl]-3-(2-hydroxy-1-methyl-ethyl)-2-methyl-thiazolo[3,2-a]pyrimidin-5-one;
7-[[5-chloro-3-(trifluoromethyl)pyrazol-1-yl]methyl]-3-(cyclopropanecarbonyl)-2-methyl-thiazolo[3,2-a]pyrimidin-5-one;
3-bromo-7-[[5-chloro-3-(trifluoromethyl)pyrazol-1-yl]
methyl]thiazolo[3,2-a]pyrimidin-5-one;
3-bromo-7-[[3-chloro-5-(trifluoromethyl)pyrazol-1-yl]
methyl]thiazolo[3,2-a]pyrimidin-5-one;
7-[(3-amino-5-chloro-pyrazol-1-yl)methyl]-3-bromo-2-methyl-thiazolo[3,2-a]pyrimidin-5-one;
7-[(5-amino-3-chloro-pyrazol-1-yl)methyl]-3-bromo-2-methyl-thiazolo[3,2-a]pyrimidin-5-one;
2-[7-[[5-chloro-3-(trifluoromethyl)pyrazol-1-yl]methyl]-2-methyl-5-oxo-thiazolo[3,2-a]pyrimidin-3-yl]acetonitrile;
N-ethyl-7-[[(5-fluoro-2-pyridyl)-methyl-amino]methyl]-5-oxo-2-(trifluoromethyl)thiazolo[3,2-a]pyrimidine-3-carboxamide;
7-[[5-chloro-3-(trifluoromethyl)pyrazol-1-yl]methyl]-3-(3,3-difluoroazetidin-1-yl)-2-(trifluoromethyl)thiazolo[3,2-a]pyrimidin-5-one;
7-[[5-chloro-3-(trifluoromethyl)pyrazol-1-yl]methyl]-2-methoxy-3-(3-pyridyl)thiazolo[3,2-a]pyrimidin-5-one;
2-[7-[[5-bromo-3-(trifluoromethyl)pyrazol-1-yl]methyl]-2-methyl-5-oxo-thiazolo[3,2-a]pyrimidin-3-yl]cyclopropanecarbonitrile;
3-chloro-7-[[5-chloro-3-(trifluoromethyl)pyrazol-1-yl]
methyl]thiazolo[3,2-a]pyrimidin-5-one;
3-chloro-7-[[3-chloro-5-(trifluoromethyl)pyrazol-1-yl]
methyl]thiazolo[3,2-a]pyrimidin-5-one;
2-acetyl-7-[[5-chloro-3-(trifluoromethyl)pyrazol-1-yl]
methyl]-N-ethyl-5-oxo-thiazolo[3,2-a]pyrimidine-3-carboxamide;
2-acetyl-7-[[3-chloro-5-(trifluoromethyl)pyrazol-1-yl]
methyl]-N-ethyl-5-oxo-thiazolo[3,2-a]pyrimidine-3-carboxamide;
7-[[5-chloro-3-(trifluoromethyl)pyrazol-1-yl]methyl]-3-(trifluoromethyl)thiazolo[3,2-a]pyrimidin-5-one;
7-[[2-fluoro-3-(trifluoromethyl)phenyl]methyl]-2-methyl-3-(1H-1,2,4-triazol-5-yl)thiazolo[3,2-a]pyrimidin-5-one;
2-[7-[[5-chloro-3-(trifluoromethyl)pyrazol-1-yl]methyl]-5-oxo-thiazolo[3,2-a]pyrimidin-3-yl]cyclopropanecarbonitrile;
3-acetyl-7-[[5-chloro-3-(trifluoromethyl)pyrazol-1-yl]
methyl]thiazolo[3,2-a]pyrimidin-5-one;
7-[[5-chloro-3-(trifluoromethyl)pyrazol-1-yl]methyl]-3-(2,2,2-trifluoroethoxy)-2-(trifluoromethyl)thiazolo[3,2-a]pyrimidin-5-one;
3-acetyl-7-[[5-chloro-3-(trifluoromethyl)pyrazol-1-yl]
methyl]-2-methoxy-thiazolo[3,2-a]pyrimidin-5-one;
3-acetyl-7-[[3-chloro-5-(trifluoromethyl)pyrazol-1-yl]
methyl]-2-methoxy-thiazolo[3,2-a]pyrimidin-5-one;
3-bromo-7-[(5-chloro-3-nitro-pyrazol-1-yl)methyl]-2-methyl-thiazolo[3,2-a]pyrimidin-5-one;
7-[[5-chloro-3-(trifluoromethyl)pyrazol-1-yl]methyl]-3-(1H-pyrazol-5-yl)-2-(trifluoromethyl)thiazolo[3,2-a]pyrimidin-5-one;
7-[[5-chloro-3-(trifluoromethyl)pyrazol-1-yl]methyl]-3-thiazol-4-yl-2-(trifluoromethyl)thiazolo[3,2-a]pyrimidin-5-one;
7-[[5-chloro-3-(trifluoromethyl)pyrazol-1-yl]methyl]-3-(5-fluoro-3-pyridyl)-2-(trifluoromethyl)thiazolo[3,2-a]pyrimidin-5-one;
7-[[5-chloro-3-(trifluoromethyl)pyrazol-1-yl]methyl]-3-propanoyl-2-(trifluoromethyl)thiazolo[3,2-a]pyrimidin-5-one;
2-[7-[(3,5-dichloropyrazol-1-yl)methyl]-2-methyl-5-oxo-thiazolo[3,2-a]pyrimidin-3-yl]cyclopropanecarbonitrile;
2-[7-[[5-chloro-3-(trifluoromethyl)pyrazol-1-yl]methyl]-2-methyl-5-oxo-thiazolo[3,2-a]pyrimidin-3-yl]propanenitrile;
2-[7-[[3-chloro-5-(trifluoromethyl)pyrazol-1-yl]methyl]-2-methyl-5-oxo-thiazolo[3,2-a]pyrimidin-3-yl]propanenitrile;
7-[[5-chloro-3-(trifluoromethyl)pyrazol-1-yl]methyl]-3-(3-fluoroazetidin-1-yl)-2-(trifluoromethyl)thiazolo[3,2-a]pyrimidin-5-one;
3-(5-chloro-3-pyridyl)-7-[[5-chloro-3-(trifluoromethyl)
pyrazol-1-yl]methyl]-2-(trifluoromethyl)thiazolo[3,2-a]pyrimidin-5-one;
7-[(3,5-dichloropyrazol-1-yl)methyl]-N-ethyl-5-oxo-2-(trifluoromethyl)thiazolo[3,2-a]pyrimidine-3-carboxamide;
3-[[3-acetyl-5-oxo-2-(trifluoromethyl)thiazolo[3,2-a]pyrimidin-7-yl]methyl-2-fluoro-benzonitrile;
7-[[5-chloro-3-(trifluoromethyl)pyrazol-1-yl]methyl]-2-(difluoromethyl)-N-ethyl-5-oxo thiazolo[3,2-a]pyrimidine-3-carboxamide;
7-[[3-chloro-5-(trifluoromethyl)pyrazol-1-yl]methyl]-2-(difluoromethyl)-N-ethyl-5-oxo thiazolo[3,2-a]pyrimidine-3-carboxamide;
(Z)-3-[7-[(N-ethyl-4-fluoro-anilino)methyl]-2-methyl-5-oxo-thiazolo[3,2-a]pyrimidin-3-yl]prop-2-enenitrile;

(E)-3-r 7-f N-ethyl-4-fluoro-anilino)methyl-2-methyl-5-oxo-thiazolo[3,2-a]pyrimidin-3-yl]prop-2-enamide;
(E)-3-[7-[[5-chloro-3-(trifluoromethyl)pyrazol-1-yl]methyl]-2-methyl-5-oxo-thiazolo[3,2-a]pyrimidin-3-yl]prop-2-enenitrile;
(Z)-3-[7-[[5-chloro-3-(trifluoromethyl)pyrazol-1-yl]methyl]-2-methyl-5-oxo-thiazolo[3,2-a]pyrimidin-3-yl]prop-2-enenitrile;
(E)-3-[7-[[5-chloro-3-(trifluoromethyl)pyrazol-1-yl]methyl]-2-methyl-5-oxo-thiazolo[3,2-a]pyrimidin-3-yl]prop-2-enamide;
N-ethyl-7-[[5-isobutyl-3-(trifluoromethyl)pyrazol-1-yl]methyl]-2-methyl-5-oxo-thiazolo[3,2-a]pyrimidine-3-carboxamide;
cis-2-[2-chloro-7-[[5-chloro-3-(trifluoromethyl)pyrazol-1-yl]methyl]-5-oxo-thiazolo[3,2-a]pyrimidin-3-yl]cyclopropanecarbonitrile;
2-[2-chloro-7-[[3-chloro-5-(trifluoromethyl)pyrazol-1-yl]methyl]-5-oxo-thiazolo[3,2-a]pyrimidin-3-yl]cyclopropanecarbonitrile;
trans-7-[[5-chloro-3-(trifluoromethyl)pyrazol-1-yl]methyl]-3-[2-(hydroxymethyl)cyclopropl]-2-(trifluoromethyl)thiazolo[3,2-a]pyrimidin-5-one;
2-[7-[(4-chloro-1-methyl-pyrazol-3-yl)methyl]-2-methyl-5-oxo-thiazolo[3,2-a]pyrimidin-3-yl]cyclopropanecarbonitrile;
cis-2-[2-methyl-5-oxo-7-[[3-(trifluoromethyl)pyrazol-1-yl]methyl]thiazolo[3,2-a]pyrimidin-3-yl]cyclopropanecarbonitrile;
cis-2-[7-[[5-bromo-3-(trifluoromethyl)pyrazol-1-yl]methyl]-2-methyl-5-oxo-thiazolo[3,2-a]pyrimidin-3-yl]cyclopropanecarbonitrile;
cis-2-[7-[[5-chloro-3-(trifluoromethyl)pyrazol-1-yl]methyl]-6-fluoro-5-oxo-2-(trifluoromethyl)thiazolo[3,2-a]pyrimidin-3-yl]cyclopropanecarbonitrile;
2-[2-methyl-7-[[1-methyl-4-(trifluoromethyl)imidazol-2-yl]methyl]-5-oxo-thiazolo[3,2-a]pyrimidin-3-yl]cyclopropanecarbonitrile;
(E)-3-[7-[(N-ethyl-4-fluoro-anilino)methyl]-2-methyl-5-oxo-thiazolo[3,2-a]pyrimidin-3-yl]prop-2-enenitrile;
7-[(4-fluorophenoxy)methyl]-3-[[2-hydroxyethyl(methyl)amino]methyl]-2-methyl-thiazolo[3,2-a]pyrimidin-5-one;
7-[(4-fluorophenoxy)methyl]-3-[(2-hydroxyethylamino)methyl]-2-methyl-thiazolo[3,2-a]pyrimidin-5-one;
2-[7-[(4-fluorophenoxy)methyl]-2-methyl-5-oxo-thiazolo[3,2-a]pyrimidin-3-yl]-N,N-dimethyl-acetamide;
7-[(2-cyano-4,5-difluoro-phenyl)methyl]-N,2-dimethyl-5-oxo-thiazolo[3,2-a]pyrimidine-3-carboxamide;
7-[(2-cyclopropyl-4,5-difluoro-phenyl)methyl]-N-ethyl-2-methyl-5-oxo-thiazolo[3,2-a]pyrimidine-3-carboxamide;
3-[2-(azetidin-1-yl)-2-oxo-ethyl]-7-[[2-fluoro-3-(trifluoromethyl)phenyl]methyl]-2-methyl-thiazolo[3,2-a]pyrimidin-5-one;
7-[(4-fluorophenoxy)methyl]-2-methyl-3-(4H-1,2,4-triazol-3-ylmethyl)thiazolo[3,2-a]pyrimidin-5-one;
2-[7-[[2-fluoro-3-(trifluoromethyl)phenyl]methyl]-2-methyl-5-oxo-thiazolo[3,2-a]pyrimidin-3-yl]-N-methyl-propanamide;
3-[7-[[2-fluoro-3-(trifluoromethyl)phenyl]methyl]-2-methyl-oxo-thiazolo[3,2-a]pyrimidin-3-yl]-N-methyl-propanamide;
7-[[5-chloro-2-(trifluoromethyl)phenyl]methyl]-N,2-dimethyl-5-oxo-thiazolo[3,2-a]pyrimidine-3-carboxamide;
7-[(5-ethyl-1,3-benzoxazol-6-yl)methyl]-N,2-dimethyl-5-oxo-thiazolo[3,2-a]pyrimidine-3-carboxamide;
7-[(3-chloropyrazol-1-yl)methyl]-N-ethyl-2-methyl-5-oxo-thiazolo[3,2-a]pyrimidine-3-carboxamide;
7-[(5-chloropyrazol-1-yl)methyl]-N-ethyl-2-methyl-5-oxo-thiazolo[3,2-a]pyrimidine-3-carboxamide;
2-[7-[(3-cyano-2-fluoro-phenyl)methyl]-2-methyl-5-oxo-thiazolo[3,2-a]pyrimidin-3-yl]-N-methyl-acetamide;
N-ethyl-7-[[2-fluoro-3-(1-hydroxypropyl)phenyl]methyl]-2-methyl-5-oxo-thiazolo[3,2-a]pyrimidine-3-carboxamide;
7-[(4,5-difluoro-2-oxazol-2-yl-phenyl)methyl]-N,2-dimethyl-5-oxo-thiazolo[3,2-a]pyrimidine-3-carboxamide;
2-fluoro-3-[(2-methyl-5-oxo-3-propanoyl-thiazolo[3,2-a]pyrimidin-7-yl)methyl]benzonitrile;
7-[[4,5-difluoro-2-(trifluoromethyl)phenyl]methyl]-N,2-dimethyl-5-oxo-thiazolo[3,2-a]pyrimidine-3-carboxamide;
7-[[2-chloro-5-(trifluoromethyl)phenyl]methyl]-N-ethyl-5-oxo-2-(trifluoromethyl)thiazolo[3,2-a]pyrimidine-3-carboxamide;
7-[[2-chloro-5-(trifluoromethyl)phenyl]methyl]-N-ethyl-2-methyl-5-oxo-thiazolo[3,2-a]pyrimidine-3-carboxamide;
7-[[2-chloro-5-(trifluoromethyl)phenyl]methyl]-2-methyl-5-oxo-N-(2,2,2-trifluoroethyl)thiazolo[3,2-a]pyrimidine-3-carboxamide;
3-[(2-chloro-3-cyclopropyl-5-oxo-thiazolo[3,2-a]pyrimidin-7-yl)methyl]-2-fluoro-benzonitrile;
7-[[2-fluoro-3-(trifluoromethyl)phenyl]methyl]-2-methyl-3-(pyrazol-1-ylmethyl)thiazolo[3,2-a]pyrimidin-5-one;
N,2-dimethyl-7-[[3-methyl-4-(trifluoromethyl)pyrazol-1-yl]methyl]-5-oxo-thiazolo[3,2-a]pyrimidine-3-carboxamide;
N,2-dimethyl-7-[[5-methyl-4-(trifluoromethyl)pyrazol-1-yl]methyl]-5-oxo-thiazolo[3,2-a]pyrimidine-3-carboxamide;
2-fluoro-3-[(8-oxo-2,3-dihydro-1H-cyclopenta[3,4]thiazolo[1,4-a]pyrimidin-6-yl)methyl]benzonitrile;
7-[[2-fluoro-3-(trifluoromethyl)phenyl]methyl]-3-[hydroxy(thiazol-2-yl)methyl]-2-methyl-thiazolo[3,2-a]pyrimidin-5-one;
2-fluoro-3-[(3-methyl-8-oxo-2,3-dihydro-1H-cyclopenta[3,4]thiazolo[1,4-a]pyrimidin-6-yl)methyl]benzonitrile;
2-[7-[(4-fluorophenoxy)methyl]-5-oxo-2-(trifluoromethyl)thiazolo[3,2-a]pyrimidin-3-yl]-N-methyl-acetamide;
2-fluoro-3-[[1-(hydroxymethyl)-8-oxo-2,3-dihydro-1H-cyclopenta[3,4]thiazolo[1,4-a]pyrimidin-6-yl]methyl]benzonitrile;
7-[[2-fluoro-3-(trifluoromethyl)phenyl]methyl]-N-(2-hydroxy-1-methyl-ethyl)-2-methyl-5-oxo-thiazolo[3,2-a]pyrimidine-3-carboxamide;
3-[[3-(2,3-dimethylcyclopropyl)-2-methyl-5-oxo-thiazolo[3,2-a]pyrimidin-7-yl]methyl]-2-fluoro-benzonitrile;
6-[[3-cyclopropyl-5-(trifluoromethyl)pyrazol-1-yl]methyl]-1-(hydroxymethyl)-2,3-dihydro-1H-cyclopenta[3,4]thiazolo[1,4-a]pyrimidin-8-one;
7-[[2-fluoro-3-(trifluoromethyl)phenyl]methyl]-2-methyl-3-(2-oxa-6-azaspiro[3,3]heptan-6-yl)thiazolo[3,2-a]pyrimidin-5-one;
N-ethyl-6-fluoro-7-[[2-fluoro-3-(trifluoromethyl)phenyl]methyl]-5-oxo-2-(trifluoromethyl)thiazolo[3,2-a]pyrimidine-3-carboxamide;

7-[(4-fluorophenoxy)methyl-5-oxo-N-(2,2,2-trifluoro-ethyl)-2-(trifluoromethyl)thiazolo[3,2-a]pyrimidine-3-carboxamide;
N-cyclopentyl-7-[[2-fluoro-3-(trifluoromethyl)phenyl]methyl]-2-methyl-5-oxo-thiazolo[3,2-a]pyrimidine-3-carboxamide;
7-(4,5-dichloropyrazol-1-yl)methyl]-N-ethyl-2-methyl-5-oxo-thiazolo[3,2-a]pyrimidine-3-carboxamide;
7-[(3,4-dichloropyrazol-1yl)methyl]-N-ethyl-2-methyl-5-oxo-thiazolo[3,2-a]pyrimidine-3-carboxamide;
N-ethyl-2-methyl-7-[[methyl(thiazol-2-yl)amino]methyl]-5-oxo-thiazolo[3,2-a]pyrimidine-3-carboxamide;
7-[(4-chloropyrazol-1-yl)methyl]-N-ethyl-2-methyl-5-oxo-thiazolo[3,2-a]pyrimidine-3-carboxamide;
N-ethyl-2-methyl-7-[[methyl-(1-methylpyrazol-4-yl)amino]methyl]-5-oxo-thiazolo[3,2-a]pyrimidine-3-carboxamide;
7-[(4-fluorophenoxy)methyl]-2-(trifluoromethyl)-3-[2-(trifluoromethyl)cyclopropyl]thiazolo[3,2-a]pyrimidin-5-one;
7-[[(3-ethoxy-2-pyridyl)-methyl-amino]methyl]-N-ethyl-2-methyl-5-oxo-thiazolo[3,2-a]pyrimidine-3-carboxamide;
7-[[(3,5-dimethylisoxazol-4-yl)-methyl-amino]methyl]-N-ethyl-2-methyl-5-oxo-thiazolo[3,2-a]pyrimidine-3-carboxamide;
3-cyclopropyl-7-[(4-fluorophenoxy)methyl]-2-(trifluoromethyl)thiazolo[3,2-a]pyrimidin-5-one;
7-[(4-fluorophenoxy)methyl]-3-pyrimidin-5-yl-2-(trifluoromethyl)thiazolo[3,2-a]pyrimidin-5-one;
7-[(4-fluorophenoxy)methyl]-3-[2-(hydroxymethyl)cyclopropyl]-2-(trifluoromethyl)thiazolo[3,2-a]pyrimidin-5-one;
7-[[2-fluoro-3-(trifluoromethyl)phenyl]methyl]-2-methyl-3-(4-methyl-1,2,4-triazol-3-yl)thiazolo[3,2-a]pyrimidin-5-one;
2-fluoro-3-[[5-oxo-2-(trifluoromethyl)-3-[2-(trifluoromethyl)cyclopropyl]thiazolo[3,2-a]pyrimidin-7-yl]methyl]benzonitrile;
N-ethyl-7-[[ethyl(4-pyridyl)amino]methyl]-2-methyl-5-oxo-thiazolo[3,2-a]pyrimidine-3-carboxamide;
N-ethyl-7-[[ethyl(3-pyridyl)amino]methyl]-2-methyl-5-oxo-thiazolo[3,2-a]pyrimidine-3-carboxamide;
7-[[5-chloro-3-(trifluoromethyl)pyrazol-1-yl]methyl]-3-(2-methoxy-3-pyridyl)-2-methyl-thiazolo[3,2-a]pyrimidin-5-one;
2-[7-[[2-fluoro-3-(trifluoromethyl)phenyl]methyl]-5-oxo-2-(trifluoromethyl)thiazolo[3,2-a]pyrimidin-3-yl]cyclopropanecarbonitrile;
7-[[3-chloro-5-(trifluoromethyl)pyrazol-1-yl]methyl]-3-isopropenyl-2 (trifluoromethyl)thiazolo[3,2-a]pyrimidin-5-one;
3-(5-chloro-3-pyridyl)-7-[[(5-chloro-2-pyridyl)-methyl-amino]methyl]-2-methyl-thiazolo[3,2-a]pyrimidin-5-one;
7-[[5-chloro-3-(trifluoromethyl)pyrazol-1-yl]methyl]-3-(3-pyridyl)-2-(trifluoromethyl)thiazolo[3,2-a]pyrimidin-5-one;
7-[[3-chloro-5-(trifluoromethyl)pyrazol-1-yl]methyl]-N-ethyl-5-oxo-2-(2,2,2-trifluoroethoxy)thiazolo[3,2-a]pyrimidine-3-carboxamide;
7-[[3-chloro-6-(trifluoromethyl)-2-pyridyl]methyl]-2-methyl-3-(2-methylcyclopropyl)thiazolo[3,2-a]pyrimidin-5-one;
7-[(5-chloro-2-pyridyl)oxymethyl]-N-ethyl-2-methyl-5-oxo-thiazolo[3,2-a]pyrimidine-3-carboxamide;
7-[[3-chloro-5-(trifluoromethyl)pyrazol-1-yl]methyl]-2-ethyl-3-(3-pyridyl)thiazolo[3,2-a]pyrimidin-5-one;
7-[[5-chloro-3-(trifluoromethyl)pyrazol-1-yl]methyl]-3-pyrrolidin-1-yl-2-(trifluoromethyl)thiazolo[3,2-a]pyrimidin-5-one;
N-ethyl-7-[[(5-methoxy-2-pyridyl)-methyl-amino]methyl]-2-methyl-5-oxo-thiazolo[3,2-a]pyrimidine-3-carboxamide;
3-(2-chloro-3-pyridyl)-7-[[5-chloro-3-(trifluoromethyl)pyrazol-1-yl]methyl]-2-methyl-thiazolo[3,2-a]pyrimidin-5-one;
3-(2-chloro-3-pyridyl)-7-[[3-chloro-5-(trifluoromethyl)pyrazol-1-yl]methyl]-2-methyl-thiazolo[3,2-a]pyrimidin-5-one;
7-[[5-chloro-3-(trifluoromethyl)pyrazol-1-yl]methyl]-3-(3-pyridyl)thiazolo[3,2-a]pyrimidin-5-one;
7-[[3-chloro-5-(trifluoromethyl)pyrazol-1-yl]methyl]-3-(3-pyridyl)thiazolo[3,2-a]pyrimidin-5-one;
7-[[5-chloro-3-(trifluoromethyl)pyrazol-1-yl]methyl]-3-(3-methoxyazetidin-1-yl)-2-(trifluoromethyl)thiazolo[3,2-a]pyrimidin-5-one;
7-[[5-chloro-3-(trifluoromethyl)pyrazol-1-yl]methyl]-3-(cyclopropylmethyl)-2-methyl-thiazolo[3,2-a]pyrimidin-5-one;
5-[7-[[2-fluoro-3-(trifluoromethyl)phenyl]ethyl]-2-methyl-5-oxo-thiazolo[3,2-a]pyrimidin-3-yl]pyridine-3-carbonitrile;
2-fluoro-3-[[3-[2-methylcyclopropyl]-5-oxo-2-(trifluoromethyl)thiazolo[3,2-a]pyrimidin-7-yl]methyl]benzonitrile;
7-[(3,5-diisopropylpyrazol-1-yl)methyl]-N-ethyl-2-methyl-5-oxo-thiazolo[3,2-a]pyrimidine-3-carboxamide;
2-[7-[(4-chloro-2-methyl-pyrazol-3-yl)methyl]-2-methyl-5-oxo-thiazolo[3,2-a]pyrimidin-3-yl]cyclopropanecarbonitrile;
7-[[5-chloro-3-(trifluoromethyl)pyrazol-1-yl]methyl]-3-(2-methylazetidin-1-yl)-2-(trifluoromethyl)thiazolo[3,2-a]pyrimidin-5-one;
cis-2-[7-[(3,5-dichloropyrazol-1-yl)methyl]-5-oxo-2-(trifluoromethyl)thiazolo[3,2-a]pyrimidin-3-yl]cyclopropanecarbonitrile;
trans-7[[5-chloro-3-(trifluoromethyl)pyrazol-1-yl]methyl]-3-[2-(2-hydroxyethyl)cyclopropyl]-2-(trifluoromethyl)thiazolo[3,2-a]pyrimidin-5-one;
3-chloro-7-[[5-chloro-3-(trifluoromethyl)pyrazol-1-yl]methyl]-2-(trifluoromethyl)thiazolo[3,2-a]pyrimidin-5-one;
cis-5-chloro-1-[[3-[2-methylcyclopropyl]-5-oxo-2-(trifluoromethyl)thiazolo[3,2-a]pyrimidin-7-yl]methyl]pyrazole-3-carbonitrile;
5-chloro-2-[[3-[(2-methylcyclopropyl]-5-oxo-2-(trifluoromethyl)thiazolo[3,2-a]pyrimidin-7-yl]methyl]pyrazole-3-carbonitrile;
7-[[5-ethoxy-3-(trifluoromethyl)pyrazol-1-yl]methyl]-N-ethyl-2-methyl-5-oxo-thiazolo[3,2-a]pyrimidine-3-carboxamide;
N-ethyl-7-[[5-isobutyl-3-(trifluoromethyl)pyrazol-1-yl]methyl]-5-oxo-2-(trifluoromethyl)thiazolo[3,2-a]pyrimidine-3-carboxamide; and
trans-2-[2-[7-[[5-chloro-3-(trifluoromethyl)pyrazol-1-yl]methyl]-5-oxo-2-(trifluoromethyl)thiazolo[3,2-a]pyrimidin-3-yl]cyclopropyl]acetonitrile;
or a pharmaceutically acceptable salt thereof.

62. A compound selected from the group consisting of 7-(4-fluorophenoxymethyl)-3-[2-(hydroxymethyl)cyclopropyl]-2-methyl-5H-[1,3]thiazolo[3,2-a]pyrimidin-5-one, or a pharmaceutically acceptable salt thereof.

63. A compound selected from the group consisting of 7-((ethyl(4-fluorophenyl)amino)methyl)-3-(2-(hydroxymethyl)cyclopropyl)-2-methyl-5H-thiazolo[3,2-a]pyrimidin-5-one, or a pharmaceutically acceptable salt thereof.

64. A compound selected from the group consisting of 6-[(N-ethyl-4-fluoro-anilino)methyl]-2,3-dihydro-1H-cyclopenta[3,4]thiazolo[1,4-a]pyrimidin-8-one, or a pharmaceutically acceptable salt thereof.

65. A compound selected from the group consisting of 3-acetyl-7-((ethyl(4-fluorophenyl)amino)methyl)-2-methyl-5H-thiazolo[3,2-a]pyrimidin-5-one, or a pharmaceutically acceptable salt thereof.

66. A compound selected from the group consisting of N-ethyl-7-(2-fluoro-3-(trifluoromethyl)benzyl)-2-methyl-5-oxo-5H-thiazolo[3,2-a]pyrimidine-3-carboxamide, or a pharmaceutically acceptable salt thereof.

67. A compound selected from the group consisting of 7-[[5-chloro-3-(trifluoromethyl)-1H-pyrazol-1-yl]methyl]-N-ethyl-2-methyl-5-oxo-5H-[1,3]thiazolo[3,2-a]pyrimidine-3-carboxamide, or a pharmaceutically acceptable salt thereof.

68. A compound selected from the group consisting of N-ethyl-7-[(N-ethyl-4-fluoro-anilino)methyl]-2-methyl-5-oxo-thiazolo[3,2-a]pyrimidine-3-carboxamide, or a pharmaceutically acceptable salt thereof.

69. A compound selected from the group consisting of 2-[7-[[5-chloro-3-(trifluoromethyl)pyrazol-1-yl]methyl]-5-oxo-2-(trifluoromethyl)thiazolo[3,2-a]pyrimidin-3-yl]cyclopropanecarbonitrile, or a pharmaceutically acceptable salt thereof.

70. A compound selected from the group consisting of 7-(3-cyano-2-fluorobenzyl)-N-ethyl-2-methyl-5-oxo-5H-thiazolo[3,2-a]pyrimidine-3-carboxamide, or a pharmaceutically acceptable salt thereof.

* * * * *